(12) United States Patent
Jouzi et al.

(10) Patent No.: US 12,092,578 B2
(45) Date of Patent: Sep. 17, 2024

(54) INTEGRATED ARRAYS FOR SINGLE-ANALYTE PROCESSES

(71) Applicant: Nautilus Subsidiary, Inc., Seattle, WA (US)

(72) Inventors: Maryam Jouzi, Hayward, CA (US); Torri Elise Rinker, San Francisco, CA (US); Pengyu Hao, Belmont, CA (US); Vadim Lobanov, Seattle, WA (US); Ryan Kempston Seghers, Kirkland, WA (US); Daniel Horner, Seattle, WA (US); Pierre Indermuhle, Berkeley, CA (US); David Stern, Mountain View, CA (US); Ezra Van Gelder, Palo Alto, CA (US); Kevin Chen, San Mateo, CA (US)

(73) Assignee: Nautilus Subsidiary, Inc., Seattle, WA (US)

(*) Notice: Subject to any disclaimer, the term of this patent is extended or adjusted under 35 U.S.C. 154(b) by 3 days.

(21) Appl. No.: 18/192,606

(22) Filed: Mar. 29, 2023

(65) Prior Publication Data

US 2023/0314324 A1    Oct. 5, 2023

Related U.S. Application Data

(60) Provisional application No. 63/485,835, filed on Feb. 17, 2023, provisional application No. 63/362,186,
(Continued)

(51) Int. Cl.
*G01N 21/64* (2006.01)
*B82Y 15/00* (2011.01)

(52) U.S. Cl.
CPC .......... *G01N 21/6452* (2013.01); *B82Y 15/00* (2013.01); *G01N 21/6428* (2013.01); *G01N 2021/6439* (2013.01)

(58) Field of Classification Search
CPC .......... G01N 21/6452; G01N 21/6428; G01N 2021/6439; B82Y 15/00
See application file for complete search history.

(56) References Cited

U.S. PATENT DOCUMENTS 8,834,797 B2   9/2014   Oldham et al.
8,927,465 B2   1/2015   Trau et al.
(Continued)

FOREIGN PATENT DOCUMENTS

JP       2002536665 A  * 10/2002
WO    WO 2002/018643 A2    3/2002
(Continued)

OTHER PUBLICATIONS

Translation of JP 2002536665 A, Oct. 29, 2002 (Year: 2002).*
(Continued)

*Primary Examiner* — Robert T. Crow
(74) *Attorney, Agent, or Firm* — Morgan, Lewis & Bockius LLP

(57) ABSTRACT

Compositions, systems, and methods are disclosed for preparing and utilizing arrays, such as single-analyte arrays containing a plurality of fiducial elements with random spatial distributions. Arrays may be prepared with pluralities of fiducial elements comprising optically active or passive moieties. Arrays containing random spatial distributions of fiducial elements may be utilized for various array-based processes that require spatial information.

30 Claims, 89 Drawing Sheets

Related U.S. Application Data filed on Mar. 30, 2022, provisional application No. 63/324,850, filed on Mar. 29, 2022.

(56) References Cited

U.S. PATENT DOCUMENTS

| | | |
|---|---|---|
| 10,473,654 B1 | 11/2019 | Mallick |
| 10,794,828 B2 | 10/2020 | Zhuang et al. |
| 10,830,703 B1* | 11/2020 | Almogy ............ G01N 21/65 |
| 11,169,368 B2 | 11/2021 | Marsh et al. |
| 11,203,612 B2 | 12/2021 | Gremyachinskiy et al. |
| 11,282,586 B2 | 3/2022 | Patel et al. |
| 11,505,796 B2 | 11/2022 | Aksel et al. |
| 2002/0125214 A1 | 9/2002 | Mirkin et al. |
| 2006/0041384 A1* | 2/2006 | Kermani ............ G01N 21/6428 |
| | | 702/19 |
| 2016/0055632 A1* | 2/2016 | Fu .................. G01N 21/6456 |
| | | 382/129 |
| 2018/0356343 A1 | 12/2018 | Neuman et al. |
| 2020/0011800 A1 | 1/2020 | Vieceli et al. |
| 2020/0248252 A1* | 8/2020 | Vieceli ............ G01N 21/6428 |
| 2020/0294763 A1 | 9/2020 | Chang |
| 2022/0017951 A1 | 1/2022 | Lyer et al. |
| 2023/0070896 A1 | 3/2023 | Joly et al. |

FOREIGN PATENT DOCUMENTS

| | | |
|---|---|---|
| WO | WO 2019/036055 | 2/2019 |
| WO | WO 2019/083856 | 5/2019 |
| WO | WO 2019/236749 | 12/2019 |
| WO | WO 2020/106889 | 5/2020 |
| WO | WO 2020/190509 | 9/2020 |
| WO | WO 2020/223368 | 11/2020 |
| WO | WO 2021/087402 | 5/2021 |
| WO | WO 2021/252800 | 12/2021 |
| WO | WO 2022/103887 | 5/2022 |
| WO | WO 2022/159520 | 7/2022 |
| WO | WO 2022/159663 | 7/2022 |
| WO | WO 2022/271983 | 12/2022 |

OTHER PUBLICATIONS

Ballard, D.H. "Generalizing the Hough Transform to Detect Arbitrary Shapes," *Pattern Recognition*, vol. 13, No. 2, p. 111-122, 1981.

Alberti, M. et al., "Biomolecular self-assembly of micrometer sized silica beads on patterned glass substrates," Applied Surface Science, 2009, 255:7759-7765.

Köhler, J. M. et al., "Selective labeling of oligonucleotide monolayers by metallic nanobeads for fast optical readout of DNA-chips," Sensors and Actuators, 2001, B 76:166-172.

Shlyapnikov, Y. et al., "Detection of microarray-hybridized oligonucleotides with magnetic beads," Analytical Biochemistry, 2010, 399:125-131.

\* cited by examiner

| 2 | 3 | 2 | 4 | 2 | 6 | 3 | 4 | 2 | 7 |
|---|---|---|---|---|---|---|---|---|---|
| 3 | 28 | 32 | 38 | 3 | 6 | 22 | 43 | 34 | 8 |
| 6 | 22 | 76 | 43 | 5 | 4 | 32 | 82 | 29 | 5 |
| 7 | 28 | 35 | 36 | 5 | 3 | 38 | 51 | 33 | 3 |
| 1 | 2 | 4 | 3 | 2 | 5 | 4 | 1 | 2 | 2 |
5 nm
5 nm
FIG. 2A
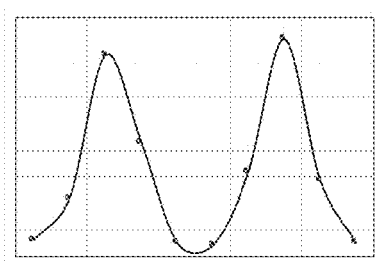
FIG. 2B
| 2 | 3 | 2 | 4 | 2 | 6 | 3 | 4 | 2 | 7 |
|---|---|---|---|---|---|---|---|---|---|
| 3 | 28 | 32 | 38 | 17 | 15 | 22 | 43 | 34 | 8 |
| 6 | 22 | 76 | 55 | 44 | 51 | 52 | 82 | 29 | 5 |
| 7 | 28 | 35 | 36 | 22 | 12 | 38 | 51 | 33 | 3 |
| 1 | 2 | 4 | 3 | 2 | 5 | 4 | 1 | 2 | 2 |
5 nm
5 nm
FIG. 2C
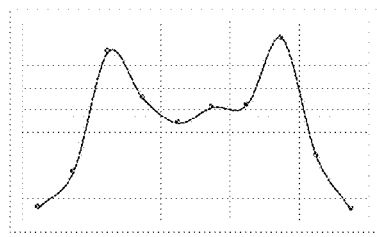
FIG. 2D

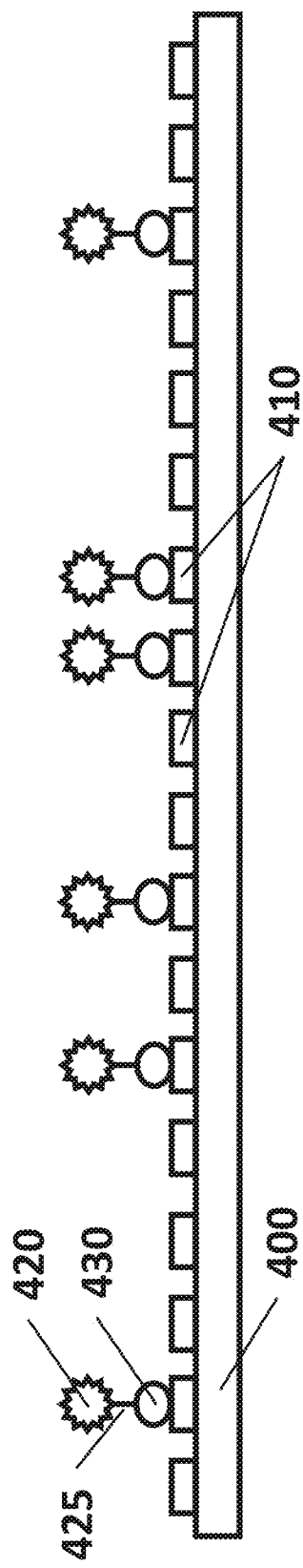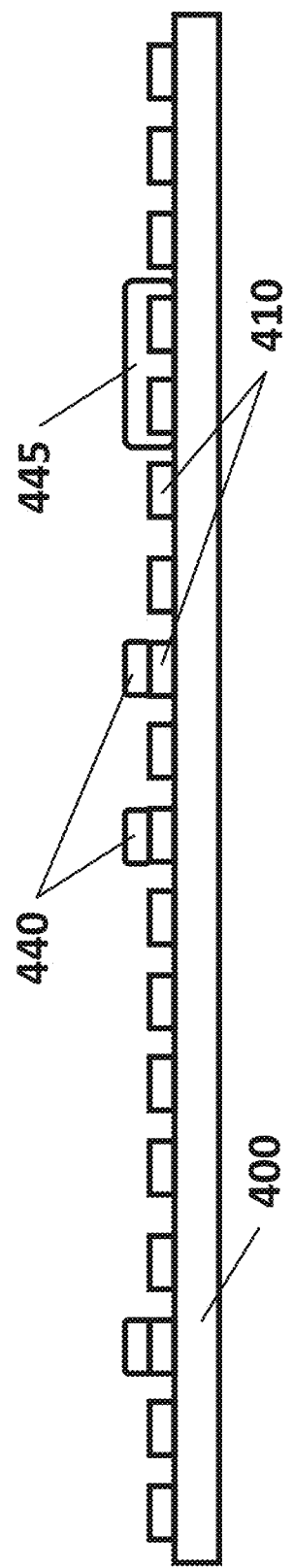

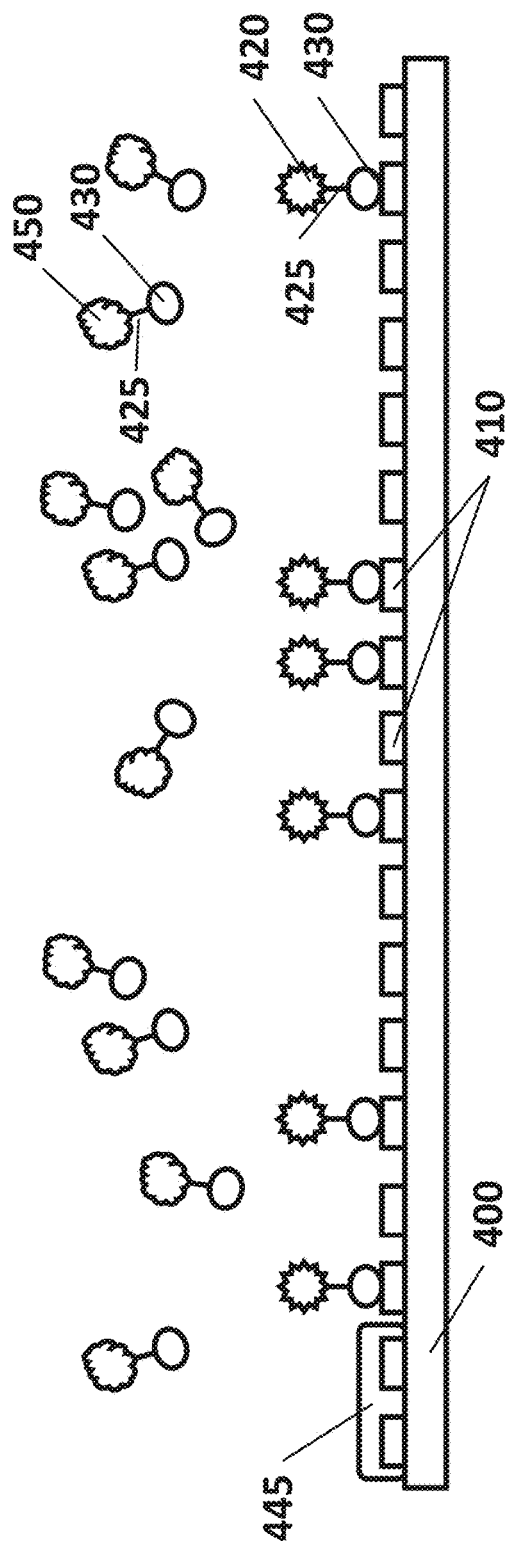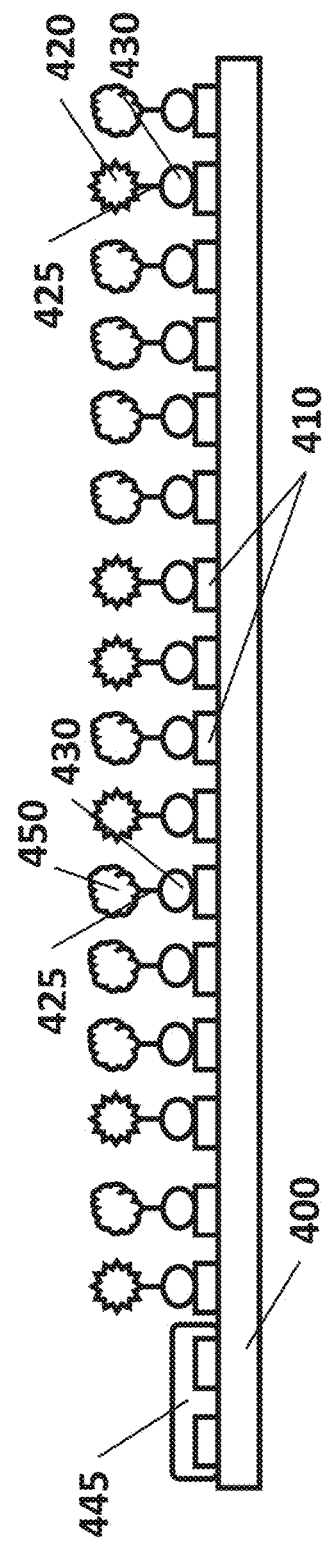

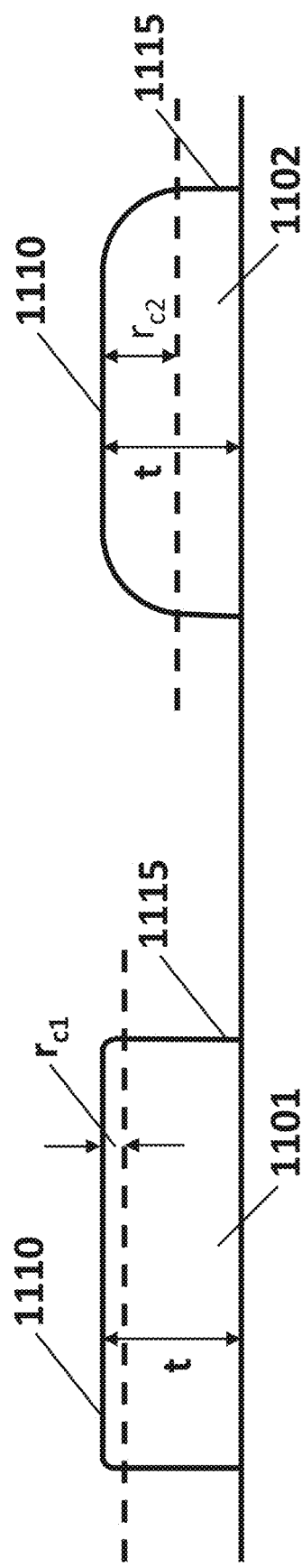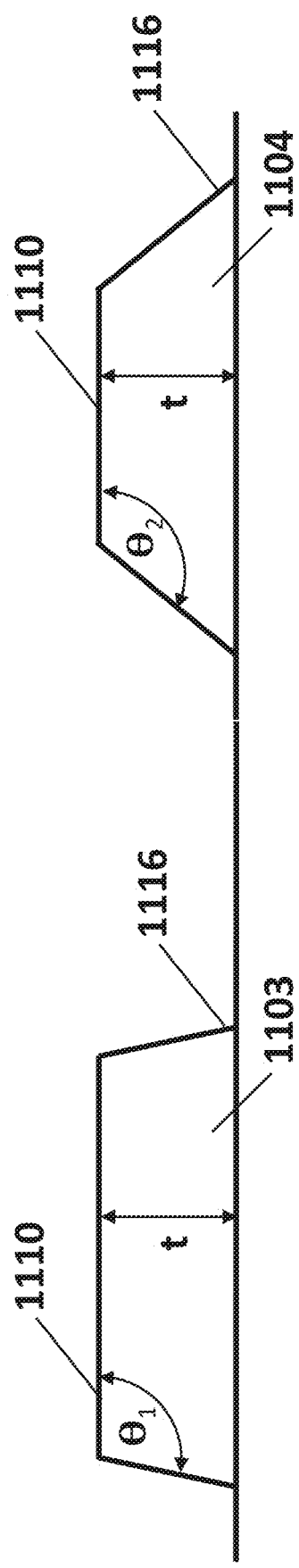
FIG. 11A
FIG. 11B

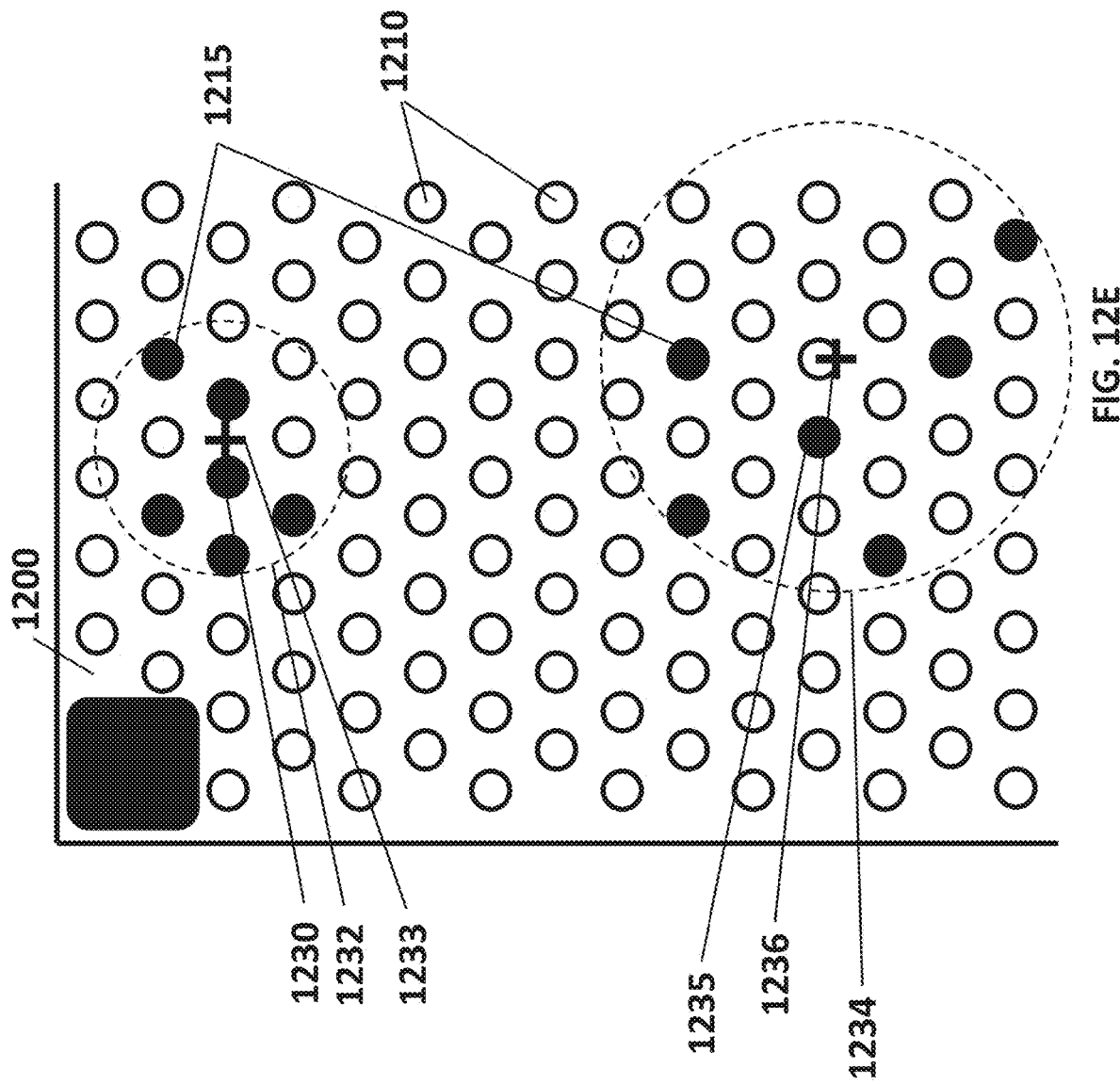

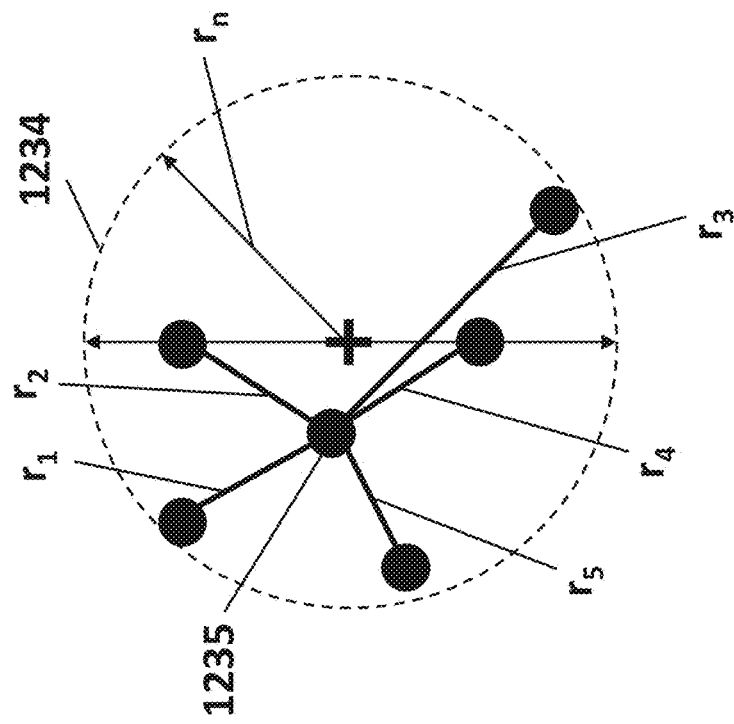
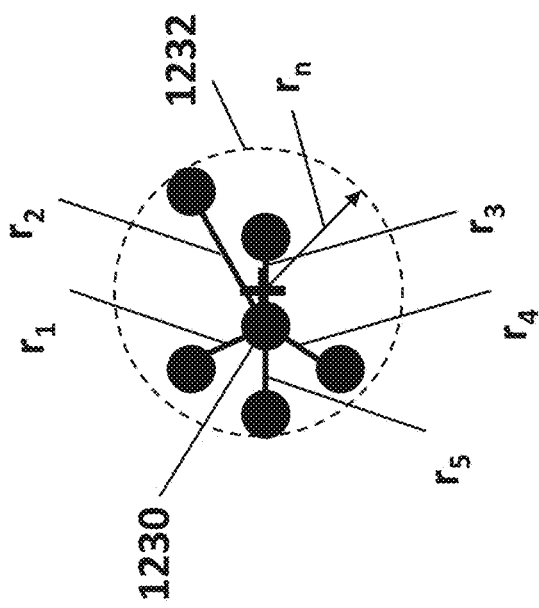
FIG. 12F

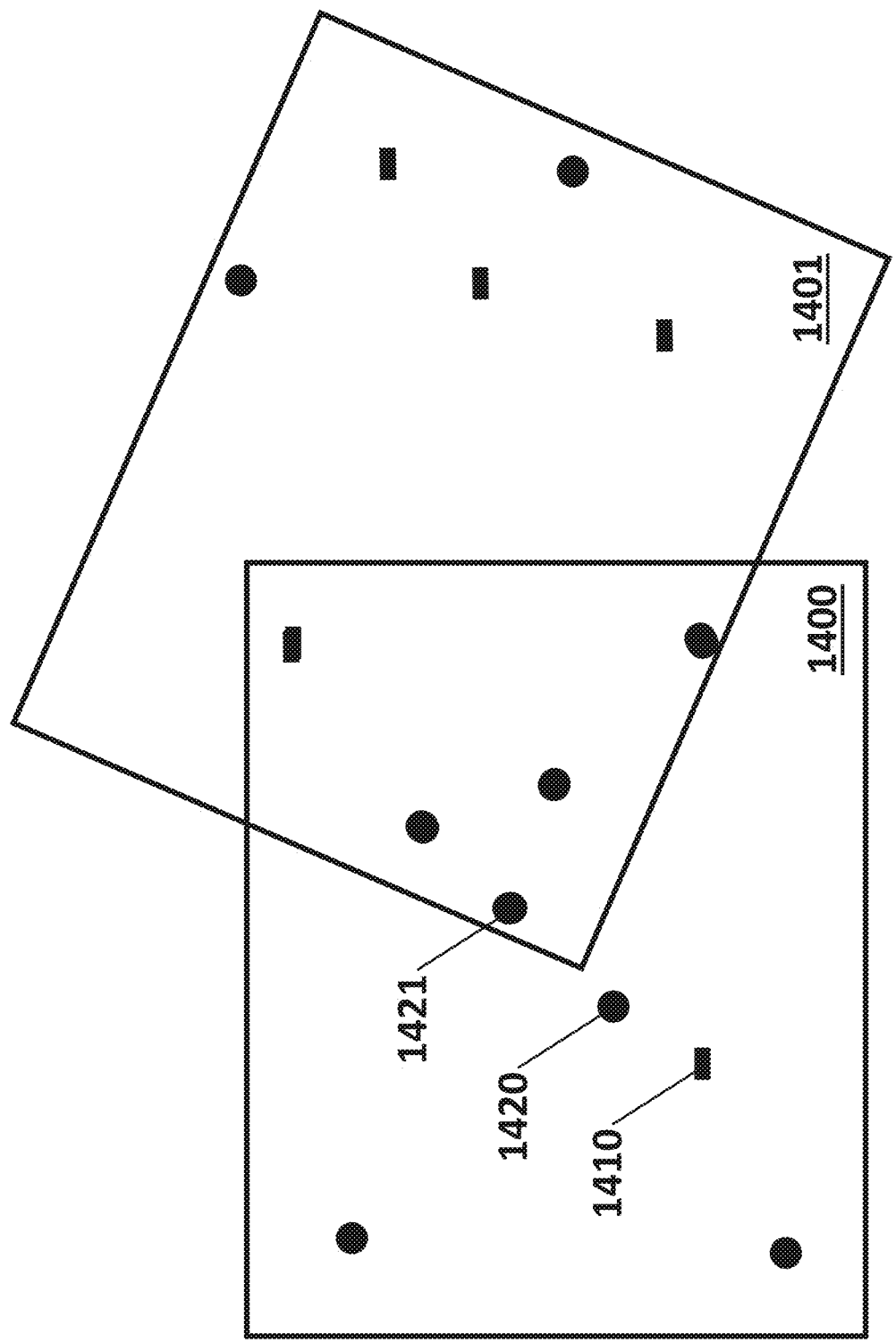

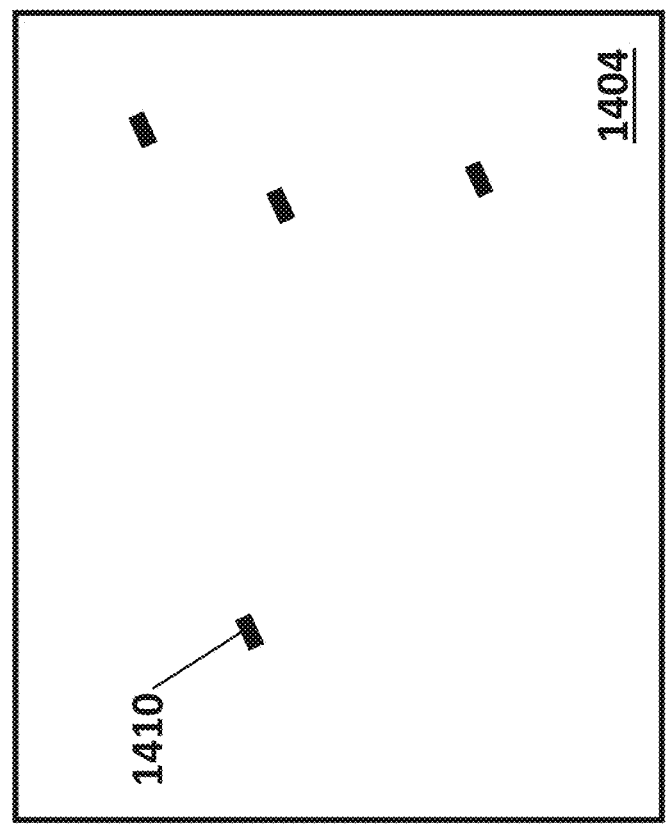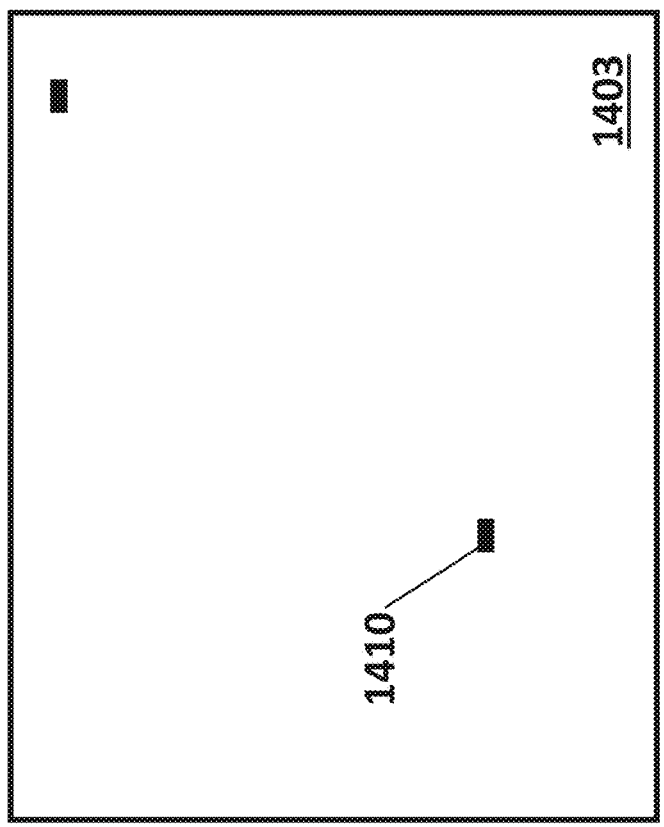
FIG. 14E

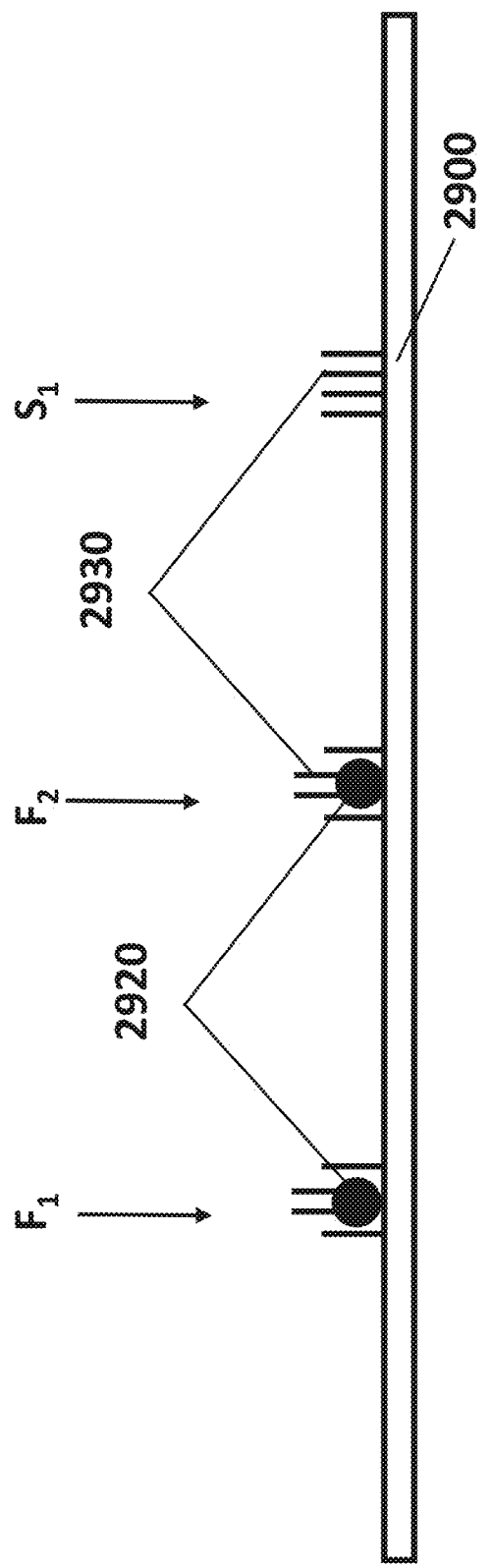

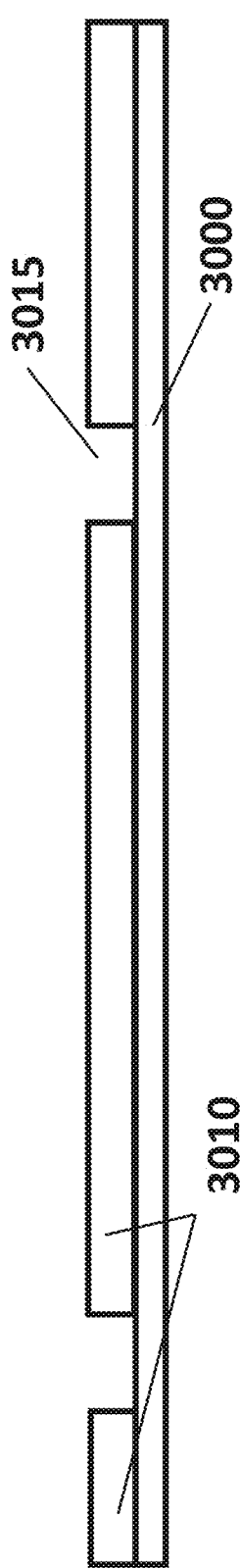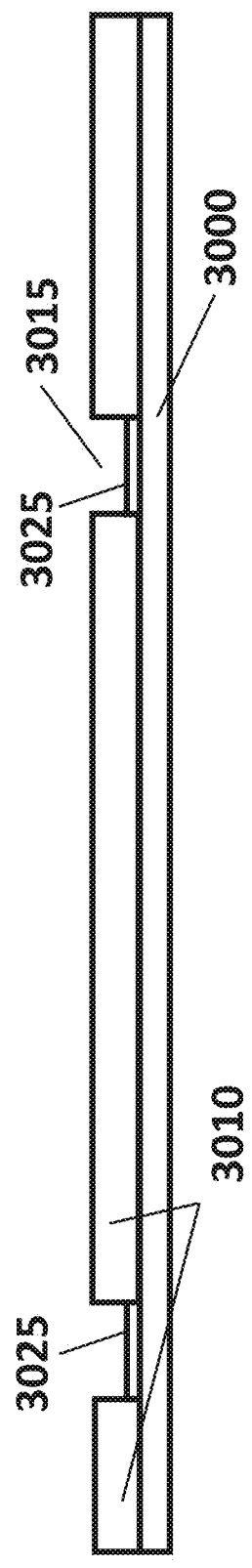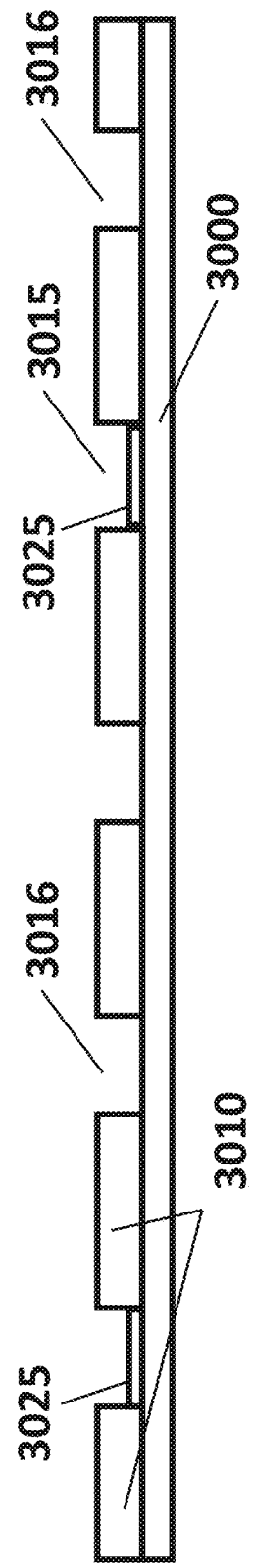

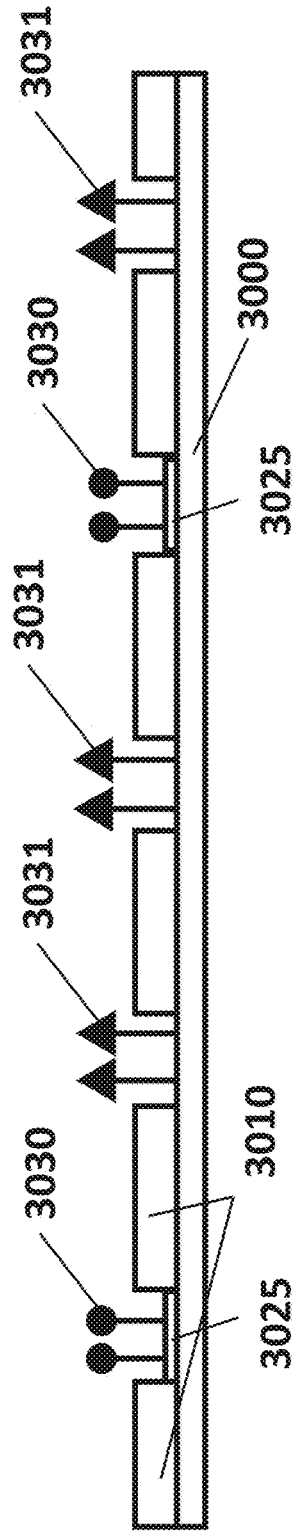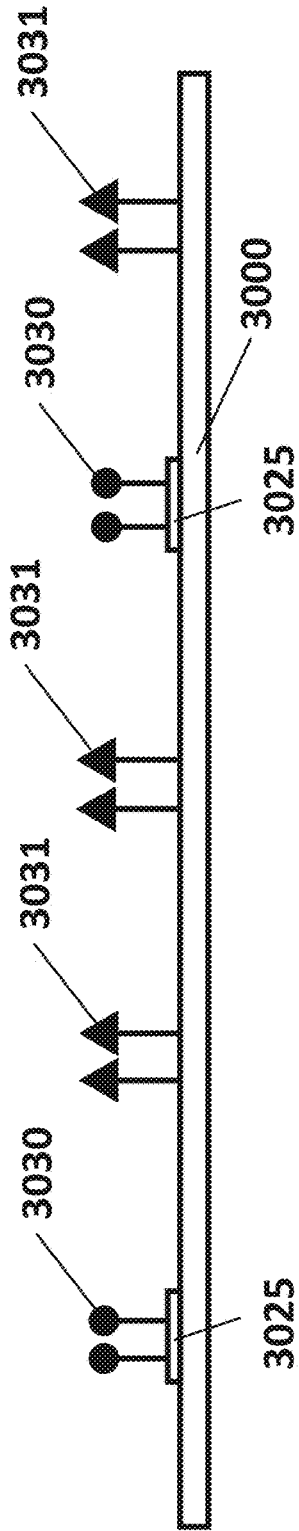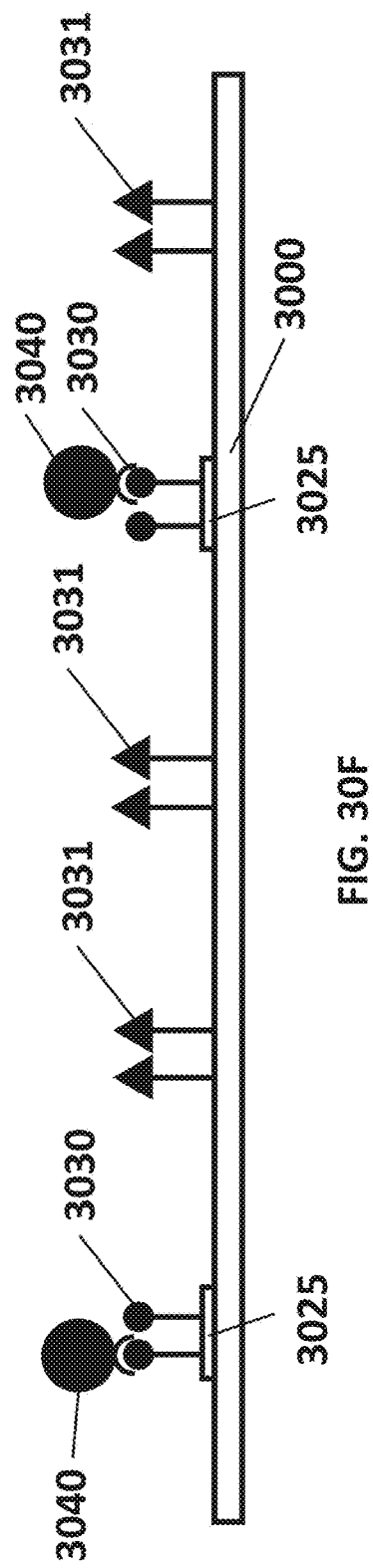

A method for registering a plurality of images of a substrate. 3600

3602
Obtain a first plurality (e.g., about 100 or more) of points within a first image in the plurality of images, the first image defining a first angular reference frame. Each respective point in the first plurality of points has respective two-dimensional coordinates defining a location of the respective point in the first image.

3604
Obtain a second plurality (e.g., about 100 or more) of points within a second image in the plurality of images, the second image defining a second angular reference frame. Each respective point in the second plurality of points has respective two-dimensional coordinates defining a location of the respective point in the second image. The first plurality of points and the second plurality of points are coplanar. At least a first subset of the first plurality of points is not represented by the second plurality of points. At least a second subset of the second plurality of points is not represented by the first plurality of points. At least a third subset of points in the first plurality of points is represented in the second plurality of points.

3606
Each point in the first plurality of points represents optical activity localized to a corresponding position on the substrate.

3608
A first subplurality of the first plurality of points arises from respective optical measurements of a plurality of fiducials on the substrate, where points corresponding to the first subplurality of points is in the second plurality of points.
A second subplurality of the first plurality of points arises from respective optical measurements of a plurality of polypeptide molecules when bound to an affinity reagent.
Each polypeptide molecule of said plurality of polypeptide molecules is coupled to a unique, spatially-separated location of a plurality of unique, spatially-separated locations on the substrate.

3610
Each point in the first plurality of points and in the second plurality of points represents an optical measurement of a corresponding position on the substrate.

3612
The optical measurement is of a fluorescence.

FIG. 36A

Vote Table

| delta y \ delta x | -4 | -3 | -2 | -1 | 0 | 1 | 2 | 3 | 4 |
|---|---|---|---|---|---|---|---|---|---|
| -4 |  |  |  |  |  |  | 1 |  |  |
| -3 |  |  |  |  |  |  |  |  |  |
| -2 |  |  |  |  | 1 |  |  |  |  |
| -1 |  |  |  |  |  | 2 |  |  |  |
| 0 |  |  |  |  |  |  |  |  |  |
| 1 |  |  |  | 1 |  |  |  |  |  |
| 2 |  |  |  |  | 1 |  |  |  |  |
| 3 |  |  |  |  |  |  |  |  |  |
| 4 |  |  |  |  |  |  |  |  |  |

FIG. 42G

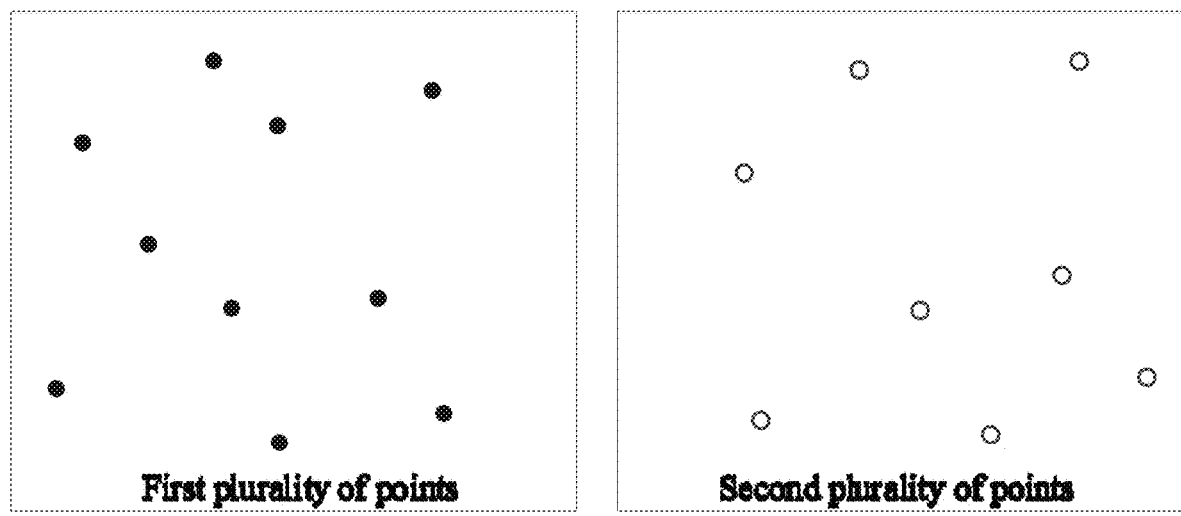
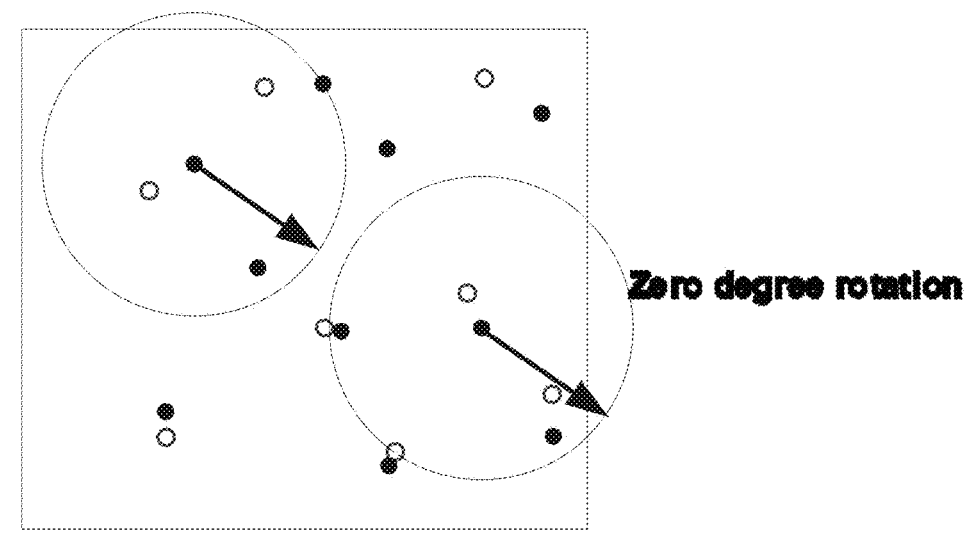
FIG. 47

INTEGRATED ARRAYS FOR SINGLE-ANALYTE PROCESSES

CROSS REFERENCE TO RELATED APPLICATIONS

This application claims priority to U.S. Provisional Application No. 63/324,850, filed on Mar. 29, 2022, U.S. Provisional Application No. 63/362,186, filed on Mar. 30, 2022, and U.S. Provisional Application No. 63/485,835, filed on Feb. 17, 2023, each of which is incorporated herein by reference in its entirety.

BACKGROUND

Single-analyte processes include certain processes in which each single analyte is uniquely resolvable by a method of interrogation, such as light microscopy or electron microscopy. A single-analyte process may utilize an optical interrogation method to identify a characteristic, property, or state of each resolvable single analyte of a single-analyte system, such as an array of single analytes. Certain single-analyte processes, such as assays of polypeptides or nucleic acids, may utilize cyclic or multi-step interrogation of each single analyte to identify a characteristic, property, or state of the single analyte.

Optical interrogation of single analytes in an array-based format can utilize multiple optical functions to ensure accurate collection of optical data. A first possible optical function may be landmarking, a function that enables position sensing and/or positional error sensing of an optical detection system relative to a known position. A second possible optical function may be image registration, a function that identifies corresponding information in two unique images. A third possible optical function may be image focusing, a function that permits an optical system to maintain a uniform focal depth across an array or a region thereof given possible local or array-wide variations in surface height and/or curvature.

Despite the wealth of insights gained from increasingly routine genomic and transcriptomic studies, there remains a large gap between the number of identified relationships between genotype and phenotype and the number of identified relationships between transcriptomes and phenotypes. Proteomics is crucial to bridging this gap as proteins constitute the main structural and functional components of cells. The proteome is perhaps the most dynamic and valuable source of functional biological insight.

However, proteome measurement technologies are significantly lagging behind next-generation DNA and RNA sequencing technologies, largely in part due to the complex nature of individual proteins and proteomes as well as the high dynamic range (~$10^9$) covered by a typical comprehensive proteomic analysis. Strikingly, roughly 10% of the proteins predicted to comprise the human proteome have never been confidently observed. Additionally, current proteomic techniques are limited in their sensitivity and throughput. A typical single experiment measures no more than 8% of the human proteome from blood or 35% from cells and tissues.

Recently, single-molecule identification has been proposed as a method to analyze small samples (including single cells) and identify rare proteins. Traditional bulk quantification techniques like mass spectrometry and immunoassays have been adapted towards detection of single proteins. In addition, several concepts have been proposed to achieve single-molecule peptide sequencing. These all use sequential processes to determine positional information from amino acids within peptides, e.g., Edman degradation or directional translocation of a peptide through a nanopore channel. See, for instance, Egertson et al., "A theoretical framework for proteome-scale single-molecule protein identification using multiaffinity protein binding reagents," bioRxiv, 2021, doi: 10.1101/2021.10.11.463967, which is hereby incorporated herein by reference in its entirety. Such approaches introduce challenges in the field of image analysis and image registration.

Thus, there is a need in the art for systems and methods that provide improved image analysis and image registration to address technical problems arising in whole proteome analysis at the single-molecule level, particularly in order to achieve high throughput and single-molecule sensitivity of intact proteins.

SUMMARY

Technical solutions (e.g., computing systems, methods, and non-transitory computer readable storage mediums) for addressing the above-identified problems in image analysis and/or image registration are provided in the present disclosure. In particular, various methods of performing image registration are described herein.

It should be understood that this summary is not an extensive overview of the present disclosure. It is not intended to identify key/critical elements of the present disclosure or to delineate the scope of the present disclosure. Its sole purpose is to present some of the aspects of the present disclosure in a simplified form as a prelude to the more detailed description that is presented later.

In an aspect, provided herein is a single-analyte array, comprising: a) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and b) a plurality of fiducial elements, wherein each fiducial element is located at a site of the plurality of sites, and wherein the plurality of fiducial elements is distributed on the solid support at random sites.

In another aspect, provided herein is a single-analyte array composition, comprising: a) a solid support, wherein the solid support comprises a plurality of addresses and one or more interstitial regions, wherein a subset of the addresses are sites that are configured to couple analytes of interest, wherein each interstitial region is configured to inhibit binding of the analytes of interest, and wherein each of the sites is separated from each other of the sites by an interstitial region of the one or more interstitial regions; b) a plurality of fiducial elements, wherein a second subset of addresses of the plurality of addresses comprises a coupled fiducial element of the plurality of fiducial elements, and wherein a spatial distribution of the second subset of addresses is random; and c) a plurality of the analytes of interest in contact with the solid support.

In another aspect, provided herein is a non-transitory computer-readable medium, comprising: a) an identification value corresponding to an identification tag of an array; and b) an array map, wherein the array map comprises a plurality of data units, in which each data unit comprises: i) a location tag, wherein the location tag comprises a datum corresponding to a site on the array; and ii) a signal datum for the site on the array, wherein the signal datum comprises information pertaining to presence or absence of a fiducial element at the site on the array.

In another aspect, provided herein is a composition, comprising: a) a solid support comprising an address with a known spatial address; b) a fiducial element coupled to the address; and c) an analyte coupled to the address; wherein the fiducial element and the analyte are spatially non-resolvable at the address at single-analyte resolution, and wherein the fiducial element and the analyte are resolvable at the address via distinguishable optical characteristics.

In another aspect, provided herein is a single-analyte system, comprising: a) a single-analyte array, as set forth herein; b) a sensing device; and c) a retaining device, wherein the retaining device is configured to position a landmarking region of the single-analyte array relative to the sensing device.

In another aspect, provided herein is a non-transitory, computer-readable medium, comprising: a) a first subarray map comprising a first plurality of data units, wherein each data unit of the first plurality of data units comprises a signal datum for the site on the array, wherein the signal datum comprises information pertaining to presence or absence of a fiducial element at the site on the first subregion of the array; and b) a second subarray map comprising a second plurality of data units, wherein each data unit of the second plurality of data units comprises a signal datum for the site on the array, wherein the signal datum comprises information pertaining to presence or absence of a fiducial element at the site on the second subregion of the array; wherein a first subset of signal data of the first plurality of data units corresponds to a first random spatial order of fiducial elements at sites of the array, wherein a second subset of signal data of the second plurality of data units corresponds to a second random spatial order of fiducial elements at sites of the array, and wherein the first random spatial order and the second random spatial order are the same.

In another aspect, provided herein is a method of registering overlapping data sets, comprising: a) obtaining a first data set of an array, as set forth herein, wherein the first data set comprises a spatial distribution of detected signals in a first field-of-view of a sensing device, wherein the first field-of-view encompasses a first plurality of sites, wherein the first plurality of sites comprises a first pattern of detected signals from a plurality of fiducial elements, and wherein a first site of the first plurality of sites is optically non-resolvable; b) obtaining a second data set of the array, wherein the second data set comprises a spatial distribution of detected signals in a second field-of-view of the sensing device, wherein the second field-of-view encompasses a second plurality of sites, wherein the second plurality of sites, wherein the second plurality of sites comprises a second pattern of detected signals from the plurality of fiducial elements, and wherein a second site of the second plurality of sites is optically non-resolvable; c) aligning the first pattern of detected signals with the second pattern of detected signals; and d) after aligning the first pattern of detected signals with the second pattern of detected signals, identifying a first address of the first site, and identifying a second address of the second site.

In another aspect, provided herein is a method of mapping an addresses of a site, comprising: a) providing a single-analyte array comprising a solid support, wherein the single-analyte array comprises a first site, a second site, and a third site, wherein the first site comprises a first address on the solid support, wherein the second site comprises a second address on the solid support, wherein the third site comprises a third address on the solid support, and wherein the first address, the second address, and the third address are resolvable at single-analyte resolution; b) coupling a first fiducial element to the third site; c) coupling a first locating moiety to the first site and a second locating moiety to the second site, wherein the locating moiety comprises a detectable label or a second fiducial element; d) detecting the first locating moiety, the second locating moiety, and the first fiducial element; and e) identifying the first address and the second address relative to the third address.

In another aspect, provided herein is a method of qualifying a single-analyte array, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; ii) a plurality of fiducial elements, wherein each fiducial element is located at a site of the plurality of sites, and wherein the plurality of fiducial elements is distributed on the solid support at spatially random addresses; b) determining a measure of spatial randomness for the plurality of fiducial elements; and c) selecting the single-analyte array if the measure of spatial randomness meets a selection criterion for the measure of spatial randomness.

In another aspect, provided herein is a method of preparing a solid support, comprising: a) providing the solid support, wherein the solid support comprises a plurality of sites, wherein each site of the plurality of sites has a unique spatial address on a surface of the solid support, and wherein each site of the plurality of sites is configured to couple a moiety to the surface of the solid support; b) depositing a plurality of fiducial elements on the solid support, wherein each fiducial element of the plurality of fiducial elements is deposited at a random site of the plurality of sites; and c) identifying a spatial distribution of the plurality of fiducial elements on the solid support, wherein the spatial distribution comprises presence or absence of a fiducial element of the plurality of fiducial elements at each address of the plurality of addresses.

In another aspect, provided herein is a method of forming a single-analyte array, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; ii) a plurality of fiducial elements, wherein each fiducial element is located at a site of the plurality of sites, and wherein the plurality of fiducial elements is distributed on the solid support at spatially random addresses; and b) depositing a plurality of single analytes on the solid support, wherein each single analyte of the plurality of single analytes is deposited at a site that does not comprise a fiducial element.

In another aspect, provided herein is a method of aligning a single-analyte array, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; ii) a plurality of fiducial elements, wherein each fiducial element is located at a site of the plurality of sites, and wherein the plurality of fiducial elements is distributed on the solid support at spatially random addresses; and iii) a landmarking fiducial element; b) setting an initial position for the single-analyte array based upon a first identification of the landmarking fiducial element relative to the detection device; c) scanning the plurality of sites of the single-analyte array with the detection device, wherein scanning the plurality of sites comprises altering a position of the detection device relative to the single-analyte array; and d) returning the single-analyte array to the initial position relative to the detection device based upon a second identification of the landmarking fiducial element relative to the detection device.

In another aspect, provided herein is a method of aligning multiple sensors, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and ii) a plurality of fiducial elements, wherein each fiducial element is located at a site of the plurality of sites, and wherein the plurality of fiducial elements is distributed on the solid support at spatially random addresses; b) identifying in a first field-of-view on a first sensor a first plurality of signals from a subset of fiducial elements of the plurality of fiducial elements, in which the first plurality of signals comprises a unique spatial pattern; c) identifying in a second field-of-view on a second sensor a second plurality of signals from the subset of fiducial elements of the plurality of fiducial elements, in which the second plurality of signals comprises the unique spatial pattern; and d) determining a spatial offset between the first field-of-view and the second field-of-view.

In another aspect, provided herein is a method of altering an optical detection device comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and ii) a plurality of fiducial elements, wherein each fiducial element is located at a site of the plurality of sites, and wherein the plurality of fiducial elements is distributed on the solid support at spatially random addresses; b) obtaining a plurality of signals from the single-analyte array using a optical detection device, in which the plurality of signals comprise a spatial pattern of a subset of the plurality of fiducial elements; c) determining an optical calibration parameter based upon the plurality of signals; and d) based upon the optical calibration parameter, altering an optical setting of the optical detection device relative to the single-analyte array.

In another aspect, provided herein is a method of utilizing a single-analyte array, comprising: a) providing the single-analyte array, wherein the single-analyte array comprises a plurality of sites, wherein each site of the plurality of sites is optically resolvable at single-analyte resolution, wherein each site of a first subset of the plurality of sites comprises a fiducial element of a plurality of fiducial elements, wherein the first subset of the plurality of sites has a random spatial distribution, wherein the single-analyte array further comprises a plurality of single analytes, wherein the plurality of single analytes is bound to a second subset of the plurality of sites, and wherein each site of the second subset of the plurality of sites comprises one and only one analyte of the plurality of single analytes, b) binding an analytical reagent to a single analyte of the plurality of single analytes, c) detecting optical signals from the first subset of the plurality of sites, d) detecting an optical signal from the analytical reagent bound to the single analyte, and e) based upon an address of the optical signal from the analytical reagent relative to the optical signals of the first subset of the plurality of sites, identifying a site of the second subset of the plurality of sites comprising the analytical reagent bound to the single analyte of the plurality of single analytes.

In another aspect, provided herein is a method of utilizing a single-analyte array, comprising: a) providing the single-analyte array, wherein the single-analyte array comprises: i) a plurality of analyte-containing sites, wherein each analyte-containing site comprises one and only one analyte, ii) a plurality of fiducial element-containing sites, wherein the plurality of fiducial element-containing sites comprises a random spatial distribution, wherein each fiducial element produces an optical signal, and wherein a ratio of analyte-containing sites to fiducial element-containing sites is at least 100:1, and iii) a plurality of analytical reagents bound to analytes at a fraction of the analyte-containing sites, wherein each analytical reagent produces an optical signal, and wherein the fraction of analyte-containing sites is no more than 50% of the analyte-containing sites, b) identifying a plurality of subdistributions of the random spatial distribution of the plurality of fiducial-element-containing sites, wherein each subdistribution of the plurality of subdistributions is unique from each other subdistribution of the plurality of subdistributions, c) detecting a plurality of optical signals from the single-analyte array, wherein the plurality of optical signals comprises optical signals from the plurality of fiducial element-containing sites and optical signals from the fraction of analyte-containing sites, and d) for each optical signal from the fraction of analyte-containing sites, determining an address on the single-analyte array of the optical signal based upon a location of the optical signal with respect to at least one subdistribution of the plurality of subdistributions of the plurality of fiducial element-containing sites.

In another aspect, provided herein is a single-analyte array, comprising: a) a solid support comprising a plurality of sites, wherein each site of the plurality of sites is optically resolvable at single-analyte resolution, b) a plurality of fiducial elements bound to a first subset of the plurality of sites, wherein the first subset of the plurality of sites comprises a random spatial distribution, and wherein the subset of the plurality of sites comprises no more than about 1% of the plurality of sites, and c) a plurality of sample analytes bound to a second subset of the plurality of sites, wherein each site of the first subset of the plurality of sites comprises one and only one fiducial element of the plurality of fiducial elements, wherein each site of the second subset of the plurality of sites comprises one and only one sample analyte of the plurality of sample analytes, wherein the random spatial distribution of the first subset of the plurality of sites comprises a plurality of unique subdistributions, and wherein each site of the second subset of the plurality of sites has known spatial distances to sites of a unique subdistribution of the plurality of unique subdistributions.

In another aspect, provided herein is a single-analyte array, comprising: a) a solid support comprising a plurality of sites, wherein each site of the plurality of sites is optically resolvable at single-analyte resolution, b) a plurality of fluorescent nanoparticles bound to a first subset of the plurality of sites, wherein each fluorescent nanoparticle of the plurality of fluorescent nanoparticles is attached to a first plurality of oligonucleotides, wherein each oligonucleotide of the first plurality of oligonucleotides comprises a first nucleotide sequence, wherein each site of the first subset of the plurality of sites comprises a second plurality of oligonucleotides, wherein each oligonucleotide of the second plurality of oligonucleotides comprises a second nucleotide sequence, wherein the first oligonucleotide sequence is complementary to the second oligonucleotide sequence, and wherein two or more oligonucleotides of the first plurality of oligonucleotides is hybridized to two or more oligonucleotides of the second plurality of oligonucleotides, and c) a plurality of analytes bound to a second subset of the plurality of sites.

In another aspect, provided herein is a method of forming a single-analyte array, comprising: a) depositing a plurality of fluorescent nanoparticles on a solid support comprising a plurality of sites, wherein the fluorescent nanoparticles bind to a first subset of the plurality of sites, wherein the first subset of the plurality of sites comprises a random spatial distribution, wherein each fluorescent nanoparticle comprises a first plurality of oligonucleotides, wherein each site of the first subset of the plurality of sites comprises a second plurality of oligonucleotides, and wherein, for each fluorescent nanoparticle, two or more oligonucleotides of the first plurality of oligonucleotides hybridize to two or more oligonucleotides of the second plurality of oligonucleotides, and b) depositing a plurality of analytes on the solid support, wherein the plurality of analytes bind to a second subset of the plurality of sites.

One aspect of the present disclosure provides a method for registering a plurality of images of a substrate, the method comprising obtaining a first plurality of points (e.g., points having two-dimensional coordinates) within a first image in the plurality of images, the first image defining a first angular reference frame, where the first plurality of points comprises about 100 or more points, and where each respective point in the first plurality of points has respective two-dimensional coordinates defining a location of the respective point in the first image. The method can further include obtaining a second plurality of points within a second image in the plurality of images, the second image defining a second angular reference frame, where the second plurality of points comprises about 100 or more points, and each respective point in the second plurality of points has respective two-dimensional coordinates defining a location of the respective point in the second image. The first plurality of points and the second plurality of points are coplanar, and optionally at least a first subset of the first plurality of points is not represented by the second plurality of points, at least a second subset of the second plurality of points is not represented by the first plurality of points, and at least a third subset of points in the first plurality of points is represented in the second plurality of points. In some cases, the first plurality of points and the second plurality of points include fiducial sites. Alternatively, none of the points in the first and second sets correspond to fiducial sites. Optionally, the first plurality of points can include only fiducial sites (e.g. lacking sites having test analytes) or the first plurality of points can include a combination of fiducial sites and test analyte sites. Similarly, the second plurality of points can include only fiducial sites (e.g. lacking sites having test analytes) or the second plurality of points can include a combination of fiducial sites and test analyte sites.

A method set forth herein can include forming a transformation data structure that includes a respective counter for each transform candidate in a plurality of transform candidates, where each transform candidate in the plurality of transform candidates includes a two-dimensional translation component and a planar rotational component, the plurality of transform candidates collectively samples between a first angle and a second angle about an axis orthogonal to the first and second plurality of points, and the plurality of transform candidates comprises about 5,000 or more different transform candidates.

A procedure can be performed that comprises, for each respective point in one of the first and second plurality of points, (i) pairing the respective point with a corresponding point in the other of the first and second plurality of points whose corresponding two-dimensional coordinates are within a query radius centered on the respective two-dimensional coordinates of the respective point thereby identifying a respective point pair. The procedure includes (ii) adding, for the respective point pair, a respective vote for each respective transform candidate in the plurality of transform candidates, having a respective angle represented by the transformation data structure, that maps the respective point onto the corresponding point, to the respective counter for the respective transform candidate in the transformation data structure. For instance, if the respective angle is zero degrees, each respective transform candidate in the plurality of transform candidates that is capable of mapping the respective point (in the first plurality of points) onto the corresponding point (in the second plurality of points) without application of a rotation (about the axis orthogonal to the first and second plurality of points) is given a vote. The procedure further includes (iii) repeating the adding (ii) for the respective point pair for each respective angle represented by the transformation data structure thereby adding additional votes for respective transform candidates identified by the adding (ii). In this way, all other angles represented by the transformation data structure are considered for the respective point pair. For instance, if the transformation data structure includes transform candidates that require a 0.25 degree rotation about the axis orthogonal to the first and second plurality of points, each respective transform candidate in the plurality of transform candidates that is capable of mapping the respective point (in the first plurality of points) onto the corresponding point (in the second plurality of points) with the application of a 0.25 degree rotation (about the axis orthogonal to the first and second plurality of points) is given a vote by virtue of the (iii) repeating. Moreover, while the enumerated steps (i), (ii) and (iii) gave votes to all transform candidates for one point pair formed by the respective point in the first plurality of points, there may exist other points within the above-described query radius of the respective point in the second plurality of points. That is, there may be other candidate point pairs for the respective point in the first plurality of points. Thus, some embodiments (iv) repeat the pairing (i), adding (ii), and repeating (iii) for the respective point with each other corresponding point in the second plurality of points that is within the query radius. As noted at the outset above, steps (i), (ii), (iii), and (iv) are performed for each point in the first plurality of points, or a predetermined subsampling of the first plurality of points. In this way, all possible transformation candidates, at possible angles, are given votes.

The method can further include registering the first and second images to each other using a respective transform candidate selected from the plurality of transform candidates in the transformation data structure based at least in part on a value of the respective counter associated with the respective transform candidate in the transformation data structure.

In some embodiments, the adding (ii) rotates a point in the respective point pair by the respective angle about the axis prior to determining each respective transform candidate in the plurality of transform candidates having the respective angle, represented by the transformation data structure, that maps the respective point onto the corresponding point.

In some embodiments, the query radius is at least 10 pixels, at least 20 pixels, or at least 50 pixels.

Another aspect of the present disclosure provides a method for registering a plurality of images of a substrate, the method comprising obtaining a first plurality of points within a first image in the plurality of images, the first image defining a first angular reference frame, where the first plurality of points comprises about 100 or more points. The method includes obtaining a second plurality of points within a second image in the plurality of images, the second image defining a second angular reference frame, where the second plurality of points comprises about 100 or more points. The first plurality of points and the second plurality of points are coplanar, and, optionally, at least a first subset of the first plurality of points is not represented by the second plurality of points, at least a second subset of the second plurality of points is not represented by the first plurality of points, and at least a third subset of points in the first plurality of points is represented in the second plurality of points. The method further comprises forming a transformation data structure that includes a respective counter for each transform candidate in a plurality of transform candidates, where each transform candidate in the plurality of transform candidates includes a two-dimensional translation component and a planar rotational component, and where the plurality of transform candidates comprises about 5,000 or more different transform candidates. In some cases, one or both of the first plurality of points and the second plurality of points (1) include only fiducial sites, (2) include only sites having test analytes, (3) lack fiducial sites, (4) lack sites having test analytes or (5) include a combination of fiducial sites and sites having test analytes.

For each respective transform candidate in the plurality of transform candidates, a procedure can be performed that comprises (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The first and second images are registered to each other using a respective transform candidate selected from the plurality of transform candidates in the transformation data structure based at least in part on a value of the respective counter associated with the respective transform candidate in the transformation data structure.

In some embodiments, a substrate that is imaged has a planar surface. In some embodiments, each image of the plurality of images is acquired from the planar surface.

In some embodiments, each image in a plurality of images comprises more than 200,000 pixels. In some embodiments, each image in a plurality of images comprises more than 500,000 pixels.

In some embodiments, each image in a plurality of images comprises at least about 500 pixels in a first dimension, each image in a plurality of images comprises at least about 500 pixels in a second dimension orthogonal to the first dimension, and each transform candidate in a plurality of transform candidates transforms one of the first image or the second image between about 1 pixel and about 300 pixels.

In some embodiments, each image in a plurality of images consists of 2048 pixels in a first dimension, each image in the plurality of images consists of 2048 pixels in a second dimension orthogonal to the first dimension, and each transform candidate in the plurality of transform candidates transforms one of the first image or the second image between about 1 pixel and about 256 pixels.

In some embodiments, each point in a first plurality of points represents optical activity localized to a corresponding position on a substrate. In some such embodiments, (i) a first subplurality of the first plurality of points arises from respective optical measurements of a plurality of fiducials on the substrate, where points corresponding to the first subplurality of points are in the second plurality of points, and (ii) a second subplurality of the first plurality of points arises from respective optical measurements of a plurality of polypeptide molecules when bound to an affinity reagent, and each polypeptide molecule of said plurality of polypeptide molecules is coupled to a unique, spatially-separated location of a plurality of unique, spatially-separated locations on the substrate. As described elsewhere herein (see, e.g., Definitions: Analytes), polypeptide molecules are exemplary analytes. A variety of other analytes set forth herein or known in the art can be used instead of, or in addition to, the polypeptide molecules exemplified herein.

In some embodiments, an affinity reagent binds to more than one unique epitope present within one or more polypeptides in a plurality of polypeptide molecules. In some embodiments, the affinity reagent comprises a known degree of binding nonspecificity (for the plurality of polypeptide molecules, for example, binding promiscuously to more than one different polypeptide molecule in the plurality of polypeptide molecules).

In some embodiments, a plurality of polypeptide molecules comprises more than 500, more than 1000, more than 2000, more than 3000, more than 5000, more than 6000, or more than 7000 different polypeptide molecules.

In some embodiments, a first subplurality represents less than 10 percent, less than 5 percent, or less than 2 percent of a plurality of points.

In some embodiments, each transform candidate in a plurality of transform candidates transforms one of a first image or a second image between about 1 pixel and about 500 pixels.

In some embodiments, a plurality of transform candidates comprises a sampling between a first limit angle and a second limit angle about the axis. In some such embodiments, the first limit angle is −0.5° and the second limit angle is +0.5°. In some embodiments, the first limit angle is −5° and the second limit angle is +5°. In some embodiments, the plurality of transform candidates samples between the first limit angle and the second limit angle with a constant step size, where the constant step size is 0.01°.

In some embodiments, a first plurality of points comprises about 200 or more, about 400 or more, about 600 or more, about 800 or more, or about 1000 or more points, and the second plurality of points comprises about 200 or more, about 400 or more, about 600 or more, about 800 or more, or about 1000 or more points.

In some embodiments, at least about 5 percent, at least about 10 percent, at least about 15 percent, at least about 20 percent, at least about 25 percent, at least about 30 percent, at least about 35 percent, or at least about 40 percent of a first plurality of points is not represented by (e.g., found in) a second plurality of points.

In some embodiments, each point in a first plurality of points occupies a corresponding single pixel in a first image; and each point in a second plurality of points occupies a corresponding single pixel in a second image.

In some embodiments, selection of a respective transform candidate in a plurality of transform candidates in a transformation data structure is based at least in part on a value of a respective counter associated with the respective transform candidate in the transformation data structure includes identifying an optimal planar rotational component by a procedure comprising, for each different candidate planar rotational component represented in the plurality of transform candidates, (i) forming a corresponding Hough two-dimensional image, where each pixel in the corresponding Hough two-dimensional image is the corresponding count of points (e.g., votes) of a respective transform candidate in the plurality of transform candidates having the different candidate planar rotational component; (ii) applying a binomial distribution cumulative distribution function across the respective counts of each transform candidate in the respective image; and (iii) computing a respective z-score of the largest peak in the respective Hough two-dimensional image, thereby forming a plurality of Hough two-dimensional images. The respective transform candidate is selected from among the plurality of transform candidates in the transformation data structure based on a respective z-score of each largest peak in each Hough two-dimensional image in the plurality of Hough two-dimensional images.

In some embodiments, a respective transform candidate is selected from among a plurality of transform candidates in a transformation data structure that is associated with a peak in a plurality of Hough two-dimensional images having the largest z-score.

In some embodiments, a method set forth herein can further comprise applying a Gaussian filter to the respective Hough two-dimensional image prior to computing the respective z-score.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is represented in (e.g., found in) the second plurality of points. In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the first plurality of points is represented in (e.g., found in) the second plurality of points.

In some embodiments, the registration is a rigid transformation.

In some embodiments, each point in the first plurality of points and in the second plurality of points represents an optical measurement of a corresponding position on the substrate. In some embodiments, the optical measurement is of a fluorescence. In some embodiments, the optical measurement is of a bioluminescence, a chemiluminescence, or a light scattering signal.

In some embodiments, each image in the plurality of images comprises at least about 500 pixels in a first dimension, and each image in the plurality of images comprises at least about 500 pixels in a second dimension orthogonal to the first dimension.

In some embodiments, each image in the plurality of images consists of 2048 pixels in a first dimension, and each image in the plurality of images consists of 2048 pixels in a second dimension orthogonal to the first dimension.

In some embodiments, the plurality of transform candidates samples between about one and about 500 pixels in a first translational dimension with a constant first step size, and the plurality of transform candidates samples between about one and about 500 pixels in a second translational dimension with a constant second step size. In some embodiments, the constant first step size and the constant second step size is the same or different. In some embodiments, the constant first step size and the constant second step size are each a single pixel. In some embodiments, the plurality of transform candidates samples between a first angle and a second angle about the axis with a third constant step size. In some embodiments, the first angle is $-0.5°$ and the second angle is $+0.5°$. In some embodiments, the first angle is $-5°$ and the second angle is $+5°$.

In some embodiments, the query radius is between 50 pixels and 500 pixels. In some embodiments, the query radius is between 100 pixels and 200 pixels.

In some embodiments, the query radius is such that it defines a circle about the respective point that contains at least 1%, at least 5%, or at least 10%, in pixels, of the total number of pixels in the respective image corresponding to the one of the first and second plurality of points that has the respective point. In some embodiments, the query radius is such that defines a circle about the respective point that contains between 1% and 50%, in pixels, of the total number of pixels in the respective image corresponding to the one of the first and second plurality of points that has the respective point. In some embodiments, the query radius is such that it defines a circle about the respective point that contains between 2% and 20%, in pixels, of the total number of pixels in the respective image corresponding to the one of the first and second plurality of points that has the respective point.

In some embodiments, each respective point in the one of the first and second plurality of points has a corresponding set of matched points in the other of the first and second plurality of points, where each respective matched point in the respective set of matched points has corresponding two-dimensional coordinates that fall within the query radius centered on the respective two-dimensional coordinates of the respective point.

In some such embodiments, the repeating (iv) repeats the pairing (i), adding (ii), and repeating (iii) for the respective point with each respective matched point in the respective set of matched points.

In some embodiments, the corresponding set of matched points comprises at least 1, at least 5, at least 10, or at least 50 points in the other of the first and second plurality of points. In some embodiments, the corresponding set of matched points comprises between 1 and 200 points in the other of the first and second plurality of points. In some embodiments, the corresponding set of matched points comprises between 10 and 100 points in the other of the first and second plurality of points.

Another aspect of the present disclosure provides a method for registering a plurality of images of a substrate, the method comprising obtaining a first plurality of points within a first image in the plurality of images, where the first plurality of points comprises about 100 or more points. The method can include obtaining a second plurality of points within a second image in the plurality of images, the second image acquired of the substrate at a different time than the first image, where the second plurality of points comprises about 100 or more points, the first plurality of points and the second plurality of points are coplanar, at least a first subset of the first plurality of points, optionally, is not represented by the second plurality of points, at least a second subset of the second plurality of points, optionally, is not represented by the first plurality of points, at least a third subset of points in the first plurality of points is represented in the second plurality of points, and each point in the first plurality of points and in the second plurality of points represents an optical measurement of a corresponding position on the substrate. The method can further include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates.

The method can include, for each respective point in one of the first and second plurality of points, attempting to pair the respective point with a corresponding point in the other of the first and second plurality of points thereby querying for a point pair and, when the point pair exists, (i) obtaining a respective vote for a respective transform candidate in the plurality of transform candidates that maps the respective point onto the corresponding point, and (ii) adding the respective vote for the respective transform candidate to the respective counter for the respective transform candidate in the transformation data structure. The first and second images are registered to each other using a respective transform candidate selected from the plurality of transform candidates in the transformation data structure based at least in part on a value of the respective counter associated with the respective transform candidate in the transformation data structure.

Another aspect of the present disclosure provides a method for registering a plurality of images of a substrate, the method comprising obtaining a first plurality of points within a first image in the plurality of images, where the first plurality of points comprises about 100 or more points. The method can include obtaining a second plurality of points within a second image in the plurality of images, where the second plurality of points comprises about 100 or more points, the first plurality of points and the second plurality of points are coplanar, at least a first subset of the first plurality of points, optionally, is not represented by the second plurality of points, at least a second subset of the second plurality of points, optionally, is not represented by the first plurality of points, at least a third subset of points in the first plurality of points is represented in the second plurality of points, and each point in the first plurality of points and in the second plurality of points represents an optical measurement of a corresponding position on the substrate. The method can further include forming a transformation data structure that includes a respective counter for each transform candidate in a plurality of transform candidates, where each transform candidate in the plurality of transform candidates includes a two-dimensional translation component, and where the plurality of transform candidates comprises about 500 or more different transform candidates.

The method can include, for each respective transform candidate in the plurality of transform candidates, performing a procedure that comprises (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The first and second images are registered to each other using a respective transform candidate selected from the plurality of transform candidates in the transformation data structure based at least in part on a value of the respective counter associated with the respective transform candidate in the transformation data structure.

Another aspect of the present disclosure provides a method for registering a plurality of images of a substrate, the method comprising obtaining a first plurality of points within a first image in the plurality of images, where the first plurality of points comprises about 100 or more points. The method can include obtaining a second plurality of points within a second image in the plurality of images, the second image acquired of the substrate at a different time than the first image, where the second plurality of points comprises about 100 or more points, the first plurality of points and the second plurality of points are coplanar, at least a first subset of the first plurality of points, optionally, is not represented by the second plurality of points, at least a second subset of the second plurality of points, optionally, is not represented by the first plurality of points, at least a third subset of points in the first plurality of points is represented in the second plurality of points, and a first subplurality of the first plurality of points arises from respective optical measurements of a plurality of fiducials on the substrate, where points corresponding to the first subplurality of points is in the second plurality of points, and a second subplurality of the first plurality of points arises from respective optical measurements of a plurality of polypeptide molecules when bound to an affinity reagent, and each polypeptide molecule of said plurality of polypeptide molecules is coupled to a unique, spatially-separated location of a plurality of unique, spatially-separated locations on the substrate.

The method can further include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. The method can further include populating the respective counter for each transform candidate in the plurality of transform candidates that is able to match respective points in one of the first and second plurality of points to corresponding points in the other of the first and second plurality of points. The first and second images can be registered to each other using a respective transform candidate selected from the plurality of transform candidates in the transformation data structure based at least in part on a value of the respective counter associated with the respective transform candidate in the transformation data structure.

In particular configurations of the methods set forth above, a point in a given image can correspond to a fiducial site or site having a test analyte. Sets of points can (1)

include only fiducial sites, (2) include only sites having test analytes, (3) lack fiducial sites, (4) lack sites having test analytes or (5) include a combination of fiducial sites and sites having test analytes.

Yet another aspect of the present disclosure provides a computing system including one or more processors and memory storing one or more programs for registering a plurality of images of a substrate. It will be appreciated that this memory can be on a single computer, a network of computers, one or more virtual machines, or in a cloud computing architecture. The one or more programs are configured for execution by the one or more processors and include instructions for performing any of the methods disclosed above.

Still another aspect of the present disclosure provides a computer readable storage medium storing one or more programs to be executed by an electronic device. The one or more programs include instructions for the electronic device to perform a method for registering a plurality of images of a substrate using any of the methods disclosed above. It will be appreciated that the computer readable storage medium can exist as a single computer readable storage medium or any number of component computer readable storage mediums that are physically separated from each other.

Other embodiments are directed to systems, portable consumer devices, and computer readable media associated with methods described herein.

In an aspect, provided herein is a single-analyte array, comprising: a) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and b) a plurality of fiducial elements, wherein each fiducial element is located at a site of the plurality of sites, and wherein the plurality of fiducial elements is distributed on the solid support at random sites.

In another aspect, provided herein is a single-analyte array composition, comprising: a) a solid support, wherein the solid support comprises a plurality of addresses and one or more interstitial regions, wherein a subset of the addresses are sites that are configured to couple analytes of interest, wherein each interstitial region is configured to inhibit binding of the analytes of interest, and wherein each of the sites is separated from each other of the sites by an interstitial region of the one or more interstitial regions; b) a plurality of fiducial elements, wherein a second subset of addresses of the plurality of addresses comprises a coupled fiducial element of the plurality of fiducial elements, and wherein a spatial distribution of the second subset of addresses is random; and c) a plurality of the analytes of interest in contact with the solid support.

In another aspect, provided herein is a non-transitory computer-readable medium, comprising: a) an identification value corresponding to an identification tag of an array; and b) an array map, wherein the array map comprises a plurality of data units, in which each data unit comprises: i) a location tag, wherein the location tag comprises a datum corresponding to a site on the array; and ii) a signal datum for the site on the array, wherein the signal datum comprises information pertaining to presence or absence of a fiducial element at the site on the array.

In another aspect, provided herein is a composition, comprising: a) a solid support comprising an address with a known spatial address; b) a fiducial element coupled to the address; and c) an analyte coupled to the address; wherein the fiducial element and the analyte are spatially non-resolvable at the address at single-analyte resolution, and wherein the fiducial element and the analyte are resolvable at the address via distinguishable optical characteristics.

In another aspect, provided herein is a single-analyte system, comprising: a) a single-analyte array, as set forth herein; b) a sensing device; and c) a retaining device, wherein the retaining device is configured to position a landmarking region of the single-analyte array relative to the sensing device.

In another aspect, provided herein is a non-transitory, computer-readable medium, comprising: a) a first subarray map comprising a first plurality of data units, wherein each data unit of the first plurality of data units comprises a signal datum for the site on the array, wherein the signal datum comprises information pertaining to presence or absence of a fiducial element at the site on the first subregion of the array; and b) a second subarray map comprising a second plurality of data units, wherein each data unit of the second plurality of data units comprises a signal datum for the site on the array, wherein the signal datum comprises information pertaining to presence or absence of a fiducial element at the site on the second subregion of the array; wherein a first subset of signal data of the first plurality of data units corresponds to a first random spatial order of fiducial elements at sites of the array, wherein a second subset of signal data of the second plurality of data units corresponds to a second random spatial order of fiducial elements at sites of the array, and wherein the first random spatial order and the second random spatial order are the same.

In another aspect, provided herein is a method of registering overlapping data sets, comprising: a) obtaining a first data set of an array, as set forth herein, wherein the first data set comprises a spatial distribution of detected signals in a first field-of-view of a sensing device, wherein the first field-of-view encompasses a first plurality of sites, wherein the first plurality of sites comprises a first pattern of detected signals from a plurality of fiducial elements, and wherein a first site of the first plurality of sites is optically non-resolvable; b) obtaining a second data set of the array, wherein the second data set comprises a spatial distribution of detected signals in a second field-of-view of the sensing device, wherein the second field-of-view encompasses a second plurality of sites, wherein the second plurality of sites, wherein the second plurality of sites comprises a second pattern of detected signals from the plurality of fiducial elements, and wherein a second site of the second plurality of sites is optically non-resolvable; c) aligning the first pattern of detected signals with the second pattern of detected signals; and d) after aligning the first pattern of detected signals with the second pattern of detected signals, identifying a first address of the first site, and identifying a second address of the second site.

In another aspect, provided herein is a method of mapping an addresses of a site, comprising: a) providing a single-analyte array comprising a solid support, wherein the single-analyte array comprises a first site, a second site, and a third site, wherein the first site comprises a first address on the solid support, wherein the second site comprises a second address on the solid support, wherein the third site comprises a third address on the solid support, and wherein the first address, the second address, and the third address are resolvable at single-analyte resolution; b) coupling a first fiducial element to the third site; c) coupling a first locating moiety to the first site and a second locating moiety to the second site, wherein the locating moiety comprises a detectable label or a second fiducial element; d) detecting the first locating moiety, the second locating moiety, and the first fiducial element; and e) identifying the first address and the second address relative to the third address.

In another aspect, provided herein is a method of qualifying a single-analyte array, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; ii) a plurality of fiducial elements, wherein each fiducial element is located at a site of the plurality of sites, and wherein the plurality of fiducial elements is distributed on the solid support at spatially random addresses; b) determining a measure of spatial randomness for the plurality of fiducial elements; and c) selecting the single-analyte array if the measure of spatial randomness meets a selection criterion for the measure of spatial randomness.

In another aspect, provided herein is a method of preparing a solid support, comprising: a) providing the solid support, wherein the solid support comprises a plurality of sites, wherein each site of the plurality of sites has a unique spatial address on a surface of the solid support, and wherein each site of the plurality of sites is configured to couple a moiety to the surface of the solid support; b) depositing a plurality of fiducial elements on the solid support, wherein each fiducial element of the plurality of fiducial elements is deposited at a random site of the plurality of sites; and c) identifying a spatial distribution of the plurality of fiducial elements on the solid support, wherein the spatial distribution comprises presence or absence of a fiducial element of the plurality of fiducial elements at each address of the plurality of addresses.

In another aspect, provided herein is a method of forming a single-analyte array, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; ii) a plurality of fiducial elements, wherein each fiducial element is located at a site of the plurality of sites, and wherein the plurality of fiducial elements is distributed on the solid support at spatially random addresses; and b) depositing a plurality of single analytes on the solid support, wherein each single analyte of the plurality of single analytes is deposited at a site that does not comprise a fiducial element.

In another aspect, provided herein is a method of aligning a single-analyte array, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; ii) a plurality of fiducial elements, wherein each fiducial element is located at a site of the plurality of sites, and wherein the plurality of fiducial elements is distributed on the solid support at spatially random addresses; and iii) a landmarking fiducial element; b) setting an initial position for the single-analyte array based upon a first identification of the landmarking fiducial element relative to the detection device; c) scanning the plurality of sites of the single-analyte array with the detection device, wherein scanning the plurality of sites comprises altering a position of the detection device relative to the single-analyte array; and d) returning the single-analyte array to the initial position relative to the detection device based upon a second identification of the landmarking fiducial element relative to the detection device.

In another aspect, provided herein is a method of aligning multiple sensors, comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and ii) a plurality of fiducial elements, wherein each fiducial element is located at a site of the plurality of sites, and wherein the plurality of fiducial elements is distributed on the solid support at spatially random addresses; b) identifying in a first field-of-view on a first sensor a first plurality of signals from a subset of fiducial elements of the plurality of fiducial elements, in which the first plurality of signals comprises a unique spatial pattern; c) identifying in a second field-of-view on a second sensor a second plurality of signals from the subset of fiducial elements of the plurality of fiducial elements, in which the second plurality of signals comprises the unique spatial pattern; and d) determining a spatial offset between the first field-of-view and the second field-of-view.

In another aspect, provided herein is a method of altering an optical detection device comprising: a) providing a single-analyte array, wherein the single-analyte array comprises: i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and ii) a plurality of fiducial elements, wherein each fiducial element is located at a site of the plurality of sites, and wherein the plurality of fiducial elements is distributed on the solid support at spatially random addresses; b) obtaining a plurality of signals from the single-analyte array using a optical detection device, in which the plurality of signals comprise a spatial pattern of a subset of the plurality of fiducial elements; c) determining an optical calibration parameter based upon the plurality of signals; and d) based upon the optical calibration parameter, altering an optical setting of the optical detection device relative to the single-analyte array.

As disclosed herein, any embodiment disclosed herein, when applicable, can be applied to any aspect.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications, patents, or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A, 2B, 2C, and 2D illustrate examples of pixel-based sensor data, in which two analytes are resolved at single-analyte resolution (FIGS. 2A and 2B), or not resolved at single-analyte resolution (FIGS. 2C and 2D), in accordance with some embodiments.

FIGS. 4A, 4B, 4C, 4D, and 4E show cross-sectional views of arrays containing pluralities of fiducial elements with random spatial distributions, and optionally analytes of interest or mapping moieties, in accordance with some embodiments.

FIGS. 5A, 5B, 5C, and 5D depict a method of forming an array comprising a random distribution of fiducial elements and a plurality of analytes of interest, in accordance with some embodiments.

FIGS. 11A and 11B displays differing morphologies of contrast-enhancing features, in accordance with some embodiments.

FIGS. 12A, 12B, 12C, 12D, 12E, and 12F show exemplary embodiments of arrays comprising ordered patterns of fiducial elements (FIGS. 12A and 12B) and fiducial elements with random spatial distributions (FIGS. 12C-12E), in accordance with some embodiments.

FIGS. 14A, 14B, 14C, 14D, 14E, 14F, and 14G illustrate alignment of data structures comprising differing fields-of-view with and without patterns of fiducial elements, in accordance with some embodiments.

FIGS. 29A, 29B, 29C, and 29D show steps of preparing a single-analyte array containing a random spatial distribution of fiducial elements at array sites, in accordance with some embodiments.

FIGS. 30A, 30B, 30C, 30D, 30E, and 30F depict steps of a method of preparing a single-analyte array containing a random spatial distribution of fiducial elements by utilizing orthogonal surface chemistries at array sites, in accordance with some embodiments.

FIG. 34A shows a scan of an array containing only fiducial elements. FIG. 34B shows a scan of an array containing fiducial elements and analytical agents bound to analytes at certain array sites.

FIGS. 36A, 36B, 36C, 36D, and 36E illustrate non-limiting methods for registering a plurality of images of a substrate, in accordance with some embodiments of the present disclosure, in which optional steps are illustrated by dashed line boxes.

FIG. 37A shows a schematic for protein identification by short-epitope mapping (PrISM). FIG. 37B shows a depiction of protein decoding resulting in identification of the protein at location A1 as EGFR.

FIG. 37C provides a schematic in which repeat sequential affinity reagent measurements on EGFR shows 5 unique binding patterns and one off-target binding event (replicate 3, HMW).

FIGS. 42A, 42B, 42C, 42D, 42E, 42F, and 42G collectively provide schematics for point-based registration using a first plurality of points, a second plurality of points, and a transformation data structure including a counter for each transform candidate in a plurality of transform candidates, in accordance with some embodiments of the present disclosure.

FIG. 46A illustrates an example plot that is not smoothed, while FIG. 46B illustrates an example plot that is smoothed using a Gaussian filter.

FIG. 47 provides a schematic illustrating a method for registering a plurality of images of a substrate, in accordance with some embodiments of the present disclosure.

DETAILED DESCRIPTION

Figure 1A:
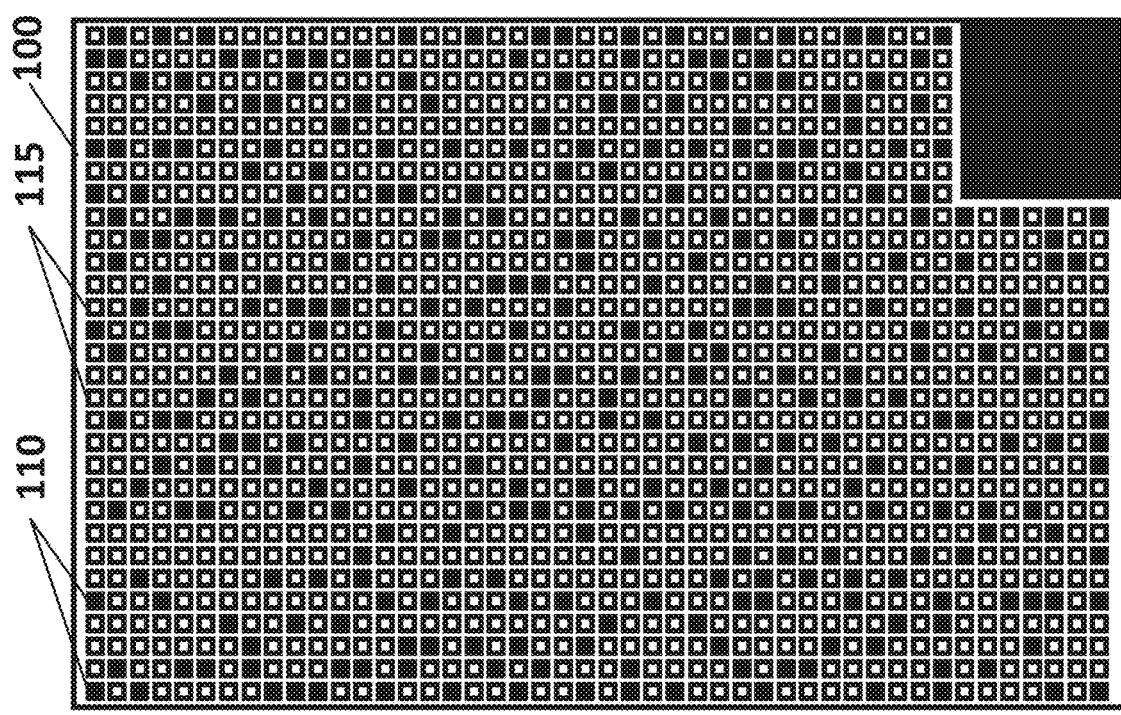
FIGS. 1A, 1C, and 1E depict regions of single-analyte arrays, in which each region comprises a fiducial element and a plurality of analyte binding sites, in which the occupancy rate of each region varies (~25%, ~2.5%, and ~0.25%, respectively), in accordance with some embodiments.

The analysis of single analytes in an array-based format can necessitate an ability to distinguish individual single analytes at high resolution and at small length scales. The detection of single analytes by an optical or electromagnetic detection system containing a pixel-based or discretized sensor can be especially challenging due to the relatively few number of pixels that can detect a signal from a single analyte and accompanying irregularities that can arise from translating a continuous phenomenon into a discretized one. Detection of a unique, isolated single analyte in a manner that resolves it from all adjacent single analytes can necessitate detection of a sufficiently strong signal from the isolated single analyte to rise above any background signal and/or system noise, as well as a surrounding region of reduced or non-existent signal so as to form an isolated signal from the isolated single-analyte. Depending upon the optical system utilized to image a plurality of single analytes, each single analyte of the plurality of single analytes may need to be sufficiently spatially separated from each other single analyte to provide sufficient separation of signal associated with each single analyte.

Accordingly, it may be advantageous to provide single analytes for single analyte processes in an array-based format. An array of single analytes may be formulated to provide sufficient organization and spatial separation to facilitate the resolvability of each single analyte on the array of single analytes. Moreover, an array may be formulated to produce a low and/or uniform level of background signal (for example, autofluorescence in a fluorescent detection system), and to minimize or mitigate the likelihood of non-specific binding of unwanted species in interstitial regions separating single analytes on the array.

Analysis of single analytes can differ from bulk or ensemble analysis of analytes in several respects. A bulk or ensemble analysis, such as an ELISA assay or Western blot, simultaneously averages measurements of each analyte within an analyte ensemble into a single measurement. Consequently, false positive and false negative measurements may be assumed to offset, thereby making the obtained average measurement the presumed average state or property of the analyte ensemble. Moreover, an average property, characteristic, or state of an analyte ensemble can often be obtained through a single measurement. In contrast, a property, characteristic, or state of a single analyte cannot be measured with as high a level of confidence by a single measurement. Moreover, in a system where a single analyte may exist in a distribution of states, the entirety of the distribution of states cannot be measured in a single measurement. The inherent likelihood of a false positive or false negative detection of a property, characteristic, or state of a single analyte means that a single measurement of a single analyte carries a probability of being correct that is less than unity. Rather, confidence in a measurement of a single analyte property, characteristic, or state can be achieved, for example, by obtaining a repeatable measurement over multiple measurements, or obtaining a series of potentially differing measurements that collectively give rise to a more certain measurement of the single analyte property, characteristic, or state.

Figure 1B:
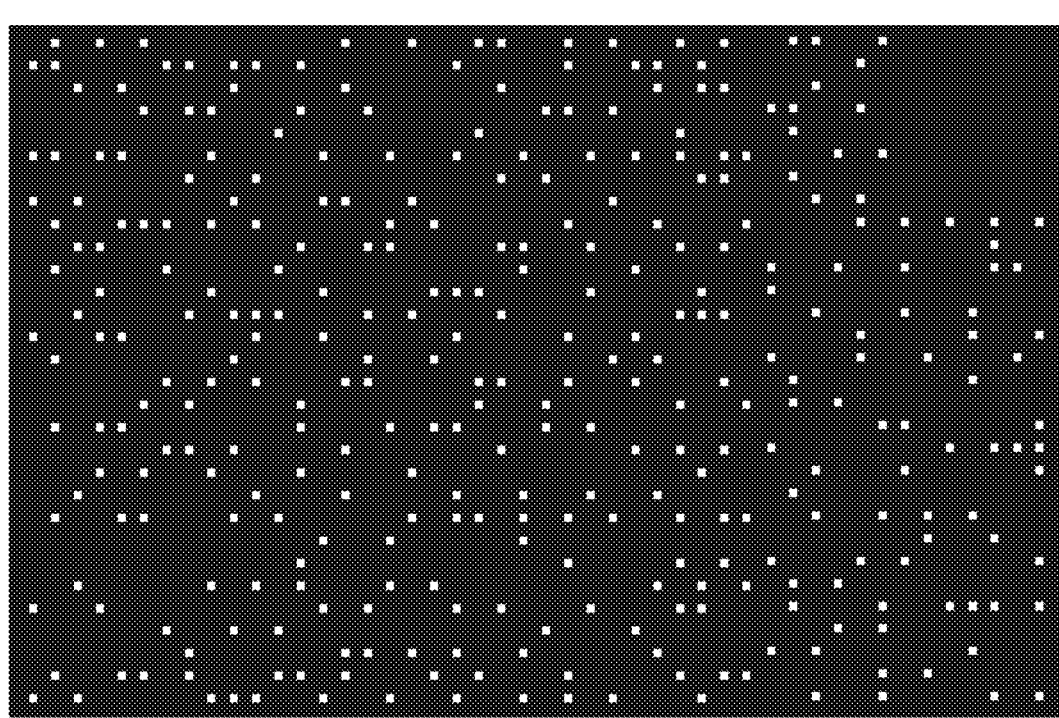
FIGS. 1B, 1D, and 1F depict simulated fluorescent image data of the arrays of FIGS. 1A, 1C, and 1E, respectively, in accordance with some embodiments.
Figure 1D:
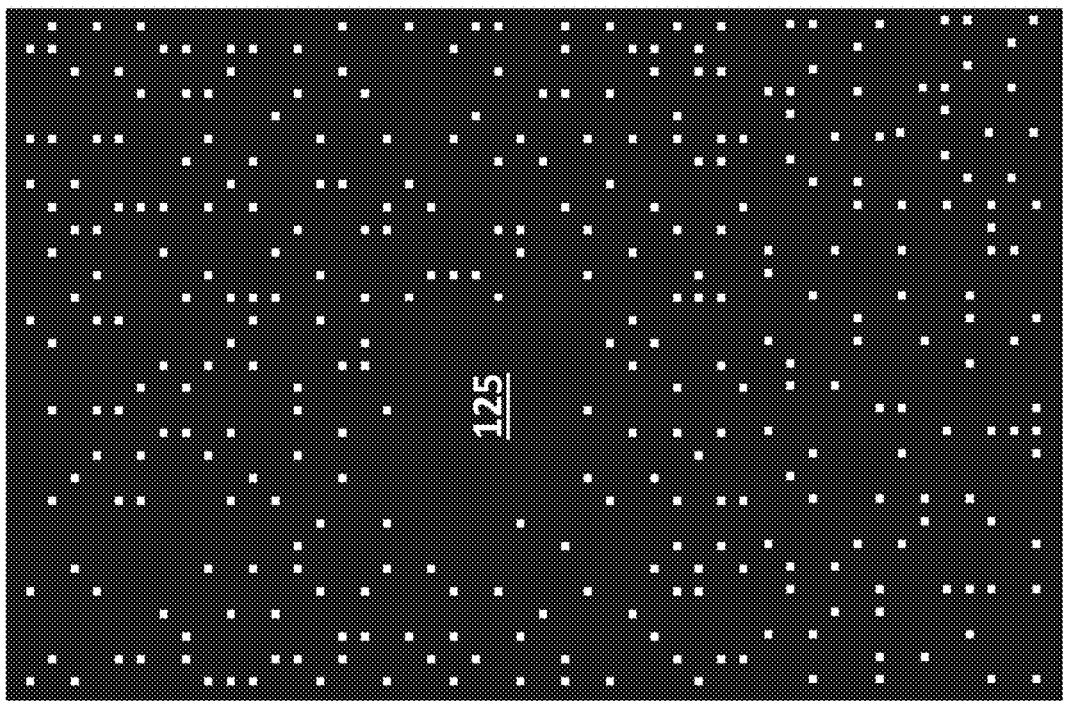
Figure 1C:
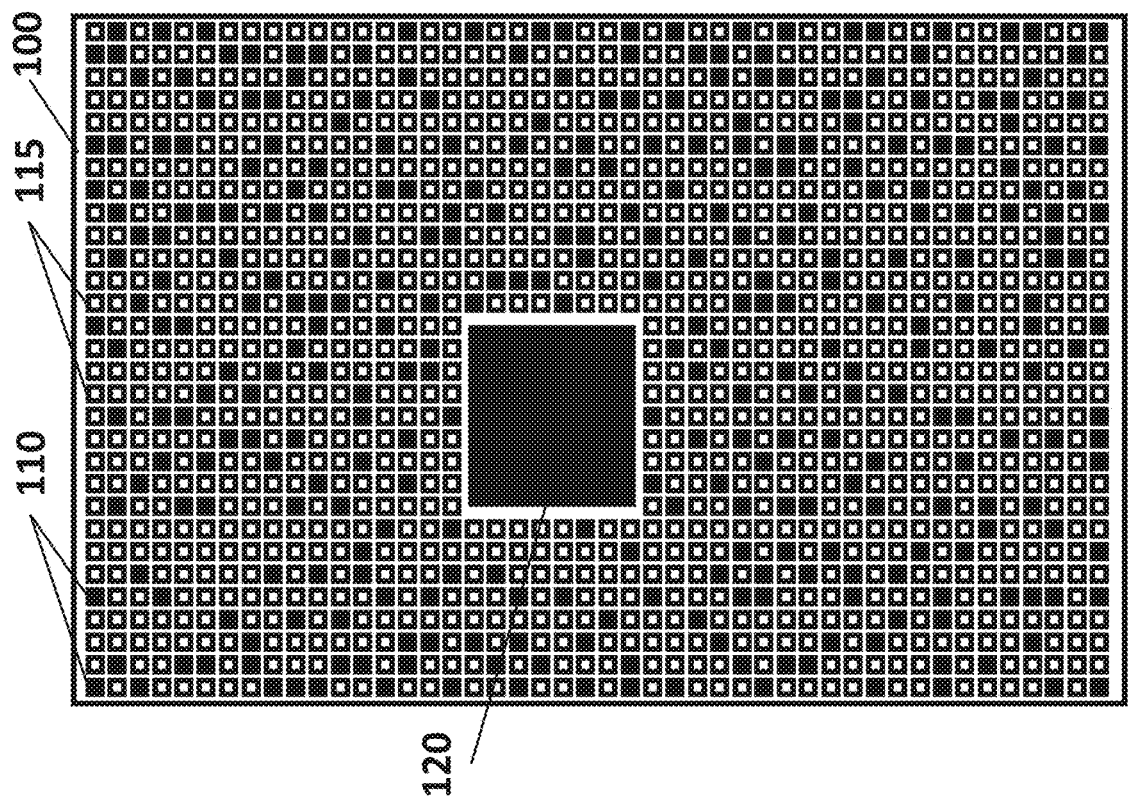
Figure 1F:
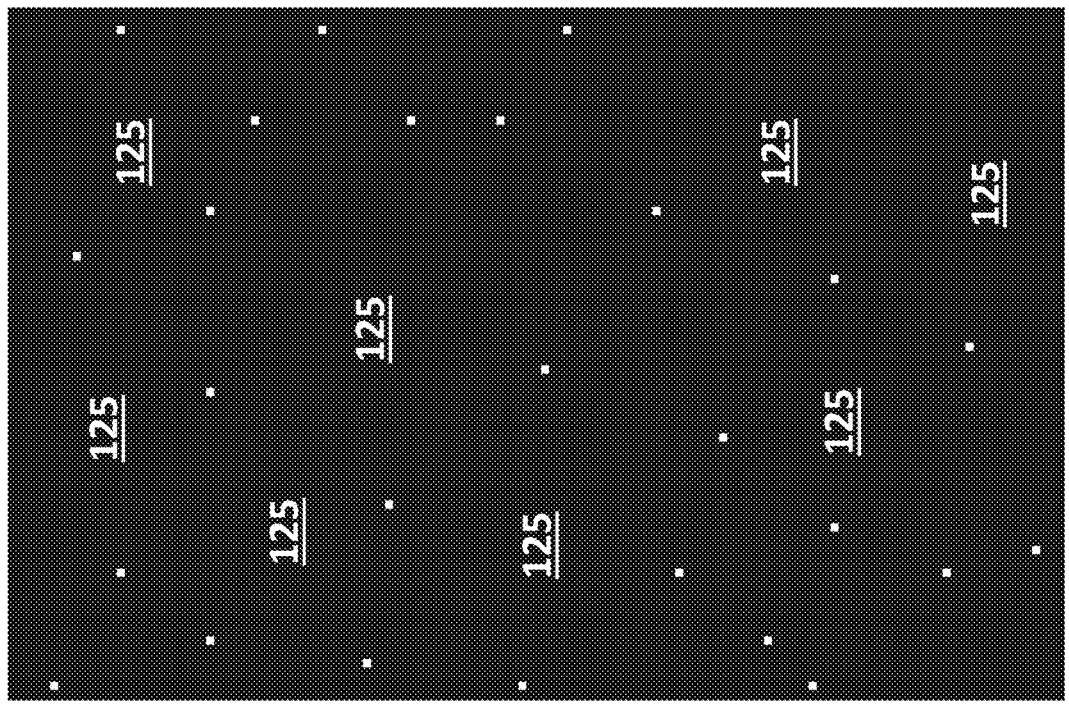
Figure 1E:
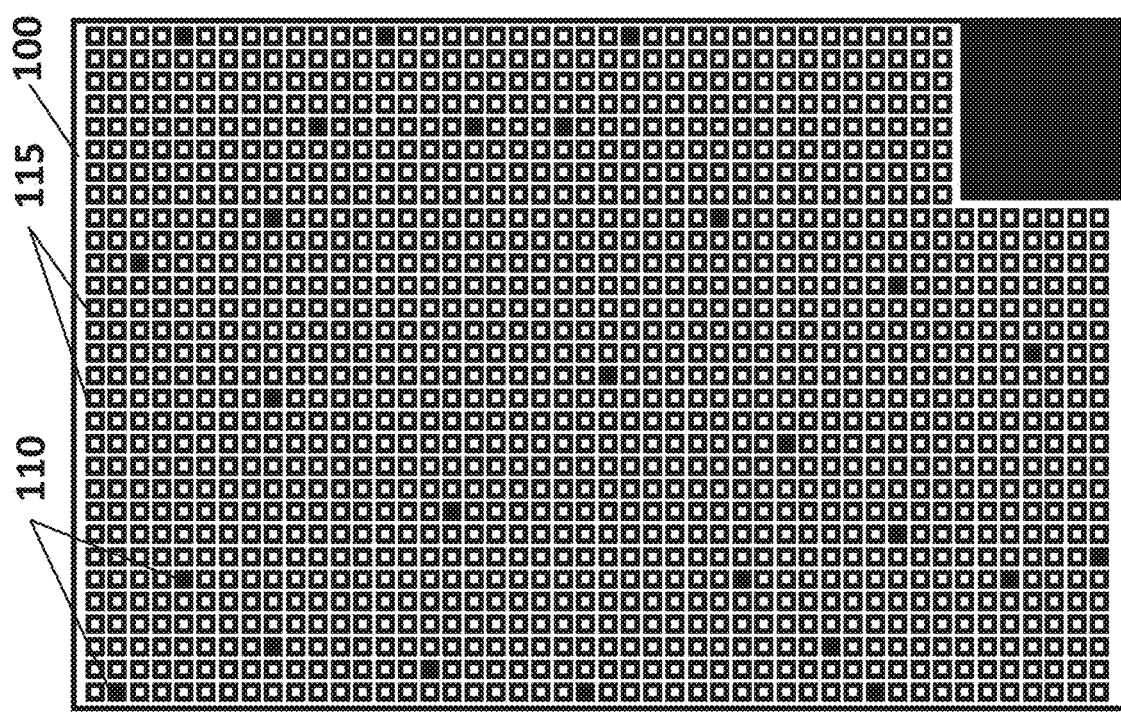

Certain single analyte assays, including many proteomic assays, may produce measurements with a low spatial information density. Low spatial information density during data collection for a single analyte assay can increase the challenge of consistently assigning data to proper single analytes. FIGS. 1A-1F illustrate an example of array-based data with differing information density. FIG. 1A depicts a solid support 100 containing a patterned array of occupied sites 110 and unoccupied sites 115, in which the sites 110 and 115 are arranged in a rectangular grid. The solid support further comprises a fiducial region 120 that may be utilized for processes such as landmarking or image registration. The occupied sites 110 have an occupancy of about 25% relative to all available sites. An array like FIG. 1A may be observed, for example, in single-analyte DNA sequencing, in which approximately 1 in 4 sites are expected to be detected for any measurement (representing the 4 possible nucleotides). FIG. 1B is a simulated detected image of the array of FIG. 1A, for example as would be detected by a measurement of fluorescence emission from each occupied site 110. The sites observed in the image can be referred to as "points" in the image. Notably, despite only 25% of sites 110 being occupied, it is possible to resolve all rows and columns of the rectangular array grid, as well as a region of no detected signal 125 corresponding to the fiducial region 120. FIGS. 1C-1D depict the same type of array and detected data as FIGS. 1A-1B, but with the position of the fiducial region 120 altered. It is still possible to identify the exact address of the fiducial region 120 in the detected data of FIG. 1D based upon an address of the region of no detected signal 125. In contrast, FIGS. 1E-1F depict a similar patterned array with an occupancy of about 2% relative to all available sites. An array like FIG. 1E may be observed, for example, in measuring affinity agent binding to protein arrays, in which only 10% of sites contain a protein that contains an epitope bound by the affinity agent, and the affinity agent has a 20% chance of binding to the protein at the array site when the epitope is present. FIG. 1F is a simulated detected image of the array of FIG. 1E. Notably, the precise address of each row and column cannot be defined, and numerous regions of the image data 125 are large enough to include the fiducial region 120 in numerous positions, creating a degree of uncertainty about the precise set of sites captured as points in the image data of FIG. 1F.

Figure 21:
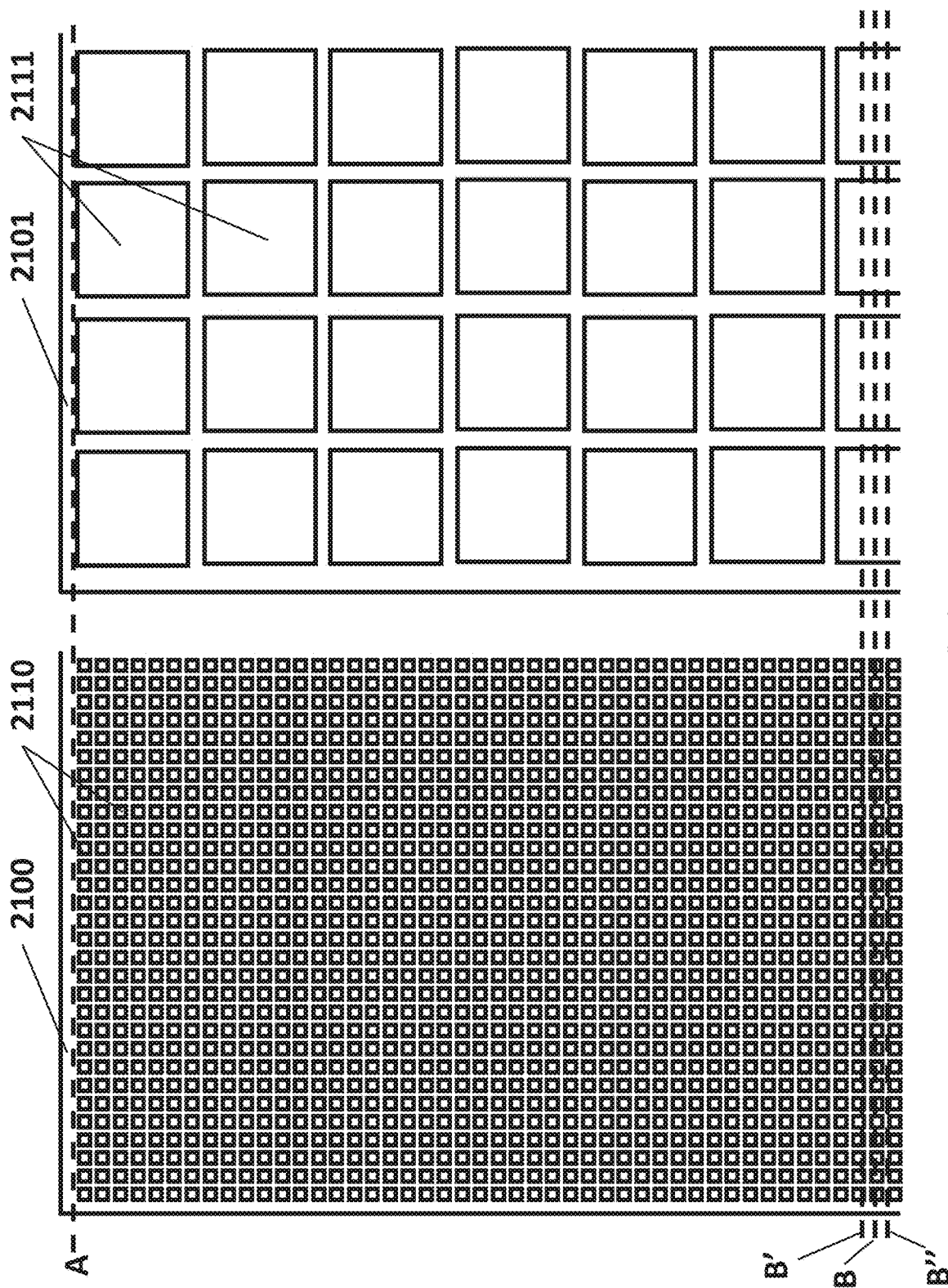
FIG. 21 depicts spatial error for a centered position of a sensing device on arrays with differing site densities, in accordance with some embodiments.

The challenge of accurately identifying a spatial address on an array at small length scales is increased by resolution and accuracy of detection methods. When resolving features with sub-micron length scales on arrays with millimeter- or even centimeter-scale aspects (for example, a $1 \times 10^9$ feature square array with array sites evenly spaced at a pitch of 1 micron would measure ~3 centimeters by 3 centimeters), a sensing device will most likely not be capable of simultaneously i) capturing all sites on the array within a single field-of-view, and ii) resolving all sites on the array such that detected signals (e.g. points) can be precisely resolved to a specific array site. Accordingly, high-resolution imaging of high-density, nanoscale arrays will typically be configured to acquire multiple images, each image being a subregion of the array and the subregions being combined to reconstruct a composite image of the array. For example, each subregion can be imaged at a micron-scale field-of-view, and the position between the array and the sensing device can be translated to sense all subregions of the array. Methods for producing relative motion between an array and a sensing device (e.g., stepper motor microstepping) can introduce a measurable uncertainty in absolute position during a sensing process. As the total distance of motion increases, the amount of spatial error potentially introduced by a motion control device increases. Likewise, as the total elapsed time of a process (e.g., motion of a system, a detection process, etc.) increases, measurement uncertainty due to the passage of time will increase. For example, transient thermal fluctuations can alter an observed field-of-view of an optical detection device during an array-based process. FIG. 21 illustrates the relationship between spatial error and sensing on high-density arrays. FIG. 21 depicts a high-density array 2100 comprising a plurality of array sites 2110 and a lower density array 2101 comprising a plurality of array sites 2111, in which the lower-density array 2101 has ~$\frac{1}{10}$ the site density of the high-density array 2100. A sensing process (e.g., optical microscopy) is configured to produce motion of a sensing device (e.g., rastering, scanning, etc.) across the arrays from a position centered on line A to a position centered on line B. However, due to an ±1% error in spatial positioning, the final centered position of the sensing device may be anywhere between line B' and line B". With respect to the lower-density array 2101, the spatial error of sensing device positioning does not produce an uncertainty in which row of sites the sensing device is centered. However, with respect to the high-density array 2100, the spatial error of sensing device positioning does produce an uncertainty in which row of sites the sensing device is centered. When considering the impact of spatial error (e.g., see FIG. 21) on sensing of arrays with low information density (e.g., see FIGS. 1E-1F), an even 1-position shift (e.g., 1-pixel shift) in alignment of a sensing device can produce a misidentification of sites at which signals are detected, thereby impacting interpretation of the collected data. Accordingly, it may be advantageous to provide fiducial elements on an array that posses one or more characteristics of: i) providing an absolute reference for position on the array, ii) providing a reference for a position at a localized region of the array relative to an absolute position, iii) providing a reference for a position at a localized region of the array relative to a relative position, and iv) providing a resolvable signal at a same length-scale as analytes of interest.

A fiducial element can be utilized to assist optical detection systems with identifying a position on an array of analytes before, during, or after optical interrogation of the array. Such fiducial elements may be utilized for several purposes (including simultaneously or sequentially) during optical interrogation, including: 1) landmarking, 2) image registration, 3) focus correction, 4) light source calibration, 5) optical sensor alignment, 6) optical calibration, 7) motion cancellation, 8) tilt correction, and 9) combinations thereof. Landmarking may include any process that aligns an optical detection system to a specific or fixed point of an interrogation target, such as an array of analytes. For example, each imaging cycle of an array of analytes may begin with a landmarking process to identify and align an optical detection device at an initial imaging address or region. Alternatively or additionally, an optical detection process may utilize landmarking at the end of an imaging cycle to confirm that an optical detection device has arrived at an intended final address or region. Landmarking information can be used to evaluate or adjust the relative positions of a detection device and an object observed by the detection device. Another potential use of landmarking information is to evaluate or adjust the relative positions for two or more subregions of an array when combined to create a composite image of the array. Image registration can include any process that is utilized to uniformly assign spatial addresses to sets of image data, including identifying points or regions of overlap between two images of the same object such as two images of the same subregion of an array, including images capturing 2-dimensional or 3-dimensional data. Image analysis that include image registration can further include the assembly of two or more images into aggregated data by data analysis processes that may: i) align overlapping images via processes such as rotation and/or tilt correction, ii) re-scale image data from one or more images, iii) standardize image data across two or more images, iv) discard redundant image data, and/or v) concatenate image data from two or more images into a single data set. Focus correction may include any process that alters a real or apparent focal point or focal plane for an optical image. Focus correction may be utilized, for example, to account for localized or broad-scale variations in surface topography on an array of analytes that affect the position of analytes bound to a surface of the array relative to an optical detection device.

Fiducial elements can be utilized on an array to provide spatial information during an optical interrogation process. A fiducial element typically comprises a distinguishable feature, material, particle, or object that is detectable and has a spatially and temporally invariant position on an array. The configuration of one or more fiducial elements on an array may depend upon the array configuration and nature of the optical detection of the array of analytes. For example, an array of analytes with spatially-large or high-signal sites (e.g., clusters of nucleic acids) may facilitate optical detection by an optical detection device with a larger field-of-view or lesser magnification. In such a configuration, a fiducial element may be utilized primarily to provide an optical ruler for identifying the address of any site on the array. Alternatively, an array of analytes with spatially-small or low-signal sites (e.g., arrays of single polypeptides) may require detection by an optical detection device with a smaller field-of-view or higher magnification. In such a configuration, a fiducial element may be utilized for landmarking due to an increased likelihood of error in image positioning caused by the smaller field-of-view relative to the movement of the optical detection device.

Moreover, fiducial elements can facilitate increased reliability and accuracy for optical interrogation of arrays of analytes with low spatial information density. Presence of distinguishable fiducial elements at known positions can provide patterns of signals or points in an image that facilitate registration of the image data with minimal or insufficient signal from analytical sources (e.g., from the binding of fluorescent moieties to analytes). In some configurations, it may be especially advantageous to provide an array with a plurality fiducial elements that have a random spatial distribution. A plurality of fiducial elements may be randomly distributed on an array such that an image registration algorithm can efficiently identify a same site or address in two images based upon pattern matching of fiducial elements, even in the absence of signals from analytical sources. As such, the random spatial distribution of fiducial elements can function as a unique signature for the object being imaged and the signature can also provide a basis for identifying a same site or address in multiple images of the site or address.

Arrays and array systems, as set forth herein, may be characterized as providing spatial information in a hierarchical structure. A hierarchical structure may refer to an array or array system comprising one or more spatially-defining elements that provide increased confidence in position when taken together than any one spatially-defining element can provide by itself. For example, a single-analyte array that is intended to be interrogated by fluorescent microscopy may comprise a plurality of array sites that are substantially non-resolvable or non-detectable at a detection wavelength of an optical sensor when no analytes and/or detection reagents are bound to the array sites. When optically interrogating such a single-analyte array, spatial position of an interrogation device (e.g., a fluorescent microscope) relative to the single-analyte array may be determined via a hierarchical information structure. For example, spatial position may be determined by one or more of: 1) data from a motion control device (e.g., coarse spatial position based upon step counts of a stepper motor), 2) data regarding position provided by a patterned fiducial material (e.g., structured silicon, deposited metal, etc.) on the single-analyte (e.g., moderately-fine spatial position), and 3) data regarding position provided by a spatially-random distribution of fiducial elements (e.g., fluorescent nanoparticles) on the single-analyte array (e.g., fine spatial position). In this example, the information obtained from any one of the three data sources may not confidently define the precise spatial position of the array relative to an interrogation device, however the simultaneous combination of the three data sources can accurately define the spatial position of the array relative to the interrogation device.

Provided herein are compositions, methods, and systems for arrays of analytes, including arrays of single analytes. The arrays may comprise one or more fiducial elements for the purposes of landmarking, image registration, and/or focus correction. In some configurations, an array of analytes may comprise a plurality of fiducial elements, in which the plurality of fiducial elements may be characterized as having a random spatial distribution on the array of analytes. In particular configurations, an array of analytes may comprise a plurality of fiducial elements comprising detectable particles that are deposited on the array of analytes by a random deposition process. In some cases, a random deposition process of fiducial elements may utilize an identical or similar deposition chemistry to a deposition process for attaching analytes to the array of analytes. Some methods of preparing arrays, as set forth herein may be characterized by the use of array surface chemistries and complementary fiducial element chemistries that provide a plurality of sites on the array surface that are configured for deposition of fiducial elements, then deposit a fiducial element at each site of a subset of the plurality of sites, thereby forming a random spatial distribution of fiducial elements on the array. Aspects of the compositions, methods and systems of the present disclosure will, in some cases, be exemplified with regard to proteins. It will be understood that those aspects can be extended to other analytes as appropriate.

Definitions

As used herein, the term "fiducial element" refers to a point of reference or measurement scale. For example, a fiducial element can be a moiety, molecule, particle, layer, or coating that comprises: i) a spatially-fixed and temporally-fixed address on an array, and ii) a moiety that is configured to provide a detectable signal at the address on the array. In some configurations, a fiducial element may be configured to provide a temporally-invariant detectable signal. In other configurations, a fiducial element may be configured to provide a temporally-variable signal. Optionally, a fiducial element may be configured to provide a detectable signal for a particular amount of time, such as the time length of an array-based process or assay, or a portion thereof (e.g., a cycle or series of cycles of the array-based process or assay). A fiducial element may be configured to emit a detectable signal subsequent to the fiducial element being contacted with an excitation source, such as an electric field, a magnetic field, heat, or a photon of light. Fiducials can include, but are not limited to, detectable labels such as fluorescent, radioactive, chemiluminescent, calorimetric, and colorimetric labels. The use of fiducial markers to stabilize and orient biological samples is described, for example, in Carter et al., *Applied Optics* 46:421-427, 2007), the entire contents of which are incorporated herein by reference. A fiducial element may comprise an optically active moiety, an optically passive moiety, or a combination thereof. Optionally, a fiducial element may comprise a fluorescent or luminescent moiety. Optionally, a fiducial element may comprise a metal or metal oxide layer. Optionally, a fiducial element may comprise two or more differing detectable labels, in which the two or more detectable labels produce two or more differing detectable signals. For example, a fiducial element may comprise two types of fluorophores, in which each type of fluorophore has a unique excitation and/or emission wavelength. A fiducial element may comprise a bead, microsphere, or nanoparticle, such as a fluorescent nanoparticle. The terms "fiducial" and "fiducial marker" are used interchangeably with the term "fiducial element" herein.

As used herein, the term "nanoparticle," when used in reference to a fiducial element, refers to a molecule or particle that is configured to bind to a site of an array and has a maximum characteristic dimension (e.g., diameter, width, length, height) of less than 1 micron. Optionally, a nanoparticle may comprise an organic material, an inorganic material, or a combination thereof. Optionally, a nanoparticle may comprise a non-biological material or a material that does not naturally arise in a biological system. Optionally, a nanoparticle may comprise an engineered or manufactured material. Optionally, a nanoparticle may be exogenous to a system from which analytes of an array, as set forth herein, are derived. A nanoparticle may comprise a non-detectable component. For example, a nanoparticle may comprise a non-detectable polymer nanoparticle to which fluorophores are affixed. In another example, a detectable inorganic nanoparticle (e.g., a quantum dot) may comprise a non-detectable polymeric shell that surrounds the detectable portion of the nanoparticle. A nanoparticle may have a characteristic dimension (e.g., diameter, width, length, height) of no more than about 950 nm, 900 nanometers (nm), 800 nm, 700 nm, 600 nm, 500 nm, 400 nm, 300 nm, 200 nm, 150 nm, 100 nm, 50 nm, 10 nm, or less than 10 nm. Alternatively or additionally, a nanoparticle may have a characteristic dimension of at least about 10 nm, 50 nm, 100 nm, 150 nm, 200 nm, 300 nm, 400 nm, 500 nm, 600 nm, 700 nm, 800 nm, 900 nm, 950 nm, or more than 950 nm.

As used herein, the term "solid support" refers to a substrate that is insoluble in aqueous liquid. Optionally, the substrate can be rigid. The substrate can be non-porous or porous. The substrate can optionally be capable of taking up a liquid (e.g. due to porosity) but will typically, but not necessarily, be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, metal oxides (e.g., zirconia, titania, alumina, etc.), inorganic glasses, optical fiber bundles, gels, and polymers.

As used herein, the term "address," when used in reference to an array, refers to a spatial coordinate on an array or a surface thereof. An address may be described by a coordinate system, such as a Cartesian coordinate system, a cylindrical coordinate system, a polar coordinate system, or a spherical coordinate system. An address may be expressed in a coordinate system with one or more, two or more, or three or more dimensions depending upon a geometry or morphology of an array, or a surface thereof. For example, an address of a substantially planar array may as a two-dimensional Cartesian coordinate (e.g., 50, −25, etc.). In another example, an address may be expressed as a three-dimensional coordinate for an array with a curved surface. A coordinate of an address may be given with respect to a reference position (e.g., a corner, edge, feature, or component of an array). An address may further comprise a temporal coordinate for a dynamic or transient system. An address may be expressed discretely (e.g., via a coordinate system) or in a continuous fashion (e.g., via a mathematical function). A discrete address may be discretized at a particular spatial and/or temporal resolution, such as a spatial and/or temporal resolution of a sensing device, or a spatial resolution of an array formation method. For example, based upon a pixel pitch of a pixel-based sensor and a magnification of an objective lens of a microscope system, an array may be discretized in a manner that each pixel of the pixel array collects a light signal from a discrete area of the array (e.g., each pixel collecting light from a 5 nanometer by 5 nanometer area). Optionally, an address can be occupied by a particular analyte (e.g. protein). An address can contain a single analyte, or it can contain a population of several analytes of the same species (e.g., an ensemble of the analytes). Alternatively, an address can include a population of different analytes. Addresses are typically discrete. Discrete addresses that neighbor each other can be contiguous, or they can be separated by interstitial spaces. An array in accordance with the present disclosure can have, for example, addresses that are separated by an average distance of less than 100 microns, 10 microns, 1 micron, 100 nm, 10 nm or less. Alternatively, or additionally, an array can have addresses that are separated by an average distance of at least 10 nm, 100 nm, 1 micron, 10 microns, 100 microns or more. The addresses can each have an area of less than 1 square millimeter, 500 square microns, 100 square microns, 10 square microns, 1 square micron, 100 square nm or less.

An array can include at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, or more addresses.

As used herein, the term "site," when used in reference to an array, means an address in an array where a particular molecule, particle, moiety, or analyte of interest is present or is configured to be present. A site can contain only a single molecule, moiety, particle, or analyte of interest, or it can contain a population of several molecules, moieties, particles, or analytes of interest of the same species (i.e. an ensemble of the molecules). Alternatively, a site can include a population of molecules, moieties, particles, or analytes of interest that are different species. Sites of an array are typically discrete. The discrete sites can be contiguous, or they can have interstitial spaces between each other. An array useful herein can have, for example, sites that are separated by less than 100 microns, 50 microns, 10 microns, 5 microns, 1 micron, or 0.5 micron. Alternatively or additionally, an array can have addresses that are separated by at least 0.5 micron, 1 micron, 5 microns, 10 microns, 50 microns or 100 microns. The sites can each have an area of less than 1 square millimeter, 500 square microns, 100 square microns, 25 square microns, 1 square micron or less.

As used herein, the term "array" refers to a population of molecules or analytes that are attached to one or more solid supports such that the molecules or analytes at one address can be distinguished from molecules or analytes at other addresses. An array can include different molecules or analytes that are each located at different addresses on a solid support. Alternatively, an array can include separate solid supports each functioning as an address that bears a different molecule or analyte, where the different molecules or analytes can be identified according to the addresses of the solid supports on a surface to which the solid supports are attached, or according to the addresses of the solid supports in a liquid such as a fluid stream. The molecules or analytes of the array can be, for example, cells, organelles, nucleic acids such as SNAPs, polypeptides, proteins, peptides, oligopeptides, enzymes, ligands, receptors such as antibodies, functional fragments of antibodies, aptamers, or therapeutic agents. The addresses of an array can optionally be optically observable and, in some configurations, adjacent addresses can be optically distinguishable when detected using a method or apparatus set forth herein. As used herein, the term "data array" refers to an ordered data structure comprising a plurality of values or coupled sets of values (e.g., a data matrix).

As used herein, the term "random," when used in reference to a plurality of moieties bound to an array, refers to a spatially- or temporally- non-deterministic distribution of the plurality of moieties. A random spatial or temporal distribution of a plurality of moieties may occur when, prior to an observation of the spatial or temporal distribution, presence or absence of a moiety at a site of an array can not be predicted with certainty. For example, a random spatial distribution of moieties or sites on a surface will typically constitute a non-repeating pattern of the moieties or sites on the surface. Optionally, a random spatial or temporal distribution of a plurality of moieties may occur when, prior to an observation of the spatial or temporal distribution, presence or absence of a moiety at a site of an array can be predicted by a probabilistic model. For example, for an array with 1000 sites that is contacted with 100 analytes, the probability of an analyte being found at any array site is $\frac{1}{10}$ assuming 100% deposition of the analytes and no surface- or analyte-specific biases for deposition, but prior to characterizing the spatial distribution of analytes on the array, the presence or absence of an analyte at any array site is uncertain. A spatially- or temporally-random distribution may be predicted by a probabilistic function, such as a Poisson distribution, a Bernoulli distribution, a normal distribution, a geometric distribution, a binomial distribution, a negative binomial distribution, or a categorical distribution.

As used herein, the term "structured nucleic acid particle" (or "SNAP") refers to a single- or multi-chain polynucleotide molecule having a compacted three-dimensional structure. The compacted three-dimensional structure can optionally have a characteristic tertiary structure. For example, a SNAP can be configured to have an increased number of interactions between regions of a polynucleotide strand, less distance between the regions, increased number of bends in the strand, and/or more acute bends in the strand, as compared to the same nucleic acid molecule in a random coil or other non-structured state. Alternatively or additionally, the compacted three-dimensional structure can optionally have a characteristic quaternary structure. For example, a SNAP can be configured to have an increased number of interactions between polynucleotide strands or less distance between the strands, as compared to the same nucleic acid molecule in a random coil or other non-structured state. In some configurations, the secondary structure (i.e. the helical twist or direction of the polynucleotide strand) of a SNAP can be configured to be more dense than the same nucleic acid molecule in a random coil or other non-structured state. SNAPs may include deoxyribonucleic acid (DNA), ribonucleic acid (RNA), peptide nucleic acid (PNA), other nucleic acid analogs, and combinations thereof. SNAPs may have naturally-arising or engineered secondary, tertiary, or quaternary structures. Exemplary SNAPs may include nucleic acid nanoballs (e.g. DNA nanoballs), nucleic acid nanotubes (e.g. DNA nanotubes), and nucleic acid origami (e.g. DNA origami). A SNAP may be functionalized to include one or more reactive handles or other moieties.

As used herein, the terms "group" and "moiety" are intended to be synonymous when used in reference to the structure of a molecule. The terms refer to a component or part of the molecule. The terms do not necessarily denote the relative size of the component or part compared to the molecule, unless indicated otherwise. A group or moiety can contain one or more atom. As used herein, the term "coupling moiety" refers to a component or part of a molecule that is configured to couple a molecule to a solid support, surface or interface. A coupling moiety may be configured to attach a molecule to a solid support by a covalent interaction, a non-covalent interaction, or a combination thereof. Optionally, a coupling moiety may be configured to form a covalent bond with a complementary moiety of an analyte, such as a Click-type reaction or a bioorthogonal reaction. Optionally, a coupling moiety may be configured to form a non-covalent interaction with a complementary moiety of an analyte, such as a hydrogen bond, an ionic bond, a van der Waals interaction, a receptor-ligand interaction, or a nucleic acid base pairing interaction. As used herein, the term "passivating moiety" refers to component or part of a surface-attached molecule that is configured to prevent or minimize the likelihood of a moiety, molecule, or particle from binding to an array surface. A passivating moiety may comprise a moiety that is configured to prevent or minimize binding to an array surface by a mechanism such as steric hindrance, electrostatic repulsion, magnetic repulsion, entropic dissociation, or a combination thereof. A passivating moiety may comprise a linear chain polymer, a branched chain polymer, or a dendrimer. An array may comprise a plurality of passivating moieties, in which the plurality of passivating moieties comprises a mixture of types of passivating moieties, such as a mixture of linear and branched polymers. As used herein, the term "anchoring moiety" refers to a moiety that is configured to couple an analyte to an array surface. Optionally, an anchoring moiety may be further configured to prevent or minimize the likelihood of direct contact between an analyte and an array surface. For example, an anchoring moiety that couples an analyte to a surface can restrain the analyte to being at least 1 nm, 10 nm, or 100 nm from the surface to which it is coupled. An anchoring moiety may comprise a structured nucleic acid particle, such as a nucleic acid origami or a nucleic acid nanoball. An anchoring moiety may comprise a non-nucleic acid molecule or particle, such as a nanoparticle.

As used herein, the term "analyte" can be used to refer to a substance, structure, moiety, component, molecule, particle, or complex thereof to be analyzed. Optionally, an analyte can be coupled to a display moiety of a molecule, when used in reference to a structured nucleic acid particle. An analyte may comprise a target for an analytical method (e.g., sequencing, identification, quantification, etc.) or may comprise a functional element such as a binding ligand or a catalyst. An analyte can be biologically active, derived from a biological source or an analog of an analyte from a biological source. An analyte may comprise a biomolecule, such as a polypeptide, polysaccharide, nucleic acid (e.g., DNA, RNA, LNA, PNA, etc.), lipid, metabolite, enzyme cofactor or a combination thereof. An analyte may comprise a non-biological molecule, such as a polymer, metal, metal oxide, ceramic, semiconductor, mineral, or a combination thereof. An analyte may comprise a complex of molecules or particles, such as a cell, an organelle (e.g., nuclei or mitochondria), or a receptor-ligand binding pair. Other exemplary analytes include non-nucleic acid analytes, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. The term "target" is used herein to refer to an analyte of interest. In some embodiments, the apparatus, systems, methods, and compositions described in this disclosure can be used to detect and analyze a wide variety of different analytes.

As used herein, the term "single analyte" refers to an analyte (e.g. protein) that is individually manipulated or distinguished from other analytes. A single analyte can be a single molecule (e.g. single protein), a single complex of two or more molecules (e.g. a single protein attached to a structured nucleic acid particle or a single protein attached to an affinity agent), a single particle, or the like. A single analyte may be resolved from other analytes based on, for example, spatial or temporal separation from the other analytes. Reference herein to a 'single analyte' in the context of a composition, apparatus or method does not necessarily exclude application of the composition, apparatus or method to multiple single analytes that are manipulated or distinguished individually, unless indicated to the contrary.

As used herein, the term "single-analyte resolution" refers to the detection of, or ability to detect, the analyte on an individual basis, for example, as distinguished from its nearest neighbor in an array. For example, an analyte or feature of an array (e.g., an interstitial region, a site, a fiducial element, an unbound moiety, a bound moiety, etc.) can be detected on an individual basis, for example, as distinguished from its nearest neighbor. Detection of a single analyte or a feature of an array at single-analyte resolution may include detection in the presence of an optical or physical source of uncertainty, such as a diffraction limit, Abbe error, spherical aberration, or chromatic aberration. Single-analyte resolution may have at least one and optionally two or more characteristics selected from: i) detecting a signal from a signal source that exceeds a signal from a background signal source, ii) detecting a signal from a first signal source that is spatially and/or temporally separated from a second signal source, iii) detecting a signal from a signal source that possesses a shape, pattern, profile, or morphology that is consistent with the signal source, iv) and iv) detecting a peak or average signal magnitude from a signal source that exceeds a threshold magnitude for detectability. The nearest neighbor of a single analyte may include a support, surface, interface, or medium with which the single analyte associates, or an adjacent analyte (whether the adjacent analyte is a single analyte or member of an ensemble of analytes). Single analyte resolution may be defined by a spatial and/or temporal length scale with respect to one or more individual analytes or features of an array. Single analyte resolution may be achieved when a detection mode is configured to observe a single analyte or a feature of an array at the spatial and/or temporal scale of the single analyte. For example, an optical fluorescence detector may be capable of resolving an analyte of at least 10 nanometers (nm) in size if a fluorescent signal from the analyte is present for at least 1 second (s). Alternatively or additionally, the optical fluorescence detector may be capable of resolving two analytes from each other when the two analytes are spatially separated by at least 10 nanometers (nm). Single analyte resolution may be associated with a spatial distribution, peak signal intensity, average signal intensity, or signal distribution obtained by a detecting device (e.g., a sensor) at a discrete spatial address. For example, a pixel-based optical detector may detect a single analyte at single-analyte resolution if an optical signal is detected at a plurality of pixels with a particular signal intensity profile, and the pixels are surrounded by a region with a signal intensity that matches an expected background intensity. FIGS. 2A-2D depict examples of a pixel-based detector results with differing signal profiles. FIG. 2A depicts exemplary signal intensity data from a pixel-based detector with each pixel representing an approximately 5 nm by 5 nm spatial region. The pixel-based detector collects physical data for an array of single analytes with a predicted size of 10-20 nm. FIG. 2B depicts a cross-sectional plot of the pixel-based signal-intensity data shown in FIG. 2A. The intensity data suggests two distinct single analytes that are distinct from the surrounding background medium and spatially separated from each other, with a size of approximately 10 to 15 nm for each single analyte. The data from FIGS. 2A-2B may be considered to have single analyte resolution. FIGS. 2C-2D depict data collected in an identical fashion to the data shown in FIGS. 2A-2B, but with a differing intensity profile. Based upon the data in FIGS. 2C-2D, the pixel-based detector might be considered to individually detect two single analytes or to detect an ensemble of two analyte. This can depend, for example, upon parameters applied to identify peaks when analyzing the data. Accordingly, the data from FIGS. 2C-2D might not be considered single analyte resolution. In some cases, signals (e.g., points) corresponding to two or more analytes or other objects (e.g., fiducial elements) may be considered spatially resolved if a spatial resolution criterion is achieved, such as the Rayleigh Criterion.

As used herein, the term "affinity agent" refers to a molecule, compound, moiety or other substance that is capable of specifically or reproducibly binding to an analyte (e.g. protein, peptide or unique identifier label) or moiety (e.g. post-translational modification of a protein). An affinity reagent can be larger than, smaller than or the same size as the analyte. An affinity reagent may form a reversible or irreversible bond with an analyte. An affinity reagent may bind with an analyte in a covalent or non-covalent manner. Affinity reagents may include reactive affinity reagents, catalytic affinity agents (e.g., kinases, proteases, etc.) or non-reactive affinity reagents (e.g., antibodies or fragments thereof). An affinity reagent can be non-reactive and non-catalytic, thereby not permanently altering the chemical structure of an analyte to which it binds. Affinity reagents that can be particularly useful for binding to proteins include, but are not limited to, antibodies or functional fragments thereof (e.g., Fab' fragments, F(ab')2 fragments, single-chain variable fragments (scFv), di-scFv, tri-scFv, or microantibodies), aptamers, affibodies, affilins, affimers, affitins, alphabodies, anticalins, avimers, miniproteins, DARPins, monobodies, nanoCLAMPs, lectins, or functional fragments thereof. The term "affinity agent" is used synonymously with the term "affinity reagent" herein.

As used herein, the term "optically active," when used in reference to a fiducial element, refers to a material, molecule, or particle that is configured to absorb a photon of light. Optionally, an optically active fiducial element may absorb photons at a single wavelength of light, multiple wavelengths of light, or a range of wavelengths of light. Optionally, an optically active fiducial element may be configured to absorb a first photon of light then subsequently emit a detectable particle, such as second photon of light or an electron. Optically active materials can include fluorophores, luminophores, dyes, pigments, fluorescent proteins, fluorescently-labeled polymers, fluorescently-labeled biomolecules, Forster resonance energy transfer (FRET) pairs, and combinations thereof. Optically active materials may be detected via a characteristic signal by any suitable method, such as confocal microscopy, total internal reflection microscopy, super-resolution microscopy, fluorescence lifetime detection, luminescence lifetime detection, infrared spectroscopy, ultraviolet spectroscopy, Raman spectroscopy, scanning electron microscopy, or x-ray photoelectron spectroscopy.

As used herein, the term "optically passive," when used in reference to a fiducial element, refers to a material, molecule or particle that is configured to reflect, refract, scatter, or transmit a photon of light or other particle (e.g., an electron, a neutron, a proton). Optionally, an optically passive fiducial element may reflect, refract, or transmit photons at a single wavelength of light, multiple wavelengths of light, or a range of wavelengths of light. In particular cases, a material, molecule, or particle may be optically active for photons with a first wavelength and optically passive for photons with a second wavelength that differs from the first wavelength. Optically passive materials may include metals, metal oxides, semiconductors, dielectric materials, and certain organic or inorganic solids. An optically passive material may comprise a metal, such as aluminum, scandium, titanium, vanadium, manganese, iron, cobalt, nickel, copper, zinc, ytrrium, zirconium, niobium, molybdenum, palladium, silver, tungsten, platinum, gold, tin, lead, or bismuth. An optically passive material may comprise a metal oxide (e.g., aluminum oxide, chromium oxide, iron oxide, nickel oxide, silicon dioxide, silver oxide, tin oxide, tungsten oxide, zinc oxide, zirconium oxide, etc.), a metal sulfide (e.g., iron sulfide, copper sulfide, nickel sulfide, lead sulfide, cobalt sulfide, silver sulfide, zinc sulfide, etc.), a metal carbide (e.g., titanium carbide, zirconium carbide, vanadium carbide, chromium carbide, molybdenum carbide, tungsten carbide, etc.) or a metal nitride (silicon nitride, titanium nitride, etc.). An optically passive material may comprise a semiconductor, such as diamond, silicon, germanium, silicon carbide, boron nitride, aluminum nitride, gallium nitride, gallium arsenide, zinc oxide, zinc selenide, tin sulfide, titanium dioxide, copper oxide, etc. An optically passive material may comprise a dielectric material, such as polytetrafluoroethylene, polyethylene, polyimide, titanium dioxide, strontium titante, barium titanate, or calcium copper titante. An optically passive moiety may be detectable via a characteristic signal by any suitable method, such as brightfield microscopy, light scattering, neutron scattering, interferometry, Mie scattering, x-ray diffraction, electron backscattering, and transmission electron microscopy.

As used herein, the term "interstitial region," when used in reference to an array, refers to a region of an array or a surface thereof that is configured to prevent or minimize the likelihood of a moiety, molecule, or particle binding to the region. An interstitial region may be configured to prevent binding of an analyte to the interstitial region. Optionally, an interstitial region may be configured to prevent non-specific binding of a moiety, molecule, or particle other than an analyte, such as an assay reagent or ionic species. An interstitial region may comprise one or more passivating moieties. An interstitial region may spatially separate a first site from a second site. Optionally, an interstitial region may spatially separate a first site from a second site by a sufficient distance to optically resolve the first site from the second site. Optionally, one or more interstitial regions may be configured on an array to provide an ordered array of sites.

Figure 3B:
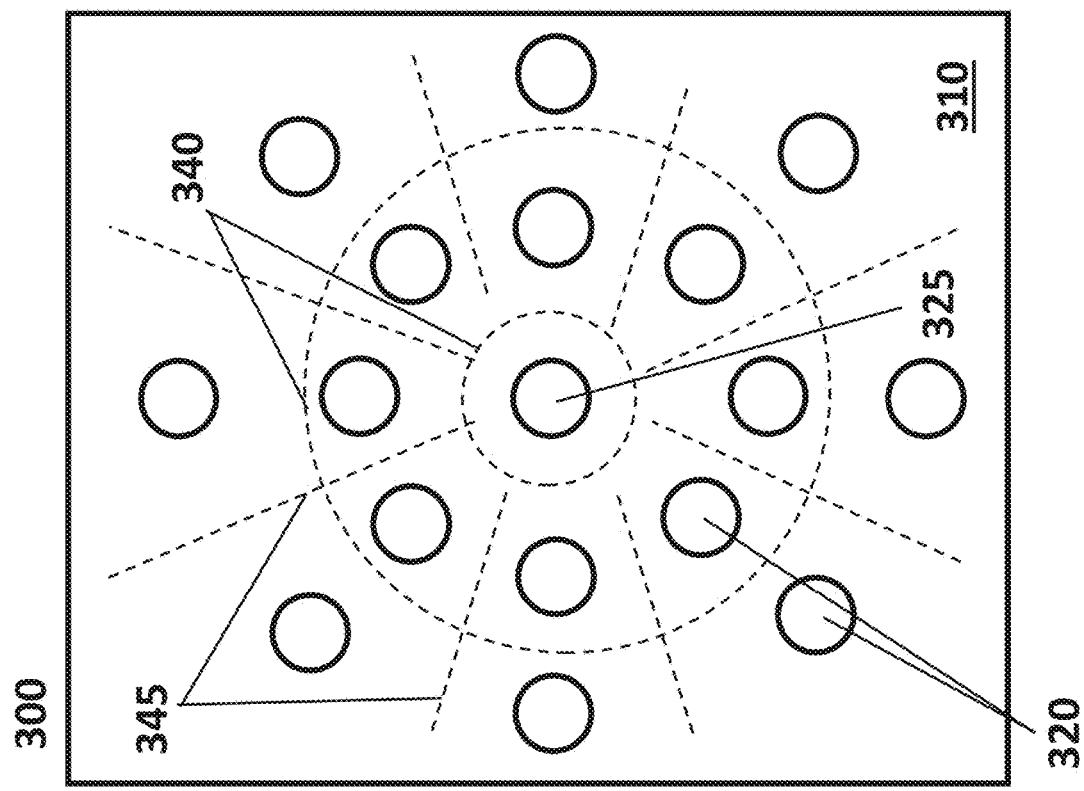
FIGS. 3A, 3B, and 3C display arrays with pluralities of sites with varying spatial configurations and interstitial regions forming streets between sites, in accordance with some embodiments.
Figure 3A:
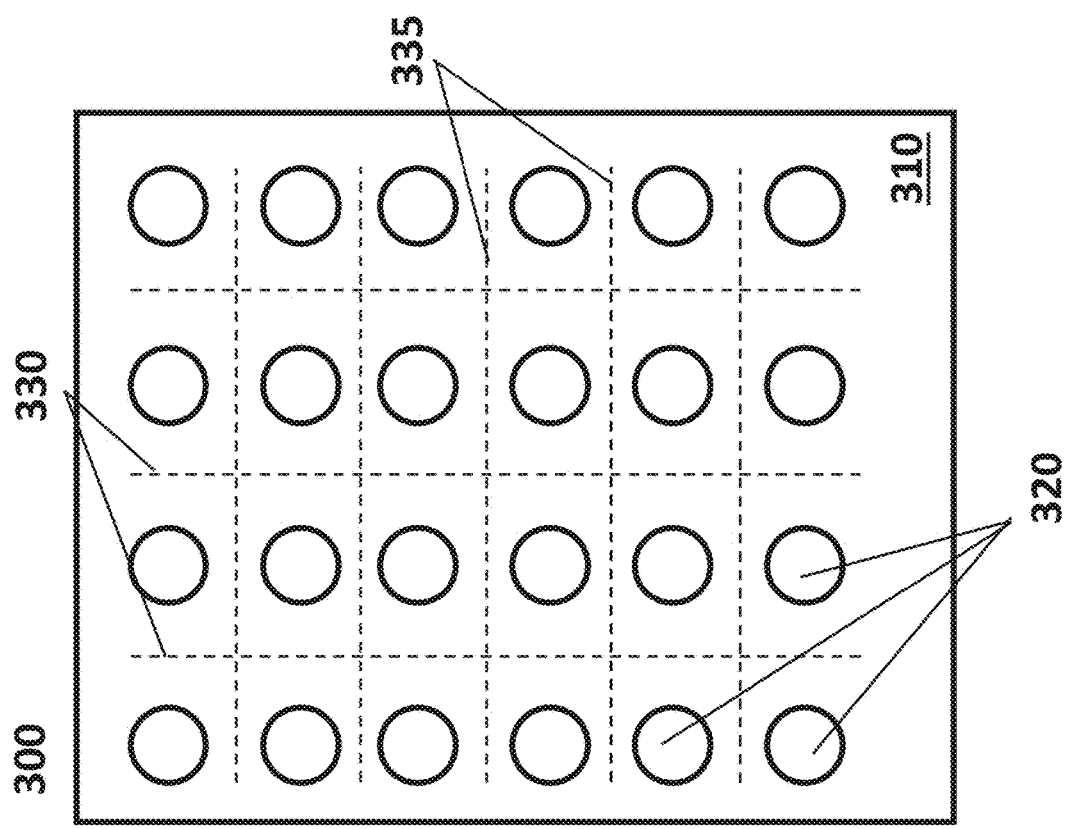

As used herein, the term "street," when used in reference to an array, refers to an interstitial region that contacts a plurality of sites. A street may provide a geometric order to a plurality of sites, such as forming columns and/or rows of sites. FIGS. 3A-3B depict examples of arrays comprising streets. FIG. 3A depicts an array 300 comprising a solid support 310 and a plurality of sites 320 with a rectangular grid of sites 320 formed by a plurality of vertically-oriented streets 330 and horizontally-oriented streets 335 (oriented along dashed lines), relative to the viewer, that separate each site 320 of the plurality of sites. FIG. 3B depicts an array 300 comprising a solid support 310 and a plurality of sites 320 with a radial grid of sites 320 formed by a plurality of concentric streets 340 and radial streets 345 (oriented along dashed lines), relative to a central site 325, that separate each site 320 of the plurality of sites.

As used herein, the terms "protein," "oligopeptide," "peptide" and "polypeptide" are used interchangeably to refer to a molecule or analyte comprising two or more amino acids joined by a peptide bond. Although the terms may optionally be used when distinguishing molecules having different characteristics, such as amino acid sequence length, molecular weight, origin of the molecule or the like, the terms are not intended to inherently delineate such distinctions in all contexts. A polypeptide may refer to a naturally-occurring molecule, or an artificial or synthetic molecule. A polypeptide may include one or more non-natural, modified amino acids, or non-amino acid linkers. A polypeptide may contain D-amino acid enantiomers, L-amino acid enantiomers or both. A polypeptide may be modified naturally or synthetically, such as by post-translational modifications.

As used herein, the terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

As used herein, the term "detectable label" refers to a moiety or substance that provides an observable characteristic. The observable characteristic can be, for example, an optical signal such as absorbance of radiation, luminescence or fluorescence emission, luminescence or fluorescence lifetime, luminescence or fluorescence polarization, or the like; Rayleigh and/or Mie scattering; binding affinity for a ligand or receptor; magnetic properties; electrical properties; charge; mass; radioactivity or the like. A label component can be a detectable chemical entity that is conjugated to or capable of being conjugated to another molecule or substance. Exemplary molecules that can be conjugated to a label component include an affinity reagent or a binding partner. A label component may produce a signal that is detected in real-time (e.g., fluorescence, luminescence, radioactivity). A label component may produce a signal that is detected off-line (e.g., a nucleic acid barcode) or in a time-resolved manner (e.g., time-resolved fluorescence). A label component may produce a signal with a characteristic frequency, intensity, polarity, duration, wavelength, sequence, or fingerprint. Exemplary labels include, without limitation, a fluorophore, luminophore, chromophore, nanoparticle (e.g., gold, silver, carbon nanotubes), heavy atom, radioactive isotope, mass label, charge label, spin label, receptor, ligand, nucleic acid barcode, polypeptide barcode, polysaccharide barcode, or the like.

As used herein, the term "identification tag," when used in reference to an array, refers to identifying information that is disposed on or within an array or a structure comprising an array. An identification tag may comprise identifying information that relates to any aspect of manufacture of an array and/or a structure comprising an array, such as serial number, lot number, date of manufacture, time of manufacture, place of manufacture, company of manufacture, or expiration date. An identification tag may be disposed on an array or a structure comprising an array by any suitable method, such as an engraving, etching, embossing, embedding, adhering, printing, or a combination thereof. An identification tag may comprise a physical embodiment, such as a sticker, a QR code, a barcode, and RFID tag, or a combination thereof.

As used herein, the term "global," when used in reference to a property or characteristic of a plurality of addresses, sites, or moieties bound thereto of an array, refers to the property or characteristic applying to or being derived from all addresses, sites, or moieties of the plurality of addresses, sites, or moieties bound thereto on the array. As used herein, the term "local," when used in reference to a property or characteristic of a plurality of addresses, sites, or moieties bound thereto of an array, refers to the property or characteristic applying to or being derived from a subset of containing less than all addresses, sites, or moieties of the plurality of addresses, sites, or moieties bound thereto on the array. For example, a global measure of randomness may refer to a measure of randomness that is determined for a spatial distribution of fiducial elements that contains every fiducial element bound to an array, whereas a local measure of randomness may refer to a measure of randomness that is determined for a spatial distribution of fiducial elements within a subregion or subarray of the array (e.g., a measure of randomness for a set of 5000 fiducial elements on an array comprising 1000000 fiducial elements).

As used herein, the term "field-of-view," when used in reference to a sensing device, refers to a dimension of a region sensed by a sensing device. A field-of-view of a sensing device may be expressed by a measure of length (e.g., diameter, radius, length, width, etc.) or area. A field-of-view may have a characteristic shape or aspect, such as rectangular, square, circular, oval, triangular, polygonal, etc. A shape or aspect of a field-of-view of a sensing device may be determined, in whole or in part, by a component of a sensing device, such as an objective lens, an aperture, or a sensor (e.g., a rectangular pixel array). A measure and/or aspect ratio of a field-of-view of a sensing device may be determined, in whole or in part, by properties of one or more components of a sensing device, such as objective lens magnification, objective lens dimension, aperture dimension, and aperture aspect ratio. A field-of-view of a sensing device may comprise a two-dimensional representation of a three-dimensional surface. A field-of-view of a sensing device may have a largest dimension (e.g., length, width, diameter) of at least about 10 nanometers (nm), 50 nm, 100 nm, 200 nm, 250 nm, 500 nm, 750 nm, 1000 nm, 1500 nm, 2000 nm, 5000 nm, 10000 nm, or more than 10000 nm. Alternatively or additionally, a field-of-view of a sensing device may have a largest dimension of no more than about 10000 nm, 5000 nm, 2000 nm, 1500 nm, 1000 nm, 750 nm, 500 nm, 250 nm, 200 nm, 100 nm, 50 nm, or less than 50 nm. A field-of-view of a sensing device may have an aspect ratio (i.e., a ratio of a largest dimension to a smallest dimension) of at least about 1:1, 5:4, 4:3, 3:2, 2:1, 3:1, 4:1, 5:1, 10:1, 15:1, 20:1, 25:1, 50:1, 100:1, 1000:1, 10000:1, or greater than 10000:1. As used herein, the term "field-of-view," when used in reference to a data structure, refers to a discrete set of data that is derived from a field-of-view of a sensing device, in which each datum corresponds to a specific address or other feature within the field-of-view of the sensing device. For example, a microscope objective can collect light from a region within its field-of-view, and the field-of-view may be discretized by collection of light on a finite pixel-based sensor. Accordingly, data from the pixel-based sensor may be converted into a data structure (e.g., an array, a digital image, etc.) with a data field-of-view that directly maps a pixel of the pixel-based array to an address of the microscope field-of-view, and in which the data structure comprises a plurality of data units pairing a spatial datum with a sensor measurement datum.

As used herein, the term "pattern," when used in reference to a spatial distribution of fiducial elements, refers to a spatial arrangement of a set or subdistribution of fiducial elements that is characteristic of the set or subdistribution. A pattern of fiducial elements may be a repeating or regular pattern if the spatial arrangement of the fiducial elements is locally or globally uniform, repeating, or regular. A pattern of fiducial elements may be an irregular, non-repeating or disordered pattern if the spatial arrangement of the fiducial elements is locally or globally random or unpredictable.

As used herein, the term "unique identifier" refers to a solid support (e.g., particle or bead), spatial address in an array, tag, label (e.g., luminophore), and/or barcode (e.g., nucleic acid barcode) that is attached to an analyte and that is distinct from other identifiers, throughout one or more steps of a process. The process can be an analytical process such as a method for detecting, identifying, characterizing or quantifying an analyte. Attachment to a unique identifier can be covalent or non-covalent (e.g., ionic bond, hydrogen bond, van der Waals forces etc.). A unique identifier can be exogenous to the analyte, for example, being synthetically attached to the analyte. Alternatively, a unique identifier can be endogenous to the analyte, for example, being attached or associated with the analyte in the native milieu of the analyte. An array can include different analytes that are each attached to different unique identifiers. An array can include different unique identifiers that are attached to the same or similar analytes. An array can include separate solid supports or separate addresses that each bear a different analyte, in which the different analytes can be identified according to the locations of the solid supports or addresses. A protein or other analyte can be attached to a unique identifier using any of a variety of means. The attachment can be covalent or non-covalent. Exemplary covalent attachments include chemical linkers such as those achieved using click chemistry or other linkages known in the art or described in US Pat. App. Pub. No. 2021/0101930 A1, which is hereby incorporated herein by reference. Non-covalent attachment can be mediated by receptor-ligand interactions (e.g., (strept)avidin-biotin, antibody-antigen, or complementary nucleic acid strands), for example, in which the receptor is attached to the unique identifier and the ligand is attached to the protein or vice versa. In particular configurations, a protein is attached to a solid support (e.g., an address in an array) via a structured nucleic acid particle (SNAP). A protein can be attached to a SNAP and the SNAP can interact with a solid support, for example, by non-covalent interactions of the DNA with the support and/or via covalent linkage of the SNAP to the support. Nucleic acid origami or nucleic acid nanoballs are particularly useful. The use of SNAPs and other moieties to attach proteins to unique identifiers such as tags or addresses in an array are set forth in US Pat. App. Pub. No. 2021/0101930 A1, which is incorporated herein by reference.

Other than in the operating examples, or where otherwise indicated, all numbers expressing quantities of ingredients or reaction conditions used herein should be understood as modified in all instances by the term "about." As used herein, the term "about," when used in connection with percentages, may mean a variance of at most ±5% of the value being referred to. For example, about 100% may mean from 95% to 105%. In some cases, "about" may mean a variance of at most ±4%, ±3%, ±2%, ±1% or ±0.5% of the value being referred to The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

Arrays Comprising Fiducial Elements

In an aspect, provided herein is a single-analyte array, comprising: a) a solid support comprising a plurality of sites, in which each site of the plurality of sites is optically resolvable at single-analyte resolution, b) a plurality of fiducial elements bound to a first subset of the plurality of sites, in which the first subset of the plurality of sites comprises a random spatial distribution, and in which the subset of the plurality of sites comprises no more than about 1% of the plurality of sites, and c) a plurality of sample analytes bound to a second subset of the plurality of sites, in which each site of the first subset of the plurality of sites comprises one and only one fiducial element of the plurality of fiducial elements, in which each site of the second subset of the plurality of sites comprises one and only one sample analyte of the plurality of sample analytes, in which the random spatial distribution of the first subset of the plurality of sites comprises a plurality of unique subdistributions, and in which each site of the second subset of the plurality of sites has known spatial distances to sites of a unique subdistribution of the plurality of unique subdistributions.

A single-analyte array may comprise a plurality of analytes obtained from a biological sample. In some cases, a plurality of analytes obtained from a biological sample may comprise biomolecules with a high degree of complexity (e.g., proteome-scale for polypeptides, genome-scale for deoxyribonucleic acids, transcriptome-scale for ribonucleic acids, etc.). A high degree of complexity for a plurality of analytes may comprise at least about 10, 50, 100, 250, 500, 1000, 2000, 5000, 10000, or more than 10000 unique or distinguishable types or species of analytes. In some cases, a single-analyte array may comprise a plurality of fiducial elements, in which the plurality of fiducial elements are obtained from a source that is exogenous to a source of a plurality of analytes. In particular cases, a plurality of fiducial elements may be obtained from a non-biological source. In particular cases, a plurality of fiducial elements may comprise manufactured or engineered moieties, molecules, or particles. In particular cases, a fiducial element of a plurality of fiducial elements may comprise a non-biological form of metal, metal oxide, semiconductor, or organic particle (e.g., graphene). In particular cases, a fiducial element of a plurality of fiducial elements may comprise a non-natural, engineered, or modified form of a biomolecule (e.g., PNAs, LNAs, fluorescently-labeled biomolecules, etc.).

A single-analyte array may comprise a plurality of fiducial elements, in which the plurality of fiducial elements are coupled to array sites, and in which the array sites comprising at least one fiducial element have a random spatial distribution. A random spatial distribution of a plurality of fiducial elements may be subdivided into subdistributions, in which each subdistribution comprises two or more sites of a plurality of sites comprising fiducial elements, and in which each subdistribution comprises a unique spatial ordering or spatial pattern of sites relative to each other subdistribution. In some cases, a random spatial distribution of a plurality of fiducial elements may be subdivided into subdistributions, in which a first subdistribution comprises a first set of sites comprising fiducial elements, in which a second subdistribution comprises a second set of sites comprising fiducial elements, and in which at least one site comprising a fiducial element is common to the first subdistribution and the second subdistribution. In other cases, a random spatial distribution of a plurality of fiducial elements may be subdivided into subdistributions, in which a first subdistribution comprises a first set of sites comprising fiducial elements, in which a second subdistribution comprises a second set of sites comprising fiducial elements, in which all sites of the first subdistribution are not in the second set of sites, and in which all sites of the second subdistribution are not in the first set of sites.

A subdistribution of a plurality of sites comprising fiducial elements may comprise at least about 2, 3, 4, 5, 6, 7, 8, 9, 10, 15, 20, 25, 30, 35, 40, 45, 50, or more than 50 sites of the plurality of sites comprising fiducial elements. Alternatively or additionally, a subdistribution of a plurality of sites comprising fiducial elements may comprise no more than about 50, 45, 40, 35, 30, 25, 20, 15, 10, 9, 8, 7, 6, 5, 4, 3, or less than 3 sites of the plurality of sites comprising fiducial elements.

Figure 32B:
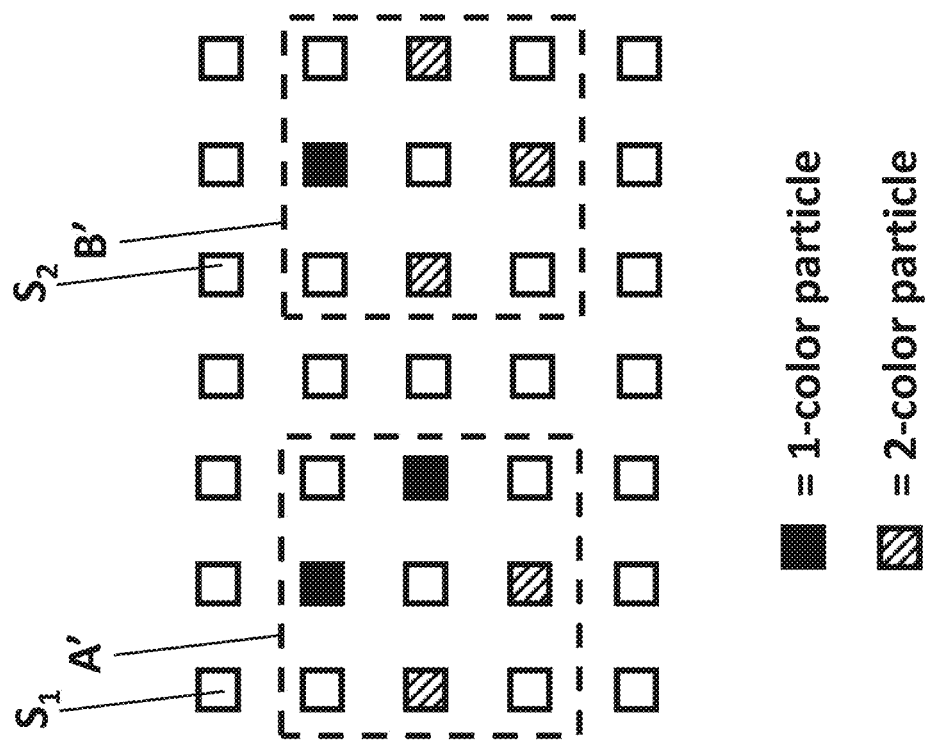
FIGS. 32A and 32B illustrate arrays with single-color or mixed single-color and multi-spectral fiducial elements to vary the spatial complexity of spatial distributions of fiducial elements, in accordance with some embodiments.
Figure 32A:
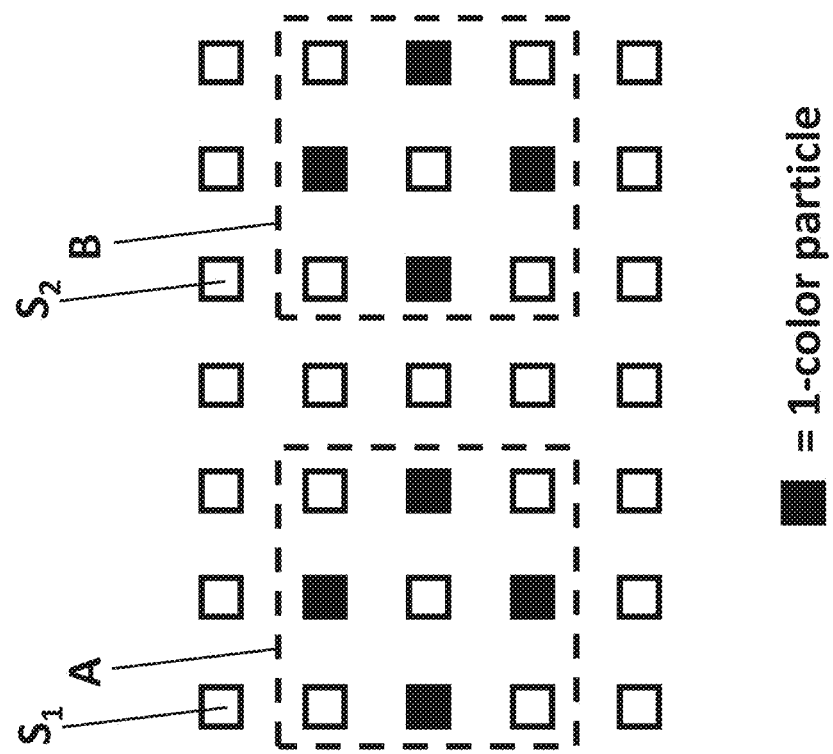

In an advantageous configuration, a single-analyte array may comprise a mixture of single-spectrum and multi-spectral fiducial elements. For example, a plurality of fiducial elements comprising a mixture of 1-color, 2-color, 3-color, and 4-color fluorescent nanoparticles may be utilized to increase the spatial complexity of a random spatial distribution of fiducial elements. FIGS. 32A-32B illustrate aspects of using a mixture of fiducial elements to increase spatial complexity of subdistributions of fiducial elements. FIG. 32A illustrates an array of sites comprising 8 sites containing fiducial elements that fluoresce in a single color (one emission wavelength). The sites containing fiducial elements are divided into subdistributions A and B. The subdistributions are spatially identical. Accordingly, sites $S_1$ and $S_2$ may not be uniquely identifiable with respect to subdistributions A and B, respectively. FIG. 32B illustrates an array of sites comprising 8 sites containing fiducial elements, with a mixture of sites comprising one-color or two-color fiducial elements. The sites containing fiducial elements are divided into subdistributions A' and B'. The subdistributions are spatially identical with respect to locations of fiducial elements, but are not spatially identical with respect to spatial distribution of one-color and two-color fiducial elements. Accordingly, sites $S_1$ and $S_2$ may be uniquely identifiable with respect to subdistributions A' and B', respectively.

An address of a site (e.g., an analyte-containing site) on a single-analyte array may be known with respect to a subdistribution of fiducial elements of a random spatial distribution of fiducial elements. An address of a site (e.g., an analyte-containing site) on a single-analyte array may be known with respect to a subdistribution of fiducial elements of a random spatial distribution of fiducial elements based upon spatial distances and/or vector directions from the site to each site of the subdistribution of fiducial elements. In some cases, an address of a site (e.g., an analyte-containing site) on a single-analyte array may be known with respect to two or more unique subdistributions of fiducial elements of a random spatial distribution of fiducial elements based upon spatial distances and/or vector directions from the site to each site of the two or more subdistributions of fiducial elements.

An address of a site (e.g., an analyte-containing site) on a single-analyte array may be a spatial distance from a site of a subdistribution of a random spatial distribution of sites comprising fiducial elements, such as at least about 10 nanometers (nm), 25 nm, 50 nm, 75 nm, 100 nm, 150 nm, 200 nm, 500 nm, 1 micron (μm), 1.5 μm, 2 μm, 3 μm, 5 μm, 10 μm, 25 μm, 50 μm, 100 μm, 250 μm, 500 μm, or more than 500 μm. Alternatively or additionally, an address of a site (e.g., an analyte-containing site) on a single-analyte array may be a spatial distance from a site of a subdistribution of a random spatial distribution of sites comprising fiducial elements, such as no more than about 500 μm, 250 μm, 100 μm, 50 μm, 25 μm, 10 μm, 5 μm, 3 μm, 2 μm, 1.5 μm, 1 μm, 500 nm, 250 nm, 150 nm, 100 nm, 75 nm, 50 nm, 25 nm, 10 nm, or less than 10 nm.

A single-analyte array composition may further comprise a plurality of analytical reagents (e.g., affinity agents, detectable labels, etc.). In some cases, a plurality of analytical reagents may be contacted with a single-analyte array. In other cases, a plurality of analytical reagents may be bound to a fraction of a plurality of analytes. In particular cases, a plurality of analytical reagents may be bound to substantially all analytes of a plurality of analytes. In other particular cases, a plurality of analytical reagents may be bound to a fraction of a plurality of analytes, such as at least about 0.000001%, 0.00001%, 0.0001%, 0.001%, 0.005%, 0.01%, 0.05%, 0.1%, 0.5%, 1%, 5%, 10%, 15%, 20%, 25%, 30%, 35%, 40%, 45%, 50%, or more than 50% of analytes of the plurality of analytes. Alternatively or additionally, a plurality of analytical reagents may be bound to a fraction of a plurality of analytes, such as no more than about 50%, 45%, 40%, 35%, 30%, 25%, 20%, 15%, 10%, 5%, 1%, 0.5%, 0.1%, 0.05%, 0.01%, 0.005%, 0.001%, 0.0001%, 0.00001%, 0.000001%, or less than 0.000001% of analytes of the plurality of analytes.

In another aspect, provided herein is a single-analyte array, comprising: a) a solid support comprising a plurality of sites, in which each site of the plurality of sites is optically resolvable at single-analyte resolution, b) a plurality of fiducial elements (e.g., fluorescent nanoparticles) bound to a first subset of the plurality of sites, in which each fiducial element of the plurality of fiducial elements is attached to a first plurality of oligonucleotides, in which each oligonucleotide of the first plurality of oligonucleotides comprises a first nucleotide sequence, in which each site of the first subset of the plurality of sites comprises a second plurality of oligonucleotides, in which each oligonucleotide of the second plurality of oligonucleotides comprises a second nucleotide sequence, in which the first oligonucleotide sequence is complementary to the second oligonucleotide sequence, and in which two or more oligonucleotides of the first plurality of oligonucleotides is hybridized to two or more oligonucleotides of the second plurality of oligonucleotides, and b) a plurality of analytes bound to a second subset of the plurality of sites.

In some configurations, a plurality of analytes is bound to a second subset of a plurality of sites by a plurality of anchoring moieties. In particular configurations, each anchoring moiety of a plurality of anchoring moieties comprises a third plurality of oligonucleotides, in which each oligonucleotide comprises a third nucleotide sequence. A third nucleotide sequence of an anchoring moiety may be identical to a first nucleotide sequence of a fiducial element. A third nucleotide sequence of an anchoring moiety may differ from a first nucleotide sequence of a fiducial element. If a third nucleotide sequence differs from a first nucleotide sequence, each site of a second subset of a plurality of sites may comprise a fourth plurality of oligonucleotides, in which each oligonucleotide of the fourth plurality of oligonucleotides comprises a fourth nucleotide sequence, and in which the fourth nucleotide sequence is complementary to the third nucleotide sequence. Accordingly, a single-analyte array may comprise a plurality of analyte-binding sites and a plurality of fiducial element-binding sites, in which the coupling chemistry of the analyte-binding sites is orthogonal to the coupling chemistry of the fiducial element-binding sites. The skilled person will readily recognize innumerable variations of such arrays utilizing coupling chemistries other than oligonucleotides, such as receptor-ligand binding pairs and/or covalent coupling pairs.

In an aspect, provided herein is a single-analyte array, comprising: a) a solid support, in which the solid support comprises a plurality of sites and one or more interstitial regions, in which each site of the plurality of sites is configured to couple an analyte, in which each interstitial region is configured to inhibit binding of an unbound moiety, and in which each site is separated from each other site by an interstitial region of the one or more interstitial regions, and b) a plurality of fiducial elements, wherein each fiducial element is located at a site of the plurality of sites, and wherein the plurality of fiducial elements is distributed on the solid support in a random order.

Figure 4C:
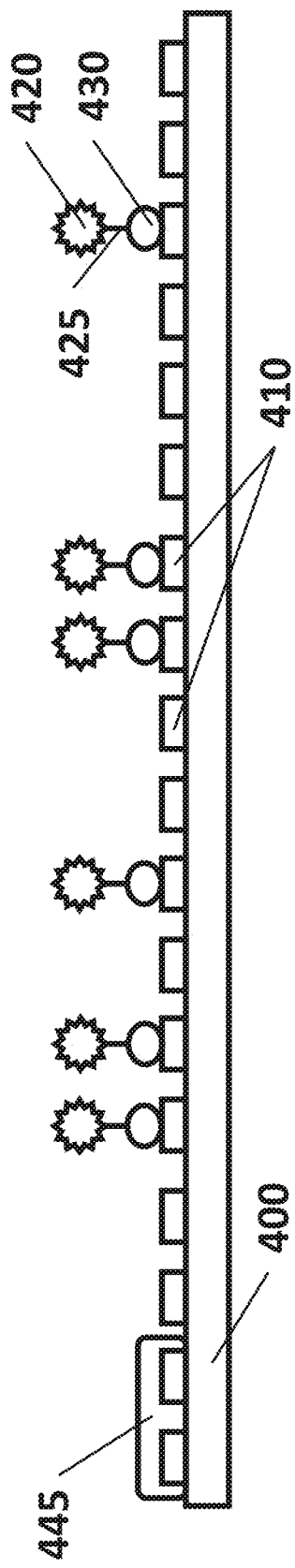
Figure 4D:
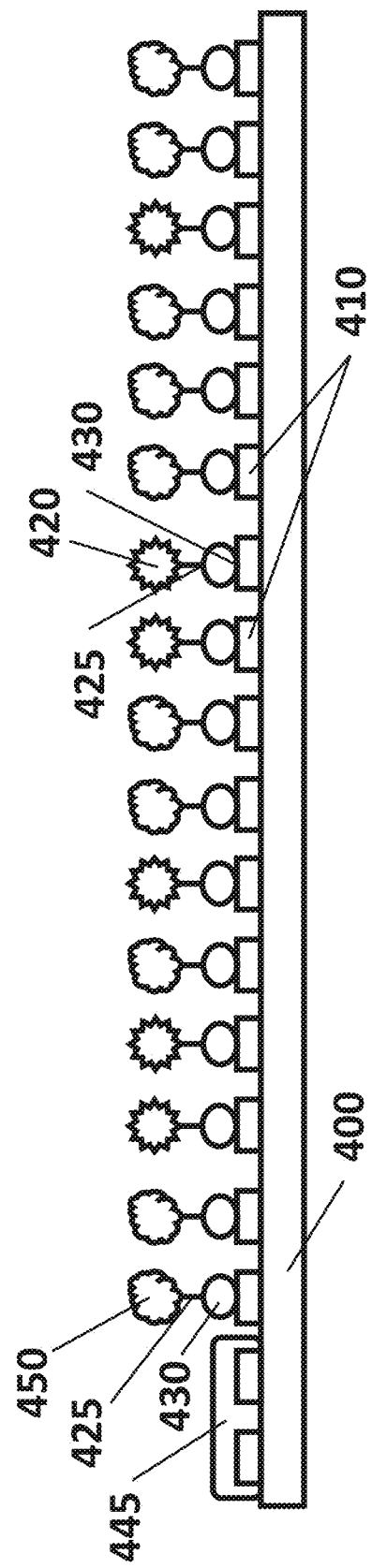
Figure 4E:
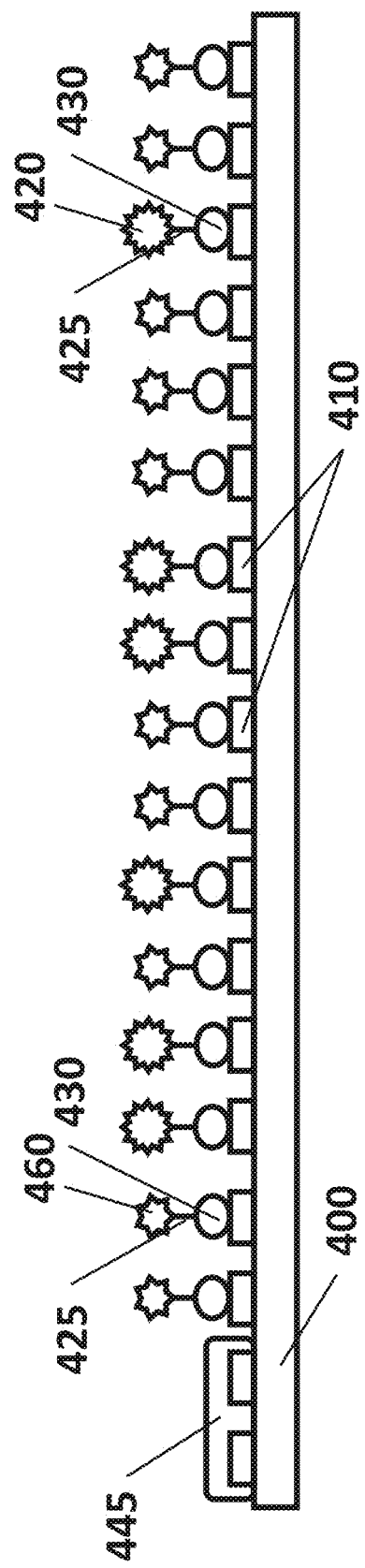

FIGS. 4A-4E illustrate exemplary embodiments of arrays comprising fiducial elements. FIG. 4A depicts a cross-sectional view of an array comprising a solid support 400, in which the solid support 400 comprises a plurality of sites 410 (e.g., analyte binding sites, fiducial element binding sites, etc.). A subset of the plurality of sites 410 are bound by fiducial elements 420. Each fiducial element 420 is coupled to a site 410 of the plurality of sites by an anchoring moiety 430, in which each fiducial element 420 is coupled to an anchoring moiety 430 by an optional attachment moiety 425. The plurality of fiducial elements has a random spatial distribution on the solid support 400 in the respect that there is no discernible repeat within the pattern of sites occupied by fiducial elements. FIG. 4B depicts a cross-sectional view of an array comprising a solid support 400, in which the solid support 400 comprises a plurality of sites 410. A subset of the plurality of sites 410 are bound by fiducial elements comprising a layer or coating, such as single-site layer fiducial elements 440 or a multi-site layer fiducial element 445. Each fiducial element is coupled to at least one site 410 of the plurality of sites. The plurality of fiducial elements has a random spatial distribution on the solid support 400 in the respect that there is no discernible repeat within the pattern of sites occupied by fiducial elements. For some methods of forming a plurality of fiducial elements comprising a layer of coating (e.g., a lithographic method), a plurality of fiducial elements comprising a layer or coating may have a random spatial distribution on an array, but a plurality of arrays may be produced with the same random spatial distribution. FIG. 4C depicts a cross-sectional view of an array comprising a solid support 400, in which the solid support 400 comprises a plurality of sites 410. The array comprises a plurality of fiducial elements, including fiducial elements 420 that are coupled to a site 410 by an anchoring moiety 430, and a multi-site layer fiducial element 445. The plurality of fiducial elements has a random spatial distribution on the solid support in the respect that there is no discernible repeat within the pattern of sites occupied by fiducial elements, and no discernible repeat within the pattern of sites occupied by fiducial elements 420 relative to the multi-site layer fiducial element 445. FIG. 4D depicts the array of FIG. 4C, in which a plurality of analytes of interest 450 have been deposited at previously-unoccupied sites 410 of the plurality of sites. Each analyte of interest 450 is coupled to a site 410 of the plurality of sites by an anchoring moiety 430, in which each analyte of interest 450 is coupled to an anchoring moiety 430 by an optional attachment moiety 425. FIG. 4E depicts the array of FIG. 4C, in which a plurality of mapping moieties 460 (e.g., fluorescently-labeled nucleic acids, reactive dyes, etc.) have been deposited at previously-unoccupied sites 410 of the plurality of sites. Each mapping moiety 460 is coupled to a site 410 of the plurality of sites by an anchoring moiety 430, in which each mapping moiety 460 is coupled to an anchoring moiety 430 by an optional attachment moiety 425.

An array, as set forth herein, may comprise a single-analyte array. A single-analyte array may comprise one or more characteristics selected from: i) comprising a plurality of sites, in which each site of the plurality of sites comprises a single analyte, and in which each single analyte is individually addressable; ii) comprising a plurality of sites, in which each site of the plurality of sites comprises one and only one single analyte, and in which each single analyte is individually addressable, iii) comprising a plurality of single analytes, in which each single analyte is resolvable from each other single analyte; and iv) comprising a plurality of single analytes, in which each single analyte is resolvable at single-analyte resolution. As used herein, the term "individually addressable," when used in reference to a site or a single analyte, refers to the ability to perform a step of a process or assay at each site or single analyte. For example, each single analyte of an array of single analytes may be individually addressable during contacting of an affinity agent if each single analyte is contactable by the affinity agent (e.g., no occlusion of a first single analyte by a second single analyte). As used herein, the term "resolvable," when used in reference to a site or a single analyte, refers to a spatial and/or temporal separation of signal(s) from the site or single analyte relative to signals from other sites or analytes.

An array may comprise a plurality of sites, in which a site of the plurality of sites may be resolvable at single-analyte resolution from all other sites in the array. In some configurations, a site may be resolvable at single-analyte resolution if a first signal from a first single analyte signal source originating from the first site is spatially distinguishable from a second signal from a second single analyte signal source originating from a second site of the plurality of sites. In particular configurations, a first signal and a second signal may be spatially distinguishable or spatially separated from a third signal originating from an interstitial region that separates the first site from the second site. For example, a first fluorescent signal from a first site may be separated from a second fluorescent signal from a second site by an interstitial region that emits a background signal, in which the background signal has a smaller peak or average magnitude than the first fluorescent signal and the second fluorescent signal. In some configurations, each site of a plurality of sites may be resolvable at single-analyte resolution.

Single analyte resolution may be achieved, in part, by providing an array with an average or minimum distance between adjacent sites. A distance between sites may be measured as a straight-line distance between the center-points of two adjacent sites. A first site and a second site located adjacent to the first site may be separated by an average or minimum distance of at least about 10 nanometers (nm), 50 nm, 100 nm, 150 nm, 200 nm, 250 nm, 300 nm, 350 nm, 400 nm, 450 nm, 500 nm, 600 nm, 700 nm, 800 nm, 900 nm, 1000 nm, 1500 nm, 2000 nm, 2500 nm, 3000 nm, 4000 nm, 5000 nm, 10000 nm, or more than 10000 nm.

Alternatively or additionally, a first site and a second site located adjacent to the first site may be separated by an average or maximum distance of no more than about 10000 nm, 5000 nm, 4000 nm, 3000 nm, 2500 nm, 2000 nm, 1500 nm, 1000 nm, 900 nm, 800 nm, 700 nm, 600 nm, 500 nm, 450 nm, 400 nm, 350 nm, 300 nm, 250 nm, 200 nm, 150 nm, 100 nm, 50 nm, 10 nm, or less than 10 nm.

An array, such as a single-analyte array, may comprise: i) a plurality of sites, in which each site of the plurality of sites is configured to couple an analyte, and ii) one or more interstitial regions, in which the one or more interstitial regions are configured to not couple an analyte. In some configurations, an array may comprise a solid support containing a plurality of sites and one or more interstitial regions. An array may comprise one or more surface chemistries that are configured to mediate an interaction between a moiety and the array. Optionally, a site of a plurality of sites on an array may comprise a moiety, molecule, particle, layer, or coating that is configured to facilitate an interaction, such as a coupling interaction, between an analyte and the site. Optionally, a site of a plurality of sites on an array may comprise a moiety, molecule, particle, layer, or coating that is configured to impede an interaction, such as a coupling interaction, between a chemical entity other than an analyte and the site. Optionally, an interstitial region on an array may comprise a moiety, molecule, particle, layer, or coating that is configured to impede an interaction, such as a coupling interaction, between an analyte and the interstitial region. Optionally, an interstitial region on an array may comprise a moiety, molecule, particle, layer, or coating that is configured to impede an interaction, such as a coupling interaction, between a chemical entity other than an analyte and the interstitial region.

A coupling moiety may be coupled to an array or a portion thereof, such as a site or an interstitial region. A coupling moiety may be covalently coupled to a solid support, or a region thereof. For example, a silane moiety with a terminal epoxide or azide group may be deposited on a glass or silicon surface via a coordination bond between the silane group and the solid support. In another example, a surface may be directly modified with reactive functional groups, such as amines, carboxylates, phosphates, or phosphonates. Alternatively, a coupling moiety may be non-covalently coupled to a solid support, or a region thereof. For example, a oligonucleotide-coated nanoparticle may be coupled to a solid support by an electrostatic or magnetic interaction. A coupling moiety may be configured to couple an analyte, such as a single analyte, to a site of a plurality of sites. In some configurations, a coupling moiety may be configured to covalently couple an analyte, such as a single analyte, to a site of a plurality of sites. For example, a coupling moiety may comprise a reactive group that is configured to form a covalent bond with a complementary reactive group that is coupled to an analyte. In particular configurations, a covalent bond may be formed by a Click-type reaction or a bioorthogonal reaction. Exemplary methods for forming covalent bonds between coupling moieties and analytes are described in U.S. Pat. No. 11,203,612 and Hermanson, *Bioconjugate Techniques,* 3$^{rd}$ Ed., 2013, each of which is incorporated by reference in its entirety. In particular configurations, a coupling moiety may be configured to non-covalently couple an analyte, such as a single analyte, to a site of a plurality of sites. Non-covalent coupling interactions may include electrostatic interactions, magnetic interactions, hydrogen bonding interactions, van der Waals interactions, nucleic acid base pair binding, receptor-ligand binding, or combinations thereof. For example, a coupling moiety may comprise an oligonucleotide that is configured to hybridize to a complementary coupling moiety coupled to an analyte. In another example, a coupling moiety may comprise a component of a receptor-ligand binding pair, such as streptavidin-biotin, SpyCatcher-SpyTag, Snoop-Catcher-SnoopTag, or SdyCatcher-SdyTag. In some configurations, a site may comprise a plurality of coupling moieties. A site may comprise a plurality of coupling moieties to increase the likelihood of at least one coupling moiety binding to an analyte. Alternatively, a site may comprise a plurality of coupling moieties to couple an analyte that comprises a plurality of complementary coupling moieties. In some configurations, each site of a subset of a plurality of sites may comprise a coupling moiety that is configured to couple an analyte, such as a single analyte. A subset of sites containing a coupling moiety of a plurality of sites may comprise at least about 5%, 10%, 15%, 20%, 25%, 30%, 35%, 40%, 45%, 50%, 55%, 60%, 65%, 70%, 75%, 80%, 85%, 90%, 95%, 99%, or more than 99% of the plurality of sites. Alternatively or additionally, a subset of sites containing a coupling moiety of a plurality of sites may comprise no more than about 99%, 95%, 90%, 85%, 80%, 75%, 70%, 65%, 60%, 55%, 50%, 45%, 40%, 35%, 30%, 25%, 20%, 15%, 10%, 5%, or less than 5% of the plurality of sites. A subset of sites containing a coupling moiety of a plurality of sites may comprise 100% of the plurality of sites. A subset of sites of a plurality of sites need not necessarily comprise a coupling moiety. For example, an array may be provided with two subsets of sites, in which a first subset comprises a coupling moiety and is configured to couple a first type of analyte, and in which a second subset comprises no coupling moiety and is configured to couple a second type of analyte. In some configurations, an array may comprise a first site and a second site, in which the first site comprises a first coupling moiety and the second site comprises a second coupling moiety, wherein a coupling complementarity of the first coupling moiety differs from a coupling complementarity of the second coupling moiety. A coupling complementarity may include reactive complementarity (e.g., reactivity of two functional groups) or non-covalent binding complementarity (e.g., nucleic acid base pair complementarity, receptor-ligand complementarity, etc.).

A passivating moiety may be coupled to an array or a portion thereof, such as a site or an interstitial region. In some configurations, an array may comprise an interstitial region, in which the interstitial region comprises a passivating moiety that is configured to inhibit binding of an unbound moiety, such as an unbound analyte or an unbound non-analyte (e.g., an assay reagent). A passivating moiety may comprise a moiety or functional group that is configured to provide a chemical property to the passivating moiety. For example, a passivating moiety may comprise a hydrophilic moiety, a hydrophobic moiety, an electrically-repulsive moiety, an electrically-attractive moiety, a magnetically repulsive moiety, a magnetically-attractive moiety, a polar moiety, a non-polar moiety, a sterically-hindering moiety, a reactive moiety, a non-reactive moiety, or a combination thereof. A passivating moiety may comprise a plurality of moieties or functional groups that are configured to provide one or more chemical properties to a passivating moiety. For example, a passivating moiety may comprise a polymer of alternating hydrophilic and electrically-repulsive moieties. A passivating moiety may comprise a linear molecular chain, a branched molecular chain, or a dendrimer. In some configurations, a passivating moiety may comprise a linear polyethylene glycol (PEG), a branched PEG, a linear alkyl moiety, a branched alkyl moiety, a fluorinated hydrocarbon, a linear polysaccharide, a branched polysaccharide, a dendrimer, or a combination thereof. In some configurations, an array may comprise a region (e.g., a site, an interstitial region) that comprises a first passivating moiety and a second passivating moiety, wherein the first passivating moiety differs from the second passivating moiety. A difference between a first passivating moiety and a second passivating moiety may comprise a difference in chemical structure (e.g., covalent ordering of atoms), a difference in a chemical property (e.g., hydrophobicity, polarity, reactivity, molecular weight, net electrical charge, etc.), a difference in surface density, a difference in binding specificity or binding affinity, or a combination thereof. In some configurations, a difference between a first passivating moiety and a second passivating moiety may comprise a difference in degree of polymer branching. In some configurations an array may comprise a site containing at least one coupling moiety and at least one passivating moiety. A site of an array may comprise a passivating moiety to prevent binding of a non-analyte to the site.

Figure 3C:
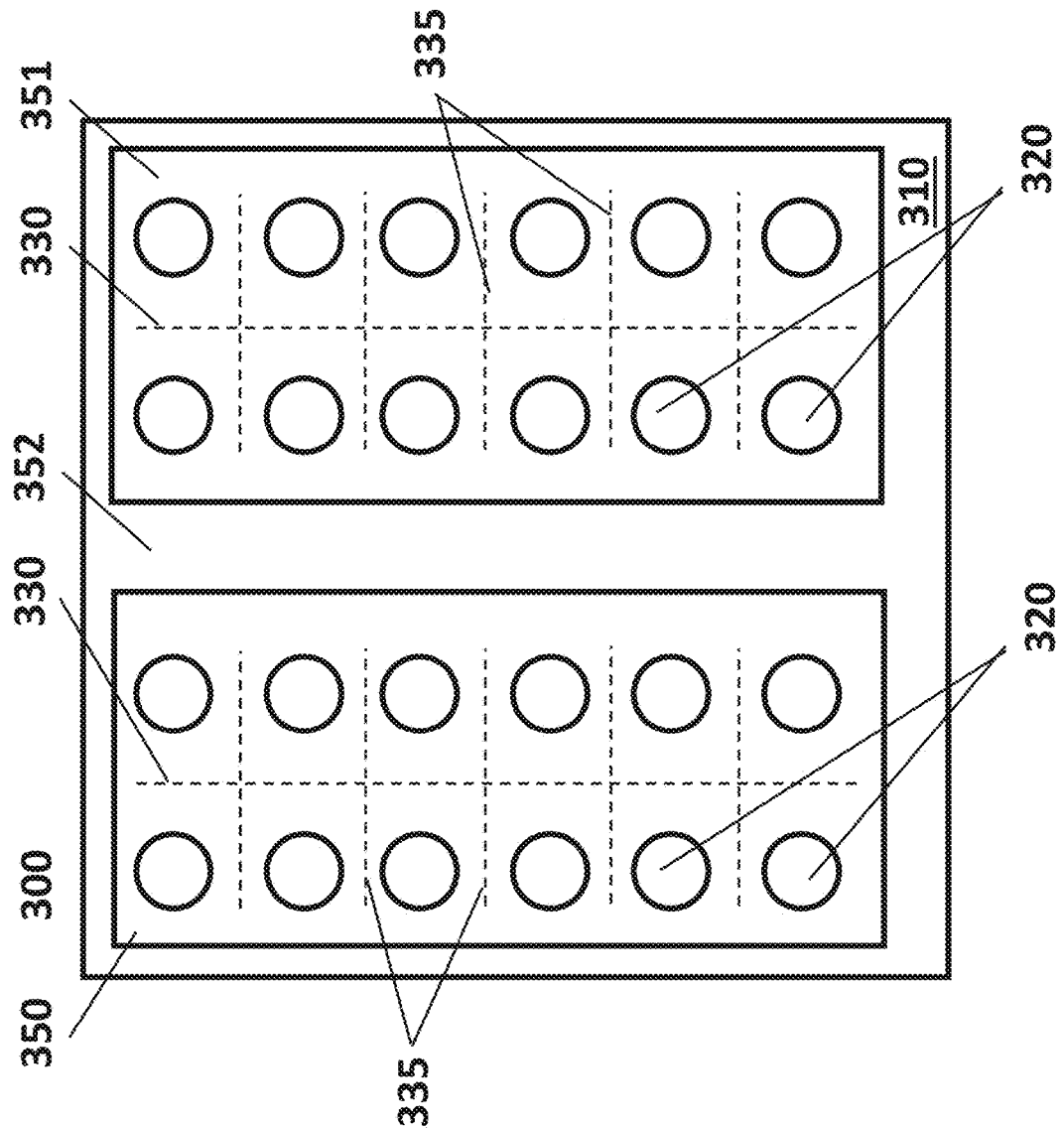

An array, such as a single-analyte array, may comprise one or more interstitial regions. In some configurations, an array may comprise a single continuous interstitial region. An interstitial region may be considered continuous if it is possible to traverse from a first address within the interstitial region to a second address in the interstitial region without passing through or crossing over a non-interstitial region. For example, an array may comprise a plurality of sites, in which each site is completely surrounded by an interstitial region. FIG. 3A illustrates an example of an array 300 comprising a plurality of sites 320 in a rectangular grid, in which it is possible to access any point within a single, continuous interstitial region via the vertical streets 330 and horizontal streets 335. In other configurations, an array may comprise two or more non-continuous interstitial regions. FIG. 3C illustrates an example of an array 300 comprising a plurality of sites 320 in rectangular grids, in which it is not possible to move from an address in a first interstitial region 350 to an address in a second interstitial region 351 without passing across a non-interstitial region 352 that completely separates the first interstitial region 350 from the second interstitial region 351.

An array, such as a single-analyte array, may comprise a region (e.g., a site, an interstitial region) containing a passivating moiety, in which the passivating moiety is configured to prevent, impede, or reduce the likelihood of an unbound moiety binding to the region. In some cases, an unbound moiety may comprise an analyte, such as a single analyte. For example, a passivating moiety may be coupled to an interstitial region to prevent an excess analyte from becoming bound to the interstitial region when analytes are deposited on an array. In another example, a passivating moiety may be coupled to an interstitial region to increase the likelihood that the analyte instead couples to a site of an array. In some cases, an unbound moiety may comprise a non-analyte, such as a cell, a macromolecule (e.g., a nucleic acid, a polypeptide, a polysaccharide, a combination thereof), a nanoparticle, a small molecule (e.g., a metabolite, a candidate therapeutic agent, a pharmaceutical compound, a binding ligand, an ionic species, a combination thereof), or a process substrate. A process substrate may comprise a moiety provided during a step of an array-based process (e.g., a synthesis, an assay, etc.). A process substrate may comprise an analyte (e.g., a component of a biomolecular complex), an affinity agent, a modifying agent, a stabilizing agent, a detection agent, or a combination thereof.

An array may comprise a solid support. In some configurations, a solid support may comprise a plurality of sites, in which the plurality of sites comprises a patterned array of sites. A patterned array of sites may be formed on a solid support by a lithographic method, such as photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, local oxidation nanolithography, deep-ultraviolet lithography, molecular self-assembly, stencil lithography, and electron-beam lithography. In some configurations, a patterned array may have a repeating pattern of sites. A repeating pattern of sites may comprise a grid pattern, such as a rectangular grid, a hexagonal grid, a polygonal grid, or a circular grid. In some configurations, a repeating pattern of sites may comprise one or more axes of symmetry. In other configurations, a repeating pattern of sites may comprise an asymmetric configuration (e.g., a trapezoid configuration, a scalene triangular configuration, etc.).

In some configurations, a solid support may comprise a plurality of sites, in which the plurality of sites comprises a non-repeating distribution of sites. A non-repeating distribution of sites may comprise a plurality of sites with no definable pattern or spatial arrangement. A non-repeating distribution of sites may comprise a plurality of sites with a disordered spatial arrangement. For example, a plurality of sites may be considered to have a disordered spatial arrangement if an average distance between centerpoints of two adjacent sites has a standard deviation that is at least about 10%, 20%, 30%, 40%, 50%, 60%, 70%, 80%, 90%, 100% or more than 100% of the average distance. A non-repeating distribution of sites may comprise a plurality of sites, in which an average distance between centerpoints of adjacent sites may be described by a statistical distribution, such as a Poisson distribution, a normal distribution, or a geometric distribution. In a particular configuration, an array may comprise a surface containing a uniform layer of coupling moieties, in which analytes are deposited randomly on the uniform layer of coupling moieties, and in which the average distance between adjacent analytes is controlled by a concentration of analytes contacted with the array.

In some configurations, a solid support, as set forth herein, may be configured to provide unbiased random deposition of fiducial elements at array sites on the solid support (i.e., each array site is equally probable to bind a fiducial element). In a particular configuration, each array site of a plurality of array sites may comprise a uniform surface chemistry that is configured to bind a fiducial element, in which each array site comprises an equal probability of binding a fiducial element. In other configurations, a solid support, as set forth herein, may be configured to provide a biased random deposition of fiducial elements at array sites on the solid support. In some particular configurations, a solid support may comprise a subset of array sites that are configured to couple a fiducial element, in which the subset of array sites comprise a spatial pattern that lacks a predictable spatial pattern. For example, an array may be patterned with a chosen subset of array sites that are provided a surface chemistry that is configured to only bind deposited fiducial elements. In other particular configurations, a solid support may comprise a plurality of array sites, in which each array site comprises a differing probability of binding a deposited fiducial element (e.g., due to non-uniformity in surface chemistry, due to manufacturing defects, etc.).

An array, such as a single-analyte array, may comprise a plurality of fiducial elements. A plurality of fiducial elements may be disposed on an array for various purposes, including at least one of: 1) landmarking an initial, intermediate, or final position on the array, 2) registering a region of overlapping data between physical data (e.g., image data) of a first region of the array and a second region of the array, and 3) providing a reference signal for a focusing device or focusing algorithm during an optical interrogation of the array. In some cases, a plurality of fiducial elements may be utilized for two or more of the aforementioned purposes during an array-based process or assay.

Design criteria for selecting materials and deposition methods for fiducial elements may depend upon the intended use of the fiducial elements. Design criteria may include one or more of: 1) required signal strength from fiducial elements; 2) required signal lifetime from fiducial elements; 3) maximum net loss of signal strength from fiducial elements over a timespan of a process, assay, or a step thereof 4) ease of deposition on an array; 5) chemical and/or structural stability of fiducial elements before, during, or after an array-based process or assay; 6) cost of fiducial elements or associated deposition methods; 7) inertness to one or more reagents that will be used during one or more assays or other processes carried out on an array, such that the one or more reagents are not modified by the fiducial elements; 8) ability to produce signals detected by hardware used to detect analytes at other sites in an array; 9) ability to produce signals that are distinct from signals produced from other sites in an array. For example, a fiducial element comprising a deposited layer of metal or metal oxide may provide a stable and sufficiently strong signal throughout an array-based process or assay, but may discourage or prohibit usage of any corrosive reagents during the process or assay. In another example, a fiducial element comprising deposited fluorescent nanoparticles may provide high fluorescent signal intensity and effective random dispersion across an array, but may experience random loss of nanoparticles from the array during the timespan of an array-based process or assay.

A fiducial element may be selected for display on an array, such as a single-analyte array, based upon the nature or characteristic of the fiducial element's interaction with electromagnetic radiation. In some configurations, a fiducial element may comprise an optically active moiety, in which the fiducial element does one or more of: 1) absorbing a photon of light, 2) emitting a photon of light, 3) transfer a photon of light from a first optically active moiety to a second optically active moiety; or 4) combinations thereof. For example, an optically active aromatic moiety may absorb a photon of impinging ultraviolet light, resulting in a detectable absence of a signal for transmission of the ultraviolet light. In another example, an optically active fluorescent moiety may be contacted with a photon of light of a first wavelength and subsequently emit a detectable photon of light of second wavelength. In another example, a first optically active photon transfer moiety may be contacted with a photon of light of a first wavelength, then transfer the photon or the energy thereof to a second optically active photon transfer moiety, thereby resulting in a detectable emission of a photon of light from the second optically active photon transfer moiety. An optically active moiety may characterized as absorbing light of a first wavelength and subsequently emitting light of a second wavelength, in which the first wavelength differs from the second wavelength. In other configurations, a fiducial element may comprise an optically passive moiety, for example, in which the fiducial element does one or more of: 1) reflecting a photon of light, 2) refracting a photon of light, 3) transmitting a photon of light, 4) scattering a photon of light, or 5) combinations thereof. For example, an array may comprise a reflective metal deposit that reflects a photon of light to a sensor that is configured to detect the photon of light. In another example, an array may be contacted with light of a particular wavelength, in which a solid support of the array is optically opaque to the particular wavelength but a fiducial region contains a material that is optically transparent to the wavelength of light. An optically passive moiety may be characterized as being contacted with light of a particular wavelength and returning a detectable amount of light of the particular wavelength. In some configurations, a fiducial element may comprise characteristics of an optically active moiety and an optically passive moiety. For example, a fluorescent moiety contacted with a light beam of a first wavelength may apparently return a signal comprising light of the first wavelength and light of a second, emitted wavelength if the light beam contains an excess amount of radiation relative to the radiant flux or radiant intensity of the fluorescent moiety.

An array, such as a single-analyte array, may comprise a plurality of fiducial elements, in which a fiducial element of the plurality of fiducial elements comprises an optically active moiety. In some configurations, an optically active moiety may comprise a light-emitting moiety, a light-absorbing moiety, a photon transfer pair, or a combination thereof. A light-emitting moiety may refer to any moiety that emits light of a detectable wavelength, such as a fluorophore or a luminophore. In some configuration, a light-emitting moiety may comprise a fluorophore that is selected from the group consisting of an organic nanoparticle, an inorganic nanoparticle, a fluorescently-labeled nucleic acid, a fluorescently-labeled polypeptide, and a combination thereof. In some configurations, an optically active moiety may comprise a photon transfer pair, in which the photon transfer pair comprises a Forster Resonant Energy Transfer (FRET) pair. FRET pairs are described in detail, for example in *The Molecular Probes Handbook* (Thermo-Fisher Scientific) and Bajar, et. al., "A Guide to Fluorescent Protein FRET Pairs," Sensors, 16, 1488, 2016, each of which is hereby incorporated by reference in its entirety.

In some configurations, a fiducial element may comprise two or more optically active moieties or optically passive moieties, in which each moiety of the two or more optically active moieties or optically passive moieties provide a detectable signal that can be distinguished (e.g., by emission wavelength, by transmission wavelength, by polarization angle, etc.) from each other moiety of the two or more optically active moieties or optically passive moieties. For example, an array site may comprise a fiducial element comprising a first fluorescently-labeled polymer nanoparticle and a second fluorescently-labeled polymer nanoparticle, in which the first fluorescently-labeled polymer nanoparticle comprises a first fluorophore with a first emission wavelength, and the second fluorescently-labeled polymer nanoparticle comprises a second fluorophore with a second emission wavelength, and in which the first emission wavelength differs from the second emission wavelength. In another example, an array site may comprise a fiducial element comprising a fluorescently-labeled polymer nanoparticle and a fluorescent nanoparticle (e.g., a quantum dot), in which the fluorescently-labeled polymer nanoparticle comprises a fluorophore with a first emission wavelength, and the fluorescent nanoparticle comprises a second emission wavelength, and in which the first emission wavelength differs from the second emission wavelength. In some configurations, a fiducial element may comprise a single moiety that is configured to produce a first detectable signal and a second detectable signal, in which the first detectable signal is distinguishable from the second detectable signal. For example, a fluorescently-labeled polymer nanoparticle may comprise a first fluorophore and a second fluorophore, in which the first fluorophore comprises a first emission wavelength and the second fluorophore comprises a second emission wavelength, and in which the first emission wavelength differs from the second emission wavelength. In another example, a fiducial element may comprise a fluorescent nanoparticle (e.g., a fluorescent nanodiamond such as an Adamas Nano Functionalized Multicolor Fluorescent Nanodiamond) that comprises two or more unique emission wavelengths. In some configurations, an array site may comprise a fiducial element that is configured to provide a first detectable signal and a second detectable signal, in which the first detectable signal is distinguishable from the second detectable signal. Such a configuration may be advantageous for applications such as calibration of excitation light sources and calibration of sensors in multi-sensor systems.

An optically active moiety, such as a fluorophore or a light-absorbing molecule, may be configured to absorb a photon of light with a characteristic wavelength. An optically active moiety may be configured to absorb a photon of light that has a wavelength of at least about 1 nanometer (nm), 10 nm, 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 900 nm, 1000 nm, 2000 nm, 3000 nm, 4000 nm, 5000 nm, 10000 nm, or more than 10000 nm. Alternatively or additionally, an optically active moiety may be configured to absorb a photon of light that has a wavelength of no more than about 10000 nm, 5000 nm, 4000 nm, 3000 nm, 2000 nm, 1000 nm, 900 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 50 nm, 10 nm, 1 nm or less than 1 nm.

An optically active moiety, such as a fluorophore or a light-absorbing molecule, may be configured to emit a photon of light with a characteristic wavelength. An optically active moiety may be configured to emit a photon of light that has a wavelength of at least about 1 nanometer (nm), 10 nm, 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 900 nm, 1000 nm, 2000 nm, 3000 nm, 4000 nm, 5000 nm, 10000 nm, or more than 10000 nm. Alternatively or additionally, an optically active moiety may be configured to emit a photon of light that has a wavelength of no more than about 10000 nm, 5000 nm, 4000 nm, 3000 nm, 2000 nm, 1000 nm, 900 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 50 nm, 10 nm, 1 nm or less than 1 nm.

A fiducial element or a component thereof (e.g., an optically active moiety, an optically passive moiety, an anchoring moiety, etc.) may be configured to have a characteristic dimension (e.g., length, width, height, diameter, circumference, etc.) that is larger, smaller, or of substantially the same dimension as a site of an array to which the fiducial element is coupled. A characteristic dimension of a fiducial element may be selected based upon one or more criteria, such as signal strength, availability of particular sizes (e.g., for manufactured particles, etc.), and chemical properties (e.g, solubility as a function of size). For example, fiducial elements comprising fluorescent nanoparticles with high signal strength may be chosen to have a diameter that is less than a diameter of an array site to minimize the likelihood of signal from the fiducial element being detected at a neighboring site. In another example, a fiducial element comprising a deposited metal layer may have a characteristic dimension that is larger than that of an array site due to limitations on minimum feature size during a lithographic deposition process. In some configurations, an optically active moiety may comprise a characteristic dimension that is smaller than a characteristic dimension of a site to which the optically active moiety is coupled. In other configurations, an optically active moiety may comprise a largest characteristic dimension that is greater than or equal to a largest characteristic dimension of a site to which the optically active moiety is coupled.

In some configurations, a largest dimension of a fiducial element or a component thereof (e.g., an optically active moiety, an optically passive moiety, an anchoring moiety, etc.) of a plurality of fiducial elements may be smaller than a largest dimension of a site at which the fiducial element is coupled. In other configurations, a largest dimension of a fiducial element or a component thereof of the plurality of fiducial elements may be larger than a largest dimension of a site at which the fiducial element is coupled. A largest dimension of a site, a fiducial element or a component thereof may comprise a length, a width, a height, a circumference, an arc length, or a diameter. In a particular configuration of a fiducial element with a largest dimension that is larger than a largest dimension of a site at which the fiducial element is coupled, the fiducial element may be coupled to two or more sites. For example, a fiducial element comprising a deposited metal layer may be deposited over two or more sites of an array. In another particular configuration of a fiducial element with a largest dimension that is larger than a largest dimension of a site at which the fiducial element is coupled, the fiducial element may be coupled to a first site and occupy, obstruct, or hinder access to a second site of an array. For example, a fluorescent microbead may be coupled to an array site and have a large enough diameter to sterically hinder an ability for other moieties to bind to one or more adjacent sites.

A fiducial element may have a characteristic dimension (e.g., length, width, height, diameter, circumference), such as an average dimension, a minimum dimension, or a maximum dimension. A fiducial element may have a characteristic dimension of at least about 10 nanometers (nm), 50 nm, 100 nm, 150 nm, 200 nm, 250 nm, 300 nm, 400 nm, 500 nm, 600 nm, 700 nm, 800 nm, 900 nm, 1000 nm, 1500 nm, 2000 nm, 3000 nm, 4000 nm, 5000 nm, 10000 nm, or more than 10000 nm. Alternatively or additionally, a fiducial element may have a characteristic dimension of no more than about 10000 nm, 5000 nm, 4000 nm, 3000 nm, 2000 nm, 1500 nm, 1000 nm, 900 nm, 800 nm, 700 nm, 600 nm, 500 nm, 400 nm, 300 nm, 250 nm, 200 nm, 150 nm, 100 nm, 50 nm, 10 nm, or less than 10 nm.

A single fiducial element may be coupled to no more than one site of a plurality of sites. A single fiducial element may be coupled to two or more sites of a plurality of sites. A single fiducial element of a plurality of fiducial elements may be coupled to at least about 1, 2, 3, 4, 5, 10, 15, 20, 25, 30, 35, 40, 50, 75, 100, or more than 100 sites. Alternatively or additionally, a single fiducial element may be coupled to no more than about 100, 75, 50, 40, 35, 30, 25, 20, 15, 10, 5, 4, 3, 2, or less than 2 sites.

A fiducial element (e.g., containing an optically active moiety, containing an optically passive moiety) may be coupled to a site of an array. In some configurations, a fiducial element may be coupled directly to a site on a solid support of an array. For example, a metal fiducial element may be formed by deposition (e.g., vapor-phase deposition, liquid-phase deposition) of the metal onto a region of a solid support, thereby forming the metal fiducial element directly on the solid support. In other configurations, a fiducial element may be coupled to a solid support by an anchoring moiety. An anchoring moiety may be characterized by one or more, two or more, three or more, four or more, five or more, or six or more of the characteristics of: 1) comprising a surface or a coupling moiety that is configured to couple to a site of an array; 2) comprising a complementary coupling moiety that is configured to couple to a coupling moiety of a site of an array; 3) comprising an attachment moiety that is configured to couple an analyte to the anchoring moiety; 4) not forming a coupling interaction with an interstitial region of an array; 5) inhibiting contact between an analyte and a site of the array or an interstitial region of the array; 6) orienting an analyte at an array site for an array-based process or assay; 7) inhibiting a deposition of a second anchoring moiety at the site of the array; 8) inhibiting a coupling of an unbound moiety at the site of the array.

A fiducial element (e.g., containing an optically active moiety, containing an optically passive moiety) may be coupled to a site of an array by an anchoring moiety, in which the anchoring moiety comprises a nucleic acid or a nanoparticle. In some configurations, an anchoring moiety may comprise a single-stranded nucleic acid. For example, an anchoring moiety may comprise an oligonucleotide that contains a complementary base pair sequence to an oligonucleotide coupling moiety that is coupled to a site of an array. In another example, a nucleic acid origami may comprise a pendant single-stranded oligonucleotide that contains a complementary base pair sequence to an oligonucleotide coupling moiety that is coupled to a site of an array. In some configurations, an anchoring moiety may comprise a structured nucleic acid particle (SNAP), such as a nucleic acid nanoball or a nucleic acid origami.

A fiducial element (e.g., containing an optically active moiety, containing an optically passive moiety) may be coupled to an anchoring moiety, in which the anchoring moiety comprises a complementary moiety that is configured to form a coupling interaction with a coupling moiety that is attached to a site of an array. In some configurations, an anchoring moiety may be coupled to a site of an array by a covalent interaction. In other configurations, an anchoring moiety may be coupled to a site of an array by a non-covalent interaction.

A fiducial element (e.g., containing an optically active moiety, containing an optically passive moiety) may be coupled to an anchoring moiety, in which the anchoring moiety comprises an attachment moiety that is configured to form a coupling interaction with a analyte. In some configurations, an anchoring moiety may be coupled to an analyte by a covalent interaction. In other configurations, an anchoring moiety may be coupled to analyte by a non-covalent interaction.

A fiducial element (e.g., containing an optically active moiety, containing an optically passive moiety) may be coupled to a site of an array without an anchoring moiety. For example, a fiducial element may be directly conjugated to a coupling moiety that is coupled to the site. In another example, a fiducial element comprising a coupled oligonucleotide may be hybridized to an oligonucleotide coupling moiety that is attached to the array site, in which the oligonucleotide contains a sequence that is complementary to a sequence of the nucleic acid analyte. In some configurations, an anchoring moiety may be coupled to a fiducial element by a covalent interaction. In other configurations, an anchoring moiety may be coupled to a fiducial element by a non-covalent interaction.

A fiducial element (e.g., containing an optically passive moiety, containing an optically active moiety) may comprise one or more layers or coatings. A fiducial element may comprise one or more layers or coatings, in which a first layer or coating and a second layer or coating contain a different material or moiety. A fiducial element may comprise one or more layers or coatings, in which a first layer or coating comprises a first organic material (e.g., a polymer, a biomolecule, etc.) and a second layer or coating comprises a second organic material. A fiducial element may comprise one or more layers or coatings, in which a first layer or coating comprises a first inorganic material and a second layer or coating comprises a second inorganic material. For example, a fiducial element may comprise a layered stack of two or more dielectric materials. A fiducial element may comprise one or more layers or coatings, in which a first layer or coating comprises an inorganic material and a second layer or coating comprises an organic material. For example, a metal fiducial layer with a planar surface may further comprise a layer of organic molecules (e.g., coupling moieties, passivating moieties) coupled to the planar surface. In some cases, a fiducial element may comprise a first layer or coating and a second layer or coating, in which the first layer or coating comprises an optically passive moiety and the second layer or coating comprises an optically active moiety. In some cases, a fiducial element may comprise a first layer or coating and a second layer or coating, in which the first layer or coating comprises an optically passive moiety and the second layer or coating comprises an optically passive moiety. In some cases, a fiducial element may comprise a first layer or coating and a second layer or coating, in which the first layer or coating comprises an optically active moiety and the second layer or coating comprises an optically active moiety.

A fiducial element may comprise an optically passive moiety. In some configurations, an optically passive moiety may comprise a particle that is deposited on an array (e.g., an organic or inorganic nanoparticle, an organic or inorganic microparticle). An optically passive moiety comprising a particle may be deposited on an array, for example, by deposition from a liquid-phase onto a surface of a solid support. In other configurations, an optically passive moiety may comprise a layer or coating that is formed or deposited on an array or a site thereof. In particular configurations, a fiducial element containing an optically passive moiety may comprise a topographical feature of the solid support, such as a raised feature (e.g., a post, platform, pillar, tube, table, etc.) or an indented feature (e.g., a well, a depression, a channel, a pore, etc.). A raised feature may be formed by any suitable method, including lithographic forming of a solid support, deposition of a material on the solid support, lithographic forming of the material deposited on the solid support, and combinations thereof. For example, a topographical feature comprising a pillar may be formed by depositing or forming a metal oxide layer on a solid support surface, then lithographically etching a pillar shape from the material by use of a photomasking technique. In another example, a topographical feature comprising a pillar may be formed by depositing a metal oxide layer on a solid support surface, then lithographically etching a pillar shape from the material and the solid support material by use of a photomasking technique. In some configurations, a topographical features may comprise a contrast-enhancing feature, in which a morphological structure of the topographical feature enhances detection of the topographical feature during an optical interrogation. In particular configurations, a topographical feature may comprise a contrast-enhancing feature comprising a sharp, acute, or non-diffuse edge between a fiducial element and a solid support. For example, a fiducial element on a silicon solid support may be formed directly from a silicon surface by lithographically forming a silicon pillar with a substantially horizontal planar face and a substantially vertical side face, in which the planar face intersects the side face at nearly a 90° angle.

FIGS. 11A and 11B show examples of contrast-enhancing features with differing morphologies. FIG. 11A depicts fiducial elements comprising raised features with planar top surfaces 1110 (e.g., deposited metals or metal oxides, lithographically formed glass or silicon, etc.). The first fiducial element 1101 and the second fiducial element 1102 have a thickness, t, that is the same for both fiducial elements. The first fiducial element 1101 and the second fiducial element 1102 each comprise a substantially horizontal top surface 1110 and a substantially vertical side surface 1115, with a transition between the top surface 1110 and the side surface 1115 having a radius of curvature. The radius of curvature $r_{d1}$ for the first fiducial element 1101 is smaller than the radius of curvature $r_{c2}$ for the second fiducial element 1102. Based upon the more abrupt transition between the top surface and the side surface of the first fiducial element 1101, the first fiducial element may have a greater optical contrast as determined by a field of reflected light. FIG. 11B depicts fiducial elements comprising raised features with planar top surfaces 1110 (e.g., deposited metals or metal oxides, lithographically formed glass or silicon, etc.). The first fiducial element 1103 and the second fiducial element 1104 have a thickness, t, that is the same for both fiducial elements. The first fiducial element 1103 and the second fiducial element 1104 each comprise a substantially horizontal top surface 1110 and an inclined side surface 1116, with a transition between the top surface 1110 and the side surface 1116 having an angle of intersection. The angle of intersection, $\theta_1$, for the first fiducial element 1103 is smaller than the radius of curvature, $\theta_2$, for the second fiducial element 1104. Based upon the more abrupt transition between the top surface and the side surface of the first fiducial element 1103, the first fiducial element may have a greater optical contrast as determined by a field of reflected light. In some configurations, an angle of intersection may be an obtuse, right, or acute angle. A right angle or an acute angle may produce a greater optical contrast than an obtuse angle on a contrast-enhancing feature.

In an advantageous configuration of an array, such as a single-analyte array, an array may comprise a plurality of fiducial elements, in which the plurality of fiducial elements comprises a first fiducial element and a second fiducial element, and in which the first fiducial element comprises an optically active moiety and the second fiducial element comprises an optically passive moiety. In some configurations, a plurality of fiducial elements may comprise a first subset of sites and a second subset of sites, wherein each site of the first subset of sites comprises an optically active moiety, and in which each site of the second subset of sites comprises an optically passive moiety. In particular configurations, a first subset of sites comprising optically active moieties may be distributed to a non-repeating pattern of sites on the solid support. In other particular configurations, a first subset of sites comprising optically active moieties may be distributed to a repeating pattern of sites on the solid support. In particular configurations, a second subset of sites comprising optically passive moieties may be distributed to a non-repeating pattern of sites on the solid support. In other particular configurations, a second subset of sites comprising optically passive moieties may be distributed to a repeating pattern of sites on the solid support. An array may be provided with a first plurality of optically active moieties and a second plurality of optically passive moieties, in which the first plurality and the second plurality comprise a fixed ratio. An array may comprise a ratio of optically active moieties to optically passive moieties of at least about 0.001:1, 0.01:1, 0.1:1, 1:1, 2:1, 5:1, 10:1, 50:1, 100:1, 500:1, 1000:1, 10000:1, 100000:1, 1000000:1, 100000000:1, 100000000:1, 1000000000:1, or more than 1000000000:1. Alternatively or additionally, an array may comprise a ratio of optically active moieties to optically passive moieties of no more than about 1000000000:1, 100000000:1, 10000000:1, 1000000:1, 100000:1, 10000:1, 1000:1, 500:1, 100:1, 50:1, 10:1, 5:1, 2:1, 1:1, 0.1:1, 0.01:1, 0.001:1, or less than 0.001:1. In some configurations, an array may comprise a landmarking region, in which a second fiducial element comprising an optically passive moiety is coupled to the landmarking region, and in which a first fiducial element comprising an optically active moiety is coupled to a region of the array other than the landmarking region.

A fiducial element of a plurality of fiducial elements may be configured to produce a detectable signal, such as emitted radiation, reflected radiation, scattered radiation, transmitted radiation, or an absence of one or more of the foregoing. A fiducial element or a component thereof may be selected, in part, based upon an average, threshold or peak magnitude of signal produced by the fiducial element. In some configurations (e.g., high-density single-analyte arrays), it may be advantageous to include a fiducial element that occupies only a single array site and produces a signal that does not produce cross-talk at neighboring sites. In other configurations (e.g., systems prone to photobleaching or photodamage), it may be advantageous to include a fiducial element that has an initially high signal magnitude to extend the lifetime of a detectable signal from the fiducial element. In some configurations, a fiducial element may be configured to produce a detectable signal, wherein the detectable signal is spatially resolvable to an area that is less than or equal to an area of a site. In other configurations, a fiducial element may be configured to produce a detectable signal, wherein the detectable signal is spatially resolvable to an area that is greater than an area of a site.

A fiducial element, such as an optically active moiety, may comprise a multi-spectral moiety, such as a multi-spectral nanoparticle. A multi-spectral moiety can refer to a molecule, particle, or moiety that produces two or more distinguishable detectable optical signals. Two or more optical signals may be distinguished by excitation wavelength, emission wavelength, or fluorescence or luminescence lifetime. A multi-spectral moiety may comprise two or more differing detectable labels. A multi-spectral moiety may comprise a first detectable label that produces a first detectable signal at a first emission wavelength, and a second detectable label that produces a second detectable signal at a second emission wavelength, in which the first emission wavelengthd differs from the second emission wavelength. A multi-spectral moiety may comprise a first detectable label that produces a first detectable signal when contacted with light of a first excitation wavelength, and a second detectable label that produces a second detectable signal when contacted with light of a second excitation wavelength, in which the first excitation wavelength differs from the second excitation wavelength. A first emission or excitation wavelength for a first detectable label of a multi-spectral moiety may differ from a second emission or excitation wavelength for a second detectable label of the multi-spectral moiety by at least about 10 nanometers (nm), 25 nm, 50 nm, 100 nm, 150 nm, 200 nm, 250 nm, 300 nm, or more than 300 nm. Alternatively or additionally, a first emission or excitation wavelength for a first detectable label of a multi-spectral moiety may differ from a second emission or excitation wavelength for a second detectable label of the multi-spectral moiety by no more than about 300 nm, 250 nm, 200 nm, 150 nm, 100 nm, 50 nm, 25 nm, 10 nm, or less than 10 nm. An example of a multi-spectral moiety is the ThermoFisher TetraSpeck™ microspheres, which fluorescently emit at 430 nm, 515 nm, 580 nm, and 680 nm wavelengths.

For particular applications of arrays, such as single-analyte assays of biomolecular arrays, it may be advantageous to further include a mapping moiety, in which the mapping moiety establishes a spatial address of each site of a plurality of sites on an array. For example, minor variations during manufacturing of an array may produce one or more sites of a plurality of sites that are located out of position relative to an expected position for a grid of sites. In another example, defects during manufacturing of an array may produce an absence of a site where a site should be located. In another example, mapping moieties may be utilized to identify an address of a site on an array with a non-repeating pattern of sites (e.g., an unstructured or unpatterned array). Additionally or alternatively, a mapping moiety may be utilized to establish an occupancy of a site by an analyte before, during, or after an array-based process or assay. For example, a fluorescently-labeled analyte may be deposited to identify both an address of a site comprising the fluorescently-labeled analyte and presence of the fluorescently-labeled analyte at the site. A mapping moiety may comprise an optically active moiety, an optically passive moiety, or a combination thereof.

A mapping moiety may be utilized at one or more times during an array-based process or assay to identify an address of a site on an array. A mapping moiety may be utilized for at least one, two, three, four, five or more purposes selected from: 1) identifying an address of a site on an array before an array process or assay; 2) identifying an address of a site on an array during an array process or assay; 3) identifying an address of a site on an array after an array process or assay; 4) determining an occupancy by an analyte of a site on an array before an array process or assay; 5) determining an occupancy by an analyte of a site on an array during an array process or assay; and 6) determining an occupancy by an analyte of a site on an array after an array process or assay.

A mapping moiety may be selected based upon its intended use during an array-based process or assay. A mapping moiety may be selected based upon a minimum, average, or maximum detectability lifetime. A detectability lifetime may be determined as a time length (e.g., minutes, hours, days, years, etc.) that a mapping moiety is detectable under process or assay conditions. Alternatively, a detectability lifetime may be determined as a number of process or assay steps or cycles that a mapping moiety is detectable. A mapping moiety may have a detectability lifetime of at least 1 second, 1 minute (min), 15 mins, 30 mins, 1 hour (hr), 3 hrs, 6 hrs, 12 hrs, 1 day, 1 week, 1 month, 1 year, or more than 1 year. Alternatively or additionally, a mapping moiety may have a detectability lifetime of no more than 1 year, 1 month, 1 week, 1 day, 12 hrs, 6 hrs, 3 hrs, 1 hr, 30 mins, 15 mins, 1 min, 1 second, or less than 1 second. A mapping moiety may have a detectability lifetime of at least 1, 5, 10, 20, 50, 75, 100, 200, 300, 500, 1000, 5000, 10000, or more than 10000 process or assay steps or cycles. Alternatively or additionally, a mapping moiety may have a detectability lifetime of no more than 10000, 5000, 1000, 500, 300, 200, 100, 75, 50, 20, 10, 5, 1, or less than 1 process or assay step or cycle. A mapping moiety may be configured to have an intended obsolescence. For example, fluorophore mapping moieties may be coupled to a site of an array with an expectation that the fluorophores will eventually become undetectable due to photobleaching. A mapping moiety may be configured to not have an intended obsolescence.

In some configurations, a mapping moiety may be configured to be permanently coupled to a site of an array. For example, a mapping moiety may comprise a complementary coupling moiety that is configured to form a covalent bond with a coupling moiety at a site of an array. In other configurations, a mapping moiety may be configured to be removed from a site of an array. For example, a mapping moiety may be configured to bind to a nucleic acid coupling moiety of a site of an array, in which the mapping moiety can be removed via denaturation of nucleic acid base pairing or a restriction enzyme assay. In some configurations, a mapping moiety may be coupled to a site of an array by a covalent interaction. In other configurations, a mapping moiety may be coupled to a site by a non-covalent interaction. In some configurations, each site of a plurality of sites of an array may comprise a mapping moiety. In some configurations, an interstitial region of one or more interstitial regions of an array may comprise no mapping moieties.

In an advantageous configuration of a single-analyte array, the single-analyte array may comprise a solid support containing a patterned grid of sites and one or more interstitial regions separating each site of the patterned grid of sites from each other site of the patterned grid of sites, in which each site of the patterned grid of sites comprises a coupling moiety and a mapping moiety. In a particular configuration of the single-analyte array, a mapping moiety is coupled directly to a site of the patterned grid of sites by an interaction with the solid support. In another particular configuration of the single-analyte array, a mapping moiety is coupled to a coupling moiety of a site of the patterned grid of sites. In another particular configuration of the single-analyte array, an anchoring moiety is coupled to a coupling moiety of a site of the single-analyte array, in which the anchoring moiety comprises a mapping moiety. In some particular configurations, an analyte is coupled to an anchoring moiety comprising a mapping moiety. In some configurations, a single-analyte array comprises a plurality of sites, in which each site comprises an anchoring moiety, in which each anchoring moiety comprises a mapping moiety, and in which each anchoring moiety is coupled to an analyte. In some configurations, a single-analyte array comprises a plurality of sites, in which each site comprises an anchoring moiety, in which each anchoring moiety comprises a mapping moiety, and in which each anchoring moiety is not coupled to an analyte. In particular configurations, a single-analyte array comprising a plurality of anchoring moieties not coupled to analytes may be subsequently contacted with a plurality of analytes, thereby coupling an analyte to each anchoring moiety of the plurality of anchoring moieties.

An array, such as a single-analyte array, may comprise a plurality of fiducial elements, in which the plurality of fiducial elements is distributed at sites of the array in a random spatial distribution. A spatial distribution of a plurality of fiducial elements at sites of an array may be considered random if the spatial distribution satisfies one or more criteria selected from: i) lacking a repeating pattern of site occupancy (e.g., 1 fiducial element coupled to a site at an exact interval of once per every 100 sites), ii) for any two random sites of a plurality of sites on an array, each site of the two possessing an equal probability of containing a coupled fiducial element, in which the probability, p, is in a range of 0%<p<100%, iii) for any site containing a coupled fiducial element, possessing a non-zero probability of having 0 sites containing a fiducial element within a radius of r, in which r>$r_o$, and in which $r_o$ is an average separation distance between array sites, iv) for any two randomly selected sites containing a coupled fiducial element, each having an average separation radius $r_{N,avg}$ for N nearest sites containing a fiducial element (e.g., 5 nearest sites to a fiducial-containing sites having an average separation radius, $r_{5,avg}$ of 450 nanometers), in which there is a non-zero-probability of $r_{N,avg}$ differing for the two randomly selected sites, v) for an array of M total sites, in which the array contains F total coupled fiducial elements (i.e., averaging 1 fiducial element per M/F sites), possessing a non-zero probability of having 0 sites containing a coupled fiducial element in a random sample of M/F sites; and vi) for an array of M total sites, in which the array contains F total coupled fiducial elements (i.e., averaging 1 fiducial element per M/F sites), possessing a non-zero probability of having 2 or more sites containing a coupled fiducial element in a random sample of M/F sites.

An array, such as a single-analyte array, may comprise a plurality of fiducial elements, in which the plurality of fiducial elements is distributed at sites of the array in a random spatial distribution, in which the random spatial distribution may be defined by a measure of randomness. A measure of randomness may comprise any suitable statistical, mathematical, or otherwise empirical measure that provides a quantitative characterization of a spatial distribution of fiducial elements on an array. In some configurations, a measure of randomness may be described by a probability distribution or a probability density function. In some configurations, a measure of randomness may comprise a parameter of a probability distribution or a probability density function (e.g., mean, median, standard deviation, variance, etc.). For example, when characterizing a spatial distribution of a plurality of fiducial elements, the average distance between a site comprising a fiducial element and a nearest site containing a coupled fiducial element may be described by a normal distribution, in which a measure of randomness for the spatial distribution comprises a parameter of the normal distribution (e.g., mean, standard deviation, coefficient of variation). In some configurations, a measure of randomness may comprise absence of a repeating pattern of spatial addresses for sites in the array.

In some cases, a measure of randomness of a spatial distribution of a plurality of fiducial elements on an array may comprise a measurement of a distance between a first fiducial element and a second fiducial element, in which the second fiducial element comprises a nearest fiducial element to the first fiducial element. For example, obtaining a measure of randomness may comprise compiling measurements of distances between a first fiducial element and each neighboring fiducial element to the first fiducial element for each fiducial element on an array, then determining a statistical distribution (e.g., Poisson distribution, normal distribution, etc.) from the compiled measurement data. In some cases, a measure of randomness of a spatial distribution of a plurality of fiducial elements on an array may comprise a likelihood of a first fiducial element and a second fiducial element being separated by a separation distance, in which the second fiducial element comprises a nearest fiducial element to the first fiducial element. In some cases, a measure of randomness of a spatial distribution of a plurality of fiducial elements on an array may comprise a measurement of a quantity of fiducial elements N within a subset of the plurality of sites containing a first fiducial element, in which the subset of the plurality of sites comprises M sites. For example, for an array with 10 fiducial elements distributed over 1000 array sites, it may be possible to identify a 10×10 cluster of array sites with 3 fiducial elements, and a 10×10 cluster of array sites with no fiducial elements if the fiducial elements have a random spatial distribution. In some cases, a measure of randomness of a spatial distribution of a plurality of fiducial elements on an array may comprise a likelihood of detecting N fiducial elements within a subset of the plurality of sites containing a first fiducial element, in which the subset of the plurality of sites comprises M sites. For example, for an array with 10 fiducial elements distributed over 1000 array sites, there may be possible a non-zero probability of identifying a 10×10 cluster of array sites with 3 fiducial elements, and a non-zero probability of identifying a 10×10 cluster of array sites with no fiducial elements if the fiducial elements have a random spatial distribution. In particular configurations, a subset of M sites for determining a measure of randomness may be contiguous (i.e., each site of the M sites having at least one neighbor site of the M sites). In other particular configurations, a subset of M sites for determining a measure of randomness may be non-contiguous.

Figure 12A:
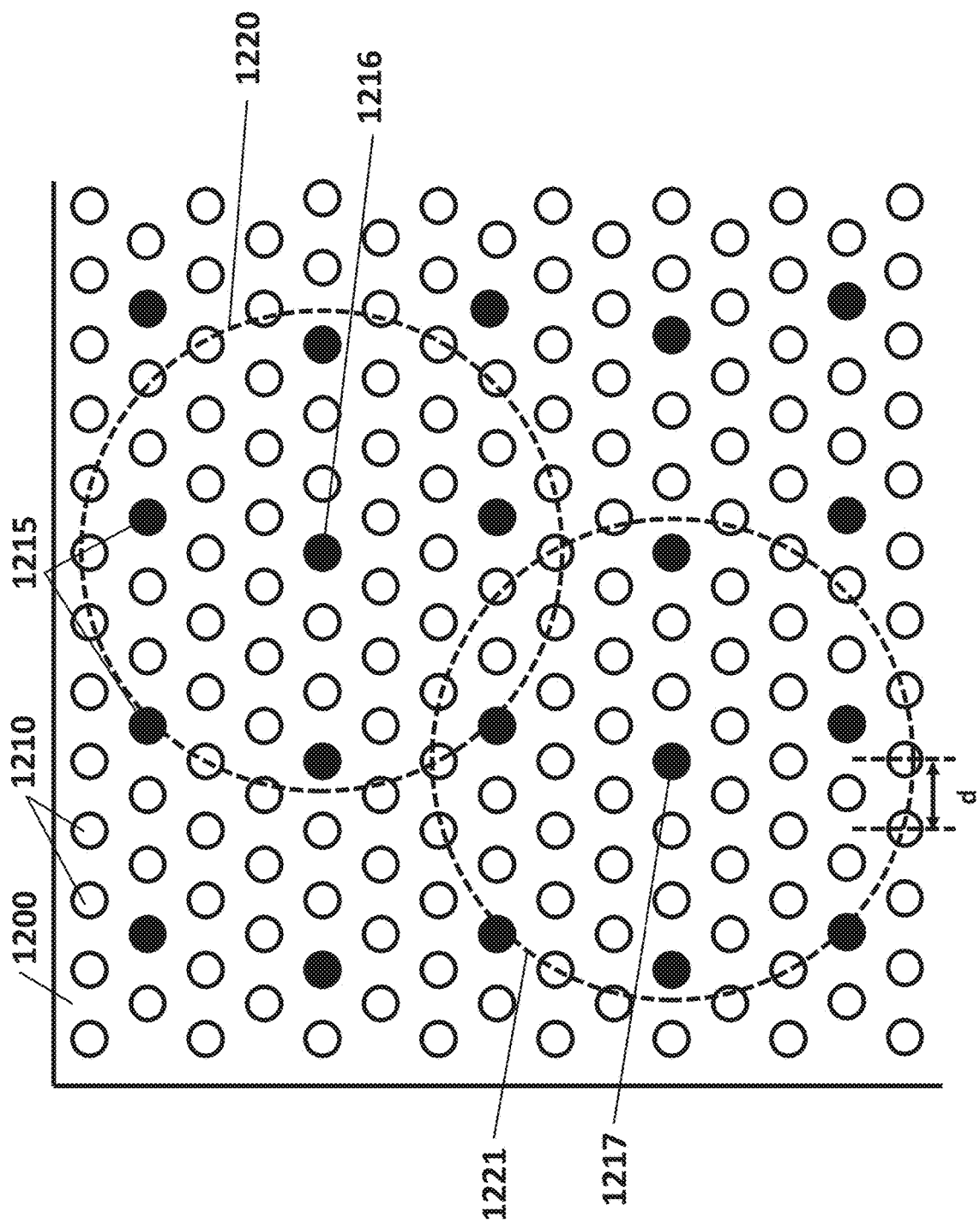
Figure 12B:
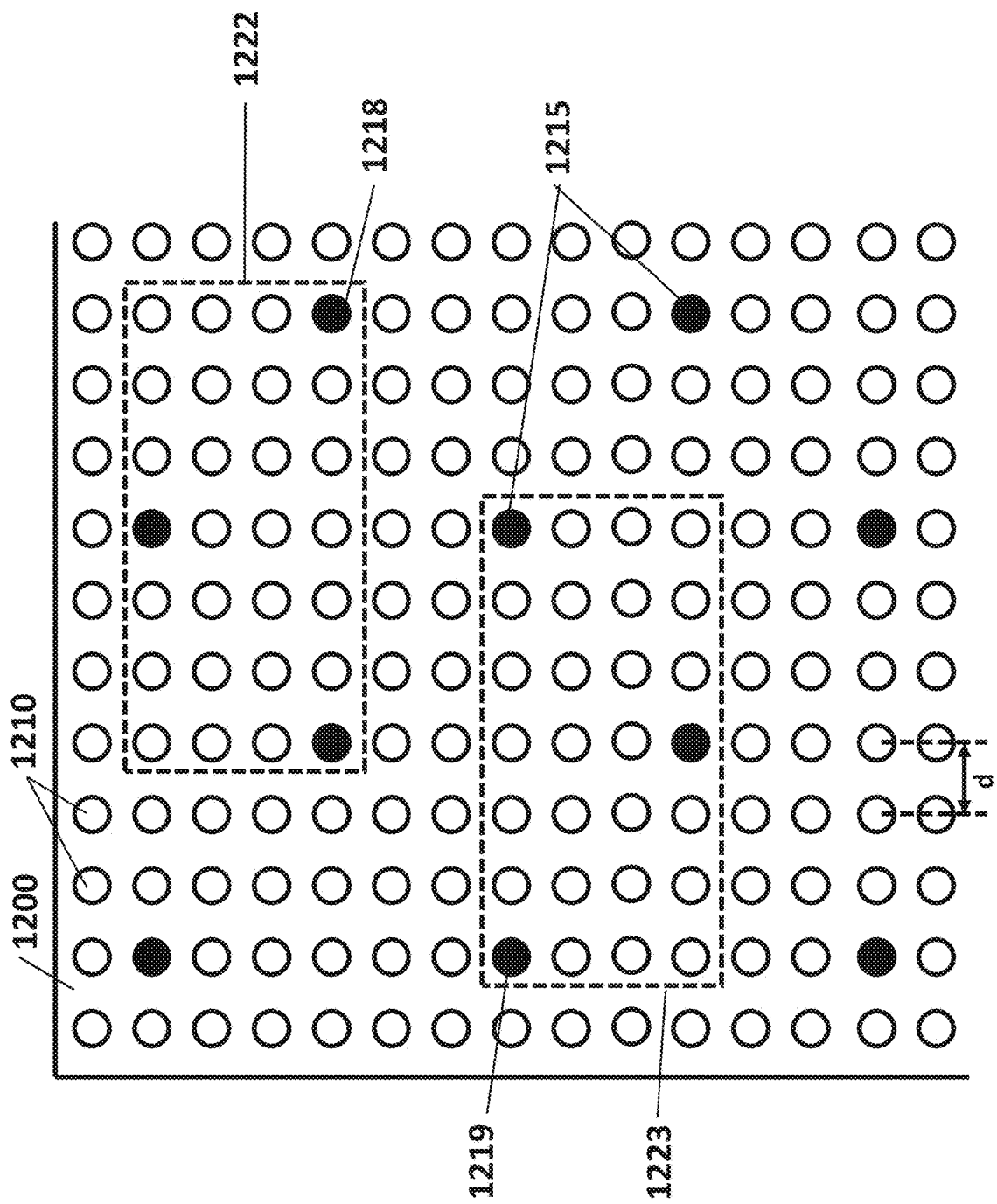

For an array with randomly deposited fiducial elements, it will be expected that no regular or repeating pattern of fiducial elements will occur over a sufficiently large number of sites. Rather, fiducial elements will form various arrangements at sites of an array that vary from one region of the array to another region. Arrangements of fiducial elements could include clusters of fiducial elements (i.e., groupings of fiducial-containing array sites with a site occupancy rate that exceeds the average site occupancy rate for the entire array) or voids of fiducial elements (i.e., groupings of sites that do not contain a fiducial element with a site occupancy rate that is less than the average site occupancy rate for the entire array). FIGS. 12A-12F demonstrate aspects associated with pattern characterization in arrays, as set forth herein. FIGS. 12A-12B depict arrays with regular or uniform patterns of occupied sites, in which each occupied site contains a moiety (e.g., a fiducial element). FIG. 12A depicts a solid support 1200 containing a plurality of sites 1210 arranged in a hexagonal grid pattern, including a subset 1215 of the plurality of sites 1210, in which each site of the subset 1215 of the plurality of sites 1210 comprises a fiducial element. The subset 1215 of the plurality of sites 1210 has a regular, predictable pattern of occupancy, in which a row with occupied sites has one occupied site exactly every three sites, and each occupied row is separated by two entirely unoccupied rows of sites. Occupied sites 1216 and 1217 are depicted as centerpoints of circles 1220 and 1221, in which circles 1220 and 1221 each have a radius of about 3d, in which d is the average separation distance between neighboring sites. Circles 1220 and 1221 each contain all or a portion of 7 occupied sites, including centerpoints 1216 and 1217. FIG. 12B depicts a solid support 1200 containing a plurality of sites 1210 arranged in a rectangular grid pattern, including a subset 1215 of the plurality of sites 1210, in which each site of the subset 1215 of the plurality of sites 1210 comprises a fiducial element. The subset 1215 of the plurality of sites 1210 has a regular, predictable pattern of occupancy, in which a row with occupied sites has one occupied site exactly every six sites, and each occupied row is separated by two entirely unoccupied rows of sites. Occupied sites 1218 and 1219 are depicted as cornerpoints of rectangles 1222 and 1223, in which rectangles 1222 and 1223 each have an aspect of about 7d by 3d, in which d is the average separation distance between neighboring sites. Rectangles 1222 and 1223 each contain 3 occupied sites, including centerpoints 1218 and 1219.

Figure 12C:
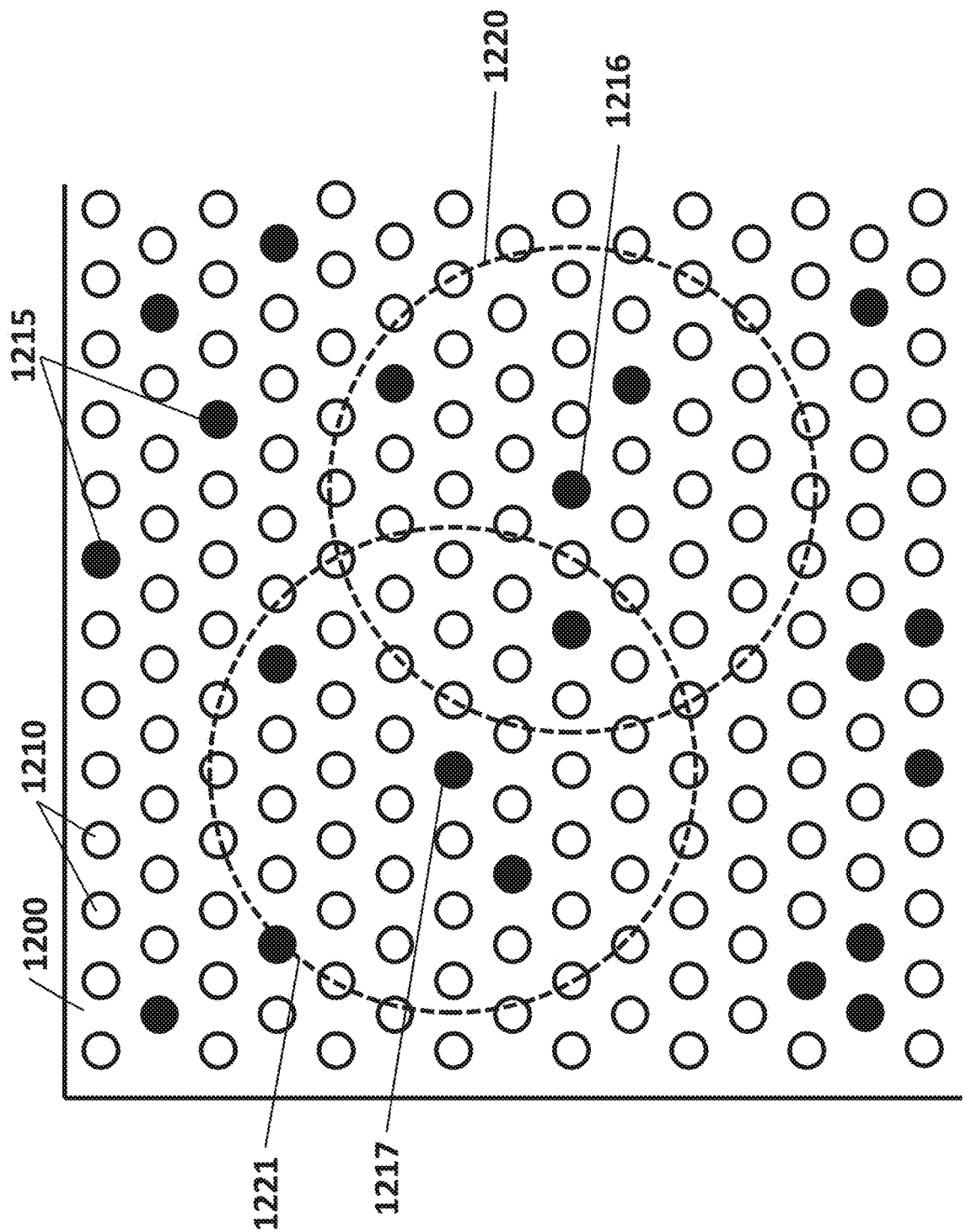
Figure 12D:
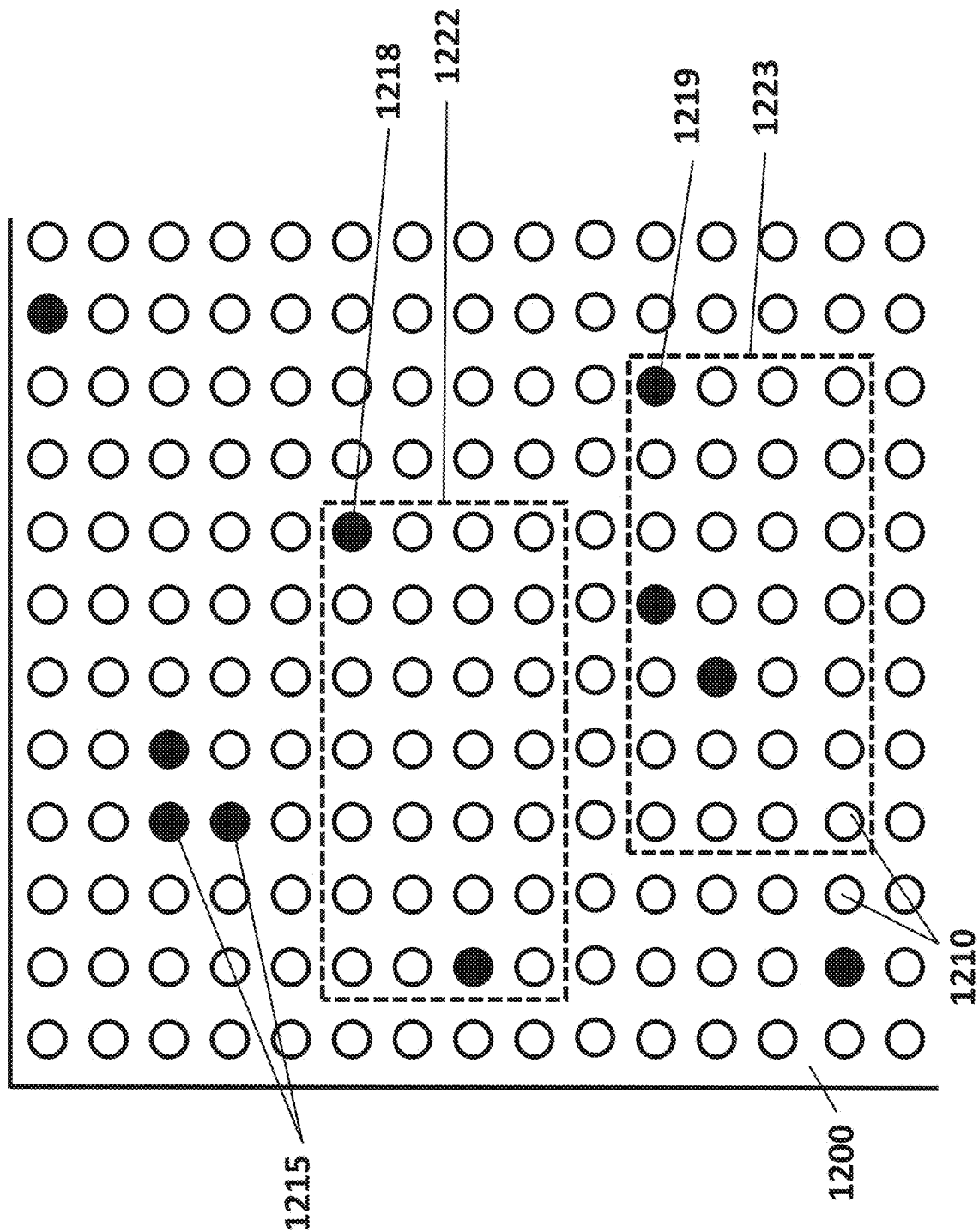

FIGS. 12C-12E illustrate arrays with random spatial distributions of occupied sites, in which each occupied site contains a moiety (e.g., a fiducial element). FIG. 12C depicts a solid support 1200 containing a plurality of sites 1210 arranged in a hexagonal grid pattern, including a subset 1215 of the plurality of sites 1210, in which each site of the subset 1215 of the plurality of sites 1210 comprises a fiducial element. The subset 1215 of the plurality of sites 1215 has no discernible repeat in the pattern of occupancy within the region of the array shown. Occupied sites 1216 and 1217 are depicted as centerpoints of circles 1220 and 1221, in which circles 1220 and 1221 each have a radius of about 3d, in which d is the average separation distance between neighboring sites. Circle 1220 contains 4 occupied sites including site 1216, and 1221 contains all or a portion of 5 occupied sites including site 1217. The difference in number of sites within a fixed radius of sites 1216 and 1217 arises due to the random spatial distribution of occupied sites of the plurality of sites 1210. FIG. 12D depicts a solid support 1200 containing a plurality of sites 1210 arranged in a rectangular grid pattern, including a subset 1215 of the plurality of sites 1210, in which each site of the subset 1215 of the plurality of sites 1210 comprises a fiducial element. The subset 1215 of the plurality of sites 1210 has no discernible repeat in the pattern of occupancy within the region of the array shown. Occupied sites 1218 and 1219 are depicted as cornerpoints of rectangles 1222 and 1223, in which rectangles 1222 and 1223 each have an aspect of about 7d by 3d, in which d is the average separation distance between neighboring sites. Rectangle 1222 contains 2 occupied sites including site 1218, and rectangle 1223 contains 3 occupied sites, including site 1219. The difference in number of sites nearby sites 1218 and 1219 arises due to the random spatial distribution of occupied sites of the plurality of sites 1210.

FIG. 12E depicts differences in patterns of spatial distribution of fiducial elements on an array. FIG. 12E illustrates a solid support 1200 containing a plurality of sites 1210 arranged in a rectangular grid pattern, including a subset 1215 of the plurality of sites 1210, in which each site of the subset 1215 of the plurality of sites 1210 comprises a fiducial element. The solid support 1200 also comprises a landmarking region containing a multi-site fiducial element 1220 in the upper corner. Occupied sites 1230 and 1235 are arbitrarily chosen central points of two clusters of occupied sites, with circles 1232 and 1234 representing circles of a minimum radius to fully capture the nearest 5 occupied sites relative to sites 1230 and 1235, respectively. Cross hatch marks 1233 and 1236 represent centerpoints of circles 1232 and 1234, respectively. FIG. 12F displays the spatial arrangements of the two clusters of occupied sites from FIG. 12E in isolation. The left cluster contains site 1230 and is enclosed by circle 1232, and the right cluster contains site 1235 and is enclosed by circle 1234. The spatial arrangements of the left cluster and the right cluster can be seen to differ in several respects. First, the distance between the central sites (1230 and 1235) and the cross hatch marks (1233 and 1236, respectively) differ in absolute measurement. Second, the radius, $r_n$, of the circle encompassing each cluster of 6 sites varies in absolute terms, indicating a greater spatial dispersity for the right cluster. Third, an average distance between a central site (1230 or 1235) and any of the other 5 sites within each cluster (marked by distances $r_1$, $r_2$, $r_3$, $r_4$, and $r_5$) differs, with the right cluster having a larger average distance to its 5 nearest neighboring occupied sites. Fourth, vector patterns between central sites (1230 and 1235) and their 5 nearest neighboring occupied sites would differ with respect to angle and magnitude for each cluster. Fifth, based upon relative locations in FIG. 12E, the left cluster would have a closer absolute distance to the landmarking region 1220 than would the right cluster.

In some configurations, a measure of randomness may comprise a measure of uniqueness for a plurality of fiducial elements or a subset thereof. A measure of uniqueness may comprise any suitable statistical, mathematical, or otherwise empirical measure that provides a quantitative characterization of a spatial arrangement of a plurality of fiducial element on an array, or a subset thereof. A measure of uniqueness may be a local measure of uniqueness. A local measure of uniqueness may comprise a quantitative characterization of a spatial arrangement of a plurality of fiducial elements within a region of an array (e.g., a region within a field-of-view of a sensing device), in which the region does not comprise all sites of the array. A measure of uniqueness may be a global measure of uniqueness. A global measure of uniqueness may comprise a quantitative characterization of a spatial arrangement of a plurality of fiducial elements encompassing all sites of the array. A local measure of uniqueness may be chosen to identify an address of a pattern on an array if additional spatial information is known. For example, an array may be sensed by a sensing device that is translated through multiple positions while capturing sensing data within a field-of-view at each position. If the position of the sensing device relative to the array is known to some degree of accuracy or confidence, a sensed spatial arrangement of fiducial elements may only need to be compared to known spatial arrangements of fiducial elements within a fixed distance of the assumed position (e.g., within 2 fields-of-view) of the sensing device. Pattern matching between a sensed spatial arrangement of fiducial elements and a known spatial arrangement of fiducial elements (e.g., an array map) may be performed utilizing a local measure of uniqueness for the sensed spatial arrangement of fiducial elements.

A measure of uniqueness for a spatial arrangement of a plurality of fiducial elements may comprise one or more quantitative characterizations of the spatial arrangement of fiducial elements. In some cases, a measure of uniqueness may comprise a set of quantitative characterizations that collectively identify and/or distinguish a spatial arrangement of fiducial elements from any other spatial arrangements of fiducial elements on an array or a region thereof. A measure of uniqueness may comprise one or more, two or more, three or more, or four or more quantitative characterizations, including but not limited to: i) a quantity of sites, N, containing a coupled fiducial element within a distance, d, of a site comprising a coupled fiducial element, ii) a radius distance of a circle that encompasses the site containing a coupled fiducial element and a quantity of sites, N, containing a coupled fiducial element, in which the N sites are the nearest N occupied sites to the site containing the coupled fiducial element, iii) a distance between a centerpoint of the circle of ii) and the site containing the coupled fiducial element, iv) a distance between a measure of absolute position (e.g., a landmarking region) and the site containing the coupled fiducial element, v) a set of N vectors defining orientation and distance between the site containing the coupled fiducial element and the N nearest occupied sites, and vi) a vector that comprises a sum of the N vectors of v), in which N is an integer greater than or equal to 1.

An array, such as a single-analyte array, may comprise a site with two or more fiducial elements co-localized at the site. For example, after depositing fluorescent nanoparticle fiducial elements on an array, at least one site of the array may comprise 2, 3, 4, 5, 6, 7, 8, 9, 10, or more than 10 fiducial elements coupled to the site. In some configurations, an array may comprise a subset of sites, in which each site of the subset of sites comprises two or more fiducial elements. In particular configurations, an array may comprise a subset of sites, in which each site of the subset of sites comprises two or more fiducial elements, and in which the subset of sites is distributed on the solid support in a random order as defined by a measure of randomness. Random order of fiducial elements on an array of sites may further include a measure of randomness for co-localization of two or more fiducial elements at a single site.

An array, such as a single-analyte array, may comprise a landmarking region. A landmarking region may comprise a feature, object, or address with a fixed position. A landmarking region may comprise a feature, structure, object, or address with a fixed position that is optically detectable. A landmarking region may be configured to provide a measure of absolute position on a single-analyte array. In some configurations, an array process or assay may utilize a landmarking region to measure a position for a beginning or an ending of a process or assay step. A step of a process or assay may comprise one or more steps selected from: 1) identifying a landmarking region of the single-analyte array, 2) aligning a component of an array system to an address on or adjacent to the landmarking region, 3) confirming an alignment of a component of an array system based upon the landmarking region, and 4) altering a position of a component of an array system based upon the address of the landmarking region. For example, an initial step of an imaging process for a single-analyte array may comprise: i) identifying a landmarking region of the single-analyte array, and ii) aligning an imaging device for image collection based upon the position of the landmarking region. In another example, a step of a photocatalyzed polymer process on a single-analyte array may comprise: i) identifying a landmarking region of the single-analyte array, and ii) aligning a photon source for photopolymerization based upon the position of the landmarking region. In another example, a final step of an array imaging process may comprise: i) identifying a landmarking region of the single-analyte array, and ii) returning an imaging device to an initial position based upon a known relation between the initial position and a position of the landmarking region.

Figure 8B:
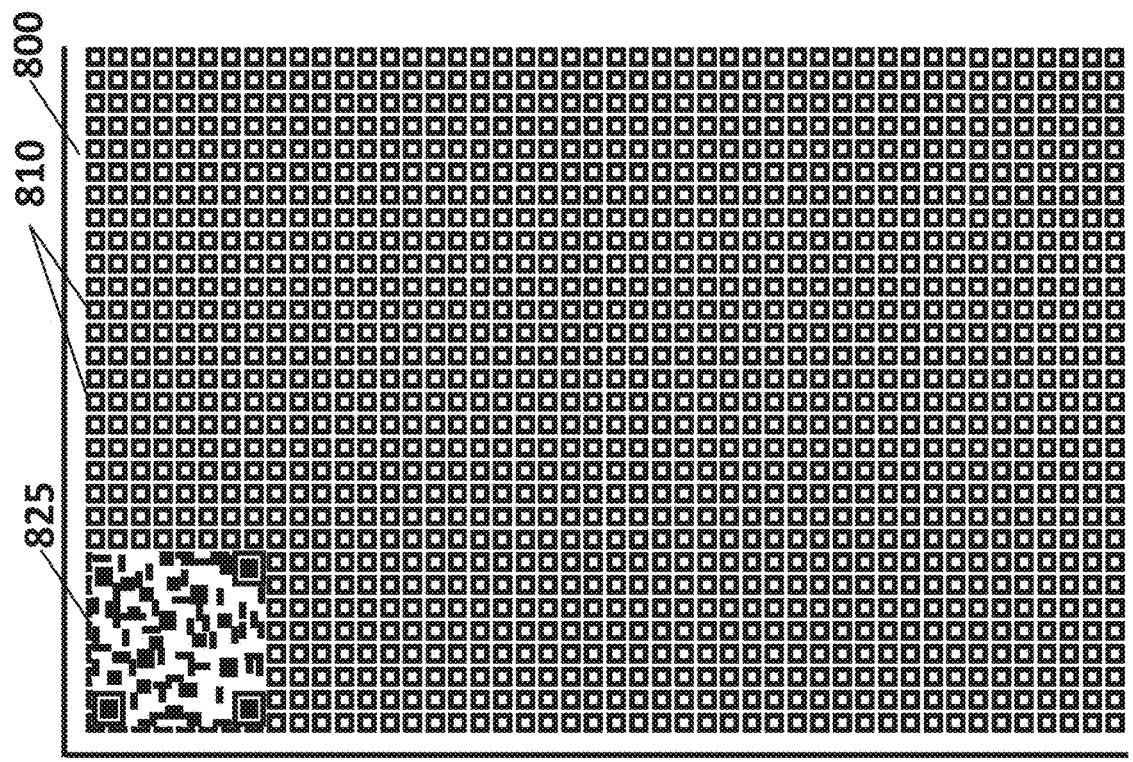
FIGS. 8A and 8B show regions of arrays comprising landmarking regions, in accordance with some embodiments.
Figure 8A:
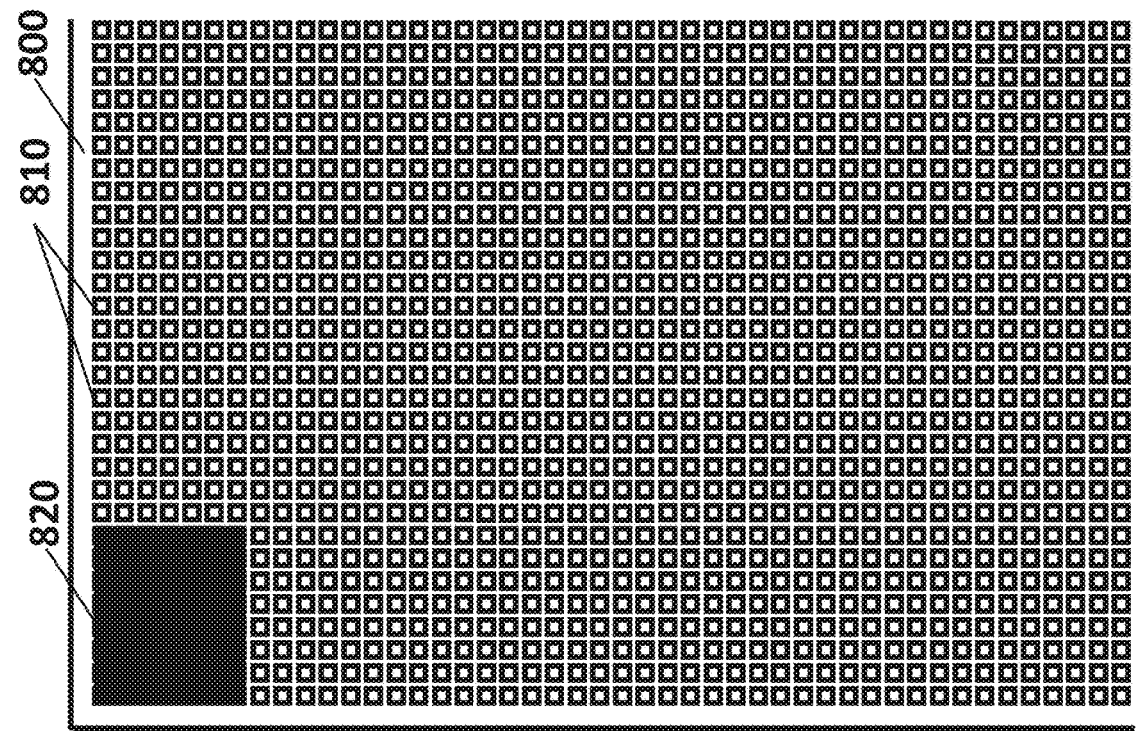

FIGS. 8A and 8B show top-down views of regions of arrays comprising landmarking regions. FIG. 8A depicts a solid support 800 comprising a plurality of sites 810 and a landmarking region (e.g., a deposited metal or metal oxide layer) in a corner of the array and near an edge of the solid support 800. FIG. 8B depicts a solid support comprising a plurality of sites 810 and a landmarking region 825 comprising a QR code, in which the landmarking region is located in a corner of the array and near an edge of the solid support 800. The QR code may serve as an identification tag for the array, and may encode one or more data of identifying information about the array.

A landmarking region may comprise a feature, structure, or object that facilitates identification of the landmarking region. In some configurations, a landmarking region may comprise a feature that is formed on a solid support of an array. For example, a raised feature or an indented feature may be formed lithographically at a corner of an array. In some configurations, a landmarking region may comprise a component of an array or a structure containing an array. In a particular configuration, a landmarking region may comprise a component of an array or a structure containing an array with an additional utility other than landmarking. For example, a structure comprising an array may comprise a hole, post, pillar, or clip that secures the structure on an array-containing device, and provides a fixed address for a landmarking region. A landmarking region may be located at a specific address of an array, such as a corner, edge, or centerpoint. In some configurations, an array comprising a plurality of sites may further comprise a landmarking region, in which one or more sites of the plurality of sites comprises a landmarking region. In a particular configuration, an array comprising a plurality of sites may further comprise a landmarking region, in which one or more sites of the plurality of sites comprises a landmarking region, and in which the landmarking region comprises a fiducial element. In a particularly advantageous configuration, an array comprising a plurality of sites may further comprise a landmarking region, in which one or more sites of the plurality of sites comprises a landmarking region, and in which the landmarking region comprises an optically passive fiducial element, such as a deposited metal fiducial element. In other configurations, a landmarking region may comprise an optically active fiducial element, such as a fluorescent nanoparticle.

A landmarking region may comprise one or more fiducial elements. A landmarking region may comprise a plurality of fiducial elements, in which the plurality of fiducial elements comprises an ordered spatial distribution. An ordered spatial distribution may refer to a plurality of fiducial elements comprise a non-random patterning in the landmarking region. An ordered spatial distribution may refer to a plurality of fiducial elements comprising at least about 50%, 60%, 70%, 80%, 90%, 95%, 99%, or substantially 100% of sites within a landmarking region. For example, a single-analyte array comprising a 1000×1000 rectangular array of sites may comprise a 10×10 landmarking region in a corner of the array with a fluorescent nanoparticle coupled to all 100 array sites of the landmarking region. In another example, a single-analyte array comprising a 1000×1000 rectangular array of sites may comprise a 10×10 landmarking region in a corner of the array with a fluorescent nanoparticle coupled to 50 array sites of the landmarking region in a regular, staggered pattern.

An array, such as a single-analyte array may comprise a plurality of sites, in which a subset of sites of the plurality of sites comprises a fiducial element. The size of a subset of sites containing a fiducial element of a plurality of sites may depend upon the size and density of the array. In some configurations, an average surface density of fiducial elements on an array may facilitate optical detection or optical data analysis for an array. For example, an array with a low spatial density of sites (e.g., no more than about 10000, 1000, 100, or 10 sites per square centimeter) may facilitate detection of each array site simultaneously within a single field-of-view of a detection device. Accordingly, in some configurations, fiducial elements need not be necessary for image registration (due to all sites being captured in one image), and fewer fiducial elements may be required on the array. Alternatively, an array with a high spatial density of sites (e.g., at least 100000, 1000000, 10000000, 100000000, or more sites per square centimeter) may necessitate detection across a plurality of higher magnification image fields. Accordingly, fiducial elements may be provided on the array in sufficient density and with a sufficient random order to facilitate image registration amongst any two images of the array.

An array, as set forth herein, may comprise a total of M sites, in which N sites of the M sites comprise a fiducial element, and in which N is less than or equal to M. An array may comprise M sites, in which M is at least about 10, 100, 1000, 10000, 100000, 1000000, 10000000, 100000000, 1000000000, 10000000000, 100000000000, 1000000000000, or more than 1000000000000 sites. Alternatively or additionally, an array may comprise a total of M sites, in which M is no more than about 1000000000000, 100000000000, 10000000000, 1000000000, 100000000, 10000000, 1000000, 100000, 10000, 1000, 100, 10, or less than 10 sites. An array may comprise a subset of N sites, in which each site of the N sites comprises a fiducial element, and in which N comprises a percentage of a total of M sites on the array, in which N comprises at least about 0.0000001%, 0.000001%, 0.00001%, 0.0001%, 0.001%, 0.01%, 0.05%, 0.1%, 0.5%, 1%, 5%, 10%, 15%, 20%, 30%, 40%, 50%, 60%, 70%, 80%, 90%, or more than 90% of the M sites. Alternatively or additionally, an array may comprise a subset of N sites, in which each site of the N sites comprises a fiducial element, and in which N comprises a percentage of a total of M sites on the array, in which N comprises no more than about 90%, 80%, 70%, 60%, 50%, 40%, 30%, 20%, 15%, 10%, 5%, 1%, 0.5%, 0.1%, 0.05%, 0.01%, 0.001%, 0.0001%, 0.00001%, 0.000001%, 0.0000001%, or less than 0.0000001% of the M sites.

An array, such as a single-analyte array, may comprise an identification tag. An identification tag may be configured to provide information to an array system regarding an array comprising the identification tag. For example, an array system may retrieve identifying information from an array comprising an identification tag to confirm that the array is configured appropriately for a process or assay to be performed on the array. In some configurations, an identification tag may comprise an on-chip label. An on-chip label may comprise one or more items of identifying information (e.g., serial number, lot number, expiration date, manufacturer, etc.). An on-chip label may be provided to an array or a structure comprising an array (e.g., a flow cell, a mechanical support, etc.) in a permanent form, such as etching or printing with an indelible ink. An on-chip label may be provided to an array or a structure comprising an array (e.g., a flow cell, a mechanical support, etc.) in a non-permanent form, such as applying an adhesive-coupled label or printing with an erasable ink. An on-chip label may be applied to a region of an array or a structure comprising an array. In some configurations, an on-chip label may be applied to a non-analyte region of an array or a structure comprising an array, in which the non-analyte region comprises no array sites. For example, an on-chip label may be applied to a portion of a casing of a flow cell, in which the portion of the casing does not contain an array or impede an optical pathway for detecting the array. In other configurations, an on-chip label may be applied to an analyte region of an array or a structure comprising an array, in which the analyte region comprises array sites. For example, an array may comprise a landmarking region comprising a fiducial element, in which the fiducial element comprises an optically passive layer that has been lithographically formed in a shape of a QR code containing identifying information. An identification tag may be affixed to an array or a housing comprising an array (e.g., a flow cell or fluidic cartridge), for example as a sticker. An identification tag may be engraved or printed on an array or a housing comprising an array.

In some configurations, an array, such as a single-analyte array, may comprise an identification tag comprising a sample identification moiety. A sample identification moiety may comprise a component of a sample comprising analytes that provides identifying information of the sample. In some configurations, a sample identification moiety may comprise a molecule derived from a sample, such as a nucleic acid, a polypeptide, a polysaccharide, a nanoparticle, a therapeutic agent, a pharmaceutical compound, or a combination thereof. In particular configurations, a sample identification moiety may comprise information on a source of a sample. For example, a polysaccharide sample identification moiety derived from a glycoprotein may contain an identifiable glycosylation pattern specific to a particular organism. In another example, a sample identification moiety may comprise a genomic, transcriptomic, proteomic, or metabolomic sample that contains identifiable information specific to a particular organism. In other configurations, a sample identification moiety may comprise a moiety added to a sample as a reference molecule or an internal standard. A reference molecule or an internal standard may comprise a naturally-occurring or synthetic molecule (e.g., a peptide, a nucleic acid, etc.) that provides information on a sample or sample processing condition. A reference molecule or an internal standard may comprise a moiety that binds to a site of an array, in which the bound moiety is configured to produce a detectable signal (e.g. a reactive molecule, a receptor moiety, a ligand, a fluorophore, a luminophore, a dye, a pigment, etc.).

An array, such as single-analyte array may comprise one or more sites of a plurality of sites that are configured to couple a sample identification moiety. In some configurations, an array, such as single-analyte array may comprise one or more sites of a plurality of sites that are coupled to a sample identification moiety. In some configurations, one or more sites that are configured to couple a sample identification moiety may be contiguous with a plurality of sites that are configured to couple an analyte. For example, sample identification moieties may be mixed with a plurality of analytes and co-deposited randomly on an array comprising a plurality of sites. In other configurations, one or more sites that are configured to couple a sample identification moiety may not be contiguous with a plurality of sites that are configured to couple an analyte. For example, a flow cell may comprise an entrance channel comprising a plurality of sites that are configured to only couple sample identification moieties, and may further comprise an array comprising a plurality of sites that are configured to only couple analytes. In some configurations, a site that is configured to couple a sample identification moiety may comprise a moiety that is configured to couple the sample identification moiety.

An array, such as a single-analyte array, may further comprise or be disposed within a structure. A structure may provide one or more utilities for an array, including: a) providing mechanical support to an array; b) providing a thermal condition to an array; c) providing a controlled chemical or physical environment to an array; d) resisting or enabling a mechanical motion (e.g., bending, rotation, translation) of an array; e) providing a pathway for transfer of a material, reagent, or fluid to an array; f) providing a mechanism for attachment of an array to an array-based device; and g) providing positioning of an array relative to a component of an array-based device (e.g., a detection device). In some configurations, an array may comprise a solid support, in which the solid support comprises a first portion comprising the array and a second portion that does not comprise the array. In a particular configuration, a portion of a solid support not comprising an array may be utilized for a second function, such as providing one or more surfaces for fastening the solid support to a device, or providing a surface for joining an additional structure to the solid support. In other configurations, an array may comprise a first solid support, in which the first solid support is disposed on or embedded within a second solid support. In particular configurations, a first solid support is disposed on or embedded within a second solid support, in which the first and the second solid support comprises a same material (e.g., a glass, a mineral, a polymer, a semiconductor, a metal, a metal oxide, etc.). In other particular configurations, a first solid support is disposed on or embedded within a second solid support, in which the first and the second solid support do not comprise a same material.

In an advantageous configuration of an array, such as a single-analyte array, the array may be disposed within a flow cell or fluidic cartridge. A flow cell or fluidic cartridge may comprise an internal volume within which an array is disposed. In some configurations, a flow cell or fluidic cartridge may comprise two or more solid supports that are joined or sealed to form the flow cell or cartridge. In a particular configuration, a flow cell or fluidic cartridge may comprise a first solid support that is joined or sealed to a second solid support, in which an array of sites is formed on the first solid support. A flow cell or fluidic cartridge may further comprise one or more fluidic ports that are configured to provide and/or remove a fluid from the flow cell or fluidic cartridge, or an internal volume or a fluidic channel thereof. A fluidic cartridge may comprise one or more fluidic channels that provide fluidic communication between a fluidic port and an internal volume of a flow cell or fluidic cartridge. In some configurations, a fluidic channel or an internal volume may comprise a site that is configured to couple a moiety (e.g., an analyte, a mapping moiety, a fiducial element, a sample identification moiety, etc.).

Figure 9:
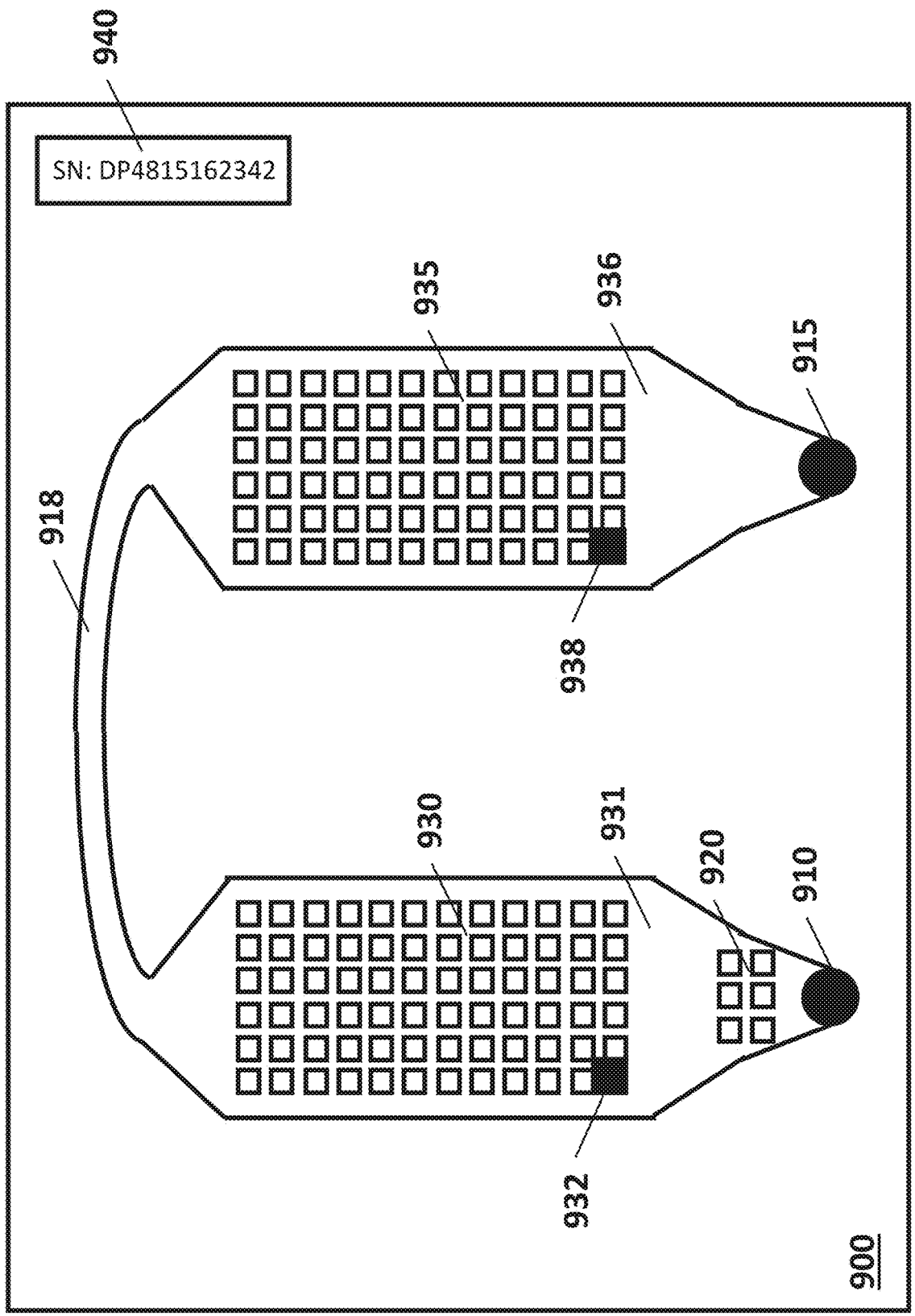
FIG. 9 depicts a top-down schematic of a fluidic cartridge comprising two arrays, in accordance with some embodiments.

In a further advantageous configuration, a flow cell or fluidic cartridge may comprise two or more internal volumes, in which each internal volume of the two or more internal volumes contains an array disposed within. In some configurations, each array may be fluidically isolated from each other array. In other configurations, a first array may be fluidically connected to a second array by a fluidic channel or an internal volume. FIG. 9 illustrates a top-down view of a fluidic cartridge comprising multiple arrays. A cartridge structure 900 comprises an inlet port 910 and an outlet port 915 that provide fluidic communication to the arrays. The cartridge structure further comprises an adhered identification tag comprising a unique serial number. A first array 930 and a second array 935 are disposed, respectively within internal volumes 931 and 936. Each array comprises a landmarking region 932 and 938 that are configured to provide an absolute spatial reference for a sensing device at the initiation or termination of a detection process. The first internal volume 931 and the second internal volume 936 are fluidically connected by a fluidic channel 918. The fluidic cartridge further comprises a small array 920 disposed adjacent to the inlet port 910 that is configured to couple one or more sample identification moieties. The sample identification moieties may be detected at the small array 920 to determine a identify, property, or state of a sample provided to an array.

In an aspect, provided herein is an array (e.g., a single-analyte array), comprising: a) a solid support, in which the solid support comprises a plurality of sites, in which each site of the plurality of sites is configured to couple an analyte, and b) a plurality of optically active fiducial elements, in which each fiducial element is located at a site of the plurality of sites, and in which the plurality of fiducial elements is distributed on the solid support in a random order. Optionally, the array is not in contact with a fluidic medium. For example, the array can be in a substantially dry state or substantially devoid of liquid. After an array comprising a plurality of randomly-ordered fluorescent nanoparticle fiducial elements is prepared, any liquid reagents utilize during array preparation may be extracted, drained, rinsed and/or dried from the array prior to storing the array. Such a composition may provide an array that is chemically stable for storage while awaiting an initiation of an array-based process or assay. In some configurations, an array may further comprise a seal, in which the seal is configured to prevent or minimize mass transfer between the array and an external environment. For example, a flow cell or fluidic cartridge may comprise one or more fluidic ports, in which the fluidic ports comprise a seal (e.g., a septum, a metal foil seal, a polymer seal, a wax seal, etc.). In a particular configuration, a sealed array may comprise a vacuum (i.e., a pressure within a sealed volume containing the array) relative to atmospheric pressure. In another particular configuration, a sealed array may comprise a controlled atmosphere (e.g., nitrogen, argon, helium, air, dehumidified air, etc.) within a sealed volume comprising the array.

An array site comprising a fiducial element may be further configured to couple an analyte. An array site comprising a fiducial element may be further configured to couple an analyte by a covalent or non-covalent interaction. It may be advantageous to couple analytes at a site comprising a fiducial element to increase the total number of analytes (e.g., single analytes) on an array. In some configurations, a fiducial element may be configured to couple an analyte. For example, a fluorescent polymer nanoparticle may be functionalized to facilitate attachment of other moieties (e.g., an analyte, passivating moieties, etc.). In particular configurations, an analyte may be coupled to a fiducial element (e.g., by a covalent interaction, by a non-covalent interaction). In some configurations, a fiducial element may be coupled to an anchoring moiety. Optionally, the anchoring moiety is further configured to couple an analyte. For example, an anchoring moiety (e.g., a nucleic acid origami, a nucleic acid nanoball, a functionalized nanoparticle) may comprise a first attachment moiety and a second attachment moiety, in which the first attachment moiety is configured to couple a fiducial element, an in which the second attachment moiety is configured to couple an analyte. In a specific configuration, an anchoring moiety may comprise a first attachment moiety and a second attachment moiety, in which the first attachment moiety and the second attachment moiety are orthogonal with respect to reactivity or binding specificity. In some configurations, a site of an array may be configured to couple a fiducial element and an analyte. In a particular configuration, an analyte and a fiducial element may be co-located at a site of an array. In a particular configuration, a site of an array may be configured to couple a first anchoring moiety and a second anchoring moiety, in which the first anchoring moiety is configured to couple a fiducial element, and in which the second anchoring moiety is configured to couple an analyte. In a particular configuration, a site of an array may be coupled to a first anchoring moiety and a second anchoring moiety, in which the first anchoring moiety is configured to couple a fiducial element, and in which the second anchoring moiety is configured to couple an analyte. In a particular configuration, a site of an array may be coupled to a first anchoring moiety and a second anchoring moiety, in which the first anchoring moiety is coupled to a fiducial element, and in which the second anchoring moiety is coupled to an analyte.

In another aspect, provided herein is an array, such as a single-analyte array, comprising: a) a solid support, in which the solid support comprises a plurality of sites, in which a subset of the sites are sites that are configured to couple analytes of interest, b) a plurality of fiducial elements, wherein a second subset of sites of the plurality of sites comprises a coupled fiducial element of the plurality of fiducial elements, and in which a spatial distribution of the second subset of sites is random, and c) a plurality of the analytes of interest in contact with the solid support.

An array, as set forth herein, may be contacted with a plurality of analytes of interest. In some configurations, an array may be contacted with a plurality of unbound analytes of interest. In other configurations, an array may be contacted with a plurality of analytes of interest, in which each analyte of interest of the plurality of analytes of interest is coupled to a site of the array. In a particular configuration, an array may be contacted with a plurality of analytes of interest, in which each analyte of interest of the plurality of analytes of interest is coupled to a site of the array, and in which each site of the array comprises no more than one analyte of interest. An array may be contacted with a plurality of analytes of interest, in which the plurality of analytes of interest comprises a cell, a polysaccharide, a polypeptide, a nucleic acid, a metabolite, a therapeutic agent, a pharmaceutical compound, or a combination thereof. In some configurations, an array may be contacted with a plurality of analytes of interest, in which the plurality of analytes of interest comprises a plurality of cells, a plurality of polysaccharides, a plurality of polypeptides, a plurality of nucleic acids, a plurality of metabolites, a plurality of therapeutic agents, or a plurality of pharmaceutical compounds. In some configurations, a plurality of analytes of interest do not comprise an analyte of interest selected from the group consisting of a cell, a polysaccharide, a polypeptide, a nucleic acid, a metabolite, a therapeutic agent, a pharmaceutical compound, and a complex thereof.

An array may be contacted with a plurality of analytes of interest, in which an analyte of interest of the plurality of analytes of interest comprises an anchoring moiety. In some configurations, an array may be contacted with a plurality of analytes of interest, in which each analyte of interest of the plurality of analytes of interest comprises an anchoring moiety. An anchoring moiety coupled to an analyte of interest may be configured to couple the analyte of interest to a site of the array. An anchoring moiety coupled to an analyte may be configured to inhibit contact of the analyte of interest with a site or an interstitial region of an array. An anchoring moiety may be configured to couple an analyte of interest to a site of an array, in which a moiety of the anchoring moiety is configured to be coupled to the site, and in which the analyte of interest does not comprise a moiety that is configured to be coupled to the site (i.e., the analyte of interest is configured to be coupled to the site only by the binding interaction of the anchoring moiety with the site, or a coupling moiety thereof). An anchoring moiety coupled to an analyte of interest may couple the analyte of interest to a site of the array. An anchoring moiety coupled to an analyte of interest may inhibit contact of the analyte of interest with a site or an interstitial region of an array. An anchoring moiety may couple an analyte of interest to a site of an array, in which a moiety of the anchoring moiety is coupled to the site, and in which the analyte of interest does not comprise a moiety that is coupled to the site (i.e., the analyte of interest is coupled to the site only by the binding interaction of the anchoring moiety with the site, or a coupling moiety thereof).

An array may comprise a plurality of fiducial elements, in which a subset of sites of a plurality of sites on the array comprises a coupled fiducial element of the plurality of fiducial elements. In some configurations, a fiducial element of a plurality of fiducial elements on an array may be coupled to an anchoring moiety. In a particular configuration, each fiducial element of a plurality of fiducial elements is coupled to an anchoring moiety. An anchoring moiety may be configured to couple a fiducial element to a site of an array. In some configurations, fiducial elements and analytes of interest are coupled to sites of an array via anchoring moieties that comprise structured nucleic acid particles. In some configurations, fiducial elements and analytes of interest are coupled to sites of an array via anchoring moieties that comprise non-nucleic acid particles.

Fiducial elements and analytes of interest may be coupled to sites of an array, in which fiducial elements may be coupled to a first type of anchoring moiety, analytes of interest may be coupled to a second type of anchoring moiety, and the first and second types of anchoring moieties may differ. In some configurations, fiducial elements may be coupled to sites of an array via anchoring moieties that comprise non-nucleic acid particles and in which analytes of interest may be coupled to sites of the array via anchoring moieties that comprise structured nucleic acid particles. In other configurations, fiducial elements may be coupled to the addresses via anchoring moieties that comprise structured nucleic acid particles and in which analytes of interest may be coupled to sites of the array via anchoring moieties that comprise non-nucleic acid particles.

An array may be contacted with a plurality of analytes of interest and/or a plurality of fiducial elements, in which the plurality of analytes of interest and/or fiducial elements are in fluidic communication with a solid support of the array. In some configurations, an array composition may comprise a fluidic medium. A fluidic medium may comprise any suitable fluidic medium for an analyte of interest or fiducial element. A fluidic medium may comprise an aqueous medium. A fluidic medium may comprise an organic medium, nonaqueous or inorganic medium. A fluidic medium may comprise a pH buffered medium. A fluidic medium may further comprise a salt, an acidic species, a basic species, a metal ionic species (e.g. $Mg^{2+}$), a non-metal ionic species, a polyatomic ionic species, a detergent species, a surfactant species, a denaturing species, a chaotropic species, an oxidizing species, a reducing species, a catalyst species, an enzyme, a reactive species, an inert species, a chelating species, or a combination thereof. A fluidic medium may comprise a multi-phase medium, such as an emulsion. A fluidic medium may include water, acetic acid, methanol, ethanol, n-propanol, isopropyl alcohol, n-butanol, formic acid, ammonia, propylene carbonate, nitromethane, dimethyl sulfoxide, acetonitrile, dimethylformamide, acetone, ethyl acetate, tetrahydrofuran, dichloromethane, chloroform, carbon tetrachloride, dimethyl ether, diethyl ether, 1-4, dioxane, toluene, benzene, cyclohexane, hexane, cyclopentane, pentane, or combinations thereof. A fluid medium may include a buffering species including, but not limited to, MES, Tris, Bis-tris, Bis-tris propane, ADA, ACES, PIPES, MOPSO, MOPS, BES, TES, HEPES, HEPBS, HEPPSO, DIPSO, MOBS, TAPSO, TAPS, TABS, POPSO, TEA, EPPS, Tricine, Gly-Gly, Bicine, AMPD, AMPSO, AMP, CHES, CAPSO, CAPS, PBS, and CABS. A fluid medium may include cationic species such as $Na^+$, $K^+$, $Ag^+$, $Cu^+$, $NH_4^+$, $Mg^{2+}$, $Ca^{2+}$, $Cu^{2+}$, $Cd^{2+}$, $Zn^{2+}$, $Fe^{2+}$, $Co^{2+}$, $Ni^{2+}$, $Cr^{2+}$, $Mn^{2+}$, $Ge^{2+}$, $Sn^{2+}$, $Al^{3+}$, $Cr^{3+}$, $Fe^{3+}$, $Co^{3+}$, $Ni^{3+}$, $Ti^{3+}$, $Mn^{3+}$, $Si^{4+}$, $V^{4+}$, $Ti^{4+}$, $Mn^{4+}$, $Ge^{4+}$, $Se^{4+}$, $V^{5+}$, $Mn^{5+}$, $Mn^{6+}$, $Se^{6+}$, and combinations thereof. A fluid medium may include anionic species such as $F^-$, $Cl^-$, $Br^-$, $ClO_3^-$, $H_2PO_4^-$, $HCO_3^-$, $HSO_4^-$, $OH^-$, $I^-$, $NO_3^-$, $NO_2^-$, $MnO_4^-$, $SCN^-$, $CO_3^{2-}$, $CrO_4^{2-}$, $Cr_2O_7^{2-}$, $HPO_4^{2-}$, $SO_4^{2-}$, $SO_3^{2-}$, $PO_4^{3-}$, and combinations thereof. A fluid medium may include a surfactant species, such as a cationic surfactant, an anionic surfactant, a zwitterionic surfactant, or an amphoteric surfactant. A fluid medium may include a surfactant species including, but not limited to, stearic acid, lauric acid, oleic acid, sodium dodecyl sulfate, sodium dodecyl benzene sulfonate, dodecylamine hydrochloride, hexadecyltrimethylammonium bromide, polyethylene oxide, nonylphenyl ethoxylates, Triton X, pentapropylene glycol monododecyl ether, octapropylene glycol monododecyl ether, pentaethylene glycol monododecyl ether, octaethylene glycol monododecyl ether, lauramide monoethylamine, lauramide diethylamine, octyl glucoside, decyl glucoside, lauryl glucoside, Tween 20, Tween 80, n-dodecyl-β-D-maltoside, nonoxynol 9, glycerol monolaurate, polyethoxylated tallow amine, poloxamer, digitonin, zonyl FSO, 2,5-dimethyl-3-hexyne-2,5-diol, Igepal CA630, Aerosol-OT, triethylamine hydrochloride, cetrimonium bromide, benzethonium chloride, octenidine dihydrochloride, cetylpyridinium chloride, adogen, dimethyldioctadecylammonium chloride, CHAPS, CHAPSO, cocamidopropyl betaine, amidosulfobetaine-16, lauryl-N,N-(dimethylammonio)butyrate, lauryl-N,N-(dimethyl)-glycinebetaine, hexadecyl phosphocholine, lauryldimethylamine N-oxide, lauryl-N,N-(dimethyl)-propanesulfonate, 3-(1-pyridinio)-1-propanesulfonate, 3-(4-tert-butyl-1-pyridinio)-1-propanesulfonate, N-laurylsarcosine, and combinations thereof. In some configurations, a fluidic medium may be configured to facilitate coupling of an analyte of interest of a plurality of analytes of interest to a site of a plurality of sites.

An array may comprise a plurality of sites, in which a first subset of sites of the plurality of sites is configured to couple an analyte, and in which a second subset of sites of the plurality of sites comprises a coupled fiducial element. In some configurations, a first subset of sites and a second subset of sites may comprise a site of a plurality of sites on an array. For example, a site comprising a coupled fiducial element may be further configured to couple an analyte of interest. In another example, a fiducial element coupled to a site may be configured to couple an analyte of interest. In some configurations, an analyte of interest may be coupled to a site of a plurality of sites on an array. In a particular configuration, an analyte of interest may be coupled to a site, in which the site does not comprise a coupled fiducial element. In another particular configuration, an analyte of interest may be coupled to a site, in which the site comprises a coupled fiducial element. In some configurations, an array may comprise a plurality of sites, in which a first subset of sites of the plurality of sites is configured to couple an analyte, in which a second subset of sites of the plurality of sites comprises a coupled fiducial element, in which each site of the first subset of sites comprises a coupled analyte, and in which no sites of the second subset of sites comprises a coupled analyte. In some configurations, an array may comprise a plurality of sites, in which a first subset of sites of the plurality of sites is configured to couple an analyte, in which a second subset of sites of the plurality of sites comprises a coupled fiducial element, in which each site of the first subset of sites comprises a coupled analyte, and in which a site of the second subset of sites comprises a coupled analyte. In some configurations, an array may comprise a plurality of sites, in which a first subset of sites of the plurality of sites is configured to couple an analyte, in which a second subset of sites of the plurality of sites comprises a coupled fiducial element, in which each site of the first subset of sites comprises a coupled analyte, and in which each site of the second subset of sites comprises a coupled analyte. In particular configurations, a site of a second subset of sites comprises only one analyte. In other particular configurations, each site of a second subset of sites comprises only one analyte. In particular configurations, a site of a second subset of sites comprises more than one analyte.

An array, such as a single-analyte array, may be contacted with an analytical reagent. An analytical reagent may facilitate a step of an array-based process or assay. For example, an array may be contacted with a plurality of affinity agents (e.g., aptamers, antibodies, etc.) for an epitope-binding assay. In another example, an array may be contacted with a plurality of monomers (e.g., nucleotides, amino acids, etc.) for a single-molecule synthesis process. In some configurations, an array may be contacted with a plurality of analytical reagents. In a particular configurations, an array may be contacted with a plurality of analytical reagents, in which the plurality of analytical reagents is in fluidic communication with the array. In some configurations, an analytical reagent of a plurality of analytical reagents may be configured to form an interaction with an analyte of interest of a plurality of analytes of interest. An analytical reagent may form an interaction with an analyte of interest selected from the group consisting of a binding interaction, a chemical modification reaction, a structural modification reaction, and a combination thereof. In some configurations, an analytical reagent of a plurality of analytical reagents may comprise an affinity agent that is configured to bind to an analyte of interest of a plurality of analytes of interest. In particular configurations, an analytical reagent of a plurality of analytical reagents may comprise an affinity agent that is configured to bind to an epitope of an analyte of interest, in which the epitope is common to at least one other analyte of interest, and in which the analyte of interest and the other analyte of interest comprises differing primary structures. In some configurations, each affinity agent of a plurality of affinity agents may be bound to an analyte of interest of a plurality of analytes of interest.

An array composition may comprise: a) a solid support, in which the solid support comprises a plurality of sites, in which a first subset of the sites are sites that are coupled to analytes of interest, and in which a fraction of the first subset of sites further comprises a detectable analytical reagent (e.g., an affinity agent) coupled to an analyte of interest, and b) a plurality of fiducial elements, wherein a second subset of sites of the plurality of sites comprises a coupled fiducial element of the plurality of fiducial elements, and in which a spatial distribution of the second subset of sites is random. In some configurations, a subarray of an array may comprise M contiguous sites, in which the subarray of M contiguous sites comprises one or more sites containing a fiducial element. In some configurations, a subarray of an array may comprise M contiguous sites, in which the subarray of M contiguous sites comprises one or more sites containing an analyte of interest coupled to an analytical reagent. A subarray may comprise M contiguous sites, in which M is at least about 10, 50, 100, 500, 1000, 5000, 10000, 50000, 100000, 500000, 1000000, or more than 1000000 sites. Alternatively or additionally, a subarray may comprise M contiguous sites, in which M is no more than about 1000000, 500000, 100000, 50000, 10000, 5000, 1000, 500, 100, 50, 10, or less than 10 sites. A subarray may comprise M contiguous sites, in which at least about 0.00001%, 0.001%, 0.01%, 0.1%, 0.5%, 1%, 5%, 10%, 50%, or more than 50% of the M sites comprises a fiducial element. Alternatively or additionally, a subarray may comprise M contiguous sites, in which no more than about 50%, 10%, 5%, 1%, 0.5%, 0.1%, 0.01%, 0.001%, 0.0001%, 0.00001%, or less than 0.00001% of the M sites comprises a fiducial element. A subarray may comprise M contiguous sites, in which at least about 0.00001%, 0.001%, 0.01%, 0.1%, 0.5%, 1%, 5%, 10%, 50%, or more than 50% of the M sites comprises an analyte of interest coupled to an analytical reagent. Alternatively or additionally, a subarray may comprise M contiguous sites, in which no more than about 50%, 10%, 5%, 1%, 0.5%, 0.1%, 0.01%, 0.001%, 0.0001%, 0.00001%, or less than 0.00001% of the M sites comprises an analyte of interest coupled to an analytical reagent.

In another aspect, provided herein is a composition, comprising: a) a solid support comprising a site with a known spatial address; b) a fiducial element coupled to the site; and c) an analyte of interest coupled to the site, in which the fiducial element and the analyte of interest are spatially non-resolvable at the site at single-analyte resolution, and in which the fiducial element and the analyte of interest are resolvable at the site via distinguishable optical characteristics. A distinguishable optical characteristic may comprise an absorbance wavelength, emission wavelength, excitation wavelength, signal intensity, luminescence lifetime, fluorescence lifetime, optical polarity, photoelectron energy, or a combination thereof. In some configurations, a composition may further comprise an analytical reagent (e.g., an affinity agent), wherein the analytical reagent is coupled to an analyte of interest. In particular configurations, an analytical reagent may comprise an optically-detectable label, wherein the optically-detectable label is configured to provide a detectable signal. In particular configurations, an optically detectable label may be configured to provide a detectable signal that is distinguishable from a detectable signal provided by a fiducial element.

Figures 6A, 6B:
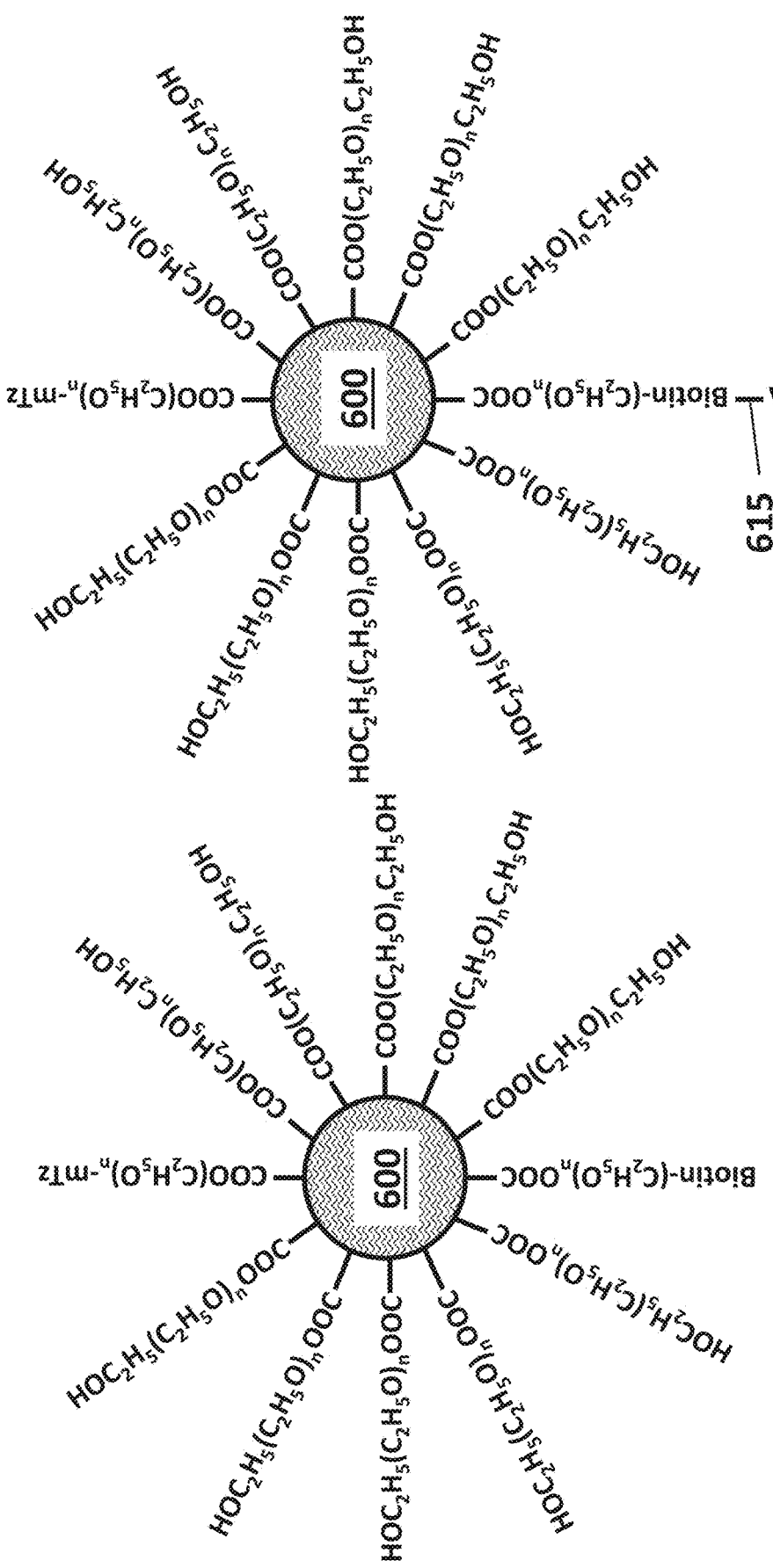
FIGS. 6A and 6B illustrate fiducial elements that are configured to bind an analyte of interest, in accordance with some embodiments.

FIGS. 6A and 6B display a composition for coupling an analyte to a fiducial element. FIG. 6A depicts a fiducial element comprising a fluorescent nanoparticle 600 (e.g., a fluorescently-labeled polymer, a quantum dot), in which the nanoparticle 600 is functionalized on an outer surface of the particle (e.g., carboxylated, aminated, azidated, epoxidated, etc.). The surface functionalities have been linked to polyethylene glycol molecules (PEG) to passivate the surface and reduce the likelihood of non-specific binding interactions. One PEG chain further comprises a terminal methyltetrazine (mTz) reactive group, and one PEG chain further comprises a terminal biotin binding group. FIG. 6B depicts the nanoparticle 600 of FIG. 6A, in which the nanoparticle has been coupled to an anchoring moiety 610 (e.g., a structured nucleic acid particle) by a streptavidin attachment moiety 615, in which the streptavidin attachment moiety 615 forms a non-covalent binding interaction with the biotin binding group. The mTz is configured to form a covalent interaction (e.g., a click-type reaction) with an analyte of interest, such as an analyte that has been functionalized with a transcyclooctylene (TCO) reactive group.

Figure 7:
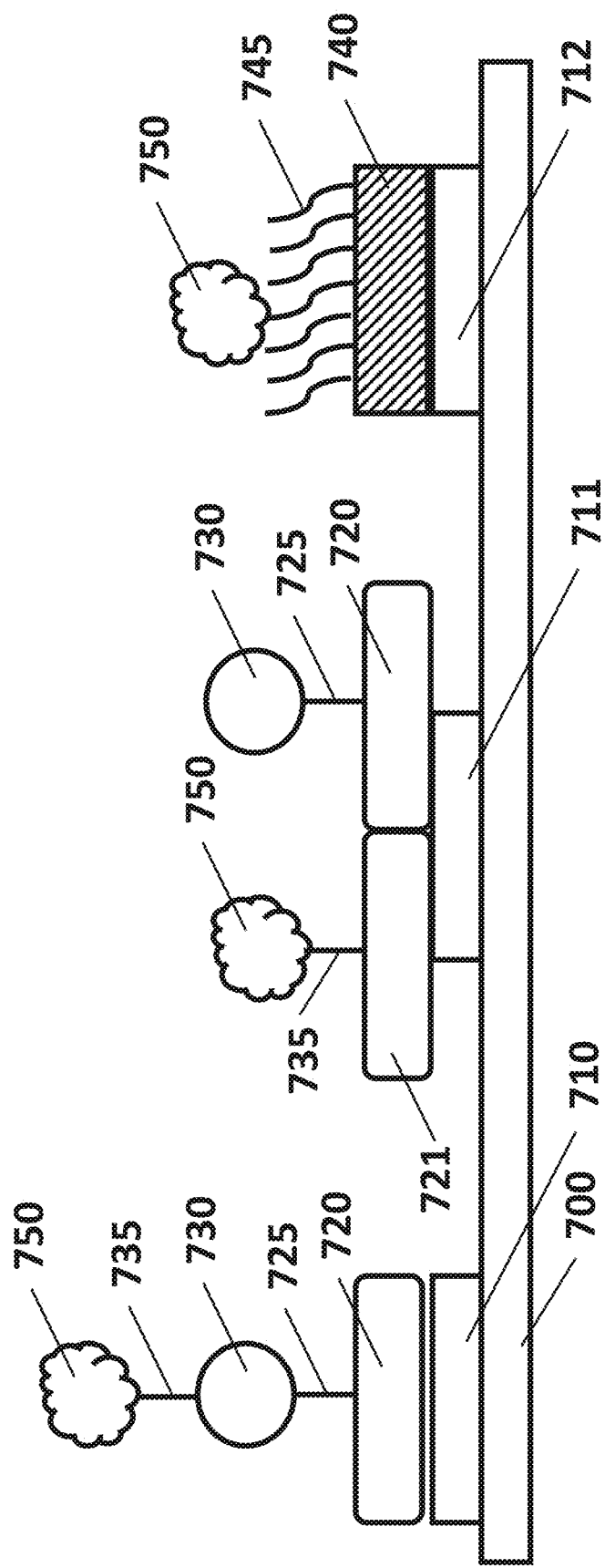
FIG. 7 displays an array comprising varying configurations of analytes of interest co-located with fiducial elements, in accordance with some embodiments.

FIG. 7 depicts exemplary embodiments of sites comprising fiducial elements and co-located analytes of interest. A solid support 700 comprises a first site 710, a second site 711, and a third site 712. The first site 710 comprises a coupled fiducial element 730 that is coupled to the first site 710 by an anchoring moiety 720. The fiducial element is coupled to the anchoring moiety 720 by an optional first attachment moiety 725. The fiducial element is further coupled to an analyte of interest 750 by an optional second attachment moiety 735. The second site 711 comprises a coupled fiducial element 730 that is coupled to the second site 711 by an anchoring moiety 720. The fiducial element is coupled to the anchoring moiety 720 by an optional first attachment moiety 725. The second site 711 further comprises an analyte of interest 750 that is coupled to the second site by a second anchoring moiety 721. The analyte of interest is coupled to the second anchoring moiety by an optional second attachment moiety 735. The third site 712 comprises a fiducial element comprising a first layer or coating 740 (e.g., metal, metal oxide, semiconductor, dielectric material, etc.) and a second layer or coating 745 (e.g., coupling moieties, passivating moieties, etc.) that is coupled to the first layer or coating 740. The second layer or coating 745 comprises a coupling moiety that coupled an analyte of interest 750 to the third site 712.

In another aspect, provided herein is a composition comprising a plurality of arrays, as set forth herein. In some configurations, a composition may comprise a first array and a second array, in which the first array comprises a first plurality of fiducial elements, in which the second array comprises a second plurality of fiducial elements, and in which a first random spatial distribution of the first plurality of fiducial elements differs from a second random spatial distribution of the second plurality of fiducial elements. In some configurations, a composition may comprise a first array and a second array, in which the first array comprises a first plurality of fiducial elements, in which the second array comprises a second plurality of fiducial elements, in which a first random spatial distribution of the first plurality of fiducial elements differs from a second random spatial distribution of the second plurality of fiducial elements, and in which a first subset of fiducial elements of the first plurality of fiducial elements has a same spatial distribution as a second subset of fiducial elements of the second plurality of fiducial elements. For example, a plurality of arrays may be produced by a method including an initial step of performing a lithographic method that forms a plurality of optically passive moieties (e.g., deposited metal layers) at fixed addresses on each array (e.g., based on a reticle pattern for the lithographic method, etc.), and a subsequent step of depositing a plurality of optically active moieties (e.g., fluorescently-labeled polymer particles) on each array of the plurality of arrays such that each array has a unique, random spatial distribution of optically active moieties.

An array, as set forth herein may comprise two or more subregions or subarrays. In some configurations, each subregion or subarray of two or more subregions or subarrays may be spatially separated or spatially divided from each other subregion or subarray of two or more subregions or subarrays. For example, an array with 1000000 array sites (e.g., a 1000×1000-site rectangular array) may be divided into 100 subarrays (e.g., 100 100×100-site rectangular arrays). In particular configurations, a first subregion or subarray may be spatially separated or spatially divided from a second subregion or subarray by a dividing interstitial region, in which the dividing interstitial region comprises a larger characteristic dimension (e.g., length, width, etc.) than the one or more interstitial regions that divide the array sites of the first subregion or subarray and/or the second subregion or subarray. In other configurations, each subregion or subarray of two or more subregions or subarrays may not be spatially separated or spatially divided from each other subregion or subarray of two or more subregions or subarrays. For example, boundaries of subregions or subarrays may be defined by optically-passive fiducial elements placed at corners of each subregion or subarray. A single-analyte array, as set forth herein, may comprise a plurality of subregions or subarrays, in which each subregion or subarray comprises one or more subdistributions of fiducial elements. A single-analyte array, as set forth herein, may comprise a plurality of subregions or subarrays, in which each subregion or subarray comprises a random spatial distribution of fiducial elements that is unique from all other subregions or subarrays.

An array, as set forth herein, may be characterized during an interrogation process to determine an occupancy rate of the array or a subregion or subarray thereof. An occupancy rate may refer to a fraction or percentage of array sites producing a detectable signal based upon detection by a detection device. For example, on an array comprising a random spatial distribution of fiducial elements, an occupancy rate may comprise a fraction or percentage of sites containing a fiducial element. In another example, on an array comprising a plurality of single analytes and a random spatial distribution of fiducial elements, in which single analytes are contacted with detectable affinity agents that are configured to bind a fraction of the single analytes, an occupancy rate may comprise a fraction or percentage of sites containing an affinity agent or a fiducial element. In some configurations, an array may comprise a plurality of subregions or subarrays, in which an occupancy rate of a first subregion or subarray and a second subregion or subarray may vary on a spatial or temporal basis. For example, an array may comprise a plurality of subarrays, in which each subarray comprises a random spatial distribution of fiducial elements, and in which the occupancy rate of fiducial elements for any subarray of the plurality of subarrays may be predicted by a probabilistic distribution (e.g., a normal distribution, a Poisson distribution, a binomial distribution, etc.). In another example, an array may comprise a plurality of subarrays, in which each subarray comprises a plurality of single analytes and a random spatial distribution of fiducial elements, in which, at a first time, a subarray comprises a first occupancy rate (e.g., 0.5) due to the binding of a first affinity agent to a first fraction of single analytes on the subarray, and in which, at a second time, the subarray comprises a second rate (e.g. 0.01) due to the binding of a second affinity agent to a second fraction of single analytes on the subarray.

During a single-analyte assay or process that utilizes a single-analyte array, as set forth herein, an analytical reagent or a plurality of analytical reagents may be bound to sites of a plurality of sites of the single-analyte array. In some cases, an analytical reagent may be non-covalently bound to a site of the plurality of sites of a single-analyte array. For example, affinity agents may be bound to polypeptides of a single polypeptide array for epitope mapping or sequencing assays. In other cases, an analytical reagent may be covalently bound to a site of a plurality of sites of a single-analyte array. For example, fluorescent nucleotides or amino acids may be present in, or incorporated into, nucleic acids or polypeptides, respectively, for single-molecule fluorosequencing assays. An analytical agent may comprise a detectable label (e.g., a fluorophore, a luminophore, a nucleic acid tag, etc), in which binding of the analytical agent to an analyte at a site of a single-analyte array can be detected by detecting a signal from the detectable label at the site of the single-analyte array.

In some cases, a plurality of analytical reagents may be bound to a plurality of analyte-containing sites. In particular cases, a plurality of analytical reagents may be bound to a subset of a plurality of analyte-containing sites. In some cases, a plurality of detectable signals from bound analytical reagents at analyte-containing sites of a single-analyte array may be insufficient to determine the address of all analyte-containing sites of the single-analyte array. A plurality of analytical reagents may be bound to a subset of a plurality of analyte-containing sites, in which the subset of analyte-containing sites comprises no more than about 50%, 45%, 40%, 35%, 30%, 25%, 20%, 15%, 10%, 5%, 1%, 0.5%, 0.1%, 0.05%, 0.01%, 0.001%, 0.0001%, 0.00001%, 0.000001%, or less than 0.000001% of a total quantity of analyte-containing sites of a single-analyte array, or a subarray thereof. Alternatively or additionally, a plurality of analytical reagents may be bound to a subset of a plurality of analyte-containing sites, in which the subset of analyte-containing sites comprises at least about 0.000001%, 0.00001%, 0.0001%, 0.001%, 0.01%, 0.05%, 0.1%, 0.5%, 1%, 5%, 10%, 15%, 20%, 25%, 30%, 35%, 40%, 45%, 50%, or more than 50% of a total quantity of analyte-containing sites of a single-analyte array, or a subarray thereof.

In some cases, an analytical agent may not be detected at an array site comprising a fiducial element. For example, a fiducial element may comprise a passivating moiety (e.g., PEGylation, a polysaccharide, a polyionic polymer, etc.) or other chemical moiety that is configured to inhibit binding of an analytical agent (e.g., an affinity agent) to the fiducial element. In other cases, an analytical agent may be detected at an array site comprising a fiducial element. For example, a fiducial element and an analyte may be co-localized at a site, in which an analytical reagent is bound to the analyte at the site. A plurality of analytical reagents may be bound to a subset of a plurality of fiducial element-containing sites, in which the subset of fiducial element-containing sites comprises no more than about 50%, 45%, 40%, 35%, 30%, 25%, 20%, 15%, 10%, 5%, 1%, 0.5%, 0.1%, 0.05%, 0.01%, 0.001%, 0.0001%, 0.00001%, 0.000001%, or less than 0.000001% of a total quantity of fiducial element-containing sites of a single-analyte array, or a subarray thereof. Alternatively or additionally, a plurality of analytical reagents may be bound to a subset of a plurality of fiducial element-containing sites, in which the subset of fiducial element-containing sites comprises at least about 0.000001%, 0.00001%, 0.0001%, 0.001%, 0.01%, 0.05%, 0.1%, 0.5%, 1%, 5%, 10%, 15%, 20%, 25%, 30%, 35%, 40%, 45%, 50%, or more than 50% of a total quantity of fiducial element-containing sites of a single-analyte array, or a subarray thereof.

In some embodiments, a fiducial marker can be present on a substrate to provide orientation of a sample (e.g., an analyte sample) on the substrate. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of capture spots on the substrate. In some embodiments, a fiducial marker can be an immobilized molecule with which a detectable analytical agent or signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the analyte sample is stained and/or contacted with analytical agents (e.g. affinity agents) to visualize or image the analyte sample on the substrate. In some embodiments, it can be advantageous to use a label or marker that can be detected using the same conditions (e.g., imaging conditions) used to detect an analyte of interest.

In some embodiments, fiducial markers are included to facilitate the orientation of an analyte sample in an image captured thereof. Any number of methods for marking an array can be used such that a marker is detectable when the substrate is imaged. For instance, a molecule, e.g., a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be stamped, attached, or synthesized on the substrate. Typically, an image of the substrate is taken, and the position of the fiducial marker on the substrate can be confirmed by viewing the image.

In some examples, fiducial markers can surround a substrate and/or an array thereon. In some embodiments, the fiducial markers allow for detection of, e.g., mirroring. In some embodiments, the fiducial markers completely surround the array. In some embodiments, the fiducial markers do not completely surround the array, for example, partially surrounding the array. In some embodiments, the fiducial markers identify the corners of the array. In some embodiments, one or more fiducial markers identify the center of the array. In some embodiments, a pattern of all, or at least a subset of addresses in an array can function as a fiducial marker. The subset can include at least 2, 3, 4, 5, 10 or more addresses of the array.

In another aspect, provided herein is an array comprising: a) a solid support comprising a plurality of sites, wherein each site is located at a unique address, and wherein each site is optically resolvable from each other site of the plurality of sites, b) a plurality of first fiducial elements, wherein each first fiducial element comprises an optically active moiety, wherein each the plurality of first fiducial elements is coupled to sites of the plurality of sites, and wherein the sites of the plurality of sites comprises a random spatial distribution, and c) one or more second fiducial elements, wherein the one or more fiducial elements comprises an optically passive moiety, and wherein the optically passive moiety comprises a reflective surface (e.g., a surface that is detectable during brightfield imaging). In some configurations, an array may comprise one or more optically passive moieties, wherein the one or more optically passive moieties comprise etched features of the solid support. In other cases, an array may comprise one or more optically passive moieties, wherein the one or more optically passive moieties comprise deposited layers (e.g. metal layers, metal oxide layers, etc.). In some configurations, the one or more optically passive moieties may be disposed on one or more sites of a plurality of sites of an array. In other configurations, the one or more optically passive moieties may be disposed on an interstitial region of an array.

A method, as set forth herein, may comprise: a) providing an array or solid support, as set forth herein, comprising one or more fiducial elements comprising an optically passive moiety (e.g., an etched feature, a reflective surface, a deposited layer, etc.), b) depositing a plurality of fiducial elements comprising optically active moieties on the array, and c) optionally depositing a plurality of analytes on the array.

A method, as set forth herein, may comprise providing an array or a solid support, as set forth herein, comprising substantially no optically passive moieties. A method, as set forth herein, may comprise providing an array or a solid support, as set forth herein, comprising substantially no optically active moieties.

Array Systems

In an aspect, provided herein is a system, comprising: a) an array, as set forth herein, b) a sensing device, and c) a retaining device, in which the retaining device is configured to position a region of the array relative to the sensing device. A system may comprise a retaining device, in which the retaining device is configured to position a landmarking region of an array relative to a sensing device. A system may comprise a retaining device, in which the retaining device is configured to position a fiducial element of a plurality of fiducial elements of an array relative to a sensing device.

Figure 10:
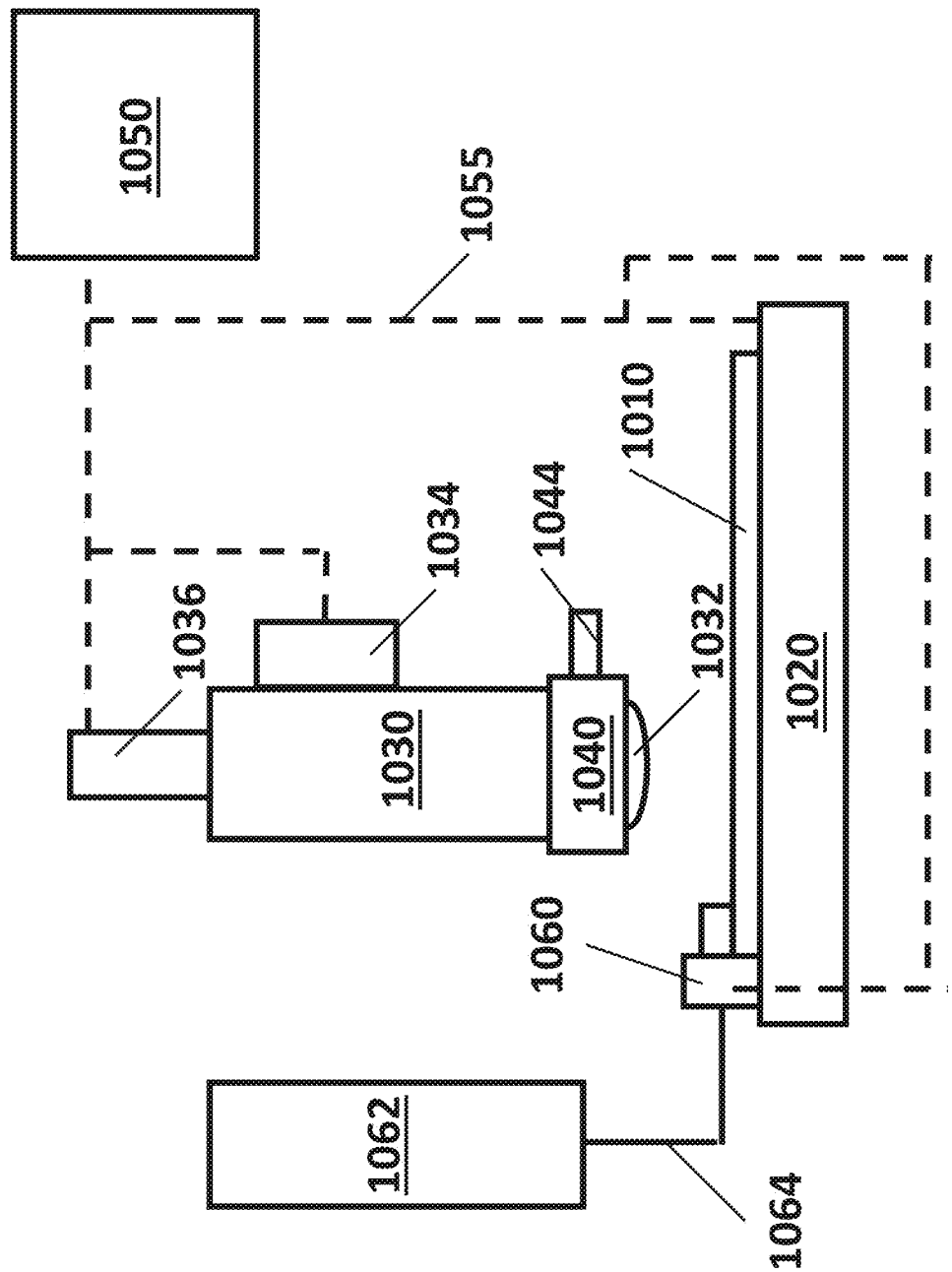
FIG. 10 illustrates components of an array-based system, including a detection system and a computer system, in accordance with some embodiments.

FIG. 10 illustrates an embodiment of an array-based system. An array 1010, as set forth herein, is mounted on a stage 1020. Optionally, stage 1020 can be functionally coupled to a motion control apparatus that provides translational motion for the array relative to a sensing device in one or both of the x and y dimensions (the xy plane being orthogonal to the axis along which signals are detected in the system). The array 1010 couples to a fluidic system 1060 which optionally comprises one or more fluid reservoirs 1062 and fluid transfer paths 1062 (e.g., tubing, piping, pumps, etc.). The array 1010 is disposed in a detection path of a sensing device. As shown, the sensing device can be an optical detection apparatus comprising an optical objective 1032, an optical sensor 1034 (e.g., a CCD, a CMOS sensor, etc.), and additional optical components 1030 (e.g., mirrors, beam-splitters, lenses, diaphragms, apertures, filters, etc.). Optionally, the system includes an excitation source 1036 (e.g., a laser, lamp, bulb, electron gun, etc.), for example, allowing luminescence detection. A sensing device may further comprise an autofocusing device 1040, including a light source 1044 for the autofocusing device 1040 along the z axis (the z axis being orthogonal to the xy plane). One or more components may have data connectivity or electrical connectivity with a computer system, as set forth herein, including one or more processors, and one or more process control units (e.g., drivers, driver boards, etc.).

Figure 13:
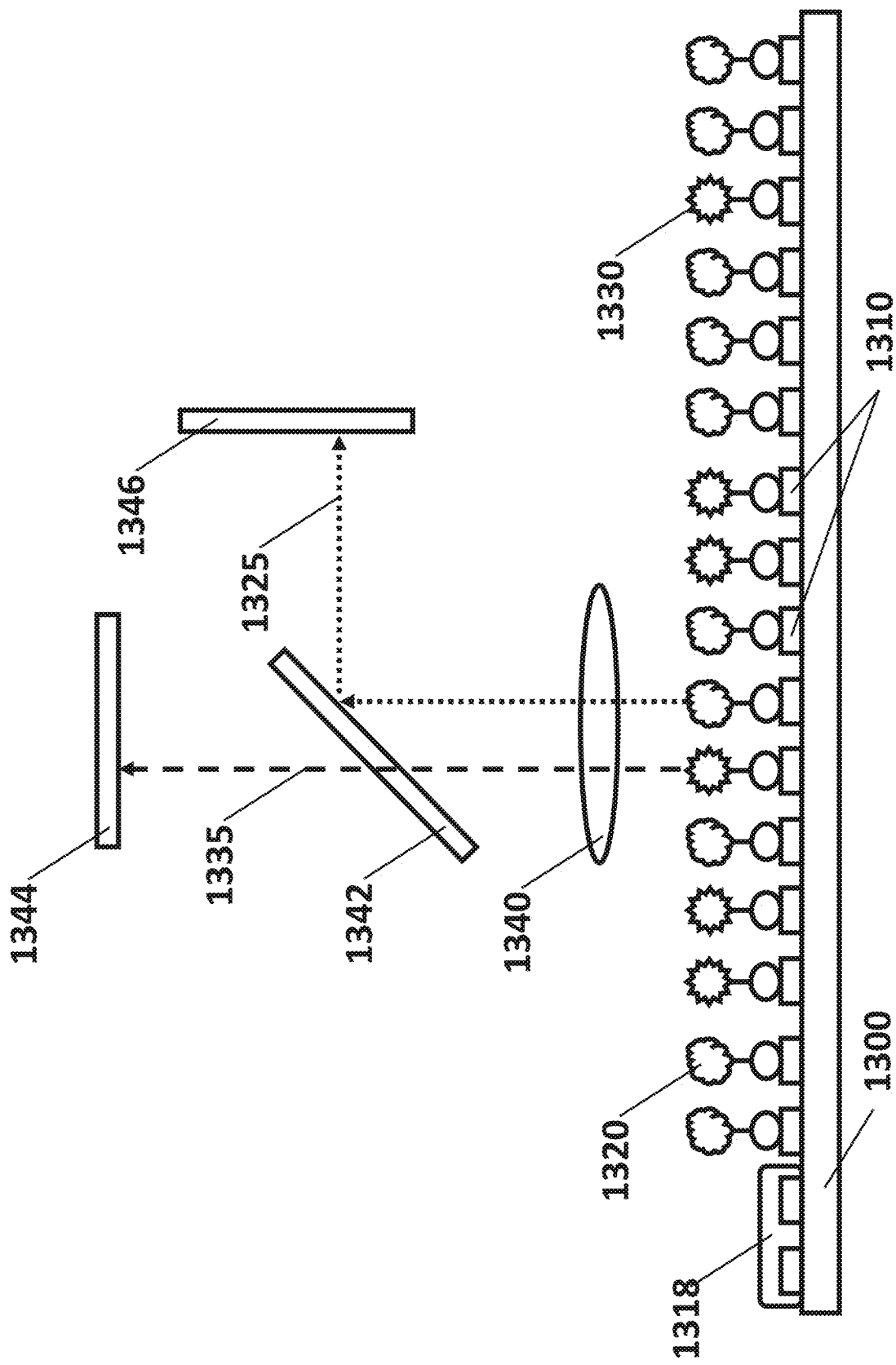
FIG. 13 depicts a multiplexed array-based sensing system, in accordance with some embodiments.

FIG. 13 illustrates an embodiment of an array-based detection system that is configured for multiplexed detection. A solid support 1300 comprises a plurality of sites 1310 and optionally a landmarking region 1318. A plurality of fiducial elements 1330 are coupled to sites 1310 of the plurality of sites in a random spatial distribution. A plurality of analytes 1320 occupy sites 1310 of the plurality of sites that do not comprise a fiducial element 1330. The analytes of interest 1320 are configured to produce a first detectable optical signal 1325 and the fiducial elements 1330 are configured to produce a second detectable optical signal 1335. A sensing device comprises an objective lens 1340 that collects optical signals 1335 from the fiducial elements 1330 and analytes of interest 1320 and transmit both signals to a optical separator 1342 (e.g., a beam-splitter, a dichroic mirror, etc.). The second detectable optical signal 1335 from a fiducial element 1330 is transmitted by the optical separator 1342 to a sensor 1344 that is configured to detect the second detectable optical signal 1335. The first detectable optical signal 1325 from an analyte of interest 1320 is relayed by the optical separator 1342 to a sensor 1346 that is configured to detect the first detectable optical signal 1325. The system may be configured to simultaneously or sequentially sense optical signals from the fiducial elements 1330 and the analytes of interest 1320.

An array-based system may comprise a retaining device that holds and/or is contacted by an array, as set forth herein.

A retaining device may possess one or more utilities, including: i) retaining an array in a fixed position relative to the retaining device, ii) fastening an array to the retaining device, iii) preventing mechanical deformation (e.g., bending, twisting, torsion, elongation) of an array, iv) providing communication with one or more physical systems (e.g., electrical, fluidic, magnetic, thermal, data, etc.), v) positioning an array relative to a sensing device, vi) sensing an array datum (e.g., address, temperature, fluid pressure, etc.), in which the array datum does not pertain to only a single site of an array, vii) communicating an array datum to a computer-based system, viii) altering (e.g., rotating, tilting, translating, etc.) a position of an array relative to a sensing device, ix) contacting an array with a fluidic system, and x) combinations thereof.

In some configurations, an array-based system may comprise a motion control system. A motion control system may comprise one or more components that alter a position of an array, as set forth herein, relative to a sensing device. A motion control system may comprise a translation stage (i.e., a device configured to provide translation along one or more of an x-axis, a y-axis, and a z-axis relative to a component of an array-based system). A motion control system may comprise a tilt stage (i.e., a device configured to provide rotation about one or more axes relative to a component of an array-based system). A motion control system may be coupled to a component of an array-based system, such as an array, a retaining device, or a sensing device. For example, a retaining device may comprise a fastening system for retaining an array at a fixed position, and a translation stage, in which the translation stage is configured to adjust a position of the retaining device relative to the sensing device, thereby adjusting the position of the array relative to the sensing device. In another example, a motion control system may be coupled to a sensing device (e.g., an optical microscope, a camera, a sensor, etc.), in which the motion control system is configured to adjust a position of the sensing device relative to an array. A motion control system may be configured to translate an array along a translation axis (e.g., x-axis, y-axis, z-axis), in which the translation axis is coplanar with a planar surface of the array. A motion control system may be configured to translate an array along a translation axis, in which the translation axis is not coplanar with a planar surface of the array. A motion control system may be configured to rotate an array along a rotation axis that is coplanar with a planar surface of an array. A motion control system may be configured to rotate an array along a rotation axis that is not coplanar with a planar surface of an array.

A motion control system may be configured to translate an array incrementally, for example in increments of no more than about 1000 nanometers (nm), 500 nm, 250 nm, 100 nm, 50 nm, 25 nm, 20 nm, 15 nm, 10 nm, 9 nm, 8 nm, 7 nm, 6 nm, 5 nm, 4 nm, 3 nm, 2 nm, 1 nm, 0.9 nm, 0.8 nm, 0.7 nm, 0.6 nm, 0.5 nm, 0.4 nm, 0.3 nm, 0.2 nm, 0.1 nm, or less than 0.1 nm. Alternatively or additionally, a motion control system may be configured to translate an array in increments of at least about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 15 nm, 20 nm, 25 nm, 50 nm, 100 nm, 250 nm, 500 nm, 1000 nm, or more than 1000 nm. A motion control system may translate an array with a positional error of no more than about 100 nm, 50 nm, 25 nm, 20 nm, 15 nm, 10 nm, 5 nm, 1 nm, 0.5 nm, 0.1 nm, or less than 0.1 nm. Alternatively or additionally, a motion control system may translate an array with a positional error of at least about 0.1 nm, 0.5 nm, 1 nm, 5 nm, 10 nm, 15 nm, 20 nm, 25 nm, 50 nm, 100 nm, or more than 100 nm.

A motion control system may be configured to tilt or rotate an array incrementally, for example in increments of no more than about 1 radian (rad), 500 milliradians (mrad), 100 mrad, 50 mrad, 10 mrad, 5 mrad, 1 mrad, 500 microradians (μrad), 250 μrad, 100 μrad, 50 μrad, 10 μrad, 5 μrad, 1 μrad, 0.5 μrad, 0.1 μrad, 0.01 μrad, 0.001 μrad, or less than 0.001 μrad. Alternatively or additionally, a motion control system may be configured to tilt or rotate an array in increments of at least about 0.001 μrad, 0.01 μrad, 0.1 μrad, 0.5 μrad, 1 μrad, 5 μrad, 10 μrad, 50 μrad, 100 μrad, 250 μrad, 500 μrad, 1 mrad, 5 mrad, 10 mrad, 50 mrad, 100 mrad, 500 mrad, 1 rad, or more than 1 rad. A motion control system may be configured to tilt or rotate an array with a rotational error of no more than about 1 radian (rad), 500 milliradians (mrad), 100 mrad, 50 mrad, 10 mrad, 5 mrad, 1 mrad, 500 microradians (gad), 250 μrad, 100 μrad, 50 μrad, 10 μrad, 5 μrad, 1 μrad, 0.5 μrad, 0.1 μrad, 0.01 μrad, 0.001 μrad, 0.0001 μrad, or less than 0.0001 μrad. Alternatively or additionally, a motion control system may be configured with a rotational error at least about 0.0001 μrad, 0.001 μrad, 0.01 μrad, 0.1 μrad, 0.5 μrad, 1 μrad, 5 μrad, 10 μrad, 50 μrad, 100 μrad, 250 μrad, 500 μrad, 1 mrad, 5 mrad, 10 mrad, 50 mrad, 100 mrad, 500 mrad, 1 rad, or more than 1 rad.

An array-based system may utilize an array comprising a landmarking region, as set forth herein. A landmarking region may comprise one or more fiducial elements. In some configurations, an array-based system may be configured to position an array relative to a sensing device based upon an address of a landmarking region on the array. An array-based system may be configured to position an array at an initial position, intermediate position, or final position relative to a sensing device based upon an address of a landmarking region on the array during an array-based process or assay, or a step thereof. For example, each detection cycle of an array-based assay may comprise a step of positioning a landmarking region within a field-of-view of a sensing device, in which the landmarking region denotes a starting point for detection by the sensing device. With respect to an alignment of an array and a sensing device, an initial position may refer to a position during a sensing process in which a first site or sites of an array are sensed by a sensing device. With respect to an alignment of an array and a sensing device, a final position may refer to a position during a sensing process in which all sites of an array have been sensed by a sensing device. For example, a sensing device may be traced in a converging, spiral-like path relative to an array of sites, thereby arriving at a final position in a central or internal region of the array when all sites have been sensed. With respect to an alignment of an array and a sensing device, an intermediate position may refer to a position during a sensing process in which less than all sites of an array have been sensed by a sensing device. In some configurations, an array may comprise a first landmarking region and a second landmarking region. In a particular configuration, an array may comprise a first landmarking region and a second landmarking region, in which a field-of-view of a sensing device in optical communication with the array comprises the first landmarking region and does not comprise the second landmarking region. In some configurations, an array may comprise a first landmarking region and a second landmarking region, in which the first landmarking region is contained in a field-of-view of a sensing device at an initial position, and the second landmarking region is contained in the field-of-view of the sensing device at a final position. In some configurations, an array may comprise a first landmarking region and a second landmarking region, in which the first landmarking region is contained in a field-of-view of a sensing device at an initial position, and the second landmarking region is contained in the field-of-view of the sensing device at an intermediate position.

An array-based system may comprise a sensing device. A sensing device may be configured to obtain a detectable signal from an array, or a site thereof. A sensing device may be configured to obtain a plurality of detectable signals, in which each detectable signal of the plurality of detectable signals is obtained from a different site of an array comprising a plurality of sites. In some configurations, a sensing device may be configured to obtain a plurality of detectable signals, in which each detectable signal of the plurality of detectable signals is obtained from a different site of an array comprising a plurality of sites, and in which each detectable signal of the plurality of detectable signals is distinguishable from each other detectable signal at single-analyte resolution. In some configurations, a sensing device may comprise an optical sensing device. In other configurations, a sensing device may comprise an electrical sensing device or a magnetic sensing device.

A sensing device of an array-based system may comprise a sensor. In some configurations, a sensing device may comprise a pixel-based sensor. Exemplary pixel-based sensors may include a charge-coupled device (CCD) sensor, or a complementary metal-on-semiconductor (CMOS) sensor. A pixel-based sensor may comprise a grid of pixels, such as a rectangular or hexagonal grid of pixels. A grid of pixels may comprise at least about 1000 pixels, 10000 pixels, 100000 pixels, 1 megapixel (Mp), 5 Mp, 10 Mp, 15 Mp, 20 Mp, 25 Mp, 30 Mp, 40 Mp, 50 Mp, 75 Mp, 100 Mp, 200 Mp, 300 Mp, 500 Mp, 1000 Mp, 5000 Mp, 10000 Mp, or more than 10000 Mp. Alternatively or additionally, a grid of pixels may comprise no more than about 10000 Mp, 5000 Mp, 1000 Mp, 500 Mp, 300 Mp, 200 Mp, 100 Mp, 75 Mp, 50 Mp, 40 Mp, 30 Mp, 25 Mp, 20 Mp, 15 Mp, 10 Mp, 5 Mp, 1 Mp, 100000 pixels, 10000 pixels, 1000 pixels, or less than 1000 pixels. A grid of pixels may comprise an aspect ratio, in which an aspect ratio comprises a ratio of a largest characteristic dimension (e.g., length, width, diameter, etc.) to a smallest characteristic dimension (e.g., length, width, diameters, etc.). A grid of pixels may comprise an aspect ratio of at least about 1:1, 5:4, 4:3, 3:2, 2:1, 5:1, 10:1, 20:1, 50:1, 100:1, 500:1, 1000:1, 10000:1, 100000:1, 1000000:1, or more than 1000000:1. Alternatively or additionally, a grid of pixels may comprise an aspect ratio of no more than about 1000000:1, 100000:1, 10000:1, 1000:1, 500:1, 100:1, 50:1, 20:1, 10:1, 5:1, 2:1, 3:2, 4:3, 5:4, or less than 5:4. A sensor may comprise a 1-dimensional grid of pixels (e.g., a single column of pixels). A pixel of a sensor may be configured to detect a particular wavelength of light, or a range of wavelengths of light. A pixel of a sensor may be configured to detect a photon of light, in which the photon comprises an emission wavelength or an excitation wavelength, as set forth herein.

A sensing device may further comprise one or more optical components. An optical component may comprise a component has one or more optical functions, including: i) collecting a detectable optical signal, ii) altering a collected optical signal, and/or iii) transmitting a detectable signal to a sensor of a sensing device. Altering a collected optical signal may include one or more optical alterations, including: i) collimating an optical beam, ii) focusing an optical beam, iii) de-focusing an optical beam, iv) scattering an optical beam, v) de-scattering an optical beam, vi) polarizing an optical beam, vii) de-polarizing an optical beam, viii) filtering an optical beam, ix) re-orienting an optical beam, and x) combinations thereof. An optical component may comprise a lens (e.g., focusing lens, de-focusing lens, collimating lens, polarizing lens, filtering lens, etc.) or mirror (dichroic mirror, reflective mirror, beam-splitter, etc.). An optical component may comprise an objective lens. An optical component may comprise an aperture, such as a rectangular or circular aperture.

An optical sensing device may be characterized by one or more parameters, such as magnification, numerical aperture, and/or field-of-view. An optical sensing device may have a characterized magnification, such as about 5×, 10×, 15×, 20×, 25×, 30×, 35×, 40×, 45×, 50×, 55×, 60×, 65×, 70×, 75×, 80×, 85×, 90×, 95×, 100×, or more than 100×. An optical sensing device may have a characterized magnification, such as at least about 5×, 10×, 15×, 20×, 25×, 30×, 35×, 40×, 45×, 50×, 55×, 60×, 65×, 70×, 75×, 80×, 85×, 90×, 95×, 100×, or more than 100×. Alternatively or additionally, an optical sensing device may have a characterized magnification, such as no more than about 100×, 95×, 90×, 85×, 80×, 75×, 70×, 65×, 60×, 55×, 50×, 45×, 40×, 35×, 30×, 25×, 20×, 15×, 10×, 5×, or less than 5×.

An optical sensing device may comprise a characterized or estimated numerical aperture. An optical sensing device may have a characterized or estimated numerical aperture of at least about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, or more than 1.5. Alternatively or additionally, an optical sensing device may comprise a characterized or estimated numerical aperture of no more than about 1.5, 1.45, 1.4, 1.35, 1.3, 1.25, 1.2, 1.15, 1.1, 1.05, 1.0, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.01, or less than 0.01.

An optical sensing device may comprise a characterized field-of-view. A field-of-view may be given as a largest dimension (e.g., length, width, diameter) of an area of an array detected by an optical sensing device. An optical sensing device may comprise a field-of-view of at least about 1 micron (µm), 5 µm, 10 µm, 50 µm, 100 µm, 500 µm, 1 millimeter (mm), 5 mm, 1 centimeter (cm), 5 cm, 10 cm, or more than 10 cm. Alternatively or additionally, an optical sensing device may comprise a field-of-view of no more than about 10 cm, 5 cm, 1 cm, 5 mm, 1 mm, 500 µm, 100 µm, 50 µm, 10 µm, 5 µm, 1 µm, or less than 1 µm. A field-of-view may be given as an area including, for example, at least 1 square micron ($\mu m^2$), 4 $\mu m^2$, 25 $\mu m^2$, 100 $\mu m^2$, 1 square millimeter ($mm^2$) 4 $mm^2$, 25 $mm^2$ 100 $mm^2$, 1 square centimeter ($cm^2$), 4 $cm^2$, 25 $cm^2$, 100 $cm^2$, or more. Alternatively or additionally, a field-of-view can be at most 100 $cm^2$, 25 $cm^2$, 4 $cm^2$, 1 $cm^2$, 100 $mm^2$, 25 $mm^2$, 4 $mm^2$, 1 $mm^2$, 100 $\mu m^2$, 25 $\mu m^2$, 4 $\mu m^2$, 1 $\mu m^2$, m or less.

A pixel-based sensor of a sensing device of an array-based system may be oriented and/or aligned with an array. In some configurations, each pixel of a pixel-based sensor may be configured to detect a detectable signal from a subarea of an array that is collected within a field-of-view of a sensing device. In some configurations, a pixel-based sensor may comprise a plurality of pixels, in which each pixel is configured to detect a detectable signal from a site of an array. In some configurations, a pixel-based sensor may comprise a plurality of pixels, in which each site of an array is detected by a pixel of the plurality of pixels. In some configurations, a pixel-based sensor may comprise a plurality of pixels, in which each site of an array is detected by a pixel of the plurality of pixels, and in which each pixel only detects a detectable signal from a single site of the array. In some configurations, a pixel-based sensor may comprise a plurality of pixels, in which each site of an array is detected by two or more pixels of the plurality of pixels. In some configurations, a pixel-based sensor may comprise a plurality of pixels, in which each site of an array is detected by two or more pixels of the plurality of pixels, and in which the two or more pixels only detect a detectable signal from a single site.

An array-based system may be configured to operate in a non-isothermal condition. A non-isothermal condition may arise in an array-based system due to heat sources or sinks, including endogenous heat sources or sinks, and/or exogenous heat sources or sinks. Endogenous heat sources or sinks may include system components such as computer processors, motors, fans, compressors, motion control devices, and heat exchangers. Exogenous heat sources or sinks may include any external sources of heat variation, including climate control systems, natural temperature variations, and unforeseen circumstances (e.g., power outages). A non-isothermal condition may affect an array-based system due to thermal expansion and/or contraction induced by temperature changes in the system. Thermal expansion and/or contraction affects may affect an array-based system due to variations in optical alignment and focusing that occur for both upstream (i.e., excitation-side) optics and downstream (i.e., emission-side) optics. For array-based systems with multi-spectral detection utilizing multiple sensors or light sources, thermal variations due to non-isothermal conditions (spatially or temporally) can cause differential changes in alignment and/or focusing between differing optical paths. A method, as set forth herein, that is implemented on an array-based system may experience a temperature change over the time course of the method with an absolute value of at least about 1° C., 2° C., 3° C., 4° C., 5° C., 10° C., 15° C., 20° C., or more than 20° C. Alternatively or additionally, a method, as set forth herein, that is implemented on an array-based system may experience a temperature change over the time course of the method with an absolute value of no more than about 20° C., 15° C., 10° C., 5° C., 4° C., 3° C., 2° C., 1° C., or less than 1° C.

An array-based system may further comprise a computer system. A computer system may comprise one or more processors that are configured to receive data from a sensing device and/or other component of an array-based system (e.g., a retaining device). A computer system may be configured to obtain data from a sensing device, in which the data comprises a detectable signal from an array site comprising a fiducial element. A computer system may be configured to obtain data from a sensing device, in which the data comprises a detectable signal from an array site comprising an analyte. A computer system may be configured to: a) obtain data comprising an optical image of an array, and b) identify presence or absence of a fiducial element at each site of a plurality of sites of the array based upon the optical image of the array. A computer system may be configured to: a) obtain data comprising a plurality of optical images of an array, and b) identify presence or absence of a fiducial element at each site of a plurality of sites of the array based upon the plurality of optical images of the array. In some configurations, a computer system may comprise a processor comprising an algorithm, in which the algorithm is configured to: a) receive data comprising an optical image of an array, and b) identify presence or absence of a fiducial element at each site of a plurality of sites of the array based upon the optical image of the array. In some configurations, a computer system may comprise a processor comprising an algorithm, in which the algorithm is configured to: a) receive data comprising a plurality of optical images of an array, and b) identify presence or absence of a fiducial element at each site of a plurality of sites of the array based upon the plurality of optical images of the array.

The present disclosure provides computer systems (e.g. computer control systems) that are programmed to implement methods, algorithms or functions set forth herein. Optionally, a computer system set forth herein can be a component of a detection system. A computer system can be programmed or otherwise configured to: (a) receive an input set forth herein such as a plurality of sensed data from one or more fields-of-view at differing addresses of an array, (b) register the plurality of sensed data from one or more fields-of-view to form a combined field-of-view, and (c) store the combined field-of-view in a data structure comprising an array map.

Figure 20:
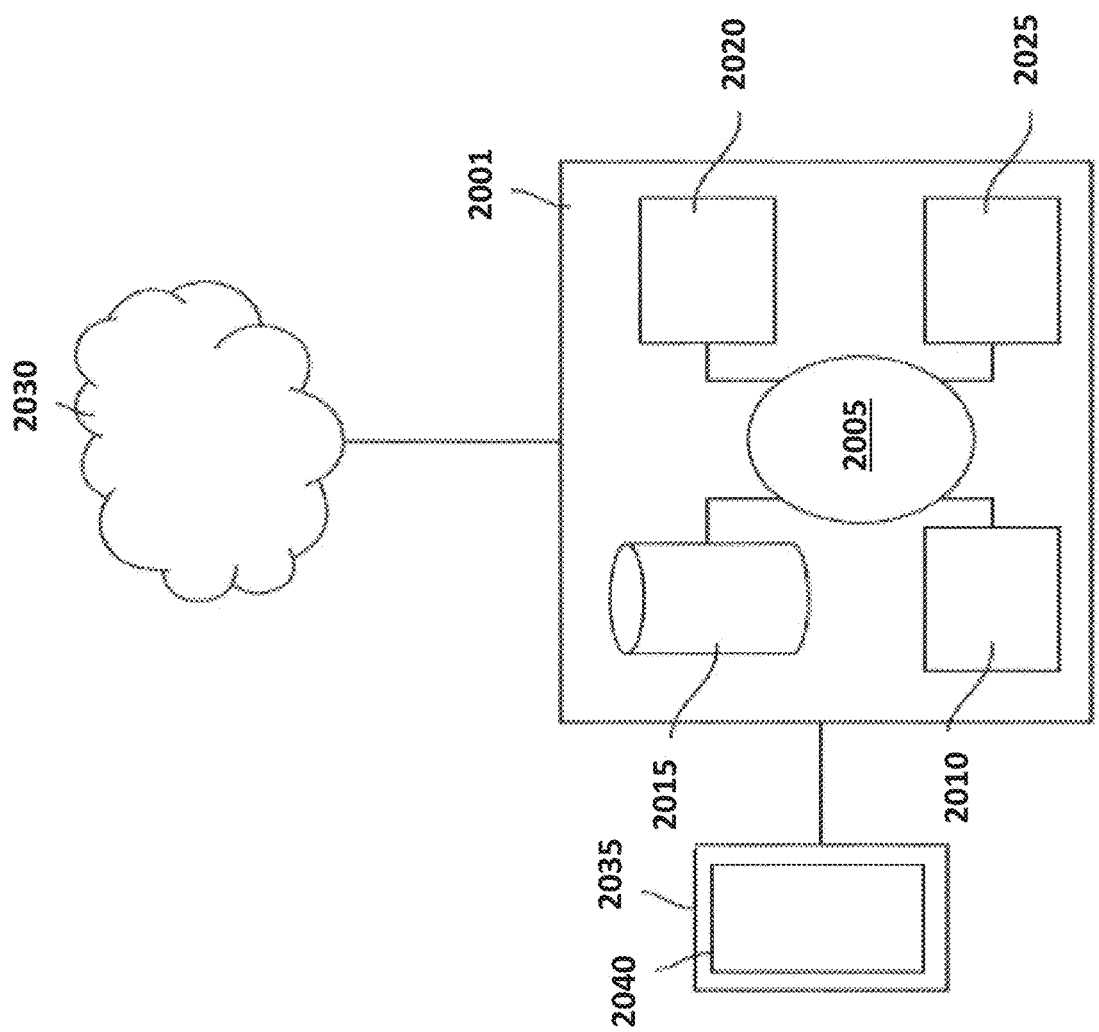
FIG. 20 shows a schematic of a computer system, in accordance with some embodiments.

FIG. 20 shows an exemplary computer system 2001. The computer system 2001 can be an electronic device of a detection system, the electronic device being integral to the detection system or remotely located with respect to the detection system. For example, the electronic device can be a mobile electronic device. The computer system 2001 includes a computer processing unit (CPU, also "processor" and "computer processor" herein) 2005, which can be a single core or multi core processor, or a plurality of processors for parallel processing. The computer system 2001 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data. The computer system 2001 can be operatively coupled to a computer network ("network") 2030 with the aid of the communication interface 2020. The network 2030 can be the Internet, an internet and/or extranet, or an intranet and/or extranet that is in communication with the Internet. The network 2030 in some cases is a telecommunication and/or data network. The network 2030 can include one or more computer servers, which can enable distributed computing, such as cloud computing. For example, one or more computer servers may enable cloud computing over the network 2030 ("the cloud") to perform various aspects of analysis, calculation, and generation of the present disclosure, such as, receiving sensed information comprising detected signals from an array, assigning detected signals to spatial addresses, storing information regarding detected signals and spatial addresses in a data structure, comparing information within a data structure to other information in the data structure of information in a different data structure, and sending and receiving data, information, or instructions from an array-based system, as set forth herein. Such cloud computing may be provided by cloud computing platforms such as, for example, Amazon Web Services (AWS), Microsoft Azure, Google Cloud Platform, and IBM cloud. The network 2030, in some cases with the aid of the computer system 2001, can implement a peer-to-peer network, which may enable devices coupled to the computer system 2001 to behave as a client or a server.

The CPU 2005 can execute a sequence of machine-readable instructions, which can be embodied in a program or software. The instructions may be stored in a memory location, such as the memory 2010. The instructions can be directed to the CPU 2005, which can subsequently program or otherwise configure the CPU 2005 to implement methods of the present disclosure. Examples of operations performed by the CPU 2005 can include fetch, decode, execute, and writeback.

The CPU 2005 can be part of a circuit, such as an integrated circuit. One or more other components of the system 2001 can be included in the circuit. In some cases, the circuit is an application specific integrated circuit (ASIC).

The storage unit 2015 can store files, such as drivers, libraries and saved programs. The storage unit 2015 can store user data, e.g., user preferences and user programs. The computer system 2001 in some cases can include one or more additional data storage units that are external to the computer system 2001, such as located on a remote server that is in communication with the computer system 2001 through an intranet or the Internet.

The computer system 2001 can communicate with one or more remote computer systems through the network 2030. For instance, the computer system 2001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2001 via the network 2030.

Methods as described herein can be implemented by way of machine (e.g., computer processor) executable code stored on an electronic storage location of the computer system 2001, such as, for example, on the memory 2010 or electronic storage unit 2015. The machine executable or machine-readable code can be provided in the form of software. During use, the code can be executed by the processor 2005. In some cases, the code can be retrieved from the storage unit 2015 and stored on the memory 2010 for ready access by the processor 2005. In some situations, the electronic storage unit 2015 can be precluded, and machine-executable instructions are stored on memory 2010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2001 can include or be in communication with an electronic display 2035 that comprises a user interface (UI) 2040 for providing, for example, user selection of algorithms, binding measurement data, candidate proteins, and databases. Examples of Uls include, without limitation, a graphical user interface (GUI) and web-based user interface.

Methods and systems of the present disclosure can be implemented by way of one or more algorithms. An algorithm can be implemented by way of software upon execution by the central processing unit 2005. The algorithm can, for example, receive information of empirical measurements of unknown proteins in a sample, compare information of empirical measurements against a database comprising a plurality of protein sequences corresponding to candidate proteins, generate probabilities of a candidate protein generating the observed measurement outcome set, and/or generate probabilities that candidate proteins are correctly identified in the sample.

The present disclosure provides a non-transitory information-recording medium that has, encoded thereon, instructions for the execution of one or more steps of the methods set forth herein, for example, when these instructions are executed by an electronic computer in a non-abstract manner. This disclosure further provides a computer processor (i.e. not a human mind) configured to implement, in a non-abstract manner, one or more of the methods set forth herein. All methods, compositions, devices and systems set forth herein will be understood to be implementable in physical, tangible and non-abstract form. The claims are intended to encompass physical, tangible and non-abstract subject matter. Explicit limitation of any claim to physical, tangible and non-abstract subject matter, will be understood to limit the claim to cover only non-abstract subject matter, when taken as a whole. Reference to "non-abstract" subject matter excludes and is distinct from "abstract" subject matter as interpreted by controlling precedent of the U.S. Supreme Court and the United States Court of Appeals for the Federal Circuit as of the priority date of this application.

Data Compositions

In another aspect, provided herein is a non-transitory computer-readable medium, comprising an array map, wherein the array map comprises a plurality of data units, in which each data unit comprises: i) a location tag, wherein the location tag comprises a datum corresponding to a site on the array; and ii) a signal datum for the site on the array, wherein the signal datum comprises information pertaining to presence or absence of a fiducial element at the site on the array.

In some configurations, provided herein is a non-transitory computer-readable medium, comprising: a) an identification value corresponding to an identification tag of an array; and b) an array map, wherein the array map comprises a plurality of data units, in which each data unit comprises: i) a location tag, wherein the location tag comprises a datum corresponding to a site on the array; and ii) a signal datum for the site on the array, wherein the signal datum comprises information pertaining to a presence, an absence, or an uncertainty thereof of a fiducial element at the site on the array.

A non-transitory, computer-readable medium may comprise a data set comprising an identification value corresponding to an identification tag of an array and an array map. An identification value may comprise one or more, two or more, three or more, or four or more data containing identifying information for an array, such as a) serial number, b) array identification number, c) lot number, d) batch number, e) manufacture date, f) manufacture location, g) expiration date, and h) a quality control metric. In some configurations, an identification value may be encrypted or cryptographically signed, in which some or all of the information contained within the identification value may be validated by a user or system with a cryptographic key for decoding the information. An identification value may be an item of identifying information that is unique to an array. For example, an array may comprise an identification tag comprising a serial number, in which the serial number is only assigned to the array comprising the identification tag. In some configuration, in which an array is not uniquely identified with an identification value, as set forth herein, an algorithm, system, or user may generate a unique identifying number (e.g., a globally-unique identifier, a universally-unique identifier, a snowflake ID, etc.) and assign all results with the unique number to facilitate disambiguation in a subsequent data-based process. An identification value may comprise a first item of identifying information and a second item of identifying information, in which the first item of identifying information or the second item of identifying information does not independently confirm an identity of an array, and in which the first item of identifying information and the second item of identifying information together confirm the identity of the array. For example, an array may be assigned a serial number based on a numeric order of manufacture during a manufacture day (e.g., . . . 51, 52, 53, 54, . . . etc.), in which the array is provided an identification tag containing the serial number and manufacture date, thereby assigning a unique identity to the array.

An identification value of an array may be stored in a database. A database comprising an identification value of an array may be in data communication with an array-based system, as set forth herein. A database containing an identification value of an array may comprise a record for the array, in which the record comprises: a) an item of information from an identification tag of an array, and b) one or more data pertaining to the array. A database record for an array may comprise one or more additional data pertaining to the array, such as: a) a raw material lot number or serial number for a material of array manufacture, b) quality control data for a raw material of array manufacture, c) a reagent lot number or serial number for a reagent of array manufacture, d) quality control data for a raw material of array manufacture, e) a manufacturing method parameter, f) post-manufacture quality control for the array, g) a lot number of serial number for a fiducial element material, h) a manufacturing method parameter for a fiducial element deposition, i) a quality control metric for an array comprising a fiducial element, and j) an array map of the array.

A non-transitory, computer-readable medium may comprise a data set comprising an array map. An array map may comprise any data structure that includes one or more data units, in which each data unit comprises a location tag for an array and a datum of physical information for each location tag in the data structure. A location tag may comprise a data form that represents a physical address on an array. A location tag may comprise a physical coordinate of an address, point, or subregion of an array (e.g., 17 μm across, 32 μm down; column 17, row 32, etc.). A location tag may comprise a categorized value that represents an address, point, or subregion of an array via an assigned reference number. For example, a data structure may comprise a plurality of location tags comprising consecutive numbers (e.g., 1, 2, 3, 4, 5, . . . , etc.), in which each consecutive number corresponds to a subregion of the array, and in which each a physical coordinate of the array corresponding to each consecutive number is searchable in a reference data structure. Physical location information may comprise a plurality of coordinates, in which each coordinate represents an address, point or subregion of an array. A coordinate of an array address may be provided with respect to a reference point or reference region (e.g., a landmarking region). A data structure for an array may be divided into data units representing subregions of the array, in which each subregion represents an area, volume, or a plurality of points of an array. A data structure for an array may be divided into a plurality of data units representing subregions based upon a layout or patterning of array sites. For example, a data structure for a rectangular grid may comprise a plurality of data units corresponding to rectangular subregions of an array, and a data structure for a hexagonal grid may comprise a plurality of data units corresponding to hexagonal subregions of an array. In some configurations, a data structure for an array may be divided into data units representing subregions of the array, in which each data unit of the data structure represents an address, point, or subregion of the array that contains a site. In a particular configuration, a data structure for an array may be divided into data units representing subregions of the array, in which each data unit of the data structure represents an address, point, or subregion of the array that contains one and only one site. In a particular configuration, a data structure for an array may be divided into data units representing subregions of the array, in which each data unit of the data structure represents an address, point, or subregion of the array that does not contain a site.

An array map may comprise any data structure that includes one or more data units, in which each data unit comprises a datum of physical information for each location tag in the data structure. A datum of physical information may comprise one or more data selected from: i) a physical measurement collected by a sensing device at an address, point, or subregion corresponding to a location tag, ii) a parameter derived from a physical measurement collected by a sensing device at an address, point, or subregion corresponding to a location tag, and iii) a categorized value assigned to a location tag based upon a physical measurement or a parameter derived from a physical measurement collected by a sensing device at an address, point, or subregion corresponding to the location tag. In some configurations, physical information data may comprise a plurality of physical measurements collected by a sensing device at an address, point, or subregion corresponding to a location tag. For example, a data unit may comprise a plurality of replicate measurements collected by a sensing device at an address, point, or subregion of an array. In another example, a subregion of an array may be sensed by a plurality of pixels on a pixel-based sensor, in which a data unit for the subregion of the array may comprise a measurement from each pixel of the plurality of pixels. In some configurations, a data unit may comprise a parameter derived from a physical measurement of a plurality of physical measurements at an address, point, or subregion of an array. A parameter derived from a physical measurement may comprise a statistical measure such as an average, a median, a standard deviation, or a coefficient of variability. A parameter derived from a physical measurement may comprise a morphological parameter, such as a center, a centroid, or a moment. For example, a subregion of an array may be sensed by a plurality of pixels on a pixel-based sensor, in which a data unit for the subregion of the array may comprise a centroid value derived from a measurement from each pixel of the plurality of pixels. A parameter derived from a physical measurement may comprise an empirical or correlated value. For example, a fluorescence intensity collected by an optical sensing device at an address on an array may be utilized to calculate a particle weight, mass, or radius based upon an empirical correlation. In some configurations, a data unit may comprise a categorized value assigned to a location tag based upon a physical measurement or a parameter derived from a physical measurement collected by a sensing device. A categorized value may comprise a classification of a plurality of classifications, such as a binary classification (e.g., ON/OFF; YES/NO; DETECTED/NOT DETECTED) or a polynary classification (e.g., YES/NO/MAYBE; DETECTED/UNCERTAIN/NOT DETECTED; DATA QUALITY HIGH/DATA QUALITY MEDIUM/DATA QUALITY LOW/DATA QUALITY UNCERTAIN; FIDUCIAL ELEMENT/AFFINITY AGENT/ANCHORING MOIETY/UNKNOWN, etc.). A categorized value may provide a classification for a site corresponding to a location tag. For example, a data structure comprising an array map for an array may comprise a plurality of data units, in which each data unit of the plurality of data units comprises a location tag corresponding to a site on the array, and in which each data unit of the plurality of units comprises a classification for a detected presence or absence of a fiducial element at the site on the array.

In some configurations, an array map may comprise an optical image or a portion thereof. In a particular configuration, an array map may comprise a composite image or a portion thereof. A composite image may comprise an image formed by combining two or more images. A composite image may combine two or more images to form a composite image of a spatial distribution of imaging data (e.g. points corresponding to addresses of the imaged array), a temporal distribution of imaging data, or a combination thereof. A composite image may comprise two or more images that are combined to display imaging data (e.g. points) from a larger imaging area than an imaging area of an image of the two or more images. For example, two images with a pixel width, w, and a common overlapping region of width, o, may be combined to form a composite image with a total width of 2w−o. In another example, two or more images may be overlayed in a data structure, in which points or other data from overlapping regions is stored cumulatively to provide more definite results when data from the overlapping region is processed. A composite image may comprise two or more images that are combined to display imaging data from a larger timespan than a timespan of an image of the two or more images. For example, a single image of a region of an array may be limited to points collected in a timespan that is substantially equal to a camera shutter speed, s, but two images of the region of the array may be collected at an interval, i, such that a composite of the images may depict points observed in the region of the array over a time span of 2s+i. In some configurations, a composite image may comprise one or more points, or regions of missing or insufficient data. In some configurations, a composite image may comprise a concatenated image. A concatenated image of an array may comprise a plurality of images that are overlayed or adjoined to form one or more images of a larger area of the array than is captured by any of the individual images within the plurality of images.

In some configurations, a composite or concatenated image may comprise an image comprising altered data. Altered data may include data that is altered by a process, such as contrast adjustment, noise filtering, background subtraction, rotation, tilting, re-scaling, cropping, aberration correction, and combinations thereof. In some configurations, a composite or concatenated image may comprise a visual rendering of a spatial distribution of moieties on an array. In some configurations a composite or concatenated image may comprise a visual rendering of an array, in which the visual rendering depicts: i) each site of a plurality of sites on the array, for example, as a point, and ii) presence or absence of a moiety at each site of the plurality of sites, for example, as presence or absence of a point. In some configurations a composite or concatenated image may comprise a visual rendering of an array, in which the visual rendering depicts: i) each site of a plurality of sites on the array, for example, as a point, and ii) presence or absence of a fiducial element at each site of the plurality of sites, for example, as presence or absence of a point. In some configurations a composite or concatenated image may comprise a visual rendering of an array, in which the visual rendering depicts: i) each site of a plurality of sites on the array, for example, as a point, and ii) presence or absence of an analyte at each site of the plurality of sites, for example, as presence or absence of a point. In some configurations a composite or concatenated image may comprise a visual rendering of an array, in which the visual rendering depicts: i) each site of a plurality of sites on the array, for example, as a point, and ii) presence or absence of an analytical reagent at each site of the plurality of sites, for example, as presence or absence of a point. In some configurations a composite or concatenated image may comprise a visual rendering of an array, in which the visual rendering depicts: i) each site of a plurality of sites on the array, for example, as a point, and ii) presence or absence of a fiducial element, analyte, or analytical reagent at each site of the plurality of sites, for example, as presence or absence of a point. In some configurations a composite or concatenated image may comprise a visual rendering of an array, in which the visual rendering depicts: i) each site of a plurality of sites on the array, for example, as a point, and ii) presence or absence of a fiducial element, and one moiety selected from an analyte and an analytical reagent, at each site of the plurality of sites.

In some configurations, an array map may comprise an artificial or synthetic data unit. An artificial data unit may comprise simulated, modelled, or inferred physical information for a location tag of an array. For example, an initial image may comprise a data unit with an indeterminate value for a measurement, in which the indeterminate value has been changed to a determinate value based upon an empirical calculation or a decision criteria to determine a finalized array map. A synthetic image may comprise one or more data units comprising physical information that has been altered from an initial physical measurement to a final physical measurement. For example, two images may be aligned to form a concatenated image by aligning a pattern of two or more fiducial elements that is common to both images, in which a first image must be partially rotated to obtain a precisely overlapping alignment between the pattern of two or more fiducial elements of the two images.

An array map may be configured to not comprise an image. In some configurations, an array map may comprise a plurality of data units that are derived from physical measurements of an array. An array map may comprise a 2-dimensional, 3-dimensional, or higher-dimension data matrix comprising a plurality of data units, in which each data unit comprises a location tag and one or more units of physical information or data derived from physical information. Physical information or data derived from physical information may be stored in a data unit as a continuous numerical value, a discrete numerical value, an alphabetic or text value, an alphanumeric value, a Boolean value, a categorical value, an enumerated value, or a combination thereof. An array map may further comprise a data unit comprising identifying information derived from an identification tag of an array.

In an advantageous configurations, an array map may comprise a data structure comprising: a) an identification value corresponding to an identification tag of an array; and b) an array map, wherein the array map comprises a first plurality of data units and a second plurality of data units, in which each data unit of the first plurality of data units comprises a location tag corresponding to a site on the array comprising a fiducial element; and in which each data unit of the second plurality of data units comprises location tag corresponding to a site on the array that does not comprise a fiducial element. In some configurations, a first plurality of data units and a second plurality of data units may be substantially equal to a total number of sites of an array.

An array map may be divided into subarray maps. A subarray map may comprise a plurality of data units from an array map, in which the plurality does not contain all data units of an array map. In some configurations, a subarray map may comprise a plurality of data units, in which the plurality of data units comprises physical information for a contiguous plurality of sites of an array. In particular configurations, a subarray map may comprise data captured within a single field-of-view of a sensing device. In other configurations, a subarray map may comprise data combined from multiple fields-of-view of a sensing device (e.g., derived from an array map of a composite or concatenated image). For example, a subarray containing data units corresponding to a contiguous 100×100 site subregion of an array may be derived from a 10000×10000 site array map.

An array map and/or one or more subarray maps may be useful for controlling a process or assay of an array-based system. An array map and/or one or more subarray maps may be utilized for an array-based process such as landmarking, image registration, and/or focus adjustment. An array map, or a subarray map thereof, may comprise a plurality of data units that provides information corresponding to a random spatial distribution of fiducial elements at sites on an array of subregion thereof. In some configurations, a plurality of data units corresponding to a spatial pattern of fiducial elements at sites of an array may be utilized for initializing, performing, controlling, or finalizing an array-based process or assay, in which the spatial pattern of fiducial elements comprises a random spatial order.

In another aspect, provided herein is a non-transitory, computer-readable medium, comprising: a) a first subarray map comprising a first plurality of data units, in which each data unit of the first plurality of data units comprises a signal datum for the site on the array, in which the signal datum comprises information pertaining to presence or absence of a fiducial element at the site on the first subregion of the array, b) a second subarray map comprising a second plurality of data units, in which each data unit of the second plurality of data units comprises a signal datum for the site on the array, in which the signal datum comprises information pertaining to presence or absence of a fiducial element at the site on the second subregion of the array, in which a first subset of signal data of the first plurality of data units corresponds to a first random spatial order of fiducial elements at sites of the array, in which a second subset of signal data of the second plurality of data units corresponds to a second random spatial order of fiducial elements at sites of the array, and in which the first random spatial order and the second random spatial order are the same.

A non-transitory, computer-readable medium comprising two subarrays may be provided, in which each subarray comprises a plurality of data units that are common to each subarray of the two or more subarrays. A plurality of data units may be common to each subarray if a common subset of signal data from a plurality of data units of each subarray comprises a signal data corresponding to a random spatial distribution of fiducial elements on a region of an array.

Figure 14A:
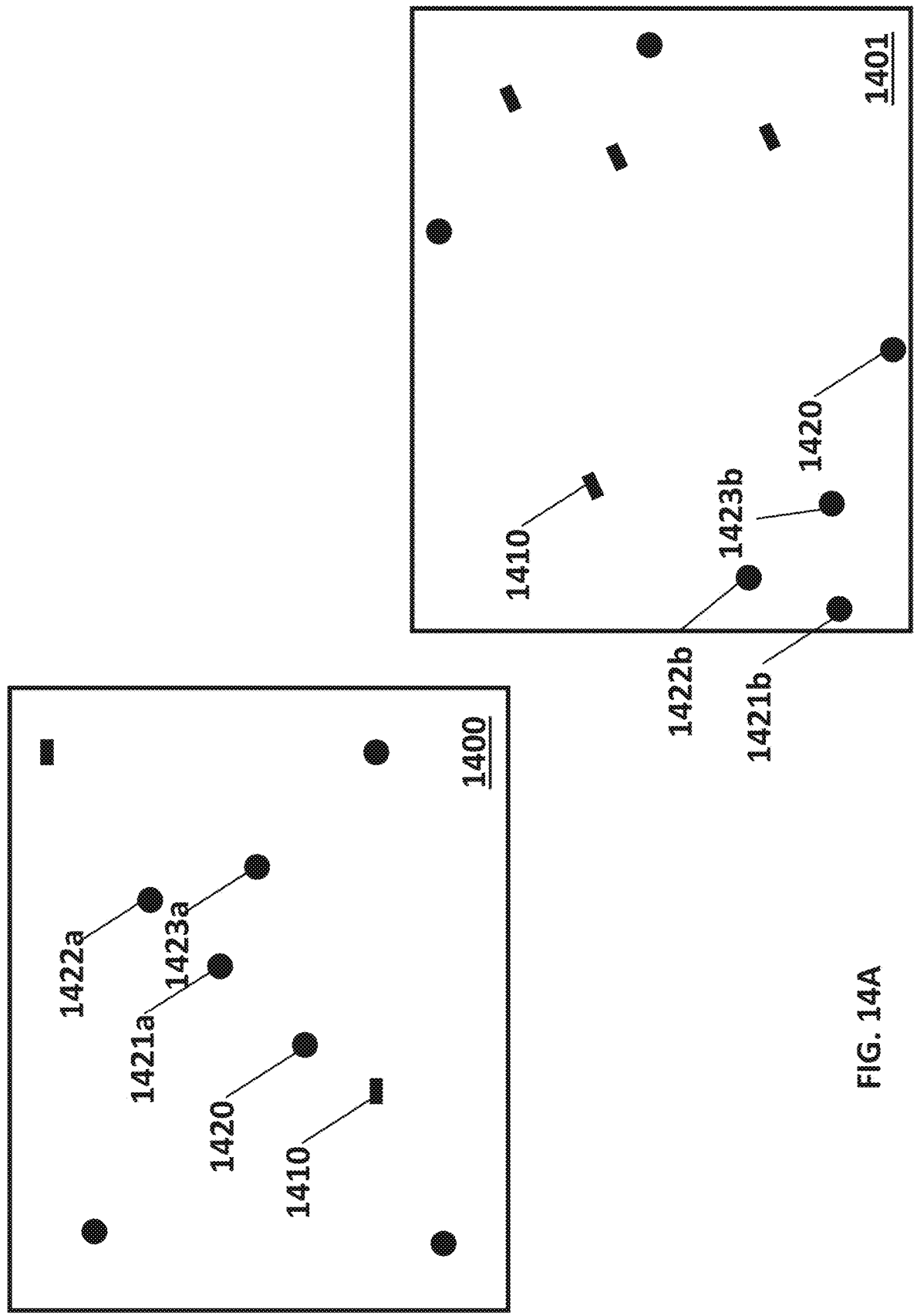
Figure 14B:
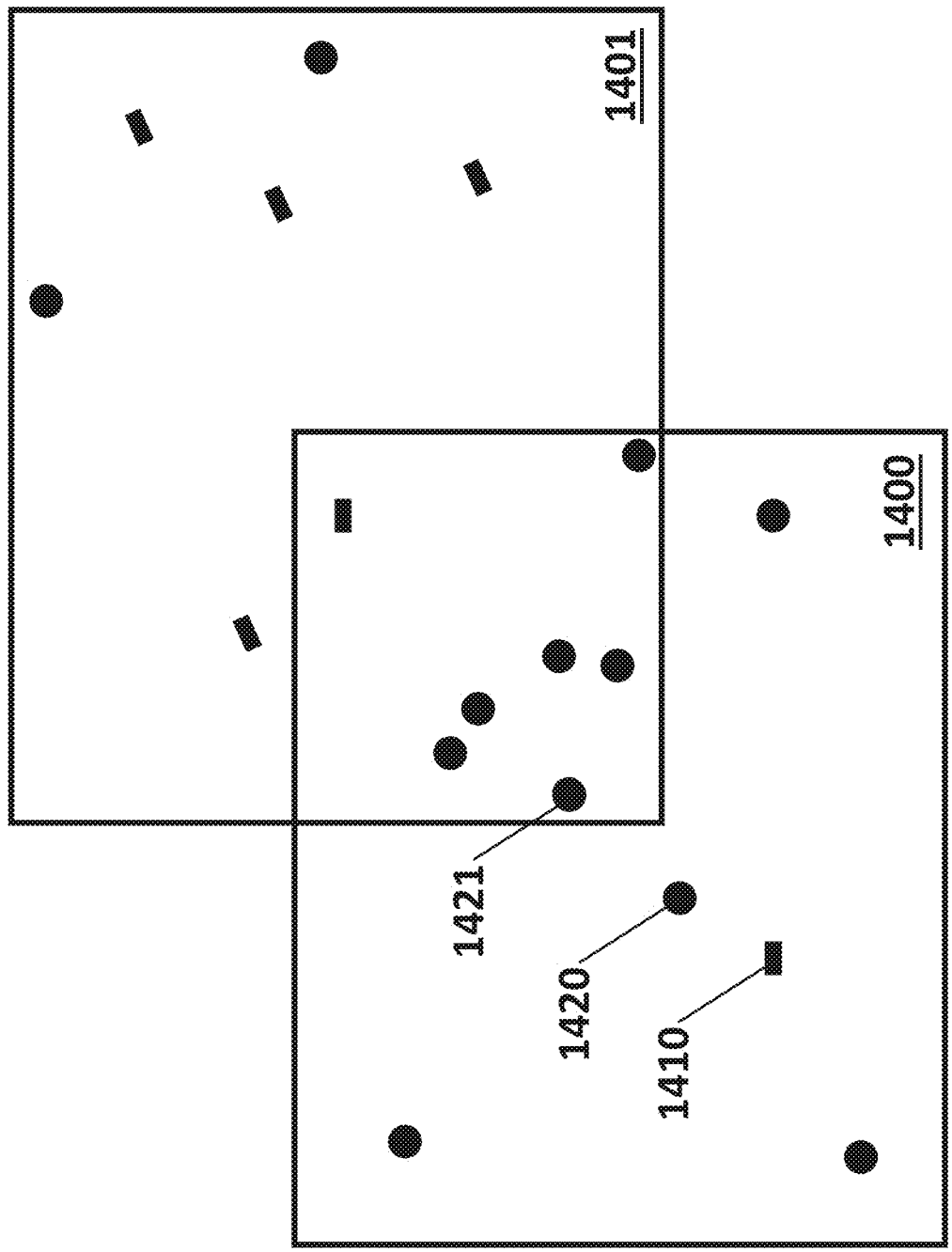
Figure 14D:
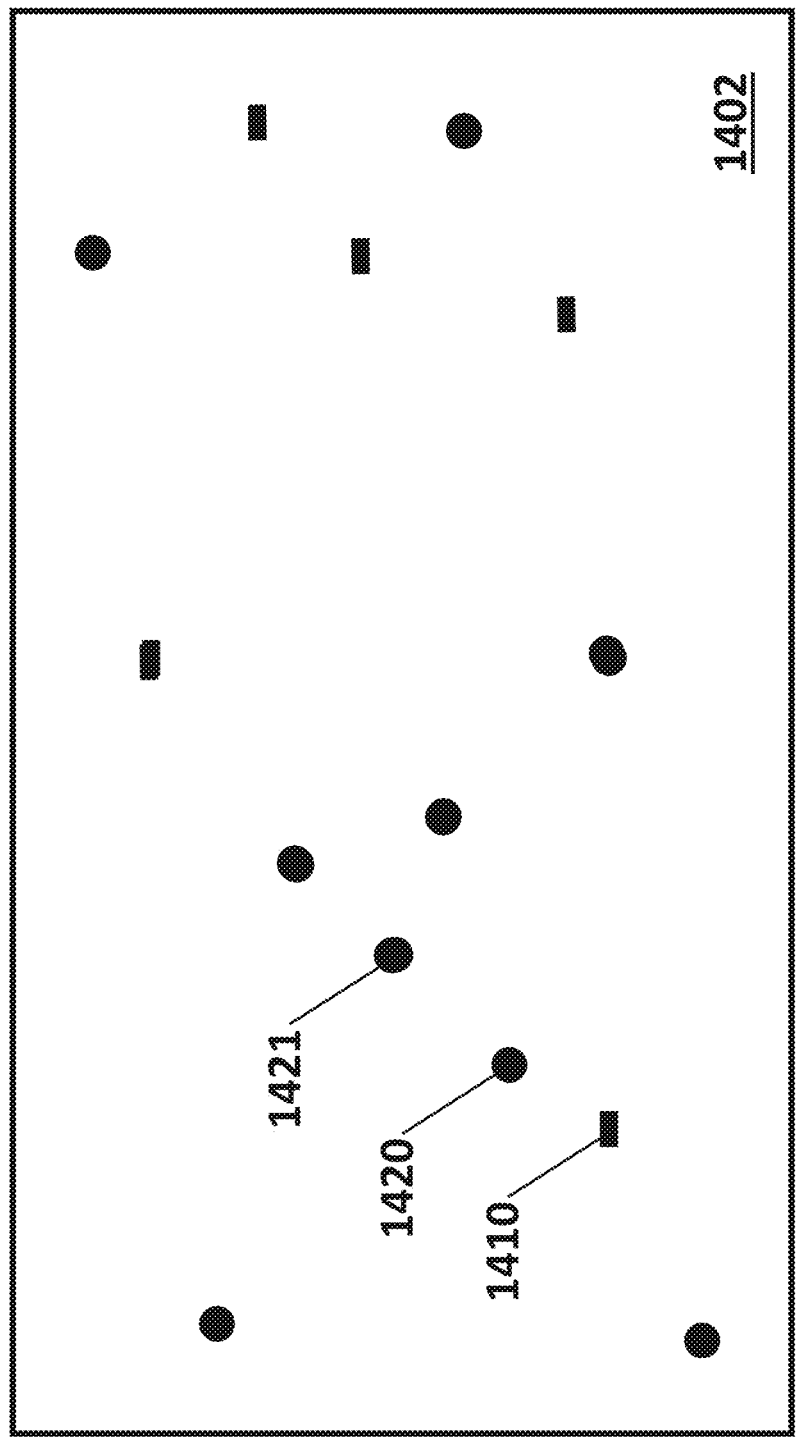

FIGS. 14A-14G depict exemplary data structures comprising different fields-of-view. FIG. 14A illustrates a graphical representation (e.g., an image) of a first field-of-view 1400 of a data structure, comprising sensed addresses and detected signals of fiducial elements 1420 and sensed addresses and detected signals of analytes of interest 1410, and a second field-of-view 1401 of a data structure, comprising sensed addresses and detected signals of fiducial elements 1420 and sensed addresses and detected signals of analytes of interest 1410. The first field-of-view 1400 and the second field-of-view 1401 may each comprise a pattern of fiducial elements whose spatial distribution is determined to match (1421a-1423a with 1421b-1423b). FIG. 14B illustrates direct alignment of the first field-of-view 1400 with the second field-of-view 1401 by overlapping of fiducial elements 1421a and 1421b. FIG. 14C illustrates clockwise rotation with a plane orthogonal to the viewer to align the pattern of fiducial elements, thereby properly aligning the spatial distribution of all detected signals in the first field-of-view 1400 with those of the second field-of-view 1401. FIG. 14D depicts a combined field-of-view 1402 that may be generated by merging (e.g., signal averaging, discarding redundant data, etc.) the overlapping data of the first field-of-view 1400 with the altered data of the second field-of-view 1401.

Figure 14F:
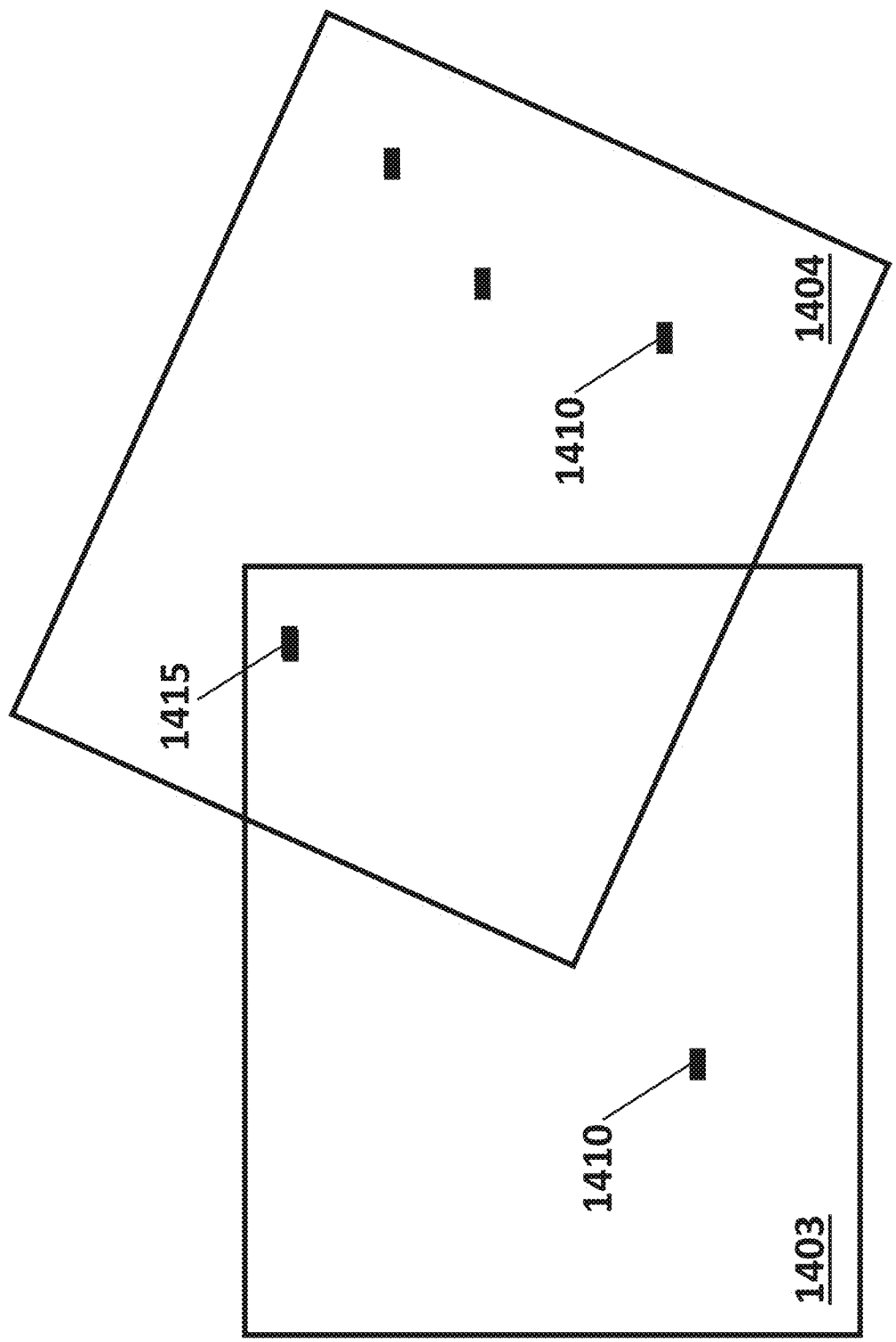
Figure 14G:
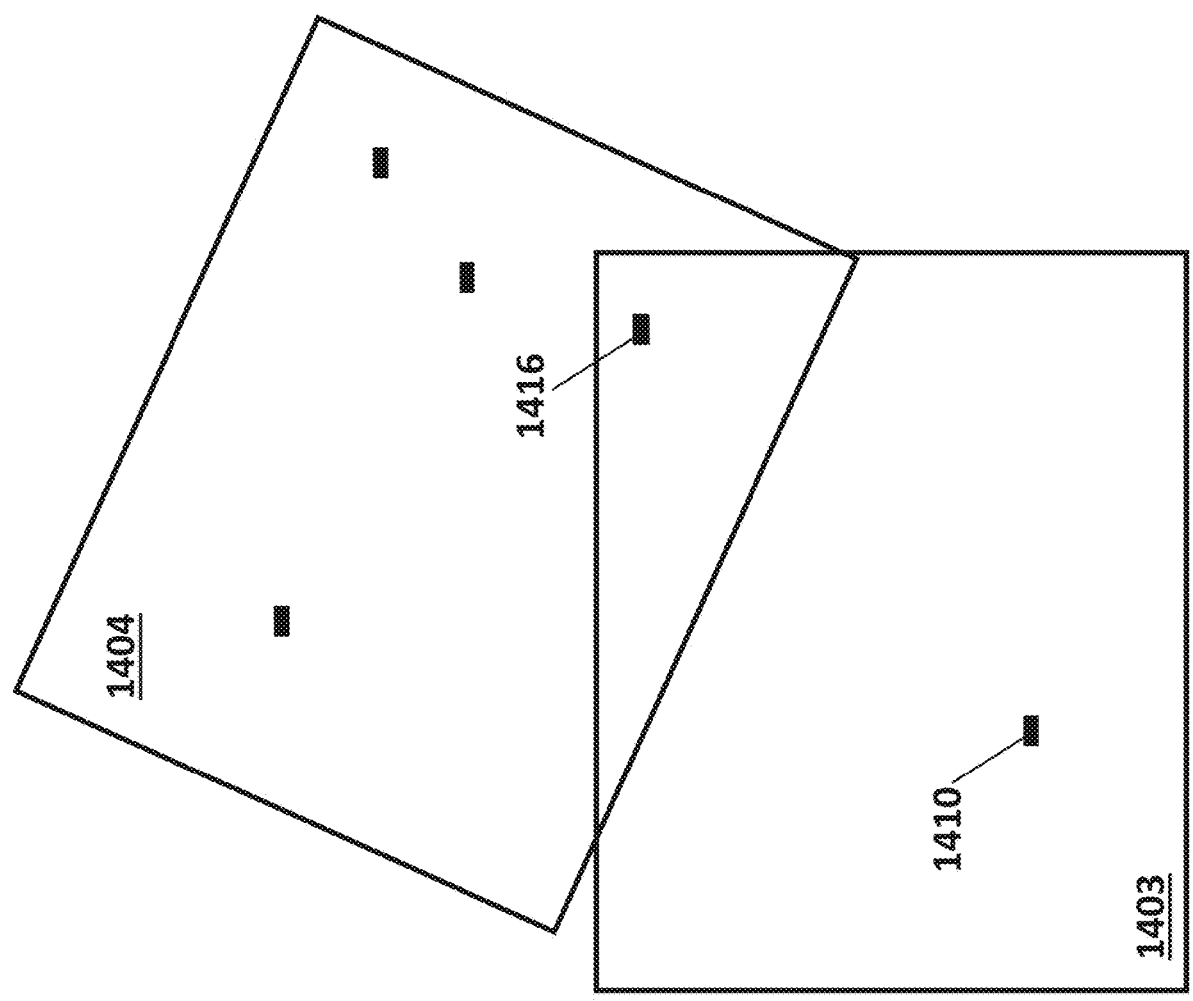

FIGS. 14E-14G depict the same data structures as FIGS. 14A-14D, but in the absence of the fiducial elements 1420. A first field-of-view 1402 and a second field-of-view 1403 only comprise data regarding sensed addresses and detected signals of analytes of interest 1410. As shown in FIGS. 14F and 14G, given the low density of signals corresponding to analytes of interest, the data from the first field-of-view 1402 and the second field-of-view 1403 can be aligned in at least two fashions. The absence of a distinct, spatially-specific (e.g., only occurring at this region of the array) pattern of fiducial elements produces uncertainty in the proper spatial alignment of the sensed data.

In some configurations of a non-transitory, computer-readable medium, a first subset of signal data of a first plurality of data units, and/or a second subset of signal data of a second plurality of data units may comprise a plurality of data units corresponding to presence of a fiducial element at a site of an array. For example, it may be necessary to have at least 3 or more signal data corresponding to presence of fiducial elements to assess if an observed pattern of fiducial elements in a first image aligns with an observed pattern of fiducial elements in a second image. In some configurations of a non-transitory, computer-readable medium, a first subset of signal data of a first plurality of data units, and/or a second subset of signal data of a second plurality of data units may comprise a plurality of data units corresponding to an absence of a fiducial element at a site of an array. For example, pattern matching of distributions of fiducial elements between a first and second image may utilize sites with no observed presence of fiducial elements rather than observed presence of fiducial elements. In some configurations of a non-transitory, computer-readable medium, a first subset of signal data of a first plurality of data units, and/or a second subset of signal data of a second plurality of data units may comprise a data unit corresponding to an absence of a fiducial element at a site of an array and a data unit corresponding to presence of a fiducial element at a site on an array.

Array and Array Data Methods

In another aspect, provided herein is a method of preparing a solid support, comprising: a) providing the solid support, in which the solid support comprises a plurality of sites, in which each site of the plurality of sites has a unique spatial address on the solid support, and in which each site of the plurality of sites is configured to couple a moiety to the solid support, and b) depositing a plurality of fiducial elements on the solid support, in which each fiducial element of the plurality of fiducial elements is deposited at a random site of the plurality of sites. In some configurations, each site of a plurality of sites may be configured to couple an analyte or a fiducial element. In some configurations, each site of a plurality of sites may comprise a coupling moiety, in which the coupling moiety is configured to couple another moiety to the solid support. In a particular configuration, each site of a plurality of sites may comprise a coupling moiety, in which the coupling moiety comprises a same chemical structure for each site of the plurality of sites. For example, a solid support may comprise a plurality of sites, in which each site comprises at least one oligonucleotide of a plurality of oligonucleotides, in which each oligonucleotide is configured to couple a complementary oligonucleotide of an anchoring moiety, and in which each oligonucleotide of the plurality of oligonucleotides comprises the same nucleotide sequence. A fiducial element of a plurality of fiducial elements deposited on a solid support may comprise an optically active moiety. A fiducial element of a plurality of fiducial elements deposited on a solid support may comprise an optically passive moiety.

In another aspect, provided herein is a method of preparing a solid support, comprising: a) providing the solid support, in which the solid support comprises a plurality of sites, in which each site of the plurality of sites has a unique spatial address on the solid support, and in which each site of the plurality of sites is configured to couple a moiety to the solid support, and b) depositing a plurality of fiducial elements on the solid support, in which the plurality of fiducial elements is deposited at a subset of the plurality of sites. In some configurations, a plurality of fiducial elements may be deposited at a subset of a plurality of sites on a solid support, in which the subset comprises a random spatial distribution. In a particular configuration, a plurality of fiducial elements may be deposited at a subset of the plurality of sites, in which each site of the plurality of sites comprises a same surface chemistry. For example, an array may comprise a plurality of sites with a same silanized monolayer that is configured to couple a moiety at each site such that there is no known bias that drives deposition of fiducial elements to particular sites. In another particular configurations, a plurality of fiducial elements may be deposited at a subset of the plurality of sites, in which each site of the subset of plurality of sites comprises a surface chemistry that couples a fiducial element, and in which the subset comprises a random spatial distribution. In another particular configuration, a plurality of fiducial elements may be deposited at a subset of the plurality of sites, in which each site of the subset of plurality of sites comprises a surface chemistry that does not couple an analyte, and in which the subset comprises a random spatial distribution. A fiducial element of a plurality of fiducial elements deposited on a solid support may comprise an optically active moiety. A fiducial element of a plurality of fiducial elements deposited on a solid support may comprise an optically passive moiety.

Figure 5A:
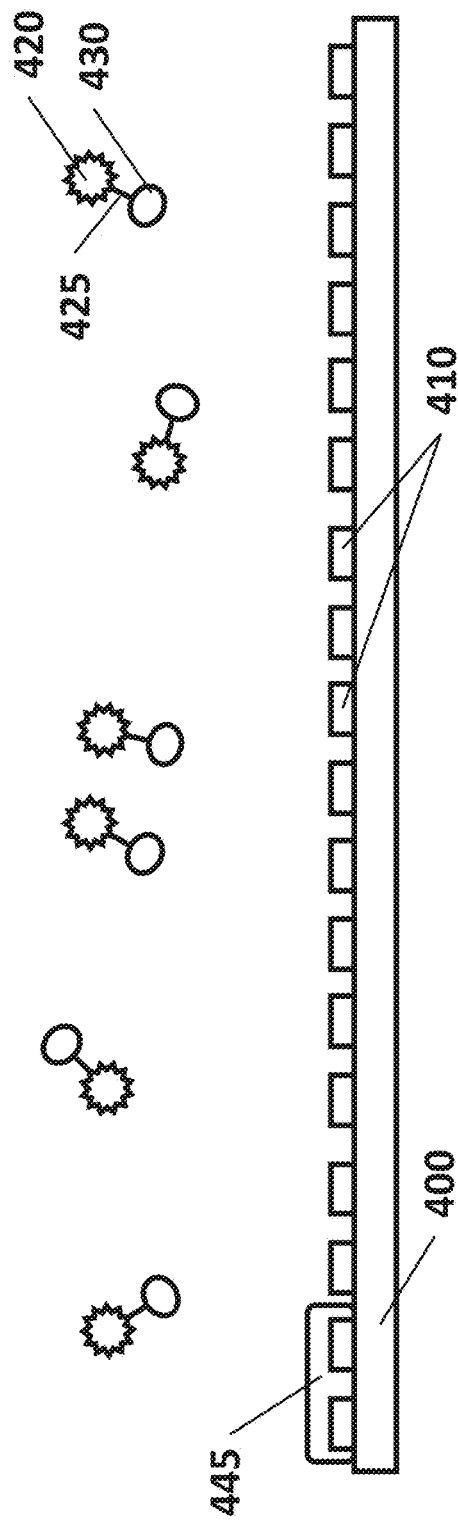
Figure 5B:
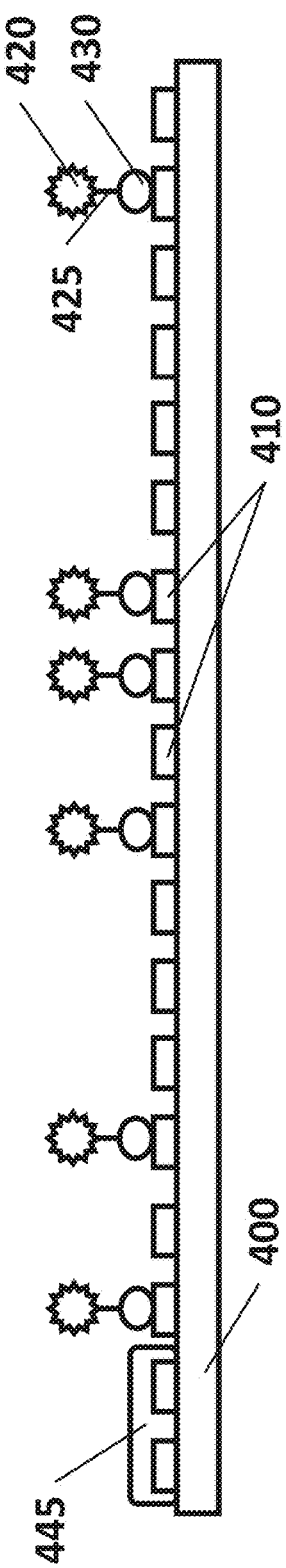

FIGS. 5A-5D illustrate a method of forming an array comprising a plurality of fiducial elements and a plurality of analytes of interest. FIG. 5A depicts a solid support 400 containing a plurality of sites 410 and a landmarking region comprising a multi-site layer fiducial element 445, in which the solid support 400 is contacted with a solution containing a plurality of fiducial elements 420 (e.g., optically active moieties, optically passive moieties). In the example shown, the solid support is in simultaneous contact with the plurality of fiducial elements 420 in the fluid phase. Alternatively, the solid support can be sequentially contacted with individual fiducial elements or subsets of fiducial elements from the plurality of fiducial elements 420. Returning to the example shown in FIG. 5A, each fiducial element 420 of the plurality of fiducial elements is coupled to an anchoring moiety 430 by an optional attachment moiety 425. Each anchoring moiety 430 is configured to couple a fiducial element 420 to a site 410 of the plurality of sites. FIG. 5B depicts the solid support 400, in which the plurality of fiducial elements 420 have been deposited at random sites 410 by the coupling of anchoring moieties 430 to sites 410. Each fiducial element 420 is coupled such that an anchoring moiety 430 mediates coupling of the fiducial element 420 to the site 410, and the fiducial element 420 is not directly coupled to the site 410. In other words, the fiducial element 420 is coupled to the site 410 via the anchoring moiety 430. FIG. 5C depicts the solid support 400 comprising the randomly distributed plurality of fiducial elements 420, which the solid support 400 is contacted with a plurality of analytes of interest 450 (e.g., polypeptides, nucleic acids, cells, etc.). Each analyte of interest 450 of the plurality of analytes of interest is coupled to an anchoring moiety 430 via an optional attachment moiety 425. Each anchoring moiety 430 is configured to couple an analyte of interest 450 to a site 410 of the plurality of sites. FIG. 5D depicts the solid support 400, in which the plurality of analytes of interest 450 have been deposited at random sites 410 by the coupling of anchoring moieties 430 to sites 410. Each analyte of interest 450 is coupled such that only an anchoring moiety 430 coupled to the analyte of interest 450 is directly coupled to the site 410, and the analyte of interest 450 is indirectly coupled to the site 410 via the anchoring moiety 430.

Figure 22B:
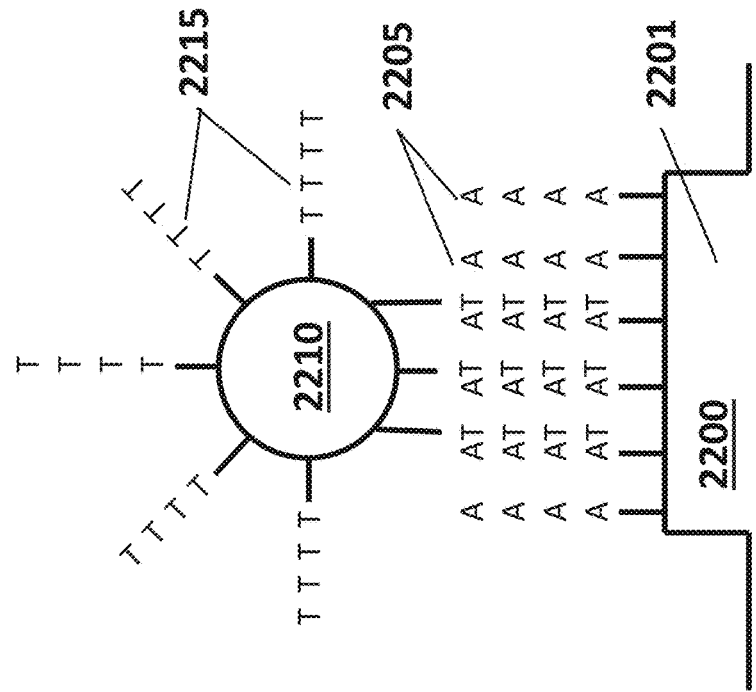
FIGS. 22A and 22B illustrate configurations of a bead-based fiducial that is configured to directly bind to an array site of a solid support, in accordance with some embodiments.
Figure 22A:
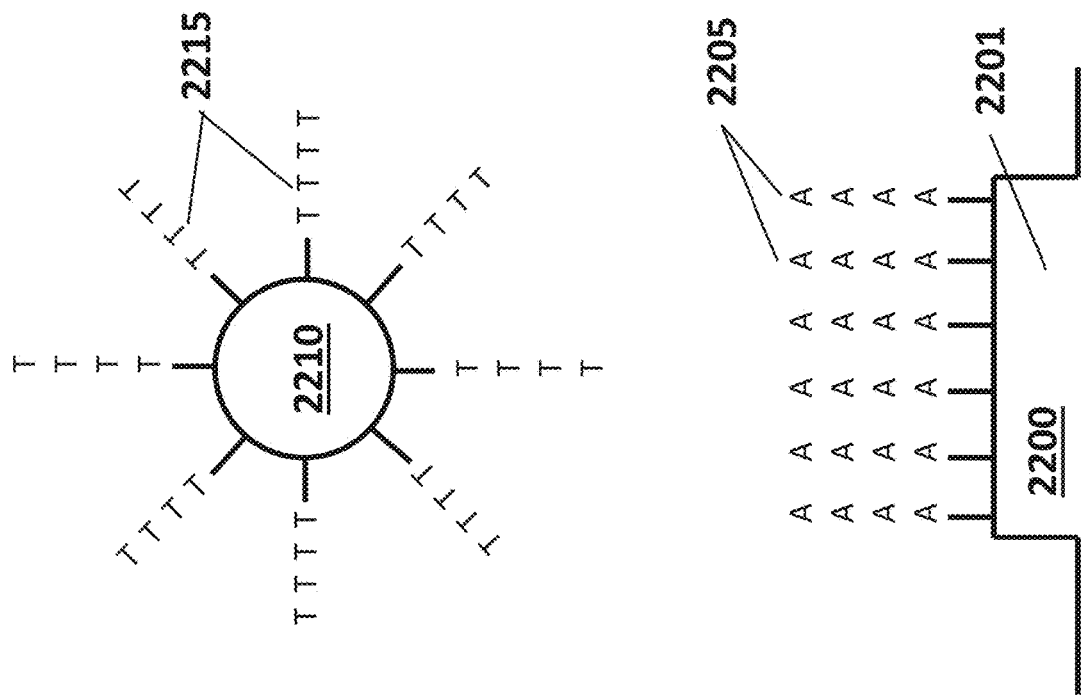

FIG. 22A-22B provide a method for direct coupling of a fiducial element to a surface of a solid support. FIG. 22A depicts a solid support 2200 containing a site 2201, in which the site 2201 comprises a plurality of surface-linked oligonucleotides 2205. The solid support 2200 is contacted with a fiducial element 2210 (e.g., an optically active moiety, an optically passive moiety, etc.) comprising a plurality of surface-coupling oligonucleotides 2215. FIG. 22B illustrates the coupling of the fiducial element 2210 to the site 2201 of the solid support 2200 by hybridizing of the surface-linked oligonucleotides 2205 to the surface-coupling oligonucleotides 2215. The skilled person will recognize innumerable variations for direct attachment of fiducial elements to a solid support, such as ligand-receptor binding pairs (e.g., streptavidin-biotin, SpyCatcher-SpyTag, etc.) or covalent attachment (e.g., Click-type reagents, NHS-amine cross-linking, epoxide-amine cross-linking, etc.). In some configurations, a method of preparing an array may comprise contacting a solid support with a plurality of fiducial elements, in which each fiducial element of the plurality of fiducial elements comprises a moiety that directly couples to the solid support, a surface thereof, or a moiety coupled thereto. In other configurations, a method of preparing an array may comprise contacting a solid support with a plurality of fiducial elements, in which each fiducial element of the plurality of fiducial elements comprises an anchoring moiety, and in which the anchoring moiety couples to the solid support, a surface thereof, or a moiety attached thereto. In other configurations, a method of preparing an array may comprise contacting a solid support with a plurality of fiducial elements, in which the plurality of fiducial elements comprises a first subset of fiducial elements that are configured to couple directly to the solid support, a surface thereof, or a moiety attached thereto, and a second subset of fiducial elements that are coupled to anchoring moieties, in which each anchoring moiety is configured to couple to the solid support, the surface thereof, or the moiety attached thereto.

Figure 15:
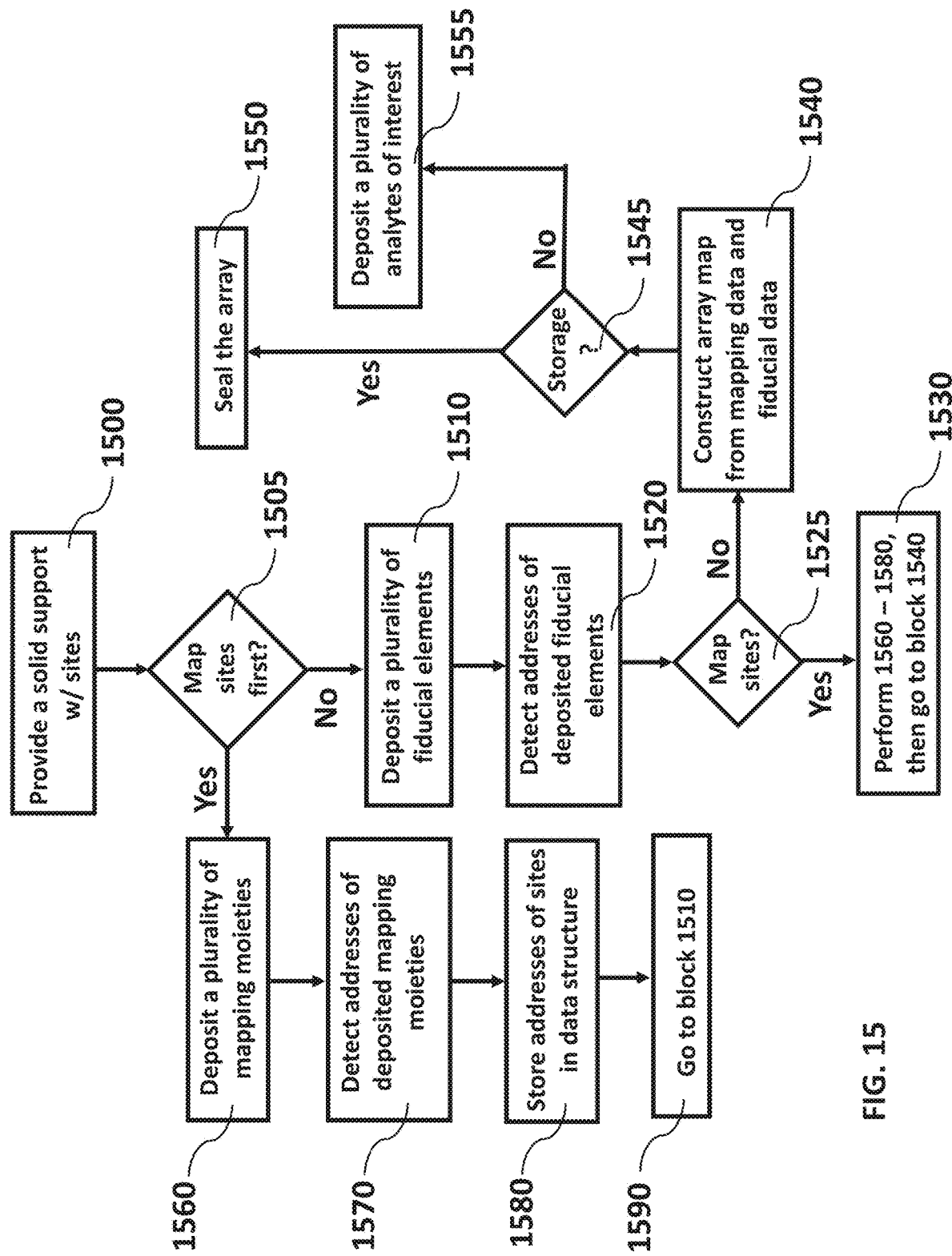
FIG. 15 displays a schematic for an array preparation and mapping process, in accordance with some embodiments.

FIG. 15 provides a schematic for a process of preparing an array, as set forth herein. In a first step 1500, a solid support comprising a plurality of sites is provided, in which each site is configured to couple a moiety (e.g., a fiducial element, an analyte of interest, a mapping moiety, etc.). Subsequently, a decision 1505 may be made regarding whether to map the addresses of each site of the plurality of sites. If the sites are not mapped initially, a plurality of fiducial elements is deposited 1510 on the provided solid support, for example by liquid-phase deposition (e.g., nanoparticles) or a vapor-phase deposition (e.g., layered metals or metal oxides, etc.). Optionally, after depositing fiducial elements on the solid support, addresses of sites comprising fiducial elements may be determined 1520 by a detection method. Another decision 1525 may be made regarding whether to map the addresses of each site of the plurality of sites. If the sites are not mapped, optionally, an array map may be constructed 1540 from the detected addresses of deposited fiducial elements. Subsequently, a decision 1545 may be made whether the array will be prepared for usage or stored for future use. If the array is to be stored, it may be sealed 1550 for increased stability. If the array is to be utilized, analytes of interest may be deposited 1555 on available sites on the solid support. If a mapping process is conducted, the mapping process may initially comprise depositing 1560 a plurality of mapping moieties on sites of the solid support. Subsequently, addresses of coupled mapping moieties on the solid support may be determined 1570 by a detection method. Optionally, addresses containing detected mapping moieties may be stored 1580 in a data structure to provide a recorded spatial arrangement of array sites. After mapping, deposition 1510 of fiducial elements may proceed if not already performed earlier in the array preparation process.

A method of preparing a solid support may comprise depositing a plurality of fiducial elements on a solid support. Depositing a plurality of fiducial elements may further comprise contacting the plurality of fiducial elements with a solid support comprising a plurality of sites. In a particular configuration, depositing a plurality of fiducial elements may comprise one or more steps of: i) providing a plurality of fiducial elements, in which each fiducial element is coupled to an anchoring moiety, and in which each anchoring moiety is coupled to a single fiducial element, ii) contacting the plurality of fiducial elements comprising anchoring moieties with a solid support comprising a plurality of sites, and iii) coupling an anchoring moiety of each fiducial element comprising a coupling moiety to a site of the plurality of sites. In some configurations, depositing a plurality of fiducial elements may further comprise contacting a fluidic medium comprising the plurality of fiducial elements with a solid support comprising a plurality of sites.

A method of preparing a solid support may further comprise one or more, or two or more steps of: i) coupling a plurality of fiducial elements (e.g., fluorescently-labeled polymers, fluorescent nanoparticles, etc.) to a plurality of anchoring moieties to form a plurality of fiducial element composites, in which each anchoring moiety of the plurality of anchoring moieties is configured to form a binding interaction with a solid support or a surface thereof, and in which each fiducial element composite of the plurality of fiducial elements composites comprises a fiducial element of the plurality of fiducial elements coupled to an anchoring moiety of the plurality of anchoring moieties, ii) separating the plurality of fiducial element composites from one or more anchoring moieties, and iii) contacting the plurality of fiducial element composites with the solid support or the surface thereof, in which the solid support comprises a plurality of sites, in which each site is configured to form a binding interaction with an anchoring moiety.

A fiducial element composite may be formed by coupling a fiducial element (e.g., an optically active moiety, an optically passive moiety, etc.) to an anchoring moiety. A fiducial element composite may be formed by a covalent or non-covalent binding interaction between a fiducial element and an anchoring moiety. For example, FIGS. 6A and 6B depict a scheme for coupling a PEGylated fluorescent polymer nanoparticle 600 to an anchoring moiety 610 via a non-covalent streptavidin-biotin attachment moiety 615. After one or more fiducial element composites are formed, the one or more fiducial element composites may be separated from uncoupled anchoring moieties by one or more separation processes. Exemplary separation processes may include high-pressure liquid chromatography, size exclusion chromatography, magnetic bead-assisted separations, affinity chromatography, dialysis, reverse osmosis, ultrafiltration, and any combination thereof. A plurality of fiducial element composites, when contacted with a solid support or when deposited at sites of an array, may comprise no more than about 10%, 5%, 1%, 0.5%, 0.1%, 0.05%, 0.01%, 0.005%, 0.001%, or less than 0.001% of uncoupled anchoring moieties relative to total anchoring moiety content on a molar basis. Alternatively or additionally, a plurality of fiducial element composites, when contacted with a solid support or when deposited at sites of an array, may comprise at least about 0.001%, 0.005%, 0.01%, 0.05%, 0.1%, 0.5%, 1%, 5%, 10%, or more than 10% of uncoupled anchoring moieties relative to total anchoring moiety content on a molar basis.

A method of preparing a solid support may comprise depositing a plurality of fiducial elements on a solid support comprising a plurality of sites, in which fiducial elements are deposited at a subset of the plurality of sites. Depositing a plurality of fiducial elements on a solid support containing a plurality of sites may comprise contacting the solid support with a quantity of fiducial elements that is smaller than a quantity of sites. For example, a plurality of fiducial elements in a fluidic medium may be quiescently contacted with a solid support containing a plurality of sites, in which a quantity of fiducial elements is about 10% of a quantity of sites. Alternatively, depositing a plurality of fiducial elements on a solid support containing a plurality of sites may comprise contacting the solid support with a quantity of fiducial elements that is larger than a quantity of sites. For example, a solid support containing a plurality of sites may be contacted by a flowing fluidic medium containing a plurality of fiducial elements, in which the total integrated flux of fiducial elements passing the solid support exceeds a total number of sites on the solid support but a flow regime limits the deposition of fiducial elements onto the solid support. A solid support may be contacted by a quantity of fiducial elements that is at least about 0.000001%, 0.00001%, 0.0001%, 0.001%, 0.01%, 0.05%, 0.1%, 0.5%, 1%, 5%, 10%, 15%, 20%, 25%, 30%, 35%, 40%, 45%, 50%, 60%, 70%, 80%, 90%, 100%, 125%, 150%, 200%, 300%, 400%, 500%, 1000%, or more than 1000% of a quantity of sites on a solid support. Alternatively or additionally, a solid support may be contacted by a quantity of fiducial elements that is no more than about 1000%, 500%, 400%, 300%, 200%, 150%, 125%, 100%, 90%, 80%, 70%, 60%, 50%, 45%, 40%, 35%, 30%, 25%, 20%, 15%, 10%, 5%, 1%, 0.5%, 0.1%, 0.05%, 0.01%, 0.001%, 0.0001%, 0.00001%, 0.000001%, or less than 0.000001% of a quantity of sites on a solid support.

Figure 29A:
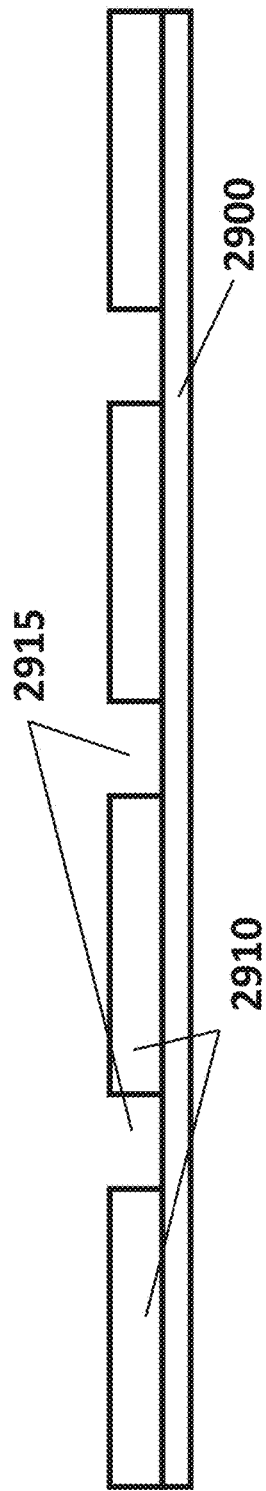
Figure 29B:
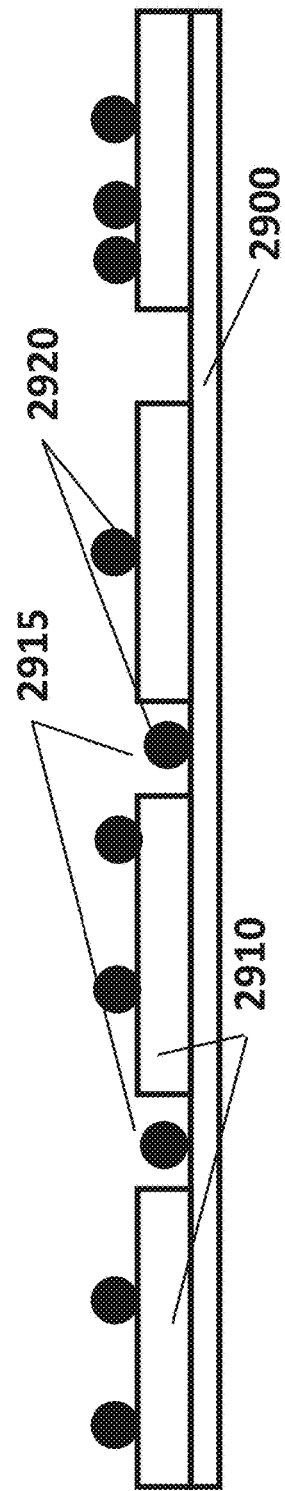
Figure 29C:
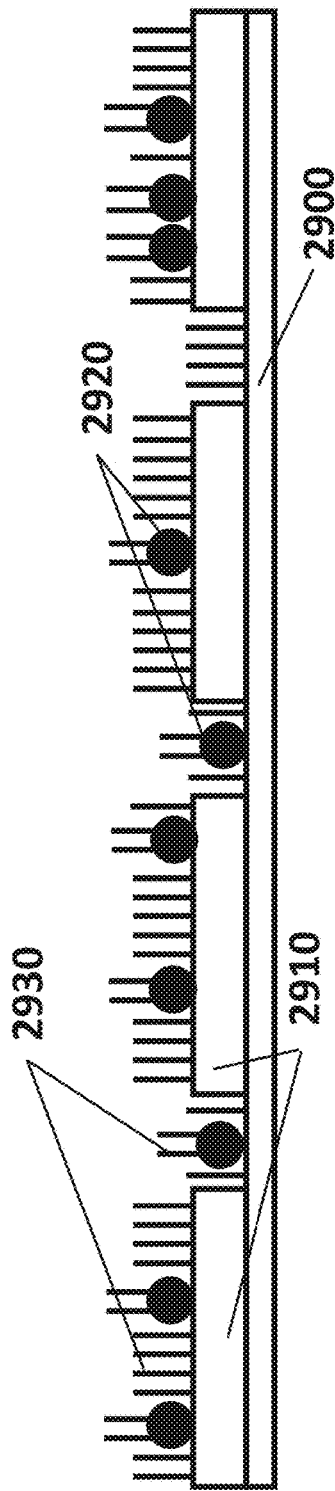

In some cases, a plurality of fiducial elements may be deposited on a single-analyte array after an array formation process. In other cases, a plurality of fiducial elements may be deposited on a single-analyte array during an array formation process, such as a during an array lithographic process or array surface chemistry deposition. FIGS. 29A-29D illustrate a method of array formation that results in a random spatial distribution of fiducial elements on a single-analyte array. FIG. 29A depicts a configuration of an array composition during a lithographic process. A solid support 2900 comprises a resist layer 2910 that has been patterned to form a series of wells 2915 in the resist layer 2910. A region of surface of the solid support 2900 is exposed in the bottom of each well 2915. FIG. 29B depicts an array composition after deposition of fiducial elements 2920 (e.g., fluorescent nanoparticles) on the solid support composition shown in FIG. 29A. The fiducial elements 2920 have become randomly deposited on the resist material 2910 and on the exposed surface regions of the solid support 2900 in the bottom of a fraction of the wells 2915. Fiducial elements 2920 deposited on the surface of the solid support 2900 within the wells 2915 may be adhered to the solid support 2900 by non-covalent interactions (e.g., electrostatic adhesion, Van der Waals interactions, etc.) and/or by covalent bonding interactions. FIG. 29C depicts an array composition after deposition of a surface chemistry on the array composition of FIG. 29B. A plurality of surface-coupled moieties 2930 are deposited on the array composition, including exposed surfaces of the resist material 2910, on fiducial elements 2920, and on exposed surfaces of the solid support 2900 in wells 2915. The deposited surface-coupled moieties 2930 may include coupling moieties (e.g., covalent coupling moieties, non-covalent coupling moieties) and/or passivating moieties (e.g., PEGylated molecules, dextrans, polyionic polymers, etc.). FIG. 29D depicts an array composition after the resist material 2910 has been stripped from the surface by a stripping method (e.g., solvent-based dissolution). The resist material 2910 is removed from the solid support 2900, providing discrete sites containing surface-coupled moieties 2930 at regions of the surface of the solid support 2900 that were previously exposed in wells 2915 of the resist material 2910. A random spatial distribution of the sites of the array contains fiducial elements 2920.

In some cases, a random spatial distribution of fiducial elements on a single-analyte array may be achieved by random deposition of fiducial elements at array sites. In other cases, a random spatial distribution of fiducial elements on a single-analyte array may be achieved by forming an array with a first set of predefined sites for analytes and a second set of predefined sites for fiducial elements, in which the second set of predefined sites have a random spatial distribution. FIGS. 30A-30F illustrate a method of forming an array with predefined sites for analytes and fiducial elements. The array utilizes orthogonal analyte and fiducial element binding chemistries to control where analytes and fiducial elements deposit on the array. FIG. 30A depicts an array composition comprising a solid support 3000 with a resist material 3010 (e.g., a photoresist, a resin, etc.) that has been patterned to form wells 3015 with a random spatial distribution. Regions of surface of the solid support 3000 are exposed in the distal portions of the wells 3015. FIG. 30B depicts an array composition after deposition of a surface coating 3025 (e.g., a metal oxide, a metal) on the surface of the solid support 3000 in each well 3015. The surface coating may be achieved by a chemical vapor deposition or chemical liquid deposition process. FIG. 30C depicts an array composition after a subsequent lithographic process forms a second set of wells 3016 in the resist material 3010. Each well 3016 exposes regions of the surface of the solid support 3000. FIG. 30D depicts an array composition after surface-coupled molecules have been deposited in wells 3015 and 3016. Wells 3015 comprising the surface coating 3025 incorporate a first species of surface-coupling moieties 3030 and wells 3016 without the surface coating incorporate a second species of surface-coupling moieties 3031. The two types of surface-coupling moieties 3030 and 3031 may be deposited sequentially or simultaneously. An exemplary system for orthogonal surface chemistries may include attaching organophosphates or organophosphonates to zirconium oxide surface coating, and attaching organosilanes to silicon oxide or silicon surfaces. The first species of surface-coupled moieties 3030 may include a first type of coupling moiety, and the second species of surface-coupled moieties 3031 may include a second type of coupling moiety, in which the first type of coupling moiety is orthogonal to the second type of coupling moiety (e.g., receptor-ligand binding pair vs. oligonucleotide). FIG. 30E depicts an array composition after stripping the resist material 3010 from the solid support 3000, thereby leaving discrete sites with orthogonal coupling chemistries. FIG. 30F depicts an array composition with fiducial elements 3040 coupled to array sites comprising the first type of surface-coupling moieties 3030, in which the fiducial elements 3040 have a random spatial distribution on the array.

Figure 31:
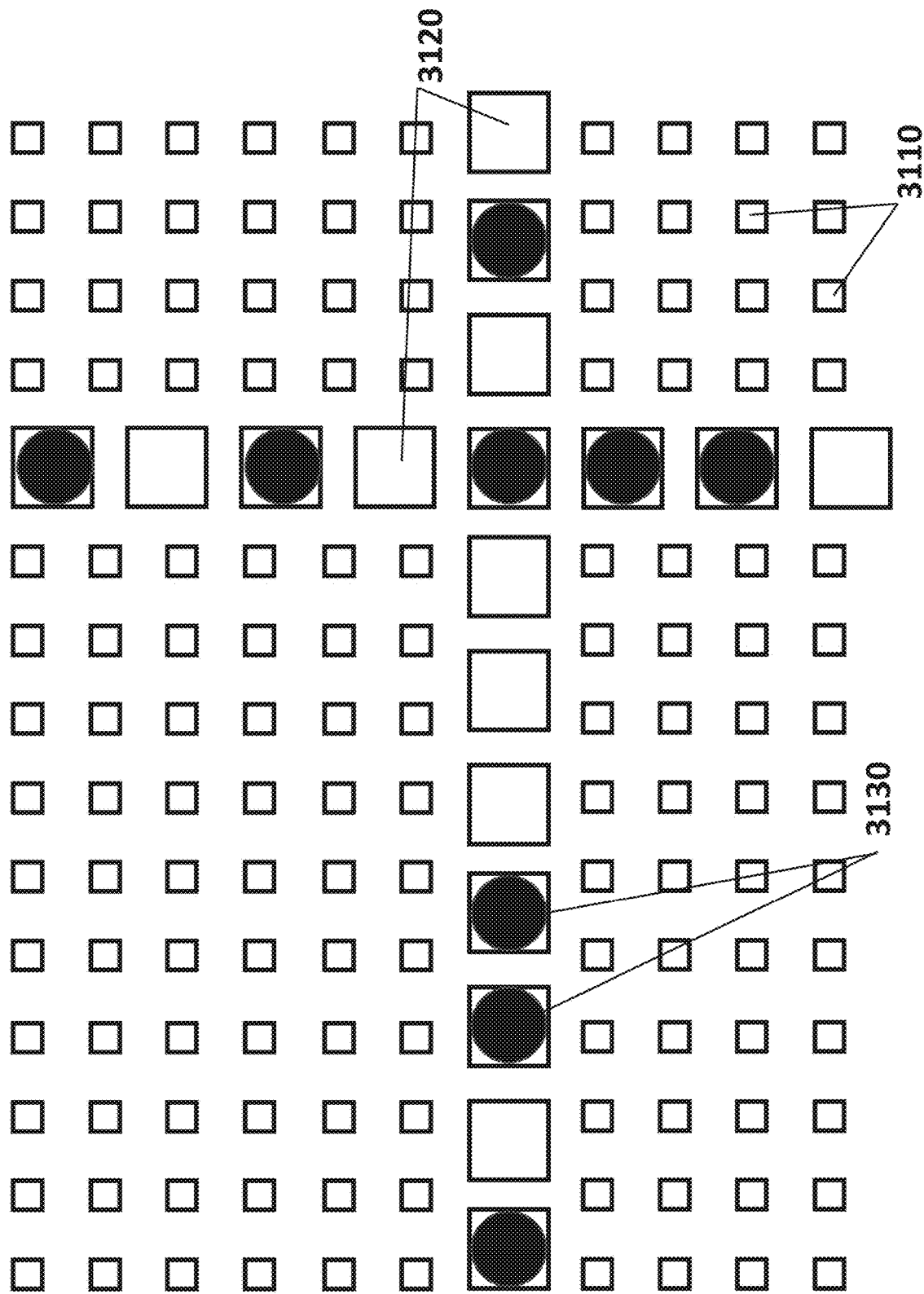
FIG. 31 displays a top-down view of a region of a single-analyte array comprising smaller analyte-binding sites and larger fiducial element-containing sites, in accordance with some embodiments.

FIG. 31 depicts a method of size exclusion to achieve a random spatial distribution of fiducial elements (e.g., fluorescent nanoparticles) on a single-analyte array. The depicted array comprises rectangular subarrays comprising analyte-binding sites 3110. Each subarray of analyte-binding sites is divided by rows or columns of fiducial element-binding sites 3120. The fiducial element-binding sites 3120 are larger than the analyte binding sites 3110. Accordingly, fiducial elements 3130 with a substantially similar characteristic dimension to the fiducial element-binding sites 3120 may preferentially bind to the fiducial element-binding sites 3120. If fiducial elements 3130 are deposited at a sufficiently low concentration such that not all fiducial element-binding sites 3120 become occupied, unique patterns or fingerprints of fiducial elements may be formed around each subarray of analyte-binding sites 3110, such that array-based processes such as image registration and/or landmarking can be performed utilizing the patterns or fingerprints of fiducial elements surrounding the subarrays. In some cases, the characteristic dimension of fiducial elements 3130 and/or fiducial element-binding sites 3120 may be chosen to be less than the pitch (i.e., inter-site spacing) of the analyte-binding sites 3110 to ensure optically resolution of the fiducial elements 3130.

A method of preparing a solid support may further comprise determining a spatial distribution of fiducial elements on a solid support. Determining a spatial distribution of fiducial elements on an array may comprise one or more steps of: i) providing a solid support comprising a plurality of sites to an array-based system comprising a sensing device; ii) detecting at each site of the plurality of sites presence of absence of a detectable signal; iii) based upon presence or absence of a detectable signal at each site, determining presence or absence of a fiducial element at each site of the plurality of sites, and iv) based upon presence or absence of a fiducial element at each site of the plurality of sites, determining a spatial distribution of fiducial elements on the solid support. In some configurations, determining a spatial distribution of fiducial elements on the solid support may further comprise determining a measure of randomness of the spatial distribution of fiducial elements on the solid support. In some configurations, determining a spatial distribution of fiducial elements on the solid support may further comprise determining an array map, as set forth herein, for the solid support. In some configurations, determining an array map may further comprise one or more steps of: i) providing an identification tag to a solid support, in which the identification tag comprises identifying information; ii) associating the identification tag, or identifying information thereof, with the array map, and iii) storing in a non-transitory, computer-readable medium a data structure comprising the array map and the identification tag or identifying information thereof.

In another aspect, provided herein is a method of preparing a solid support, comprising: a) providing the solid support, in which the solid support comprises a plurality of sites, in which each site of the plurality of sites has a unique spatial address on the solid support, and in which each site of the plurality of sites is configured to couple a moiety to the solid support, b) forming a first fiducial element on the solid support, in which the fiducial element comprises an optically passive moiety, and c) depositing a plurality of fiducial elements on the solid support, in which each fiducial element of the plurality of fiducial elements is deposited at a subset of the plurality of sites. In some configurations, forming a first fiducial element on the solid support may comprise forming a plurality of fiducial elements on the solid support, in which each fiducial element of the plurality of fiducial elements comprises an optically passive moiety. In some configurations, forming a first fiducial element on the solid support may be performed before depositing a plurality of fiducial elements on the solid support. In other configurations, forming a first fiducial element on the solid support need not be performed before depositing a plurality of fiducial elements on the solid support.

A method of preparing a solid support may comprise forming a first fiducial element on the solid support, in which the first fiducial element comprises an optically passive moiety. A fiducial element comprising an optically passive moiety may be formed on a solid support by a lithographic method (e.g., photolithography, nanoimprint lithography, etc.). A fiducial element comprising an optically passive moiety may be formed on a solid support by depositing the optically passive moiety on the solid support (e.g., chemical vapor deposition, atomic layer deposition, chemical liquid deposition, etc.).

A first fiducial element may be formed on a site of a solid support. A first fiducial element may be formed on a plurality of sites. For example, a fiducial element comprising a reflective metal layer may be formed on a region of a solid support that would contain 4 sites if the fiducial element was not present. A first fiducial element need not necessarily be formed on a site of a solid support. For example, a fiducial element comprising an optically passive moiety may be formed at a region of a solid support that does not comprise sites, such as an edge of grid of sites, a boundary of a solid support, or an internal region of a solid support that is not configured to couple an analyte. A first fiducial element may be formed on a landmarking region of a solid support. A plurality of fiducial elements comprising optically passive moieties may be formed on a solid support. In some configurations, a plurality of fiducial elements (e.g., comprising optically passive moieties, comprising optically active moieties) may be formed on a solid support, in which the plurality of fiducial elements comprises a random spatial distribution. For example, fiducial elements may be formed by a lithographic method (e.g., photolithography) that utilizes a reticle with openings placed in random but pre-determined spatial addresses. In other configurations, a plurality of fiducial elements (e.g., comprising optically passive moieties, comprising optically passive moieties) may be formed on a solid support, in which the plurality of fiducial elements comprises a non-random spatial distribution. For example, a nanoscale or microscale ruler may be formed on a solid support by depositing one or more fiducial elements at a fixed interval (e.g., 1 fiducial element at each 50 μm interval).

A method of preparing a solid support may further comprise removing a fluidic medium from the solid support. A fluidic medium may be removed from a solid support by any suitable method, such as pressure-driven flow (e.g., vacuum removal of a fluid, capillary flow), passive drainage (e.g., gravity-driven flow), fluid displacement, or evaporation. A liquid fluidic medium may be removed until no liquid fluid is contacted with a solid support. In some cases, a fluidic medium may be removed from a solid support after depositing a plurality of fiducial elements. In particular cases, removal of a fluidic medium need not remove any deposited fiducial elements on a solid support. A method of preparing a solid support may further comprise fluidically sealing an array or a solid support thereof. In some cases, sealing an array or a solid support thereof may comprise sealing a structure (e.g., a flow cell, a fluidic cartridge) comprising the array or solid support thereof. In some cases, an array or a solid support thereof may be sealed with a fluidic medium in contact with the array of solid support thereof. In other cases, an array or a solid support thereof may be sealed with a fluidic medium not in contact with the array of solid support thereof. A fluidic medium may include a gas fluidic medium or a liquid fluidic medium. An array or a solid support thereof may be sealed to prevent exchange of a fluidic medium. For example, a sealed array may be sealed to prevent exchange of a nitrogen atmosphere in contact with the array with an external air atmosphere. In another example, a sealed array may be sealed to prevent exchange of a nitrogen atmosphere in contact with the array with a liquid medium external to the array.

In another aspect, provided herein is a method of forming an array, comprising: a) providing an array, wherein the array comprises: i) a solid support, in which the solid support comprises a plurality of sites and one or more interstitial regions, in which each site of the plurality of sites is configured to couple an analyte (e.g., single analytes), in which each interstitial region is configured to inhibit binding of an unbound moiety, and in which each site is separated from each other site by an interstitial region of the one or more interstitial regions, and ii) a plurality of fiducial elements, in which each fiducial element is located at a site of the plurality of sites, and in which the plurality of fiducial elements is distributed on the solid support at spatially random addresses, and b) depositing a plurality of analytes on the solid support, in which each single analyte of the plurality of analytes is deposited at a site that does not comprise a fiducial element. In some cases, providing an array may be performed before depositing a plurality of analytes on the solid support. In other cases, depositing a plurality of analytes on the solid support may be performed before providing an array.

A method of forming an array may comprise depositing a plurality of analytes (e.g., single analytes) on the solid support. In some cases, an analyte of a plurality of analytes may be coupled to an anchoring moiety. In some cases, each analyte of a plurality of analytes may be coupled to an anchoring moiety. In some cases, a fiducial element is coupled to a solid support by a first anchoring moiety, and an analyte is coupled to the solid support by a second anchoring moiety, in which the first anchoring moiety and the second anchoring moiety comprise the same chemical structure. In other cases, a fiducial element is coupled to a solid support by a first anchoring moiety, and an analyte is coupled to the solid support by a second anchoring moiety, in which the first anchoring moiety and the second anchoring moiety do not comprise the same chemical structure.

A method of forming an array may further comprise coupling an analyte to a site comprising a fiducial element of a plurality of fiducial elements. A method of forming an array may further comprise coupling an analyte to a fiducial element of a plurality of fiducial elements. In some cases, providing an array comprising a plurality of fiducial elements may further comprise coupling an analyte to a fiducial element of the plurality of fiducial elements. In some cases, a method of forming an array may comprise: i) depositing a first plurality of analytes on the solid support, in which each analyte of the first plurality of analytes is deposited at a site that does not comprise a fiducial element, and ii) depositing a second plurality of analytes on the solid support, in which each analyte of the second plurality of analytes is deposited at a site that comprises a fiducial element. An analyte may be coupled to a fiducial element by a covalent interaction or a non-covalent interaction.

In another aspect, provided herein is a method of forming an array, comprising: a) providing an array, wherein the array comprises a solid support, in which the solid support comprises a plurality of sites and one or more interstitial regions, in which each site of the plurality of sites is configured to couple a moiety, in which each interstitial region is configured to inhibit binding of an unbound moiety, and in which each site is separated from each other site by an interstitial region of the one or more interstitial regions, and b) depositing a plurality of moieties on the solid support, in which the plurality of moieties comprises a plurality of analytes and a plurality of fiducial elements. A plurality of moieties may be provided in an optimal ratio of analytes to fiducial elements, such as at least about 1:1, 2:1, 5:1, 10:1, 50:1, 100:1, 500:1, 1000:1, 5000:1, 10000:1, 50000:1, 100000:1, 500000:1, 1000000:1, or more than 1000000:1. Alternatively or additionally, a plurality of moieties may be provided in an optimal ratio of analytes to fiducial elements, such as no more than about 1000000:1, 500000:1, 100000:1, 50000:1, 10000:1, 5000:1, 1000:1, 500:1, 100:1, 50:1, 10:1, 5:1, 2:1, 1:1, or less than 1:1.

In another aspect, provided herein is a method of mapping an array, comprising: a) providing an array, wherein the array comprises a solid support, in which the solid support comprises a plurality of sites and one or more interstitial regions, in which each site of the plurality of sites is configured to couple an analyte (e.g., single analytes), in which each interstitial region is configured to inhibit binding of an unbound moiety, and in which each site is separated from each other site by an interstitial region of the one or more interstitial regions, and b) depositing a mapping moiety of a plurality of mapping moieties at each site of the plurality of sites. In some cases, a method of mapping an array may further comprise one or more steps of: c) detecting presences or absences of detectable signals from mapping moieties over a region of an array, in which the region of the array comprises each site of the plurality of sites, d) assigning a location tag to each address of the region of the array comprising presence of a detectable signal from a mapping moiety; and e) storing each location tag in a non-transitory, computer-readable medium. In some cases, a method of mapping an array may comprise depositing a first mapping moiety of a plurality of mapping moieties at each site of the plurality of sites, in which a second mapping moiety of the plurality of mapping moieties is not deposited at an interstitial region of the one or more interstitial regions.

A method of mapping an array may comprise depositing a mapping moiety of a plurality of mapping moieties at each site of the plurality of sites. In some cases, after depositing a plurality of mapping moieties on a solid support, each site may comprise one and only one mapping moiety. In other cases, after depositing a plurality of mapping moieties on a solid support, each site may comprise a plurality of mapping moieties. In some cases, depositing a plurality of mapping moieties on a solid support may comprise depositing a plurality of fluorescent mapping moieties. In some cases, depositing a plurality of mapping moieties on a solid support may comprise coupling a fluorescent mapping moiety to a coupling moiety of a site of an array. In some cases, depositing a plurality of mapping moieties on a solid support may comprise covalently coupling a fluorescent mapping moiety to a coupling moiety of a site of an array. For example, a plurality of fluorescent dye molecules may be conjugated to coupling moieties of array sites by a Click-type reaction. In other cases, depositing a plurality of mapping moieties on a solid support may comprise non-covalently coupling a fluorescent mapping moiety to a coupling moiety of a site of an array. For example, a plurality of nanoparticles may be electrostatically coupled to coupling moieties of array sites. In some cases, a plurality of mapping moieties may comprise a plurality of detectably-labeled anchoring moieties (e.g., structured nucleic acid particles, nucleic acid origami, nucleic acid nanoballs, etc.). In some cases, a plurality of mapping moieties may comprise one or more fiducial elements (e.g., fluorescent nanoparticles).

In an advantageous method of mapping an array, the method may comprise: a) providing an array comprising a solid support, in which the single-analyte array comprises a first site and a second site, in which the first site comprises a first address on the solid support, in which the second site comprises a second address on the solid support, and in which the first address and the second address are resolvable at single-analyte resolution, b) coupling a fiducial element to the second site, c) coupling a mapping moiety to the first site, in which the mapping moiety comprises a detectable label d) detecting the mapping moiety and the fiducial element; and identifying the first address relative to the second address.

In another aspect, provided herein is a method of forming an array map, comprising one or more, two or more, three or more, four or more, or five or more steps of: a) providing an array, wherein the array comprises: i) a solid support, in which the solid support comprises a plurality of sites and one or more interstitial regions, in which each site of the plurality of sites is configured to couple an analyte (e.g., single analytes), in which each interstitial region is configured to inhibit binding of an unbound moiety, and in which each site is separated from each other site by an interstitial region of the one or more interstitial regions, and ii) a plurality of fiducial elements, in which each fiducial element is located at a site of the plurality of sites, and in which the plurality of fiducial elements is distributed on the solid support at spatially random addresses, b) providing a non-transitory, computer-readable medium comprising a data structure, in which the data structure comprises a plurality of data units, in which each data unit comprises a location tag for a site of the plurality of sites, and in which each site of the plurality of sites comprises a data unit in the data structure; c) detecting presence or absence of a detectable signal of a fiducial element at each site of the plurality of sites, d) determining a detection data set, in which the detection data set comprises a unit of physical information for each site of the plurality of sites, in which each unit of physical information relates to the detected presence or absence of the fiducial element at each site of the plurality of sites; e) adding the detection data set to the data structure, and 0 relating each unit of the detection data set with a data unit of the plurality of data units. In some cases, a unit of physical information may comprise a value or magnitude of a physical measurement collected by a sensing device. In other cases, a unit of physical information may comprise a categorized value (e.g., DETECTED/NOT DETECTED).

A method, as set forth herein, may comprise one or more steps of detecting signals from fiducial elements at sites of an array (e.g., cyclical or serial detection of arrays may comprise multiple detection steps). In some cases, a method may comprise one or more steps of: i) contacting an array comprising a plurality of optically active moieties with light of a first wavelength, and ii) after contacting the array with the light of the first wavelength, detecting at sites of the array signals comprising light a second wavelength, wherein the first wavelength and the second wavelength differ. In some cases, a method may comprise one or more steps of: i) contacting an array comprising an optically passive moiety with light of a first wavelength, and ii) after contacting the array with the light of the first wavelength, detecting at an address of the array a signal, wherein the signal comprises light of the first wavelength. In some cases, a method may comprise one or more steps of: i) detecting signals from a plurality of optically active moieties at sites of a plurality of sites, and ii) detecting a signal from an optically passive moiety. In particular cases, steps i) and ii) may occur simultaneously. In other cases, steps i) and ii) may occur sequentially. In yet other cases, steps i) and ii) may occur cyclically.

In another aspect, provided herein is a method of aligning an array, comprising: a) providing an array, in which the array comprises: i) a solid support, in which the solid support comprises a plurality of sites and one or more interstitial regions, in which each site of the plurality of sites is configured to couple an analyte, in which each interstitial region is configured to inhibit binding of an unbound moiety, and in which each site is separated from each other site by an interstitial region of the one or more interstitial regions, ii) a plurality of fiducial elements, in which each fiducial element is located at a site of the plurality of sites, and in which the plurality of fiducial elements is distributed on the solid support at spatially random addresses; and iii) a landmarking fiducial element, b) identifying a position for the array relative to a sensing device based upon a first identification of the landmarking fiducial element relative to the sensing device, c) altering a position of the sensing device relative to the array; and d) based upon a second identification of the landmarking fiducial element relative to the detection device, determining a position or an offset of the array relative to the position. In some cases, altering a position of a sensing device relative to an array may comprise rastering, translating, rotating, or tilting a sensing device relative to an array. In some cases, a method of aligning an array may comprise adjusting a position of the array relative to an initial position or a final position. For example, when performing iterative scans of an array with a detection device, the array may be returned at the end of a scan to an initial position based upon the identification of a landmarking fiducial element. In another example, when performing iterative scans of an array with a detection device, an initial position of a detection device may be determined relative to a landmarking fiducial element before a first scan, and an offset relative to the initial position of the detection device may be determined before a second scan rather than adjusting the array back to the initial position.

Figure 16:
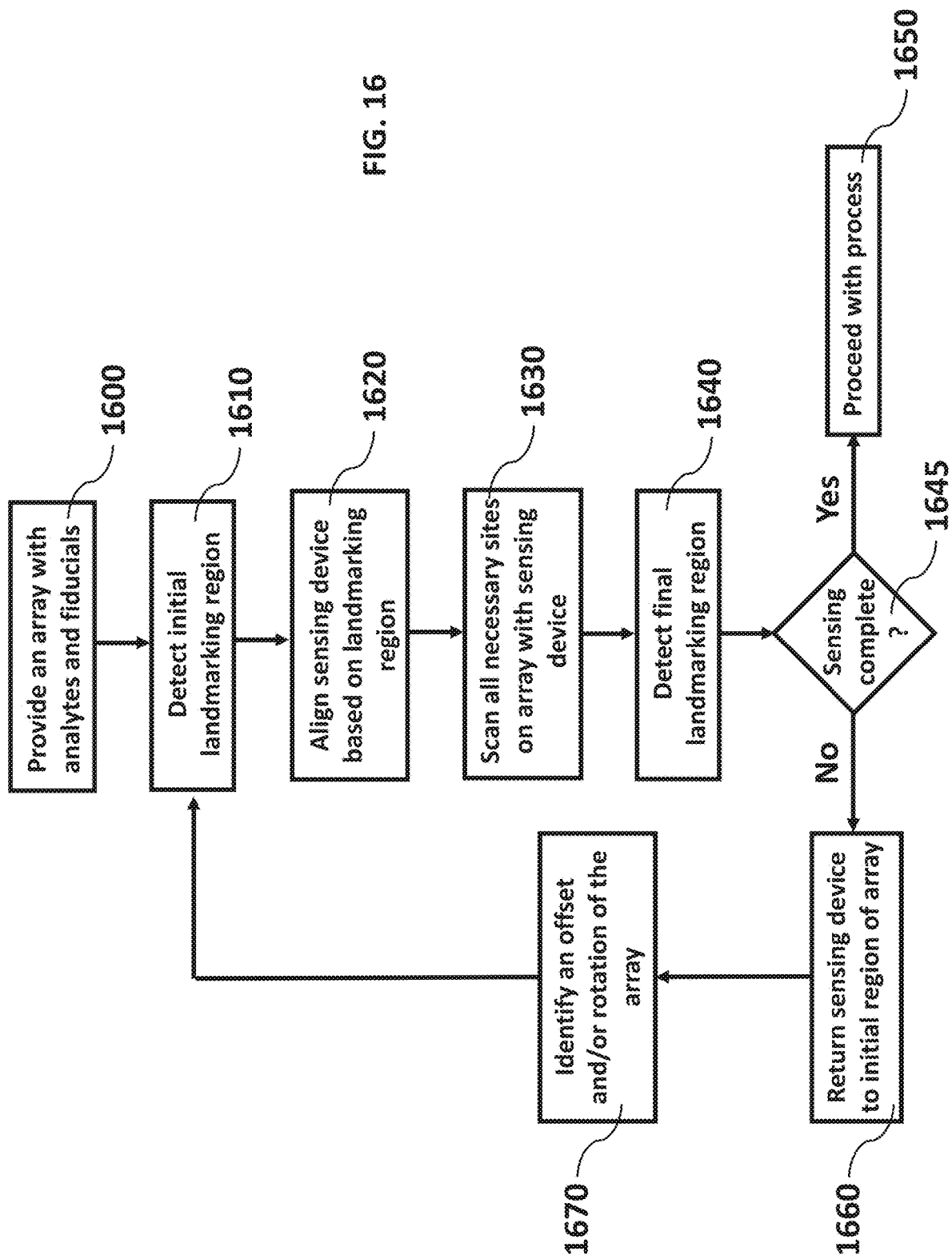
FIG. 16 shows a schematic for a landmarking process, in accordance with some embodiments.

FIG. 16 provides a schematic depicting a landmarking process, as set forth herein. In an initial step 1600, an array comprising a plurality of fiducial elements and, optionally, analytes of interest is provided. Optionally, to initiate a sensing process, an initial landmarking region may be detected 1610 by a sensing device. The sensing device may be aligned 1620 with the array based upon a sensed relative position between the initial landmarking region and the sensing device. Subsequently, the array may be scanned 1630 to detect presence or absence of a signal at each site on the array that is necessary for a process or assay (e.g., all sites, a subset of all sites, etc.). Optionally, a landmarking process may comprise a step of detecting 1640 an intermediate or final landmarking region. In some cases, a landmarking process may include at least one of steps 1610 and 1640. In particular cases, a landmarking process may include both steps 1610 and 1640. After scanning 1630 all necessary sites of the array, a decision 1645 may be made if a sensing process is complete. If the sensing process is complete, any further steps of the array-based process may be performed 1650. If the sensing process is not complete, the sensing device may be returned 1660 to the initial landmarking region or an intermediate region, then iterating the landmarking process until sensing is complete. Optionally, an offset and/or rotation of a position of the array may be determined 1670 relative to a sensing device based upon the location of a landmarking region. In some cases, an array may be positioned at an absolute initial position based upon the location of a landmarking region (i.e., fine alignment of the array). In other cases, an array may be initially positioned at a variable position relative to a landmarking region provided that the offset and/or rotation of the array relative to a sensing device does not exceed a set limit for detection, such as less than 10%, 5%, 1%, 0.5%, 0.1%, or less than 0.1% positional error relative to the landmarking region (i.e., coarse alignment of the array).

Figure 19A:
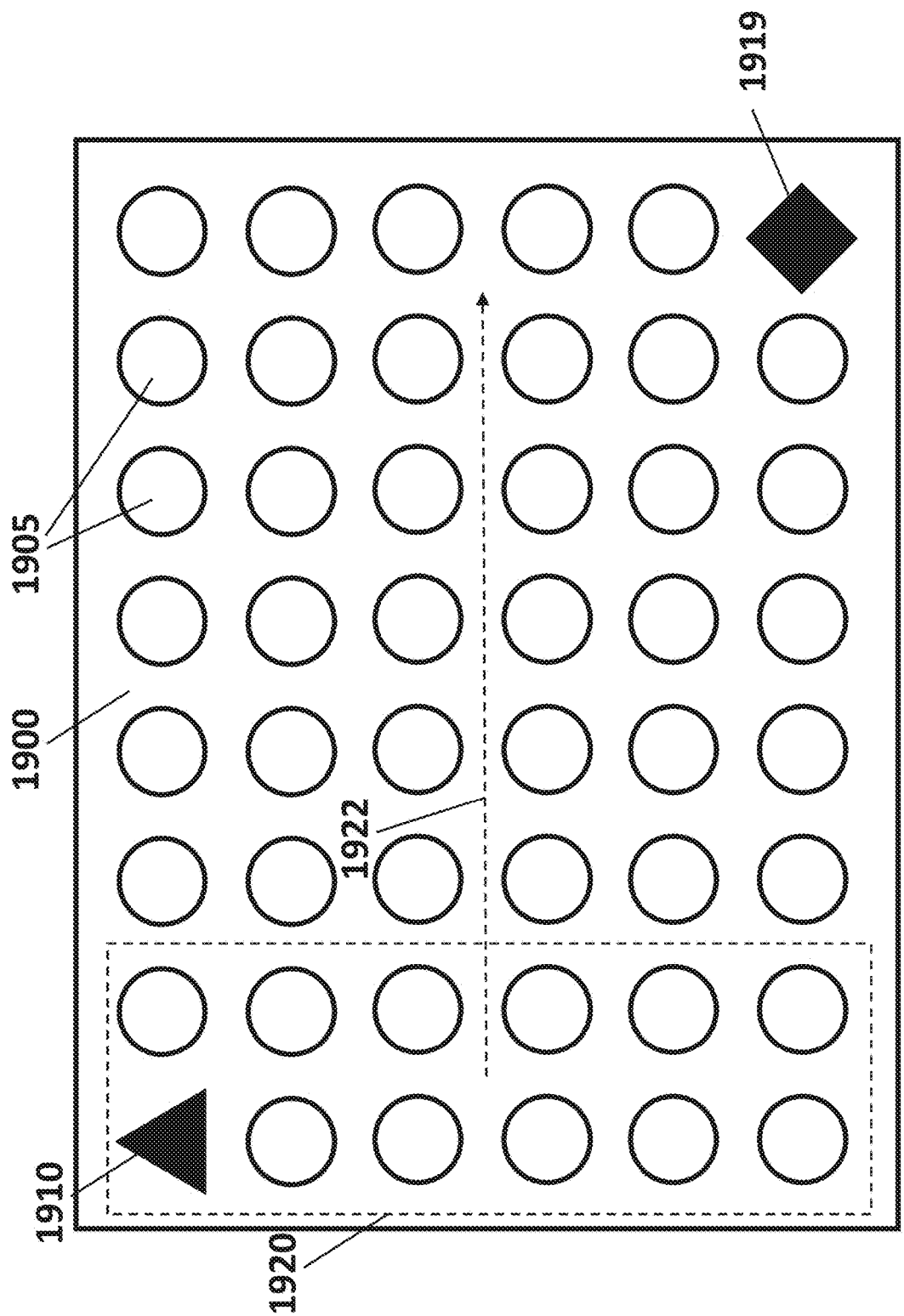
FIGS. 19A and 19B display methods for utilizing landmarking regions for alignment and control of sensing devices, in accordance with some embodiments.
Figure 19B:
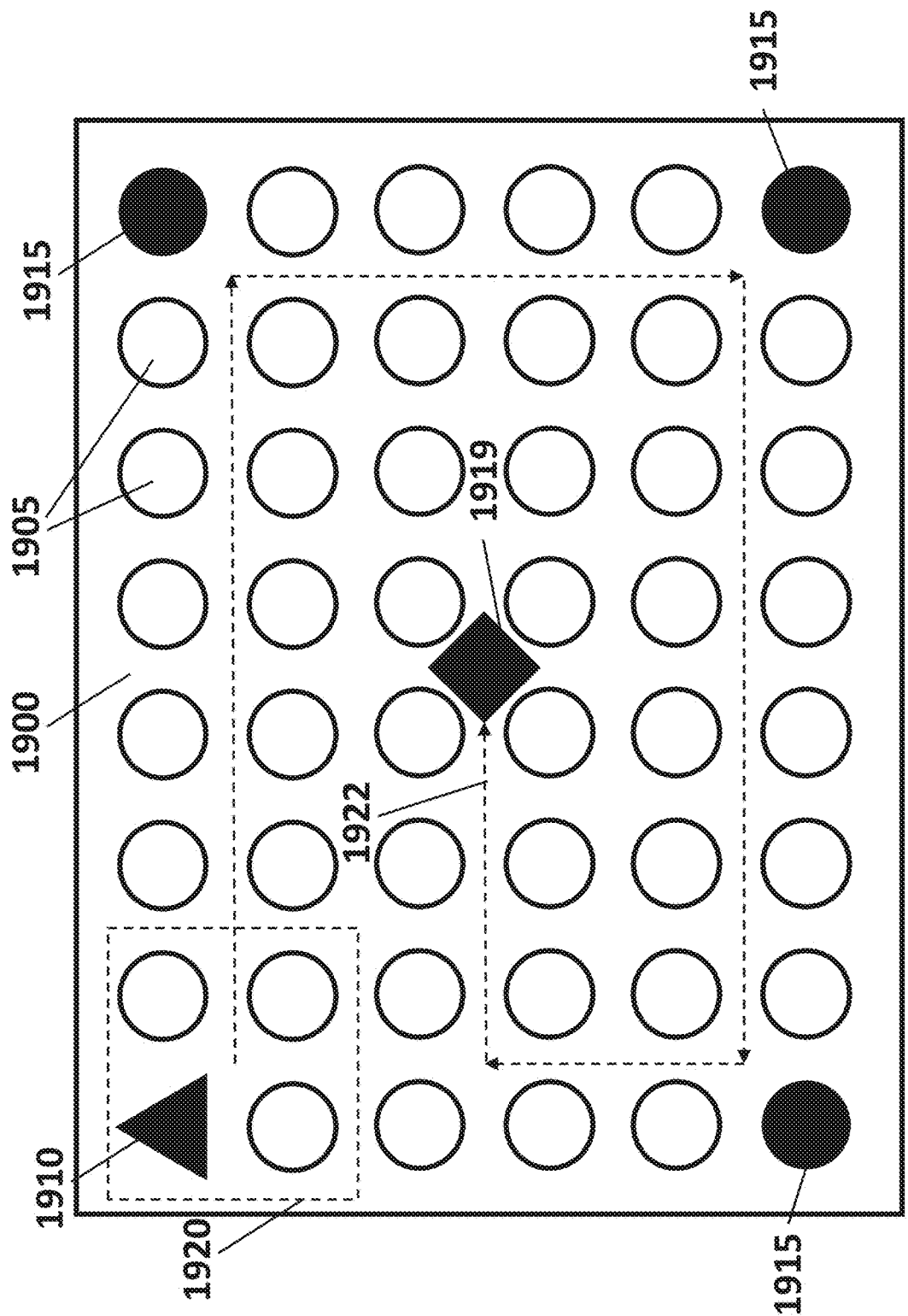

FIGS. 19A and 19B illustrate methods of utilizing initial, intermediate, and final landmarking regions for spatial reference. FIG. 19A depicts a solid support 1900 comprising a plurality of sites 1905, an initial landmarking region 1910 and a final landmarking region 1919. A sensing device has a field-of-view depicted by box 1920. The field-of-view 1920 is initially adjusted to an initial subset of sites based upon alignment with the initial landmarking region 1910. The sensing device is scanned across the plurality of sites 1905 in direction 1922 until reaching the final landmarking region 1919. FIG. 19B depicts a solid support 1900 comprising a plurality of sites 1905, an initial landmarking region 1910, intermediate landmarking regions 1915, and a final landmarking region 1919. A sensing device has a field-of-view depicted by box 1920. The field-of-view 1920 is initially adjusted to an initial subset of sites based upon alignment with the initial landmarking region 1910. The sensing device is rastered across the plurality of sites 1905 in direction 1922. Intermediate landmarking regions 1915 may be detected to identify regions in an image acquired by the sensing device. In some cases, the sensing device can be configured to alter the raster pattern of the sensing device based upon detection of landmarking regions 1915. The sensing device is rastered along path 1922 until the final landmarking region 1919 is reached. Optionally, the sensing device can be configured to stop restoring upon sensing landmarking region 1919. Alternatively, the sensing device can be configured to stop restoring after traveling a preset distance.

In another aspect, provided herein is a method of altering or calibrating an optical detection device comprising: a) providing a single-analyte array, wherein the single-analyte array comprises: i) a solid support, in which the solid support comprises a plurality of sites and one or more interstitial regions, in which each site of the plurality of sites is configured to couple an analyte, in which each interstitial region is configured to inhibit binding of an unbound moiety, and in which each site is separated from each other site by an interstitial region of the one or more interstitial regions; and ii) a plurality of fiducial elements, in which each fiducial element is located at a site of the plurality of sites, and in which the plurality of fiducial elements is distributed on the solid support at spatially random addresses, b) obtaining a plurality of signals from the single-analyte array using a optical detection device, in which the plurality of signals comprise a spatial pattern of a subset of the plurality of fiducial elements, c) determining an optical calibration parameter based upon the plurality of signals, and d) based upon the optical calibration parameter, altering an optical setting of the optical detection device relative to the single-analyte array.

Figure 25:
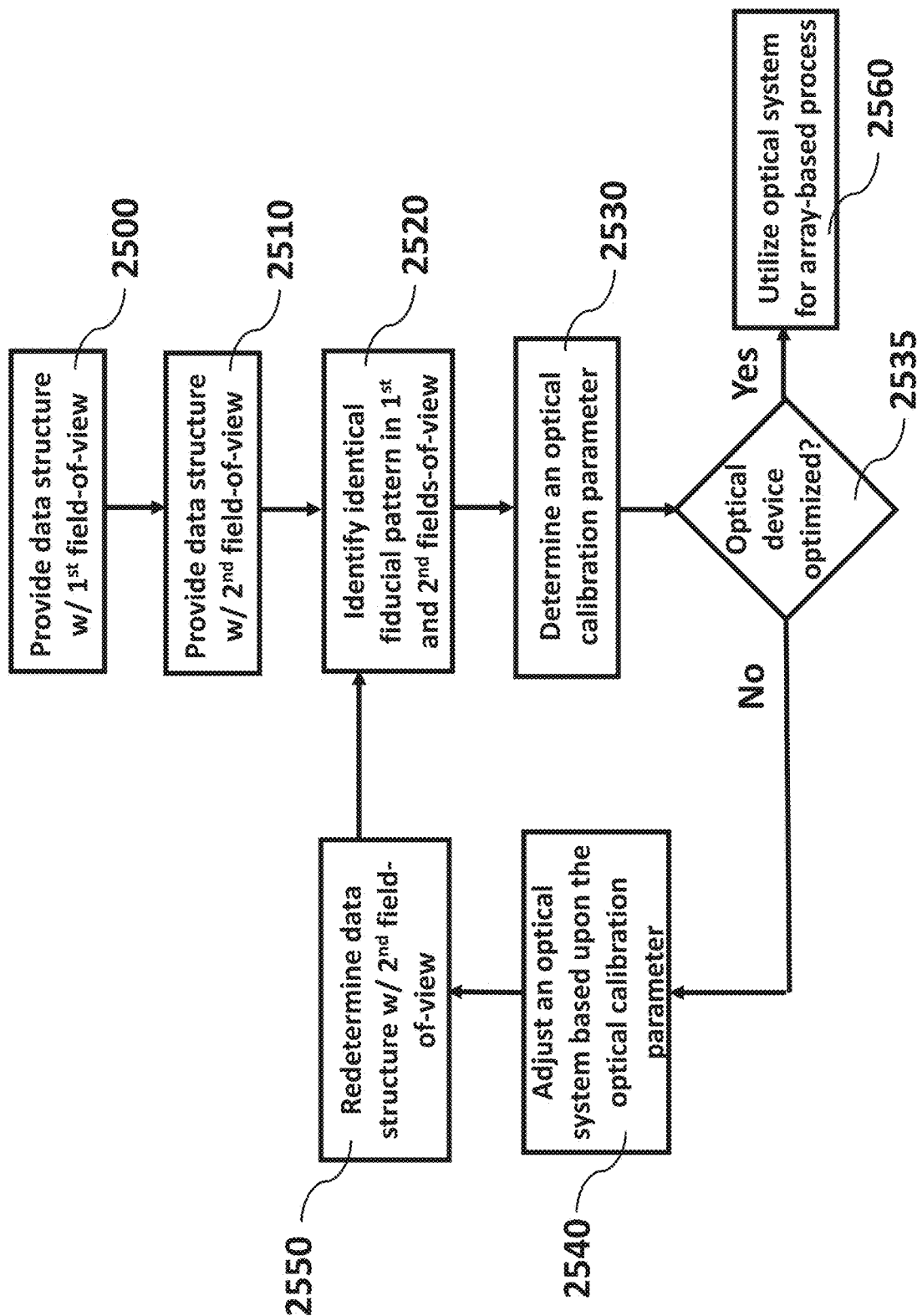
FIG. 25 depicts a schematic of a process for calibrating or altering an optical detection system utilizing fiducial elements, in accordance with some embodiments.

FIG. 25 displays a flowchart for a process of altering or calibrating an optical detection system. In a first step, a first data structure comprising a first field-of-view from an optical sensor may be provided 2500. In a second step, a second data structure comprising a second field-of-view from an optical sensor may be provided 2510. In a third step, a spatial pattern of signals from fiducial elements that is common to the first field-of-view and the second field-of-view may be identified 2520. In a fourth step, an optical calibration parameter may be determined 2530 based upon a comparison of the spatial pattern of signals in the first field-of-view to the spatial pattern of signals in the second field-of-view. A comparison of the spatial patterns of signals in the first field-of-view to the spatial pattern of signals in the second field-of-view may comprise comparing a difference between the spatial patterns of signals in the first field-of-view and the spatial pattern of signals in the second field-of-view (e.g., a difference in focus, a difference in brightness, a difference in contrast, a difference in shape or morphology, a difference in tilt, a difference in rotation, a difference in excitation light source power density, a difference in excitation light source power spatial or temporal distribution, etc.). In some cases, an optical calibration parameter may comprise an image quality metric (e.g., sharpness, noise, dynamic range, contrast, distortion, exposure, etc.). Based upon a determined optical calibration parameter, it may be decided if an optical detection system is optimized 2535. If the optical detection system is optimized, the optical detection system may be utilized 2560 for an array-based process. If the optical detection system is not optimized, optionally, the optical detection system may be adjusted 2540 based upon the determined optical calibration parameter (e.g., adjusting a working distance, adjusting an excitation light source, recalibrating an optical sensor, etc.). After adjusting the optical detection system based upon the optical calibration parameter, the second data structure comprising the second field-of-view may be re-collected 2560. The re-collected second data structure may be utilized to determine the optical calibration parameter again. In some cases, the first data structure may comprise a reference field-of-view, such as a field-of-view of an array captured at a time before an array-based process is initiated.

In another aspect, provided herein is a method of registering overlapping data sets, comprising: a) obtaining a first data set of an array, in which the first data set comprises a spatial distribution of detected signals in a first field-of-view of a sensing device, in which the first field-of-view encompasses a first plurality of sites, in which the spatial distribution of detected signals comprises a pattern of detected signals from a plurality of fiducial elements, and in which a spatial location of an address of a site of the first plurality of sites is known with respect to the pattern of detected signals from the plurality of fiducial elements, b) obtaining a second data set of the array, in which the second data set comprises a spatial distribution of detected signals in a second field-of-view of the sensing device, in which the second field-of-view encompasses a second plurality of sites, in which the second plurality of sites comprises the pattern of detected signals from the plurality of fiducial elements, and in which the second field-of-view comprises the site of the first plurality of sites, c) aligning the pattern of detected signals from the first data set with the pattern of detected signals from the second data set, and d) after aligning the pattern of detected signals from the first data set with the pattern of detected signals from the second data set, determining a presence or absence of a signal at the site of the plurality of sites in the second data set. In some cases, a first data set may comprise only detected signals from fiducial elements. In some cases, a second data set may comprise detected signals from fiducial elements and analytical reagents bound to analytes at analyte-containing sites.

Figure 17:
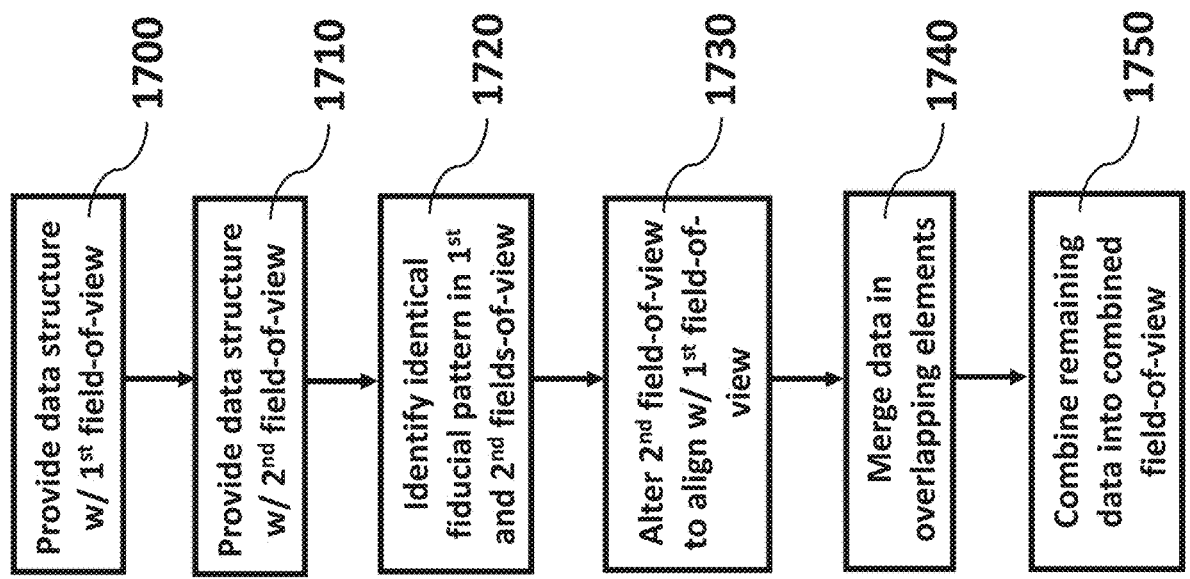
FIG. 17 depicts a schematic for an data registration process, in accordance with some embodiments.

FIG. 17 provides a schematic representation of a fiducial-based image registration process. In a first step, a data structure may be provided 1700, in which the data structure comprises a first field-of-view. In a second step, a data structure may be provided 1710, in which the data structure comprises a second field-of-view. Subsequently, the first field-of-view and the second field-of-view may be compared 1720 to identify an identical or near-identical spatial pattern of fiducial elements that is common to both fields-of-view, for example as determined by an image processing algorithm that is configured to register spatial information from images. Optionally, an image processing algorithm may utilize a local or global measure of uniqueness for a pattern of fiducial elements when registering two images. Optionally, before or after identifying a common pattern of fiducial elements, the second field-of-view may undergo one or more data alterations (e.g., rescaling, rotation, tilting, etc.) to properly align 1730 the common pattern. In some cases, a method of motion correction or tilt correction (e.g., due to vibration, due to thermal fluctuations, etc.) may comprise an image registration method containing one or more of steps 1700-1730. Optionally, after aligning 1730 the first field-of-view and the second field-of-view, overlapping data elements may be merged 1740 (e.g., signal averaged, discarding data from one field-of-view, etc.). Optionally, after merging 1740 the overlapping data elements, the first field-of-view and the second field-of-view may be combined 1750 to form a combined field-of-view.

Figure 28B:
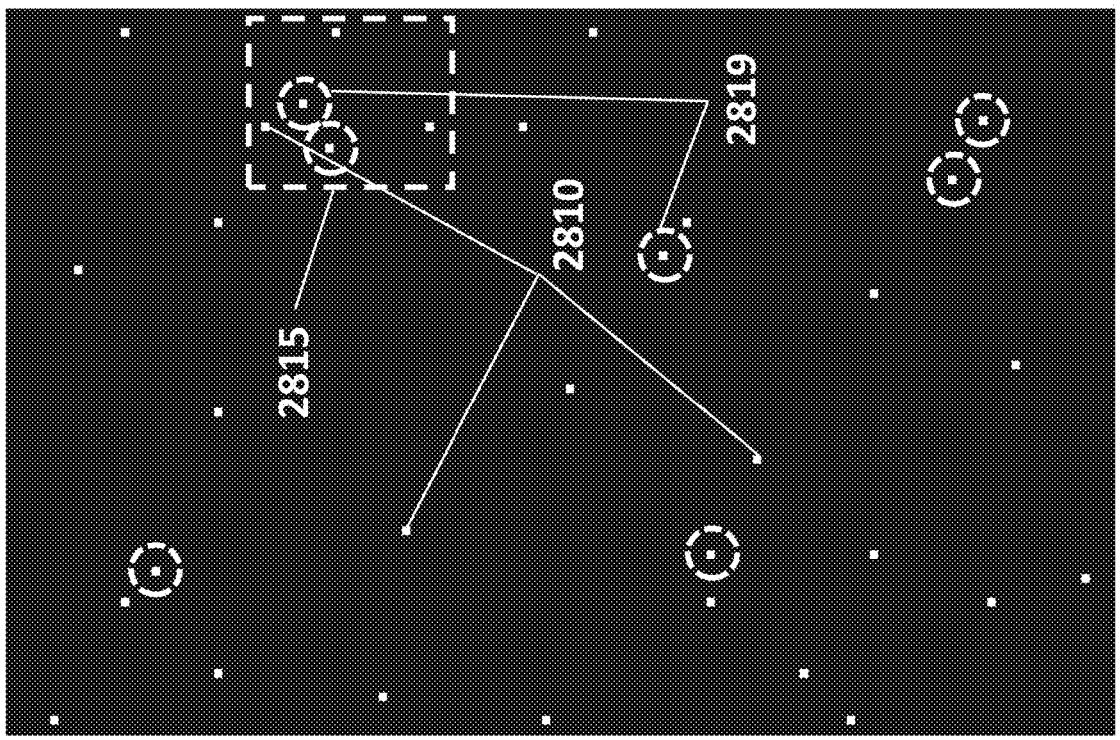
FIGS. 28A, 28B, and 28C illustrate simulated fluorescent image data of single-analyte arrays during an assay involving binding of an analytical reagent to particular array sites, in accordance with some embodiments.
Figure 28A:
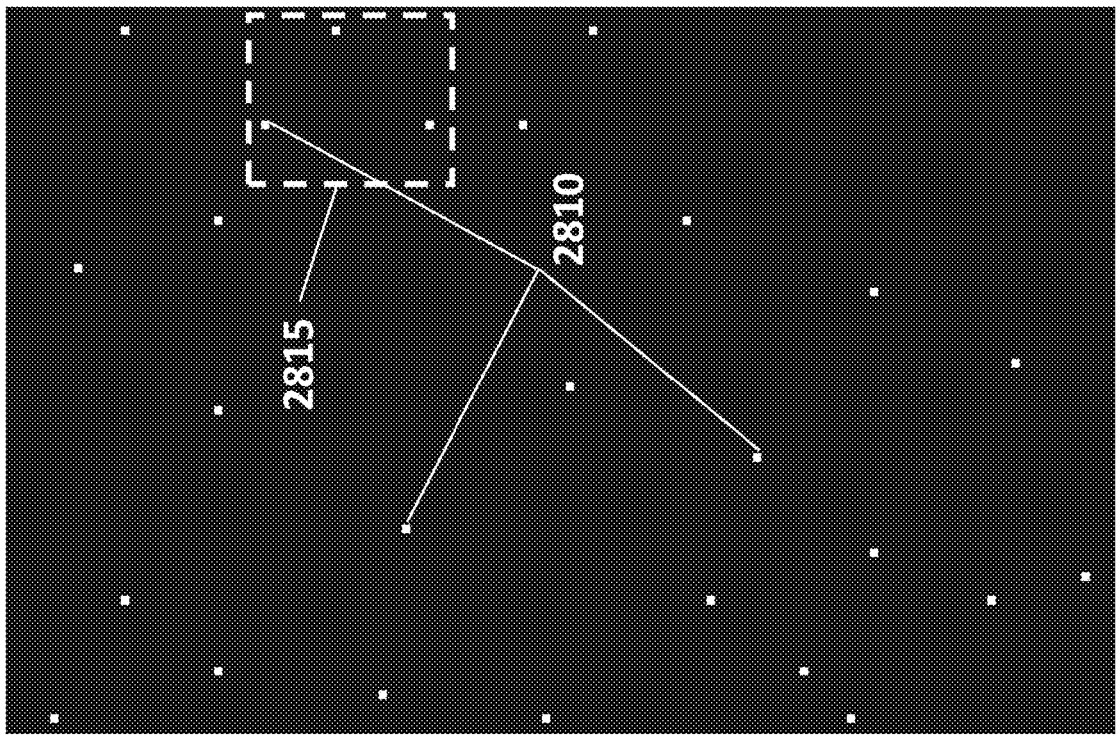
Figure 28D:
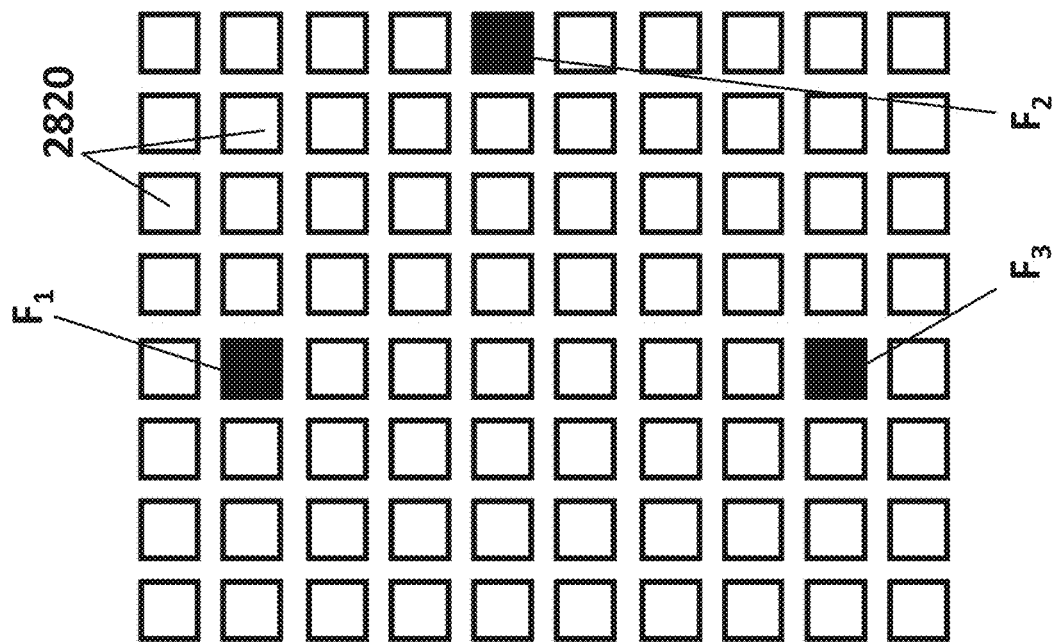
FIGS. 28D, 28E, 28F, and 28G depict spatial distributions of fiducial elements and analytical reagents in a subregion of FIGS. 28A, 28B, and 28C, respectively, in accordance with some embodiments.
Figure 28C:
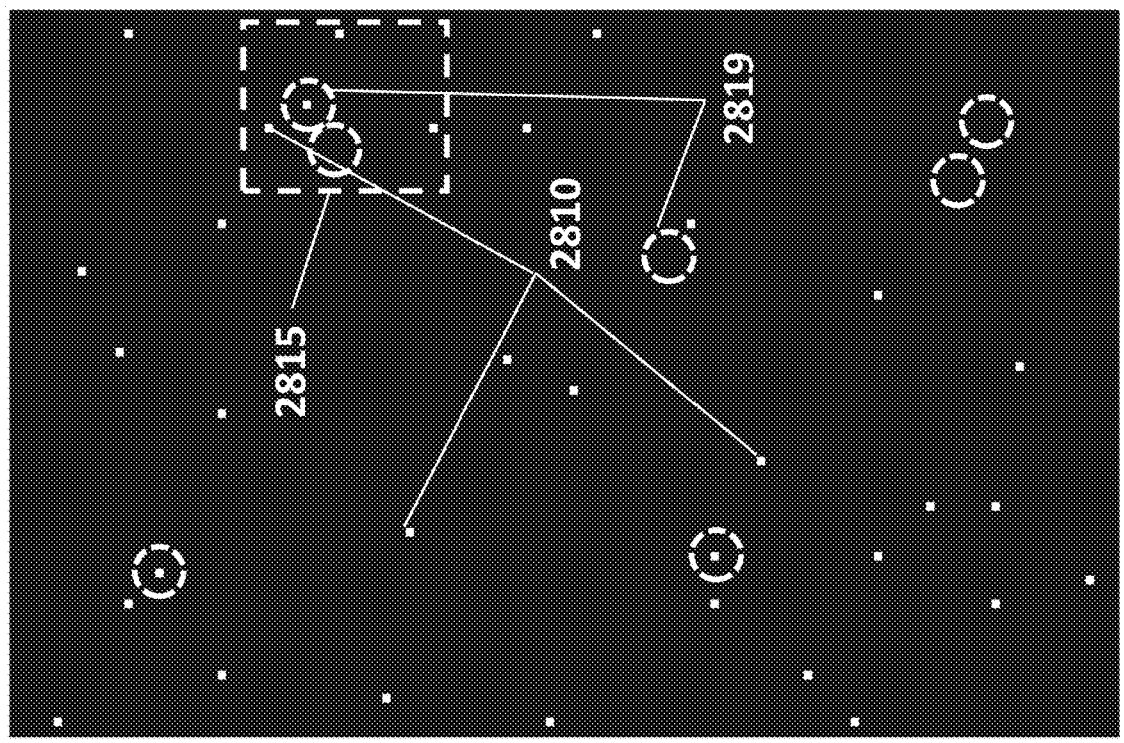

FIGS. 28A-28G depict additional aspects of data registration, in accordance with some embodiments. FIGS. 28A-28C illustrate simulated image data for fluorescent imaging of a single-analyte array during various steps of an array-based process. FIG. 28A depicts a simulated image of a single-analyte array containing a plurality of sites, in which a first subset of the plurality of sites with a random spatial distribution provide optical signals 2810 (e.g., fluorescent light emission, fluorescence lifetime) due to the presence of a fiducial element at each site of the first subset of the plurality of sites. A subregion of the array containing a subdistribution of the first subset of the plurality of sites is enclosed by box 2815. The relative positions of points 2810 from fiducial elements within the subregion 2815 is unique relative to any other possible subdistribution of points from fiducial elements in FIG. 28A. FIG. 28B depicts simulated image data for the single-analyte array of FIG. 28A after binding a first analytical agent that selectively binds a first fraction of analytes on the single-analyte array. The distribution of points 2810 from fiducial elements remains unchanged relative to the observed points shown in FIG. 28A. Additional points 2819 (e.g., optical signals form fluorescent light emission, fluorescence lifetime) are observed at a second subset of sites (points highlighted in circles 2819) of the plurality of sites of the single-analyte array due to the binding of first analytical agents (e.g., affinity agents) to analytes at the second subset of sites. FIG. 28C depicts simulated image data for the single-analyte array of FIG. 28A after binding a second analytical agent that selectively binds a second fraction of analytes on the single-analyte array. The distribution of points 2810 from fiducial elements remains unchanged relative to the observed points shown in FIG. 28A. Additional points (e.g., optical signals from fluorescent light emission, fluorescence lifetime) are observed at a third subset of sites of the plurality of sites of the single-analyte array due to the binding of second analytical agents (e.g., affinity agents) to analytes at the second subset of sites. The highlighted circles from FIG. 28B remain at the same addresses in FIG. 28C to highlight that certain addresses of the second subset of sites also belong to the third subset of sites, while certain other addresses of the second subset of sites are not found in the third subset of sites.

Figure 28F:
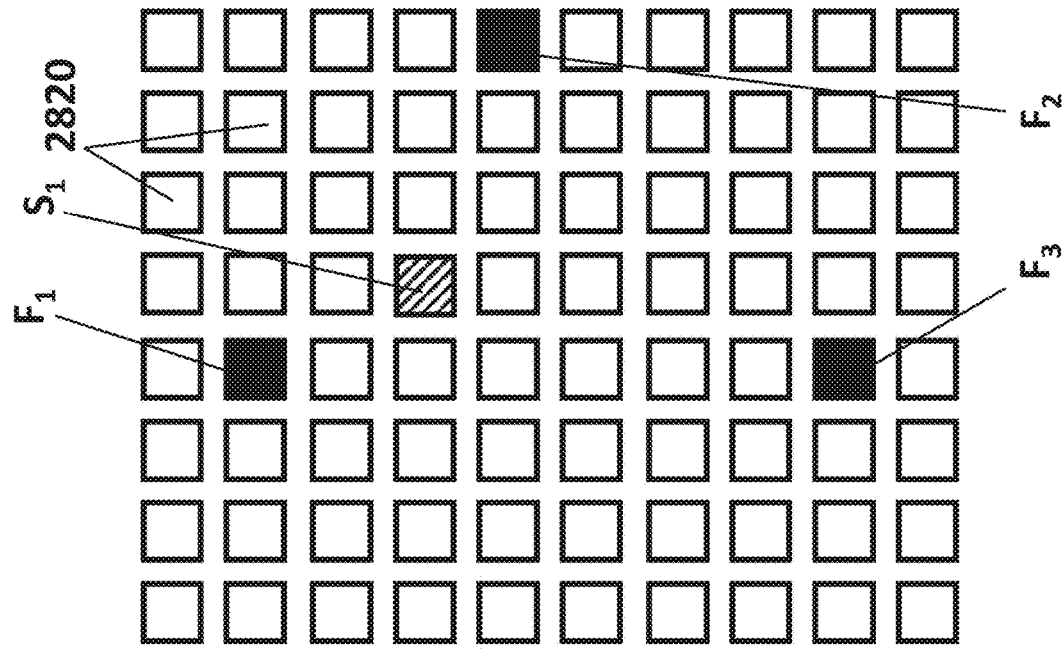
Figure 28E:
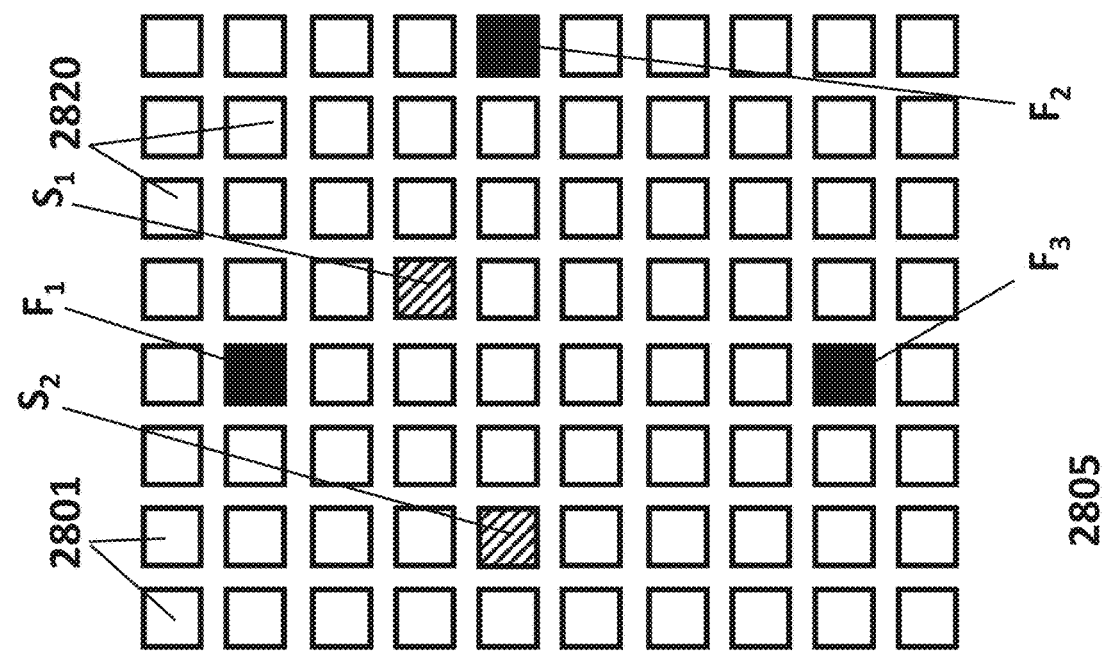
Figure 28G:
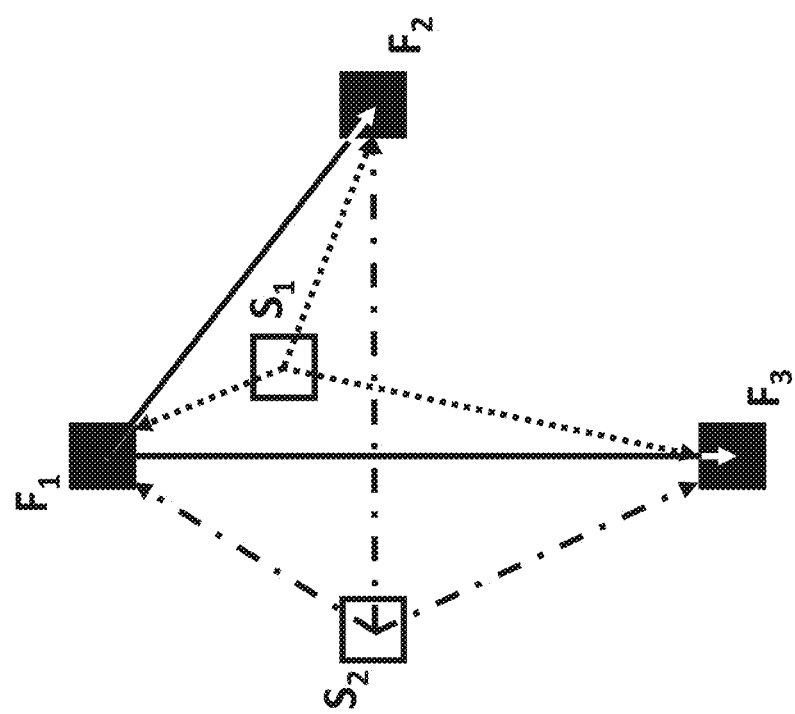

FIGS. 28D-28F depict top-down views of patterned array surfaces corresponding to the subregion 2815 highlighted in FIGS. 28A-28C, respectively. The single-analyte array comprises a rectangular array of sites 2820. As shown in FIG. 28D, within the subregion 2815 of FIGS. 28A-28C, a subdistribution of fiducial elements ($F_1$, $F_2$, $F_3$) can be mapped onto the rectangular array grid. FIG. 28E depicts the observed data of FIG. 28B, in which signals from analytical agents are observed at sites $S_1$ and $S_2$, which addresses can be mapped onto the rectangular array grid. FIG. 28F depicts the observed data of FIG. 28C, in which a signal from an analytical agent is observed at site $S_1$, which address can be mapped onto the rectangular array grid. FIG. 28G depicts an aspect of identifying the addresses of sites $S_1$ and $S_2$ relative to fiducial elements $F_1$, $F_2$, and $F_3$. Each site of the array can be identified, for example with respect to a vector direction and magnitude relative to a fiducial element. Combined sets of vector magnitudes and directions with respect to unique subdistributions of fiducial elements can increase confidence or decrease measurement uncertainty in the observation (e.g., presence of a signal, absence of a signal) at each array address of a single-analyte array. Accordingly, a presence or absence of an optical signal at each site of a single-analyte array can be determined based upon relative positions of analyte-containing sites with respect to subdistributions of fiducial elements when the fiducial elements have a random spatial distribution on the single-analyte array.

A method of registering spatially overlapping data sets may utilize a first data set comprising a first plurality of sites, and a second data set comprising a second plurality of sites, in which a site of the first plurality of sites or a site of the second plurality of sites is non-resolvable (e.g., optically non-resolvable). In some cases, an address of a first site of a first plurality of sites or an address of a second site of a second plurality of sites may be non-resolvable based upon a ratio of a magnitude of a detected signal from a first site or a second site to a magnitude of a detected background signal or a signal-to-noise ratio. A ratio of a magnitude of a signal from a first site or a second site to a magnitude of a detected background signal may be considered non-resolvable if the ratio is less than about 5:1, 4:1, 3:1, 2.5:1, 2:1, 1.5:1, 1.25:1, 1.2:1, 1.1:1, 1.05:1, 1:1, or less than 1:1. Alternatively or additionally a detected background signal may be considered non-resolvable if the ratio is greater than about 1:1, 1.05:1, 1.1:1, 1.2:1, 1.25:1, 1.5:1, 2:1, 2.5:1, 3:1, 4:1, 5:1, or more than 5:1.

A method of registering spatially overlapping data sets may further comprise: a) collecting a first data set of an array on an array-based system comprising a sensing device; and b) collecting a second data set of the array on the array-based system comprising a sensing device. In some cases, a sensing device of an array-based system may comprise a sensor, in which the sensor comprises a pixel array containing a plurality of pixels (e.g., a camera-based optical system). In particular cases, collecting a first data set or collecting a second data set may comprise distinguishing signal intensities at each pixel of a plurality of pixels of a pixel array. For example, distinguishing signal intensities at each pixel of a plurality of pixels of a pixel array may comprise identifying, inferring, or interpolating intensity peaks or any other signal parameter and corresponding the intensity peaks or any other signal parameter to addresses of an array. In some cases, signal intensities may comprise signal magnitudes of signals derived from signal sources. A signal source may comprise an analyte or an affinity agent bound to an analyte. A signal source may comprise a fiducial element.

A method of registering spatially overlapping data sets may utilize a first data set comprising detected signals from a first plurality of sites and a second data set comprising detected signals from a second plurality of sites. A first plurality of sites or a second plurality of sites may comprise at least about 100, 500, 1000, 5000, 10000, 50000, 100000, 500000, 1000000, 10000000, 100000000, 1000000000, or more than 1000000000 sites. Alternatively or additionally, a first plurality of sites or a second plurality of sites may comprise no more than about 1000000000, 100000000, 10000000, 1000000, 500000, 100000, 50000, 10000, 5000, 1000, 500, 100, or less than 100 sites. A first plurality of sites may comprise the same number of sites as a second plurality of sites. A first plurality of sites need not necessarily comprise the same number of sites as a second plurality of sites.

A data set may comprise detected signals from an array, in which one or more sites are non-resolvable. A site may be non-resolvable if i) it does not comprise a signal source that produces a detectable signal, ii) an insufficient number of neighboring or adjacent sites are optically resolvable, iii) a detection method may introduce a significant source of spatial and/or signal measurement uncertainty (e.g., chromatic aberration, spherical aberration, etc.), or iv) a combination thereof. A data set may comprise detected signal from a plurality of sites, in which addresses of at least about 10%, 15%, 20%, 25%, 30%, 35%, 40%, 45%, 50%, 55%, 60%, 65%, 70%, 75%, 80%, 85%, 90%, 95%, 99%, 99.9%, 99.99%, 99.999%, 99.9999%, 99.99999%, or more than 99.99999% of sites of the plurality of sites are non-resolvable in the data set. Alternatively or additionally, a data set may comprise detected signal from a plurality of sites, in which addresses of no more than about 99.99999%, 99.9999%, 99.999%, 99.99%, 99.9%, 99%, 95%, 90%, 85%, 80%, 75%, 70%, 65%, 60%, 55%, 50%, 45%, 40%, 35%, 30%, 25%, 20%, 15%, 10%, or less than 10% of sites of the plurality of sites are non-resolvable in the data set.

A method of registering spatially overlapping data sets may utilize a first data set comprising a first field-of-view, and a second data set comprising a second field-of-view. A field-of-view may refer to a subset of a plurality of sites contained in a data set, in which the subset of the plurality of sites comprises all sites or less than all sites of the plurality of sites on an array. For example, a pixel array-based camera for a microscope system may capture an image with a field-of-view determined by, in whole or in part, an aspect ratio of pixels on the pixel array and a magnification of the microscope system, in which an aspect ratio of the subset of sites captured in the camera field-of-view is substantially the same as the aspect ratio of the pixel array, and in which the absolute width and/or length of the pixel array is proportional to the pixel array width and/or length divided by the magnification. Accordingly, sources in system variability, such as variations in working distance of a sensing device and variations in a surface morphology of a solid support may produce differences in absolute dimension of field-of-views between images collected on a sensor with a fixed aspect ratio. In some cases, a method of registering two overlapping data sets may comprise altering a data set to produce a uniform absolute dimension for both data sets. In some cases, a first field-of-view of a first data set may have the same aspect ratio as a second field-of-view of a second data set. In a particular case, a first field-of-view may have the same absolute dimension (e.g., length, width, height, depth, angle of orientation, etc.) as a second field-of-view. In another particular case, a first field-of-view may have a different absolute dimension as a second field-of-view. In some cases, a method may further comprise rescaling a first data set or a second data set to comprise the same absolute dimension. In some cases, a first field-of-view may be rotated within a same plane relative to a second field-of-view. In a particular case, a method may further comprise rotating a first field-of-view or a second field-of-view to align with each other within the same plane of orientation. In some cases, a first field-of-view may be tilted (i.e., rotated out of a plane relative to a common axis) relative to a second field-of-view. In a particular case, a method may further comprise re-tilting a first field-of-view- or a second field-of-view to align with each other within the same plane of orientation.

A method of registering spatially overlapping data sets may comprise aligning a first pattern of fiducial elements with a second pattern of fiducial elements, in which the aligning further comprises: i) altering the second data set to form an altered second pattern of fiducial elements; and ii) aligning the first pattern of fiducial elements with the altered second pattern of fiducial elements. Aligning data sets may refer to any suitable method of comparison of spatial information patterns, including overlaying of spatial data or mathematical comparison of spatial information similarity. In some cases, altering a second data set may comprise altering spatial information of the second data set. For example, altering spatial information of a second data set may comprise a rotational transformation of spatial data within a focal plane, a rotational transformation of spatial data into or out of a focal plane, re-scaling the spatial data of the second data set, correction of optical distortion (e.g., chromatic aberration, spherical aberration, pincushion distortion, etc.), or a combination thereof. A spatial transformation may be accomplished by a data analysis algorithm (e.g., matrix algebra, a Hamiltonian transformation, etc.). In some cases, altering a second data set may comprise altering signal information of the second data set. For example, altering signal information of a second data set may comprise filtering signal information, reducing noise of signal information, subtracting background from signal information, altering contrast of signal information, or a combination thereof. An alteration of signal information may be performed by a data analysis algorithm (e.g., an image analysis program, etc.).

A method of registering spatially overlapping data sets may further comprise identifying presence or absence of a detected signal at each site of a first plurality of sites and/or a second plurality of sites. Identifying presence or absence of a detected signal at each site of a first plurality of sites and/or a second plurality of sites may comprise one or more steps of: i) determining an address for each site of the first plurality of sites and second plurality of sites, ii) determining presence or absence of a detected signal at each address of each site of the first plurality of sites and the second plurality of sites, iii) optionally removing a background signal from each address of each site of the first plurality of sites and the second plurality of sites, and iv) in a non-transitory, computer-readable medium, associating a value associated with the presence or absence of the detected signal at each address of each site of the first plurality of sites and the second plurality of sites with a value for the address of each site of the first plurality of sites and the second plurality of sites.

A method of registering spatially overlapping data sets may comprise a method of registering overlapping image sets. A first data set or a second data set of overlapping data sets may be derived from image data. In some cases, image data may comprise unaltered image data. Unaltered image data may comprise image data collected directly from an imaging device. In some cases, image data may comprise altered image data. Altered image data may comprise data that has been modified in one or more ways, for example by a data analysis algorithm. In some cases, image data may comprise a data structure derived from an image, in which the data structure comprises a plurality of data units, in which each data unit comprises: i) an address of a plurality of addresses, and ii) a detected signal at the address of the plurality of addresses. In a particular case, a data unit of image data may comprise an address of a plurality of addresses, in which the address of the plurality of addresses corresponds to a pixel of a pixel array of a sensing device. In another particular case, a data unit of image data may comprise an address of a plurality of addresses, in which the address of the plurality of addresses corresponds to a fractional pixel of a pixel array of a sensing device, or a first fractional portion of a first pixel and a second fractional portion of a second pixel of a pixel array of a sensing device.

In some cases, a method of registering two spatially overlapping data sets may further comprise repeating the method of registering the two overlapping data sets with a third data set, in which the third data set comprises a spatial distribution of detected signals in a third field-of-view of a sensing device, in which the third field-of-view encompasses a third plurality of sites, in which the third plurality of sites comprises a third pattern of detected signals from a plurality of fiducial elements, optionally in which a third site of the third plurality of sites is optically non-resolvable, and in which the third data set is registered with a data set (e.g., a first data set, a second data set, a combined data set comprising the first data set and the second data set). In some cases, a method of registering overlapping data sets may further comprise sequentially registering a non-combined data set with a combined data set, in which the combined data set comprises registered data from two or more data sets. In some cases, a method of registering overlapping data sets may further comprise, after registering the overlapping data sets, determining an array map based upon the overlapping data sets by a method, as set forth herein. In particular cases, an array map may comprise a first plurality of addresses, in which each address of the first plurality of addresses comprises a fiducial element. In another particular case, an array map may comprise a second plurality of addresses, in which each address of the second plurality of addresses comprises a signal from an analyte signal source. In some cases, an analyte signal source may comprise an analyte. In other cases, an analyte signal source may comprise an analytical reagent (e.g., an affinity agent, a reactant, etc.) bound to an analyte.

A method of registering spatially overlapping data sets may comprise aligning a first pattern of a first plurality of fiducial elements with a second pattern of a second plurality of fiducial elements. A first pattern of a first plurality of fiducial elements and a second pattern of a second plurality of fiducial elements may be the same pattern based upon a measure of randomness or uniqueness, as set forth herein. In some cases, a measure of randomness or uniqueness for a pattern of a plurality of fiducial elements may be a local measure of randomness or uniqueness. For example, a pattern of a plurality of fiducial elements may be a unique pattern within about 1, 2, 3, 4, 5, 6, 7, 8, 9, 10 fields-of-view of the plurality of fiducial elements. In other cases, a measure of randomness or uniqueness may be a global measure of randomness or uniqueness. For example, a pattern of fiducial elements may be unique to all possible patterns of fiducial elements on an entire array.

Figure 23B:
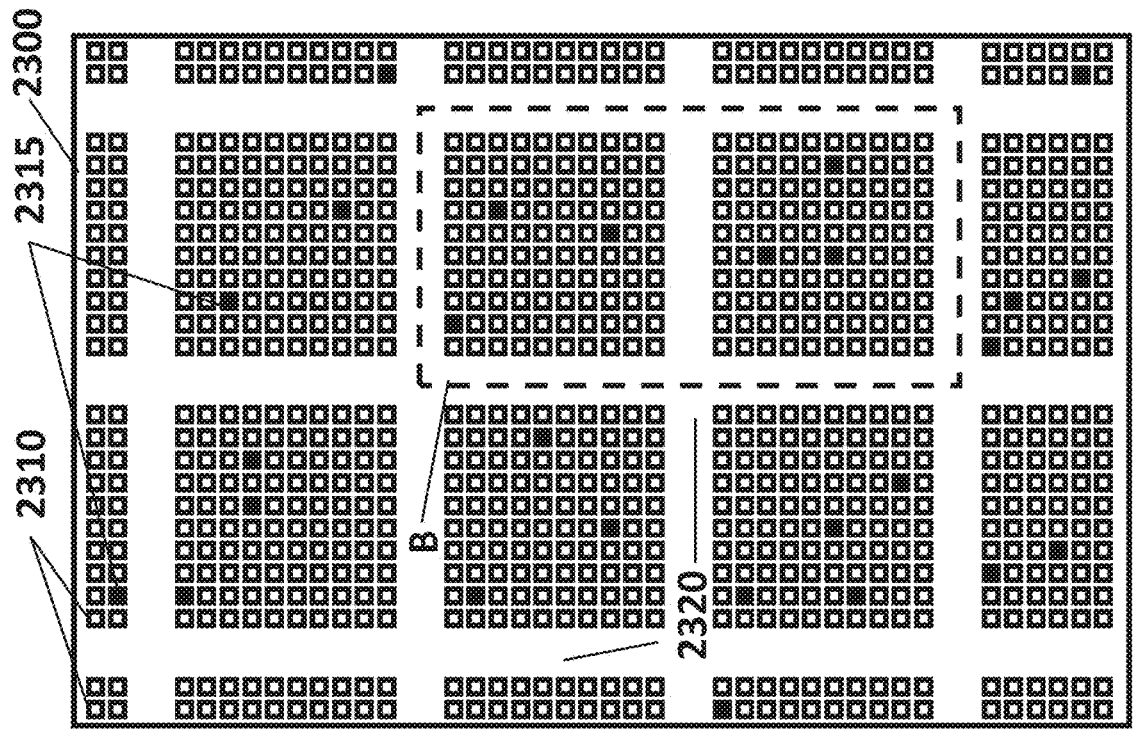
FIGS. 23A and 23B display depicted images of a group of subarrays of an array collected at a first time and a second time, respectively, in accordance with some embodiments.
Figure 23A:
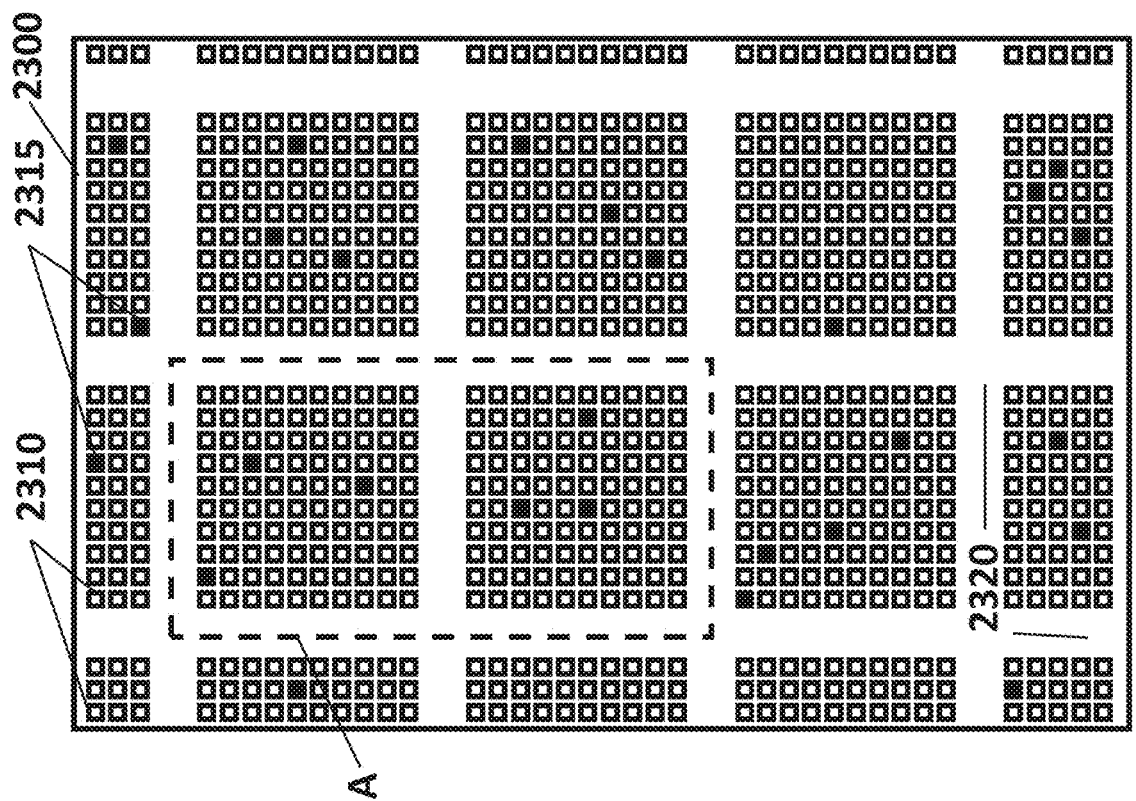

A method of registering two data structures may comprise comparing a first data structure to a second data structure, in which the first data structure differs from the second data structure spatially, temporally, or a combination thereof. For example, a method of registering a first data structure to a second data structure may comprise identifying a spatial region that is common to both data structures by identifying a fiducial element or a pattern of two or more fiducial elements that is common to both data structures. In another example, a method of registering a first data structure collected at a first time to a second data structure collected at a second time may comprise identifying a spatial region that is common to both data structures by identifying a fiducial element or a pattern of two or more fiducial elements that is common to both data structures. FIGS. 23A and 23B depict an example of images that can be registered by a method of time-dependent image registration. FIG. 23A depicts an image of an array comprising a solid support 2300 containing a plurality of array sites 2310, in which the array sites are patterned into rectangular subarrays of 10×10, with each subarray separated by an interstitial lane 2320 that contains no array sites 2310. Optionally, an interstitial lane 2320 between subarrays may comprise a landmarking fiducial element (e.g., an optically passive moiety, an optically active moiety, etc.) that provides a coarse measure of spatial position on the array. The array comprises a plurality of fiducial elements (e.g., optically passive moieties, optically active moieties, etc.) that are deposited in a random spatial pattern at a subset of arrays sites 2315. FIG. 23B depicts a second image of the same array as FIG. 23A, captured at a different time (e.g., a later step of an array-based process). The image of FIG. 23B is spatially-displaced relative to the image of FIG. 23A such that the images need to be registered to identify the same spatial regions contained in each image. The box A in FIG. 23A can be seen to enclose the same two subarrays as the box B in FIG. 23B, as determined by the substantially identical patterns of array sites comprising fiducial elements 2315 in the two subarrays in both images. In some cases, a spatially-dependent and/or temporally-dependent method of registering two data structures may comprise one or more steps of: a) providing a first data structure and a second data structure, b) identifying a portion of data from the first data structure that is also common to a portion of data from the second data structure based upon a fiducial element or a pattern of fiducial elements common to both data structures, and c) after identifying the common portion of data, manipulating data in the first data structure and/or the second data structure (e.g., compiling or aggregating data from both data structures, combining data from both data structures, cancelling or replacing data from one of the data structures, merging the common data from both data structures into a new data structure, combinations thereof, etc.).

In another aspect, provided herein is a method of utilizing a single-analyte array, comprising: a) providing the single-analyte array, in which the single-analyte array comprises a plurality of sites, in which each site of the plurality of sites is optically resolvable at single-analyte resolution, in which each site of a first subset of the plurality of sites comprises a fiducial element of a plurality of fiducial elements, in which the first subset of the plurality of sites has a random spatial distribution, in which the single-analyte array further comprises a plurality of single analytes, in which the plurality of single analytes is bound to a second subset of the plurality of sites, and in which each site of the second subset of the plurality of sites comprises one and only one single analyte of the plurality of single analytes, b) binding an analytical reagent to a single analyte of the plurality of single analytes, c) detecting optical signals from the first subset of the plurality of sites, d) detecting an optical signal from the analytical reagent bound to the single analyte, and e) based upon an address of the optical signal from the analytical reagent relative to the optical signals of the first subset of the plurality of sites, identifying a site of the second subset of the plurality of sites comprising the analytical reagent bound to the single analyte of the plurality of single analytes.

In another aspect, provided herein is a method of utilizing a single-analyte array, comprising: a) providing the single-analyte array, in which the single-analyte array comprises: i) a plurality of analyte-containing sites, in which each analyte-containing site comprises one and only one analyte, ii) a plurality of fiducial element-containing sites, in which the plurality of fiducial element-containing sites comprises a random spatial distribution, in which each fiducial element produces an optical signal, and in which a ratio of analyte-containing sites to fiducial element-containing sites is at least 100:1, and iii) a plurality of analytical reagents bound to analytes at a fraction of the analyte-containing sites, in which each analytical reagent produces an optical signal, and in which the fraction of analyte-containing sites is no more than 50% of the analyte-containing sites, b) identifying a plurality of subdistributions of the random spatial distribution of the plurality of fiducial-element-containing sites, in which each subdistribution of the plurality of subdistributions is unique from each other subdistribution of the plurality of subdistributions, c) detecting a plurality of optical signals from the single-analyte array, in which the plurality of optical signals comprises optical signals from the plurality of fiducial element-containing sites and optical signals from the fraction of analyte-containing sites, and d) for each optical signal from the fraction of analyte-containing sites, determining an address on the single-analyte array of the optical signal based upon a location of the optical signal with respect to at least one subdistribution of the plurality of subdistributions of the plurality of fiducial element-containing sites. In some cases, a ratio of analyte-containing sites to fiducial element-containing sites is at least about 1:1, 5:1, 10:1, 50:1, 100:1, 500:1, 1000:1, 5000:1, 10000:1, 50000:1, 100000:1, 500000:1, 1000000:1, or more than 1000000:1. Alternatively or additionally, a ratio of analyte-containing sites to fiducial element-containing sites is no more than about 1000000:1, 500000:1, 100000:1, 50000:1, 10000:1, 5000:1, 1000:1, 500:1, 100:1, 50:1, 10:1, 5:1, 1:1, or less than 1:1.

A method, as set forth herein, may comprise one or more steps of forming and/or providing a single-analyte array. Forming and/or providing a single-analyte array may comprise the steps of: i) coupling a plurality of fiducial elements to a first subset of a plurality of sites; and ii) coupling a plurality of single analytes to a second subset of the plurality of sites. Accordingly, a single-analyte array may comprise a plurality of analyte-containing sites and a plurality of fiducial element-containing sites. In some cases, a plurality of fiducial elements may be coupled to a single-analyte array before a plurality of analytes is coupled to the array. In other cases, a plurality of fiducial elements may be coupled to a single-analyte array after a plurality of analytes is coupled to the array. In some cases, a plurality of fiducial elements and a plurality of analytes may be coupled to a single-analyte array simultaneously. For example, an admixture comprising a plurality of analytes and a plurality of fiducial elements may be contacted with a single-analyte array, thereby simultaneously depositing the analytes and fiducial elements on the array.

In some single-analyte assays, such as the identification of polypeptides from a proteome-scale sample (e.g., a sample with potentially at least 1000 unique types of polypeptides), utilization of a single-analyte array can involve at least one step of collecting information from each site of a plurality of sites of the single-analyte such that the collected information can be resolved for each site of the plurality of sites. Accordingly, a single-analyte method may comprise: i) identifying an address of each site of a plurality of sites of a single-analyte array, and ii) identifying a presence or absence of a detectable signal from each site of the plurality of sites. In some cases, presence of signal, absence of signal, and/or magnitude of signal intensity or strength may provide information on an analyte at a site of a single-analyte array. Accordingly, utilization of single-analyte arrays, as set forth herein, may comprise transferring information, processing information, and/or analyzing information regarding single analytes with a computer-based data analysis algorithm (e.g., an image analysis algorithm), in which the computer-based data analysis is integrated with one or more physical single-analyte processes, including: 1) forming an interaction (e.g., a binding interaction) between a single analyte and an analytical reagent, 2) providing a signal-generating excitation (e.g., light illumination, chemical substrate interaction) by a signal detection system to a single-analyte or an analytical agent comprising a detectable label, 3) transmitting or emitting a detectable signal from a single-analyte, analytical agent, or a detectable label attached thereto, and 4) detecting in a spatial fashion with a sensing device (e.g., a pixel-based array) a detectable signal from a single-analyte, an analytical agent, or a detectable label attached thereto.

A method, as set forth herein, may comprise detecting optical from a first plurality of sites, in which the first plurality of sites comprises a plurality of fiducial elements. In some cases, detecting optical signals of a first subset of the plurality of sites may comprises: iii) contacting a single-analyte array with electromagnetic radiation, in which the electromagnetic radiation comprises light of a wavelength that produces optical signals from the fiducial elements; and iv) after contacting the single-analyte array with electromagnetic radiation, detecting the optical signals from fiducial elements of the plurality of fiducial elements at sites of the first subset of the plurality of sites. A method may further comprise detecting an analytical agent bound to a single analyte at an analyte-containing site, in which detecting the analytical reagent bound to the single analyte further comprises: v) contacting a single-analyte array with electromagnetic radiation, in which the electromagnetic radiation comprises light of an excitation wavelength of a detectable label coupled to the analytical reagent. In some cases, an excitation wavelength of a detectable label bound to an analytical reagent is the same wavelength as an excitation wavelength that produces an optical signal from a fiducial element of the plurality of fiducial elements. In other cases, an excitation wavelength of a detectable label bound to an analytical reagent differs from an excitation wavelength that produces an optical signal from a fiducial element of the plurality of fiducial elements. Accordingly, a method may comprise providing light of a single excitation wavelength to a single-analyte array, or providing light of two or more excitation wavelengths, either simultaneously or sequentially. In some cases, detecting an analytical reagent bound to a single analyte may further comprise: vi) detecting addresses of optical signals from sites of a first subset of the plurality of sites, in which the first subset of the plurality of sites comprises a plurality of fiducial elements (e.g., a plurality of fiducial elements with a random spatial distribution). In some cases, identifying a site of a second subset of the plurality of sites comprising an analytical reagent bound to a single analyte may comprise: vii) providing addresses of optical signals from sites of a first subset of a plurality of sites to an image analysis algorithm; viii) matching a spatial distribution of the addresses of the optical signals from sites of the first subset of the plurality of sites to a known subdistribution of the first subset of the plurality of sites using the image analysis algorithm; and ix) based upon the address of the optical signal from the analytical reagent relative to the known subdistribution of the first subset of the plurality of sites, identifying the site of the second subset of the plurality of sites.

Some methods may comprise a step of identifying each site of a plurality of sites of a single-analyte array. Mapping may be performed, for example, to identify damaged or defective sites (e.g., sites that do not bind analytes or fiducial elements) or determine minor variances in address location that deviate from a predicted location based upon an array gridding pattern (e.g., rectangular grid, hexagonal grid, circular grid, etc.). A method may further comprise: f) for each site of a plurality of sites, identifying an address of the site on a single-analyte array. In some cases, identifying an address of the site on a single-analyte array may comprise: x) for a site of the plurality of sites of the single-analyte array, coupling a mapping moiety to the site, and xi) detecting an address of a detectable signal from the mapping moiety (e.g., a detectable signal from a detectable label coupled to the mapping moiety).

A method, as set forth herein, may comprise multiplexed detection of analytical agents bound to single analytes. Two types of affinity agents with differing binding specificities may be coupled to sites of a plurality of sites of a single-analyte array, in which the two types of affinity agents are distinguishable based upon detectable signals (e.g., a first emission wavelength and a differing second emission wavelength). In some cases, binding an analytical reagent to a single analyte of a plurality of single analytes may comprise binding a first analytical reagent to a first single analyte, and binding a second analytical reagent to a second single analyte. In particular cases, a first analytical reagent may comprise a first detectable label with a first excitation wavelength, a second analytical reagent may comprise a second detectable label with a second excitation wavelength, in which the first excitation wavelength differs from the second excitation wavelength. In some cases, a fiducial element of a plurality of fiducial elements may produce a first optical signal in the presence of light of a first excitation wavelength, and produces a second optical signal in the presence of light of a second excitation wavelength. In some cases, a first analytical agent and a second analytical agent may be co-located at a same site of a plurality of sites (e.g., both bound to a same analyte). In other cases, a first analytical reagent may be bound to a first analyte at a first site, and a second analytical agent may be bound to a second analyte at a second site.

A multiplexed detection method may utilize a first subset of a plurality of sites, in which each site of the first subset of the plurality of sites comprises a multi-spectral moiety, as set forth herein (e.g., a multi-spectral nanoparticle). In some cases, detecting an analytical reagent bound to an analyte may comprise binding a first analytical reagent to a first single analyte of the plurality of single analytes, and binding a second analytical reagent to a second single analyte of the plurality of single analytes, wherein the first analytical reagent produces an optical signal at a first excitation wavelength, wherein the second analytical reagent produces an optical signal at a second excitation wavelength, and wherein the first excitation wavelength differs from the second excitation wavelength. In some cases, a multi-spectral moiety may produce a first optical signal at the first excitation wavelength and a second optical signal at the second excitation wavelength. For example, a multi-spectral moiety may be configured to fluoresce at the same emission wavelengths as differing analytical reagents utilized during a step of a multiplexed detection step. Such a method may be advantageous for confirming optical parameters such as focus at each emission wavelength when signals of differing wavelengths are detected simultaneously.

A method, as set forth herein, may comprise, before binding an analytical reagent to a single analyte, identifying a random spatial distribution of a first subset of the plurality of sites, in which the first subset of the plurality of sites comprises a plurality of fiducial elements. Identifying a random spatial distribution of a first subset of the plurality of sites may comprise detecting optical signals from fiducial elements at the first subset of the plurality of sites. A method may further comprise identifying two or more subdistributions of a first subset of the plurality of sites, in which each subdistribution of the two or more subdistributions comprises a locally and/or globally unique spatial distribution relative to the single-analyte array. In some cases, identifying two or more subdistributions of a first subset of the plurality of sites may comprise one or more steps of: 1) providing detectable signals from the first subset of the plurality of sites to an image analysis algorithm, and 2) determining addresses on the single-analyte array for each detectable signal from the first subset of the plurality of sites, and 3) calculating with the image analysis algorithm measures of uniqueness for each subdistribution of the two or more subdistributions.

A method of utilizing a single-analyte array may further comprise obtaining information from an identification tag associated with the single-analyte array (e.g., a barcode, a QR code, etc.). In some cases, a method may comprise one or more steps of: 1) obtaining a datum of information from an identification tag associated with a single-analyte array, 2) based upon the datum of information, receiving spatial distribution information (e.g., from a database, server, etc.) for a first subset of sites of a plurality of sites, wherein the first subset of the plurality of sites comprises fiducial elements, 3) detecting on the single-analyte array a spatial distribution of the first subset of the plurality of sites, and 4) comparing the spatial distribution information to the detected spatial distribution of the first subset of the plurality of sites. In some cases, comparing spatial distribution information to a detected spatial distribution of a first subset of the plurality of sites may comprise: 1) identifying a difference between spatial distribution information and a detected spatial distribution of a first subset of the plurality of sites, and 2) pausing a single-analyte assay or process. For example, a difference may arise between a prior-measured or known spatial distribution of fiducial elements and a measured spatial distribution of fiducial elements on a single-analyte array due to damage during manufacture, shipping, or storage, or due to counterfeiting of the array. In some cases, comparing spatial distribution information to a detected spatial distribution of a first subset of the plurality of sites may comprise: 1) identifying a match between spatial distribution information and a detected spatial distribution of a first subset of the plurality of sites, and 2) continuing a single-analyte assay or process. In some cases, a method may further comprise: xii) providing a datum from an identification tag to a database; and xiii) after providing the datum to the database, obtaining an array map, as set forth herein, comprising the first subset of the plurality of sites. In particular cases, a method may further comprise matching signals from a first subset of a plurality of sites to an array map of a first subset of the plurality of sites. In other particular cases, a method may further comprise determining differences between signals from a first subset of a plurality of sites to an array map of a first subset of the plurality of sites.

A method of utilizing an array, as set forth herein, may be performed in a cyclical or sequential fashion. A method of utilizing an array may comprise repeating one or more steps, as set forth herein, at least once. In some cases, a method of utilizing an array may comprise repeating a step or a set of steps, as set forth herein, at least about 1, 2, 3, 4, 5, 10, 15, 20, 25, 30, 35, 40, 45, 50, 75, 100, 125, 150, 175, 200, 250, 300, 350, 400, 450, 500, 600, 700, 800, 900, 1000, or more than 1000 times. Alternatively or additionally, a method of utilizing an array may comprise repeating a step or a set of steps, as set forth herein, no more than about 1000, 900, 800, 700, 600, 500, 450, 400, 350, 300, 250, 200, 175, 150, 125, 100, 75, 50, 45, 40, 35, 30, 25, 20, 15, 10, 5, 4, 3, 2, or less than 2 times.

In another aspect, provided herein is a method of adjusting a focal parameter of a sensing device, comprising: a) providing an array, wherein the array comprises: i) a solid support, in which the solid support comprises a plurality of sites and one or more interstitial regions, in which each site of the plurality of sites is configured to couple an analyte (e.g., single analytes), in which each interstitial region is configured to inhibit binding of an unbound moiety, and in which each site is separated from each other site by an interstitial region of the one or more interstitial regions, and ii) a plurality of fiducial elements, in which each fiducial element is located at a site of the plurality of sites, and in which the plurality of fiducial elements is distributed on the solid support at spatially random addresses, b) detecting a detectable signal of a fiducial element of the plurality of fiducial elements; c) based upon the detectable signal, adjusting a focal parameter of the sensing device. A focal parameter may comprise a focal depth, a focal plane, a focal point, or a working depth. In some cases, detecting a detectable signal of a fiducial element of the plurality of fiducial elements may comprise detecting a plurality of detectable signals of a subset of a plurality of fiducial elements.

Figure 18:
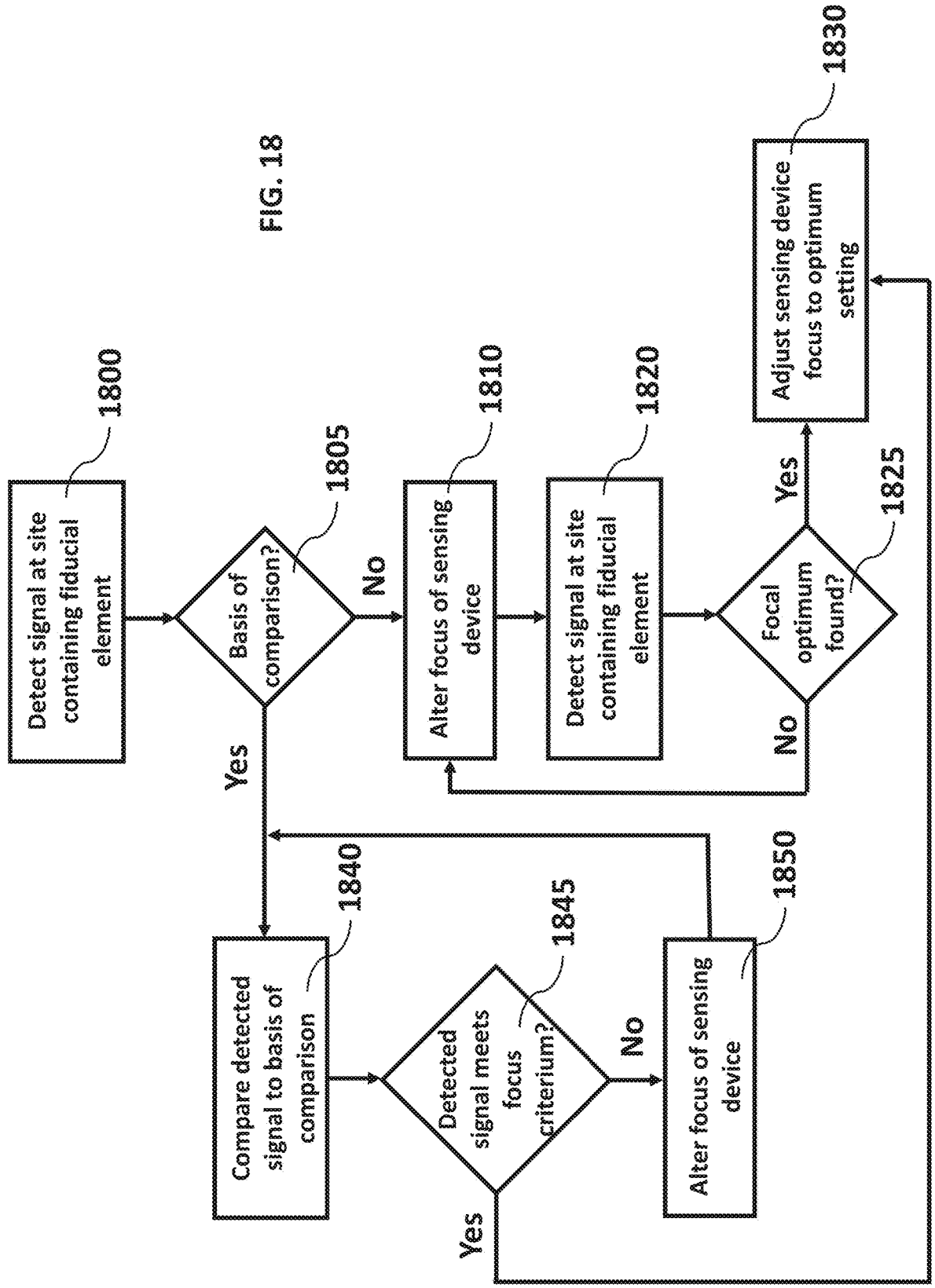
FIG. 18 illustrates a schematic for an optical focus process, in accordance with some embodiments.

FIG. 18 displays a schematic representation of a focal adjustment method that utilizes a fiducial element. In an initial step, a signal may be detected at an address comprising a fiducial element. Subsequently, a decision may be made regarding whether there is a known basis of comparison with which to compare the detected signal (e.g., a known signal strength or morphology, a signal sharpness metric, etc.). If a basis of comparison exists, the detected signal is compared 1840 to the basis of comparison. Subsequently, a decision 1845 may be made if the detected signal meets a focus criterion (e.g., within a threshold percentage of a value of the basis for comparison). If not, a focal parameter (e.g., working distance) of a sensing device is altered 1850, and the process is iterated until the focus criterion is met 1845. Once the focus criterion is met, the sensing device is adjusted 1830 to the determined parameter. If a basis for comparison does not exist, a focus parameter (e.g., working distance) of a sensing device is altered 1810, for example by a fixed amount or a pre-set amount. After adjusting the focal parameter 1810, a signal from the fiducial element is detected again 1820. Subsequently, a decision 1825 may be made regarding whether a focal optimum has been achieved (e.g., by signal magnitude, by signal morphology, etc.). If an optimum has not been determined, the process may be iterated until an optimum is achieved. If an optimum has been achieved, the sensing device will be adjusted 1830 to the determined optimal focal parameter.

A method of adjusting a focal parameter may comprise detecting a detectable signal of a fiducial element of a plurality of fiducial elements, in which the fiducial element comprises an optically passive moiety. A method of adjusting a focal parameter may comprise detecting a detectable signal of a fiducial element of a plurality of fiducial elements, in which the fiducial element comprises an optically active moiety. In some cases, detecting a detectable signal of a fiducial element of the plurality of fiducial elements may comprise detecting a plurality of detectable signals of a subset of a plurality of fiducial elements, in which the subset of the plurality of fiducial elements comprises an optically passive moiety and an optically active moiety.

A method of adjusting a focal parameter may comprise, based upon a detectable signal of a fiducial element, adjusting a focal parameter of a sensing device. In some cases, a detectable signal may comprise a signal magnitude (e.g., a peak photon count, an average photon count, a peak electron count, an average electron count, a total signal lifetime, a derivative of a signal lifetime, etc.). In some cases, a detectable signal may comprise a signal morphology. In a particular case, a detectable signal of a fiducial element may be detected on a plurality of pixels of a pixel-based sensor, in which each pixel of the plurality of pixels detects a signal magnitude, and in which a signal morphology comprises a spatial distribution of signal magnitudes detected by the plurality of pixels.

A method of adjusting a focal parameter may comprise, based upon a detectable signal of a fiducial element, adjusting a focal parameter of a sensing device, in which adjusting a focal parameter of a sensing device comprises optimizing the detectable signal of the fiducial element. In some cases, optimizing a detectable signal of a fiducial element may comprise detecting an optimal detectable signal (e.g., a peak signal magnitude, a peak average signal magnitude, a characteristic signal magnitude, etc.). For example, a detectable signal of a fiducial element may be optimized at a focal depth that corresponds to a peak fluorescence signal for the fiducial element. In another example, a detectable signal of a fiducial element may be optimized at a focal depth that corresponds to a known or characterized optimal signal value (e.g., a value obtained from a reference, database, or via prior measurement). In some cases, optimizing a detectable signal of a fiducial element may comprise detecting an optimal signal morphology of the fiducial element. For example, a detectable signal of a fiducial element may be optimized at a focal depth that corresponds to a characteristic morphology (e.g., a resolved shape, a closest fit to a known or characterized signal morphology, etc.). Adjusting a focal parameter of a sensing device may comprise one or more, two or more, or three or more steps of: b) detecting a first detectable signal of a fiducial element of the plurality of fiducial elements; c) adjusting a focal parameter of the sensing device; d) detecting a second detectable signal of the fiducial element, e) comparing the first detectable signal and the second detectable signal, and 0 based upon comparing the first detectable signal and the second detectable signal, adjusting the focal parameter of the sensing device. In some cases, comparing a first detectable signal and a second detectable signal may comprise comparing the first detectable signal to the second detectable signal. For example, a peak signal magnitude of a first signal may be compared to a peak signal magnitude of a second signal to determine which setting of a sensing device produced the larger peak signal. In other cases, comparing a first detectable signal and a second detectable signal may comprise comparing the first detectable signal and the second detectable signal to a known, characterized, or stored value for a detectable signal of the fiducial element. For example, a first signal morphology and a second signal morphology of a fiducial element may be compared to a prior measured signal morphology to determine which setting of a sensing device produces a signal that most closely fits an expected signal morphology.

A method, as set forth herein, may comprise determining a measure of randomness or uniqueness for a spatial distribution of a plurality of fiducial elements. In some cases, a measure of randomness or uniqueness may be determined in order to assess a quality control metric of an array. In some cases, a measure of randomness or uniqueness may be determined in order to identify unique patterns of fiducial elements for use an array-based process, such as image registration. In some cases, a measure of randomness or uniqueness may comprise a local measure of randomness or uniqueness. A local measure of randomness or uniqueness may refer to a measure of randomness or uniqueness that is calculated for a plurality of fiducial elements within a region of an array, in which the region contains less than all sites of the array. For example, a local measure of randomness or uniqueness may comprise a measure of uniqueness for a spatial distribution of a set of 10 fiducial elements within a 100×100 region of a 10000×10000 site array. In some cases, a measure of randomness or uniqueness may comprise a global measure of randomness or uniqueness. A global measure of randomness or uniqueness may refer to a measure of randomness or uniqueness that is calculated for a plurality of fiducial elements within a region of an array, in which the region contains all sites of the array.

Obtaining a measure of randomness or uniqueness may comprise detecting addresses for each fiducial element on an array, or a subset thereof. For example, addresses of each fluorescent fiducial element on an array may be determined by analyzing one or more images of an array obtained by fluorescence microscopy. Obtaining a measure of randomness or uniqueness may further comprise statistically analyzing addresses data for a plurality of fiducial elements on an array, or a subset thereof. In some cases, determining a measure of randomness or uniqueness may comprise determining a statistical measure for an array comprising a plurality of fiducial elements, then comparing the statistical measure to a same statistical measure for a perfectly ordered array comprising the plurality of fiducial elements.

Determining a measure of randomness or uniqueness may comprise one or more, or two or more steps of: a) determining presence or absence of a fiducial element at each site of a plurality of sites on an array; b) determining a spatial relationship between a first site comprising a first fiducial element and a second site comprising a second fiducial element; c) determining a spatial relationship between the first site comprising the first fiducial element and a third site that does not comprise a fiducial element, and d) based upon determining a spatial relationship, determining a measure of randomness or uniqueness of a spatial distribution of fiducial elements. A spatial relationship may be determined between a site comprising a fiducial element and at least about 1, 2, 3, 4, 5, 10, 20, 50, 100, 500, 1000, 10000, 100000, 1000000, 10000000, or more than 10000000 other sites comprising a fiducial element. Alternatively or additionally, a spatial relationship may be determined between a site comprising a fiducial element and no more than about 10000000, 1000000, 100000, 10000, 1000, 500, 100, 50, 20, 10, 5, 4, 3, 2, or less than 2 other sites comprising a fiducial element. A spatial relationship may be determined between a site comprising a fiducial element and at least about 1, 2, 3, 4, 5, 10, 20, 50, 100, 500, 1000, 10000, 100000, 1000000, 10000000, or more than 10000000 other sites not comprising a fiducial element. Alternatively or additionally, a spatial relationship may be determined between a site comprising a fiducial element and no more than about 10000000, 1000000, 100000, 10000, 1000, 500, 100, 50, 20, 10, 5, 4, 3, 2, or less than 2 other sites not comprising a fiducial element.

In some configurations, determining a measure of randomness or uniqueness for a spatial distribution of a plurality of fiducial elements may comprise determining a quantity of sites comprising two or more fiducial elements. In some configurations, determining a measure of randomness or uniqueness for a spatial distribution of a plurality of fiducial elements may comprise determining a likelihood of a site comprising two or more fiducial elements. In some configurations, a measure of randomness or uniqueness may comprise a measurement of an average distance between a first site comprising two or more fiducial elements and a second site comprising one or more fiducial elements, wherein the first fiducial element comprises only one fiducial element, wherein the second site comprises two or more fiducial elements, and wherein the second site is a nearest site comprising two or more fiducial elements to the first site. In some cases, a measure of randomness or uniqueness may comprise a measurement of an average distance between a first site of the subset of the plurality of sites and a second site of the subset of the plurality of sites, in which the first fiducial element comprises two or more fiducial elements, in which the second site comprises two or more fiducial elements, and in which the second site is a nearest site comprising two or more fiducial elements to the first site. In some cases, a measure of randomness or uniqueness may comprise a likelihood that a sampling of M sites of a plurality of sites comprises N sites comprising two or more fiducial elements.

In some cases, determining a measure of randomness for a spatial distribution of a plurality of fiducial elements, as set forth herein, may comprise determining a measure of randomness based upon a metric derived from information theory (e.g., a Kolmogorov complexity, an information entropy, etc.). A measure of randomness derived from information theory may comprise a global measure of randomness or a local measure of randomness. Determining a measure of randomness for a spatial distribution of a plurality of fiducial elements may comprise determining a minimum size of a data structure that is necessary to fully describe the spatial distribution of the plurality of fiducial elements. Determining a measure of randomness for a spatial distribution of a plurality of fiducial elements may comprise determining a compressibility of a data structure that is necessary to fully describe the spatial distribution of the plurality of fiducial elements. In some cases, a method, as set forth herein, may comprise one or more steps of: 1) detecting on a detection device a plurality of signals from a plurality of fiducial elements on an array, as set forth herein, 2) storing the plurality of signals in a data structure, as set forth herein, 3) providing the data structure to an analysis algorithm, and 4) determining a measure of randomness for a subset of the plurality of signals.

A method, as set forth herein, may comprise a step of identifying a measure of uniqueness, as set forth herein, for a spatial arrangement of a plurality of fiducial elements. In some cases, a measure of uniqueness for a spatial arrangement of a plurality of fiducial elements may be determined before a subsequent array-based process or assay (e.g., before an image registration process). Identifying a measure of uniqueness may comprise one or more, two or more, or three or more steps of: a) providing an array map, as set forth herein, b) identifying a plurality of fiducial elements, c) calculating a measure of uniqueness, as set forth herein, for the plurality of fiducial elements, and d) storing in a data structure an address and the measure of uniqueness for the plurality of fiducial elements. A method, as set forth herein, may comprise a step of identifying a spatial arrangement of a plurality of fiducial elements based upon a measure of uniqueness for the plurality of fiducial elements. Identifying a spatial arrangement of a plurality of fiducial elements may comprise one or more, two or more, three or more, four or more, five or more, or six or more steps of: a) providing a first data structure comprising a field-of-view of a sensing device, in which the field-of-view comprises a plurality of detected signal from fiducial elements at addresses in the field-of-view; b) providing a second data structure comprising a plurality of data units, in which each data unit comprises an address and a measure of uniqueness for a spatial arrangement of a plurality of fiducial elements; c) identifying a spatial arrangement of a plurality of fiducial elements of the first data structure, d) altering a spatial arrangement of the plurality of fiducial elements of the first data structure (e.g., rotating, tilting, re-scaling, etc.) e) determining a measure of uniqueness for the spatial arrangement of the plurality of fiducial elements of the first data structure; f) comparing the measure of uniqueness for the spatial arrangement of the plurality of fiducial elements of the first data structure to one or more measures of uniqueness of the second data structure; and g) identifying presence or absence of a match between a spatial arrangement of the first data structure and a spatial arrangement of the second data structure. In some cases, a first spatial arrangement and a second spatial arrangement may be considered to match if a first measure of uniqueness for the first spatial arrangement is within about $\pm 0.01\%$, $\pm 0.05\%$, $\pm 0.1\%$, $\pm 0.5\%$, $\pm 1\%$, $\pm 2\%$, $\pm 3\%$, $\pm 4\%$, or within about $\pm 5\%$ of a second measure of uniqueness for the second spatial arrangement. In a particular cases, in which a measure of uniqueness comprises two or more quantitative characterizations of a spatial arrangement, a first spatial arrangement and a second spatial arrangement may be considered to match if each of the two or more quantitative characterizations for the first spatial arrangement are within about $\pm 0.01\%$, $\pm 0.05\%$, $\pm 0.1\%$, $\pm 0.5\%$, $\pm 1\%$, $\pm 2\%$, $\pm 3\%$, $\pm 4\%$, or within about $\pm 5\%$ of each of the two or more quantitative characterizations for the second spatial arrangement.

In another aspect, provided herein is a method of identifying an array, comprising one or more, two or more, three or more, or four or more steps of: a) providing an array, in which the array comprises a plurality of sites, in which the array comprises an identification tag comprising a unit of identifying information, in which a subset of the plurality of sites comprises a plurality of fiducial elements, and in which the subset of the plurality of sites comprises a random spatial distribution; b) providing a stored array map and one or more units of stored identifying information for the array on a non-transitory, computer-readable medium; c) by a method provided herein, determining a measured array map for the array; d) determining the unit of identifying information from the identification tag of the array; and e) comparing the unit of identifying information and the measured array map to the stored identifying information and the stored array map. In some cases, a method may comprise, based upon comparing a unit of identifying information and a measured array map to a stored identifying information and a stored array map, discontinuing an array-based process or assay that utilizes an array. For example, if identifying information and a measured array map are found not to correspond to a stored array map for the array, the array may be discarded or blocked from a usage on an array-based system (e.g., due to damage, due to counterfeiting, etc.). In other cases, a method may comprise, based upon comparing a unit of identifying information and a measured array map to a stored identifying information and a stored array map, continuing an array-based process or assay that utilizes an array.

In some cases, a method of identifying an array may further comprise one or more steps of: a) preparing a sample comprising an analyte and a sample identification moiety, b) storing in a non-transitory, computer-readable medium a data structure comprising a stored unit of information related to a sample identification moiety, c) depositing the sample on the array, d) detecting a unit of information related to a sample identification moiety, and e) comparing the unit of information related to the sample identification moiety to the stored unit of information related to the sample identification moiety. In some cases, a unit of information related to a sample identification moiety may comprise a property of the sample identification (e.g., an identity, a structure, a sequence, etc.) or a property related to the presence of the sample identification moiety (e.g., a detectable signal, presence of a reactive product, an absence of a reactive product, presence of a binding interaction, an absence of a binding interaction, etc.). In some cases, a method may comprise, based upon comparing a unit of information related to a sample identification moiety and a stored unit of information related to a sample identification moiety, discontinuing an array-based process or assay that utilizes an array. For example, if a polypeptide sample identification moiety is unexpectedly not found when a stored property of the sample identification moiety indicates it should be, an assay may be discontinued due to a possible corruption of a sample or array. In other cases, a method may comprise, based upon comparing a unit of information related to a sample identification moiety and a stored unit of information related to a sample identification moiety, continuing an array-based process or assay that utilizes an array.

In another aspect, provided herein is a method of calibrating or aligning multiple sensors, comprising: a) providing a single-analyte array, in which the single-analyte array comprises: i) a solid support, in which the solid support comprises a plurality of sites and one or more interstitial regions, in which each site of the plurality of sites is configured to couple an analyte, in which each interstitial region is configured to inhibit binding of an unbound moiety, and in which each site is separated from each other site by an interstitial region of the one or more interstitial regions; and ii) a plurality of fiducial elements, in which each fiducial element is located at a site of the plurality of sites, and in which the plurality of fiducial elements is distributed on the solid support at spatially random addresses, b) identifying in a first field-of-view on a first sensor a first plurality of signals from a subset of fiducial elements of the plurality of fiducial elements, in which the first plurality of signals comprises a unique spatial pattern, c) identifying in a second field-of-view on a second sensor a second plurality of signals from the subset of fiducial elements of the plurality of fiducial elements, in which the second plurality of signals comprises the unique spatial pattern, and d) determining a spatial offset between the first field-of-view and the second field-of-view. Such a method may be useful in an array-based system with multiple optical sensors (e.g., sensors for different wavelengths of light), in which fields-of-view of each optical sensor may differ or may deviate relative to each other over time.

Figure 24:
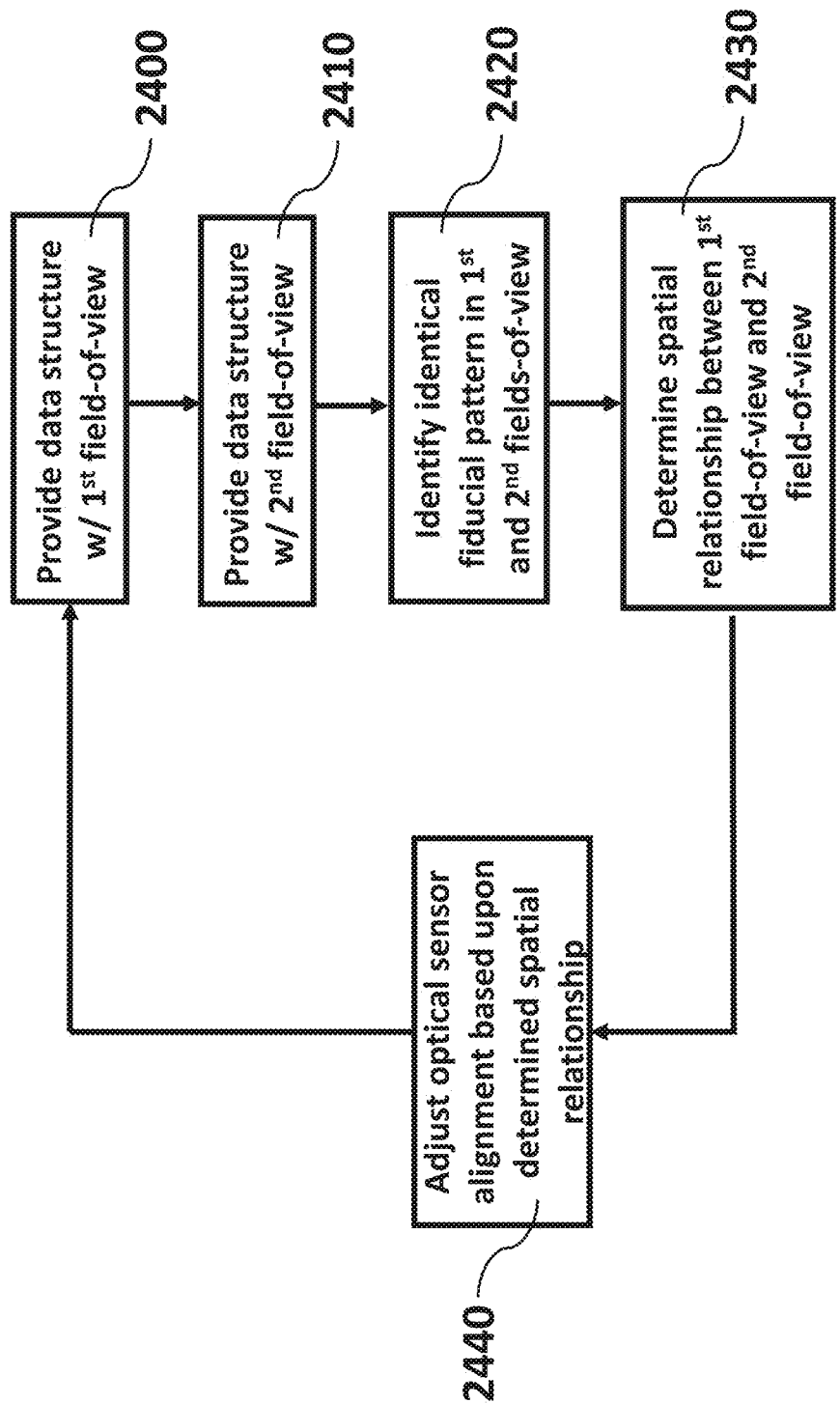
FIG. 24 shows a schematic of process for calibrating or aligning sensors of a multi-sensor optical system utilizing fiducial elements, in accordance with some embodiments.

FIG. 24 displays a flowchart depicting a process for aligning multiple optical sensors. In a first step, a first data structure comprising a $1^{st}$ field-of-view of a first sensor may be provided 2400. In a second step, a second data structure comprising a $2^{nd}$ field-of-view of a second sensor may be provided 2410. In a third step, a spatial pattern of signals from fiducial elements may be identified 2420 in the first data structure and the second data structure, thereby determining a common spatial location between the $1^{st}$ field-of-view and the $2^{nd}$ field-of-view. In a fourth step, a spatial relationship (e.g., a distance offset, rotation, tilt, etc.) may be determined 2430 between the $1^{st}$ field-of-view and the $2^{nd}$ field-of-view based upon the difference in spatial location of the spatial pattern of signal from fiducial elements in the $1^{st}$ field-of-view and the $2^{nd}$ field-of view. Optionally, in a fifth step, one or both optical sensors may be realigned 2440 based upon the determined spatial relationship between the fields-of-view of the first sensor and the second sensor. Optionally, after realigning one or both sensors, the sensor alignment method of steps 2400-2430 may be repeated to determine the new relative alignment between sensors. Optionally, a sensor calibration method may comprise utilizing the spatial relationship between the fields-of-view of the first sensor and the second sensor for data analysis without realigning one or both sensors.

In another aspect, provided herein is a method of forming a single-analyte array, comprising: a) depositing a plurality of fluorescent nanoparticles on a solid support comprising a plurality of sites, in which the fluorescent nanoparticles bind to a first subset of the plurality of sites, in which the first subset of the plurality of sites comprises a random spatial distribution, in which each fluorescent nanoparticle comprises a first plurality of oligonucleotides, in which each site of the first subset of the plurality of sites comprises a second plurality of oligonucleotides, and in which, for each fluorescent nanoparticle, two or more oligonucleotides of the first plurality of oligonucleotides hybridize to two or more oligonucleotides of the second plurality of oligonucleotides, and b) depositing a plurality of analytes on the solid support, in which the plurality of analytes bind to a second subset of the plurality of sites. In some cases, deposition of a plurality of fluorescent nanoparticles may occur before deposition of a plurality of analytes. In other cases, deposition of a plurality of fluorescent nanoparticles may occur after deposition of a plurality of analytes. In yet other cases, deposition of a plurality of fluorescent nanoparticles and a plurality of analytes may occur simultaneously. A method may further comprise: i) combining a plurality of fluorescent nanoparticles and a plurality of analytes to form a mixture, and ii) after combining, contacting the mixture to the solid support.

Acquiring and Processing Pixel-Based Information

In some embodiments, systems and methods set forth herein generate or manipulate pixel information acquired by a light sensing device from an array of analytes. The systems and methods are exemplified herein in the context of light sensing devices. Various configurations of the systems and methods can be extended to other detection devices. For example, systems, methods and algorithms set forth herein in the context of classifying the pixel subcomponents of light sensing device can be applied to individual subcomponents of other detectors such as transistors of FET, ISFET or other electronic detectors, or nanopores of a nanopore array.

Processing of pixel information may be performed using one or more instruments and instrument controls. Such instrument controls may include hardware and/or software to acquire data and process the data using one or more algorithms. The instruments may include light-sensing devices such as scientific-grade CMOS cameras, TDI cameras or other imaging devices. The light sensing devices can optionally be coupled with one or more excitation sources, for example, lasers, light emitting diodes (LEDs), arc lamps or other energy sources. The instrument can optionally include sample handling components, such as a stage configured to position an array or other sample with respect to a detection device. In some configurations, a stage and detector (e.g., light sensing device) can be translated relative to each other, for example, to facilitate scanning an area of an array or other sample that is larger than the detector's field of view (e.g., translation in one or both of the X and Y dimensions), or to adjust focus (e.g., translation along the Z dimension during autofocus or manual focus). The translation system can optionally include one or more X-Y translation gages and/or Z translation stage configured to move a sample an array) and one or more light sensing devices (e.g., cameras) with respect to each other, thereby acquiring a scanned image of the sample. The instrument can optionally include a fluid handling systems (e.g., a microfluidics system and/or liquid handling robot) to deliver sample fluids into a flow cell and onto a functionalized surface where data acquisition is performed. Optionally, the fluid handling system can be configured to remove samples from a flow cell or functionalized surface. In some embodiments, X-Y stages and/or Z stages are used to transport a sample to and from various portions of a fluid handling system. In some embodiments, the system comprises a plurality of such X-Y stages and/or Z stages, for example, either to achieve increased parallelism of sample handling or to dedicate each stage to a certain physical area of the system. As an example, additional hardware may be used to transfer components of the system, such as flow cells, from one stage to another. The instrument can further include a temperature control system. For example, temperature control can be provided by controlling temperature of an internal chamber that houses an array or other fluidic component. Alternatively or additionally, an array or other fluidic component can be placed into contact with a thermally conductive surface that is temperature controlled, such as the surface of a stage. Exemplary components that can be adapted for use in an instrument set forth herein are described, for example, in WO 04/018,497; WO 07/123,744; U.S. Pat. Nos. 10,858,703; 7,329,492; 7,211,414; 7,057,026; 7,31,019; 7,405,281; or U.S. Pat. App. Pub. No. 2008/0108082 A1, each of which is incorporated herein by reference in its entirety.

Instrument controls may include commercially available or custom hardware, including software (e.g., drivers) necessary to control and operate the hardware. For example, such drivers may be configured to prepare light sensing devices (e.g., cameras) to acquire a sequence of one or more images, and then trigger the light sensing devices to acquire image data at certain times or time intervals. A set of drivers may be constructed (e.g., conforming to public specifications) to encode the desired functionality of associated hardware such as detection and/or fluidics instruments. For example, liquid handling systems may use microfluidics to transfer reagents onto a surface, and then signals can be acquired from analytes or binding agents with which they interact (e.g., an image acquisition system may acquire image data of the surface of an array using light sensing devices). An exemplary detection system may comprise one or more cameras, one or more lasers, a stage and an actuator to effect relative motion between the stage and optics. In some embodiments, drivers are configured to control a plurality of different hardware components in concert to acquire pixel information of an array of biological, chemical, or physical entities (e.g., using a set of a few hundred affinity binding reagents on proteins of interest in a sample that is immobilized on a surface).

Pixel information (e.g., camera image data) acquired according to a method set forth herein may be in a suitable format for downstream computational processing, such as color (e.g., RGB) or gray scale images, where individual pixels of the pixel information include an intensity of light at one or more wavelengths (e.g., corresponding to differently colored lasers or fluorescence channels). Optionally, the acquired pixel information can include metadata such as wavelength of luminescence emission detected, wavelength of excitation energy used to produce luminescence, pixel position, excitation exposure time, focus metrics, information acquired from tri autofocus system, environmental conditions experienced by the light sensing device such as temperature or vibration, timing of detection relative to shifting of electrons in a charge-coupled device (CCD) operating in time delay integration (TDI) mode, relative location of pixels with respect to the motion of a stage (e.g., information received from an encoder), levels of background signals, correction for background signals, corrections for aberrations in the optical train used to transmit radiation to the pixel, or the like. In particular configurations, analytes or other moieties (e.g., anchoring moieties, analytical reagents) can be located on the surface of a solid support, for example, at sites in an array. At each location where image data is acquired (e.g., a site in an array of analytes), a set of single-channel, dual-channel, or multiple-channel images can be acquired. An image can be acquired at different stages of array processing. For example, an image can be acquired to identify the location of sites in an array prior to delivering an analytical reagent or other assay reagent to the array. Accordingly, pixel information acquired from a light sensing device that observes an array can include metadata including, for example, characteristics of a fluid in contact with the array, such as temperature, composition, refractive index or viscosity; location of the array or sites in the array derived from a stage encoder or image registration algorithm; cycle number for a multicycle process carried out on the array; or the like. Optionally, an image can be acquired to detect the presence of a given affinity binding reagent (e.g., after introducing the affinity binding reagent into the sample, such as by incubation).

Optionally, a scanning technique (e.g., raster scanning, line scanning or step-and-shoot scanning) is used to image array fields that are larger than the field of view for the detection optics. One or both of the optics and array can be moved relative to the other to achieve scanning. For example, light sensing devices can be moved across an experimental surface to capture images at the desired locations, times or time intervals. Images of array subregions or data derived therefrom can be combined into a larger image or aggregated dataset before or after any image processing steps set forth herein.

Whether or not a scanning technique is used, a method or system of the present disclosure can be configured to detect one or more detectable species (e.g., analytes, analytical reagents, anchoring moieties), for example, in an array of sites that are attached to the detectable species. In some configurations, two or more different detectable species can be simultaneously present in an array (or other format for presenting detectable species) and the different detectable species can be detected based on characteristics that are distinguishable by the detector being used. For example, acquiring dual-channel or multiple-Channel images may advantageously allow, for example, two different labeled affinity agents to be imaged (e.g., each affinity agent species being imaged using a different channel of the multiple channels). Multichannel detection of distinguishable detectable species can provide an advantage of increasing speed and/or efficiency of operation because, in many systems, delivering a mixture of distinguishable detectable species to an array and imaging the array via multiple channels is faster than serially delivering individual detectable species to the array and imaging the array in a single channel after each delivery. For configurations in which two or more different analytical agents are in simultaneous contact with an analyte array, the two or more analytical agents can be selected to have a low likelihood of influencing binding of each other to one or more analytes suspected of being on the array. For example, different analytical agents can bind to different analytes in a sample (e.g., affinity agents that do not bind to the same polypeptide) or the different analytical agents can hind to epitopes or moieties in an analyte that are spatially separated from each other in the analyte structure.

In some configurations, the process may comprise repeated measurements or image acquisition operations by looping over a set of colors (e.g., repeated measurements using different excitation wavelengths or emission wavelengths), then over a set of locations, then over a set of binding agents. In another exemplary configuration, the process may comprise repeated measurements or image acquisition operations by looping over a set of binding agents, then over a set of locations, then over a set of colors (e.g., excitation or emissions wavelengths). The image(s) obtained from each individual cycle of a multi-cycle process can optionally be registered to a common coordinate system via an image registration process. Image registration methods may be exemplified herein in the context of "mapping" which can be used to identify the location of sites that are occupied by detectable species (e.g., analytical agents, analytes and/or anchoring moieties) with reference to a common coordinate system. In some cases, a detectable species can be detected via a first channel that is configured to acquire signals from an analyte and/or anchoring moiety without necessarily detecting an analytical agent attached to the analyte. Alternatively, a process may not comprise acquiring images via a first channel, and instead may comprise acquiring images via a second detection channel that is configured to acquire signals from an analytical agent without necessarily detecting an analyte and/or anchoring moiety to which the analytical agents is coupled. A plurality of analytical agents (e.g., N affinity agents) may be processed all together simultaneously, thereby enabling N-channel imaging to be performed, all for N different analytical agent channels. Mapping can be performed using images from the first channel and/or second channel. Alternatively or additionally to processing images using mapping, the image(s) obtained from each individual cycle of a multi-cycle process can optionally be processed using analytical agent finding to identify or locate binding events at sites of an array. Mapping and analytical agent finding are set forth in further detail below.

When a detection process of the present disclosure comprises repeated measurements or image acquisition operations for a set of locations (e.g., repeated passes over an area of landing sites on a SNAP array), the imaging pattern may change from pass to pass. In some configurations, one pass employs detection via a first detection channel to detect a first type of luminescent label) and another pass employs detection via a second detection channel. The imaging pattern can change due to differences in the detection channels such as intensity of signals detected, presence or characteristics of wavelength-dependent optical aberrations, wavelength-dependent differences in focus, and thermal focus drift. In some cases, changes from pass to pass may be due to the use of analytical reagents that respectively hind different sites in an array due, to differences in specificity of the binding agents for the different analytes present at the respective sites. A site may produce signal in a first image of an array due to binding of a first analytical reagent to an analyte at the site. Upon replacement of the first analytical reagent with a second analytical reagent, signal is not expected to be produced at the site if the second analytical reagent does not bind the analyte at the site (and if the first reagent is properly removed by the replacement procedure). Thus, images of an array that are acquired after delivery of different detectable species can have a different pattern of signal producing sites (e.g., sites bound to an analytical reagent) and non-signal producing sites (e.g., sites not bound to an affinity agent). Imaging patterns acquired from two scans can also differ due to hardware operational variance. For example, in a first pass, the imaging may be performed from the left or top of the array to the right or bottom of the array (e.g., over a given row, respectively, whereas for a second pass, the imaging may be performed in reverse, from the right or bottom of the array to the left or top of the array (e.g., over another given row), respectively. As another example, the imaging pattern may comprise a spiral pattern, such as starting from the outside locations and proceeding inward, or starting from the inside locations and proceeding outward.

Individual sites in an array may be in one of multiple different states. For example, a given site may be empty. Alternatively, a site may be occupied by an anchoring moiety, but not occupied by an analyte. Alternatively, a site may be occupied by an anchoring moiety and also occupied by an analyte. Optionally, the analyte and/or anchoring moiety may have a detectable label or may be devoid of any label. The present disclosure provides methods for determining the state of the individual sites in the array. For illustrative purposes, configurations of the methods are exemplified herein using analyte-binding sites as exemplary array sites, proteins as exemplary analytes, anchoring moieties as exemplary linkers for attaching proteins to landing sites, and affinity agents as exemplary analytical reagents. In some embodiments, detecting components of an array (e.g., an array of analytes) is based at least in part on acquired pixel information and includes a mapping process for determining a plurality of locations corresponding to locations of sites, anchoring moieties, and/or analytes in an array. In some embodiments, detecting components of an array of analyte is based at least in part on acquired pixel information and includes a process of determining whether an analytical reagent has bound to analyte present at one or more of the sites. This process may be referred to as "reagent finding". The outputs of mapping and reagent finding steps may be combined as part of a pixel information acquisition process. Compositions and methods exemplified herein with respect to anchoring moieties can utilize any of a variety of regions on a solid support or sites in an array whether anchoring moieties are present or not.

It will be appreciated by the skilled person that aspects of "mapping" and "reagent finding" algorithms may overlap or be interchangeable. In some respects, mapping and reagent finding both can comprise acquiring image information and interpreting spatial information based upon the locations of discrete signals or clusters thereof from the image information. Accordingly, aspects of image analysis that are exemplified herein with respect to mapping or reagent finding may be applied to the alternative operation.

In some configurations, mapping or reagent finding may be performed to process an image that is acquired from an array of sites, for example, an array including an irregular pattern of sub-arrays where one or more regions of the pattern is interrupted by a subregion lacking landing sites (e.g., a center knock out, that can optionally function as a fiducial). Mapping can produce a set of pixel coordinates for every landing site (e.g., location on the surface where an affinity binding reagent may have landed and bound to an entity) that exists in an image or portion(s) of an image. The pixel coordinates may correspond to one or more pixels and/or may have a sub-pixel precision. For example, if an image has 2048/2048 pixels, the coordinate space may comprise any continuous value from 0 to 2048 (e.g., a given coordinate may be, for example, (12.25218, 28.28922905)). Mapping or reagent finding may comprise identifying every sub-array (or other region) in an image based on analyzing a regular or periodic pattern of the image, so that a seat of landing sites where analytes of interest may be found can be determined. This process may include accounting for noise that may be present in the acquired image data (e.g., by applying a de-noising, filtering, or background subtraction operation to the data).

Optionally, mapping or reagent finding may comprise preprocessing image data to clean up or correct any artifacts. For example, one or more lens or other optical component used in an optical detection device may introduce some amount of non-linear artifacts into the acquired image data, which may be removed. For example, an operation to correct fish-eye aberrations, focus aberrations or other optical aberrations may be applied to the images to obtain a normal perspective. In another example, preprocessing can be used to correct for non-uniformity of illumination such as correction of radial components, linear components or a superposition of radial and linear components that produce artifacts when detecting luminescence signals. Preprocessing can be used in some systems to correct for characteristics of individual pixels that may affect detection accuracy. In a particular configuration, a parameterized function can be fit to the overall intensity for an individual pixel and then a number of standard deviations for the pixel value above or below that function can be determined. The number of standard deviations can be represented by a standard score (e.g., z score). The parameterized function can be based, for example, on empirical background measurements acquired prior to performing an analytical measurement or while performing an analytical measurement. Alternatively or additionally, a parameterized function can derive from modeled properties of a system or selected component parts.

Optionally, mapping or reagent finding may comprise processing image data to account for rotational effects in the image (e.g., a de-rotation operation). For example, the surface of a solid support may have sub-arrays in a regular pattern, which facilitates the alignment (e.g., northeast/southwest alignment) of the image acquired from the surface. Therefore, a de-rotation operation may be performed to account for rotational misalignment of the hardware relative to the surface. For example, this de-rotation may be performed by applying a two-dimensional (2-D) transform, such as a Fourier transform (e.g., a discrete Fourier transform or a continuous Fourier transform) or a fast Fourier transform (FFT) (e.g., a discrete FFT or a continuous FFT) to the image data, to obtain an image signal in the frequency domain. The image signals in the frequency domain may be analyzed to identify high-intensity frequency signals at locations where frequencies of landing sites may be expected to be high (e.g., based on a known spacing of the array). By drawing lines from the origin to such locations, a set of angles may be measured, and statistical measures such as mean or median, may be used to combine the set of angles into a single angle. The image may then be de-rotated using the single angle by software processing of the image data. Further, the results of the 2-dimensional FFT may be used to not only determine the rotation angle within the image, but also the zoom amount. At different levels of zoom, the distance between the landing sites in an image of the chip may vary, which may change the frequency of the signal, which in turn may change the areas where the strongest frequency responses are located. By measuring the distance of these areas from the origin in the EFT result image, the observed spacing of the landing sites may be determined. This information may be used to construct a template, which may be applied by sliding across the entire image to determine the locations where the strongest response is measured. This may advantageously increase the robustness and reliability of measurements, since the application of a template having a degree of mismatch with the spacing observed in the image may produce spurious and/or erroneous results. Optionally, detectable features (e.g., signals from anchoring moieties, analytes, or analytical reagents) in an image can be sharpened by deconvolving with a small, localized kernel which exemplifies an ideal detectable signal. A point spread function can be used for convolving the features with the kernel.

Optionally, mapping or reagent finding may comprise locating and identifying sub-arrays based on image data. For example, a template of an optimal image may be created, and specific positions and/or magnification levels may be measured from such a template. These possible templates may then be applied to empirical image data to identify which template produces the strongest match. For example, matches may be evaluated using a statistical measure or metric, such as a correlation (e.g., a Pearson correlation coefficient), to assess the quality of a match with an image. Alternatively, matches may be evaluated using other methods of assessing the match, such as a dot product or any number of distance metrics.

Upon identifying a template for an array image, the locations of the sites may be identified. Alternatively, the image data may be collapsed into two one-dimensional (1-D) sums of pixels in a column, and then the resulting graphs may be used to find sub-arrays. This may be performed using summation algorithms, such as calculating a sum, mean, and/or median. A fast Fourier transform may be applied to the summed-histogram data to identify a regular pattern of high-intensity; and low-intensity values, wherein high-intensity; values indicate where landing sites in a column align, and low-intensity values lie in between. In some embodiments, the phase of the highest frequency component from the FFT is used to determine an offset of the landing sites from the set of pixels in the image. For example, the grid of landing sites may be determined to be offset by at least about +1-2 pixels, 1.8 pixels, 1.6 pixels, 1.5 pixels, 1.4 pixels, 1.2 pixels, 1.0 pixel, 0.8 pixels, 0.6 pixels 0.5 pixels, 0.4 pixels, 0.2 pixels, or relative to the first pixel in the image.

In some configurations of the methods or systems set forth herein, the location and spacing of landing sites can be determined in view of the Nyquist limitation. For some images, spacing between landing sites can be calculated using the fast Fourier transform (FFT). Other calculation methods may be preferred, for example, in cases where resolution is affected by or approaches the Nyquist limitation. This be the case for some systems where the spacing between landing sites is less than 2 pixels. In some embodiments, determining the landing site spacing comprises interpolating and then performing the discrete Fourier transform (DFT) operation.

Mapping or reagent finding may comprise performing one or more de-noising operations. This process may include accounting for noise that may be present in the acquired image data (e.g., by applying a de-noising, filtering, or background subtraction operation to the data).

The mapping and/or reagent finding methods set forth herein are particularly useful for registering or otherwise characterizing arrays in which sites are spatially arranged in a repeating, uniform or periodic pattern, such as a rectilinear grid or hexagonal grid. In some embodiments, methods and systems of the present disclosure are applied to "non-gridded" arrays of biological, chemical, or physical entities. Such arrays can be configured as high-density, single-molecule arrays. For example, such an array may have SNAPS present at sites that are not necessarily arranged in a repeating, uniform or periodic grid. In some cases, non-gridded arrays can be registered using a method other than a mapping or reagent finding method set forth herein. For example, non-gridded arrays can optionally be registered based on comparison and alignment of sites across multiple images of the array, for example, images acquired in the course of a multicycle process set forth herein. Even if mapping or reagent finding is not used to register images from a non-gridded array, the presence or absence of a detectable label at particular sites can be determined using a analytical reagent detection algorithm set forth herein.

Moreover, an analytical reagent detection algorithm may be applied to images acquired from a site detection channel to locate the site centers, for example, rather than applying a mapping approach.

In some embodiments, methods and systems of the present disclosure are applied to arrays of analytes that have a fixed (e.g., periodic) spacing between sites, but are not shaped like a square grid. For example, the array may be arranged similar to a square with the corners trimmed in somewhat, for purposes of facilitating image processing to align a sub-array. As another example, one or more sites of a grid may be removed (e.g., randomly) from an image to facilitate the localization and/or identification of a sub-array. A particularly useful arrangement is a hexagonal grid of sites. A hexagonal arrangement of sites can be advantageous in providing a higher density of sites in a given area while retaining a pitch (i.e., center-to-center spacing of nearest neighbor landing sites) that allows neighboring sites to be resolved. An array grid can further include fiducial elements as set forth herein, that interrupt or intervene an otherwise regular repeating pattern Fiducial elements can be used to register multiple images of an array with respect to each other by a method set forth herein. Alternatively or additionally, the relative shape, relative size or relative orientation of two or more sub-regions of an array can be used as a fiducial for registering multiple images of the array with respect to each other. The sub-regions can occur in a single field of view or in a composite image obtained by knitting together images from multiple fields of view.

In some embodiments, methods and systems of the present disclosure are applied to arrays of analytes using unlabeled moieties (e.g., anchoring moieties, analytes, analytical reagents). Labeled moieties can be used instead of, or in addition to, unlabeled moieties. For example, a small amount of labeled anchoring moieties (e.g., about 0.1%, 0.2%, 0.3%, 0.4%, 0.5%, 0.6%, 0.7%, 0.8%, 0.9%, or 1%) may be mixed into a plurality of otherwise unlabeled anchoring moieties or into a plurality of anchoring moieties having a label that is detected in a different channel, such as the channel used to detect analytical reagents. The labeled anchoring moieties may be considered as "reference moieties" for image alignment. A label on the reference moieties can be detected in the same channel used to detect analytical reagents and/or in a channel that is different from an analytical reagent channel. For example, anchoring moieties ma be deposited, and the analytical reagent channel may be imaged prior to passing any analytical reagents over the chip to detect the random pattern of reference moieties at each subarray. Alternatively or additionally, reference moieties can have a label that is detected in a channel other than the channel used to detect analytical reagents. A random pattern of reference moieties may be used to uniquely identify each subarray. As another example, a pattern of reference moieties may be used to easily determine the location of one or more subarray. This may be done, for example, as follows: prior to the experiment being run, use bright field imaging and a highly accurate mapping algorithm to grid every subarray. This may be a time-consuming process, bra produces an accurate gridding for each subarray. Next, anchoring moieties may be deposited, and the reference moieties may be imaged, to determine the relationship between each reference moiety pattern and each highly accurate mapping alignment. In future runs, the reference moiety image (which was collected when imaging analytical reagents) may be used to localize the subarray. When performing the protein decoding, the reference moieties may be ignored, since they may all be measured as positive light-up events.

Reagent finding, may be performed to determine a set of coordinates where analytical reagents (e.g., affinity agents) are located, e.g., locations in images where affinity agents appear to bind their target analytes. The analytical reagent detection (e.g., reagent finding) may comprise performing a thresholding operation to binarize the image data. For example, fixed or adaptive thresholding may be applied to binarize the image data (e.g., such that individual pixels are designated as ON or OFF, indicative of an event being present or absent, respectively) image data used for locating analytical reagents can be based on the raw pixel values for pixels in the image. Alternatively or additionally, image data can be based on a function or algorithmically determined score for the pixels in an image. For example, a standard score (e.g., z score) derived from a parameterized function fined to the overall intensity for individual pixels can be used. A connected components analysis may be performed, such that pixels in close proximity are clustered together, while disconnected pixels (not in close proximity to other pixels) are placed into separate clusters. The clusters may be analyzed to determine whether or not a given cluster is a reagent event (e.g., a positive result indicative of a site where an analytical reagent has bound), a reagent non-event (e.g., a negative result indicative of a site where an analytical reagent is not bound), or an indeterminate event (e.g., an indeterminate result that is not indicative of whether or not an analytical reagent is bound at the site). In some embodiments, the cluster analysis comprises performing a size-based filtering, enrichment, or exclusion of a subset of the clusters based on their size. For example, clusters that are too small (e.g., smaller than a given lower threshold) or too large (e.g., larger than a given higher threshold) may be excluded as non-events, while clusters that fall into a given range (e.g., between a given lower threshold and a given higher threshold) may be included as reagent events, thereby producing a set of coordinates where reagent events are found. The reagent finding may overcome challenges with identifying binding events, especially in cases where the image data has a low signal-to-noise ratio (SNR), such that the signal is, just above the background noise level. This approach may be referred to as an "object-first" analytical reagent detection approach.

Alternatively, analytical reagent detection (e.g., reagent finding) may be performed using a "site-first" approach as follows, which may be able to handle some difficult cases more elegantly. In the "site-first" approach, rather than treating mapping and reagent finding as being parallel operations, such operations may instead be performed serially, such that the results of the mapping (e.g., the coordinates for each, and optionally every, site) are used to assist with performing analytical reagent finding. Analyte-binding sites are array sites that are capable of attaching (e.g., covalently or non-covalently) to an anchoring moiety, analyte, or other entity. The methods exemplified herein for sites can be carried out using other array sites (e.g., sites comprising fiducial elements). The "site-first" approach leverages the fact that since the expected locations of the sites in the analytical reagent channel image may be known a priori (even though they may not be observed on that image), the locations where analytical reagents are searched for may be restricted, focused, or confined to a certain range of pixels in proximity to (e.g., centered around) the site coordinates, rather than across the entire image. In particular, this approach may advantageously avoid certain false-negative failure modes, such as those arising in cases in which a plurality of analytical reagents (e.g., two analytical reagents) happen to be located in proximity to each other, and appear during processing as a single larger cluster of pixels. Aberrantly large clusters may be discarded or filtered out based on the application of size thresholds (e.g., because they have a larger size than the maximum upper-limit size threshold for a single site or analytical reagent). Withthe "site-first" approach, such large clusters may be split apart into the individual (e.g., two or more) constituent analytical reagents because the regions being analyzed may only include a portion (e.g., half) of the large cluster at a time. Image data used for the site first approach can be based on the raw pixel values for pixels in the image and/or a function or algorithmically determined score for the pixels in the image.

A method of the present disclosure can include a step of processing a set of pixels (e.g., a cluster of pixels) using a trained algorithm (e.g., a classifier) in order to classify each of the clusters. The clusters can be classified, for example, as an event of interest, a non-event of interest, or an indeterminate event. Other exemplary classifications include confidence level that an entity has been detected by the pixels, confidence level that a reaction or other process has been detected by the pixels, a count of the number of entities or processes detected by the pixels, or a probability distribution of the number of entities or processes detected by the pixels. The event of interest can be presence of a binding agent bound to an analyte of interest, presence of a signal producing label added to an analyte of interest in an enzymatic or chemical reaction, presence of a signal produced from a reporter molecule in the presence of an analyte of interest, or the like. For ease of illustration, pixel processing may be exemplified below in the context of reagent events. However, the pixel processing methods can be applied to other events of interest such as events arising from a protein detection assay.

In some embodiments, analytical reagent detection (e.g., reagent finding) may comprise processing a set of pixels (e.g., a cluster of pixels) using a trained algorithm (e.g., a classifier) in order to classify each of the clusters as a reagent event, a reagent non-event, or an indeterminate event. A classifier may comprise a machine learning algorithm such as a supervised machine learning algorithm, a semi-supervised machine learning algorithm, or an unsupervised machine learning algorithm. A classifier may comprise a classification and regression tree (CART) algorithm. A classifier may comprise, for example, a support vector machine (SVM), a linear regression, a logistic regression, a nonlinear regression, a neural network, a Random Forest, a deep learning algorithm, a naïve Bayes classifier, or a combination thereof. A classifier may comprise an unsupervised machine learning algorithm, e.g., clustering analysis (e.g., k-means clustering, hierarchical clustering, mixture models, DBSCAN, OPTICS algorithm), principal component analysis, independent component analysis, non-negative matrix factorization, singular value decomposition, anomaly detection (e.g., local outlier factor), neural network (e.g., autoencoder, deep belief network, Hebbian learning, generative adversarial network, self-organizing map, convolutional neural network), expectation-maximization algorithm, method of moments, or a combination thereof.

A classifier may be configured to accept a plurality of input variables and to produce one or more output values based on the plurality of input variables. The plurality of input variables may comprise data indicative of a set of clusters of pixels, which may or may not correspond to events of interest such as analytical reagent binding events. For example, an input variable may comprise a set of one or more pixels corresponding to each of the sets of clusters of pixels. The pixels may be represented by, for example, an intensity value (e.g., selected from among a range of possible intensity Values) representative of a detected or measured signal an optical detection or measurement) at a given location. The input values may be calculated or extracted based on performing image analysis of the set of clusters of pixels, such as an indication of a size (e.g., diameter or perimeter), shape (e.g., circularity or symmetry), contrast, texture, or other physical attribute or image attribute of a cluster.

Input values for a classifier may comprise features (e.g. points) that are extruded from an image using various image processing techniques and algorithms. For example, the features may comprise values derived from a convolution of the image with a kernel encoding the expected shape of one or more regions of interest such as a region where a reagent event has occurred. As another example, the features may comprise values normalized to a calculated background signal in an image. For example, the background signal may be determined by fining a distribution to the intensity in the non-patterned region of an array (e.g., where minimal analytical reagent binding is expected to be measured), and pixel intensities may be normalized to a number of counts above background (e.g., a number of standard deviations above background if a normal distribution is fitted). Such a feature may be useful because it "normalizes" the intensity values against values that may vary with experimental conditions, such as changes in exposure time (e.g., double the exposure time may result in double the intensity counts). As another example, the features may comprise aspects of the data acquisition protocol (e.g., components of the imaging system, an exposure time of the image acquisition, the wavelength at which the image was acquired, etc.). In some embodiments, separate classifiers are trained for each of a plurality of imaging systems.

A classifier may have one or more possible output values, each comprising one of a fixed number of possible values a linear classifier, a logistic regression classifier, etc.) indicating a classification of the cluster as an event of interest (e.g., a reagent event), a non-event of interest (e.g., a reagent non-event), or an indeterminate event. The classifier may comprise a binary classifier, such that each of the one or more output values comprises one of two values {0, 1}, {positive, negative}, or {event, non-event}, {present, absent}) indicating a classification of the cluster as an event of interest (e.g., a reagent event) or a non-event of interest (e.g., a reagent non-event). The classifier may be another type of classifier, such that each of the one or more output values comprises one of more than two values {0, 1, 2}, {positive, negative, or indeterminate}, or {present, absent, or unknown}) indicating a classification of the cluster as an event of interest (e.g., a reagent event), a non-event of interest (e.g., a reagent non-event), or an indeterminate event. The output values may comprise descriptive labels, numerical values, or a combination thereof. Some of the output values may comprise descriptive labels. Such descriptive labels may provide an identification or indication of the cluster, and may comprise, for example, event, non-event, positive, negative, or indeterminate/unknown.

Some of the output values may comprise numerical values, such as binary, integer, or continuous values. Such binary output values may comprise, for example, {0, 1}. Such integer output values may comprise, for example, {0, 1, 2}. Such continuous output values may comprise, for example, a probability value of at least 0 and no more than 1 (e.g., of the classification of the cluster as an event of interest, such as a reagent event, a non-event of interest, such as a reagent non-event, or an indeterminate event). Such continuous output values may comprise, for example, an un-normalized probability value of at least 0. Such continuous output values may comprise, for example, an un-normalized probability value of at least 0. Such continuous output values may comprise, for example, an indication of a size (e.g., diameter or perimeter), shape (e.g., circularity), contrast, texture, or other physical attribute or image attribute of a cluster. Some numerical values may be mapped to descriptive labels, for example, by mapping 1 to "positive" and 0 to "negative." Output value need not be a numerical value. For example, the output value can be a binary outcome (e.g., yes/no), a categorical outcome (e.g., analytical reagent hound, non-specific binding event, no analytical reagent bound, or apparent sample defect), or a continuous outcome (e.g., size of array site). For discrete outputs, distributions can be determined for the characteristic being measured. Distributions can be modeled according to a statistical or stochastic distribution, such as a Poisson, binomial, beta-binomial, discrete Weibull, geometric, hypergeometric, or negative binomial behavior distribution. Categorical data can be modeled, for example, by a categorical distribution (e.g., an assignment of probabilities to each class) or a multinomial distribution. A modeling outcomes can be a mixtures of distributions (e.g., a gaussian mixture which is a distribution composed of two or more gaussians), or a non-parametric distribution such as a normalized histogram, a kernel density estimate derived from a histogram, or a non-parametric discrete distribution converted into a continuous distribution by interpolation.

Some of the output values may be assigned based on one or more cutoff values. For example, a binary classification of clusters may assign an output value of "positive" or 1 if the sample indicates that the cluster has at least a 50% probability of being an actual event, such as a reagent event. For example, a binary classification of samples may assign an output value of "negative" or 0 if the sample indicates that the cluster has less than a 30% probability of being an actual reagent event (or equivalently, at least a 30% probability of being a reagent non-event). In this case, a single cutoff value of 50% is used to classify clusters into one of the two possible binary output values. Examples of single cutoff values may include about 1%, 2%, 5%, 10%, 20%, 30%, 40%, 50%, 60%, 70%, 80%, 90%, 95%, 98%, or 99%.

As another example, a classification of clusters may assign an output value of "positive" or 1 if the cluster has a probability of being an actual event (e.g., a reagent event) of at least about 30%, 60%, 70%, 80%, 90%, 95%, 98%, or 99%. The classification of clusters may assign an output value of "positive" or 1 if the sample indicates that the subject has a probability of producing an actual event (e.g., a reagent event) of more than 50%, 60%, 70%, 80%, 90%, 95%, 98%, or 99% or more. The classification of clusters may assign an output value of "negative" or 0 if the cluster has a probability of being an actual event (e.g., a reagent event) of less than 50%, 40%, 30%, 20%, 10%, 5%, 2%, 1% or less. The classification of clusters may assign an output value of "indeterminate" or 2 if the cluster has not been classified as "positive." "negative," 1, or 0. In this case, a set of two cutoff values can be used to classify clusters into one of the three possible output values (e.g., a first, smaller cutoff value and a second, larger cutoff value). Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify clusters into one of n+1 possible output values, where n is any positive integer.

A classifier may be trained with a plurality of independent training samples. Each of the independent training samples may include pixel information acquired from a single pixel, a cluster of pixels, a group of pixels that acquires signal from a site in an array, a collection of pixels (and/or pixel clusters) that acquires signals from multiple sites in an array, a collection of pixels (and/or pixel clusters) that acquire signals from a region of sites in an array, a collection of pixels (and/or pixel clusters) that acquire signals from a collection of spatially disparate sites in an array, or pixels (and/or pixel clusters) that acquire signals from an entire array. The data can include one or more known output values corresponding to the foregoing. Independent training samples may comprise the data and associated outputs obtained from a plurality of different images, experimental runs, experimental conditions, equipment, etc. Independent training samples may comprise data and associated outputs obtained at a plurality of different time points from the same sample. The data may have been acquired from the sample after treatment with different analytical reagents or other differing conditions. Alternatively, independent training samples may comprise data and associated outputs obtained at a plurality of different time points from different samples. The data may have been acquired from the different samples after treatment with different analytical reagents or other differing conditions. Independent training samples may be associated with presence of an event of interest such as a reagent event (e.g., training samples comprising clusters of pixels and associated outputs obtained from imaging a plurality of known reagent events). Independent training samples may be associated with absence of an event of interest, such as absence of a reagent event (e.g., training samples comprising clusters of pixels and associated outputs obtained from imaging a plurality of known reagent non-events).

A classifier may be trained with at least about 2, 100, 500, 1 thousand, 5 thousand, 10 thousand, 20 thousand, 30 thousand, 40 thousand, 50 thousand 100 thousand, 200 thousand, 300 thousand, 400 thousand, 500 thousand, 1 million, 2 million, 3 million, 4 million, 5 million, 10 million, 100 million, 1 billion or more independent training samples. The independent training samples may comprise samples associated with presence of events of interest, such as reagent events, and/or samples associated with absence of an event of interest, such as reagent non-events. Alternatively or additionally to the lower limits of the ranges set forth above, a classifier may be trained with no more than about 1 billion, 100 million, 10 million, 1 million, 800 thousand, 500 thousand, 250 thousand, 100 thousand, 50 thousand, 10 thousand, 1 thousand, 500, 250, 100, 50, or 2 independent training samples. The training samples may be associated with presence of an event of interest (e.g., reagent events) or alternatively, the training samples mar be associated with absence of events of interest (e.g., reagent non-events). In some embodiments, the cluster of pixels being classified is independent of samples used to train the classifier.

A classifier may be trained with a first number of independent training samples associated with presence of one or more events of interest (e.g., reagents events) and a second number of independent training samples associated with an absence of one or more events of interest (e.g., reagents non-events). The first number of independent training samples associated with presence of one or more events of interest (e.g., reagents events) may be no more than the second number of independent training samples associated with an absence of the one or more events of interest (e.g., reagents events). The first number of independent training samples associated with presence of one or more events of interest (e.g., reagent events) may be equal to the second number of independent training samples associated with an absence of the one or more events of interest (e.g., reagent events). The first number of independent training samples associated with presence of one or more events of interest (e.g., reagent events) may be greater than the second number of independent training samples associated with an absence of the one or more events of interest (e.g., reagent events).

A classifier may be configured to detect or identify one or more events of interest and/or non-events of interest (e.g., reagent events and/or reagent non-events) with an accuracy of at least about 50%, 60%, 70%, 80%, 85%, 90%, 95%, 96%, 97%, 98%, 99%, or more; for at least about 50, 100, 200, 300, or more independent samples. The accuracy of detecting or identifying one or more events of interest (e.g., reagent events) by the classifier may be calculated as the percentage of independent test samples (e.g., clusters that are reagent events or reagent non-events) that are correctly identified or classified as being an event of interest (e.g., a reagent event) or a non-event of interest (e.g., a reagent non-event), respectively.

A classifier may be configured to detect or identify one or more events of interest (e.g., reagent events) with a positive predictive value (PPV) of at least about 5%, 10%, 20%, 30%, 40%, 50%, 60%, 70%, 80%, 90%, 95%, 96%, 97%, 98%, 99%, 99.9%, 99.99%, 99.999%, or more. The PPV of detecting or identifying one or more events of interest (e.g., reagent events) by the classifier may be calculated as the percentage of clusters identified or classified as events of interest (e.g., reagent events) that correspond to clusters that truly are events of interest (e.g., reagent events). A PPV may also be referred to as a precision.

A classifier may be configured to detect or identify one or more non-events of interest (e.g., reagent non-events) with a negative predictive value (NPV) of at least about 5%, 10%, 20%, 30%, 40%, 50%, 75%, 80%, 90%, 95%, 99%, 99.9%, 99.99%, 99.999%, or more. The NPV of detecting or identifying non-events of interest (e.g., reagent non-events) by the classifier may be calculated as the percentage of clusters identified or classified as non-events of interest (e.g., not being reagent events) that correspond to clusters that truly are non-events of interest (e.g., reagent non-events).

A classifier may be configured to detect or identify events of interest (e.g., reagent events) with a sensitivity of at least about 5%, 10%, 20%, 30%, 40%, 50%, 60%, 70%, 80%, 90%, 95%, 96%, 97%, 98%, 99%, 99.9%, 99.99%, 99.999%, or more. The sensitivity of detecting or identifying events of interest (e.g., reagent events) by the classifier may be calculated as the percentage of independent test samples associated with presence of events of interest (e.g., reagent events) that are correctly identified or classified as events of interest (e.g., reagent events). A sensitivity may also be referred to as a recall.

A classifier may be configured to detect or identify non-events of interest (e.g., reagent non-events) with a specificity of at least about 5%, 10%, 20%, 30%, 40%, 50%, 60%, 70%, 80%, 90%, 95%, 96%, 97%, 98%, 99%, 99.9%, 99.99%, 99.999%, or more. The specificity of detecting or identifying the non-events of interest (e.g., reagent non-events) by the classifier may be calculated as the percentage of independent test samples associated with absence of events of interest (e.g., reagent non-events) that are correctly identified or classified as not being events of interest (e.g., as being reagent non-events).

A classifier may be adjusted or tuned to improve the performance, accuracy, PPV, NPV, sensitivity, specificity, or combination thereof, of detecting or identifying one or more events of interest (e.g., reagent events), or one or more non-events of interest (e.g., reagent non-events). The classifier may be adjusted or tuned by adjusting parameters of the classifier a set of cutoff values used to classify a duster of pixels as described elsewhere herein, or eights of a neural network). The classifier may be adjusted or tuned continuously during the training process or after the training process has completed. For example, re-training or continuous training can be carried out using data obtained from analytical measurements. For example, assays run on a system used by an end user, such as a researcher or clinician, can provide scientific or clinical output to the end user, and can also transmit training data to a computer that is configured to train the system.

After a classifier is initially trained, a subset of the inputs may be identified (for example, as most influential or most important) to be included for making high-quality classifications. For example, a subset of the set of input variables may be identified as most influential or most important to be included for making high-quality classifications or identifications of one or more events of interest (e.g., reagent events) and/or non-events of interest (e.g., reagent non-events). The set of input variables or a subset thereof may be ranked based on metrics indicative of each input variable's influence or importance toward making high-quality classifications or identifications of an event of interest (e.g., reagent event) or non-event of interest (e.g., reagent non-event). Such metrics may be used to reduce, in some cases significantly, the number of input variables (e.g., predictor variables) that may be used to train the classifier to a desired performance level (e.g., based on a desired minimum accuracy, PPV, NPV, sensitivity, specificity, or combination thereof). In some configurations, a set of inputs can be divided into a first subset of the inputs that is used to train a machine learning algorithm, a second set of the inputs can be used to validate the machine learning algorithm and a third set of the inputs can be used to test the machine learning algorithm. The inputs can be used, for example, to select underlying models for the machine learning algorithm or to tune hyperparameters within those models.

In some embodiments, a cluster of pixels being classified is independent of samples used to train a classifier. For example, the training datasets used to train a classifier may be distinct from the test datasets to which the classifier is applied. As another example, an expansive collection of training datasets may be used to train a base classifier, and that base classifier may be used as an initial starting point UN analysis of any individual dataset. The base classifier may be further refined over time, based on acquisition parameters of the dataset or using an expectation maximization approach prior to application to that dataset.

For example, if training an algorithm with a plurality comprising several dozen or hundreds of input variables in the classifier results in an accuracy of classification of more than 99%, then training the training algorithm instead with a selected subset of no more than about 2, 3, 4, 5, 6, 7, 8, 9, 10, 20, 30, 40, 50, or 100 such most influential or most important input variables among the plurality may result in decreased but still acceptable accuracy of classification (e.g., at least about 70%, 80%, 90%, 95%, 96%, 97%, or 98%).

Optionally, a classifier can be calibrated to account for changes that occur (or that are expected to occur) over the course of use for an imaging system. For example, an analyte, or ensemble of analytes, that is present at a site of an array may demonstrate a loss of signal over the course of a series of detection steps. Ibis may be the case, for example, due to photobleaching by excitation sources used for luminescence detection, or due to chemical degradation after long term exposure, or repeated exposure, to particular solvents, reagents or conditions. Alternatively, signal gain may occur due to accumulation of signal producing contaminants in the observation field of an imaging device. For example, contaminants may accumulate at a site of an array causing an increase in apparent signal produced by the site. As an alternative or addition to employing calibration of a classifier, the subject to be observed by an imaging system can be refreshed, for example, by replacing a degraded analyte, supplementing with additional analyte, or removal of contaminants. By way of more specific example, an array of labeled anchoring moieties and/or analytes can be imaged multiple times over the course of a method set forth herein and then the labeled anchoring moieties and/or analytes can be replaced for subsequent imaging steps. A different classifier can be applied to images before and after the refresh as appropriate to the changes or trends known or suspected to occur before and after the refresh.

The pixel information of image data may be stored in a binary format, optionally along with metadata. The metadata may include pertinent information about the measurement conditions for each image, such as the instrument (e.g., identified via serial number) from which data was acquired, the flow cell or other vessel (e.g., identified via bar code) that was detected by the instrument, the identity of one or more reagent lots used during detection, a timestamp (e.g., date or time) when pixel information was acquired, the chip coordinates, the experiment or run globally unique identifier (GUID) or universally unique identifier (UUID) number), and other pertinent information such as the software version, under which the image data was acquired. Alternatively to a binary signal, the signal may store two pieces of information per landing site: a binary value indicative of a binding event or non-event, and another binary value indicative of whether the signal is determinate (ON or OFF) or indeterminate (unknown). The intensity value of each pixel may be retained for downstream analyses. Alternatively, the intensity value of each pixel may be discarded and not retained for downstream analyses. In some embodiments, a degree of confidence (10%, etc) of each class being correct is stored along with the binarized data. The degree of confidence may account for spatial and/or temporal effects and/or variations of confidence as part of experimental flow.

In some embodiments, event detection (e.g., reagent finding) may comprise performing an image segmentation (e.g., to solve an image segmentation problem). For example, a goal of an image segmentation problem may be to detect patterns in an image and to "segment" the image into sections corresponding to each pattern. The image segmentation may be performed using various suitable unsupervised clustering approaches and/or various suitable image segmentation algorithms (e.g., using random Mackay fields).

In some embodiments, images may be subjected to processing (e.g., using various suitable image processing algorithms) to remove or "censor" image artifacts. For example, image artifacts may comprise substantial areas of pixels with saturated intensity values (e.g., at a 100% intensity value or a 0% intensity value). These may appear in the image as, for example, large bright "bubbles", which may overlap with (e.g., obscure) multiple sites. Therefore, image processing algorithms may be applied to detect and remove such artifacts from analysis in event detection (e.g., analytical reagent detection); this may include "censoring" or excluding the associated landing sites from the downstream decoding analysis. In another example, sites for which position cannot be determined confidently can be censored and treated as artifacts. As another example, a trained classifier configured to perform event detection (e.g., analytical reagent detection) may comprise classes for detection, identification, or classification of artifacts which may be expected to be observed in images.

Upon completion of operations for locating sites or regions of interest in an image (e.g., mapping) and for detecting events of interest (e.g., reagent finding), the two output sets may be combined to determine the nearest site (e.g., an analyte-binding site) where an analyte of interest (e.g., a protein of interest) may be found, given a detected event (e.g., a reagent event). This approach can be particularly useful in a censored decoding approach in which non-binding events are not considered to be informative. Alternatively, non-binding events can be included in the output sets and used to determine the nearest site for a feature on a substrate (e.g., a feature such as a site in an array). If such a nearest site (e.g., landing site) is in close enough proximity to a region of interest in an image, the event (e.g., analytical reagent binding) may be considered to have occurred at the site (e.g., the analytical reagent hound to an analyte at the site) or to not have occurred as the case may be. Conversely, if such a nearest site (e.g., analyte-binding site) is not in close enough proximity to a region of interest (e.g., is too far away) in an image, the event (e.g., analytical reagent, binding) may be considered to not have occurred at the site (e.g., a non-specific binding event has occurred for the analytical reagent). Brighter detectable moieties, although generally easier to detect, may produce greater positional uncertainty, for example, due to signal cross-talk with pixels that detect an adjacent detectable moiety. This can be exacerbated when adjacent detectable moieties are both relatively bright, resulting in cross talk with each other to yield apparent overlap or merging of sites in an image.

A simple threshold of distance may be applied to determine whether or not a dose proximity condition is satisfied. Alternatively or additionally, probability distributions and/or confidence levels may be analyzed to determine whether or not the close proximity condition is satisfied. The threshold may be set by performing control experiments based on a known input, to acquire image data indicating binding event locations, which allows distance calibration based on the physical layout and setup of the measurement conditions. As another example, the distance threshold for localizing an analytical reagent to a site may take into account quality metrics from a mapping algorithm (e.g., how confident the gridding algorithm is of the localization at each location), the resolution of the image sensor, and the signal-to-noise (SNR) ratio of features used to localize the landing site and/or analytical reagent. For example, a bright detectable moiety may have a higher likelihood of being accurately characterized than a dim detectable moiety. A distance threshold can optionally be set based on the amount of distortion present in various points or regions in a field of view. For example, distortions can be used as points of reference for determining relative distances between sites or features in the field of view. In another example, distances can be adjusted to account for distortions that may otherwise introduce errors in in distance determinations. A distance threshold can optionally be set based on noise or censored artifacts in an image. A distance threshold can be in the form of a value or a function when used for determining the proximity of sites or features in an image.

For each site (e.g., site attached to an analyte or other entity) in a given image, an event of interest (e.g., a binding event) or non-event of interest can be determined. Therefore, a per-image map can be produced, which provides a binary signal of whether an entity (e.g., an analyte) is present at a given location. However, a binary signal need not necessarily be used. For example, the presence or absence of an entity at a given location can be represented by a value in a continuous range of values, by a probability value, or by categorical data. A suitable decoding algorithm, as described elsewhere herein, may be performed on the per-image binding map to identify entities (e.g., analytes) in a sample and/or quantities of entities in the sample. In some configurations, images from adjacent regions of an array can be stitched together or otherwise registered with respect to each other. The combined image can be mapped, decoded or processed as set forth herein. Conversely, an image can be subdivided into image regions, and the resulting subregions can be mapped, decoded or processed as set forth herein.

In some embodiments, a system of the present disclosure may comprise commercially available or custom hardware configured to perform image processing (e.g., CPU offloads or FPGAs to perform custom operations). Some or all of the instrument control and/or image processing methods set forth herein can be performed remote from the instrument being used. For example, the methods can be performed on a dedicated co-processor, such as CPUs within a computer, OPUS, FPGAs, real-time microcontrollers, separate computer, or cloud instance. In some configurations, one or more of the hardware components that performs all or part of an instrument control and/or image processing method can be a component part that is physically associated with the instrument.

In some embodiments, an algorithm, as set forth herein, may be selected and performed using one or more computers (e.g., either locally or on the cloud). The one or more computers may be configured to enable horizontal scalability, such that the algorithm can be parallelized by being split up across a plurality of independent processors for independent computational processing. For example, an algorithm may be parallelized based on analyzing each site among a plurality of sites independently. Therefore, the location on a chip may be treated as a trivial scaling dimension. Optionally, the location on a Chip may be treated as a set of scaling dimensions which allow for maximal or complete independence of the data being processed. In some embodiments, data to be processed may be re-dimensionalized (e.g., by slicing and inverting the data before processing it using the algorithm). The re-dimensionalizing of the data may be performed in some cases, for example, when the temporal order of data acquisition does not represent the same dimension as one of the scaling dimensions.

Image Analysis by General Hough Transform

As described above, the proteome provides a valuable source of functional biological insight, such as understanding the structural and functional cellular components underlying various phenotypes. One general method for elucidating the proteome includes whole proteome analysis at the single-molecule level, such as single-molecule peptide sequencing.

Figure 37A:
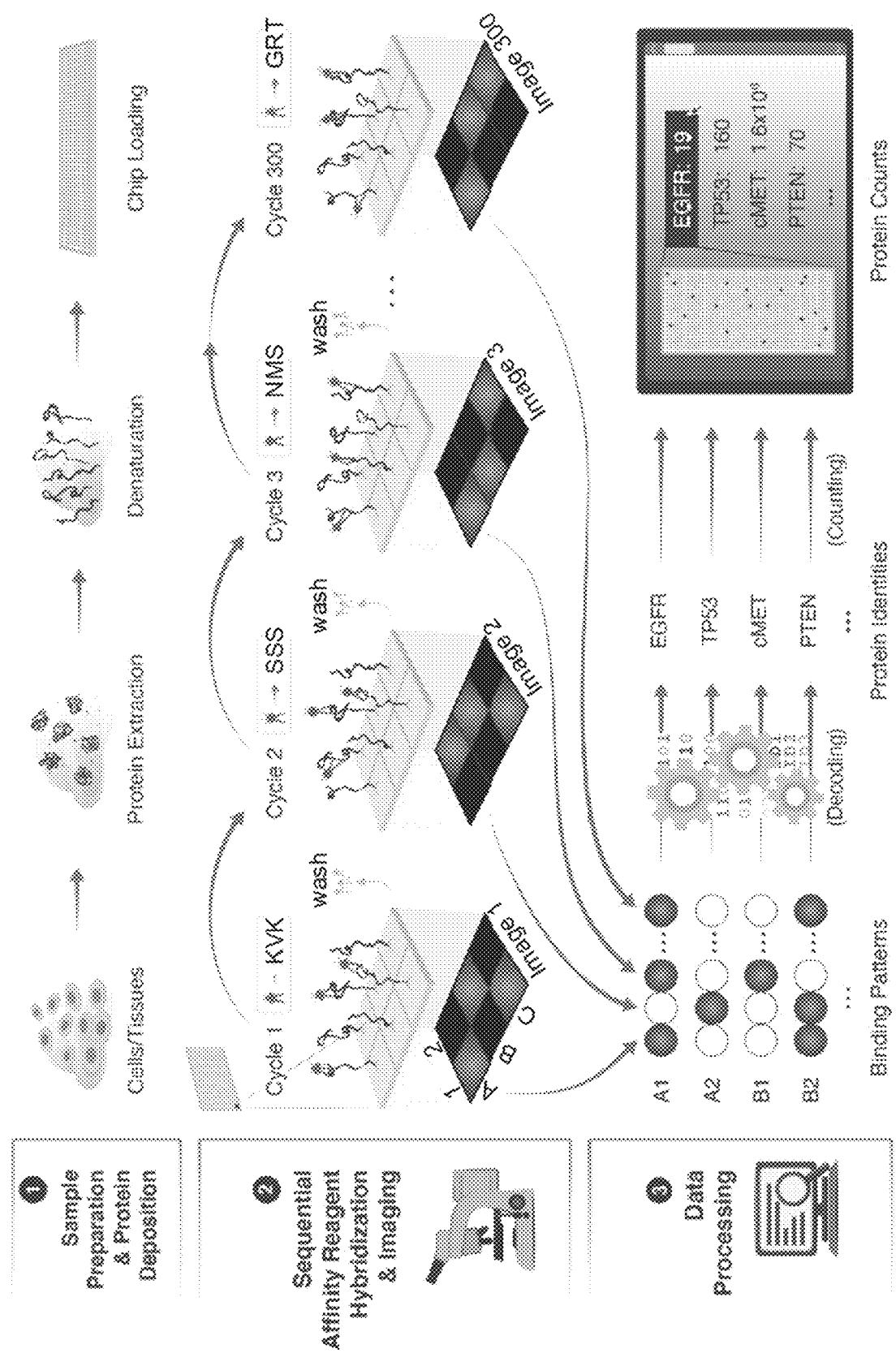
FIGS. 37A, 37B, and 37C collectively illustrate systems and methods for analyte identification, in accordance with some embodiments of the present disclosure.
Figure 38:
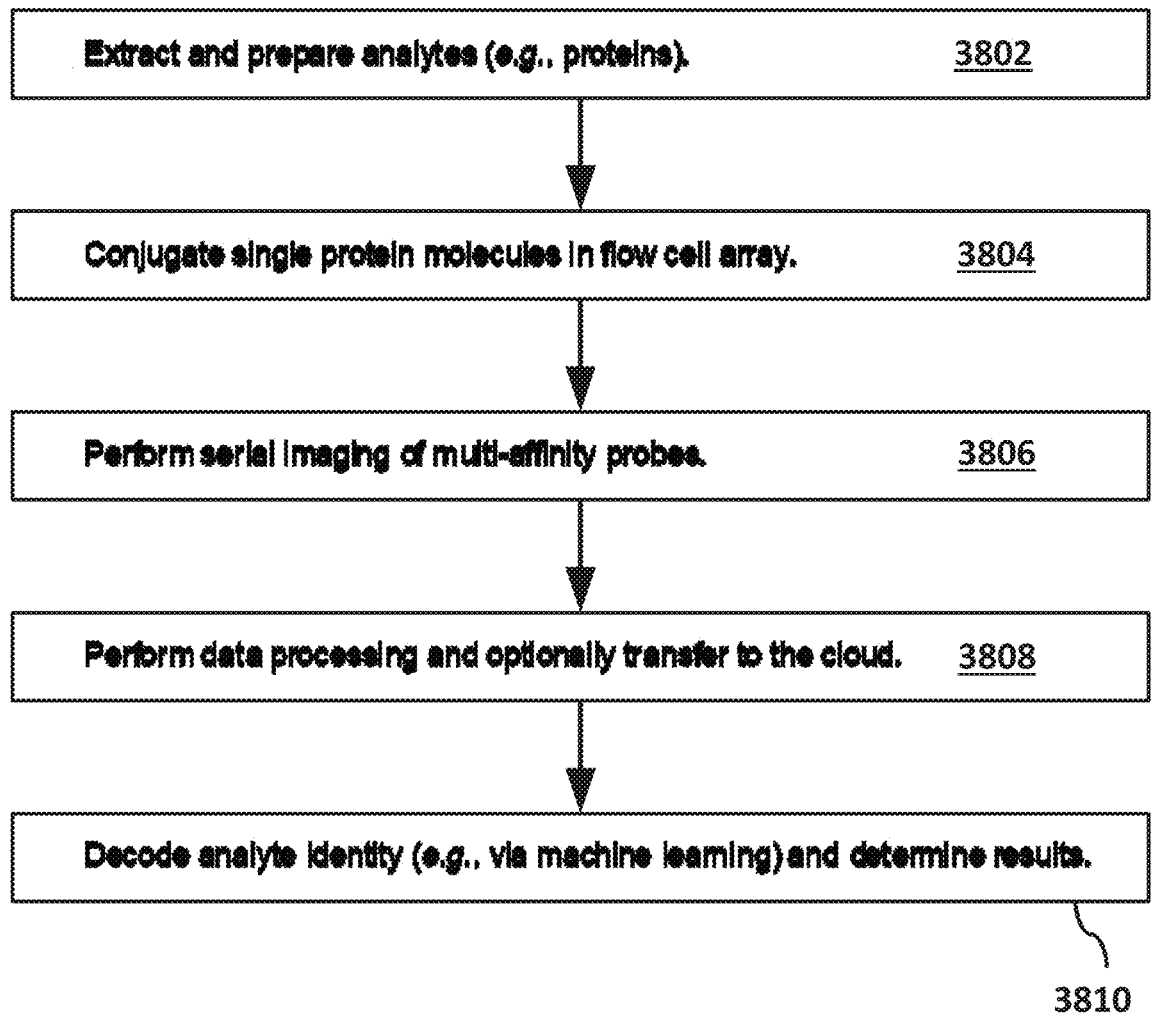
FIG. 38 illustrates an example workflow for analyte identification, in accordance with an embodiment of the present disclosure.

In an example embodiment for single-molecule proteome analysis, rapid identification and quantification of proteins at the single molecule level is performed using an experimental workflow 3800 as shown in FIGS. 37A and 38. Proteins are extracted from the sample (3802) and conjugated (3804) intact, but under denaturing conditions, onto a substrate (e.g., a chip) including a hyper-dense single-molecule array. On this substrate, no more than one protein molecule is present per predefined position (e.g., landing pad) on the array and each position is optically resolvable. Affinity reagents (antibodies, aptamers, or small proteins) are labeled with fluorophores to allow for optical detection of single-protein molecule binding events, and then passed over the substrate (e.g., chip). One affinity reagent is used per cycle, and each reagent is washed off the substrate before the next one is added. Integrated fluidics and imaging allows for high resolution multi-cycle imaging of individual binding events at scale (3806). Binding of affinity reagents to proteins produces a bind/no-bind outcome series for each protein, which can be used to infer the identity of the protein. Since there is only one protein per predefined position (e.g., landing pad), direct counting can be used to quantify each protein in the sample.

Figure 37B:
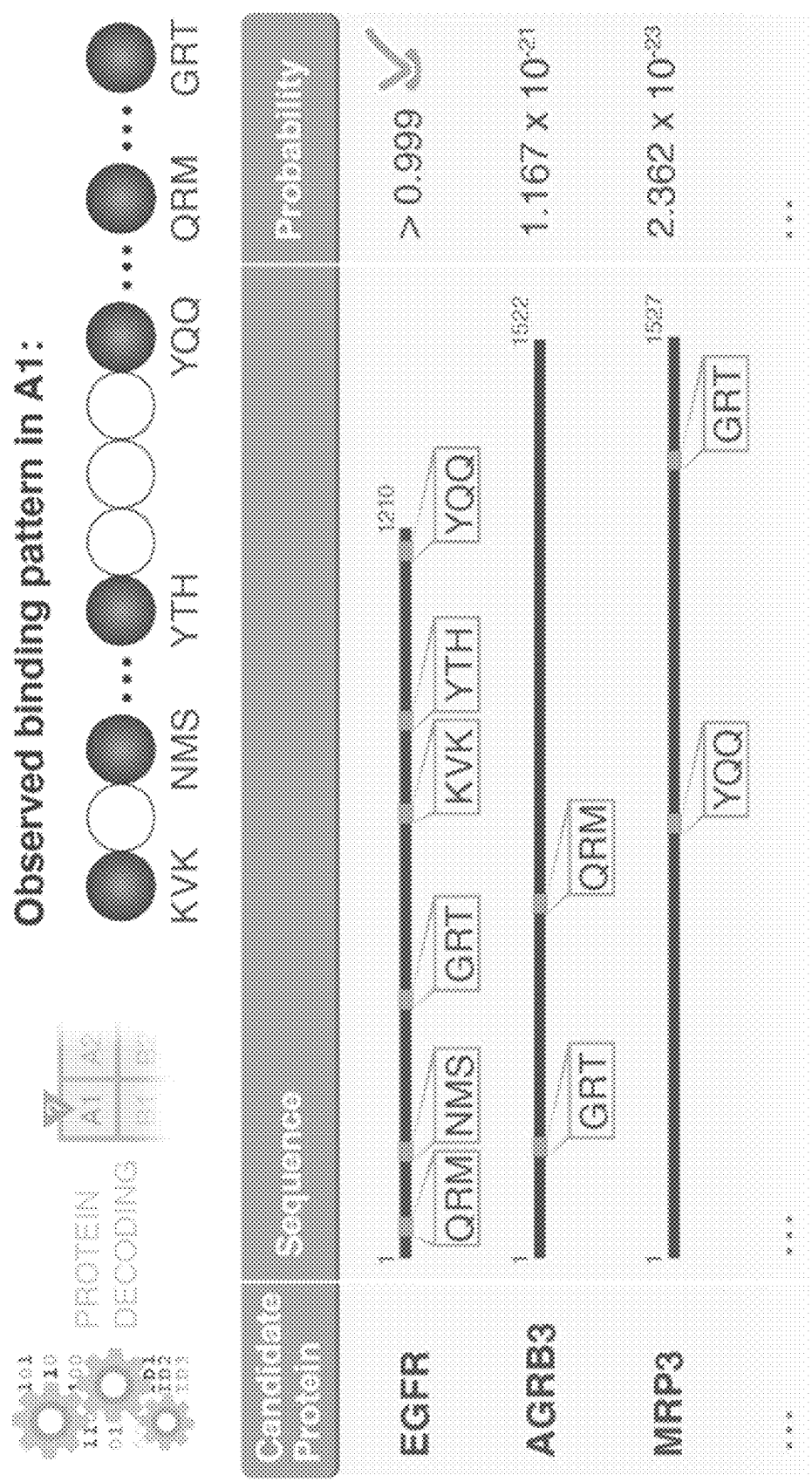

In some instances, identifying the total number (e.g., tens of thousands) of different proteins in a proteome would require a prohibitively large number of traditional highly specific affinity reagents. However, in some implementations set forth herein, the affinity reagents that are used in each cycle include affinity reagents that bind short, linear epitopes (e.g., trimers) with moderate specificity, such that each affinity reagent binds many proteins (e.g., "multi-affinity" binding reagents). While the binding of a single multi-affinity reagent is typically not sufficient to identify a given protein, sequential probing using a series of multi-affinity reagents can decode many proteins, as discussed below. In this approach, each new affinity reagent that is introduced in a cycle of binding and imaging provides additional evidence and gradually narrows the list of possible protein identities by creating protein-specific binding patterns or "signatures", as shown in FIG. 37B (408). In some implementations, this approach is referred to as Protein Identification by Short-epitope Mapping (PrISM).

Figure 37C:
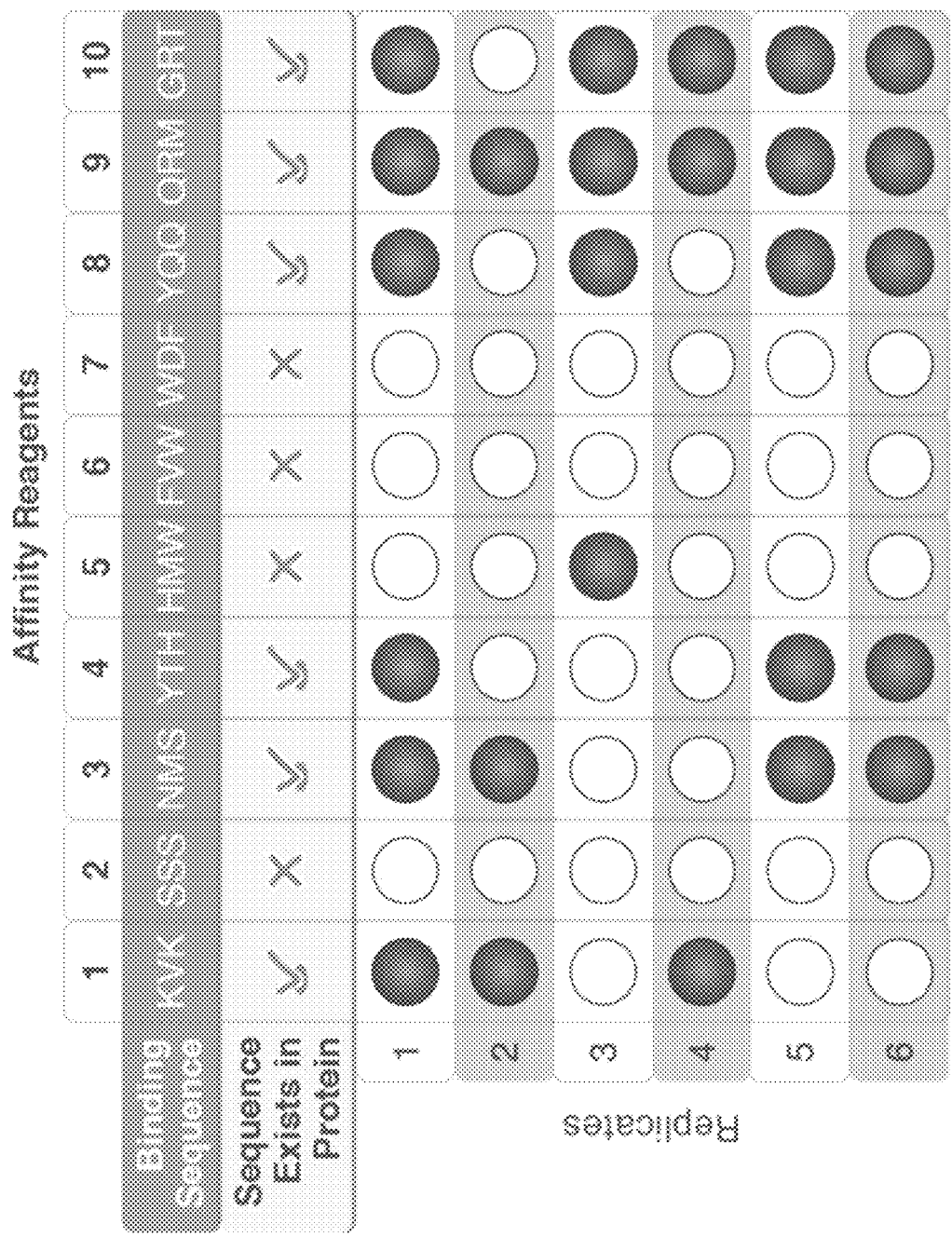

In some embodiments, a respective protein has more than one binding pattern or "signature." Generally, this is due to the fact that binding is stochastic; an affinity reagent will not always bind every protein containing its target epitope when making single-molecule measurements. Furthermore, each affinity reagent may bind to off-target epitopes with similarity to the target epitope. Therefore, measuring the same protein multiple times can produce a different binding pattern each time, as shown in FIG. 37C. To account for this stochasticity, a probabilistic binding model can be used in which each affinity reagent binds with a primary probability to a protein containing one copy of its target epitope and with an equal or lower probability to a protein containing one copy of an off-target epitope. For instance, in some implementations, the binding model defines a probability of 0.5 for on-target binding to a primary epitope and a probability of 0.5 for binding to an off-target epitope. This is because many factors could prevent binding of an affinity reagent to its epitope, e.g., native protein structure, localized protein structure due to micro-folding or incomplete denaturation in proteins that were subjected to denaturing conditions, post-translational modifications and binding kinetics. This can be used to determine a final binding pattern for an unknown protein at the respective predefined position, which can be decoded resulting in identification of the protein (3810).

See, for instance, Egertson et al., "A theoretical framework for proteome-scale single-molecule protein identification using multiaffinity protein binding reagents," bioRxiv, 2021, doi: 10.1101/2021.10.11.463967, which is hereby incorporated herein by reference in its entirety.

Referring again to FIG. 37A, the sequential probing and imaging of proteins exposed to the series of multi-affinity reagents results in a series of images of the substrate (e.g., a chip having an array of single-molecule positions, with no more than one protein molecule at each position). In some implementations, the images are registered (e.g., aligned) in order to collapse the protein binding patterns represented over all of the images in the series of images into binding pattern vectors specific to protein molecules at different positions. For instance, as illustrated in Steps 2 and 3 of FIG. 37A, a substrate (e.g., a chip) comprises, at each respective position in a plurality of positions (e.g., A1, A2, B1, B2, C1, and C2), a respective unknown protein. Each image in a series of images of the substrate (e.g., image 1, image 2, image 3, . . . image 300) is obtained for a corresponding cycle in a plurality of cycles, in which the substrate is exposed to a respective affinity reagent labeled with a fluorophore (e.g., cycle 1: KVK, cycle 2: SSS, cycle 3: NMS, . . . cycle 300: GRT).

Accordingly, each respective image in the series of images includes, at each respective position in the plurality of positions, a respective signal due to binding of affinity reagent or absence of signal from any affinity reagent. As such, presence or absence of signal at a given position in an image from a given cycle indicates binding status (e.g., bind/no-bind) of the corresponding protein at the given position probed by the respective affinity reagent for the given cycle. In other words, each respective image in the series of images captures binding events for the protein molecules on the substrate with the respective affinity reagent at the corresponding cycle. In some embodiments, the binding status (e.g., bind/no-bind) of the unknown protein at position A1 on the substrate is localized and determined for each respective image in the series of images (e.g., A1 in image 1, image 2, image 3, and image 300), and can then be used to generate the binding pattern vector illustrated in FIG. 37B.

However, issues can arise during image registration and alignment, particularly when aligning the features of the substrate captured during imaging. For instance, detectable moieties coupled to affinity reagents can produce detectable signals upon binding to protein molecules, which can be imaged (e.g., protein molecule-affinity reagent binding patterns such as fluorescent spots at each position on the array). In other embodiments, features of the substrate captured by imaging can include various spatial or visual indicators, such as fiducials and/or beads that are affixed to the substrate. In either case, changes in the position of the substrate relative to an imaging device can occur between the capturing of a first and second image, such as motion of the stage of a microscope on which the substrate is placed or movement resulting from the application of one or more affinity reagents or washing steps. In some instances, even slight movements can occur between respective image captures for two or more cycles in the plurality of cycles, such that, over time, the coordinate location of a respective feature (e.g., corresponding to a predefined position, a landing pad, a fiducial, a bead, etc.) on the substrate changes, in each image in the series of images. Such difficulties become more significant for an array of features as feature size and pitch decrease. For example, at resolutions and scales used for detection of single-molecule arrays, even vibration of the array or imaging device can result in significant changes in position of features between two images of the array.

Difficulties can result from the fact that coordinates of positions are limited to image size (e.g., 2048 by 2048 pixels), which can result in imprecise localization of imaged features or points (e.g., detected binding events such as fluorescent spots corresponding to protein molecules at predefined positions, fiducials, beads, etc.) or inconsistent coordinates between images. Other issues can occur due to differences in the number of points between two images to be registered. For example, the number of protein molecules on the substrate to which a first affinity reagent binds can be different from the number of protein molecules on the substrate to which a second affinity reagent binds and, as a result, the two corresponding images to be registered include two different patterns of points. In some cases, one of the first and second images can have a relatively smaller number of points (e.g., 100 points) while the other of the first and second images has a relatively larger number of points (e.g., 10,000). Additionally, in some cases, one or more points in a first image are not present in a second image, due to the loss of one or more identifiable features on the substrate (e.g., protein molecules on landing pads, fiducials, beads, etc.) between cycles, such as loss from handling, washing, or reagent flow. This type of problem is sometimes referred to generally as "point cloud registration."

Advantageously, the present disclosure provides systems and methods that allow for improved registration of a plurality of images of a substrate. In an example embodiment, a generalized Hough transform is applied to a point registration problem for a first image and a second image, obtained as described above in the workflow illustrated in FIGS. 37A and 38. The first image has a first plurality of points (e.g., a first point set), and the second image has a second plurality of points (e.g., a second point set), where registration between the first plurality of points and the second plurality of points is desired. For each point A in one of the first and the second images, all neighboring points B in the other of the first and the second images are localized to form a "point pair" or "matched points" (e.g., point pairs $A:B_1, \ldots A:B_n$, for each respective point A in the one image and each respective point B of n neighboring points B in the other image). For each point pair, the spatial relationship (e.g., the pixel offset between the positions of point A and point B) are determined and a vote is added to the transform implied by the spatial relationship. In this way, the spatial relationship of each point pair is used to vote for all of the implied (e.g., candidate) transforms between the two point sets.

The final registration is obtained based on the number of votes obtained for each candidate transform in the plurality of candidate transforms. For example, in some embodiments, the candidate transform that receives the most votes is selected for the final transformation. In some implementations, the determining the final registration also includes computing a score that estimates the probability that the highest-voted transform is non-random using a binomial distribution cumulative distribution function (CDF). This measure provides the probability that a candidate transform receives a certain number of votes given a random distribution of votes over all candidate transforms.

In some embodiments, the systems and methods disclosed herein provide image registration using a rigid transformation (e.g., where the features of the substrate are generally stationary). Advantageously, such methods produce nearly exact correspondence when correctly transformed, such that the features of the substrate can be correctly aligned to within the accuracy of the disclosed method (e.g., approximately 1 pixel). Moreover, in some implementations, the presently disclosed systems and methods utilize a point-based registration process, rather than a pixel-space based algorithm that compares pixels between images to determine transforms. A common mechanism includes selecting many regions of interest (ROIs) in a first image, using cross-correlation to identify best matches in a second image, and determining a consensus among best match offsets. However, such pixel-based approaches can be limited as images become increasingly different. For instance, as described in Example 7 below, the systems and methods disclosed herein improve upon conventional methodology by increasing the accuracy and consistency of registration over traditional methods such as image-based (e.g., pixel-based) cross-correlation, with higher numbers of true positives, higher numbers of true negatives, and lower numbers of false positives.

Accordingly, this disclosure provides systems, methods, and apparatuses for image registration, specifically for registering a plurality of images of a substrate. For sake of clarity and demonstration, systems, methods, and apparatuses of the present disclosure are exemplified herein in the context of imaging protein analytes, for example, in the context of assays wherein optically labelled affinity reagents are bound to the proteins. It will be understood that other analytes can be detected instead and other assay methods can be used instead including, for example, those set forth herein or those known in the art.

Methods, as set forth herein, may include one or more steps of performing an image analysis algorithm, for example to process pixel-based sensor data. In particular cases, it may be advantageous to include a General Hough Transform (GHT) method in an image analysis algorithm for purposes such as image registration, data classification, and mapping. General aspects of applying GHT analysis to data obtained from arrays, as set forth herein, are exemplified in the following embodiments, although aspects of image acquisition, processing, an/or analysis may be applicable to other methods.

Figure 35:
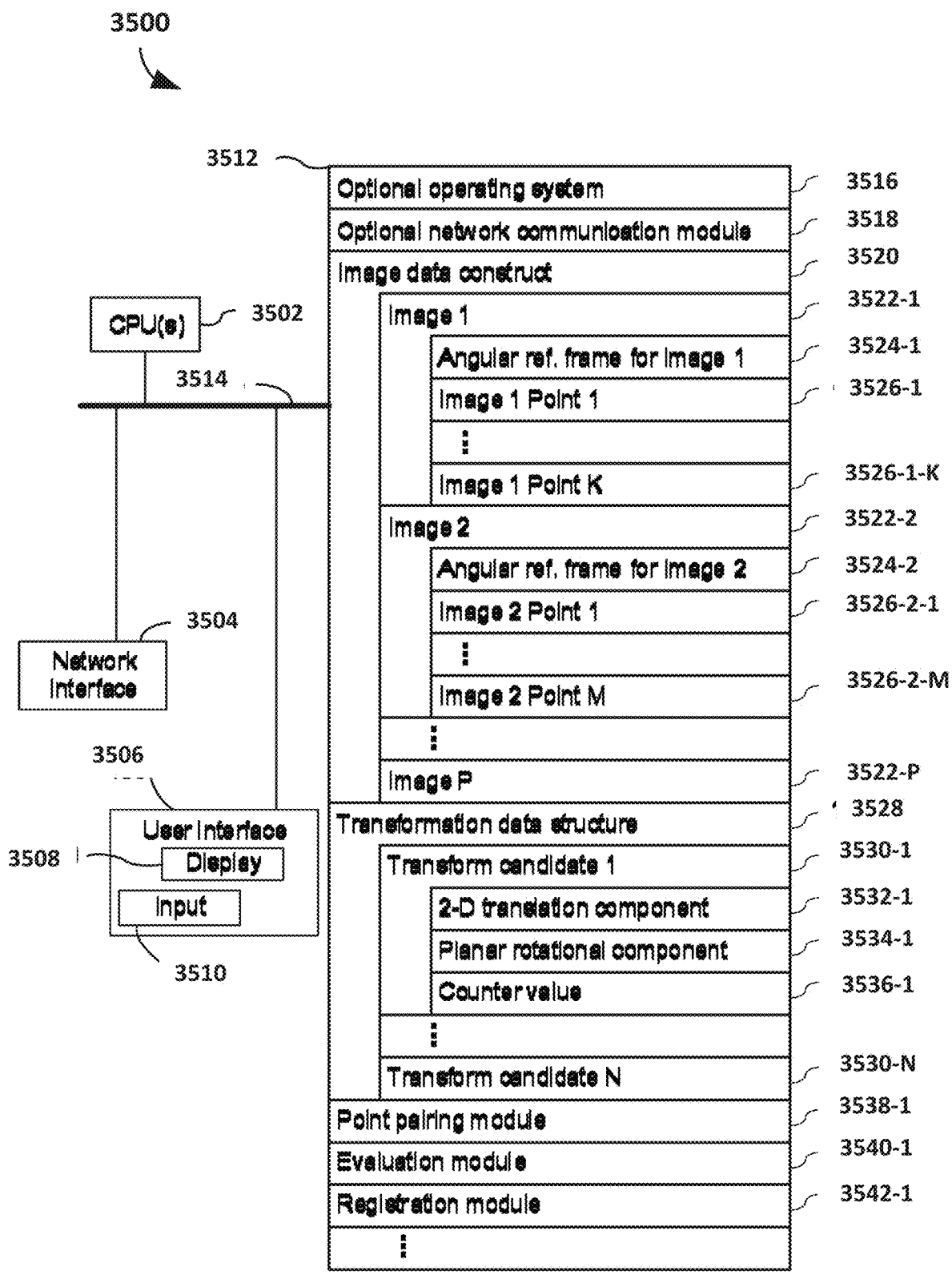
FIG. 35 illustrates an example block diagram illustrating a computing device in accordance with some embodiments of the present disclosure.

FIG. 35 illustrates a block diagram illustrating an exemplary, non-limiting system 3500 for registering a plurality of images of a substrate or an array set thereupon in accordance with some implementations. The system 3500 in some implementations includes one or more processing units CPU(s) 3502 (also referred to as processors), one or more network interfaces 3504, a user interface 3506, a memory 3512, and one or more communication buses 3514 for interconnecting these components. The communication buses 3514 optionally include circuitry (sometimes called a chipset) that interconnects and controls communications between system components. The memory 3512 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 3512 optionally includes one or more storage devices remotely located from the CPU(s) 3502. The memory 3512, or alternatively the non-volatile memory device(s) within the memory 3512, comprises a non-transitory computer readable storage medium. It will be appreciated that this memory 3512 can be distributed across one or more computers. In some implementations, the memory 3512 or alternatively the non-transitory computer readable storage medium stores the following programs, modules and data structures, or a subset thereof: a) an optional operating system 3516, which includes procedures for handling various basic system services and for performing hardware dependent tasks; b) an optional network communication module (or instructions) 3518 for connecting the device 3500 with other devices, or a communication network; c) an image data construct 3520 comprising a plurality of images 3522 (e.g., 3522-1, 3522-2, . . . 35122-P) of a substrate, including: i) a first image 3522-1 defining a first angular reference frame 3524-1 and a first plurality of points 3526 (e.g., 3526-1-1, . . . 3526-1-K); and ii) a second image 3522-2 defining a second angular reference frame 124-2 and a second plurality of points 3526 (e.g., 3526-2-1, . . . 3526-2-M), where the first plurality of points and the second plurality of points are coplanar, and where at least a first subset of the first plurality of points is not represented by the second plurality of points, at least a second subset of the second plurality of points is not represented by the first plurality of points, and at least a third subset of points in the first plurality of points is represented in the second plurality of points; d) a transformation data structure 3528 including, for each respective transform candidate 3530 in a plurality of transform candidates (e.g., 3530-1, . . . 3530-N), a respective two-dimensional translation component 3532 (e.g., 3532-1), a respective planar rotational component 3534 (e.g., 3534-1), and a respective counter 3536 (e.g., 3536-1), where the plurality of transform candidates collectively samples between a first angle and a second angle about an axis orthogonal to the first and second plurality of points; e) a point pairing module 3538 for performing a procedure that comprises, for each respective point in one of the first 3526-1 and second plurality of points 3526-2, (i) pairing the respective point with a corresponding point in the other of the first 3526-1 and second plurality of points 3526-2 whose corresponding two-dimensional coordinates are within a query radius centered on the respective two-dimensional coordinates of the respective point thereby identifying a respective point pair and, (ii) adding, for the respective point pair, a respective vote for each respective transform candidate 3530 in the plurality of transform candidates, having a respective angle represented by the transformation data structure, that maps the respective point onto the corresponding point, to the respective counter 3536 for the respective transform candidate in the transformation data structure; f) an evaluation module 3540 for repeating the adding (ii) for the respective point pair for each respective angle represented by the transformation data structure 3528 thereby adding additional votes for respective transform candidates 3530 identified by the adding (ii), and (iv) repeating the pairing (i), adding (ii), and repeating (iii) for the respective point with each other corresponding point in the second plurality of points that is within the query radius; and g) a registration module 3542 for registering the first 3522-1 and second images 3522-2 to each other using a respective transform candidate 3530 selected from the plurality of transform candidates in the transformation data structure 3528 based at least in part on a value of the respective counter 3536 associated with the respective transform candidate in the transformation data structure.

In some implementations, the user interface 3506 includes an input device (e.g., a keyboard, a mouse, a touchpad, a track pad, and/or a touch screen) 3510 for a user to interact with the system 3500 and a display 3508.

In some implementations, one or more of the above identified elements are stored in one or more of the previously mentioned memory devices and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 3512 optionally stores a subset of the modules and data structures identified above. Furthermore, in some embodiments, the memory stores additional modules and data structures not described above. In some embodiments, one or more of the above identified elements is stored in a computer system, other than that of system 3500, that is addressable by system 3500 so that system 3500 may retrieve all or a portion of such data when needed.

Although FIG. 35 shows an exemplary system 3500, the figure is intended more as functional description of the various features that may be present in computer systems than as a structural schematic of the implementations described herein. In practice, and as recognized by those of ordinary skill in the art, items shown separately could be combined and some items could be separated.

While a system in accordance with the present disclosure has been disclosed with reference to FIG. 35, methods in accordance with the present disclosure are now detailed with reference to FIGS. 36A, 36B, 36C, 36D, and 36E.

I. Specific Embodiments

This disclosure also provides methods and systems for registering a plurality of images of a substrate, as described above (e.g., for single-molecule proteome analysis). Provided below are detailed descriptions and explanations of various embodiments of the present disclosure. These embodiments are non-limiting and do not preclude any alternatives, variations, changes, and substitutions that can occur to those skilled in the art from the scope of this disclosure.

Details of a method 200 for registering a plurality of images of a substrate will now be provided with reference to FIGS. 36A, 36B, 36C, 36D, and 36E, in accordance with some embodiments of the present disclosure. In some embodiments, the method is performed at a computer system comprising one or more processing cores and a memory. Accordingly, one aspect of the present disclosure provides a method 200 for registering a plurality of images 3522 (e.g., 3522-1, 3522-2, ... 3522-P) of a substrate.

Point Sets.

Referring to Block 3602, the method 3600 comprises obtaining a first plurality of points 3526 (e.g., 3526-1-1, ... 3526-1-K) within a first image 3522-1 in the plurality of images, the first image defining a first angular reference frame 3524-1. In some embodiments, the first plurality of points comprises about 100 or more points. In some embodiments, each respective point in the first plurality of points has respective two-dimensional coordinates defining a location of the respective point in the first image.

In some embodiments, the substrate or array set thereupon is planar. In some embodiments, the substrate comprises a plurality of fiducial elements, as set forth herein. In some embodiments, the plurality of fiducial elements comprises any suitable indicator that denotes a point of reference on a respective substrate. In some embodiments, the plurality of fiducial elements comprises one or more fiducial marks (e.g., spots).

In some embodiments, the substrate comprises a plurality of unique, spatially-separated locations (e.g., addresses in an array of addresses). In some embodiments, each unique spatially-separated location corresponds to a candidate location for a respective analyte (e.g., a polypeptide molecule). In other words, in some embodiments, each unique spatially-separated location is a position on the substrate to which a single respective analyte (e.g., polypeptide molecule) can attach (e.g., a landing pad and/or a candidate polypeptide binding site). In some embodiments, each respective unique spatially-separated location includes an anchoring moiety, such as a structured nucleic acid particle (SNAP). For example, each respective unique spatially-separated location can be an address to which a SNAP is covalently or non-covalently attached. See, for example, U.S. Pat. Nos. 11,203,612 and 11,505,796, each of which is incorporated herein by reference. In some embodiments, the substrate comprises a plurality of analytes, where each respective analyte in the plurality of analytes is coupled to (e.g., bound to) a different respective unique spatially-separated location in all or a subset of the plurality of unique spatially-separated locations.

In some embodiments, the substrate comprises a plurality of analytes. In some embodiments, the plurality of analytes of the substrate comprises five or more analytes, ten or more analytes, fifty or more analytes, one hundred or more analytes, five hundred or more analytes, 1000 or more analytes, 2000 or more analytes, or between 2000 and 100,000 analytes. Each of the analytes can optionally be attached to an individual address in an array on the substrate.

In some embodiments, the plurality of analytes comprises at least 5, at least 10, at least 20, at least 50, at least 100, at least 200, at least 300, at least 400, at least 500, at least 600, at least 700, at least 800, at least 900, at least 1000, at least 2000, at least 3000, at least 5000, at least 6000, at least 7000, at least 8000, at least 9000, at least 10,000, at least 20,000, at least 30,000, at least 40,000, at least 50,000, at least 100,000, at least 500,000, or at least 1,000,000 analytes. Alternatively or additionally, the plurality of analytes comprises no more than 5,000,000, no more than 1,000,000, no more than 500,000, no more than 100,000, no more than 50,000, no more than 20,000, no more than 10,000, no more than 5000, no more than 3000, no more than 2000, no more than 1000, no more than 500, no more than 100, or no more than 50 analytes. Each of the analytes can optionally be attached to an individual address in an array on the substrate.

In some embodiments, each respective point in the first plurality of points has a corresponding set of two-dimensional coordinates within the respective image. In some embodiments, the first plurality of points is planar. In some such embodiments, the first plurality of points is coplanar with the substrate. In some embodiments, each image of the plurality of images is acquired from the planar surface (e.g., of the substrate).

In some embodiments, the first plurality of points includes at least 2, at least 3, at least 4, at least 5, at least 6, at least 7, at least 8, at least 9, at least 10, at least 20, at least 50, at least 100, at least 1000, at least 5000, at least 10,000, at least 20,000, at least 50,000, at least 100,000, at least 500,000, or at least 1,000,000 points. Alternatively or additionally, the first plurality of points includes no more than 5,000,000, no more than 1,000,000, no more than 500,000, no more than 100,000, no more than 50,000, no more than 10,000, no more than 1000, no more than 100, no more than 50, no more than 20, or no more than 10 points.

Referring to Block 204, the method further includes obtaining a second plurality of points 3526 (e.g., 3526-2-1, ... 3526-2-M) within a second image 3522-2 in the plurality of images, the second image defining a second angular reference frame 3524-2, where each respective point in the second plurality of points has respective two-dimensional coordinates defining a location of the respective point in the second image and where the first plurality of points and the second plurality of points are coplanar. In some embodiments, at least some points in one of the first and second plurality of points is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points. In some embodiments, the second plurality of points comprises about 100 or more points.

In some embodiments, each respective point in the second plurality of points has a corresponding set of two-dimensional coordinates within the respective image. As described above, in some embodiments, the second plurality of points is planar (e.g., coplanar with the substrate and/or with the first plurality of points). In some embodiments, the second plurality of points is not coplanar with the first plurality of points and/or with the substrate.

In some embodiments, the second plurality of points includes at least 2, at least 3, at least 4, at least 5, at least 6, at least 7, at least 8, at least 9, at least 10, at least 20, at least 50, at least 100, at least 1000, at least 5000, at least 10,000, at least 20,000, at least 50,000, at least 100,000, at least 500,000, at least 1,000,000, or at least 5,000,000 points. Alternatively or additionally, the second plurality of points includes no more than 10,000,000, no more than 5,000,000, no more than 1,000,000, no more than 500,000, no more than 100,000, no more than 50,000, no more than 10,000, no more than 1000, no more than 100, no more than 50, no more than 20, or no more than 10 points.

In some embodiments, the first and second plurality of points have the same or a different number of points. In some embodiments, the first plurality of points has fewer points than the second plurality of points. In some embodiments, the second plurality of points has fewer points than the first plurality of points.

For instance, in some embodiments, the first plurality of points comprises about 2 or more, about 10 or more, about 20 or more, about 50 or more, about 100 or more, about 200 or more, about 400 or more, about 600 or more, about 800 or more, or about 1000 or more points, and the second plurality of points comprises about 2 or more, about 10 or more, about 20 or more, about 50 or more, about 100 or more, about 200 or more, about 400 or more, about 600 or more, about 800 or more, or about 1000 or more points.

In some embodiments, the first plurality of points comprises about 20 or more, about 100 or more, about 500 or more, about 1000 or more, about 5000 or more, about 10,000 or more, about 100,000 or more, or about 1,000,000 or more points, and the second plurality of points comprises about 20 or more, about 100 or more, about 500 or more, about 1000 or more, about 5000 or more, about 10,000 or more, about 100,000 or more, or about 1,000,000 or more points. Alternatively or additionally, the first plurality of points comprises about 5,000,000 or less, about 1,000,000 or less, about 100,000 or less, about 10,000 or less, about 1000 or less, or about 100 or less points, and the second plurality of points comprises about 5,000,000 or less, about 1,000,000 or less, about 100,000 or less, about 10,000 or less, about 1000 or less, or about 100 or less points.

In some embodiments, the first plurality of points corresponds to a plurality of fiducials in an array, a plurality of sites having target analytes, or a combination thereof. Alternatively or additionally, the second plurality of points corresponds to a plurality of fiducials in an array, a plurality of sites having target analytes, or a combination thereof.

In some embodiments, the first plurality of points does not include any points corresponding to fiducials in an array, and/or the second plurality of points does not include any points corresponding to fiducials in an array. Alternatively or additionally, the first plurality of points does not include any points corresponding to sites having target analytes in an array, and/or the second plurality of points does not include any points corresponding to sites having target analytes in an array.

As described above, in some embodiments, at least a first subset of the first plurality of points is not represented by (e.g., is not found in) the second plurality of points. In some such embodiments, points in one plurality of points that are not represented in another plurality of points are not found in the other plurality of points. In other words, a point in a first set of points (e.g., a point in point set A), having respective two-dimensional coordinates defining its location in a first image (e.g., relative to a substrate), that is not represented in a second set of points (e.g., point set B) does not have a corresponding point in the second set of points that has the same two-dimensional coordinates relative to the substrate. Thus, in some such embodiments, at least the first subset of the first plurality of points is unique to the first plurality of points. Put another way, in some embodiments, at least the first subset of points is found in the first plurality of points but not in the second plurality of points.

Moreover, in some embodiments, at least a second subset of the second plurality of points is not represented by (e.g., is not found in) the first plurality of points. Similar to the first subset of the first plurality of points, in some such embodiments, points in the second plurality of points that are not represented by the first plurality of points are found in the second plurality of points but not in the first plurality of points. In other words, a point in a second set of points (e.g., a point in point set B), having respective two-dimensional coordinates defining its location in a second image (e.g., relative to a substrate), that is not represented in a first set of points (e.g., point set A) does not have a corresponding point in the first set of points that has the same two-dimensional coordinates relative to the substrate. Thus, in some such embodiments, at least the second subset of the second plurality of points is unique to the second plurality of points. Put another way, in some embodiments, at least the second subset of points is found in the second plurality of points but not in the first plurality of points.

Additionally, in some embodiments, at least a third subset of points in the first plurality of points is represented in the second plurality of points. In some such embodiments, points in the third subset of points are found in both the first plurality of points and the second plurality of points. For example, in some embodiments, points in the third subset of points have corresponding two-dimensional coordinates defining their location in the first image, as well as corresponding two-dimensional coordinates defining their location in the second image. Put another way, in some embodiments, the at least the third subset of points is shared between the first and second plurality of points.

An illustrative example can be described using two point sets A and B. In some cases, some points in point set A are not found in point set B, and/or some points in point set B are not found in point set A. Alternatively, or additionally, some points can be found in both point set A and point set B. The appearance, in image A or image B, of points that are unique to point set A or point set B can be due to transient optical measurements obtained for a plurality of analytes bound to an affinity reagent specific to image A or image B, as appropriate. The appearance, in image A and image B, of points that are common to both point set A and point set B can be due to features on the substrate that are nontransient, such as fiducial elements or spatially-separated locations (e.g., analyte-binding sites and/or anchoring moieties). Transient optical measurements, fiducial elements, and spatially-separated locations that can result in the capture and imaging of one or more points in a plurality of points are further described elsewhere herein.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is not represented by (e.g., found in) the second plurality of points. In some embodiments, at least about 5 percent, at least about 10 percent, at least about 15 percent, at least about 20 percent, at least about 25 percent, at least about 30 percent, at least about 35 percent, or at least about 40 percent of the second plurality of points is not represented by (e.g., found in) the first plurality of points.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is represented by (e.g., found in) the second plurality of points. In some embodiments, at least about 5 percent, at least about 10 percent, at least about 15 percent, at least about 20 percent, at least about 25 percent, at least about 30 percent, at least about 35 percent, or at least about 40 percent of the second plurality of points is represented by (e.g., found in) the first plurality of points.

In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the first plurality of points is not represented by (e.g., found in) the second plurality of points. In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the second plurality of points is not represented by (e.g., found in) the first plurality of points.

In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the first plurality of points is represented by (e.g., found in) the second plurality of points. In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the second plurality of points is represented by (e.g., found in) the first plurality of points.

Images

In some embodiments, the plurality of images includes at least 2, at least 3, at least 4, at least 10, at least 20, at least 50, at least 100, at least 500, at least 1000, at least 2000, or at least 5000 images. Alternatively or additionally, the plurality of images includes no more than 10,000, no more than 5000, no more than 1000, no more than 100, no more than 50, or no more than 10 images.

In some embodiments, the plurality of images includes at least a first subset of images of a first region of the substrate and a second subset of images of a second region of a substrate that is different from the first region. For instance, as described in Example 1 below, in some embodiments, the plurality of images includes images obtained by scanning across all or a portion of the substrate. In some embodiments, a first respective image in the plurality of images is of the same or an overlapping region of the substrate as another image in the plurality of images.

In some embodiments, each respective image in the plurality of images is obtained at a different point in time. For example, each respective image in the plurality of images can be obtained from a given substrate at a different point in time such as before and after a step in a method of detecting or manipulating analytes.

In some embodiments, a respective image in the plurality of images comprises any of the embodiments disclosed herein as for the first and/or the second image. In some embodiments, each respective image in the plurality of images comprises any of the embodiments disclosed herein as for the first and/or the second image. For example, in some embodiments, the plurality of images further includes a third image, where the third image is coplanar with the first and the second images and includes a respective third plurality of points. Thus, in some embodiments, each respective image in the plurality of images includes a corresponding plurality of points. In some embodiments, each respective plurality of points corresponding to a respective image in the plurality of images has the same or a different number of points as any other respective plurality of points corresponding to another respective image in the plurality of images. In some embodiments, a respective plurality of points corresponding to a respective image in the plurality of images includes any number of points as described herein for the first and/or the second plurality of points.

In some embodiments, a respective image (e.g., the first image and/or the second image) comprises a plurality of pixels. In some embodiments, each image in the plurality of images comprises more than 200,000 pixels. In some embodiments, each image in the plurality of images comprises more than 500,000 pixels.

In some embodiments, the plurality of pixels includes at least 100, at least 500, at least 1000, at least 5000, at least 10,000, at least 50,000, at least 100,000, at least 500,000, at least $1\times10^6$, at least $2\times10^6$, at least $3\times10^6$, at least $5\times10^6$, at least $8\times10^6$, at least $1\times10^7$, at least $1\times10^8$, at least $1\times10^9$, at least $1\times10^{10}$, or at least $1\times10^{11}$ pixels. Alternatively or additionally, the plurality of pixels includes no more than $1\times10^{12}$, no more than $1\times10^{11}$, no more than $1\times10^{10}$, no more than $1\times10^9$, no more than $1\times10^8$, no more than $1\times10^7$, no more than $1\times10^6$, no more than 100,000, no more than 10,000, or no more than 1000 pixels.

In some embodiments, a respective image in the plurality of images has a first dimension and a second dimension orthogonal to the first dimension, where the number of pixels in the first dimension and the number of pixels in the second dimension are the same or different For example, in some embodiments, each image in the plurality of images comprises at least about 500 pixels in a first dimension, and each image in the plurality of images comprises at least about 500 pixels in a second dimension orthogonal to the first dimension. In some embodiments, each image in the plurality of images consists of 2048 pixels in a first dimension, and each image in the plurality of images consists of 2048 pixels in a second dimension orthogonal to the first dimension.

In some embodiments, each image in the plurality of images comprises at least about 200, at least about 400, at least about 800, at least about 1500, at least about 2000, at least about 5000, at least about 10,000 pixels in a first dimension, and each image in the plurality of images comprises at least about 200, at least about 400, at least about 800, at least about 1000, at least about 2000, at least about 5000, at least about 10,000 pixels in a second dimension. Alternatively or additionally, each image in the plurality of images comprises no more than 20,000, no more than 10,000, no more than 5000, no more than 2000, no more than 1000, no more than 800, or no more than 400 pixels in a first dimension, and each image in the plurality of images comprises no more than 20,000, no more than 10,000, no more than 5000, no more than 2000, no more than 1000, no more than 800, or no more than 400 pixels in a second dimension.

In some embodiments, a respective image (e.g., the first image and/or the second image) has an image size between 1 KB and 1 MB, between 1 MB and 0.5 GB, between 0.5 GB and 5 GB, between 5 GB and 10 GB, or greater than 10 GB. In some embodiments, the first image and the second image have the same or different image sizes. In some embodiments, a respective image in the plurality of images has the same or different image size from any other image in the plurality of images.

In some embodiments, each point in the first plurality of points occupies a corresponding single pixel in the first image, and each point in the second plurality of points occupies a corresponding single pixel in the second image. In some embodiments, each point in the first plurality of points occupies one or more adjacent pixels in the first image. In some embodiments, each point in the second plurality of points occupies one or more adjacent pixels in the second image. In some embodiments, each point in the first plurality of points occupies a corresponding plurality of adjacent pixels (e.g., 2, 3, 4, 5, 6, 7, 8, 9, 10 pixels, or between 2 and 100 pixels) in the first image, and each point in the second plurality of points occupies a corresponding plurality of adjacent pixels (e.g., 2, 3, 4, 5, 6, 7, 8, 9, 10 pixels, or between 2 and 100 adjacent pixels) in the second image.

As described above, in some embodiments, each respective point in a respective plurality of points (e.g., the first and/or the second plurality of points) has a corresponding set of two-dimensional coordinates within the respective image (e.g., the first and/or the second image). Accordingly, in some embodiments, a respective point in a respective image corresponds to one pixel or a plurality of adjacent pixels in the respective image, where the location (e.g., coordinates) of the one pixel or the location of the plurality of adjacent pixels for the respective point within the respective image is known. For instance, in some embodiments, each respective pixel in the plurality of pixels for a respective image has a set of two-dimensional coordinates within the respective image. In embodiments where a point corresponds to a plurality of adjacent pixels, the center of the plurality of adjacent pixels is used as the two-dimensional coordinates of the point. In embodiments where a point corresponds to a single pixel, the coordinates of the single pixel is used as the two-dimensional coordinates of the point.

In some embodiments, the plurality of images includes a respective image of the substrate comprising a plurality of analytes (e.g., polypeptides). For instance, in some embodiments, the plurality of images includes a respective image of the substrate comprising a plurality of analytes (e.g., polypeptide molecules) bound to an analytical reagent (e.g., an affinity reagent). In some embodiments, the plurality of images includes a respective image of the substrate comprising a plurality of fiducial elements. In some embodiments, each respective image in the plurality of images comprises an indication of the locations (e.g., optical measurements) of the plurality of fiducial elements, as further described herein. For instance, in some embodiments, the substrate comprises the plurality of fiducial elements, such that each image in the plurality of images of the substrate includes the plurality of fiducial elements, or a subset thereof. Accordingly, in some embodiments, each of the first image and the second image includes the plurality of fiducial elements or the subset thereof.

In some embodiments, the plurality of images includes a respective image of the substrate comprising a visual indication of one or more fiducial elements and not comprising a visual indication of analyte signal (e.g., polypeptide molecules bound to affinity reagents). For example, in some embodiments, the plurality of images includes a "fiducial only" reference image that displays one or more visual indications (e.g., optical measurements) corresponding to the one or more fiducial elements but does not display any visual indications (e.g., signals obtained from polypeptide molecules bound to affinity reagents) corresponding to analytes.

In some embodiments, the plurality of images includes a respective image of the substrate comprising, for each unique spatially-separated location in a plurality of unique spatially-separated locations on the substrate, a respective indication (e.g., an optical measurement) of the respective location. In some embodiments, each respective image in the plurality of images comprises the indication of each unique spatially-separated location in the plurality of unique spatially-separated locations on the substrate. In some embodiments, one or more respective images in the plurality of images comprises the indication of each unique spatially-separated location in the plurality of unique spatially-separated locations on the substrate.

In some embodiments, each unique spatially-separated location corresponds to a candidate location for a respective analyte (e.g., polypeptide molecule). In other words, in some embodiments, each unique spatially-separated location is a position on the substrate to which a single respective analyte molecule can bind (e.g., a site and/or a candidate analyte binding site). In some embodiments, each respective unique spatially-separated location is, or includes, an anchoring moiety, such as a SNAP.

In some embodiments, the plurality of images includes a respective image of the substrate comprising the plurality of indications of the unique spatially-separated locations on the substrate but does not include optical measurements of analytes (e.g., polypeptide molecules bound to affinity reagents). For example, in some embodiments, the plurality of images includes a "position only" reference image that displays one or more visual indications (e.g., optical measurements) of the plurality of spatially-separated locations on the substrate (e.g., sites and/or anchoring moieties) even when analytes have not bound to the respective locations (e.g., a reference image that provides the locations of candidate analyte binding sites on the substrate).

In some embodiments, a respective image in the plurality of images comprises a plurality of fiducial elements, a plurality of unique spatially-separated locations (e.g., addresses) on the substrate, a plurality of analytes (e.g., polypeptide molecules bound to an affinity reagent), or any combination thereof. For instance, in some embodiments, a respective image in the plurality of images comprises a plurality of fiducial elements and a plurality of unique spatially-separated locations on the substrate but does not comprise a plurality of analyte molecules bound to an analytical reagent (e.g., a reference image indicating the positions of fiducial elements and of candidate analyte binding sites (e.g., anchoring moieties)). In some embodiments, a respective image in the plurality of images comprises a plurality of fiducial elements and a plurality of analytes (e.g., polypeptide molecules) bound to an analytical reagent (e.g., an affinity reagent). In some embodiments, a respective image in the plurality of images comprises a plurality of fiducial elements, a plurality of unique spatially-separated locations on the substrate, and a plurality of analytes (e.g., polypeptide molecules) bound to an analytical reagent (e.g., an affinity reagent).

In some embodiments, a respective image in the plurality of images comprises any suitable feature of a substrate and/or of a plurality of analytes thereon, including but not limited to fiducial elements, unique spatially-separated locations, analytes (e.g., polypeptides), analytical reagents (e.g., affinity reagents), and/or detectable markers, as disclosed elsewhere herein. In some embodiments, a respective image in the plurality of images comprises any other feature of a substrate and/or of a plurality of analytes thereon that can be obtained as a result of sample preparation, substrate preparation, analyte labeling, and/or image acquisition, as will be apparent to one skilled in the art.

In some embodiments, one or more features of the substrate and/or of a plurality of analytes thereon (e.g., a plurality of fiducial elements, a plurality of unique spatially-separated locations on the substrate, and/or a plurality of polypeptide molecules bound to an affinity reagent) are represented in a respective image, in the plurality of images, as points in a respective plurality of points.

For instance, in some implementations, each point in a respective plurality of points for a respective image represents optical activity localized to a corresponding position on the substrate, where the optical activity indicates the one or more features of the substrate and/or of a plurality of analytes thereon (e.g., a plurality of fiducial elements, a plurality of unique spatially-separated locations on the substrate, and/or a plurality of analytes bound to an analytical reagent). Optical activity and optical measurement thereof are described further below.

Optical Measurement and Detection

Referring to Block 3606, in some embodiments, each point in the first plurality of points represents optical activity localized to a corresponding position on the substrate. In some embodiments, each point in the second plurality of points represents optical activity localized to a corresponding position on the substrate. Referring to Block 3610, in some embodiments, each point in the first plurality of points and in the second plurality of points represents an optical measurement of a corresponding position on the substrate. For instance, in some embodiments, optical measurements are obtained of optical activity (e.g., fluorescence, bioluminescence, chemiluminescence, and/or light scattering).

Referring to Block 3608, in some embodiments, a first subplurality of the first plurality of points arises from respective optical measurements of a plurality of fiducial elements on the substrate, where points corresponding to the first subplurality of points are in the second plurality of points, and a second subplurality of the first plurality of points arises from respective optical measurements of a plurality of analytes (e.g., polypeptide molecules) when bound to an analytical reagent (e.g., an affinity agent), and each analyte of the plurality of analytes is coupled to a unique, spatially-separated location (e.g., a site and/or a candidate analyte binding site) of a plurality of unique, spatially-separated locations on the substrate.

Thus, as described above (see, e.g., the section entitled "Images," above), the first image and the second image both include a subplurality of points corresponding to the plurality of fiducial elements, and the first image includes at least a second subplurality of points corresponding to analyte signals (e.g., the plurality of polypeptide molecules when bound to an affinity reagent). In some embodiments, the second subplurality of points (e.g., corresponding to analyte signals in the first image) is not in the second plurality of points (e.g., analyte signal patterns in the first image are not duplicated in the second image).

In some embodiments, the first subplurality (e.g., points corresponding to the plurality of fiducial elements) represents less than 10 percent, less than 5 percent, or less than 2 percent of the first plurality of points. In some embodiments, the first subplurality represents less than 20 percent, less than 15 percent, less than 10 percent, less than 8 percent, less than 5 percent, less than 2 percent, or less than 1 percent of the first plurality of points. Alternatively or additionally, the first subplurality represents at least 0.1 percent, at least 0.5 percent, at least 1 percent, at least 2 percent, at least 5 percent, or at least 10 percent of the first plurality of points.

Similarly, in some embodiments, a first subplurality of the second plurality of points arises from respective optical measurements of a plurality of fiducial elements on the substrate, where points corresponding to the first subplurality of points are in the first plurality of points, and a second subplurality of the second plurality of points arises from respective optical measurements of a plurality of polypeptide molecules when bound to an affinity reagent, and each polypeptide molecule of said plurality of polypeptide molecules is coupled to a unique, spatially-separated location of a plurality of unique, spatially-separated locations on the substrate. In some embodiments, the second subplurality of points (e.g., corresponding to analyte signals in the second image) is not in the first plurality of points (e.g., analyte signal patterns in the second image are not duplicated in the first image).

In some embodiments, the first subplurality (e.g., points corresponding to the plurality of fiducial elements) represents less than 10 percent, less than 5 percent, or less than 2 percent of the second plurality of points. In some embodiments, the first subplurality represents less than 20 percent, less than 15 percent, less than 10 percent, less than 8 percent, less than 5 percent, less than 2 percent, or less than 1 percent of the second plurality of points. Alternatively or additionally, the first subplurality represents at least 0.1 percent, at least 0.5 percent, at least 1 percent, at least 2 percent, at least 5 percent, or at least 10 percent of the second plurality of points.

In some embodiments, as described above, the substrate comprises the plurality of fiducial elements, such that the first image and the second image each include a respective first subplurality of points corresponding to the plurality of fiducial elements in the respective image (e.g., fiducial elements are visible in both the first and second images).

In some embodiments, the second subplurality of the first plurality of points corresponds to transient optical measurements in the first image obtained for a plurality of analytes (e.g., polypeptide molecules) bound to a first analytical reagent (e.g., a first affinity agent). For instance, as described above, in some embodiments, the substrate comprises a plurality of a polypeptide molecules, where each respective polypeptide molecule in the plurality of polypeptide molecules is coupled to a unique, spatially-separated location on the substrate (e.g., a site and/or a an anchoring moiety) and is further bound to an affinity reagent.

In some embodiments, the second subplurality of the first plurality of points is specific to the first image (e.g., is not in the second image). This can occur, for example, at least in part because transient optical measurements that correspond to the first analytical reagent are only obtained when the substrate is exposed to the first analytical reagent during capture of the first image. Similarly, in some embodiments, the second subplurality of the second plurality of points corresponds to transient optical measurements in the second image obtained for a plurality of analytes (e.g., polypeptide molecules) bound to a second analytical reagent (e.g., a second affinity agent) that is different from the first analytical reagent. Moreover, in some embodiments, the second subplurality of the second plurality of points is specific to the second image (e.g., is not in the first image). This can occur, for example, at least in part because transient optical measurements that correspond to the second analytical reagent are only obtained when the substrate is exposed to the second analytical reagent during capture of the second image.

In some embodiments, an analytical reagent comprises a detectable label or marker (e.g., a labeled probe or "lobe"). In some embodiments, the detectable marker is selected from the group consisting of an antibody, a fluorescent label (e.g., a fluorophore), a radioactive label, a chemiluminescent label, a calorimetric label, a colorimetric label, and/or a combination thereof. For instance, in some embodiments, the detectable marker is selected from the group consisting of: live/dead stain, trypan blue, periodic acid-Schiff reaction stain, Masson's trichrome, Alcian blue, van Gieson, reticulin, Azan, Giemsa, Toluidine blue, isamin blue, sudan black and osmium, acridine orange, Bismarck brown, carmine, Coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or a combination thereof. In some embodiments, different detectable markers are used for obtaining the first image and the second image. In some embodiments, a different detectable marker is used for obtaining each respective image in the plurality of images. In some embodiments, the same detectable marker is used for obtaining one or more images in the plurality of images.

In some embodiments, an analytical reagent comprising an affinity agent has affinity for (e.g., binds to) one or more epitopes in an analyte (e.g., a polypeptide molecule). In some embodiments, the affinity agent binds to more than one unique epitope present within one or more analyte in the plurality of analytes.

In particular configurations, an analyte can be detected using one or more affinity agents having known or measurable binding affinity for the analyte. For example, an affinity agent can bind an analyte to form a complex and a signal produced by the complex can be detected. An analyte that is detected by binding to a known affinity agent can be identified based on the known or predicted binding characteristics of the affinity agent. For example, an affinity agent that is known to selectively bind a candidate analyte suspected of being in a sample, without substantially binding to other analytes in the sample, can be used to identify the candidate analyte in the sample merely by observing the binding event. This one-to-one correlation of affinity agent to candidate analyte can be used for identification of one or more analytes.

In some embodiments, an analytical reagent comprising an affinity agent binds to at least 2, at least 3, at least 5, at least 10, at least 20, at least 30, or at least 50 unique epitopes present within one or more analytes (e.g., polypeptides) in the plurality of analytes. Alternatively or additionally, the analytical reagent binds to no more than 100, no more than 50, no more than 20, no more than 10, or no more than 5 unique epitopes present within one or more analytes in the plurality of analytes. In some embodiments, the analytical reagent binds to only one unique epitope present within one or more analytes in the plurality of analytes.

In some embodiments, an affinity agent comprises a known degree of binding nonspecificity. For example, the affinity agent can be promiscuous for a plurality of different proteins. In some cases, the affinity agent is promiscuous with respect to binding the same epitope in the different proteins. In some cases, the affinity agent is promiscuous with respect to binding different epitopes.

In some embodiments, an affinity reagent binds to an epitope comprising at least 2, at least 3, at least 4, or at least 5 residues. Alternatively or additionally, the affinity agent binds to an epitope comprising no more than 10, no more than 8, no more than 5, or no more than 3 residues.

In some embodiments, the plurality of images comprises, for each respective analytical reagent in a plurality of analytical reagents, a corresponding image including respective optical measurements of the plurality of analytes (e.g., polypeptide molecules) when bound to the respective analytical agent. Thus, in some such implementations, the plurality of images comprises a first image that includes respective optical measurements for a first analytical agent, a second image that includes respective optical measurements for a second analytical reagent, a third image that includes respective optical measurements for a third analytical reagent, and so on.

In some embodiments, the plurality of analytical reagents comprises at least 2, at least 5, at least 10, at least 20, at least 50, at least 80, at least 100, at least 300, or at least 500 species of analytical reagent. Alternatively or additionally, the plurality of affinity reagents comprises no more than 1000, no more than 500, no more than 300, no more than 100, no more than 50, no more than 20, or no more than 10 species of analytical reagent. A first species of analytical reagent may be distinguished from a second species of analytical reagent with respect to, for example, type of reagent (reactive, non-reactive, antibody, aptamer, etc.), binding specificity, binding promiscuity, and combinations thereof. In some embodiments, a first respective analytical reagent comprises the same or a different detectable marker as a second respective analytical reagent in the plurality of analytical reagents. Any embodiments for a first respective analytical reagent disclosed herein can apply to any other respective analytical reagent in a plurality of analytical reagents, as will be apparent to one skilled in the art.

In some embodiments, a respective analytical reagent in a plurality of analytical reagents binds to all or a subset of a plurality of analytes (e.g., the plurality of polypeptide molecules). For example, in some implementations, a respective analytical reagent binds to a unique epitope present within a subset of the plurality of analytes (e.g., polypeptide molecules). In some embodiments, a first respective analytical reagent binds to a unique epitope present within a first respective subset of the plurality of analytes (e.g., polypeptide molecules), and a second respective analytical reagent binds to a unique epitope present within a second respective subset of the plurality of analytes (e.g., polypeptide molecules), where the first and the second subset of analytes are different (e.g., the first and the second subset of analytes differ by at least one analyte).

Accordingly, in some embodiments, for each respective image corresponding to presence of a respective analytical reagent, the respective subplurality of the respective plurality of points arising from optical measurements of the plurality of analytes when bound to the respective analytical reagent (e.g., an optical pattern) corresponds uniquely to the respective analytical reagent. For instance, in an example implementation, a first image comprises a respective first optical pattern (e.g., a subplurality of the respective plurality of points in the first image), and a second image comprises a respective second optical pattern (e.g., a subplurality of the respective plurality of points in the second image), where the first optical pattern and the second optical pattern are different. The first optical pattern and the second optical pattern can differ due to the presence of different analytical reagents bound to an array of addresses on the substrate when the respective images are acquired, the different analytical reagents binding to analytes (e.g., protein analytes) at a different pattern of the addresses. In some implementations, a first optical pattern and a second optical pattern are the same.

In some embodiments, the plurality of analytes (e.g., polypeptide molecules) comprises at least 100, at least 500, at least 1000, at least 2000, at least 3000, at least 5000, at least 6000, at least 7000, at least 10,000, or at least 20,000 different species of analytes. Alternatively or additionally, the plurality of analytes comprises no more than 50,000, no more than 20,000, no more than 10,000, no more than 5000, no more than 1000, or no more than 500 different species of analytes.

The first and second image can be obtained using any analyte detection assay known in the art including, but not limited to those set forth herein. For instance, in some embodiments, the first and second image are obtained using any protein or nucleic acid detection assay known in the art.

As described above, in some embodiments, a respective image in a plurality of images can contain one or more respective sub pluralities of points corresponding to one or more of a plurality of fiducial elements, a plurality of unique, spatially-separated locations, and a plurality of transient optical measurements obtained for a plurality of analytes (e.g., polypeptide molecules) bound to an analytical reagent (e.g., an affinity agent). In some implementations, the plurality of images comprises one or more images comprising a respective subplurality of points arising from optical measurements of a plurality of analytes when bound to a respective analytical reagent. For instance, as described above with reference to FIGS. 37A-C and 38, the plurality of images can include a first image of optical measurements from a first analytical reagent, a second image of optical measurements from a second analytical reagent, a third image of optical measurements from a third analytical reagent, and so on. Any number of images in the plurality of images, and any corresponding number of analytical reagent-specific sub pluralities of points (e.g., binding patterns), can be obtained, as will be apparent to one skilled in the art.

In some such embodiments, each respective image in the plurality of images includes a first subplurality of points corresponding to one or more fiducial elements. In some embodiments, each respective image in the plurality of images further includes a unique affinity reagent-specific subplurality of points (e.g., binding pattern). Accordingly, in some such embodiments, points corresponding to fiducial elements are visible in each image in the plurality of images, whereas points corresponding to transient analyte detection data (e.g., transient optical measurements obtained for a plurality of polypeptide molecules bound to an affinity reagent) are visible only in the respective image or images corresponding to the respective analyte detection moiety (e.g., an affinity reagent that is uniquely captured in a respective cycle, in a plurality of cycles, when the respective affinity agent is washed over the substrate).

In some embodiments, in the plurality of images, at least one respective image is a reference fiducial image, where the respective plurality of points in the reference fiducial image comprises the first subplurality of points corresponding to the fiducial elements and does not comprise points arising from optical measurements of a plurality of analytes (e.g., polypeptide molecules) when bound to an analytical reagent (e.g., a fiducial-only scan).

In some embodiments, in the plurality of images, at least one respective image is a reference location image that contains a third subplurality of points corresponding to the unique, spatially-separated locations on the substrate for analyte binding and does not comprise points arising from optical measurements of a plurality of analytes when bound to an analytical reagent (e.g., a SNAP-location only scan).

In some embodiments, the plurality of images includes any combination of the images described herein, including reference fiducial images, reference location images, and/or analyte binding images, and any substitutions, modifications, additions, deletions, and/or combinations thereof, as will be apparent to one skilled in the art.

Obtaining Images

Referring to Block 3612, in some embodiments, the optical measurement is of a fluorescence. In some embodiments, the optical measurement is of a bioluminescence, a chemiluminescence, or a light scattering signal.

In some embodiments, the obtaining a respective image in the plurality of images (e.g., the first image and/or the second image) is performed using any suitable imaging technique, and any substitutions, modifications, additions, deletions, and/or combinations thereof, as will be apparent to one skilled in the art.

For instance, in some embodiments, a respective image (e.g., the first image and/or the second image) is acquired using transmission light microscopy (e.g., bright field transmission light microscopy, dark field transmission light microscopy, oblique illumination transmission light microscopy, dispersion staining transmission light microscopy, phase contrast transmission light microscopy, differential interference contrast transmission light microscopy, emission imaging, etc.). See, for example, Methods in Molecular Biology, 2018, *Light Microscopy Method and Protocols*, Markaki and Harz eds., Humana Press, New York, New York, ISBN-13: 978-1493983056, which is hereby incorporated by reference.

In some embodiments, fluorescence imaging is used to acquire a respective image (e.g., the first image and/or the second image) of the substrate. As used herein, the term "fluorescence imaging" refers to imaging that relies on the excitation and re-emission of light by fluorophores, regardless of whether they are added experimentally to the sample and bound to antibodies (or other compounds) or naturally occurring features of the sample. For instance, fluorescence imaging includes, but is not limited to, immunohistochemistry imaging and/or immunofluorescence imaging.

Accordingly, in some embodiments, a respective image (e.g., the first image and/or the second image) is obtained by bright-field microscopy, immunohistochemistry, or fluorescence microscopy. In some embodiments, a respective image (e.g., the first image and/or the second image) is obtained by immunofluorescence microscopy.

In some embodiments, a respective image (e.g., the first image and/or the second image) is acquired using confocal microscopy, two-photon imaging, wide-field multiphoton microscopy, single plane illumination microscopy or light sheet fluorescence microscopy. See, for example, *Adaptive Optics for Biological Imaging*, 2013, Kubby ed., CRC Press, Boca Raton, Florida; and *Confocal and Two-Photon Microscopy: Foundations, Applications and Advances*, 2002, Diaspro ed., Wiley Liss, New York, New York; and *Handbook of Biological Confocal Microscopy*, 2002, Pawley ed., Springer Science+Business Media, LLC, New York, New York each of which is hereby incorporated by reference.

In some embodiments, the obtaining the first image and/or the second image is performed using bioluminescence imaging (BLI), including but not limited to bioluminescence tomography (BLT) and/or bioluminescence resonance energy transfer. In some embodiments, the obtaining the first image and/or the second image is performed using chemiluminescence imaging (CLI), including but not limited to nanoprobe-based CL imaging, isothermal amplification-based CL imaging, integrated CL imaging, peroxyoxalate chemiluminescence (POCL) polymer-based CL imaging, inorganic material-based CL imaging, and/or dioxetane-based CL imaging. See, for example, Yan et al., "Chemiluminescence and Bioluminescence Imaging for Biosensing and Therapy: In Vitro and In Vivo Perspectives," Theranostics 2019; 9(14): 4047-4065, doi: 10.7150/thno.33228, which is hereby incorporated herein by reference in its entirety. Advantageously, bioluminescence and chemiluminescence imaging techniques do not use an external light source and thus can be used to avoid photobleaching, background interference and/or autoluminescence that can occur when using external light-dependent imaging techniques. As a result, bioluminescence and chemiluminescence imaging techniques can be used to provide increased sensitivity, efficiency, and high signal-to-noise ratio.

In some embodiments, the obtaining the first image and/or the second image is performed using light scattering spectroscopy (e.g., dynamic light scattering spectroscopy, static light scattering spectroscopy, and/or elastic light scattering spectroscopy). See, e.g., Park et al., "Static and dynamic light scattering of healthy and malaria-parasite invaded red blood cells," J. of Biomedical Optics 2010; 15(2), 020506, doi: 10.1117/1.3369966, which is hereby incorporated herein by reference in its entirety.

In some embodiments, the same imaging technique is used for obtaining the first image and the second image. In some embodiments, different imaging techniques are used for obtaining the first image and the second image. In some embodiments, a respective image (e.g., the first image and/or the second image) is obtained using any imaging technique appropriate for the type of analytical reagent and/or detectable marker used, as will be apparent to one skilled in the art.

In some embodiments, the obtaining the first image includes any of the embodiments disclosed herein with respect to the obtaining the second image. In some embodiments, the obtaining the second image includes any of the embodiments disclosed herein with respect to the obtaining the first image. Similarly, in some embodiments, the first image includes any of the embodiments disclosed herein with respect to the second image. In some embodiments, the second image includes any of the embodiments disclosed herein with respect to the first image.

In some embodiments, each respective image in the plurality of images is obtained using the same or different methods as described herein for the first and/or the second image.

An image can be obtained in any electronic image file format, including but not limited to JPEG/JFIF, TIFF, Exif, PDF, EPS, GIF, BMP, PNG, PPM, PGM, PBM, PNM, WebP, HDR raster formats, HEIF, BAT, BPG, DEEP, DRW, ECW, FITS, FLIF, ICO, ILBM, IMG, PAM, PCX, PGF, JPEG XR, Layered Image File Format, PLBM, SGI, SID, CDS, CPT, PSD, PSP, XCF, PDN, CGM, SVG, PostScript, PCT, WMF, EMF, SWF, XAML, and/or RAW. In some embodiments, a respective image (e.g., the first image and/or the second image) is obtained in any electronic color mode, including but not limited to grayscale, bitmap, indexed, RGB, CMYK, HSV, lab color, duotone, and/or multichannel. In some embodiments, the image is manipulated (e.g., stitched, compressed and/or flattened). In some embodiments, a respective image is a color image. In some embodiments, a respective image is a monochrome image.

In some embodiments, the method further comprises modifying a respective image (e.g., the first image and/or the second image) prior to the registration of the first image and the second image. In some embodiments, the modifying an image comprises adjusting a brightness of the image, adjusting a contrast of the image, flipping the image, rotating the image, cropping the image, zooming a view of the image, panning across the image, or overlaying a grid onto the respective image.

In some embodiments, the modifying an image comprises preprocessing the image. For example, in some embodiments, preprocessing is performed on the first image and/or the second image. In some embodiments, the preprocessing includes matching pixelwise resolution (e.g., upsampling and/or downsampling), mirror image flipping, and angular rotation.

In some embodiments, the method further comprises performing a normalization of pixel values within a respective image (e.g., the first and/or the second image). In some embodiments, the normalization is a log normalization.

Other suitable methods of image normalization and modification are contemplated, including smoothing, noise reduction, color normalization, contrast stretching, histogram stretching, Reinhard method, Macenko method, stain color descriptor (SCD), complete color normalization and structure preserving color normalization (SPCN), as will be apparent to one skilled in the art. See, e.g., Roy et al., "Novel Color Normalization Method for Hematoxylin & Eosin Stained Histopathology Images," 2019 IEEE Access 7: 2169-3536; doi: 10.1109/ACCESS.2019.2894791, which is hereby incorporated herein by reference in its entirety.

Transformation Data Structure

Referring to Block 214, the method further includes forming a transformation data structure 3528 that includes a respective counter 3536 for each transform candidate 3530 in a plurality of transform candidates (e.g., 3530-1, . . . 3530-N), where each transform candidate in the plurality of transform candidates includes a two-dimensional translation component 3532 and a planar rotational component 3534, and the plurality of transform candidates collectively samples between a first angle and a second angle about an axis orthogonal to the first and second plurality of points. In some embodiments, the plurality of transform candidates comprises about 5,000 or more different transform candidates.

In some embodiments, the plurality of transform candidates comprises at least about 100, at least about 500, at least about 1000, at least about 2000, at least about 5000, at least about 7500, at least about 10,000, at least about 15,000, or at least about 20,000 different transform candidates. Alternatively or additionally, the plurality of transform candidates comprises no more than 50,000, no more than 20,000, no more than 10,000, no more than 5000, no more than 2000, no more than 1000, or no more than 500 different transform candidates.

In some embodiments, the two-dimensional translation component comprises a distance corresponding to a first dimension (e.g., an x-axis) and a distance corresponding to a second dimension orthogonal to the first dimension (e.g., a y-axis). Accordingly, in some embodiments, the two-dimensional translation component comprises a delta x and a delta y indicating a distance in each of the x and y dimensions. In some embodiments, the two-dimensional translation component uses one of the first image and the second image as a reference point (e.g., a starting point) from which the distance in the first and the second dimensions are measured. Thus, in an example implementation, a two-dimensional translation component is (−1, 1) using the first image as a reference point, indicating that the second image is shifted relative to the first image by −1 units along the x-axis (e.g., to the left), and by +1 units along the y-axis (e.g., up). In another example implementation, a two-dimensional translation component is (3, −2) using the second image as a reference point, indicating that the first image is shifted relative to the second image by +3 units along the x-axis (e.g., to the right), and by −2 units along the y-axis (e.g., down). In some embodiments, the distance is measured using any suitable unit (e.g., pixels, millimeters, etc.).

In some embodiments, the planar rotational component refers to an angle by which the first and second images (e.g., the first and second plurality of points) are rotated relative to each other from their initial relative orientation. In some embodiments, the planar rotational component uses one of the first image and the second image as a reference point (e.g., a starting point) from which the rotation between the two images is measured. For instance, in an example implementation, a planar rotational component is 1° using the first image as a reference point, indicating that the second image is rotated (within the plane defined by the first and second images) relative to the first image by 1° (e.g., clockwise or counterclockwise).

Accordingly, in some embodiments, each respective transform candidate in the plurality of transform candidates indicates a two-dimensional translation (e.g., −1 pixels across, 1 pixel up) and a rotation (e.g., 1°). FIG. 42G illustrates an example transformation data structure including a plurality of transform candidates each having a respective first planar rotational component (e.g., all having the same rotation) and a respective different two-dimensional translation component (e.g., [−4, −4], [−2, 1], [3, 1], [0, 3], etc.).

In some embodiments, the transformation data structure comprises one or more tables, where each element in the table corresponds to a respective transform candidate. For instance, in some embodiments, the transformation data structure comprises, for each respective angle in a plurality of rotation angles represented by the transformation data structure, a respective table (such as the one illustrated in FIG. 42G) corresponding to the respective angle, each respective table comprising a subset of the plurality of transform candidates each having the respective planar rotational component corresponding to the respective angle and a respective different two-dimensional translation component. In some embodiments, the transformation data structure comprises one or more vectors or tensors, where each element in the vector or tensor corresponds to a respective transform candidate.

Referring to Block 3616, in some embodiments, each transform candidate in the plurality of transform candidates transforms one of the first image or the second image between about 1 pixel and about 500 pixels.

In some embodiments, each transform candidate in the plurality of transform candidates transforms one of the first image or the second image at least 1, at least 2, at least 5, at least 10, at least 20, at least 50, at least 100, at least 200, at least 500, or at least 1000 pixels. Alternatively or additionally, each transform candidate in the plurality of transform candidates transforms one of the first image or the second image no more than 2000, no more than 1000, no more than 500, no more than 100, no more than 50, no more than 10, or no more than 5 pixels.

In some embodiments, each transform candidate in the plurality of transform candidates transforms one of the first image or the second image a distance that is at least about 0.05%, at least about 0.1%, at least about 0.5%, at least about 1%, at least about 2%, at least about 5%, at least about 10%, at least about 20%, at least about 30%, or at least about 50% of the total image size (e.g., in a first and/or a second dimension). Alternatively or additionally, each transform candidate in the plurality of transform candidates transforms one of the first image or the second image a distance that is no more than 80%, no more than 50%, no more than 30%, no more than 20%, no more than 10%, no more than 5%, no more than 2%, no more than 1%, or no more than 0.5% of the total image size (e.g., in the first and/or the second dimension).

Accordingly, in an example embodiment, a respective image has dimensions of 500 pixels by 500 pixels, and a respective transform candidate for the respective image transforms the image up to 50% (250 pixels) along the first and/or the second dimension. In another example embodiment, a respective image has dimensions of 1000 pixels by 1000 pixels, and a respective transform candidate for the respective image transforms the image up to 0.1% (1 pixel) along the first and/or the second dimension. Referring to Block 3618, in yet another example embodiment, each image in the plurality of images comprises at least about 500 pixels in a first dimension, each image in the plurality of images comprises at least about 500 pixels in a second dimension orthogonal to the first dimension, and each transform candidate in the plurality of transform candidates transforms one of the first image or the second image between about 1 pixel and about 300 pixels. Referring to Block 3620, in some embodiments, each image in the plurality of images consists of 2048 pixels in a first dimension, each image in the plurality of images consists of 2048 pixels in a second dimension orthogonal to the first dimension, and each transform candidate in the plurality of transform candidates transforms one of the first image or the second image between about 1 pixel and about 256 pixels. As noted by the transformation data structure illustrated in FIG. 40G, where Cartesian coordinates are used, such transformations include a first transformation component (e.g., a transformation in an X-axis) by some number of pixel(s) and a second transformation component (e.g., a transformation in a Y-axis) orthogonal to the first transformation component by some number of pixel(s). In such instances, it is possible for the first or second transformation component to be null. In such instances, it is also possible for the first or second transformation component to be other than null, i.e., the first transformation component may indicate a transformation (e.g., translation) of 1 or more pixels along an X-coordinate as well as a transformation (e.g., translation) of 1 or more pixels along an orthogonal Y-coordinate to realize the full transformation of the transform candidate. Moreover, the transform candidate may specify a rotation angle in addition to the first and second transformation component.

In some embodiments, the transformation data structure represents a plurality of rotation angles. For instance, in some embodiments, the plurality of transform candidates collectively samples a plurality of rotation angles, where the corresponding planar rotational component of each respective transform candidate in the plurality of transform candidates represents a respective rotation angle in the plurality of rotation angles.

In some embodiments, the plurality of angles comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, or at least 50 angles. Alternatively or additionally, the plurality of angles comprises no more than 100, no more than 50, no more than 30, no more than 20, no more than 15, no more than 10, or no more than 5 angles.

In some embodiments, the plurality of transform candidates collectively samples between a first angle and a second angle. For instance, referring to Block 3622, in some embodiments, the plurality of transform candidates comprises a sampling between a first limit angle and a second limit angle about the axis.

In some embodiments, the first limit angle is at least about −20°, at least about −15°, at least about −10°, at least about −8°, at least about −5°, at least about −2°, at least about −1°, at least about −0.5°, at least about −0.1°, at least about −0.05°, at least about −0.01°, or at least about −0.005°. Alternatively or additionally, the second limit angle is no more than about 20°, no more than about 15°, no more than about 10°, no more than about 8°, no more than about 5°, no more than about 2°, no more than about 1°, no more than about 0.5°, no more than about 0.1°, no more than about 0.05°, no more than about 0.01°, or no more than about 0.005°.

Referring to Block 3624, in some embodiments, the first limit angle is −0.5° and the second limit angle is +0.5°. Referring to Block 3626, the first limit angle is −5° and the second limit angle is +5°. In some embodiments, the plurality of transform candidates samples between another range of angles starting no lower than −20° and ending no higher than 20°.

In some embodiments, the plurality of transform candidates samples between the first limit angle and the second limit angle with a constant step size. For instance, referring to Block 3628, in some embodiments, the plurality of transform candidates samples between the first limit angle and the second limit angle with a constant step size, where the constant step size is 0.01°.

In some embodiments, the constant step size is at least about 0.001°, at least about 0.005°, at least about 0.01°, at least about 0.05°, at least about 0.1°, at least about 0.5°, or at least about 1°. Alternatively or additionally, the constant step size is no more than about 2°, no more than about 1°, no more than about 0.5°, no more than about 0.1°, no more than about 0.05°, no more than about 0.01°, or no more than about 0.005°.

In some embodiments, the plurality of transform candidates samples between the first limit angle and the second limit angle with a step size that is not constant. For instance, in some embodiments, angles closer to zero rotation are more finely sampled than angles further away from zero rotation.

In some embodiments, as described above, the transformation data structure includes a respective counter for each transform candidate in the plurality of transform candidates. In some embodiments, the counter indicates a number of point pairs that are represented by the respective transform candidate. As used interchangeably herein, a point pair or "matching points" refers to a pair of points that includes (i) a respective point from one of the first and second plurality of points corresponding to the first and second image (e.g., a starting or seeking point in a respective starting image) and (ii) a corresponding point from the other of the first and second plurality of points corresponding to the first and second image (e.g., a matching or comparison point in a respective comparison image).

In some embodiments, the counter for each respective transform candidate indicates a number of times the transform candidate described the two-dimensional translation and the planar rotational component of the points in a point pair, for each point pair in a plurality of point pairs. Point pairs are further described, for instance, in the section entitled "Point pairs," below.

Point Pairs

Referring to Block 3630, the method further includes, for each respective point in one of the first 3526-1 and second plurality of points 3526-2, (i) pairing the respective point with a corresponding point in the other of the first 3526-1 and second plurality of points 3526-2 whose corresponding two-dimensional coordinates are within a query radius centered on the respective two-dimensional coordinates of the respective point, thereby identifying a respective point pair. The method further includes (ii) adding, for the respective point pair, a respective vote for each respective transform candidate 3530 in the plurality of transform candidates, having a respective angle represented by the transformation data structure, that maps the respective point onto the corresponding point, to the respective counter for the respective transform candidate in the transformation data structure.

Generally, point pairs are paired between any two images in the plurality of images (e.g., a first image and a second image). As described above, in some embodiments, a point pair refers to a pair of points that includes a respective point from a first image (e.g., a starting point) and a corresponding point in a second image (e.g., a matching point or matched point). Advantageously, point pairs can be used to determine the corresponding positions, within each respective image in the pair of images, of features on a substrate that are captured in both images, thus allowing the images to be co-registered.

In some embodiments, a "point pair" is obtained when the corresponding point overlaps the starting point. In some embodiments, a point pair is obtained when the corresponding point is within a predefined search radius (e.g., a query radius) of the starting point. In some such embodiments, a point pair is obtained when the corresponding point is within a predefined number of pixels from the starting point.

In some embodiments, a first respective point (e.g., a starting point) can be selected from the first image and the corresponding point (e.g., the matching point) can be selected from the second image. In some embodiments, a first respective point (e.g., a starting point) can be selected from the second image and the corresponding point (e.g., the matching point) can be selected from the first image. Thus, in some embodiments, identifying a point pair can be performed by searching for the corresponding positions of the first image's points in the second image, or by searching for the corresponding positions of the second image's points in the first image.

FIGS. 42A-42F illustrate an example process of identifying point pairs and adding the respective vote for the respective transform candidate that maps the respective point (e.g., the starting point) onto the corresponding point (e.g., the matching point) to the counter in the transformation data structure. For instance, in FIGS. 42A-42F, two points in a first plurality of points corresponding to a first image (e.g., points A1 and A2) are each paired with three points in a second plurality of points corresponding to a second image (e.g., points B1, B2, and B3).

Figure 42A:
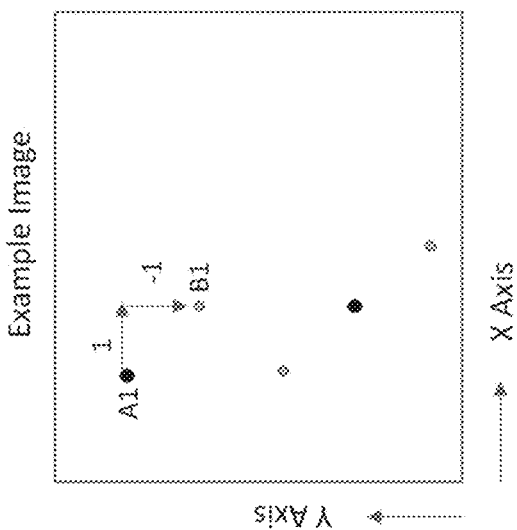
Figure 42B:
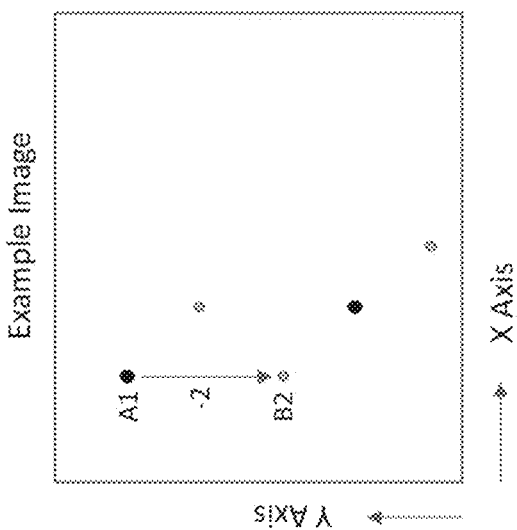
Figure 42C:
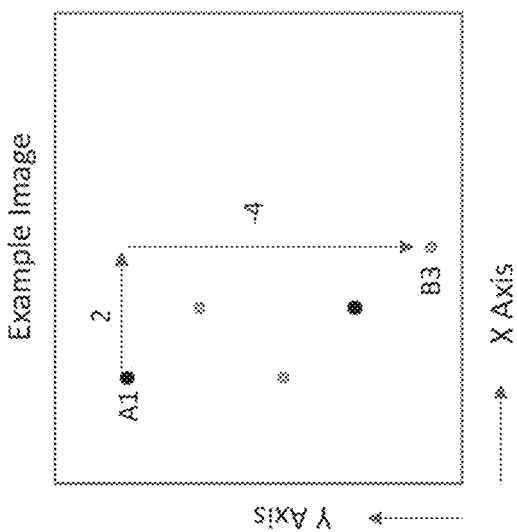
Figure 42F:
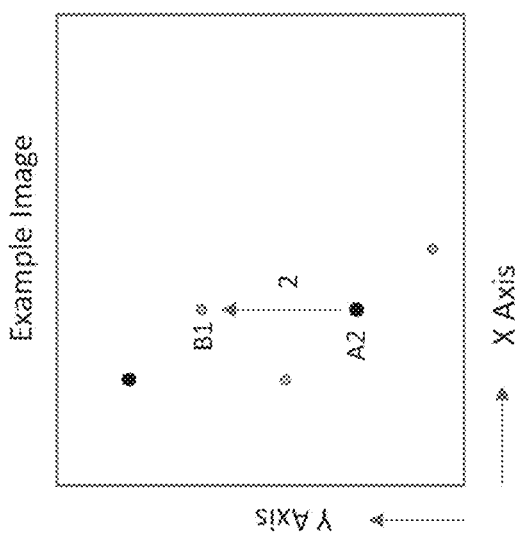
Figure 42E:
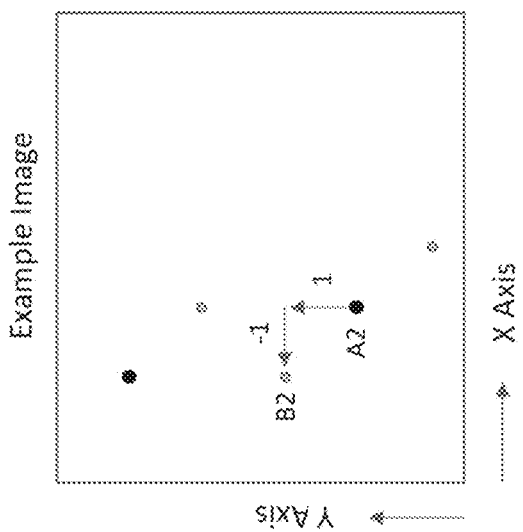
Figure 42D:
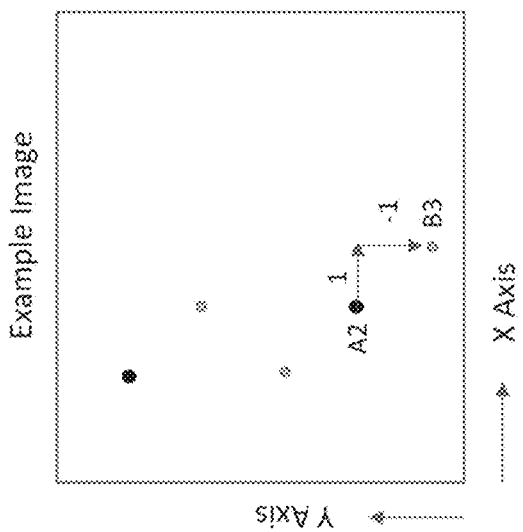

FIG. 42A illustrates, for a given respective angle (e.g., a first rotation angle of) 0°, for a first point pair A1-B1, the difference between the two points can be represented by a transform candidate having a two-dimensional translation component of (+1, −1), where the nomenclature is (x, y), where x represents the number of pixels translated along the X Axis and y represents the number of pixels translated along the Y Axis, and a planar rotational component of 0°. This process can be repeated for each point pair in the plurality of point pairs in FIG. 42B (point pair A1-B2: (0, −2)), FIG. 42C (point pair A1-B3: (+2, −4)), FIG. 42D (point pair A2-B3: (+1, −1)), FIG. 42E (point pair A2-B2: (−1, +1)), and FIG. 42F (point pair A2-B1: (0, +2)).

In some embodiments, as described above, the counter indicates the number of point pairs that are represented (e.g., that can be mapped onto each other) by the respective transform candidate. Accordingly, FIG. 42G illustrates an example transformation data structure including counters for a plurality of transform candidates having a planar rotational component of 0° (e.g., the respective angle of 0° represented by the transformation data structure). Each transform candidate that mapped points in a point pair onto each other was given a respective vote. Accordingly, one vote was given to each of the transforms corresponding to point pairs illustrated in FIGS. 42B, 42C, 42E, and 42F, while two votes were given to the transform corresponding to the point pairs illustrated in FIGS. 42A and 42D (+1, −1).

In some embodiments, querying for a matched point uses a predefined search radius or query radius. In particular, for a selected point in one of the first and the second plurality of points (e.g., a starting point in point set A), the use of a query radius allows the identification of point pairs without the need for performing a search and comparison with every other point in the other of the first and the second plurality of points (e.g., every other point in point set B). This advantageously limits the number of point pairs that are searched, compared, and voted for, reduces the size of the resulting transformation data structure, and thus beneficially allows for point-based image registration with lower computational burden.

In some embodiments, the using a query radius comprises determining a query radius around a starting point in a respective starting image (e.g., one of the first image and the second image) and limiting the search for corresponding points (e.g., matching points) within that radius in the corresponding comparison (e.g., the other of the first and the second image).

In some embodiments, as described above, the query radius is centered on the respective two-dimensional coordinates of the respective point (e.g., the starting point) in the one of the first and second plurality of points. In other words, when the starting point is a point A1 in point set A, the query radius is centered on the two-dimensional coordinates of point A1, and the method includes searching for every corresponding point in point set B that falls within the query radius as overlaid onto point set B.

In some embodiments, the query radius is expected to be small (e.g., a few pixels), such as where at least the first image and the second image are obtained without intentional movement of the substrate relative to an image capture device (e.g., when taking multiple fluorescent images of the same analyte area on the substrate). In some embodiments, alignment of the first image and the second image can be used to identify, collapse, and decode different fluorescent signals at the same position for analyte identification.

In some embodiments, the query radius is at least 10 pixels, at least 20 pixels, or at least 50 pixels. In some embodiments, the query radius is between 50 pixels and 500 pixels. In some embodiments, the query radius is between 100 pixels and 200 pixels.

In some embodiments, the query radius is at least 0.01, at least 0.05, at least 0.1, at least 0.5, at least 1, at least 2, at least 5, at least 10, at least 20, at least 50, at least 100, at least 200, at least 500, at least 1000, or at least 1500 pixels. Alternatively or additionally, the query radius is no more than 2000, no more than 1000, no more than 500, no more than 100, no more than 50, no more than 10, no more than 5, or no more than 1 pixels.

In some embodiments, the query radius is defined based on the size of one or both of the first and the second image. For instance, in some embodiments, the query radius is such that it defines a circle about the respective point that contains at least about 0.05%, at least about 0.1%, at least about 0.5%, at least about 1%, at least about 2%, at least about 5%, at least about 10%, at least about 20%, at least about 30%, or at least about 50% of the total number of pixels in the first and/or the second image. Alternatively or additionally, the query radius is such that it defines a circle about the respective point that contains no more than 80%, no more than 50%, no more than 30%, no more than 20%, no more than 10%, no more than 5%, no more than 2%, no more than 1%, or no more than 0.5% of the total number of pixels in the first and/or the second image.

In some embodiments, the query radius is such that it defines a circle about the respective point that contains at least 1%, at least 5%, or at least 10%, in pixels, of the total number of pixels in the respective image corresponding to the one of the first and second plurality of points that has the respective point. In some embodiments, the query radius is such that it defines a circle about the respective point that contains at least about 0.05%, at least about 0.1%, at least about 0.5%, at least about 1%, at least about 2%, at least about 5%, at least about 10%, at least about 20%, at least about 30%, or at least about 50%, in pixels, of the total number of pixels in the respective image corresponding to the one of the first and second plurality of points that has the respective point. Alternatively or additionally, the query radius is such that it defines a circle about the respective point that contains no more than 80%, no more than 50%, no more than 30%, no more than 20%, no more than 10%, no more than 5%, no more than 2%, no more than 1%, or no more than 0.5%, in pixels, of the total number of pixels in the respective image corresponding to the one of the first and second plurality of points that has the respective point.

In some embodiments, the query radius is such that it defines a circle about the respective point that contains between 1% and 50%, in pixels, of the total number of pixels in the respective image corresponding to the one of the first and second plurality of points that has the respective point. In some embodiments, the query radius is such that it defines a circle about the respective point that contains between 2% and 20%, in pixels, of the total number of pixels in the respective image corresponding to the one of the first and second plurality of points that has the respective point.

In some embodiments, the query radius is between 1% and 50%, in pixels, of a dimension of the respective image corresponding to the one of the first and second plurality of points that has the respective point. In some embodiments, the query radius is between 2% and 20%, in pixels, of a dimension of the respective image corresponding to the one of the first and second plurality of points that has the respective point. For instance, in an example embodiment, the respective image for a starting point A1 has dimensions of 2048 pixels in a first dimension and 2048 pixels in a second dimension orthogonal to the first dimension, and the query radius is about 5%, in pixels, of a dimension of the respective image (e.g., the query radius is about 100 pixels). In another example embodiment, the respective image for a starting point A1 has dimensions of 2048 pixels in a first dimension and 2048 pixels in a second dimension orthogonal to the first dimension, and the query radius is about 6.25%, in pixels, of a dimension of the respective image (e.g., the query radius is about 128 pixels).

As described above, in some embodiments, the query radius around a starting point in a first point set encompasses a certain number of corresponding points in a second point set. For instance, in some such embodiments, the query radius defines the number of points in a point set B that can be paired with a respective starting point A1 in point set A, based on their proximity to the two-dimensional coordinates of A1. Points in point set B falling within the query radius of A1 can be termed, for instance, the set of matched points for A1.

Accordingly, in some embodiments, each respective point in the one of the first and second plurality of points has a corresponding set of matched points in the other of the first and second plurality of points, where each respective matched point in the respective set of matched points has corresponding two-dimensional coordinates that fall within the query radius centered on the respective two-dimensional coordinates of the respective point.

In some embodiments, the corresponding set of matched points comprises at least 1, at least 5, at least 10, or at least 50 points in the other of the first and second plurality of points. For instance, in some embodiments, the corresponding set of matched points (e.g., that falls within the query radius) comprises at least about 1, at least about 2, at least about 3, at least about 5, at least about 10, at least about 20, at least about 30, at least about 50, at least about 100, at least about 200, at least about 500, at least about 1000, or at least about 2000 points. Alternatively or additionally, the corresponding set of matched points (e.g., that falls within the query radius) comprises no more than 5000, no more than 2000, no more than 1000, no more than 500, no more than 100, no more than 50, or no more than 10 points.

In some embodiments, the corresponding set of matched points comprises between 1 and 200 points in the other of the first and second plurality of points. In some embodiments, the corresponding set of matched points comprises between 10 and 100 points in the other of the first and second plurality of points. In some embodiments, querying for a matched point does not comprise using a query radius.

Rotation Angles

Referring to Block 3632, the method further includes repeating the adding (ii) for the respective point pair for each respective angle represented by the transformation data structure 3528 thereby adding additional votes for respective transform candidates 3530 identified by the adding (ii), and (iv) repeating the pairing (i), adding (ii), and repeating (iii) for the respective point with each other corresponding point in the second plurality of points that is within the query radius.

In some embodiments, the respective angle represented by the transformation data structure is 0°, as described above with reference to FIGS. 42A-42F. Thus, a first iteration of the (i) pairing and (ii) adding, referring again to Block 3630, is performed at a rotation angle of 0° or no rotation, and the transform candidates used for the (ii) adding, map the respective point to the corresponding point using the two-dimensional translation component only. However, in some embodiments, rotation is applied to one of the point sets (e.g., one of the first and second plurality of points), such that the transform candidates used for the (ii) adding, utilize both the two-dimensional translation component and the planar rotational component to map the respective point to the corresponding point.

Figure 44:
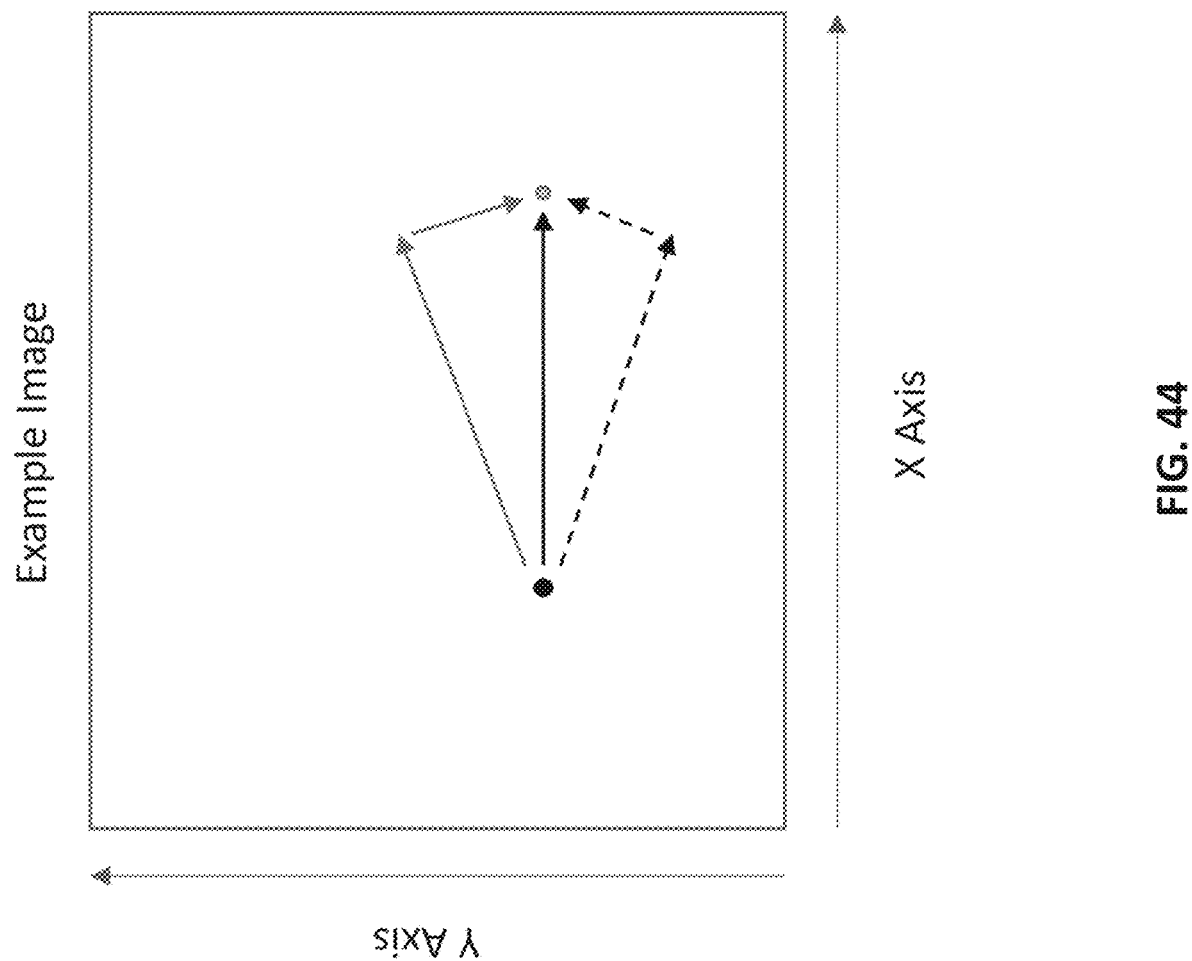
FIG. 44 illustrates transform candidates including a two-dimensional translation component and a planar rotation component, such that transforms between points (e.g., vector offsets) can be represented by more than one possible transform candidates.

An example of different transform candidates having different planar rotational components (e.g., corresponding to different respective angles represented by the transformation data structure) is illustrated in FIG. 44. For instance, the final vector offset (e.g., final transform) between a pair of points can be explained by more than one combination of rotation and translation (e.g., transform candidates having a planar rotational component and a two-dimensional translation component). Three different possible transforms are provided that can explain the relationship between the two points, beginning with a starting point in black and a matching point in gray, where each relationship comprises a vector (e.g., two-dimensional translation component) and an angle (e.g., planar rotation component). Accordingly, the solid gray line represents a transform candidate having a rotation angle of −30° and a two-dimensional translation component of (45,10); the solid black line represents a transform candidate having a rotation angle of 0° and a two-dimensional translation component of (50, 0); and the dashed black line represents a transform candidate having a rotation angle of 30° and a two-dimensional translation component of (45, −10). However, in many embodiments of the present disclosure, the range of rotation angles that is sampled is such that additional point pairs are not identified for such additional transform candidates at these other rotation angles.

Figure 45:
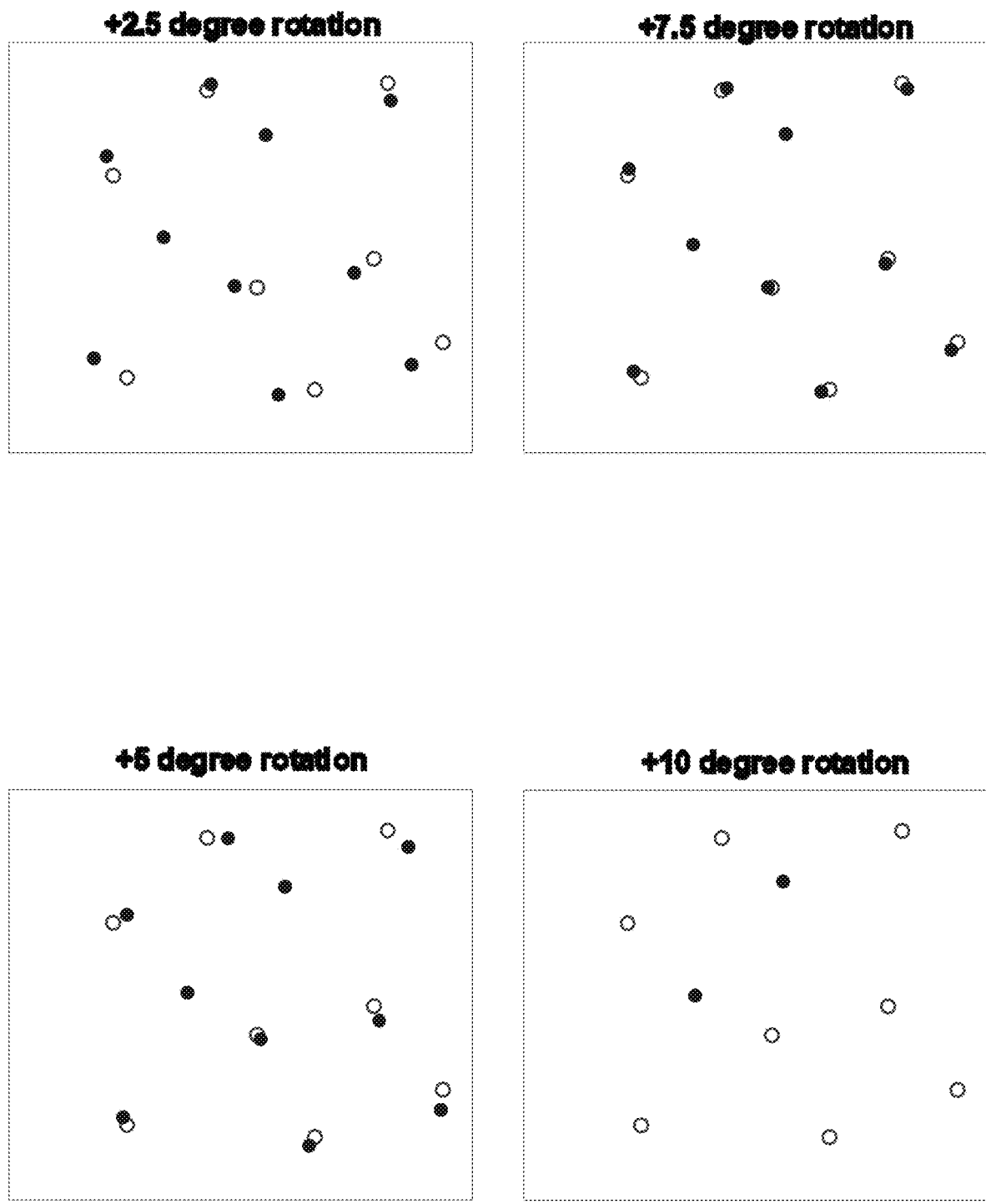
FIG. 45 illustrates applying a transform candidate including a planar rotational component to a first plurality of points (e.g., solid black points) relative to a second plurality of points (e.g., white outlined points), for each respective angle in a plurality of angles represented by a transformation data structure.

FIG. 45 further illustrates how different offsets between a first plurality of points (shown in solid black) and a second plurality of points (shown in white with black outlines) are achieved at different angles. The planar rotational component is applied to the first plurality of points (solid black points) relative to the second plurality of points (white outlined points), for each respective angle in a plurality of angles represented by a transformation data structure (e.g., +2.5° rotation, +5° rotation, +7.5° rotation and +10° rotation of solid black points relative to white outlined points).

In some embodiments, the first and second angular reference frames define a first rotational orientation of the respective first and second images. Accordingly, in some embodiments, rotation by a respective angle comprises rotating one of the first and the second plurality of points about the axis orthogonal to the (coplanar) first and second plurality of points, relative to its respective angular reference frame, while keeping the other of the first and second plurality of points fixed. In such manner, transform candidates corresponding to the respective angle (e.g., transform candidates having the respective planar rotational component corresponding to the respective angle) can be evaluated. In some embodiments, rotation by a respective angle comprises rotating the first plurality of points about the axis while keeping the second plurality of points fixed. In some embodiments, rotation by a respective angle comprises rotating the second plurality of points about the axis while keeping the first plurality of points fixed.

Figure 36B:
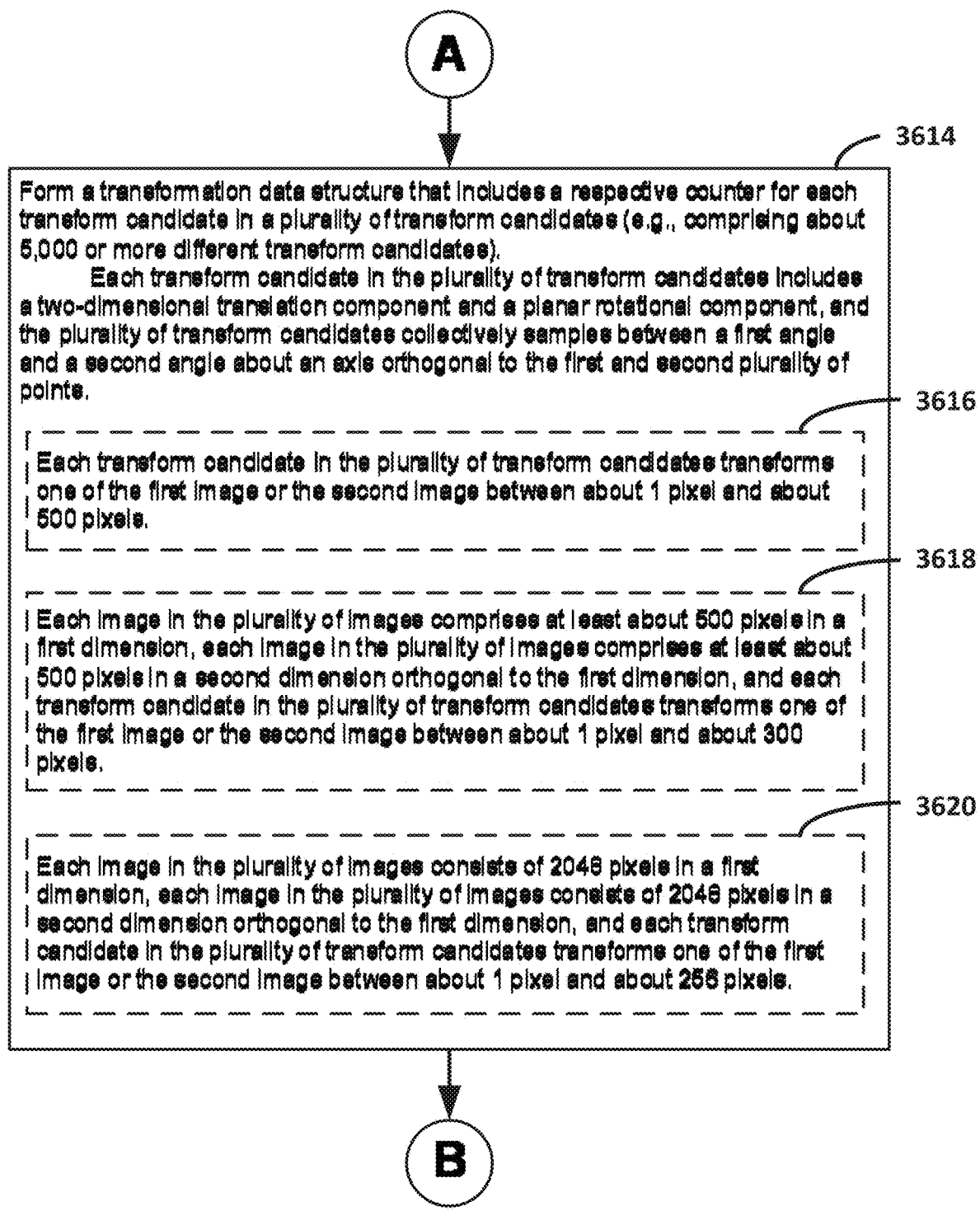
Figure 36C:
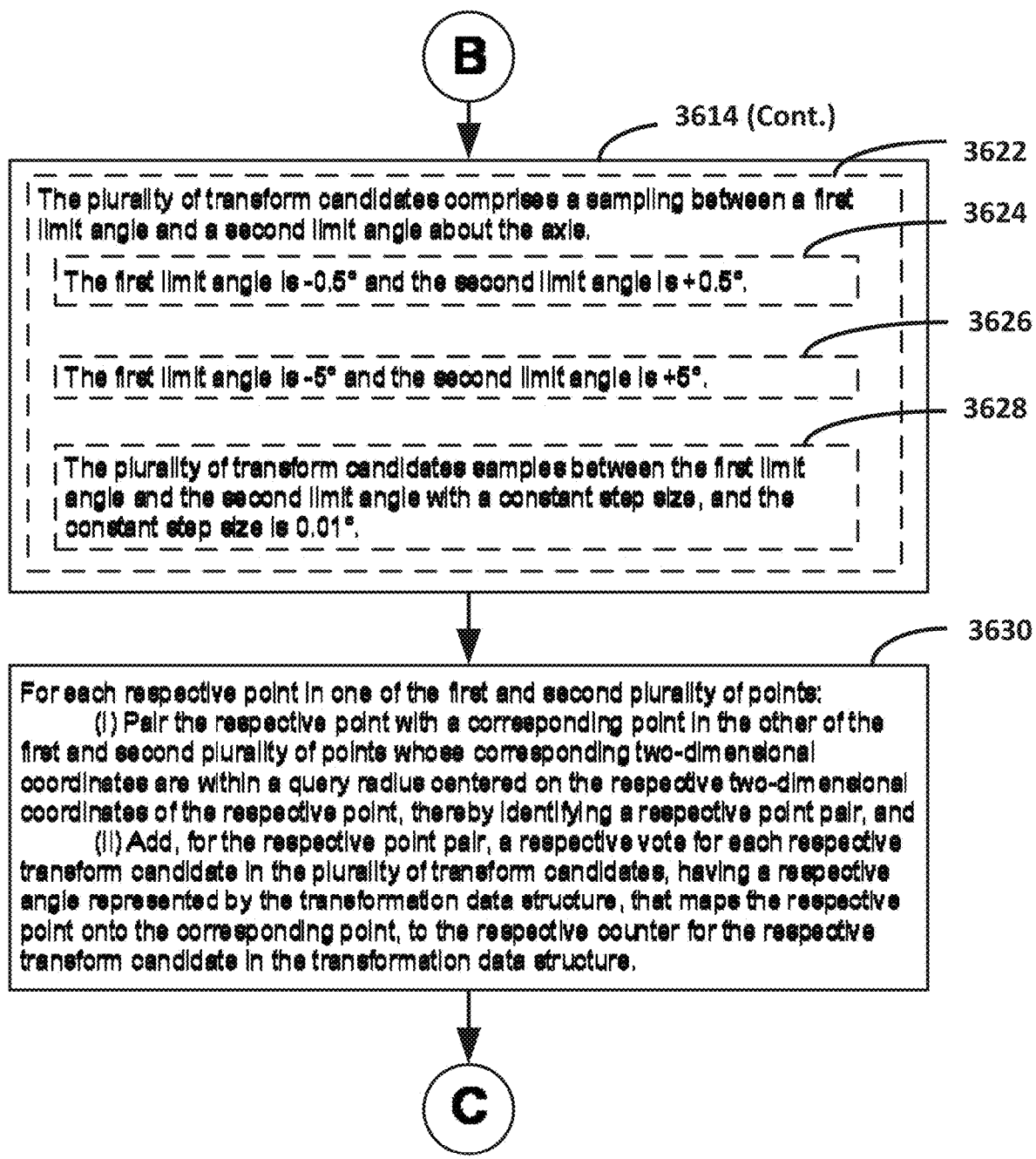
Figure 36D:
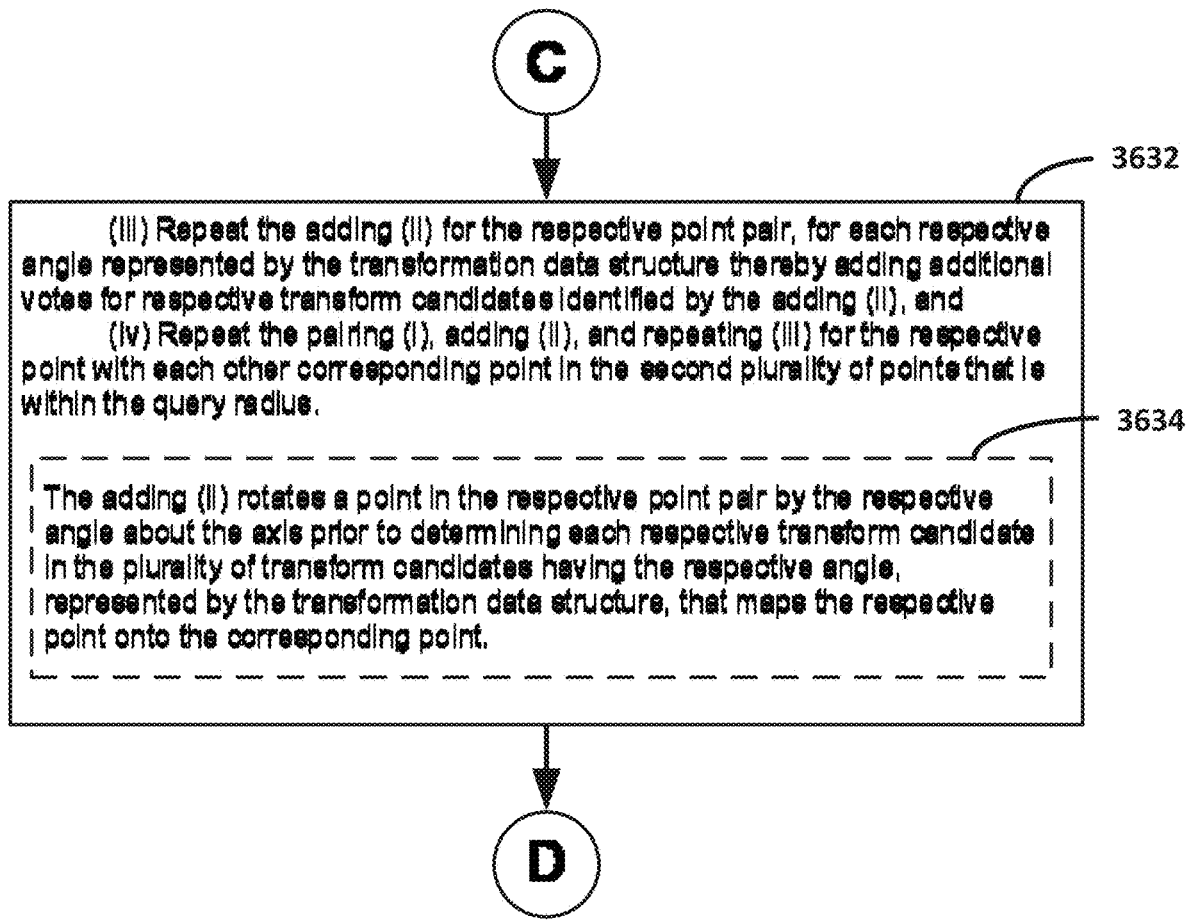
Figure 36E:
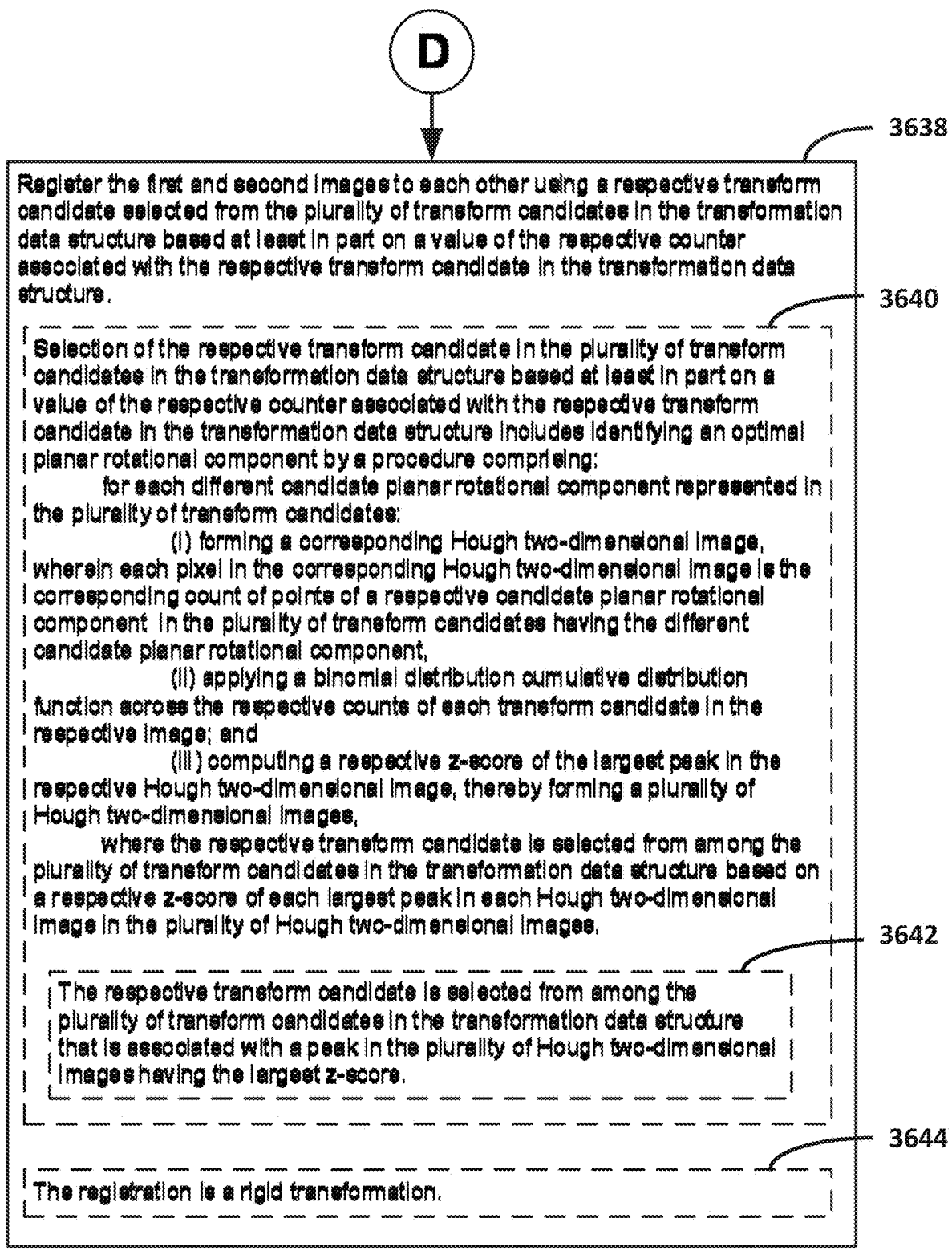

For instance, referring to Block 3634 of FIG. 36D, in some embodiments, the adding (ii) rotates a point in the respective point pair by the respective angle about the axis prior to determining each respective transform candidate in the plurality of transform candidates having the respective angle, represented by the transformation data structure, that maps the respective point onto the corresponding point. In some embodiments, this process can be repeated for each respective angle in a plurality of angles represented by the transformation data structure. Angles represented by the transformation data structure are further described in the section entitled "Transformation data structure," above.

Any suitable method of evaluating transform candidates at each respective angle represented by the transformation data structure, such that each point pair is evaluated at each respective angle, can be employed.

In some embodiments, the method further includes, for each respective angle represented by the transformation data structure, repeating the adding (ii) for the respective point pair by rotating a point in the respective point pair by the respective angle about the axis, prior to determining each respective transform candidate in the plurality of transform candidates having the respective angle, represented by the transformation data structure, that maps the respective point onto the corresponding point.

Various methods for adding votes for transform candidates using rotations are possible, as detailed in the following example embodiments.

In some embodiments, the evaluating the first and second plurality of points at each respective angle represented by the transformation data structure comprises, for each respective point pair identified for a first angle in the plurality of angles: rotating a point in the respective point pair from one of the first angular reference frame or the second angular reference frame by a difference of the respective angle and the first angle about the axis; obtaining, after the rotating, a respective vote for a respective transform candidate in the plurality of transform candidates that maps the pair of points of the respective point pair onto each other; and adding the respective vote for the respective transform candidate to the respective counter for the respective transform candidate in the transformation data structure.

Accordingly, in some such embodiments, a plurality of point pairs are identified for the first angle, and a rotation is applied to the vectors corresponding to the identified point pairs for each respective angle other than the first angle (e.g., by rotating one of the points corresponding to the transform candidate around the axis), thereby obtaining a vote for a new transform candidate corresponding to the respective angle (e.g., having the respective planar rotational component), and updating the transformation data structure with votes for the new transform candidate. In other words, in some such embodiments, a plurality of point pairs are identified at a first relative rotational orientation, and votes for transform candidates are obtained by applying rotations to each previously identified point pair.

In some alternative embodiments, the evaluating the first and second plurality of points at each respective angle other than the first angle represented by the transformation data structure comprises, for each respective point in one of the first and the second plurality of points, selecting the respective point (e.g., a starting point), searching for a matched point in the other of the first and the second plurality of points (e.g., the comparison point), and, when a point pair exists, performing a procedure comprising: for each of the angles in the plurality of angles represented by the transformation data structure, rotating one of the images by the respective angle such that the relative rotational orientation between the first and second images differs from their initial relative orientations by the respective angle; adding a vote for the respective transform candidate that represents the point pair at the respective angle; repeating the rotating and voting for each angle in the plurality of angles until no more rotations can be performed for the respective point pair; and repeating the selecting, searching, rotating and voting, for each point in the plurality of points in the starting image.

Accordingly, in some such embodiments, point pairs are searched for and determined one at a time, and all possible rotations are performed in view of an existing point pair, such that votes for transform candidates at each possible rotation are obtained and added to the transformation data structure for a given point pair before performing the procedure for a subsequent point pair.

In some embodiments, the evaluating the first and second plurality of points at each respective angle other than the first angle represented by the transformation data structure comprises: for each respective point in one of the first and second plurality of points, where the second plurality of points is rotated about the axis from the second angular reference frame by the respective angle, attempting to pair the respective point with a corresponding point in the other of the first and second plurality of points thereby querying for a point pair and, when the point pair exists, (i) obtaining a respective vote for a respective transform candidate in the plurality of transform candidates, having the respective angle, that maps the respective point onto the corresponding point, and (ii) adding the respective vote for the respective transform candidate to the respective counter for the respective transform candidate in the transformation data structure.

In other words, the method can include, for each of the angles in the plurality of angles, rotating one of the first and second plurality of points by the respective angle and performing a procedure comprising, for each point in one of the first and second plurality of points, selecting the respective point (e.g., a starting point), searching for a matched point in the other of the images (e.g., the comparison point), and, when a point pair exists, adding a vote for the respective transform candidate that represents the point pair. The method includes repeating the searching and voting for each possible point pair in the pair of images, rotated relative to their starting relative orientations by the respective angle until no more point pairs can be made for the respective angle. The method then includes repeating the rotating, searching, and voting, for each angle in the plurality of angles.

Accordingly, in some such embodiments, the images are rotated relative to each other one angle at a time, and all possible point pairs are searched for and determined based on the rotated images, such that votes for transform candidates between each possible point pair are obtained and added to the transformation data structure for a given rotation angle before proceeding to the next rotation.

In some embodiments, the rotating can occur using any axis that is orthogonal to the first and second plurality of points, at any position within the image, as long as all rotations in the plurality of rotations are performed consistently around the same axis. In some embodiments, the axis can be defined at any pixel or any coordinate location in the image (e.g., a center of an image, a corner of an image, etc.), and the images can be rotated, relative to each other, around the axis at that location.

In some embodiments, the transformation data structure includes multiple sub-structures for each rotation angle (e.g., buckets). For instance, in some embodiments, the transformation data structure includes a different table for each rotation angle. For instance, FIG. 42G illustrates a first table for a first rotation angle, but the transformation data structure can include additional tables, thereby generating a plurality of tables corresponding to different represented angles. In some such embodiments, the plurality of tables consists of the same number of tables as the number of rotation angles represented by the transformation data structure. In some embodiments, the plurality of tables comprises more tables or fewer tables than the number of rotation angles represented by the transformation data structure.

In an illustrative example, the method includes defining a set of angle "buckets" (e.g., 10 buckets corresponding to a set of angles ranging between −0.5° and +0.5° with a constant step size of 0.1°). A voting table (as illustrated in FIG. 42G) is generated for each angle in the set of angles. The procedure of querying for point pairs, obtaining votes for transform candidates, and adding votes for transform candidates to counters, is then performed, thereby populating each respective voting table in the set of voting tables. Final transforms are then selected across all of the voting tables corresponding to the set of angles.

In some embodiments, the transformation data structure is not subdivided into a plurality of voting tables. In some embodiments, the transformation data structure is a single table, vector, or tensor.

In some embodiments, the method does not include rotation (e.g., does not comprise performing the evaluating at each respective angle represented by the transformation data structure), and the method is performed for only the first angle. In some embodiments, the transformation data structure represents a single angle (e.g., the first angle).

In some embodiments, the method further comprises flipping (e.g., obtaining a mirror image of) one of the first image and the second image, and repeating the evaluating the first and second plurality of points at each respective angle represented by the transformation data structure for the flipped image relative to the other (e.g., unflipped) image. Thus, each possible orientation of the first image relative to the second image is sampled by the method. In some embodiments, the method does not comprise flipping.

In some embodiments, as described above, the method includes (iv) repeating the pairing (i), adding (ii), and repeating (iii) for the respective point with each other corresponding point in the second plurality of points that is within the query radius.

For instance, in some implementations, each respective point in the one of the first and second plurality of points (e.g., point A1 in point set A) has a corresponding set of matched points in the other of the first and second plurality of points that falls within the query radius centered on the respective two-dimensional coordinates of the respective point (e.g., corresponding points in point set B that are within the query radius of point A1). Thus, in some implementations, the repeating (iv) repeats the pairing (i), adding (ii), and repeating (iii) for the respective point with each respective matched point in the respective set of matched points.

In some embodiments, the corresponding set of matched points comprises at least 2, at least 5, at least 10, or at least 50 points in the other of the first and second plurality of points, and the repeating (iv) is performed at least 2, at least 5, at least 10, or at least 50 times. In some embodiments, the corresponding set of matched points comprises between 2 and 200 points in the other of the first and second plurality of points, and the repeating (iv) is performed between 2 and 200 times. In some embodiments, the corresponding set of matched points comprises between 10 and 100 points in the other of the first and second plurality of points, and the repeating (iv) is performed between 10 and 100 times. In some embodiments, for a respective point in the one of the first and second plurality of points (e.g., a point A1 in point set A), the repeating (iv) is performed at least as many times as the number of points in the corresponding set of matched points.

In some implementations, the pairing (i) and adding (ii) is repeated, for each respective point pair for the respective point (e.g., point A1 matched with every other point in point set B within the query radius), for each respective angle represented by the transformation data structure. Any of the methods and embodiments for adding votes for transform candidates using rotations disclosed herein are contemplated, as well as any substitutions, modifications, additions, deletions, and/or combinations thereof, as will be apparent to one skilled in the art.

Moreover, in some embodiments, the method comprises performing the (i) pairing, (ii) adding, (iii) repeating, and (iv) repeating, for each respective point in the one of the first and second plurality of points. As an illustrative example, FIGS. 42A-F illustrates a plurality of points (points A1 and A2) in a first point set (point set A). The pairing (e.g., with points in a second point set B) and adding of votes is performed for each point in the first point set (e.g., for point A1 and again for point A2). Any of the methods and embodiments for a first respective point (e.g., a first starting point A1 in point set A) disclosed herein are also contemplated with respect to any subsequent respective point (e.g., starting points A2, A3, A4, etc.), as well as any substitutions, modifications, additions, deletions, and/or combinations thereof, as will be apparent to one skilled in the art.

Selecting Transform Candidates

Referring to Block 3638, the method further includes registering the first 3522-1 and second images 3522-2 to each other using a respective transform candidate 3530 selected from the plurality of transform candidates in the transformation data structure 3528 based at least in part on a value of the respective counter 3536 associated with the respective transform candidate in the transformation data structure.

In some embodiments, the selected transform candidate is selected based on the highest vote for a respective angle (e.g., the first angle) represented by the transformation data structure. Thus, in some such embodiments, the selected transform candidate represents the most prevalent transform for the respective angle. For instance, when the transformation data structure is a table (e.g., representing one or more angles), the highest voting table entry is selected as the final (e.g., best) transform.

Referring again to FIG. 42G, the transformation data structure is represented as a voting table that represents only one angle (e.g., an angle of 0 degrees or no rotation). Accordingly, in some embodiments, rotation is not taken into account and the selected transform candidate used to register the first and second image is the highest voting table entry. In other words, the delta x and delta y (e.g., dx, dy) of the highest voting table entry is the highest voted relationship between points in the first plurality of points (image A) and points in the second plurality of points (image B).

Figure 43:
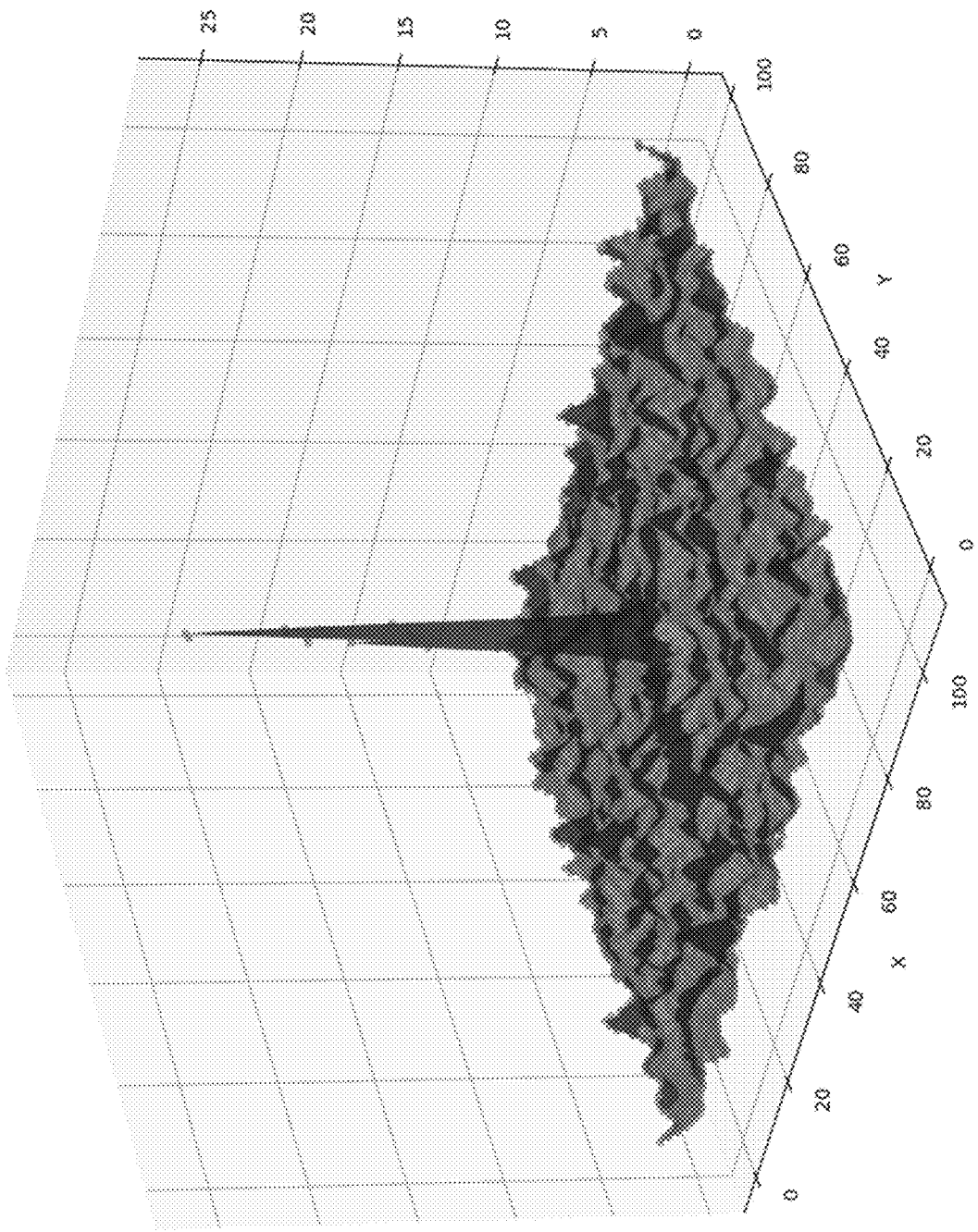
FIG. 43 illustrates an example three-dimensional image that represents a plurality of transform candidates in a transformation data structure, in accordance with an embodiment of the present disclosure. Each pixel in the three-dimensional image indicates a value for a corresponding counter associated with a respective transform candidate in the transformation data structure.

FIG. 43 illustrates another representation of the transformation data structure as a three-dimensional image. The three-dimensional image shows the pixel values (e.g., the corresponding count of points for the respective transform candidate in the plurality of transform candidates that corresponds to the respective pixel) along the z-axis as a z-score. The highest peak, as determined by the z-score, is the final selected transform.

In some embodiments, the selected transform candidate is selected based on the highest vote across all of the angles in the plurality of angles represented by the transformation data structure.

For instance, referring to Block 3640, selection of the respective transform candidate in the plurality of transform candidates in the transformation data structure based at least in part on a value of the respective counter associated with the respective transform candidate in the transformation data structure includes identifying an optimal planar rotational component by a procedure comprising, for each different candidate planar rotational component represented in the plurality of transform candidates: (i) forming a corresponding Hough two-dimensional image, where each pixel in the corresponding Hough two-dimensional image is the corresponding count of points of a respective transform candidate in the plurality of transform candidates having the different candidate planar rotational component, (ii) applying a binomial distribution cumulative distribution function across the respective counts of each transform candidate in the respective image; and (iii) computing a respective z-score of the largest peak in the respective Hough two-dimensional image, thereby forming a plurality of Hough two-dimensional images, where the respective transform candidate is selected from among the plurality of transform candidates in the transformation data structure based on a respective z-score of each largest peak in each Hough two-dimensional image in the plurality of Hough two-dimensional images.

In some embodiments, a respective Hough two-dimensional image is a voting table (e.g., as illustrated in FIG. 42G). In some embodiments, as described above, each pixel in the corresponding Hough two-dimensional image is the corresponding count of votes of a respective transform candidate in the plurality of transform candidates having the different candidate planar rotational component.

Accordingly, in some such embodiments, each respective Hough two-dimensional image in the plurality of Hough two-dimensional images is a respective voting table in a plurality of voting tables, where each respective voting table is for a different respective angle in the plurality of angles represented by the transformation data structure.

In some embodiments, the method includes determining a subset of top transform candidates, where each top transform candidate is selected as the highest voted transform candidate from each respective Hough two-dimensional image. In some such embodiments, the final selected transform candidate is selected from the subset of top transform candidates, thereby selecting the highest voted transform candidate across every angle in the plurality of angles represented by the transformation data structure. Thus, referring to Block 3642, in some embodiments, the respective transform candidate is selected from among the plurality of transform candidates in the transformation data structure that is associated with a peak in the plurality of Hough two-dimensional images having the largest z-score.

In some embodiments, the method comprises generating a plot based on a respective z-score of each largest peak in each Hough two-dimensional image in the plurality of Hough two-dimensional images.

Figure 46A:
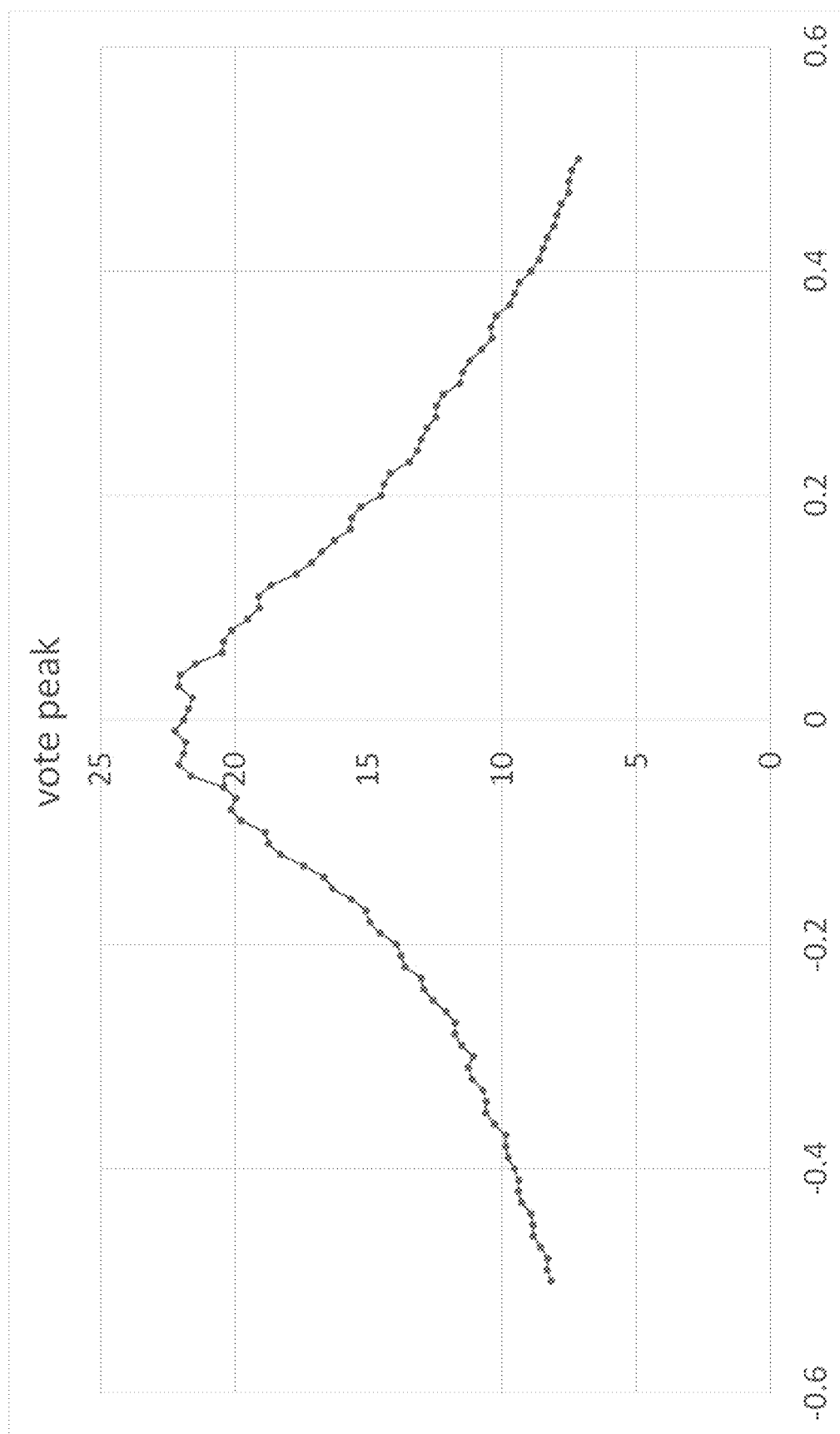
FIGS. 46A and 46B illustrate plots of a plurality of peaks, each respective peak indicating the largest z-score in a respective Hough two-dimensional image in a plurality of Hough two-dimensional images, where each Hough two-dimensional image is associated with a respective angle in a plurality of angles represented by a transformation data structure.
Figure 46B:
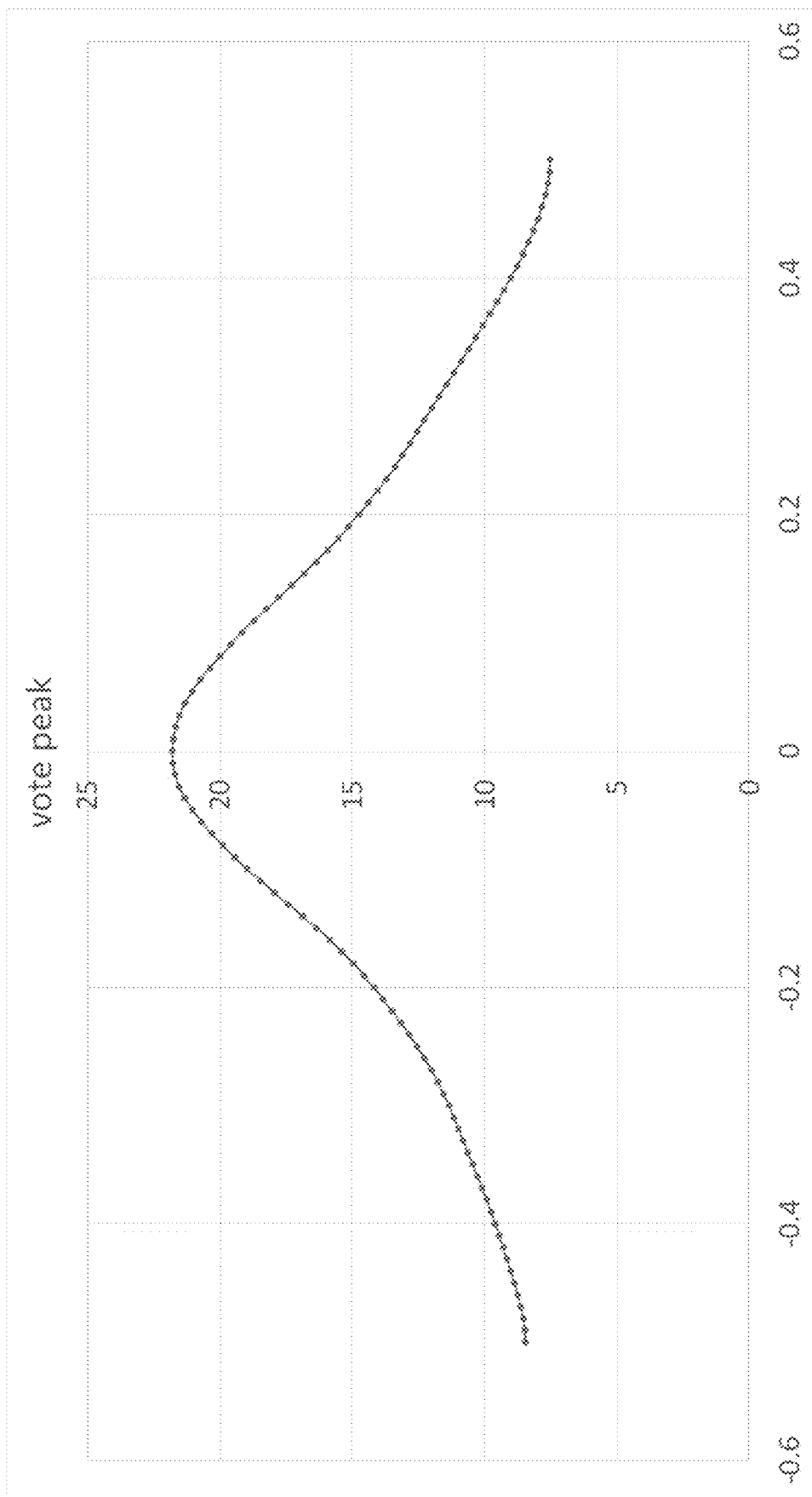

For instance, FIGS. 46A-B illustrate examples of two-dimensional plots where each point represents a maximum value obtained from a different Hough two-dimensional image (a respective z-score of the largest peak in the respective Hough two-dimensional image). The x-axis denotes each angle assessed by the evaluation (e.g., each angle represented by the transformation data structure), and the y-axis denotes the value of each largest peak (e.g., the highest count of votes) over all of the transform candidates having the planar rotational component corresponding to the respective angle. Thus, the plots in FIGS. 46A-B illustrate the subset of peak transform candidates for each angle, and, in some embodiments, the final selected transform candidate is selected as the peak of the subset of peaks.

In some embodiments, the method further comprises smoothing each respective Hough two-dimensional image in the plurality of Hough two-dimensional images. For instance, in some embodiments, the method further comprises applying a Gaussian filter to the respective Hough two-dimensional image prior to computing the respective z-score.

In some embodiments, the method comprises smoothing the plot comprising the maximum values obtained from different Hough two-dimensional images. For instance, FIG. 46A illustrates a plot that is not smoothed, while FIG. 46B illustrates a plot that is smoothed.

In some embodiments, where the transformation data structure does not subdivide transform candidates based on angle (e.g., where there are not multiple tables to choose from and where all counter values are contained within a single table or vector), the method comprises selecting the final transform candidate based on the value (e.g., selecting the highest value) for all transform candidates in the transformation data structure.

In some embodiments, the method includes weighting one or more votes in the transformation data structure. For instance, in some embodiments, the selecting comprises obtaining a value for each respective counter associated with each respective transform candidate in the transformation data structure, where the value is determined using a first subset of votes and a second subset of votes in the plurality of votes. In some embodiments, the first subset of votes is weighted, and the second subset of votes is unweighted. In some embodiments, weighted votes can be weighted using the same or different weights. For instance, a first weighted vote can be weighted using a first parameter and a second weighted vote can be weighted using a second parameter (e.g., votes that are weighted more heavily and votes that are weighted less heavily).

In some embodiments, a respective vote is weighted depending on the type of point pair for which the vote is obtained. For instance, in some embodiments, votes obtained for point pairs representing the first subplurality of points (e.g., fiducial elements) in a first or a second plurality of points are weighted more heavily, whereas votes obtained for point pairs representing a second subplurality of points (e.g., optical measurements of a plurality of polypeptide molecules when bound to an affinity reagent) are weighted less heavily.

As described above, in some implementations, the determining the final registration also includes computing a score that estimates the probability that the highest-voted transform is non-random (e.g., using a binomial distribution cumulative distribution function (CDF)). This measure provides the probability that a candidate transform receives a certain number of votes given a random distribution of votes over all candidate transforms. Thus, in some embodiments, the method further includes determining a probability that the alignment of points in one of the first and the second plurality of points over points in the other of the first and the second plurality of points is random. In some embodiments, the score is at least 0.95, at least 0.96, at least 0.97, at least 0.98, at least 0.99, at least 0.999, or at least 0.9999. In some embodiments, the score is between 0.95 and 1.

Referring to Block 3644, in some embodiments, the registration is a rigid transformation. Generally, a rigid transformation allows only for translation and rotation.

In some embodiments, the transformation is a similarity transform. A similarity transformation allows for translation, rotation and isotropic (equal-along-each-axis) scaling.

In some embodiments, the transformation is a non-rigid transform that comprises anisotropic scaling and skewing of the first and/or second plurality of points. In some embodiments the non-rigid transform is an affine transformation (e.g., that allows for translation, rotation, scale, and shear). In embodiments that allow skewing, more than one angle is needed for each transform candidate to describe the angular displacement between the first and second images associated with the transform candidate. For instance, in some embodiments the first angle is the rotation angle discussed above and the second angle is the angular difference between the plane of the first image and the plane of the second image.

In some embodiments, the determining the final registration comprises taking a tolerance into account. In some embodiments, the tolerance is for an angle (e.g., an angle tolerance). In some embodiments, the tolerance is for a two-dimensional translation component (e.g., a translation tolerance). In some embodiments, the angle tolerance is at least 0.01°, at least 0.05°, at least 0.1°, at least 0.5°, at least 1°, at least 1.5°, at least 2°, or at least 2.5°. Alternatively or additionally, the angle tolerance is no more than 3°, no more than 2°, no more than 1°, no more than 0.5°, no more than 0.1°, or no more than 0.05°. In some embodiments, the translation tolerance is at least 1, at least 2, at least 3, at least 4, at least 5, at least 6, at least 7, or at least 8 pixels. Alternatively or additionally, the translation tolerance is no more than 10, no more than 8, no more than 5, or no more than 3 pixels. In some embodiments, the translation tolerance is within a percentage of the total distance of the final selected transform. For instance, in some embodiments, the translation tolerance is at least 1%, at least 2%, at least 3%, at least 4%, at least 5%, at least 6%, at least 7%, or at least 8% of the total distance of the final selected transform. Alternatively or additionally, the translation tolerance is no more than 10%, no more than 8%, no more than 5%, or no more than 3% of the total distance of the final selected transform.

Another aspect of the present disclosure provides a method for registering a plurality of images 3522 (e.g., 3522-1, 3522-2, . . . 3522-P) of a substrate, the method comprising obtaining a first plurality of points 3526 (e.g., 3526-1-1, . . . 3526-1-K) (e.g., comprising about 100 or more points) within a first image 3522-1 in the plurality of images, the first image defining a first angular reference frame 3524-1. The method further comprises obtaining a second plurality of points 3526 (e.g., 3526-2-1, . . . 3526-2-M) (e.g., comprising about 100 or more points) within a second image 3522-2 in the plurality of images, the second image defining a second angular reference frame 3524-2, where the first plurality of points and the second plurality of points are coplanar. In some embodiments, at least some points in one of the first and second plurality of points is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

A method set forth herein can include forming a transformation data structure 3528 that includes a respective counter 3536 for each transform candidate 3530 in a plurality of transform candidates (e.g., 3530-1, . . . 3530-N) (e.g., comprising about 5000 or more different transform candidates), where each transform candidate in the plurality of transform candidates includes a two-dimensional translation component 3532 and a planar rotational component 3534. For each respective transform candidate 3530 in the plurality of transform candidates, the method includes performing a procedure that comprises: (i) superimposing the first 3526-1 and second plurality of points 3526-2 onto each other using the respective transform candidate 3530 to form a respective candidate superposition, and (ii) for each respective point, in the first plurality of points, adding to the respective counter 3536 for the transform candidate 3530 in the transformation data structure 3528, a single vote when the respective point overlaps a corresponding point from the second plurality of points in the respective candidate superposition.

The first image 3522-1 and second image 3522-2 are registered to each other using a respective transform candidate 3530 selected from the plurality of transform candidates in the transformation data structure 3528 based at least in part on a value of the respective counter 3536 associated with the respective transform candidate in the transformation data structure.

Accordingly, in some embodiments, the counter indicates a number of points from a first respective plurality of points (e.g., one of the first and second plurality of points corresponding to the first and second image) that successfully query a second respective plurality of points (e.g., the other of the first and second plurality of points corresponding to the first and second image) such that a point pair can be obtained, given a respective transform candidate. Thus, in some embodiments, the counter for each respective transform candidate indicates the number of successful point pairs that can be achieved using the respective transform candidate.

FIG. 47 illustrates an example implementation including a first plurality of points (solid black points; top left panel), a second plurality of points (white points with black outlines; top right panel), and a respective candidate superposition (bottom panel) obtained by superimposing the first and second plurality of points onto each other using a respective transform candidate (x, y, 0°). Accordingly, in some such implementations, the number of overlapping points obtained from the respective candidate superposition provides the value that is added to the transformation data structure in the counter corresponding to the respective transform candidate.

In some embodiments, the plurality of transform candidates samples between about one and about 500 pixels in a first translational dimension with a constant first step size; and the plurality of transform candidates samples between about one and about 500 pixels in a second translational dimension with a constant second step size. In some embodiments, the constant first step size and the constant second step size is the same or different. In some embodiments, the first step size and the second step size are not constant.

In some embodiments, the constant first step size is at least 1, at least 5, at least 10, at least 50, at least 100, at least 500, at least 1000, or at least 5000 pixels. Alternatively or additionally, the constant first step size is no more than 10,000, no more than 5000, no more than 1000, no more than 500, no more than 100, no more than 50, no more than 10 pixels, no more than 5 pixels, no more than 4 pixels, no more than 3 pixels, no more than 2 pixels, or no more than a single pixel.

In some embodiments, the constant second step size is at least 1, at least 5, at least 10, at least 50, at least 100, at least 500, at least 1000, or at least 5000 pixels. Alternatively or additionally, the constant second step size is no more than 10,000, no more than 5000, no more than 1000, no more than 500, no more than 100, no more than 50, no more than 10 pixels, no more than 5 pixels, no more than 4 pixels, no more than 3 pixels, no more than 2 pixels, or no more than a single pixel.

In some embodiments, the constant first step size and the constant second step size are each a single pixel.

In some embodiments, the plurality of transform candidates samples between a first angle and a second angle about the axis with a third constant step size. In some embodiments, the first angle is $-0.5°$ and the second angle is $+0.5°$. In some embodiments, the first angle is $-5°$ and the second angle is $+5°$.

In some implementations, any of the embodiments for point sets, images, optical measurements, transformation data structures, point pairs, rotation angles, and selection of transform candidates disclosed herein is similarly applicable to the above method, as will be apparent to one skilled in the art.

In some embodiments, the method further includes performing a registration of a third image onto the first image. In some embodiments, the method further includes performing a registration of a fourth image onto the first image. In some embodiments, the method includes performing a registration of a third image onto the second image. In some embodiments, the method includes performing a registration of a fourth image onto the second image.

In some embodiments, the method includes performing a registration of any image in the plurality of images onto any other image in the plurality of images, using any of the methods disclosed herein. For instance, as described above, the plurality of images can include images that are obtained at different points in time and/or images that are obtained of the same or overlapping regions of the substrate. Downstream applications obtained by registering each image in a plurality of images to each other are described elsewhere herein, such as in Example 7. Further uses for registering a plurality of images to each other are described in Egertson et al., "A theoretical framework for proteome-scale single-molecule protein identification using multiaffinity protein binding reagents," bioRxiv, 2021, doi: 10.1101/2021.10.11.463967, which is hereby incorporated herein by reference in its entirety.

In some implementations, any of the embodiments for point sets, images, optical measurements, transformation data structures, point pairs, rotation angles, and selection of transform candidates disclosed herein with respect to registering the first and the second images are similarly applicable to the registration of any one image in the plurality of images to any other image in the plurality of images, and any substitutions, modifications, additions, deletions, and/or combinations thereof, as will be apparent to one skilled in the art.

II. Additional Embodiments

Another aspect of the present disclosure provides a computer system comprising one or more processors, memory, and one or more programs, where the one or more programs are stored in the memory and are configured to be executed by the one or more processors. The one or more programs include instructions for registering a plurality of images of a substrate by a method comprising obtaining a first plurality of points (e.g., comprising about 100 or more points) within a first image in the plurality of images, the first image defining a first angular reference frame. The method further comprises obtaining a second plurality of points (e.g., comprising about 100 or more points) within a second image in the plurality of images, the second image defining a second angular reference frame, where the first plurality of points and the second plurality of points are coplanar. In some embodiments, at least some points in one of the first and second plurality of points is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can further include forming a transformation data structure that includes a respective counter for each transform candidate in a plurality of transform candidates (e.g., about 5,000 or more different transform candidates), where each transform candidate in the plurality of transform candidates includes a two-dimensional translation component and a planar rotational component and the plurality of transform candidates collectively samples between a first angle and a second angle about an axis orthogonal to the first and second plurality of points.

For a first angle represented by the transformation data structure, the method can include performing a procedure that comprises: for each respective point in one of the first and second plurality of points, where the second plurality of points is rotated about the axis from the second angular reference frame by the first angle, attempting to pair the respective point with a corresponding point in the other of the first and second plurality of points thereby querying for a point pair and, when the point pair exists, (i) obtaining a respective vote for a respective transform candidate in the plurality of transform candidates, having the first angle, that maps the respective point onto the corresponding point, and (ii) adding the respective vote for the respective transform candidate to the respective counter for the respective transform candidate in the transformation data structure.

The method can further include evaluating the first and second plurality of points at each respective angle other than the first angle represented by the transformation data structure thereby adding additional votes for respective transform candidates identified by the evaluating to the respective counter; and registering the first and second images to each other using a respective transform candidate selected from the plurality of transform candidates in the transformation data structure based at least in part on a value of the respective counter associated with the respective transform candidate in the transformation data structure.

Another aspect of the present disclosure provides a computer readable storage medium storing one or more programs, the one or more programs comprising instructions that, when executed by an electronic device with one or more processors and a memory, cause the electronic device to perform a method for registering a plurality of images of a substrate. The method can include obtaining a first plurality of points (e.g., comprising about 100 or more points) within a first image in the plurality of images, the first image defining a first angular reference frame. The method can further include obtaining a second plurality of points (e.g., comprising about 100 or more points) within a second image in the plurality of images, the second image defining a second angular reference frame, where the first plurality of points and the second plurality of points are coplanar. In some embodiments, at least some points in one of the first and second plurality of points is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can further include forming a transformation data structure that includes a respective counter for each transform candidate in a plurality of transform candidates (e.g., about 5,000 or more different transform candidates), where each transform candidate in the plurality of transform candidates includes a two-dimensional translation component and a planar rotational component and the plurality of transform candidates collectively samples between a first angle and a second angle about an axis orthogonal to the first and second plurality of points.

For a first angle represented by the transformation data structure, the method can include performing a procedure that comprises: for each respective point in one of the first and second plurality of points, where the second plurality of points is rotated about the axis from the second angular reference frame by the first angle, attempting to pair the respective point with a corresponding point in the other of the first and second plurality of points thereby querying for a point pair and, when the point pair exists, (i) obtaining a respective vote for a respective transform candidate in the plurality of transform candidates, having the first angle, that maps the respective point onto the corresponding point, and (ii) adding the respective vote for the respective transform candidate to the respective counter for the respective transform candidate in the transformation data structure.

The method can further include evaluating the first and second plurality of points at each respective angle other than the first angle represented by the transformation data structure thereby adding additional votes for respective transform candidates identified by the evaluating to the respective counter; and registering the first and second images to each other using a respective transform candidate selected from the plurality of transform candidates in the transformation data structure based at least in part on a value of the respective counter associated with the respective transform candidate in the transformation data structure.

Yet another aspect of the present disclosure provides a computer system comprising one or more processors, memory, and one or more programs, where the one or more programs are stored in the memory and are configured to be executed by the one or more processors. The one or more programs can include instructions for registering a plurality of images of a substrate, by a method comprising obtaining a first plurality of points (e.g., comprising about 100 or more points) within a first image in the plurality of images, the first image defining a first angular reference frame. The method can further include obtaining a second plurality of points (e.g., comprising about 100 or more points) within a second image in the plurality of images, the second image defining a second angular reference frame, where the first plurality of points and the second plurality of points are coplanar. In some embodiments, at least some points in one of the first and second plurality of points is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates (e.g., comprising about 5,000 or more different transform candidates), where each transform candidate in the plurality of transform candidates includes a two-dimensional translation component and a planar rotational component.

For each respective transform candidate in the plurality of transform candidates, the method can include performing a procedure that comprises: (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The method can further include registering the first and second images to each other using a respective transform candidate selected from the plurality of transform candidates in the transformation data structure based at least in part on a value of the respective counter associated with the respective transform candidate in the transformation data structure.

Still another aspect of the present disclosure provides a computer readable storage medium storing one or more programs, the one or more programs comprising instructions that, when executed by an electronic device with one or more processors and a memory, cause the electronic device to perform a method for registering a plurality of images of a substrate. The method can include obtaining a first plurality of points (e.g., comprising about 100 or more points) within a first image in the plurality of images, the first image defining a first angular reference frame. The method can further include obtaining a second plurality of points (e.g., comprising about 100 or more points) within a second image in the plurality of images, the second image defining a second angular reference frame, where the first plurality of points and the second plurality of points are coplanar. In some embodiments, at least some points in one of the first and second plurality of points is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates (e.g., comprising about 5,000 or more different transform candidates), where each transform candidate in the plurality of transform candidates includes a two-dimensional translation component and a planar rotational component.

For each respective transform candidate in the plurality of transform candidates, the method can include performing a procedure that comprises: (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The method further comprises registering the first and second images to each other using a respective transform candidate selected from the plurality of transform candidates in the transformation data structure based at least in part on a value of the respective counter associated with the respective transform candidate in the transformation data structure.

III. Additional Aspects

In some embodiments, the method is performed without rotating the first and/or the second image relative to the other. For instance, in some embodiments, the transformation data structure represents a single angle of 0°.

Accordingly, another aspect of the present disclosure provides a method for registering a plurality of images of a substrate, the method comprising obtaining a first plurality of points within a first image in the plurality of images, where the first plurality of points comprises about 100 or more points; and obtaining a second plurality of points within a second image in the plurality of images, the second image acquired of the substrate at a different time than the first image, where the second plurality of points comprises about 100 or more points, the first plurality of points and the second plurality of points are coplanar, at least some points in one of the first and second plurality of points, optionally, is not in the other of the first and second plurality of points, and each point in the first plurality of points and in the second plurality of points represents an optical measurement of a corresponding position on the substrate. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. For each respective point in one of the first and second plurality of points, the method can include attempting to pair the respective point with a corresponding point in the other of the first and second plurality of points thereby querying for a point pair and, when the point pair exists, (i) obtaining a respective vote for a respective transform candidate in the plurality of transform candidates that maps the respective point onto the corresponding point, and (ii) adding the respective vote for the respective transform candidate to the respective counter for the respective transform candidate in the transformation data structure. The first and second images can be registered to each other using a respective transform candidate selected from the plurality of transform candidates in the transformation data structure based at least in part on a value of the respective counter associated with the respective transform candidate in the transformation data structure.

Another aspect of the present disclosure provides a method for registering a plurality of images of a substrate, the method comprising obtaining a first plurality of points within a first image in the plurality of images, where the first plurality of points comprises about 100 or more points; and obtaining a second plurality of points within a second image in the plurality of images, where the second plurality of points comprises about 100 or more points, the first plurality of points and the second plurality of points are coplanar, at least some points in one of the first and second plurality of points, optionally, is not in the other of the first and second plurality of points, and each point in the first plurality of points and in the second plurality of points represents an optical measurement of a corresponding position on the substrate. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates, where each transform candidate in the plurality of transform candidates includes a two-dimensional translation component, and where the plurality of transform candidates comprises about 500 or more different transform candidates.

For each respective transform candidate in the plurality of transform candidates, the method can include performing a procedure that comprises (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The first and second images can be registered to each other using a respective transform candidate selected from the plurality of transform candidates in the transformation data structure based at least in part on a value of the respective counter associated with the respective transform candidate in the transformation data structure.

In some embodiments, the substrate has a planar surface. In some embodiments, each image in the plurality of images comprises more than 200,000 pixels. In some embodiments, each image in the plurality of images comprises more than 500,000 pixels. In some embodiments, each image in the plurality of images comprises at least about 500 pixels in a first dimension, each image in the plurality of images comprises at least about 500 pixels in a second dimension orthogonal to the first dimension, and each transform candidate in the plurality of transform candidates transforms one of the first image or the second image between about 1 pixel and about 300 pixels. In some embodiments, each image in the plurality of images consists of 2048 pixels in a first dimension, each image in the plurality of images consists of 2048 pixels in a second dimension orthogonal to the first dimension, and each transform candidate in the plurality of transform candidates transforms one of the first image or the second image between about 1 pixel and about 256 pixels.

In some embodiments, a first subplurality of the first plurality of points arises from respective optical measurements of a plurality of fiducial elements on the substrate, where points corresponding to the first subplurality of points is in the second plurality of points, and a second subplurality of the first plurality of points arises from respective optical measurements of a plurality of analytes (e.g., polypeptide molecules) when bound to an analytical reagent (e.g., an affinity agent), and each analyte of said plurality of analytes is coupled to a unique, spatially-separated location of a plurality of unique, spatially-separated locations on the substrate.

In some embodiments, the analytical reagent binds to more than one unique epitope present within one or more analytes in the plurality of analytes. In some embodiments, the affinity reagent comprises a known degree of binding nonspecificity.

In some embodiments, said plurality of analytes comprises more than 500, more than 1000, more than 2000, more than 3000, more than 5000, more than 6000, or more than 7000 different polypeptide molecules.

In some embodiments, the first subplurality represents less than 10 percent, less than 5 percent, or less than 2 percent of the first plurality of points.

In some embodiments, each transform candidate in the plurality of transform candidates transforms one of the first image or the second image between about 1 pixel and about 500 pixels.

In some embodiments, the first plurality of points comprises about 200 or more, about 400 or more, about 600 or more, about 800 or more, or about 1000 or more points, and the second plurality of points comprises about 200 or more, about 400 or more, about 600 or more, about 800 or more, or about 1000 or more points.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is not found in the second plurality of points.

In some embodiments, each point in the first plurality of points occupies a corresponding single pixel in the first image; and each point in the second plurality of points occupies a corresponding single pixel in the second image.

In some embodiments, selection of the respective transform candidate in the plurality of transform candidates in the transformation data structure based at least in part on a value of the respective counter associated with the respective transform candidate in the transformation data structure includes: (i) forming a corresponding Hough two-dimensional image, wherein each pixel in the corresponding Hough two-dimensional image is the corresponding count of points of a respective transform candidate in the plurality of transform candidates; (ii) applying a binomial distribution cumulative distribution function across the respective counts of each transform candidate in the respective image; and (iii) computing a respective z-score of the largest peak in the respective Hough two-dimensional image, where the respective transform candidate is selected from among the plurality of transform candidates in the transformation data structure based on a respective z-score of a largest peak in the Hough two-dimensional image. In some embodiments, the respective transform candidate is selected from among the plurality of transform candidates in the transformation data structure that is associated with a peak in the Hough two-dimensional image having the largest Z-score.

In some embodiments, the method further comprises applying a Gaussian filter to the respective Hough two-dimensional image prior to computing the respective z-score.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is found in the second plurality of points.

In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the first plurality of points is found in the second plurality of points.

In some embodiments, the registration is a rigid transformation.

In some embodiments, each point in the first plurality of points and in the second plurality of points represents an optical measurement of a corresponding position on the substrate. In some embodiments, the optical measurement is of a fluorescence. In some embodiments, the optical measurement is of a bioluminescence, a chemiluminescence, or a light scattering signal.

In some embodiments, each image in the plurality of images comprises at least about 500 pixels in a first dimension, and each image in the plurality of images comprises at least about 500 pixels in a second dimension orthogonal to the first dimension.

In some embodiments, each image in the plurality of images consists of 2048 pixels in a first dimension, and each image in the plurality of images consists of 2048 pixels in a second dimension orthogonal to the first dimension.

In some embodiments, the plurality of transform candidates samples between about one and about 500 pixels in a first translational dimension with a constant first step size; and the plurality of transform candidates samples between about one and about 500 pixels in a second translational dimension with a constant second step size. In some embodiments, the constant first step size and the constant second step size is the same or different. In some embodiments, the constant first step size and the constant second step size are each a single pixel.

Another aspect of the present disclosure provides a computer system comprising one or more processors, memory, and one or more programs, where the one or more programs are stored in the memory and are configured to be executed by the one or more processors, the one or more programs including instructions for registering a plurality of images of a substrate. The instructions can perform a method comprising obtaining a first plurality of points within a first image in the plurality of images, where the first plurality of points comprises about 100 or more points; and obtaining a second plurality of points within a second image in the plurality of images, the second image acquired of the substrate at a different time than the first image, where the second plurality of points comprises about 100 or more points, the first plurality of points and the second plurality of points are coplanar, at least some points in one of the first and second plurality of points, optionally, is not in the other of the first and second plurality of points, and each point in the first plurality of points and in the second plurality of points represents an optical measurement of a corresponding position on the substrate. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. For each respective point in one of the first and second plurality of points, the method can include attempting to pair the respective point with a corresponding point in the other of the first and second plurality of points thereby querying for a point pair and, when the point pair exists, (i) obtaining a respective vote for a respective transform candidate in the plurality of transform candidates that maps the respective point onto the corresponding point, and (ii) adding the respective vote for the respective transform candidate to the respective counter for the respective transform candidate in the transformation data structure. The first and second images can be registered to each other using a respective transform candidate selected from the plurality of transform candidates in the transformation data structure based at least in part on a value of the respective counter associated with the respective transform candidate in the transformation data structure.

Another aspect of the present disclosure provides a computer readable storage medium storing one or more programs, the one or more programs comprising instructions that, when executed by an electronic device with one or more processors and a memory, cause the electronic device to perform a method for registering a plurality of images of a substrate. The method can include obtaining a first plurality of points within a first image in the plurality of images, where the first plurality of points comprises about 100 or more points; and obtaining a second plurality of points within a second image in the plurality of images, the second image acquired of the substrate at a different time than the first image, where the second plurality of points comprises about 100 or more points, the first plurality of points and the second plurality of points are coplanar, at least some points in one of the first and second plurality of points, optionally, is not in the other of the first and second plurality of points, and each point in the first plurality of points and in the second plurality of points represents an optical measurement of a corresponding position on the substrate. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. For each respective point in one of the first and second plurality of points, the method can include attempting to pair the respective point with a corresponding point in the other of the first and second plurality of points thereby querying for a point pair and, when the point pair exists, (i) obtaining a respective vote for a respective transform candidate in the plurality of transform candidates that maps the respective point onto the corresponding point, and (ii) adding the respective vote for the respective transform candidate to the respective counter for the respective transform candidate in the transformation data structure. The first and second images can be registered to each other using a respective transform candidate selected from the plurality of transform candidates in the transformation data structure based at least in part on a value of the respective counter associated with the respective transform candidate in the transformation data structure.

Still another aspect of the present disclosure provides a computer system comprising, one or more processors, memory, and one or more programs, where the one or more programs are stored in the memory and are configured to be executed by the one or more processors, the one or more programs including instructions for registering a plurality of images of a substrate. The instructions can perform a method comprising obtaining a first plurality of points within a first image in the plurality of images, where the first plurality of points comprises about 100 or more points; and obtaining a second plurality of points within a second image in the plurality of images, where the second plurality of points comprises about 100 or more points, the first plurality of points and the second plurality of points are coplanar, at least some points in one of the first and second plurality of points, optionally, is not in the other of the first and second plurality of points, and each point in the first plurality of points and in the second plurality of points represents an optical measurement of a corresponding position on the substrate. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates, where each transform candidate in the plurality of transform candidates includes a two-dimensional translation component, and where the plurality of transform candidates comprises about 500 or more different transform candidates. For each respective transform candidate in the plurality of transform candidates, the method can include performing a procedure that comprises (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The first and second images can be registered to each other using a respective transform candidate selected from the plurality of transform candidates in the transformation data structure based at least in part on a value of the respective counter associated with the respective transform candidate in the transformation data structure.

Yet another aspect of the present disclosure provides a computer readable storage medium storing one or more programs, the one or more programs comprising instructions that, when executed by an electronic device with one or more processors and a memory, cause the electronic device to perform a method for registering a plurality of images of a substrate. The method can include obtaining a first plurality of points within a first image in the plurality of images, where the first plurality of points comprises about 100 or more points; and obtaining a second plurality of points within a second image in the plurality of images, where the second plurality of points comprises about 100 or more points, the first plurality of points and the second plurality of points are coplanar, at least some points in one of the first and second plurality of points, optionally, is not in the other of the first and second plurality of points, and each point in the first plurality of points and in the second plurality of points represents an optical measurement of a corresponding position on the substrate. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points.

The method can include forming a transformation data structure that includes a respective counter for each transform candidate in a plurality of transform candidates, where each transform candidate in the plurality of transform candidates includes a two-dimensional translation component, and where the plurality of transform candidates comprises about 500 or more different transform candidates. For each respective transform candidate in the plurality of transform candidates, the method can include performing a procedure that comprises (i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition. The first and second images can be registered to each other using a respective transform candidate selected from the plurality of transform candidates in the transformation data structure based at least in part on a value of the respective counter associated with the respective transform candidate in the transformation data structure.

IV. Additional Aspects Including Fiducial Elements

In some embodiments, as described above, the substrate comprises a plurality of fiducial elements. Advantageously, the plurality of fiducial elements can be used to perform registration of the plurality of images.

Accordingly, another aspect of the present disclosure provides a method for registering a plurality of images of a substrate, the method comprising obtaining a first plurality of points within a first image in the plurality of images, where the first plurality of points comprises about 100 or more points; and obtaining a second plurality of points within a second image in the plurality of images, the second image acquired of the substrate at a different time than the first image, where the second plurality of points comprises about 100 or more points, the first plurality of points and the second plurality of points are coplanar, and at least some points in one of the first and second plurality of points, optionally, is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points. A first subplurality of the first plurality of points arises from respective optical measurements of a plurality of fiducial elements on the substrate, where points corresponding to the first subplurality of points is in the second plurality of points, and a second subplurality of the first plurality of points arises from respective optical measurements of a plurality of analytes (e.g., polypeptide molecules) when bound to an analytical reagent (e.g., an affinity agent), and each analyte of said plurality of analytes is coupled to a unique, spatially-separated location of a plurality of unique, spatially-separated locations on the substrate.

The method can include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. The method can include populating the respective counter for each transform candidate in the plurality of transform candidates that is able to match respective points in one of the first and second plurality of points to corresponding points in the other of the first and second plurality of points. The first and second images can be registered to each other using a respective transform candidate selected from the plurality of transform candidates in the transformation data structure based at least in part on a value of the respective counter associated with the respective transform candidate in the transformation data structure.

In some embodiments, points are matched between a first image and a second image using any of the methods disclosed above (see, e.g., the section entitled "Point pairs," above). In some embodiments, points are matched between a first image and a second image using any methods known in the art.

In some embodiments, the substrate has a planar surface.

In some embodiments, each image in the plurality of images comprises more than 200,000 pixels. In some embodiments, each image in the plurality of images comprises more than 500,000 pixels. In some embodiments, each image in the plurality of images comprises at least about 500 pixels in a first dimension, each image in the plurality of images comprises at least about 500 pixels in a second dimension orthogonal to the first dimension, and each transform candidate in the plurality of transform candidates transforms one of the first image or the second image between about 1 pixel and about 300 pixels. In some embodiments, each image in the plurality of images consists of 2048 pixels in a first dimension, each image in the plurality of images consists of 2048 pixels in a second dimension orthogonal to the first dimension, and each transform candidate in the plurality of transform candidates transforms one of the first image or the second image between about 1 pixel and about 256 pixels.

In some embodiments, the analytical reagent binds to more than one unique epitope present within one or more analytes in the plurality of analytes. In some embodiments, the analytical reagent comprises a known degree of binding nonspecificity.

In some embodiments, said plurality of analytes comprises more than 500, more than 1000, more than 2000, more than 3000, more than 5000, more than 6000, or more than 7000 different analytes.

In some embodiments, the first subplurality represents less than 10 percent, less than 5 percent, or less than 2 percent of the first plurality of points.

In some embodiments, each transform candidate in the plurality of transform candidates transforms one of the first image or the second image between about 1 pixel and about 500 pixels.

In some embodiments, the first plurality of points comprises about 200 or more, about 400 or more, about 600 or more, about 800 or more, or about 1000 or more points, and the second plurality of points comprises about 200 or more, about 400 or more, about 600 or more, about 800 or more, or about 1000 or more points.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is not found in the second plurality of points.

In some embodiments, each point in the first plurality of points occupies a corresponding single pixel in the first image; and each point in the second plurality of points occupies a corresponding single pixel in the second image.

In some embodiments, selection of the respective transform candidate in the plurality of transform candidates in the transformation data structure based at least in part on a value of the respective counter associated with the respective transform candidate in the transformation data structure includes: (i) forming a corresponding Hough two-dimensional image, wherein each pixel in the corresponding Hough two-dimensional image is the corresponding count of points of a respective transform candidate in the plurality of transform candidates; (ii) applying a binomial distribution cumulative distribution function across the respective counts of each transform candidate in the respective image; and (iii) computing a respective z-score of the largest peak in the respective Hough two-dimensional image, where the respective transform candidate is selected from among the plurality of transform candidates in the transformation data structure based on a respective z-score of a largest peak in the Hough two-dimensional image. In some embodiments, the respective transform candidate is selected from among the plurality of transform candidates in the transformation data structure that is associated with a peak in the Hough two-dimensional image having the largest Z-score.

In some embodiments, the method further comprises applying a Gaussian filter to the respective Hough two-dimensional image prior to computing the respective z-score.

In some embodiments, at least about 5 percent, at least about 10 percent, at least about 15 percent, at least about 20 percent, at least about 25 percent, at least about 30 percent, at least about 35 percent, or at least about 40 percent of the first plurality of points is found in the second plurality of points. In some embodiments, between about 5 percent and about 10 percent, between about 15 percent and about 20 percent, between about 25 percent and about 30 percent, between about 35 percent and about 40 percent, between about 20 percent and about 90, or between about 5 percent and about 99 percent of the first plurality of points is found in the second plurality of points.

In some embodiments, the registration is a rigid transformation.

In some embodiments, the optical measurements are of fluorescence. In some embodiments, the optical measurements are of bioluminescence, a chemiluminescence, or a light scattering signal.

In some embodiments, each image in the plurality of images comprises at least about 500 pixels in a first dimension, and each image in the plurality of images comprises at least about 500 pixels in a second dimension orthogonal to the first dimension. In some embodiments, each image in the plurality of images consists of 2048 pixels in a first dimension, and each image in the plurality of images consists of 2048 pixels in a second dimension orthogonal to the first dimension.

Yet another aspect of the present disclosure provides a computer system comprising one or more processors, memory, and one or more programs, where the one or more programs are stored in the memory and are configured to be executed by the one or more processors, the one or more programs including instructions for registering a plurality of images of a substrate. The instructions can perform a method comprising obtaining a first plurality of points within a first image in the plurality of images, where the first plurality of points comprises about 100 or more points; and obtaining a second plurality of points within a second image in the plurality of images, the second image acquired of the substrate at a different time than the first image, where the second plurality of points comprises about 100 or more points, the first plurality of points and the second plurality of points are coplanar, and at least some points in one of the first and second plurality of points, optionally, is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points. A first subplurality of the first plurality of points arises from respective optical measurements of a plurality of fiducial elements on the substrate, where points corresponding to the first subplurality of points is in the second plurality of points, and a second subplurality of the first plurality of points arises from respective optical measurements of a plurality of analytes when bound to an analytical reagent, and each analyte of said plurality of analytes is coupled to a unique, spatially-separated location of a plurality of unique, spatially-separated locations on the substrate.

The method can include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. The method can include populating the respective counter for each transform candidate in the plurality of transform candidates that is able to match respective points in one of the first and second plurality of points to corresponding points in the other of the first and second plurality of points. The first and second images can be registered to each other using a respective transform candidate selected from the plurality of transform candidates in the transformation data structure based at least in part on a value of the respective counter associated with the respective transform candidate in the transformation data structure.

Still another aspect of the present disclosure provides a computer readable storage medium storing one or more programs, the one or more programs comprising instructions that, when executed by an electronic device with one or more processors and a memory, cause the electronic device to perform a method for registering a plurality of images of a substrate. The method can include obtaining a first plurality of points within a first image in the plurality of images, where the first plurality of points comprises about 100 or more points; and obtaining a second plurality of points within a second image in the plurality of images, the second image acquired of the substrate at a different time than the first image, where the second plurality of points comprises about 100 or more points, the first plurality of points and the second plurality of points are coplanar, and at least some points in one of the first and second plurality of points, optionally, is not in the other of the first and second plurality of points. For instance, in some embodiments, at least a first subset of the first plurality of points is not represented by the second plurality of points, at least a second subset of the second plurality of points is not represented by the first plurality of points, and at least a third subset of points in the first plurality of points is represented in the second plurality of points. A first subplurality of the first plurality of points arises from respective optical measurements of a plurality of fiducial elements on the substrate, where points corresponding to the first subplurality of points is in the second plurality of points, and a second subplurality of the first plurality of points arises from respective optical measurements of a plurality of analytes (e.g., polypeptide molecules) when bound to an analytical reagent (e.g., an affinity agent), and each analyte of said plurality of analytes is coupled to a unique, spatially-separated location of a plurality of unique, spatially-separated locations on the substrate.

The method can include forming a transformation data structure that includes a respective counter for each transform candidate in a plurality of transform candidates, where each transform candidate in the plurality of transform candidates includes a two-dimensional translation component, and the plurality of transform candidates comprises about 500 or more different transform candidates. The method can include populating the respective counter for each transform candidate in the plurality of transform candidates that is able to match respective points in one of the first and second plurality of points to corresponding points in the other of the first and second plurality of points. The first and second images can be registered to each other using a respective transform candidate selected from the plurality of transform candidates in the transformation data structure based at least in part on a value of the respective counter associated with the respective transform candidate in the transformation data structure.

Yet another aspect of the present disclosure provides a computing system including one or more processors and memory storing one or more programs for registering a plurality of images of a substrate. It will be appreciated that this memory can be on a single computer, a network of computers, one or more virtual machines, or in a cloud computing architecture. The one or more programs are configured for execution by the one or more processors and include instructions for performing any of the methods, workflows, processes, or embodiments disclosed herein, and/or any substitutions, modifications, additions, deletions, and/or combinations thereof, as will be apparent to one skilled in the art.

Still another aspect of the present disclosure provides a computer readable storage medium storing one or more programs to be executed by an electronic device. The one or more programs include instructions for the electronic device to perform a method for registering a plurality of images of a substrate using any of the methods, workflows, processes, or embodiments disclosed herein, and/or any substitutions, modifications, additions, deletions, and/or combinations thereof, as will be apparent to one skilled in the art. It will be appreciated that the computer readable storage medium can exist as a single computer readable storage medium or any number of component computer readable storage mediums that are physically separated from each other.

Polypeptide Assays

The present disclosure provides compositions, apparatus and methods that can be useful for characterizing sample components, such as proteins, nucleic acids, cells or other species, by obtaining multiple separate and non-identical measurements of the sample components. In particular configurations, the individual measurements may not, by themselves, be sufficiently accurate or specific to make the characterization, but an aggregation of the multiple non-identical measurements can allow the characterization to be made with a high degree of accuracy, specificity and confidence. For example, the multiple separate measurements can include subjecting the sample to reagents that are promiscuous with regard to recognizing multiple components of the sample. Accordingly, a first measurement carried out using a first promiscuous reagent may perceive a first subset of sample components without distinguishing one component from another. A second measurement carried out using a second promiscuous reagent may perceive a second subset of sample components, again, without distinguishing one component from another. However, a comparison of the first and second measurements can distinguish: (i) a sample component that is uniquely present in the first subset but not the second; (ii) a sample component that is uniquely present in the second subset but not the first; (iii) a sample component that is uniquely present in both the first and second subsets; or (iv) a sample component that is uniquely absent in the first and second subsets. The number of promiscuous reagents used, the number of separate measurements acquired, and degree of reagent promiscuity (e.g. the diversity of components recognized by the reagent) can be adjusted to suit the component diversity expected for a particular sample.

The present disclosure provides assays that are useful for detecting one or more analytes. Exemplary assays are set forth herein in the context of detecting proteins. Those skilled in the art will recognize that methods, compositions and apparatus set forth herein can be adapted for use with other analytes such as nucleic acids, polysaccharides, metabolites, vitamins, hormones, enzyme co-factors and others set forth herein or known in the art. Particular configurations of the methods, apparatus and compositions set forth herein can be made and used, for example, as set forth in U.S. Pat. No. 10,473,654 or US Pat. App. Pub. Nos. 2020/0318101 A1 or 2020/0286584 A1, each of which is incorporated herein by reference. Exemplary methods, systems and compositions are set forth in further detail below.

A composition, apparatus or method set forth herein can be used to characterize an analyte, or moiety thereof, with respect to any of a variety of characteristics or features including, for example, presence, absence, quantity (e.g. amount or concentration), chemical reactivity, molecular structure, structural integrity (e.g. full length or fragmented), maturation state (e.g. presence or absence of pre- or pro-sequence in a protein), location (e.g. in an analytical system, subcellular compartment, cell or natural environment), association with another analyte or moiety, binding affinity for another analyte or moiety, biological activity, chemical activity or the like. An analyte can be characterized with regard to a relatively generic characteristic such as the presence or absence of a common structural feature (e.g. amino acid sequence length, overall charge or overall pKa for a protein) or common moiety (e.g. a short primary sequence motif or post-translational modification for a protein). An analyte can be characterized with regard to a relatively specific characteristic such as a unique amino acid sequence (e.g. for the full length of the protein or a motif), an RNA or DNA sequence that encodes a protein (e.g. for the full length of the protein or a motif), or an enzymatic or other activity that identifies a protein. A characterization can be sufficiently specific to identify an analyte, for example, at a level that is considered adequate or unambiguous by those skilled in the art.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids. Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA). Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The analyte can include a nucleic acid capable of functioning as a component of a gene editing reaction, such as, for example, clustered regularly interspaced short palindromic repeats (CRISPR)-based gene editing.

In certain embodiments, an analyte is extracted from a live cell. Processing conditions can be adjusted to ensure that a biological sample remains live during analysis, and analytes are extracted from (or released from) live cells of the sample. Live cell-derived analytes can be obtained only once from the sample or can be obtained at intervals from a sample that continues to remain in viable condition.

An analyte can be characterized with regard to a relatively generic characteristic such as the presence or absence of a common structural feature (e.g., amino acid sequence length, overall charge or overall pKa for a protein) or common moiety (e.g., a short primary sequence motif or post-translational modification for a protein). An analyte can be characterized with regard to a relatively specific characteristic such as a unique amino acid sequence (e.g., for the full length of the protein or a motif), an RNA or DNA sequence that encodes a protein (e.g., for the full length of the protein or a motif), or an enzymatic or other activity that identifies a protein. A characterization can be sufficiently specific to identify an analyte, for example, at a level that is considered adequate or unambiguous by those skilled in the art.

In some embodiments, one or more analytes (e.g., in an analyte sample) are contacted with affinity agents. In some embodiments, one or more analytes (e.g., in an analyte sample) are prepared by staining. For example, to facilitate visualization, analyte samples can be stained and/or contacted using a wide variety of affinity agents, stains, and/or staining techniques. In some embodiments, for example, an analyte sample can be stained using any number of stains, including but not limited to, acridine orange, Bismarck brown, carmine, Coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or a combination thereof. The analyte sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the analyte sample is stained using a detectable label (e.g., radioisotopes, fluorophores, chemiluminescent compounds, bioluminescent compounds, and dyes). In some embodiments, an analyte sample is stained using only one type of stain or one technique. In some embodiments, an analyte sample is stained using two or more different types of stains, or two or more different staining techniques. In some embodiments, an analyte sample is not stained, for example, lacking one or more type of stain or label set forth herein.

In particular configurations, a protein can be detected using one or more affinity agents having known or measurable binding affinity for the protein. For example, an affinity agent can bind a protein to form a complex and a signal produced by the complex can be detected. A protein that is detected by binding to a known affinity agent can be identified based on the known or predicted binding characteristics of the affinity agent. For example, an affinity agent that is known to selectively bind a candidate protein suspected of being in a sample, without substantially binding to other proteins in the sample, can be used to identify the candidate protein in the sample merely by observing the binding event. This one-to-one correlation of affinity agent to candidate protein can be used for identification of one or more proteins. However, as the protein complexity (i.e. the number and variety of different proteins) in a sample increases, or as the number of different candidate proteins to be identified increases, the time and resources to produce a commensurate variety of affinity agents having one-to-one specificity for the proteins approaches limits of practicality.

Methods set forth herein, can be advantageously employed to overcome these constraints. In particular configurations, the methods can be used to identify a number of different candidate proteins that exceeds the number of affinity agents used. For example, the number of candidate proteins identified can be at least 5×, 10×, 25×, 50×, 100× or more than the number of affinity agents used. This can be achieved, for example, by (1) using promiscuous affinity agents that bind to multiple different candidate proteins suspected of being present in a given sample, and (2) subjecting the protein sample to a set of promiscuous affinity agents that, taken as a whole, are expected to bind each candidate protein in a different combination, such that each candidate protein is expected to be encoded by a unique profile of binding and non-binding events. Promiscuity of an affinity agent is a characteristic that can be understood relative to a given population of proteins. Promiscuity can arise due to the affinity agent recognizing an epitope that is known to be present in a plurality of different candidate proteins suspected of being present in the given population of unknown proteins. For example, epitopes having relatively short amino acid lengths such as dimers, trimers, or tetramers can be expected to occur in a substantial number of different proteins in the human proteome. Alternatively or additionally, a promiscuous affinity agent can recognize different epitopes (e.g. epitopes differing from each other with regard to amino acid composition or sequence), the different epitopes being present in a plurality of different candidate proteins. For example, a promiscuous affinity agent that is designed or selected for its affinity toward a first trimer epitope may bind to a second epitope that has a different sequence of amino acids when compared to the first epitope.

Although performing a single binding reaction between a promiscuous affinity agent and a complex protein sample may yield ambiguous results regarding the identity of the different proteins to which it binds, the ambiguity can be resolved when the results are combined with other identifying information about those proteins. The identifying information can include characteristics of the protein such as length (i.e. number of amino acids), hydrophobicity, molecular weight, charge to mass ratio, isoelectric point, chromatographic fractionation behavior, enzymatic activity, presence or absence of post translational modifications or the like. The identifying information can include results of binding with other promiscuous affinity agents. For example, a plurality of different promiscuous affinity agents can be contacted with a complex population of proteins, wherein the plurality is configured to produce a different binding profile for each candidate protein suspected of being present in the population. In this example, each of the affinity agents can be distinguishable from the other affinity agents, for example, due to unique labeling (e.g. different affinity agents having different luminophore labels), unique spatial address (e.g. different affinity agents being located at different addresses in an array), and/or unique time of use (e.g. different affinity agents being delivered in series to a population of proteins). Accordingly, the plurality of promiscuous affinity agents produces a binding profile for each individual protein that can be decoded to identify a unique combination of epitopes present in the individual protein, and this can in turn be used to identify the individual protein as a particular candidate protein having the same or similar unique combination of epitopes. The binding profile can include observed binding events as well as observed non-binding events and this information can be evaluated in view of the expectation that particular candidate proteins produce a similar binding profile, for example, based on presence and absence of particular epitopes in the candidate proteins.

In some configurations, distinct and reproducible binding profiles may be observed for one or more unknown proteins in a sample. However, in many cases one or more binding events produces inconclusive or even aberrant results and this, in turn, can yield ambiguous binding profiles. For example, observation of binding outcome for a single-molecule binding event can be particularly prone to ambiguities due to stochasticity in the behavior of single molecules when observed using certain detection hardware. The present disclosure provides methods that provide accurate protein identification despite ambiguities and imperfections that can arise in many contexts. In some configurations, methods for identifying, quantitating or otherwise characterizing one or more proteins in a sample utilize a binding model that evaluates the likelihood or probability that one or more candidate proteins that are suspected of being present in the sample will have produced an empirically observed binding profile. The binding model can include information regarding expected binding outcomes (e.g. binding or non-binding) for binding of one or more affinity reagent with one or more candidate proteins. The information can include an a priori characteristic of a candidate protein, such as presence or absence of a particular epitope in the candidate protein or length of the candidate protein. Alternatively or additionally, the information can include empirically determined characteristics such as propensity or likelihood that the candidate protein will bind to a particular affinity reagent. Accordingly, a binding model can include information regarding the propensity or likelihood of a given candidate protein generating a false positive or false negative binding result in the presence of a particular affinity reagent, and such information can optionally be included for a plurality of affinity reagents.

Methods set forth herein can be used to evaluate the degree of compatibility of one or more empirical binding profiles with results computed for various candidate proteins using a binding model. For example, to identify an unknown protein in a sample of many proteins, an empirical binding profile for the protein can be compared to results computed by the binding model for many or all candidate proteins suspected of being in the sample. In some configurations of the methods set forth herein, identity for the unknown protein is determined based on a likelihood of the unknown protein being a particular candidate protein given the empirical binding pattern or based on the probability of a particular candidate protein generating the empirical binding pattern. Optionally a score can be determined from the measurements that are acquired for the unknown protein with respect to many or all candidate proteins suspected of being in the sample. A digital or binary score that indicates one of two discrete states can be determined. In particular configurations, the score can be non-digital or non-binary. For example, the score can be a value selected from a continuum of values such that an identity is made based on the score being above or below a threshold value. Moreover, a score can be a single value or a collection of values. Particularly useful methods for identifying proteins using promiscuous reagents, serial binding measurements and/or decoding with binding models are set forth, for example, in U.S. Pat. No. 10,473,654 US Pat. App. Pub. No. 2020/0318101 A1 or Egertson et al., BioRxiv (2021), DOI: 10.1101/2021.10.11.463967, each of which is incorporated herein by reference.

The present disclosure provides compositions, apparatus and methods for detecting one or more proteins. A protein can be detected using one or more affinity agents having binding affinity for the protein. The affinity agent and the protein can bind each other to form a complex and, during or after formation, the complex can be detected. The complex can be detected directly, for example, due to a label that is present on the affinity agent or protein. In some configurations, the complex need not be directly detected, for example, in formats where the complex is formed and then the affinity agent, protein, or a label component that was present in the complex is detected.

Many protein detection methods, such as enzyme linked immunosorbent assay (ELISA), achieve high-confidence characterization of one or more protein in a sample by exploiting high specificity binding of antibodies, aptamers or other binding agents to the protein(s) and detecting the binding event while ignoring all other proteins in the sample. ELISA is generally carried out at low plex scale (e.g. from one to a hundred different proteins detected in parallel or in succession) but can be used at higher plexity. ELISA methods can be carried out by detecting immobilized binding agents and/or proteins in multiwell plates, on arrays, or on particles in microfluidic devices. Exemplary plate-based methods include, for example, the MULTI-ARRAY technology commercialized by MesoScale Diagnostics (Rockville, Maryland) or Simple Plex technology commercialized by Protein Simple (San Jose, CA). Exemplary, array-based methods include, but are not limited to those utilizing Simoa® Planar Array Technology or Simoa® Bead Technology, commercialized by Quanterix (Billerica, MA). Further exemplary array-based methods are set forth in U.S. Pat. Nos. 9,678,068; 9,395,359; 8,415,171; 8,236,574; or 8,222,047, each of which is incorporated herein by reference. Exemplary microfluidic detection methods include those commercialized by Luminex (Austin, Texas) under the trade name xMAP® technology or used on platforms identified as MAGPIX®, LUMINEX® 100/200 or FEXMAP 3D®.

Other detection methods that can also be used, for example at low plex scale, include procedures that employ SOMAmer reagents and SOMAscan assays commercialized by Soma Logic (Boulder, CO). In one configuration, a sample is contacted with aptamers that are capable of binding proteins with specificity for the amino acid sequence of the proteins. The resulting aptamer-protein complexes can be separated from other sample components, for example, by attaching the complexes to beads (or other solid support) that are removed from other sample components. The aptamers can then be isolated and, because the aptamers are nucleic acids, the aptamers can be detected using any of a variety of methods known in the art for detecting nucleic acids, including for example, hybridization to nucleic acid arrays, PCR-based detection, or nucleic acid sequencing. Exemplary methods and compositions are set forth in U.S. Pat. Nos. 7,855,054; 7,964,356; 8,404,830; 8,945,830; 8,975,026; 8,975,388; 9,163,056; 9,938,314; 9,404,919; 9,926,566; 10,221,421; 10,239,908; 10,316,321 10,221,207 or 10,392,621, each of which is incorporated herein by reference.

In some detection assays, a protein can be cyclically modified and the modified products from individual cycles can be detected. In some configurations, a protein can be sequenced by a sequential process in which each cycle includes steps of detecting the protein and removing one or more terminal amino acids from the protein. Optionally, one or more of the steps can include adding a label to the protein, for example, at the amino terminal amino acid or at the carboxy terminal amino acid. In particular configurations, a method of detecting a protein can include steps of (i) exposing a terminal amino acid on the protein; (ii) detecting a change in signal from the protein; and (iii) identifying the type of amino acid that was removed based on the change detected in step (ii). The terminal amino acid can be exposed, for example, by removal of one or more amino acids from the amino terminus or carboxyl terminus of the protein. Steps (i) through (iii) can be repeated to produce a series of signal changes that is indicative of the sequence for the protein.

In a first configuration of a cyclical protein detection method, one or more types of amino acids in the protein can be attached to a label that uniquely identifies the type of amino acid. In this configuration, the change in signal that identifies the amino acid can be loss of signal from the respective label. For example, lysines can be attached to a distinguishable label such that loss of the label indicates removal of a lysine. Alternatively or additionally, other amino acid types can be attached to other labels that are mutually distinguishable from lysine and from each other. For example, lysines can be attached to a first label and cysteines can be attached to a second label, the first and second labels being distinguishable from each other. Exemplary compositions and techniques that can be used to remove amino acids from a protein and detect signal changes are those set forth in Swaminathan et al., *Nature Biotech.* 36:1076-1082 (2018); or U.S. Pat. Nos. 9,625,469 or 10,545,153, each of which is incorporated herein by reference. Methods and apparatus under development by Erisyon, Inc. (Austin, TX) may also be useful for detecting proteins.

In a second configuration of a cyclical protein detection method, a terminal amino acid of a protein can be recognized by an affinity agent that is specific for the terminal amino acid or specific for a label moiety that is present on the terminal amino acid. The affinity agent can be detected on the array, for example, due to a label on the affinity agent. Optionally, the label is a nucleic acid barcode sequence that is added to a primer nucleic acid upon formation of a complex. For example, a barcode can be added to the primer via ligation of an oligonucleotide having the barcode sequence or polymerase extension directed by a template that encodes the barcode sequence. The formation of the complex and identity of the terminal amino acid can be determined by decoding the barcode sequence. Multiple cycles can produce a series of barcodes that can be detected, for example, using a nucleic acid sequencing technique. Exemplary affinity agents and detection methods are set forth in US Pat. App. Pub. No. 2019/0145982 A1; 2020/0348308 A1; or 2020/0348307 A1, each of which is incorporated herein by reference. Methods and apparatus under development by Encodia, Inc. (San Diego, CA) may also be useful for detecting proteins.

Cyclical removal of terminal amino acids from a protein can be carried out using an Edman-type sequencing reaction in which a phenyl isothiocyanate reacts with a N-terminal amino group under mildly alkaline conditions (e.g. about pH 8) to form a cyclical phenylthiocarbamoyl Edman complex derivative. The phenyl isothiocyanate may be substituted or unsubstituted with one or more functional groups, linker groups, or linker groups containing functional groups. An Edman-type sequencing reaction can include variations to reagents and conditions that yield a detectable removal of amino acids from a protein terminus, thereby facilitating determination of the amino acid sequence for a protein or portion thereof. For example, the phenyl group can be replaced with at least one aromatic, heteroaromatic or aliphatic group which may participate in an Edman-type sequencing reaction, non-limiting examples including: pyridine, pyrimidine, pyrazine, pyridazoline, fused aromatic groups such as naphthalene and quinoline), methyl or other alkyl groups or alkyl group derivatives (e.g., alkenyl, alkynyl, cyclo-alkyl). Under certain conditions, for example, acidic conditions of about pH 2, derivatized terminal amino acids may be cleaved, for example, as a thiazolinone derivative. The thiazolinone amino acid derivative under acidic conditions may form a more stable phenylthiohydantoin (PTH) or similar amino acid derivative which can be detected. This procedure can be repeated iteratively for residual protein to identify the subsequent N-terminal amino acid. Many variations of Edman-type degradation have been described and may be used including, for example, a one-step removal of an N-terminal amino acid using alkaline conditions (Chang, J. Y., *FEBS LETTS.*, 1978, 91(1), 63-68). In some cases, Edman-type reactions may be thwarted by N-terminal modifications which may be selectively removed, for example, N-terminal acetylation or formylation (e.g., see Gheorghe M. T., Bergman T. (1995) in *Methods in Protein Structure Analysis*, Chapter 8: Deacetylation and internal cleavage of Proteins for N-terminal Sequence Analysis. Springer, Boston, MA. doi.org/10.1007/978-1-4899-1031-8_8).

Non-limiting examples of functional groups for substituted phenyl isothiocyanate may include ligands (e.g. biotin and biotin analogs) for known receptors, labels such as luminophores, or reactive groups such as click functionalities (e.g. compositions having an azide or acetylene moiety). The functional group may be a DNA, RNA, peptide or small molecule barcode or other tag which may be further processed and/or detected.

The removal of an amino terminal amino acid using Edman-type processes can utilize at least two main steps, the first step includes reacting an isothiocyanate or equivalent with protein N-terminal residues to form a relatively stable Edman complex, for example, a phenylthiocarbamoyl complex. The second step can include removing the derivatized N-terminal amino acid, for example, via heating. The protein, now having been shortened by one amino acid, may be detected, for example, by contacting the protein with a labeled affinity agent that is complementary to the amino terminus and examining the protein for binding to the agent, or by detecting loss of a label that was attached to the removed amino acid.

Edman-type processes can be carried out in a multiplex format to detect, characterize or identify a plurality of proteins. A method of detecting a protein can include steps of (i) exposing a terminal amino acid on a protein at an address of an array; (ii) binding an affinity agent to the terminal amino acid, where the affinity agent includes a nucleic acid tag, and where a primer nucleic acid is present at the address; (iii) extending the primer nucleic acid, thereby producing an extended primer having a copy of the tag; and (iv) detecting the tag of the extended primer. The terminal amino acid can be exposed, for example, by removal of one or more amino acids from the amino terminus or carboxyl terminus of the protein. Steps (i) through (iv) can be repeated to produce a series of tags that is indicative of the sequence for the protein. The method can be applied to a plurality of proteins on the array and in parallel. Whatever the plexity, the extending of the primer can be carried out, for example, by polymerase-based extension of the primer, using the nucleic acid tag as a template. Alternatively, the extending of the primer can be carried out, for example, by ligase- or chemical-based ligation of the primer to a nucleic acid that is hybridized to the nucleic acid tag. The nucleic acid tag can be detected via hybridization to nucleic acid probes (e.g. in an array), amplification-based detections (e.g. PCR-based detection, or rolling circle amplification-based detection) or nuclei acid sequencing (e.g. cyclical reversible terminator methods, nanopore methods, or single molecule, real time detection methods). Exemplary methods that can be used for detecting proteins using nucleic acid tags are set forth in US Pat. App. Pub. No. 2019/0145982 A1; 2020/0348308 A1; or 2020/0348307 A1, each of which is incorporated herein by reference.

A protein can optionally be detected based on its enzymatic or biological activity. For example, a protein can be contacted with a reactant that is converted to a detectable product by an enzymatic activity of the protein. In other assay formats, a first protein having a known enzymatic function can be contacted with a second protein to determine if the second protein changes the enzymatic function of the first protein. As such, the first protein serves as a reporter system for detection of the second protein. Exemplary changes that can be observed include, but are not limited to, activation of the enzymatic function, inhibition of the enzymatic function, attenuation of the enzymatic function, degradation of the first protein or competition for a reactant or cofactor used by the first protein. Proteins can also be detected based on their binding interactions with other molecules such as proteins, nucleic acids, nucleotides, metabolites, hormones, vitamins, small molecules that participate in biological signal transduction pathways, biological receptors or the like. For example, a protein that participates in a signal transduction pathway can be identified as a particular candidate protein by detecting binding to a second protein that is known to be a binding partner for the candidate protein in the pathway.

The presence or absence of post-translational modifications (PTM) can be detected using a composition, apparatus or method set forth herein. A PTM can be detected using an affinity agent that recognizes the PTM or based on a chemical property of the PTM. Exemplary PTMs that can be detected, identified or characterized include, but are not limited to, myristoylation, palmitoylation, isoprenylation, prenylation, farnesylation, geranylgeranylation, lipoylation, flavin moiety attachment, Heme C attachment, phosphopantetheinylation, retinylidene Schiff base formation, dipthamide formation, ethanolamine phosphoglycerol attachment, hypusine, beta-Lysine addition, acylation, acetylation, deacetylation, formylation, alkylation, methylation, C-terminal amidation, arginylation, polyglutamylation, polyglyclyation, butyrylation, gamma-carboxylation, glycosylation, glycation, polysialylation, malonylation, hydroxylation, iodination, nucleotide addition, phosphoate ester formation, phosphoramidate formation, phosphorylation, adenylylation, uridylylation, propionylation, pyrolglutamate formation, S-glutathionylation, S-nitrosylation, S-sulfenylation, S-sulfinylation, S-sulfonylation, succinylation, sulfation, glycation, carbamylation, carbonylation, isopeptide bond formation, biotinylation, carbamylation, oxidation, reduction, pegylation, ISGylation, SUMOylation, ubiquitination, neddylation, pupylation, citrullination, deamidation, elminylation, disulfide bridge formation, proteolytic cleavage, isoaspartate formation, racemization, and protein splicing.

PTMs may occur at particular amino acid residues of a protein. For example, the phosphate moiety of a particular proteoform can be present on a serine, threonine, tyrosine, histidine, cysteine, lysine, aspartate or glutamate residue of the protein. In other examples, an acetyl moiety can be present on the N-terminus or on a lysine; a serine or threonine residue can have an O-linked glycosyl moiety; an asparagine residue can have an N-linked glycosyl moiety; a proline, lysine, asparagine, aspartate or histidine amino acid can be hydroxylated; an arginine or lysine residue can be methylated; or the N-terminal methionine or at a lysine amino acid can be ubiquitinated.

In some configurations of the apparatus and methods set forth herein, one or more proteins can be detected on a solid support. For example, protein(s) can be attached to a support, the support can be contacted with detection agents (e.g. affinity agents) in solution, the agents can interact with the protein(s), thereby producing a detectable signal, and then the signal can be detected to determine the presence of the protein(s). In multiplexed versions of this approach, different proteins can be attached to different addresses in an array, and the probing and detection steps can occur in parallel. In another example, affinity agents can be attached to a solid support, the support can be contacted with proteins in solution, the proteins can interact with the affinity agents, thereby producing a detectable signal, and then the signal can be detected to determine presence, quantity or characteristics of the proteins. This approach can also be multiplexed by attaching different affinity agents to different addresses of an array.

Proteins, affinity agents or other objects of interest (e.g., fiducial elements) can be attached to a solid support via covalent or non-covalent bonds. For example, a linker can be used to covalently attach a protein or other object of interest to an array. A particularly useful linker is a structured nucleic acid particle such as a nucleic acid nanoball (e.g. a concatemeric amplicon produced by rolling circle replication of a circular nucleic acid template) or a nucleic acid origami. For example, a plurality of proteins can be conjugated to a plurality of structured nucleic acid particles, such that each protein-conjugated particle forms an address in the array. Exemplary linkers for attaching proteins, or other objects of interest, to an array or other solid support are set forth in US Pat. App. Pub. No. 2021/0101930 A1, which is incorporated herein by reference.

A protein can be detected based on proximity of two or more affinity agents. For example, the two affinity agents can include two components each: a receptor component and a nucleic acid component. When the affinity agents bind in proximity to each other, for example, due to ligands for the respective receptors being on a single protein, or due to the ligands being present on two proteins that associate with each other, the nucleic acids can interact to cause a modification that is indicative of the two ligands being in proximity. Optionally, the modification can be polymerase catalyzed extension of one of the nucleic acids using the other nucleic acid as a template. As another option, one of the nucleic acids can form a template that acts as splint to position other nucleic acids for ligation to an oligonucleotide. Exemplary methods are commercialized by Olink Proteomics AB (Uppsala Sweden) or set forth in U.S. Pat. Nos. 7,306,904; 7,351,528; 8,013,134; 8,268,554 or 9,777,315, each of which is incorporated herein by reference.

A method or apparatus of the present disclosure can optionally be configured for optical detection (e.g. luminescence detection). Analytes or other entities can be detected, and optionally distinguished from each other, based on measurable characteristics such as the wavelength of radiation that excites a luminophore, the wavelength of radiation emitted by a luminophore, the intensity of radiation emitted by a luminophore (e.g. at particular detection wavelength (s)), luminescence lifetime (e.g. the time that a luminophore remains in an excited state) or luminescence polarity. Other optical characteristics that can be detected, and optionally used to distinguish analytes, include, for example, absorbance of radiation, resonance Raman, radiation scattering, or the like. A luminophore can be an intrinsic moiety of a protein or other analyte to be detected, or the luminophore can be an exogenous moiety that has been synthetically added to a protein or other analyte. The term "imaging" is used herein to refer to any method of obtaining an image, e.g., a microscope image.

A method or apparatus of the present disclosure can use a light sensing device that is appropriate for detecting a characteristic set forth herein or known in the art. Particularly useful components of a light sensing device can include, but are not limited to, optical sub-systems or components used in nucleic acid sequencing systems. Examples of useful sub systems and components thereof are set forth in US Pat. App. Pub. No. 2010/0111768 A1 or U.S. Pat. Nos. 7,329,860; 8,951,781 or 9,193,996, each of which is incorporated herein by reference. Other useful light sensing devices and components thereof are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference. Light sensing devices and components that can be used to detect luminophores based on luminescence lifetime are described, for example, in U.S. Pat. Nos. 9,678,012; 9,921,157; 10,605,730; 10,712,274; 10,775,305; or 10,895,534, each of which is incorporated herein by reference.

Luminescence lifetime can be detected using an integrated circuit having a photodetection region configured to receive incident photons and produce a plurality of charge carriers in response to the incident photons. The integrated circuit can include at least one charge carrier storage region and a charge carrier segregation structure configured to selectively direct charge carriers of the plurality of charge carriers directly into the charge carrier storage region based upon times at which the charge carriers are produced. See, for example, U.S. Pat. Nos. 9,606,058, 10,775,305, and 10,845,308, each of which is incorporated herein by reference. Optical sources that produce short optical pulses can be used for luminescence lifetime measurements. For example, a light source, such as a semiconductor laser or LED, can be driven with a bipolar waveform to generate optical pulses with FWHM durations as short as approximately 85 ps having suppressed tail emission. See, for example, in U.S. Pat. No. 10,605,730, which is incorporated herein by reference.

For configurations that use optical detection (e.g. luminescent detection), one or more analytes (e.g. proteins) may be immobilized on a surface, and this surface may be scanned with a microscope to detect any signal from the immobilized analytes. The microscope itself may include a digital camera or other luminescence detector configured to record, store, and analyze the data collected during the scan. A luminescence detector of the present disclosure can be configured for epiluminescent detection, total internal reflection (TIR) detection, waveguide assisted excitation, or the like.

A light sensing device may be based upon any suitable technology, and may be, for example, a charged coupled device (CCD) sensor that generates pixilated image data based upon photons impacting addresses in the device. It will be understood that any of a variety of other light sensing devices may also be used including, but not limited to, a detector array configured for time delay integration (TDI) operation, a complementary metal oxide semiconductor (CMOS) detector, an avalanche photodiode (APD) detector, a Geiger-mode photon counter, a photomultiplier tube (PMT), charge injection device (CID) sensors, JOT image sensor (Quanta), or any other suitable detector. Light sensing devices can optionally be coupled with one or more excitation sources, for example, lasers, light emitting diodes (LEDs), arc lamps or other energy sources known in the art.

An optical detection system can be configured for single molecule detection. For example, waveguides or optical confinements can be used to deliver excitation radiation to addresses of a solid support where analytes are located. Zero-mode waveguides can be particularly useful, examples of which are set forth in U.S. Pat. Nos. 7,181,122, 7,302,146, or 7,313,308, each of which is incorporated herein by reference. Analytes can be confined to surface features, for example, to facilitate single molecule resolution. For example, analytes can be distributed into wells having nanometer dimensions such as those set forth in U.S. Pat. Nos. 7,122,482 or 8,765,359, or US Pat. App. Pub. No 2013/0116153 A1, each of which is incorporated herein by reference. The wells can be configured for selective excitation, for example, as set forth in U.S. Pat. Nos. 8,798,414 or 9,347,829, each of which is incorporated herein by reference. Analytes can be distributed to nanometer-scale posts, such as high aspect ratio posts which can optionally be dielectric pillars that extend through a metallic layer to improve detection of an analyte attached to the pillar. See, for example, U.S. Pat. Nos. 8,148,264, 9,410,887 or 9,987,609, each of which is incorporated herein by reference. Further examples of nanostructures that can be used to detect analytes are those that change state in response to the concentration of analytes such that the analytes can be quantitated as set forth in WO 2020/176793 A1, which is incorporated herein by reference.

An apparatus or method set forth herein need not be configured for optical detection. For example, an electronic detector can be used for detection of protons or charged labels (see, for example, US Pat. App. Pub. Nos. 2009/0026082 A1; 2009/0127589 A1; 2010/0137143 A1; or 2010/0282617 A1, each of which is incorporated herein by reference in its entirety). A field effect transistor (FET) can be used to detect analytes or other entities, for example, based on proximity of a field disrupting moiety to the FET. The field disrupting moiety can be due to an extrinsic label attached to an analyte or affinity agent, or the moiety can be intrinsic to the analyte or affinity agent being used. Surface plasmon resonance can be used to detect binding of analytes or affinity agents at or near a surface. Exemplary sensors and methods for attaching molecules to sensors are set forth in US Pat. App. Pub. Nos. 2017/0240962 A1; 2018/0051316 A1; 2018/0112265 A1; 2018/0155773 A1 or 2018/0305727 A1; or U.S. Pat. Nos. 9,164,053; 9,829,456; 10,036,064, each of which is incorporated herein by reference.

In some configurations of the compositions, apparatus and methods set forth herein, one or more proteins can be present on a solid support, where the proteins can optionally be detected. For example, a protein can be attached to a solid support, the solid support can be contacted with a detection agent (e.g. affinity agent) in solution, the affinity agent can interact with the protein, thereby producing a detectable signal, and then the signal can be detected to determine the presence, absence, quantity, a characteristic or identity of the protein. In multiplexed versions of this approach, different proteins can be attached to different addresses in an array, and the detection steps can occur in parallel, such that proteins at each address are detected, quantified, characterized or identified. In another example, detection agents can be attached to a solid support, the support can be contacted with proteins in solution, the proteins can interact with the detection agents, thereby producing a detectable signal, and then the signal can be detected to determine the presence of the proteins. This approach can also be multiplexed by attaching different probes to different addresses of an array.

In multiplexed configurations, different proteins can be attached to different unique identifiers (e.g. addresses in an array), and the proteins can be manipulated and detected in parallel. For example, a fluid containing one or more different affinity agents can be delivered to an array such that the proteins of the array are in simultaneous contact with the affinity agent(s). Moreover, a plurality of addresses can be observed in parallel allowing for rapid detection of binding events. A plurality of different proteins can have a complexity of at least 5, 10, 100, $1 \times 10^3$, $1 \times 10^4$, $1 \times 10^5$ or more different native-length protein primary sequences. Alternatively or additionally, a proteome, proteome subfraction or other protein sample that is analyzed in a method set forth herein can have a complexity that is at most $1 \times 10^5$, $1 \times 10^4$, $1 \times 10^3$, 100, 10, 5 or fewer different native-length protein primary sequences. The total number of proteins of a sample that is detected, characterized or identified can differ from the number of different primary sequences in the sample, for example, due to the presence of multiple copies of at least some protein species. Moreover, the total number of proteins of a sample that is detected, characterized or identified can differ from the number of candidate proteins suspected of being in the sample, for example, due to the presence of multiple copies of at least some protein species, absence of some proteins in a source for the sample, or loss of some proteins prior to analysis.

A protein can be attached to a unique identifier using any of a variety of means. The attachment can be covalent or non-covalent. Exemplary covalent attachments include chemical linkers such as those achieved using click chemistry or other linkages known in the art or described in U.S. patent application Ser. No. 17/062,405, which is incorporated herein by reference. Non-covalent attachment can be mediated by receptor-ligand interactions (e.g. (strept)avidin-biotin, antibody-antigen, or complementary nucleic acid strands), for example, wherein the receptor is attached to the unique identifier and the ligand is attached to the protein or vice versa. In particular configurations, a protein is attached to a solid support (e.g. an address in an array) via a structured nucleic acid particle (SNAP). A protein can be attached to a SNAP and the SNAP can interact with a solid support, for example, by non-covalent interactions of the DNA with the support and/or via covalent linkage of the SNAP to the support. Nucleic acid origami or nucleic acid nanoballs are particularly useful. The use of SNAPs and other moieties to attach proteins to unique identifiers such as tags or addresses in an array are set forth in U.S. patent application Ser. Nos. 17/062,405 and 63/159,500, each of which is incorporated herein by reference.

The methods, compositions and apparatus of the present disclosure are particularly well suited for use with proteins. Although proteins are exemplified throughout the present disclosure, it will be understood that other analytes can be similarly used. Exemplary analytes include, but are not limited to, biomolecules, polysaccharides, nucleic acids, lipids, metabolites, hormones, vitamins, enzyme cofactors, therapeutic agents, candidate therapeutic agents or combinations thereof. An analyte can be a non-biological atom or molecule, such as a synthetic polymer, metal, metal oxide, ceramic, semiconductor, mineral, or a combination thereof.

One or more proteins that are used in a method, composition or apparatus herein, can be derived from a natural or synthetic source. Exemplary sources include, but are not limited to biological tissues, fluids, cells or subcellular compartments (e.g. organelles). For example, a sample can be derived from a tissue biopsy, biological fluid (e.g. blood, sweat, tears, plasma, extracellular fluid, urine, mucus, saliva, semen, vaginal fluid, synovial fluid, lymph, cerebrospinal fluid, peritoneal fluid, pleural fluid, amniotic fluid, intracellular fluid, extracellular fluid, etc.), fecal sample, hair sample, cultured cell, culture media, fixed tissue sample (e.g. fresh frozen or formalin-fixed paraffin-embedded) or product of a protein synthesis reaction. A protein source may include any sample where a protein is a native or expected constituent. For example, a primary source for a cancer biomarker protein may be a tumor biopsy sample or bodily fluid. Other sources include environmental samples or forensic samples.

Exemplary organisms from which proteins or other analytes can be derived include, for example, a mammal such as a rodent, mouse, rat, rabbit, guinea pig, ungulate, horse, sheep, pig, goat, cow, cat, dog, primate, non-human primate or human; a plant such as *Arabidopsis thaliana*, tobacco, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Proteins can also be derived from a prokaryote such as a bacterium, *Escherichia coli*, staphylococci or *Mycoplasma pneumoniae*; an archae; a virus such as Hepatitis C virus, influenza virus, coronavirus, or human immunodeficiency virus; or a viroid. Proteins can be derived from a homogeneous culture or population of the above organisms or alternatively from a collection of several different organisms, for example, in a community or ecosystem.

In some cases, a protein or other biomolecule can be derived from an organism that is collected from a host organism. For example, a protein may be derived from a parasitic, pathogenic, symbiotic, or latent organism collected from a host organism. A protein can be derived from an organism, tissue, cell or biological fluid that is known or suspected of being linked with a disease state or disorder (e.g., cancer). Alternatively, a protein can be derived from an organism, tissue, cell or biological fluid that is known or suspected of not being linked to a particular disease state or disorder. For example, the proteins isolated from such a source can be used as a control for comparison to results acquired from a source that is known or suspected of being linked to the particular disease state or disorder. A sample may include a microbiome or substantial portion of a microbiome. In some cases, one or more proteins used in a method, composition or apparatus set forth herein may be obtained from a single source and no more than the single source. The single source can be, for example, a single organism (e.g. an individual human), single tissue, single cell, single organelle (e.g. endoplasmic reticulum, Golgi apparatus or nucleus), or single protein-containing particle (e.g., a viral particle or vesicle).

A method, composition or apparatus of the present disclosure can use or include a plurality of proteins having any of a variety of compositions such as a plurality of proteins composed of a proteome or fraction thereof. For example, a plurality of proteins can include solution-phase proteins, such as proteins in a biological sample or fraction thereof, or a plurality of proteins can include proteins that are immobilized, such as proteins attached to a particle or solid support. By way of further example, a plurality of proteins can include proteins that are detected, analyzed or identified in connection with a method, composition or apparatus of the present disclosure. The content of a plurality of proteins can be understood according to any of a variety of characteristics such as those set forth below or elsewhere herein.

A plurality of proteins can be characterized in terms of total protein mass. The total mass of protein in a liter of plasma has been estimated to be 70 g and the total mass of protein in a human cell has been estimated to be between 100 pg and 500 pg depending upon cells type. See Wisniewski et al. *Molecular & Cellular Proteomics* 13:10.1074/mcp.M113.037309, 3497-3506 (2014), which is incorporated herein by reference. A plurality of proteins used or included in a method, composition or apparatus set forth herein can include at least 1 pg, 10 pg, 100 pg, 1 ng, 10 ng, 100 ng, 1 µg, 10 µg, 100 µg, 1 mg, 10 mg, 100 mg or more protein by mass. Alternatively or additionally, a plurality of proteins may contain at most 100 mg, 10 mg, 1 mg, 100 µg, 10 µg, 1 µg, 100 ng, 10 ng, 1 ng, 100 pg, 10 pg, 1 pg or less protein by mass.

A plurality of proteins can be characterized in terms of percent mass relative to a given source such as a biological source (e.g. cell, tissue, or biological fluid such as blood). For example, a plurality of proteins may contain at least 60%, 75%, 90%, 95%, 99%, 99.9% or more of the total protein mass present in the source from which the plurality of proteins was derived. Alternatively or additionally, a plurality of proteins may contain at most 99.9%, 99%, 95%, 90%, 75%, 60% or less of the total protein mass present in the source from which the plurality of proteins was derived.

A plurality of proteins can be characterized in terms of total number of protein molecules. The total number of protein molecules in a *Saccharomyces cerevisiae* cell has been estimated to be about 42 million protein molecules. See Ho et al., *Cell Systems* (2018), DOI: 10.1016/j.cels.2017.12.004, which is incorporated herein by reference. A plurality of proteins used or included in a method, composition or apparatus set forth herein can include at least 1 protein molecule, 10 protein molecules, 100 protein molecules, $1\times10^4$ protein molecules, $1\times10^6$ protein molecules, $1\times10^8$ protein molecules, $1\times10^{10}$ protein molecules, 1 mole ($6.02214076\times10^{23}$ molecules) of protein, 10 moles of protein molecules, 100 moles of protein molecules or more. Alternatively or additionally, a plurality of proteins may contain at most 100 moles of protein molecules, 10 moles of protein molecules, 1 mole of protein molecules, $1\times10^{10}$ protein molecules, $1\times10^8$ protein molecules, $1\times10^6$ protein molecules, $1\times10^4$ protein molecules, 100 protein molecules, 10 protein molecules, 1 protein molecule or less.

A plurality of proteins can be characterized in terms of the variety of full-length primary protein structures in the plurality. For example, the variety of full-length primary protein structures in a plurality of proteins can be equated with the number of different protein-encoding genes in the source for the plurality of proteins. Whether or not the proteins are derived from a known genome or from any genome at all, the variety of full-length primary protein structures can be counted independent of presence or absence of post translational modifications in the proteins. A human proteome is estimated to have about 20,000 different protein-encoding genes such that a plurality of proteins derived from a human can include up to about 20,000 different primary protein structures. See Aebersold et al., *Nat. Chem. Biol.* 14:206-214 (2018), which is incorporated herein by reference. Other genomes and proteomes in nature are known to be larger or smaller. A plurality of proteins used or included in a method, composition or apparatus set forth herein can have a complexity of at least 2, 5, 10, 100, $1\times10^3$, $1\times10^4$, $2\times10^4$, $3\times10^4$ or more different full-length primary protein structures. Alternatively or additionally, a plurality of proteins can have a complexity that is at most $3\times10^4$, $2\times10^4$, $1\times10^4$, $1\times10^3$, 100, 10, 5, 2 or fewer different full-length primary protein structures.

In relative terms, a plurality of proteins used or included in a method, composition or apparatus set forth herein may contain at least one representative for at least 60%, 75%, 90%, 95%, 99%, 99.9% or more of the proteins encoded by the genome of a source from which the sample was derived. Alternatively or additionally, a plurality of proteins may contain a representative for at most 99.9%, 99%, 95%, 90%, 75%, 60% or less of the proteins encoded by the genome of a source from which the sample was derived.

A plurality of proteins can be characterized in terms of the variety of primary protein structures in the plurality including transcribed splice variants. The human proteome has been estimated to include about 70,000 different primary protein structures when splice variants ae included. See Aebersold et al., *Nat. Chem. Biol.* 14:206-214 (2018), which is incorporated herein by reference. Moreover, the number of the partial-length primary protein structures can increase due to fragmentation that occurs in a sample. A plurality of proteins used or included in a method, composition or apparatus set forth herein can have a complexity of at least 2, 5, 10, 100, $1\times10^3$, $1\times10^4$, $7\times10^4$, $1\times10^5$, $1\times10^6$ or more different primary protein structures. Alternatively or additionally, a plurality of proteins can have a complexity that is at most $1\times10^6$, $1\times10^5$, $7\times10^4$, $1\times10^4$, $1\times10^3$, 100, 10, 5, 2 or fewer different primary protein structures.

A plurality of proteins can be characterized in terms of the variety of protein structures in the plurality including different primary structures and different proteoforms among the primary structures. Different molecular forms of proteins expressed from a given gene are considered to be different proteoforms. Proteoforms can differ, for example, due to differences in primary structure (e.g. shorter or longer amino acid sequences), different arrangement of domains (e.g. transcriptional splice variants), or different post translational modifications (e.g. presence or absence of phosphoryl, glycosyl, acetyl, or ubiquitin moieties). The human proteome is estimated to include hundreds of thousands of proteins when counting the different primary structures and proteoforms. See Aebersold et al., *Nat. Chem. Biol.* 14:206-214 (2018), which is incorporated herein by reference. A plurality of proteins used or included in a method, composition or apparatus set forth herein can have a complexity of at least 2, 5, 10, 100, $1\times10^3$, $1\times10^4$, $1\times10^5$, $1\times10^6$, $5\times10^6$, $1\times10^7$ or more different protein structures. Alternatively or additionally, a plurality of proteins can have a complexity that is at most $1\times10^7$, $5\times10^6$, $1\times10^6$, $1\times10^5$, $1\times10^4$, $1\times10^3$, 100, 10, 5, 2 or fewer different protein structures.

A plurality of proteins can be characterized in terms of the dynamic range for the different protein structures in the sample. The dynamic range can be a measure of the range of abundance for all different protein structures in a plurality of proteins, the range of abundance for all different primary protein structures in a plurality of proteins, the range of abundance for all different full-length primary protein structures in a plurality of proteins, the range of abundance for all different full-length gene products in a plurality of proteins, the range of abundance for all different proteoforms expressed from a given gene, or the range of abundance for any other set of different proteins set forth herein. The dynamic range for all proteins in human plasma is estimated to span more than 10 orders of magnitude from albumin, the most abundant protein, to the rarest proteins that have been measured clinically. See Anderson and Anderson *Mol Cell Proteomics* 1:845-67 (2002), which is incorporated herein by reference. The dynamic range for plurality of proteins set forth herein can be a factor of at least 10, 100, $1\times10^3$, $1\times10^4$, $1\times10^6$, $1\times10^8$, $1\times10^{10}$, or more. Alternatively or additionally, the dynamic range for plurality of proteins set forth herein can be a factor of at most $1\times10^{10}$, $1\times10^8$, $1\times10^6$, $1\times10^4$, $1\times10^3$, 100, 10 or less.

A method set forth herein can be carried out in a fluid phase or on a solid phase. For fluid phase configurations, a fluid containing one or more proteins can be mixed with another fluid containing one or more affinity agents. For solid phase configurations one or more proteins or affinity agents can be attached to a solid support. One or more components that will participate in a binding event can be contained in a fluid and the fluid can be delivered to a solid support, the solid support being attached to one or more other component that will participate in the binding event.

A method of the present disclosure can be carried out at single analyte resolution. Alternatively to single-analyte resolution, a method can be carried out at ensemble-resolution or bulk-resolution. Bulk-resolution configurations acquire a composite signal from a plurality of different analytes or affinity agents in a vessel or on a surface. For example, a composite signal can be acquired from a population of different protein-affinity agent complexes in a well or cuvette, or on a solid support surface, such that individual complexes are not resolved from each other. Ensemble-resolution configurations acquire a composite signal from a first collection of proteins or affinity agents in a sample, such that the composite signal is distinguishable from signals generated by a second collection of proteins or affinity agents in the sample. For example, the ensembles can be located at different addresses in an array. Accordingly, the composite signal obtained from each address will be an average of signals from the ensemble, yet signals from different addresses can be distinguished from each other.

A composition, apparatus or method set forth herein can be configured to contact one or more proteins (e.g. an array of different proteins) with a plurality of different affinity agents. For example, a plurality of affinity agents (whether configured separately or as a pool) may include at least 2, 5, 10, 25, 50, 100, 250, 500 or more types of affinity agents, each type of affinity agent differing from the other types with respect to the epitope(s) recognized. Alternatively or additionally, a plurality of affinity agents may include at most 500, 250, 100, 50, 25, 10, 5, or 2 types of affinity agents, each type of affinity agent differing from the other types with respect to the epitope(s) recognized. Different types of affinity agents in a pool can be uniquely labeled such that the different types can be distinguished from each other. In some configurations, at least two, and up to all, of the different types of affinity agents in a pool may be indistinguishably labeled with respect to each other. Alternatively or additionally to the use of unique labels, different types of affinity agents can be delivered and detected serially when evaluating one or more proteins (e.g. in an array).

A method of the present disclosure can be performed in a multiplex format. In multiplexed configurations, different proteins can be attached to different unique identifiers (e.g. the proteins can be attached to different addresses in an array). Multiplexed proteins can be manipulated and detected in parallel. For example, a fluid containing one or more different affinity agents can be delivered to a protein array such that the proteins of the array are in simultaneous contact with the affinity agent(s). Moreover, a plurality of addresses can be observed in parallel allowing for rapid detection of binding events. A plurality of different proteins can have a complexity of at least 5, 10, 100, $1\times10^3$, $1\times10^4$, $2\times10^4$, $3\times10^4$ or more different native-length protein primary sequences. Alternatively or additionally, a proteome or proteome subfraction that is analyzed in a method set forth herein can have a complexity that is at most $3\times10^4$, $2\times10^4$, $1\times10^4$, $1\times10^3$, 100, 10, 5 or fewer different native-length protein primary sequences. The plurality of proteins can constitute a proteome or subfraction of a proteome. The total number of proteins that is detected, characterized or identified can differ from the number of different primary sequences in the sample from which the proteins are derived, for example, due to the presence of multiple copies of at least some protein species. Moreover, the total number of proteins that are detected, characterized or identified can differ from the number of candidate proteins suspected of being present, for example, due to the presence of multiple copies of at least some protein species, absence of some proteins in a source for the proteins, or loss of some proteins prior to analysis.

A particularly useful multiplex format uses an array of proteins and/or affinity agents. A polypeptide, anchoring group, polypeptide composite or other analyte can be attached to a unique identifier, such as an address in an array, using any of a variety of means. The attachment can be covalent or non-covalent. Exemplary covalent attachments include chemical linkers such as those achieved using click chemistry or other linkages known in the art or described in US Pat. App. Pub. No. 2021/0101930 A1, which is incorporated herein by reference. Non-covalent attachment can be mediated by receptor-ligand interactions (e.g. (strept) avidin-biotin, antibody-antigen, or complementary nucleic acid strands), for example, in which the receptor is attached to the unique identifier and the ligand is attached to the protein or vice versa. In particular configurations, a protein is attached to a solid support (e.g. an address in an array) via a structured nucleic acid particle (SNAP). A protein can be attached to a SNAP and the SNAP can interact with a solid support, for example, by non-covalent interactions of the DNA with the support and/or via covalent linkage of the SNAP to the support. Nucleic acid origami or nucleic acid nanoballs are particularly useful. The use of SNAPs and other moieties to attach proteins to unique identifiers such as tags or addresses in an array are set forth in US Pat. App. Pub. No. 2021/0101930 A1, which is incorporated herein by reference.

In some embodiments, a solid support allows for positioning of one or more analytes (e.g., proteins) or affinity agents. A solid support can have a surface onto which one or more analytes or affinity agents can be affixed (e.g., a chip, solid array, a bead, a slide, a coverslip, etc.). Optionally, the solid support can be rigid. The solid support can be non-porous or porous. The solid support can optionally be capable of taking up a liquid (e.g., due to porosity) but will typically, but not necessarily, be sufficiently rigid that the substrate does not swell substantially when taking up the liquid and does not contract substantially when the liquid is removed by drying. A nonporous solid support is generally impermeable to liquids or gases. Exemplary solid support include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, gels, and polymers. In some cases, a solid support comprises silicon, fused silica, quartz, mica, or borosilicate glass. In particular configurations, a flow cell contains the solid support such that fluids introduced to the flow cell can interact with a surface of the solid support to which one or more components of a binding event (or other reaction) is attached. In addition, in some embodiments, a solid support functions as a support for direct or indirect attachment of the one or more analytes or affinity agents.

A solid support or a surface thereof may be configured to display an analyte or a plurality of analytes. A solid support may contain one or more patterned, formed, or prepared surfaces that contain at least one address for displaying an analyte. In some cases, a solid support may contain one or more patterned, formed, or prepared surfaces that contain a plurality of addresses, with each address configured to display one or more analytes. Accordingly, an array as set forth herein may comprise a plurality of analytes coupled to a solid support or a surface thereof. In some configurations, a solid support or a surface thereof may be patterned or formed to produce an ordered or patterned array of addresses. The deposition of analytes on the ordered or patterned array of addresses may be controlled by interactions between the solid support and the analytes such as, for example, electrostatic interactions, magnetic interactions, hydrophobic interactions, hydrophilic interactions, covalent interactions, or non-covalent interactions. Accordingly, the coupling of an analyte at each address of an array may produce an ordered or patterned array of analytes whose average spacing between analytes is determined based upon the tolerance of the ordering or patterning of the solid support and the size of an analyte-binding region for each address. An ordered or patterned array of analytes may be characterized as having a regular geometry, such as a rectangular, triangular, polygonal, or annular grid. In other configurations, a solid support or a surface thereof may be non-patterned or non-ordered. The deposition of analytes on the non-ordered or non-patterned array of addresses may be controlled by interactions between the solid support and the analytes, or inter-analyte interactions such as, for example, steric repulsion, electrostatic repulsion, electrostatic attraction, magnetic repulsion, magnetic attraction, covalent interactions, or non-covalent interactions.

A solid support or a surface thereof may contain one or more structures or features. A structure or feature may comprise an elevation, profile, shape, geometry, or configuration that deviates from an average elevation, profile, shape, geometry, or configuration of a solid support or surface thereof. A structure or feature may be a raised structure or feature, such as a ridge, post, pillar, or pad, if the structure or feature extends above the average elevation of a surface of a solid support. A structure or feature may be a depressed structure, such as a channel, well, pore, or hole, if the structure or feature extends below the average elevation of a surface of a solid support. A structure or feature may be an intrinsic structure or feature of a substrate (i.e., arising due to the physical or chemical properties of the substrate, or a physical or chemical mechanism of formation), such as surface roughness structures, crystal structures, or porosity. A structure or feature may be formed by a method of processing a solid support. In some configurations, a solid support or a surface may be processed by a lithographic method to form one or more structures or features. A solid support or a surface thereof may be formed by a suitable lithographic method, including, but not limited to photolithography, Dip-Pen nanolithography, nanoimprint lithography, nanosphere lithography, nanoball lithography, nanopillar arrays, nanowire lithography, immersion lithography, neutral particle lithography, plasmonic lithography, scanning probe lithography, thermochemical lithography, thermal scanning probe lithography, local oxidation nanolithography, molecular self-assembly, stencil lithography, laser interference lithography, soft lithography, magnetolithography, stereolithography, deep ultraviolet lithography, x-ray lithography, ion projection lithography, proton-beam lithography, or electron-beam lithography.

A solid support or surface may comprise a plurality of structures or features (e.g., raised features, indented features, functionalized regions, non-functionalized regions, etc.). A plurality of structures or features may comprise an ordered or patterned array of structures or features. A plurality of structures or features may comprise an non-ordered, non-patterned, or random array of structures or features. A structure or feature may have an average characteristic dimension (e.g., length, width, height, diameter, circumference, etc.) of at least about 1 nanometer (nm), 5 nm, 10 nm, 20 nm, 30 nm, 40 nm, 50 nm, 75 nm, 100 nm, 150 nm, 200 nm, 250 nm, 300 nm, 400 nm, 500 nm, 750 nm, 1000 nm, or more than 1000 nm. Alternatively or additionally, a structure or feature may have an average characteristic dimension of no more than about 1000 nm, 750 nm, 500 nm, 400 nm, 300 nm, 250 nm, 200 nm, 150 nm, 100 nm, 75 nm, 50 nm, 40 nm, 30 nm, 20 nm, 10 nm, 5 nm, 1 nm, or less than 1 nm. An array of structures or features may have an average pitch, in which the pitch is measured as the average separation between respective centerpoints of neighboring structures or features. An array may have an average pitch of at least about 1 nm, 5 nm, 10 nm, 20 nm, 30 nm, 40 nm, 50 nm, 75 nm, 100 nm, 150 nm, 200 nm, 250 nm, 300 nm, 400 nm, 500 nm, 750 nm, 1 micron ($\mu$m), 2 $\mu$m, 5 $\mu$m, 10 $\mu$m, 50 $\mu$m, 100 $\mu$m, or more than 100 $\mu$m. Alternatively or additionally, an array may have an average pitch of no more than about 100 $\mu$m, 50 $\mu$m, 10 $\mu$m, 5 $\mu$m, 1 $\mu$m, 750 nm, 500 nm, 400 nm, 300 nm, 250 nm, 200 nm, 150 nm, 100 nm, 75 nm, 50 nm, 40 nm, 30 nm, 20 nm, 10 nm, 5 nm, 1 nm, or less than 1 nm. A dimension or pitch of a structure or feature of an array may be determined based upon or in concert with a detection system that is configured to interrogate the array. For example, a pitch of a plurality of array sites may be determined based upon a magnification, working distance, and/or sensor position of an optical detection system such that each array site corresponds to a single pixel of a pixel array of the sensor. In another example, a feature dimension of an array site may be sufficiently small enough to be captured fully within an M×N block of pixels of a pixel array (e.g., a pixel block with an aspect of 3×3, 4×4, 5×5, 2×3, 3×4, 4×5, etc.).

A solid support or a surface thereof may include a base substrate material and, optionally, one or more additional materials that are contacted or adhered with the substrate material. A solid support may comprise one or more additional materials that are deposited, coated, or inlayed onto the substrate material. Additional materials may be added to the substrate material to alter the properties of the substrate material. For example, materials may be added to alter the surface chemistry (e.g., hydrophobicity, hydrophilicity, non-specific binding, electrostatic properties), alter the optical properties (e.g., reflective properties, refractive properties), alter the electrical or magnetic properties (e.g., dielectric materials, conducting materials, electrically-insulating materials), or alter the heat transfer characteristics of the substrate material. Additional materials contacted or adhered with a substrate material may be ordered or patterned onto the substrate material to, for example, locate the additional material at addresses or locate the additional material at interstitial regions between addresses. Exemplary additional materials may include metals (e.g., gold, silver, copper, etc.), metal oxides (e.g., titanium oxide, silicon dioxide, alumina, iron oxides, etc.), metal nitrides (e.g., silicon nitride, aluminum nitride, boron nitride, gallium nitride, etc.), metal carbides (e.g., tungsten carbide, titanium carbide, iron carbide, etc.), metal sulfides (e.g., iron sulfide, silver sulfide, etc.), and organic moieties (e.g., polyethylene glycol (PEG), dextrans, chemically-reactive functional groups, etc.).

A method of the present disclosure can include the step of coupling one or more analytes to a solid support or a surface thereof prior to performing a detection step set forth herein. The coupling of one or more analytes to a solid support surface may include covalent or non-covalent coupling of the one or more analytes to the solid support. Covalent coupling of an analyte to a solid support can include direct covalent coupling of an analyte to a solid support (e.g., formation of coordination bonds) or indirect covalent coupling between a reactive functional group of the analyte and a reactive functional group that is coupled to the solid support (e.g., a CLICK-type reaction). Non-covalent coupling can include the formation of any non-covalent interaction between an analyte and a solid support, including electrostatic or magnetic interactions, or non-covalent bonding interactions (e.g., ionic bonds, van der Waals interactions, hydrogen bonding, etc.). The skilled person will readily recognize that the particular analyte and the choice of solid support can affect the selection of a coupling chemistry for the compositions and methods set forth herein.

Accordingly, a coupling chemistry may be selected based upon the criterion that it provides a sufficiently stable coupling of an analyte to a solid support for a time scale that meets or exceeds the time scale of a method as set forth herein. For example, a polypeptide identification method can require a coupling of the analyte to the solid support for a sufficient amount of time to permit a series of empirical measurements of the analyte to occur. An analyte may be continuously coupled to a solid support for an observable length of time such as, for example, at least about 1 minute, 1 hour (hr), 3 hrs, 6 hrs, 12 hrs, 1 day, 1.5 days, 2 days, 3 days, 1 week (wk), 2 wks, 3 wks, 1 month, or more. The coupling of an analyte to a solid support can occur with a solution-phase chemistry that promotes the deposition of the analyte on the solid support. Coupling of an analyte to a solid support may occur under solution conditions that are optimized for any conceivable solution property, including solution composition, species concentrations, pH, ionic strength, solution temperature, etc. Solution composition can be varied by chemical species, such as buffer type, salts, acids, bases, and surfactants. In some configurations, species such as salts and surfactants may be selected to facilitate the formation of interactions between an analyte and a solid support. Covalent coupling methods for coupling an analyte to a solid support may include species such as catalyst, initiators, and promoters to facilitate particular reactive chemistries.

Coupling of an analyte to a solid support may be facilitated by a mediating group. A mediating group may modify the properties of the analyte to facilitate the coupling. Useful mediating groups have been set forth herein (e.g., structured nucleic acid particles). In some configurations, a mediating group can be coupled to an analyte prior to coupling the analyte to a solid support. Accordingly, the mediating group may be chosen to increase the strength, control, or specificity of the coupling of the analyte to the solid support. In other configurations, a mediating group can be coupled to a solid support prior to coupling an analyte to the solid support. Accordingly, the mediating group may be chosen to provide a more favorable coupling chemistry than can be provided by the solid support alone.

Exemplary mediating groups (e.g., linkers) for attaching proteins, or other objects of interest, to an array or other solid support are set forth in US Pat. App. Pub. No. 2021/0101930 A1, which is hereby incorporated herein by reference in its entirety.

EXAMPLES

Example 1: Polypeptide Identification Assay

An array is prepared for a polypeptide identification assay. The array is patterned onto a surface of a silicon solid support utilizing a photolithography method. The array comprises 100000000 array sites that are patterned into rectangular subarrays of 100×100 sites. Each array site comprises a characteristic diameter of about 300 nanometers, with a pitch of about 1 micron between each array site. Each subarray is separated from neighboring subarrays by interstitial lanes that do not comprise array sites. Interstitial lanes comprise etched silicon fiducial elements at regular intervals. Each etched silicon fiducial element comprises a cross pattern with a substantially planar top surface that is configured to be detectable by reflection of white light. Each array sites comprises a substantially uniform layer of oligonucleotides that are configured to hybridize to complementary oligonucleotides of polypeptide anchoring groups. Interstitial regions between array sites are PEGylated to minimize non-specific binding of entities between array sites. The array is disposed within a fluidic cartridge that permits controlled delivery and extraction of fluids to the array through a fluidic system that couples to the fluidic cartridge.

Prior to a polypeptide identification assay, the array is contacted with a fluidic medium comprising fluorescently-labeled polymer nanoparticles, with each polymer nanoparticle having a fluorescent emission wavelength of about 517 nanometers (nm). Each fluorescently-labeled polymer nanoparticle is covalently coupled to a structured nucleic acid particle comprising a DNA origami structure. Each DNA origami structure further comprises a plurality of single-stranded oligonucleotides that are complementary to the oligonucleotides coupled to each array site. A total quantity of fluorescently-labeled polymer nanoparticles is sufficient to provide a total surface occupancy rate of about 0.1% relative to the total quantity of array sites (i.e., about 100000 array sites containing a coupled fluorescently-labeled polymer nanoparticle). The fluidic medium comprising the fluorescently-labeled polymer nanoparticles is incubated on the array for sufficient time to randomly deposit the polymer nanoparticles at array sites of the array. After depositing the fluorescently-labeled polymer nanoparticles on the array, the array is rinsed by a rinsing fluid, then imaged by fluorescent microscopy under an excitation light field of about 493 nm. The array is imaged in a linescan mode utilizing TDI imaging. Fluorescent emission from array sites comprising fluorescently-labeled polymer nanoparticles is detected on a pixel-based array, and the detected imaging data is transferred to a processor comprising an image analysis algorithm. The fluorescence data is utilized to determine an array map comprising spatial locations of array sites comprising coupled fluorescently-labeled polymer nanoparticles. The array map further comprises locations of etched silicon fiducial elements in interstitial lanes. A second image analysis algorithm identifies patterns of deposited fluorescently-labeled polymer nanoparticles for each subarray of the array and stores the pattern data in a data structure comprising the array map.

A polypeptide identification assay is initiated by coupling polypeptides to the array containing the randomly deposited fluorescently-labeled polymer nanoparticles. The array is contacted with a fluorescent medium comprising a plurality of polypeptides. Each polypeptide is coupled to a structured nucleic acid nanoparticle. The structure of the structured nucleic acid nanoparticle is substantially the same as the structure of the structured nucleic acid nanoparticle coupled to the fluorescently-labeled polymer nanoparticles. The polypeptides are incubated on the array, thereby depositing polypeptides at unoccupied array sites by coupling of the structured nucleic acid particles to the array sites. After depositing polypeptides at unoccupied array sites, the array is rinsed with a rinsing fluidic medium. The array is subsequently contacted with a fluidic medium comprising internal standard polypeptides. Each internal standard polypeptide further comprises a reactive Click-type functional group that is configured to form a covalent interaction with a complementary functional group on each fluorescently-labeled polymer nanoparticle. The fluidic medium containing the internal standard polypeptides is incubated for sufficient time to permit coupling of internal standard polypeptides to at least 75% of fluorescently-labeled polymer nanoparticles. The array is rinsed again with a rinsing fluid to remove unbound internal standard polypeptides from the array.

After completing polypeptide deposition, a polypeptide identification assay is performed on the array. The polypeptide identification assay comprises 300 cycles of affinity agent binding and detection. Each cycle of the 300 cycles comprises the steps of: 1) incubating the array with a fluidic medium comprising a plurality of fluorescently-labeled affinity agents that are configured to couple polypeptides of the polypeptide array, 2) rinsing the array to remove unbound affinity agents after incubation, 3) imaging the polypeptide array by fluorescent microscopy to identify array sites comprising coupled affinity agents and/or fluorescently-labeled polymer nanoparticles, and 4) stripping bound affinity agents from the array via incubation in a stripping fluidic medium. Each cycle of the 300 cycles utilizes a pool of affinity agents in which each affinity agent is configured to couple an epitope that can be found in at least one polypeptide on the polypeptide array. Each affinity agent may be further characterized by a binding promiscuity in the respect that the affinity agent may bind to one or more additional epitopes other than the epitope to which it has a highest binding affinity. Each affinity agent of each affinity pool is fluorescently-labeled with a fluorophore that is excited at a wavelength of about 650 nm and emits at a wavelength of about 663 nm. During each cycle of the 300 cycles, the entire array is imaged by linescan TDI imaging under excitation by two lasers with about 493 nm (for fiducial imaging) and 650 nm excitation wavelengths (for affinity agent imaging), respectively. The optical imaging system also utilizes an autofocus device that utilizes reflection of light from a white light source off etched fiducial elements to determine optimal focus of the system. Emission signals at about 517 nm and 663 nm are captured on separate pixel-based array sensors. Fluorescent signal data is obtained at both wavelengths for the entirety of each array during each cycle of the 300 cycles. Fluorescent signal data is transferred to a processor comprising an image analysis algorithm that is configured to identify array sites producing a fluorescent signal.

Fluorescent signal data is analyzed for each cycle. The image analysis algorithm utilize detected patterns of fluorescently-labeled polymer nanoparticles (as determined from the 517 nm imaging data) and detected etched fiducial elements to identify subarrays by registering patterns of detected polymer nanoparticles against the array map. After identifying subarrays, corresponding 663 nm fluorescence data from each subarray is bucketed into a data structure for the subarray. The identification of subarrays and bucketing of affinity agent detection data for each cycle is repeated for each cycle of the 300 cycles. After image analysis is completed for each cycle of the 300 cycles, subarray data is provided to a polypeptide identity decoding algorithm. A pattern of affinity agent binding (e.g., binding/no binding/uncertain binding) for each site of each subarray is provided to the decoding algorithm. The pattern of affinity agent binding is utilized to determine a most probable identity for a polypeptide at the array site. Each array site of each subarray is analyzed to provide single-analyte identification of each polypeptide on the array.

Example 2. Arrays Containing Optically Active Moieties

Optically active moieties comprising fluorescently-labeled polymer nanoparticles were deposited on arrays to form random dispersions of the optically active moieties. Each array was formed by the deposition of ThermoFisher carboxylate-modified FluoSpheres™ labeled with 647 nm fluorescent dyes (40 nanometer average particle size). The FluoSpheres as provided were diluted via suspension in a buffer comprising 5 mM Tris-HCl— pH 8.0, 205 mM NaCl, 1 mM EDTA, and 12.5 mM $MgCl_2$ at $10^7$-fold and $10^8$-fold dilutions.

Figure 26B:
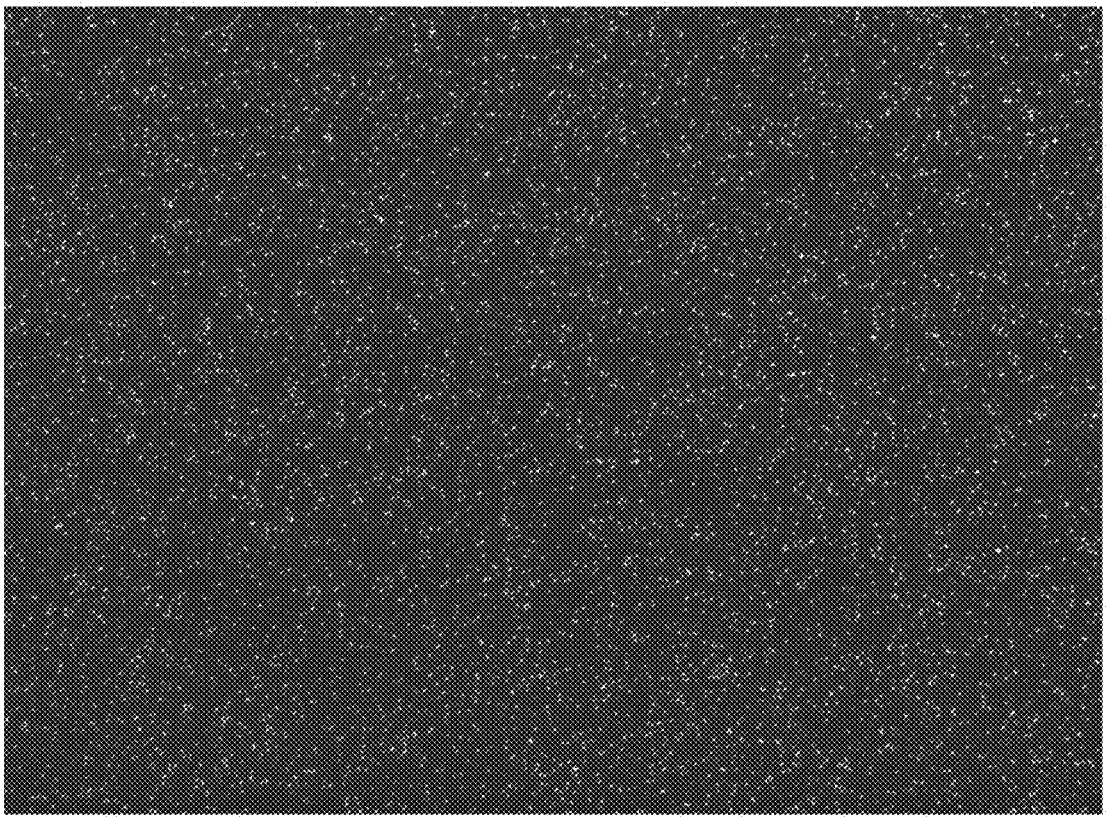
FIGS. 26A, 26B, 26C, and 26D display fluorescence microscopy imaging data of fluorescently-labeled polymer nanoparticles deposited on unpatterned and patterned array in random spatial distributions.
Figure 26A:
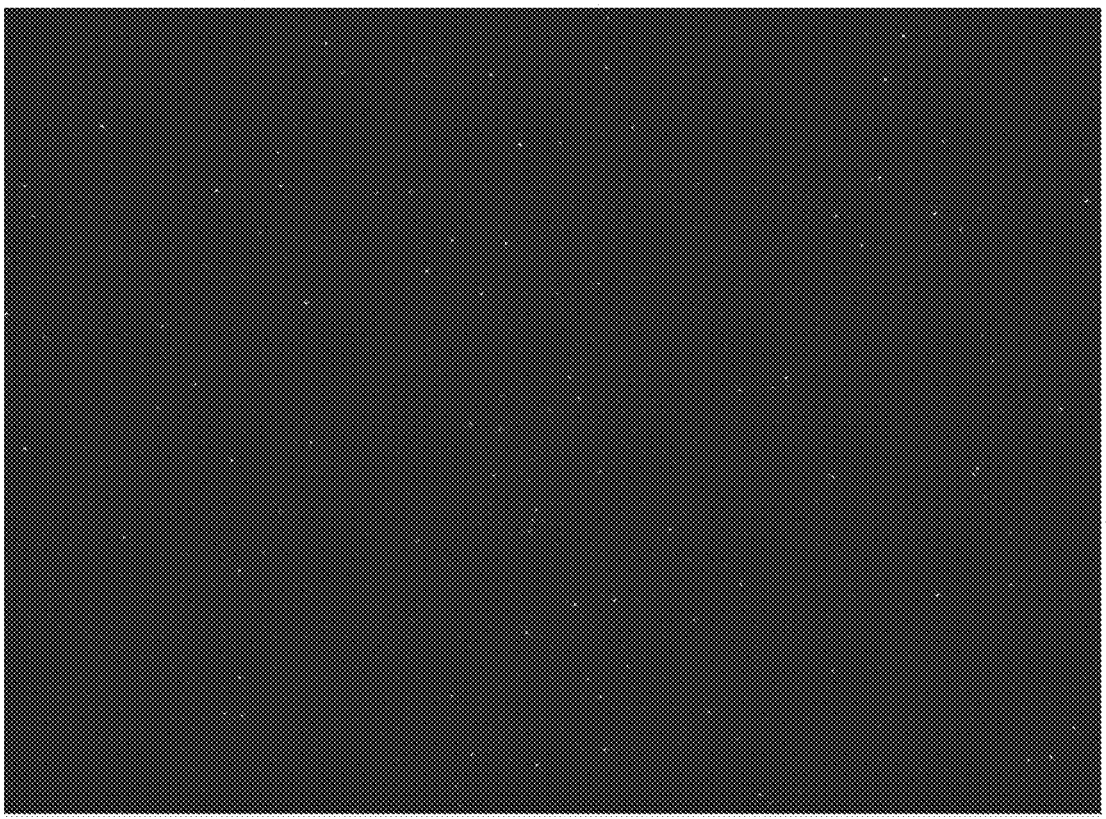

FluoSpheres were deposited on unpatterned arrays. The arrays comprised a planar glass surface with a uniform surface layer comprising (3-aminopropyl) trimethoxysilane (APTMS). FluoSpheres were incubated on a first and a second unpatterned array at the dilutions of $10^7$-fold and $10^8$-fold, respectively, for 10 minutes. After deposition, unbound FluoSpheres were rinsed from the arrays. After rinsing, each array was imaged by confocal fluorescence microscopy using a 647 nm laser light source. Images were collected for both arrays to identify the spatial distribution of FluoSpheres deposited on each array. FIGS. 26A and 26B display representative images of deposited FluoSpheres on unpatterned arrays at $10^8$-fold and $10^7$-fold dilutions, respectively. The array incubated with the higher concentration contained a higher surface concentration of deposited FluoSpheres. The spatial distribution of deposited FluoSpheres appears random, with no discernible short-range or long-range order in the set of array sites on which the FluoSpheres were deposited.

Figure 26D:
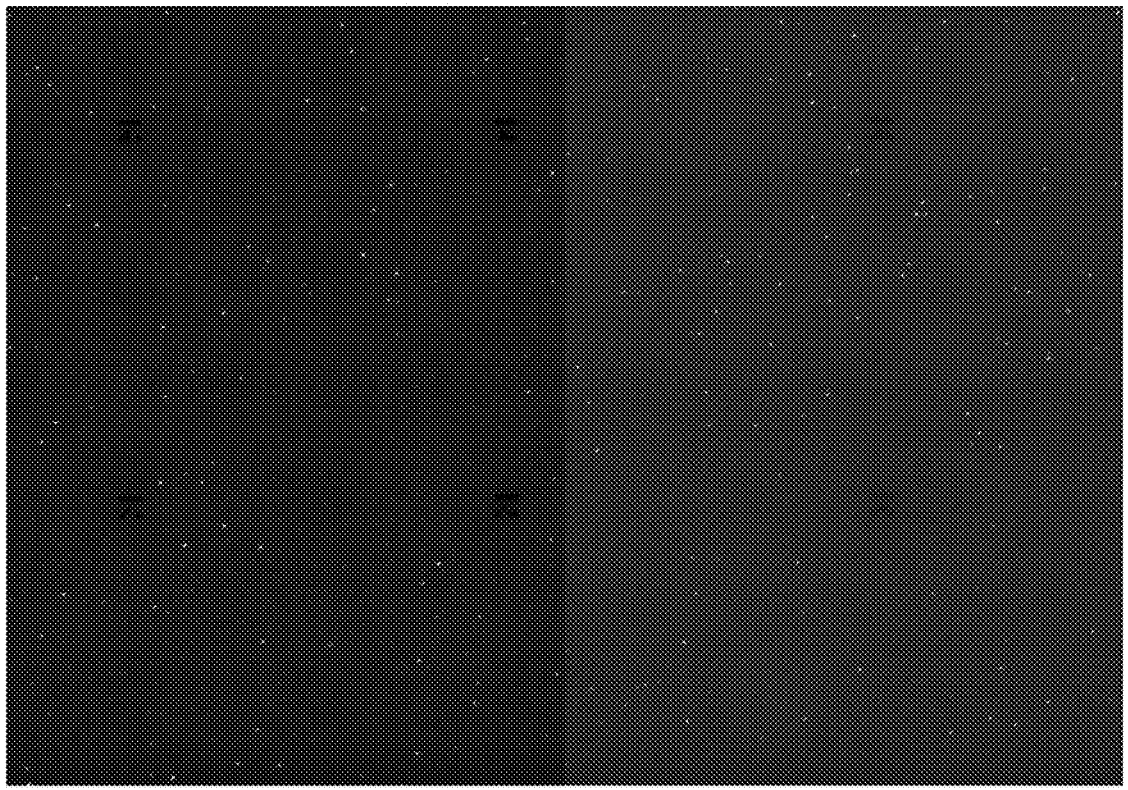
Figure 26C:
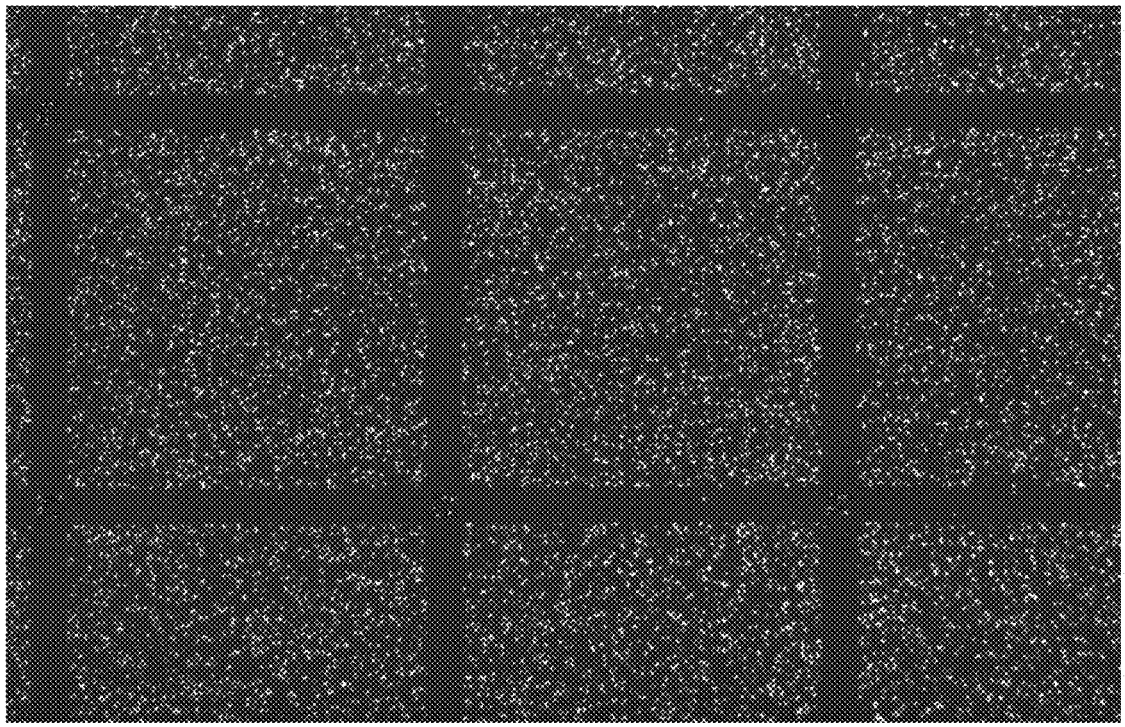

FluoSpheres were also deposited on patterned arrays. Each patterned array comprised a planar glass substrate with an array of sites formed in a substantially uniform rectangular pattern. The array sites were separated in subarrays, in which each subarray comprised a square field of array sites with substantially uniform spacing. Each subarray was separated from each other subarray by a lane that contained no binding sites. Each array site comprised an APTMS surface layer coupled to the glass substrate. FluoSpheres were incubated on a first and a second patterned array at the dilutions of $10^7$-fold and $10^8$-fold, respectively, for 10 minutes. After deposition, unbound FluoSpheres were rinsed from the arrays. After rinsing, each array was imaged by confocal fluorescence microscopy using a 647 nm laser light source. Images were collected for both arrays to identify the spatial distribution of FluoSpheres deposited on each array. FIGS. 26C and 26D display representative images of deposited FluoSpheres on patterned arrays at $10^8$-fold and $10^7$-fold dilutions, respectively. The array incubated with the higher concentration contained a higher surface concentration of deposited FluoSpheres. The spatial distribution of deposited FluoSpheres appears random, with no discernible short-range or long-range order in the set of array sites on which the FluoSpheres were deposited. Moreover, FluoSpheres were not observed substantially to not bind to regions not comprising APTMS (i.e., interstitial regions and lanes).

Example 3. Array Containing Patterned Fiducial Elements

An array was formed on a glass substrate by a lithographic process. The patterned array comprised a planar glass substrate with an array of sites formed in a substantially uniform rectangular pattern. The array sites were separated in subarrays, in which each subarray comprised a square field of array sites with substantially uniform spacing. Each subarray was separated from each other subarray by a lane that contained no uniformly patterned binding sites. Patterned fiducial elements were formed during the same lithographic process that formed the array sites. Each fiducial element was located in a lane at the junction where four corners of adjacent subarrays met. Each fiducial element had a unique two-dimensional pattern that distinguished it from each other lithographically-formed fiducial element. Each array site comprised an APTMS surface layer coupled to the glass substrate.

Figure 27B:
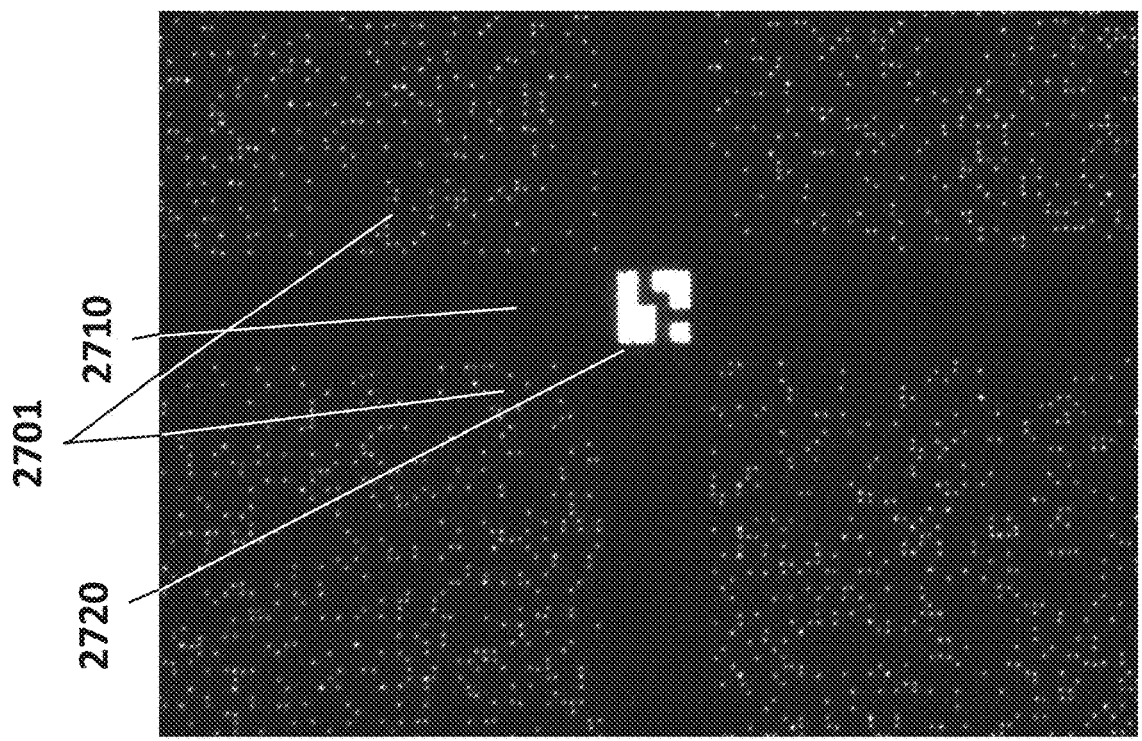
FIGS. 27A and 27B display fluorescence microscopy imaging data of lithographically-formed glass fiducial elements with unique spatial patterns on a patterned array.
Figure 27A:
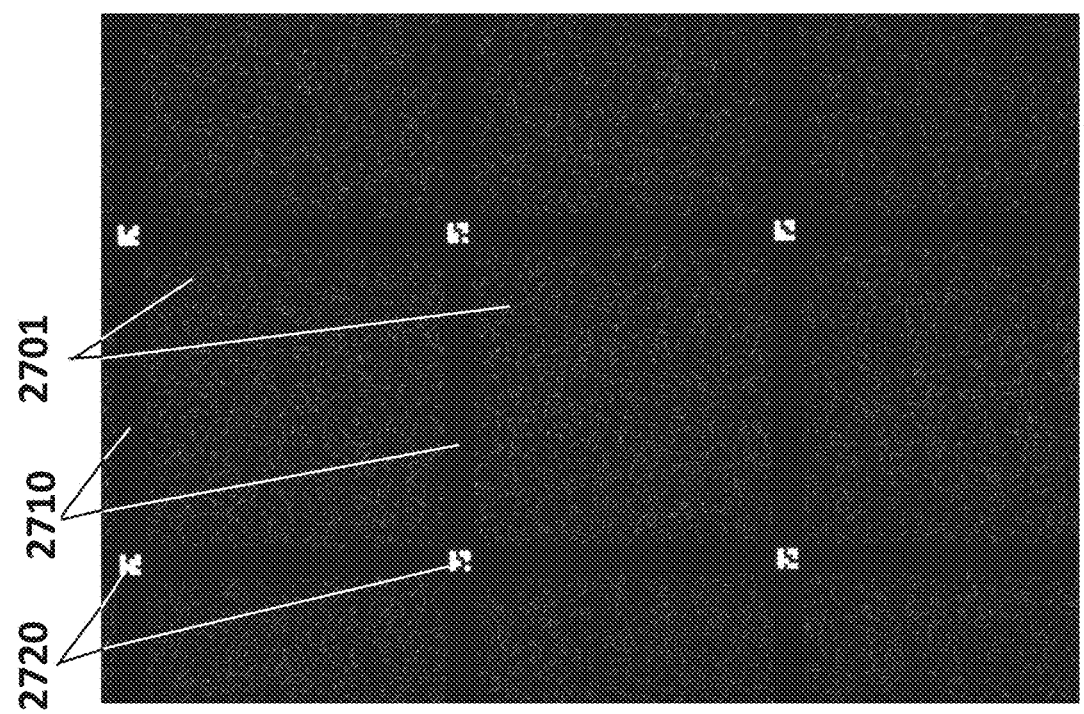

Arrays were contacted with fluorescently-labeled structured nucleic acid particles (SNAPs). Each SNAP comprised multiple Alexa-Fluor 488 fluorescent labels. The SNAPs were incubated on each array at a concentration of 50 picoMolar (pM) for 15 minutes. After incubation, unbound SNAPs were rinsed from the array. FIG. 27A depicts a view of multiple subarrays 2701 imaged by fluorescence microscopy after irradiation at a wavelength of 488 nanometers (nm). The rectangular pattern of array sites is observed to be illuminated by emission of fluorescent signals from array sites comprising bound SNAPs. The fiducial elements 2720 in the lanes 2710 are also visible due to emission of fluorescent signals from SNAPs bound to the fiducial elements. FIG. 27B depicts a higher magnification view of the array imaged in FIG. 27B.

Example 4. Preparation of Modified Fluorescent Nanoparticles

Fluorescently-labeled polymer nanoparticles comprising a PEGylated passivation layer and oligonucleotides were prepared. Carboxyl-functionalized, fluorescently-labeled polystyrene nanoparticles were prepared in a two-step process to provide the passivation layer and the surface-displayed oligonucleotide coupling moieties. Methods of nanoparticle preparation were adapted from Stawicki, C. M., et al. "Modular Fluorescent Nanoparticle DNA probes for Detection of Peptides and Proteins." *Scientific Reports*, 11, 2022, 1-15, which is herein incorporated by reference in its entirety.

30 µL of 3 µM carboxyl-functionalized polystyrene microspheres from Bangs Laboratories or ThermoFisher Fluospheres™ (100 nm average diameter) were sonicated briefly to suspend the nanoparticles in solution (separate preparations were made for microspheres with 505 nm and 660 nm emission wavelengths). The microsphere solution was mixed with 500 µL of EDC solution (100 mM EDC in 20 mM MES and 500 mM NaCl, pH 6.0) and 500 µL of NHS solution (200 mM NHS in 20 mM MES and 500 mM NaCl, pH 6.0). The mixture was sonicated, then placed in a shaker at 800 rpm for 1 hour at 24° C. Reacted fluorescent microspheres were collected by centrifugation, then transferred into 1 mL of pH 7.4 PBS solution. 475 µL of $CH_3$—$PEG_2K$—$NH_2$ molecules (200 mg/mL in 1×PBS solution) and 25 µL of $N_3$—$PEG_2K$—$NH_2$ molecules were mixed with the microspheres in the PBS solution. The mixture was placed in a shaker at 800 rpm for 12 hours at 24° C. Reacted fluorescent microspheres were collected by centrifugation, then transferred into 500 µL of pH 7.4 PBS solution. PEGylated microspheres in PBS solution were mixed with DBCO-functionalized oligonucleotides with a 1.5× excess of oligonucleotides and allowed to undergo a Copper-free click-type reaction. The mixture was placed in a shaker at 800 rpm for 24 hours at 24° C. The oligo-modified microspheres were collected by centrifugation and stored in 1×PBS solution.

During preparation of oligo-modified fluorescent microspheres, nanoparticle characteristics were measured by dynamic light scattering (DLS) and Zeta potential. Carboxyl-functionalized microspheres were measured to have an average diameter of 104 nm via DLS, and a Zeta potential of −36 mV. After the PEGylation reaction step, functionalized microspheres were measured to have an average diameter of 128 nm via DLS, and a Zeta potential of −15 mV. The final oligonucleotide-functionalized microspheres were measured to have a 129 nm average diameter via DLS, and a Zeta potential of −22 mV.

Example 5. Preparation of Patterned Arrays with Distributions of Fiducial Elements Oligonucleotide-functionalized microspheres as described in Example 4 were deposited on patterned arrays. Patterned chips were prepared via photolithography of silicon wafers to form patterned arrays with ~100 nm array sites with 1 μm of pitch between adjacent array sites. Each array site comprised a plurality of organosilane surface-coupled moieties, with each organosilane surface-coupled moiety comprising a PEGylated passivating linker and a terminal oligonucleotide. The terminal oligonucleotide of each surface-coupled moiety comprised a nucleotide sequence that was complementary to the nucleotide sequence of the oligonucleotides attached to the fluorescently-labeled microspheres described in Example 4.

Figure 33B:
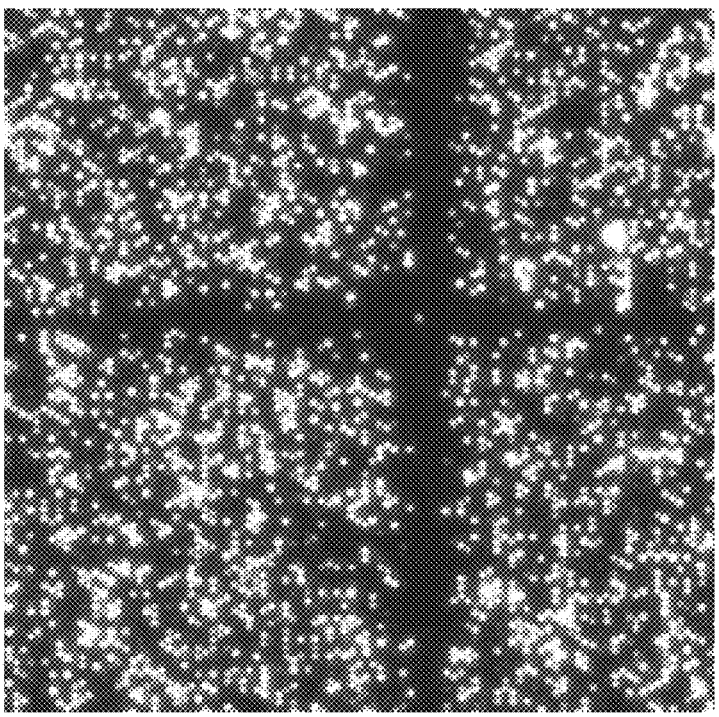
FIGS. 33A, 33B, 33C, 33D, 33E, and 33F show fluorescent microscopy images of patterned arrays comprising deposited fluorescent nanoparticle fiducial elements.
Figure 33A:
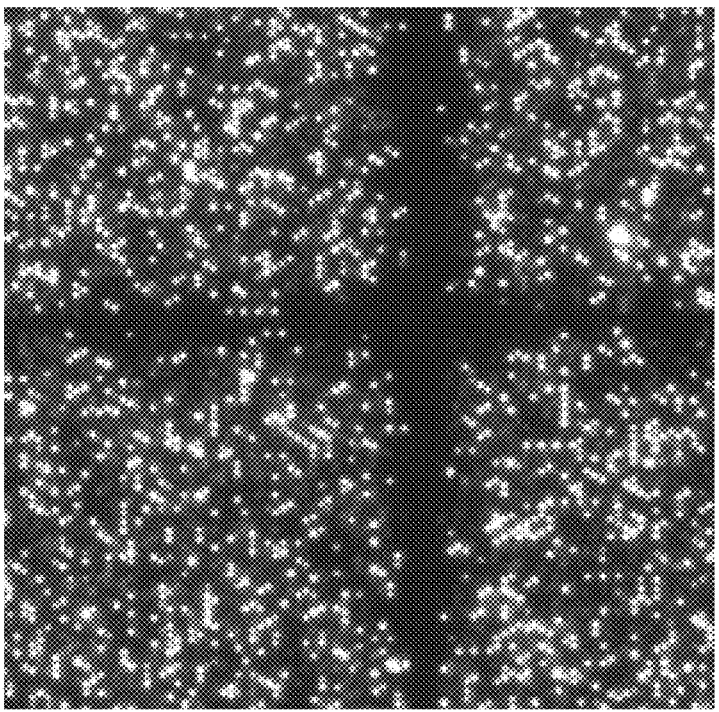
Figure 33D:
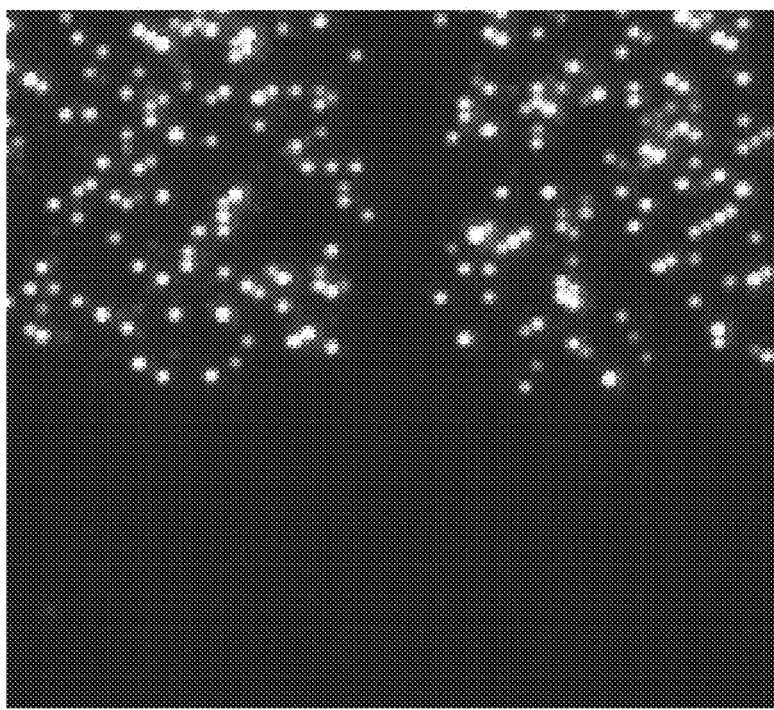
Figure 33C:
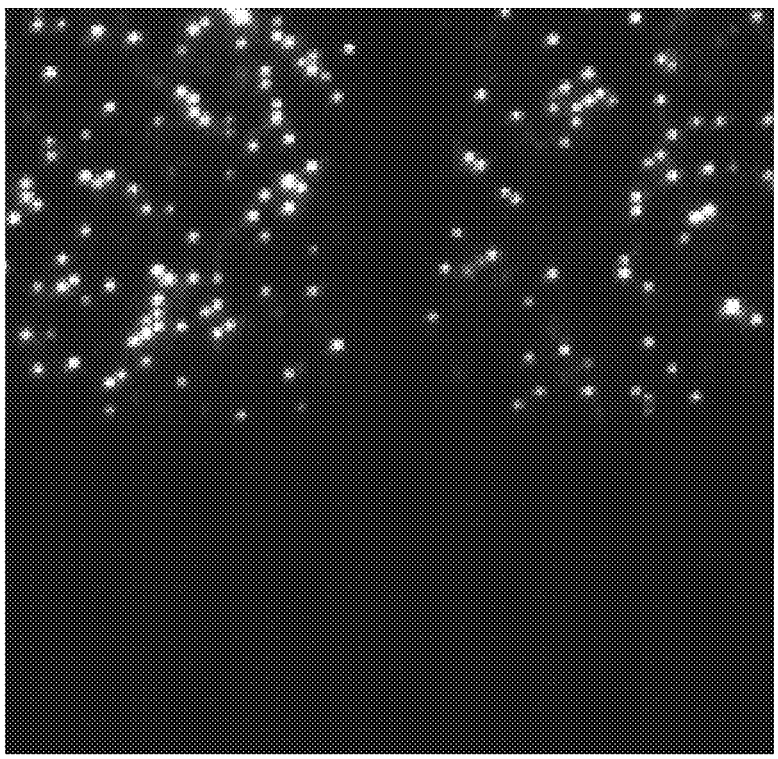
Figure 33F:
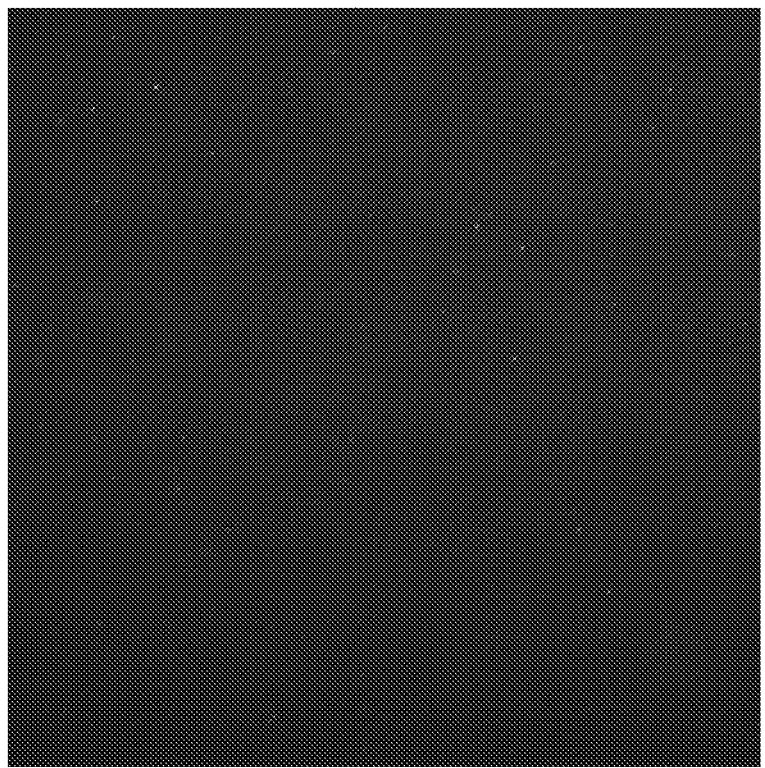
Figure 33E:
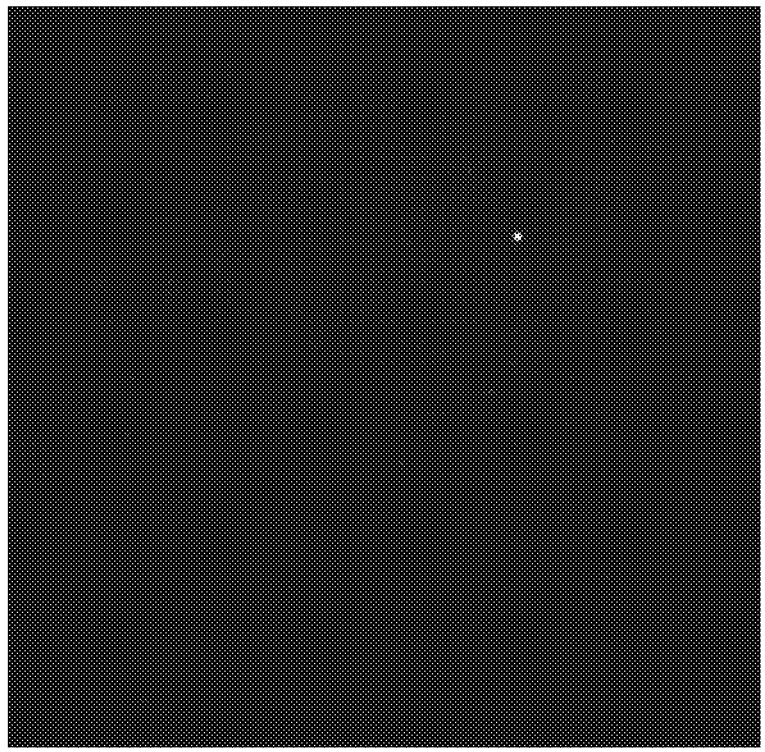

A first 1:1 mixture of fluorescently-labeled microspheres of 505 nm and 660 nm emission wavelengths was prepared with an overall concentration of 1 nM microspheres. A second 1:1 mixture of fluorescently-labeled microspheres of 505 nm and 660 nm emission wavelengths was prepared with an overall concentration of 1 nM microspheres, in which the microspheres were modified with oligonucleotides that were not complementary to the surface-coupled oligonucleotides of the patterned arrays (negative control). The first and second mixture were incubated on separate patterned arrays for 60 mins. After incubation, unbound microspheres were rinsed from array surfaces with a rinse buffer containing 10 mM HEPES buffer, 120 mM sodium chloride, 10 mM magnesium chloride, 5 mM potassium chloride, and 10% sodium dodecyl sulfate, pH 7.4. Arrays were imaged via confocal scanning fluorescence microscopy using 488 nm and 647 nm excitation light sources. FIGS. 33A and 33B display fluorescence microscopy data for arrays incubated with the first microsphere mixture at 505 nm and 660 nm emission, respectively. Specific binding of microspheres to array sites is observed. FIGS. 33C and 33D display fluorescence microscopy data for arrays incubated with the first microsphere mixture at 505 nm and 660 nm emission, respectively, with the sensor positioned over an interstitial region of the array (i.e., no binding sites). Interstitial regions can be observed on the left sides of images, as well as bisecting two subarrays through the center right of the images. Little or no binding of microspheres is observed in the interstitial regions (containing an HMDS coating and no surface-coupled oligonucleotides). FIGS. 33E and 33F display fluorescence microscopy data for arrays incubated with the second microsphere mixture at 505 nm and 660 nm emission, respectively. Minimal binding of the non-complementary microspheres to array sites is observed, indicating that the specificity of binding observed on arrays of incubated with the first mixture arise from nucleic acid hybridization interactions rather than orthogonal binding of microspheres to array sites. It would be expected that loading concentrations below 1 nM of complementary microspheres on the patterned arrays would produce lesser array site occupancy than that observed in FIGS. 33A and 33B.

Example 6. Image Registration on Patterned Arrays Containing Fiducial Elements Oligonucleotide-modified fluorescent microspheres with a 660 nm emission wavelength were prepared by the method of Example 4. Microspheres were deposited on patterned arrays at varying concentrations, then peptide analytes were deposited at unoccupied array sites. Arrays were subsequently cycled through 28 cycles of affinity agent binding, fluorescent imaging, and affinity agent removal. After 28 cycles, fluorescent images were analyzed by an image analysis algorithm to determine if sites with peptide-affinity agent co-localization could be successfully registered over the full range of binding cycles.

Table I lists experimental conditions for 4 conditions tested. Each array was prepared by incubating fluorescent microspheres at the desired concentration with an array for 30 mins. After microsphere incubation, unbound microspheres were rinsed from arrays with a rinsing buffer containing 10 mM HEPES buffer, 120 mM sodium chloride, 10 mM magnesium chloride, 5 mM potassium chloride, and 10% sodium dodecyl sulfate, pH 7.4. After microsphere deposition, single peptide targets were deposited on the arrays at a 150 pM concentration. Each peptide target was attached to an anchoring moiety comprising a structured nucleic acid particle (SNAP), in which the SNAP contained a plurality of surface-coupling oligonucleotides with identical binding nucleotide sequences as the fluorescent microspheres. SNAPs with peptide targets were incubated on the arrays for 30 mins. After peptide target incubation, unbound SNAPs were rinsed from arrays with a rinsing buffer containing 10 mM HEPES buffer, 120 mM sodium chloride, 10 mM magnesium chloride, 5 mM potassium chloride, and 0.1 wt % Tween-20, pH 7.4. For each cycle of affinity agent binding, affinity agents were incubated at 5 nM (anti-DTR antibody) or 10 nM (B1 aptamer) for 10 mins. Affinity agents were bound in a buffer containing 10 mM HEPES buffer, 120 mM sodium chloride, 10 mM magnesium chloride, 5 mM potassium chloride, 1% PF-127 surfactant, and 1 mg/mL sheared salmon DNA, pH 7.4. After affinity agent incubation, unbound affinity agents were rinsed from arrays with a rinsing buffer containing 10 mM HEPES buffer, 120 mM sodium chloride, 10 mM magnesium chloride, 5 mM potassium chloride, and 0.1 wt % Tween-20, pH 7.4. Imaging of each array following affinity agent incubation was performed by confocal scanning microscopy utilizing a 647 nm light source for fluorophore excitation of fiducial elements and bound affinity agents. After fluorescent imaging, bound affinity agents were removed by incubation of arrays with a removal buffer containing 10 mM MES buffer, 10% sodium dodecyl sulfate, 10 mM magnesium chloride, pH 5.5. The affinity agent removal buffer was incubated for 10 mins, then the arrays were rinsed with a buffer containing 10 mM HEPES buffer, 120 mM sodium chloride, 10 mM magnesium chloride, 5 mM potassium chloride, and 10% sodium dodecyl sulfate, pH 7.4. Additional aspects of SNAP and affinity agent structure and utilization are described in U.S. Pat. No. 11,505,796B2 and U.S. Patent Publication No. 20220162684A1, each of which is herein incorporated by reference in its entirety.

TABLE I

Image registration testing conditions

| Array | Peptide Target Sequence | Affinity Agent | Microsphere Deposition Concentration (pM) |
|---|---|---|---|
| 1 | DTR | anti-DTR AB | 0.05 |
| 2 | HHH | B1 aptamer | 0.01 |
| 3 | DTR | anti-DTR AB | 0.05 |
| 4 | HHH | B1 aptamer | 0.01 |

Figure 34B:
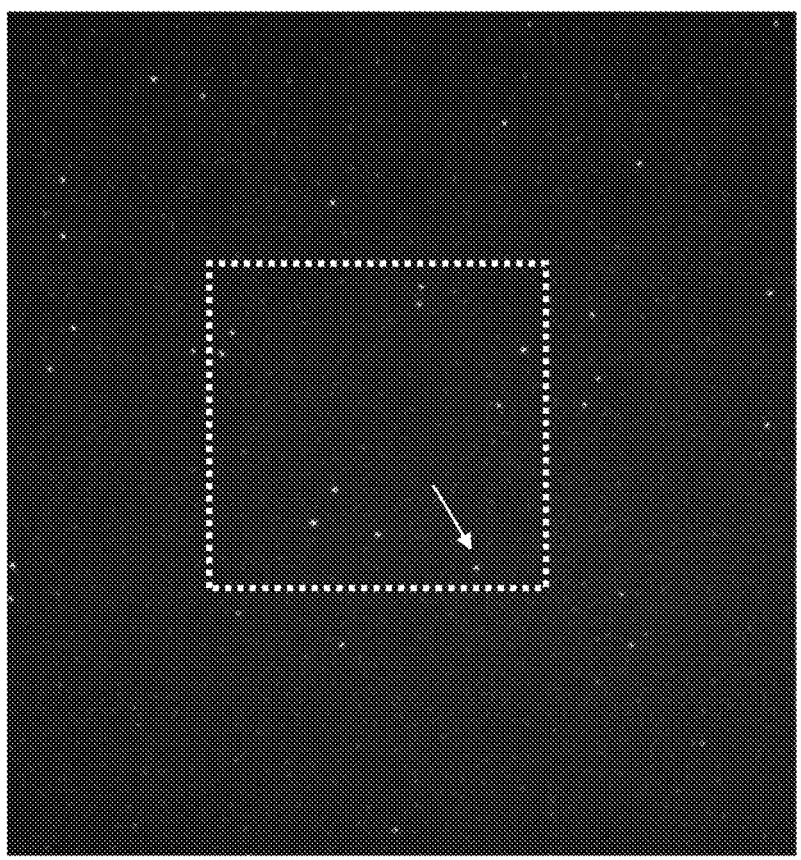
FIGS. 34A and 34B show fluorescent microscopy images of patterned arrays comprising fiducial elements.
Figure 34A:
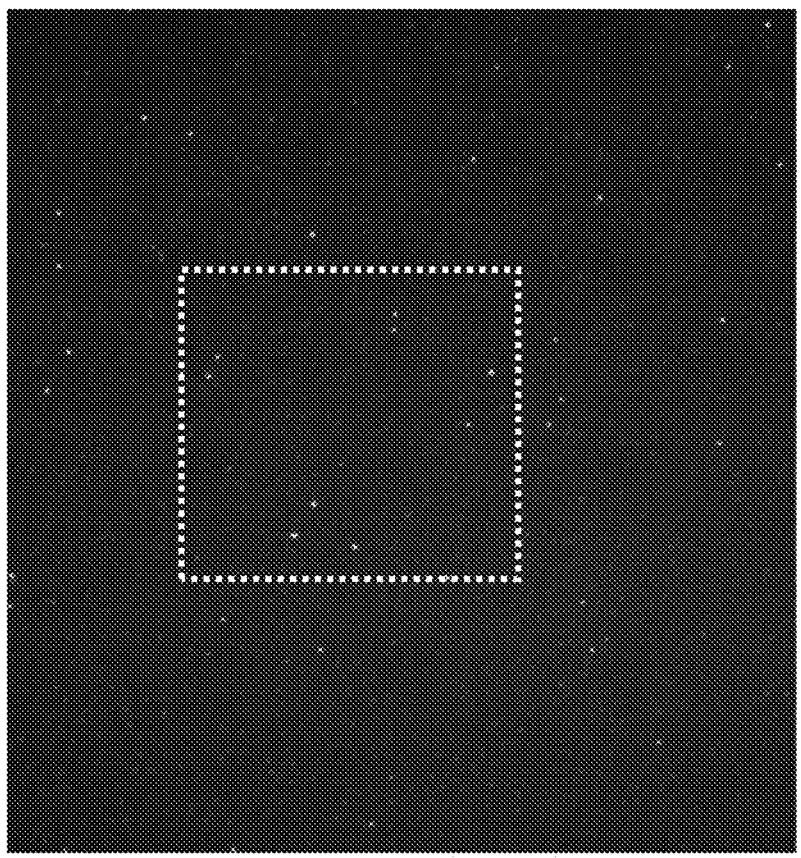

FIGS. 34A and 34B depict exemplary array images from after microsphere deposition and after the 28$^{th}$ affinity agent binding cycle, respectively, for the array containing microspheres deposited at 0.05 pM and HHH peptide targets. FIG. 34A displays an image of an array containing a random spatial distribution of fluorescent microspheres. FIG. 34B displays an image of the fluorescent microspheres and some additional sites producing signals due to incomplete removal of affinity agents from peptide targets. A dashed box is used in both figures to highlight a subdistribution of 9 fluorescent microsphere fiducial elements with a random spatial distribution. A site producing a signal due to incomplete removal of an affinity agent is highlighted by an arrow in FIG. 34B. By direct comparison, it can be observed that virtually all sites containing fiducial elements, as determined from FIG. 34A, are observed to produce a fluorescent signal after the 28$^{th}$ binding cycle, suggesting a high degree of microsphere binding stability throughout the serial binding, rinsing, and stripping steps of the assay. Fluorescent images of each array were provided to an image analysis algorithm. For all arrays, it was found that fluorescent signals due to co-localization of affinity agents and peptide targets could be registered to array sites successfully. Accordingly, deposition of fiducial elements at 0.01 pM concentration was found to be sufficient for preparing single-analyte arrays.

Example 7: Validation of Point Registration Approach

A validation assay was performed for a method of registering a plurality of images of a substrate, in accordance with some embodiments of the present disclosure. The validation assay included an accuracy unit test, a false-positives unit test, an integration test, and a manual validation.

The accuracy unit test included a process comprising 1) generating random points in a first image (image A), 2) generating random points in a second image B, 3) generating a random rigid transform, 4) applying that transform to points in image A, 5) adding those transformed points to image B, and 6) running and checking the result of an image registration algorithm, in accordance with an embodiment of the present disclosure (e.g., a generalized Hough transform (GHT) point-based registration method), to verify whether it matched the expected transform. Accordingly, 100 random points were generated in image A and 1000 random points were generated in image B. The 100 random points in image A were transformed with a random offset (dx, dy) having a radius of 45 pixels, a random angle from −0.5° to +0.5°, and a random point jitter having a radius 0.5 pixels. The transformed points from image A were then added to the 1000 points in image B, and the image registration algorithm was performed for images A and B over 1000 iterations. The accuracy unit test was observed to successfully perform registration of image A and image B over the 1000 iterations, indicating that the image registration method was able to satisfactorily identify true positives.

The false-positives unit test included a process comprising 1) generating random points in a first image A, 2) generating random points in a second image B, and 3) running and checking the result of the image registration algorithm (e.g., the GHT point-based registration method) to verify that no correspondence was found (e.g., no false-positives). As described above, 100 random points were generated in image A and 1000 random points were generated in image B, and the image registration algorithm was performed for images A and B over 1000 iterations. The false-positives unit test was observed to correctly indicate failures of registration between image A and image B over the 1000 iterations, indicating that the image registration method was able to satisfactorily produce a low or zero number of false positives.

The integration test performed a run of a data set of labeled probe ("lobe") detection output CSV files from real experiments. A set of images from a single lane-scan on an imaging instrument were deemed to have a geometric relationship because the instrument moves with fixed steps between images (e.g., where a respective lane encompasses all or a part of a row or column across the surface of a substrate). Thus, the second (and subsequent) scans of the same lane were deemed to have relationships between all the image positions. Accordingly, the integration test was performed to check that those relationships were within expected tolerances of the stage motion, which the image registration method was deemed to have satisfactorily passed.

The manual validation was performed for a series of images obtained from a reference set. The reference set included images obtained by stepping an imaging instrument across the length of a lane (e.g., encompassing all or a part of a row or column across the surface of a substrate), for each lane in a set of four lanes (e.g., "A," "B," "C," and "D"). Each respective lane included 30 different regions, or "steps," along the length of the lane. Moreover, for each respective "step" of each respective lane, the series of images included a corresponding subset of 10 images, each respective image in the subset of 10 images corresponding to a different labeled probe ("lobe") to which the substrate was exposed. Accordingly, image registration was performed for images corresponding to various pairs of lobes (e.g., LOBE05 vs. LOBE10), at each respective step across each respective lane. An image-based cross-correlation algorithm was used as a baseline for comparison against the GHT point-based registration method, performed in accordance with an embodiment of the present disclosure. For both methods, when a successful image registration was obtained, the consistency of output transform offsets and rotations was verified. When the image registration indicated a mixed set (e.g., where some "steps" indicated failures and some "steps" indicated successes), the images were inspected to confirm correctness.

Figure 39A:
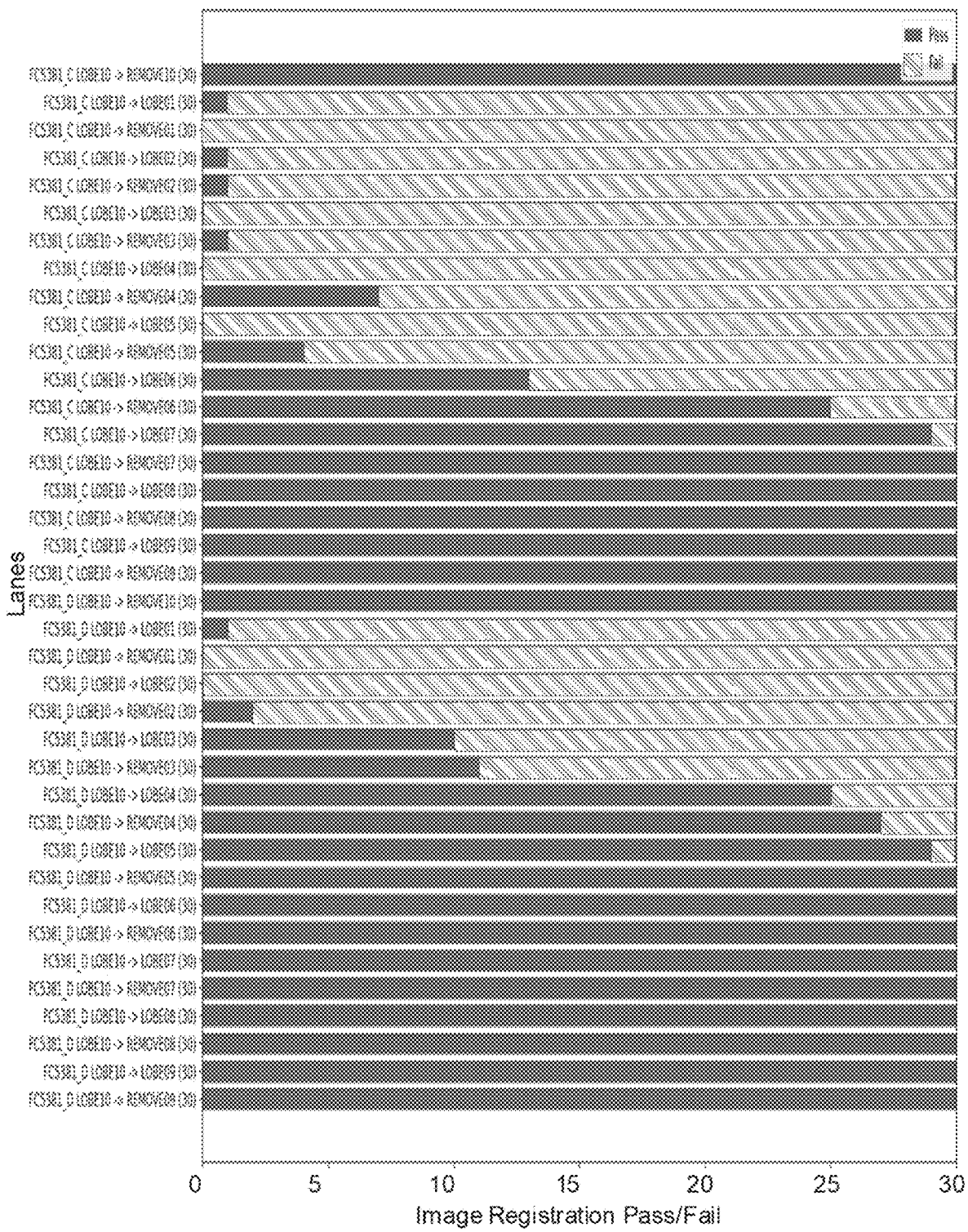
FIGS. 39A, 39B, 39C, and 39D illustrate image registration pass/fail plots indicating performance of a baseline, image-based cross-correlation registration algorithm and a GHT point-based image registration method in accordance with an embodiment of the present disclosure.
Figure 39B:
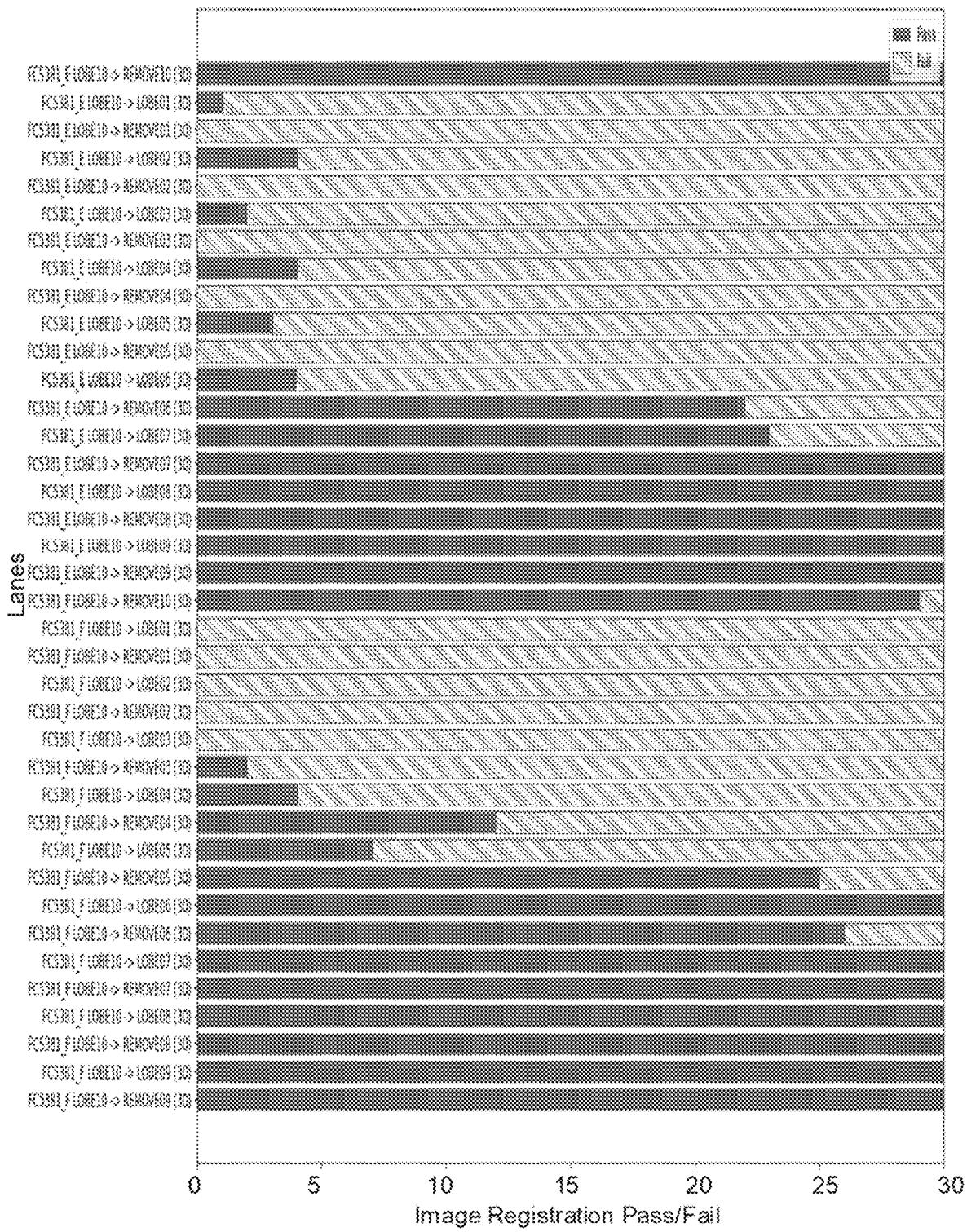

Baseline plots from the image-based cross-correlation registration algorithm are shown in FIGS. 39A-B. Each respective comparison of lobe pairs for a given lane is represented as a respective row ("Lanes") in the plot, where steps along the respective lane are denoted by the x-axis (0-30). Success or failure of registration is indicated, by the shading of each step in the row (e.g., boxes with solid shading: pass; boxes with hatched pattern: fail). FIGS. 39A-B show significant failure rates for a large proportion of comparisons using the baseline cross-correlation registration algorithm.

Figure 39C:
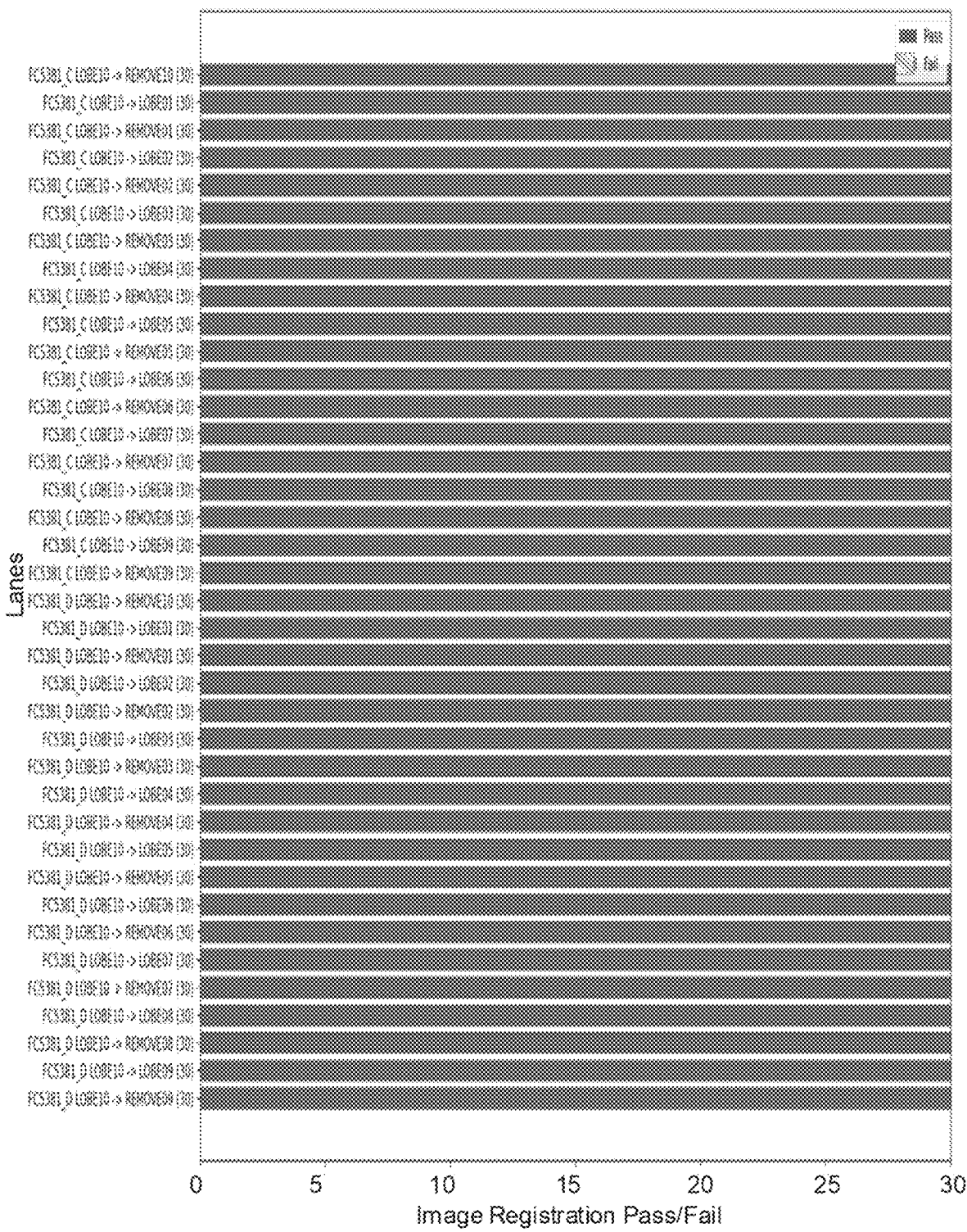
Figure 39D:
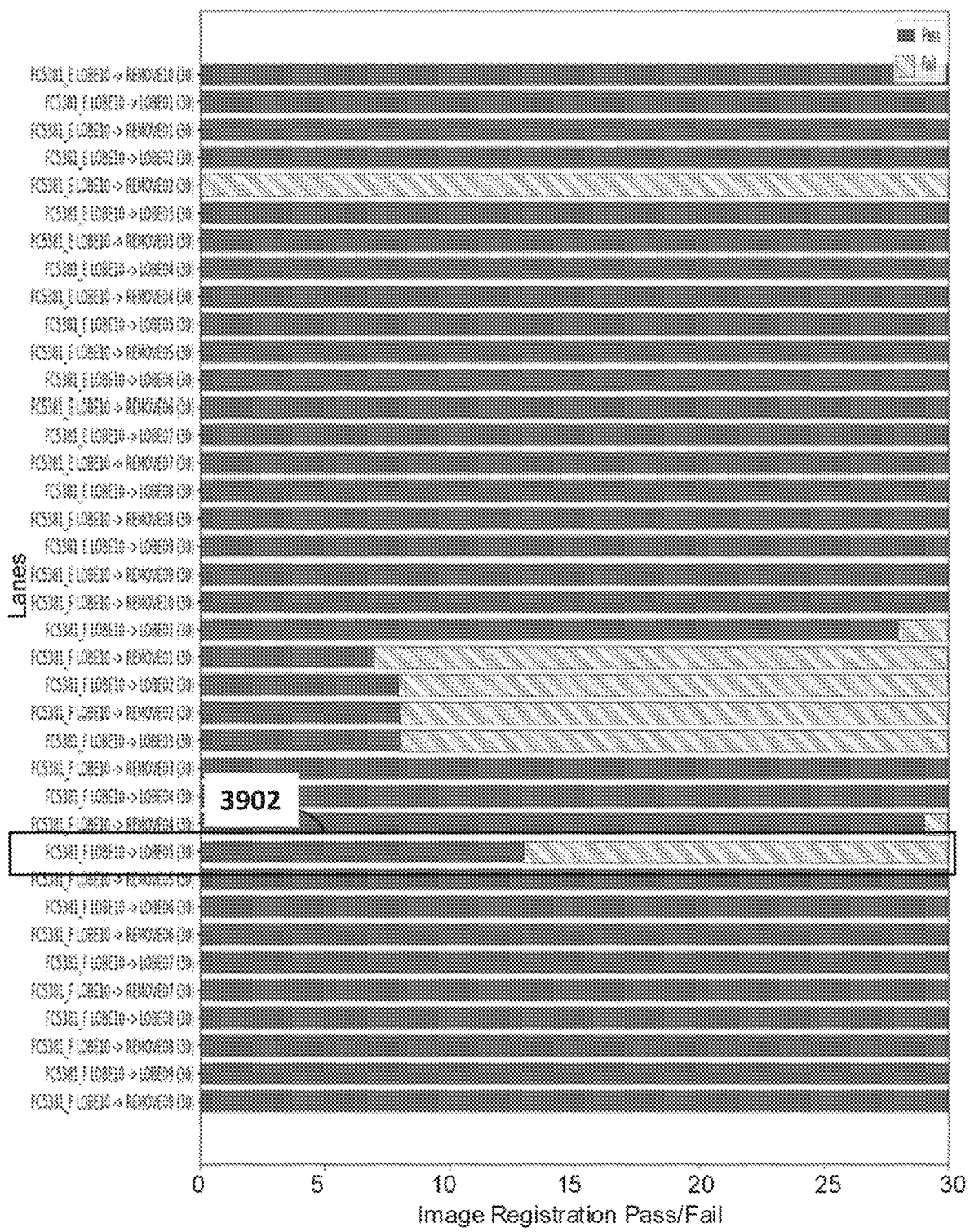

In contrast, corresponding plots for the GHT point-based image registration method are shown in FIGS. 39C-D.

Figure 41A:
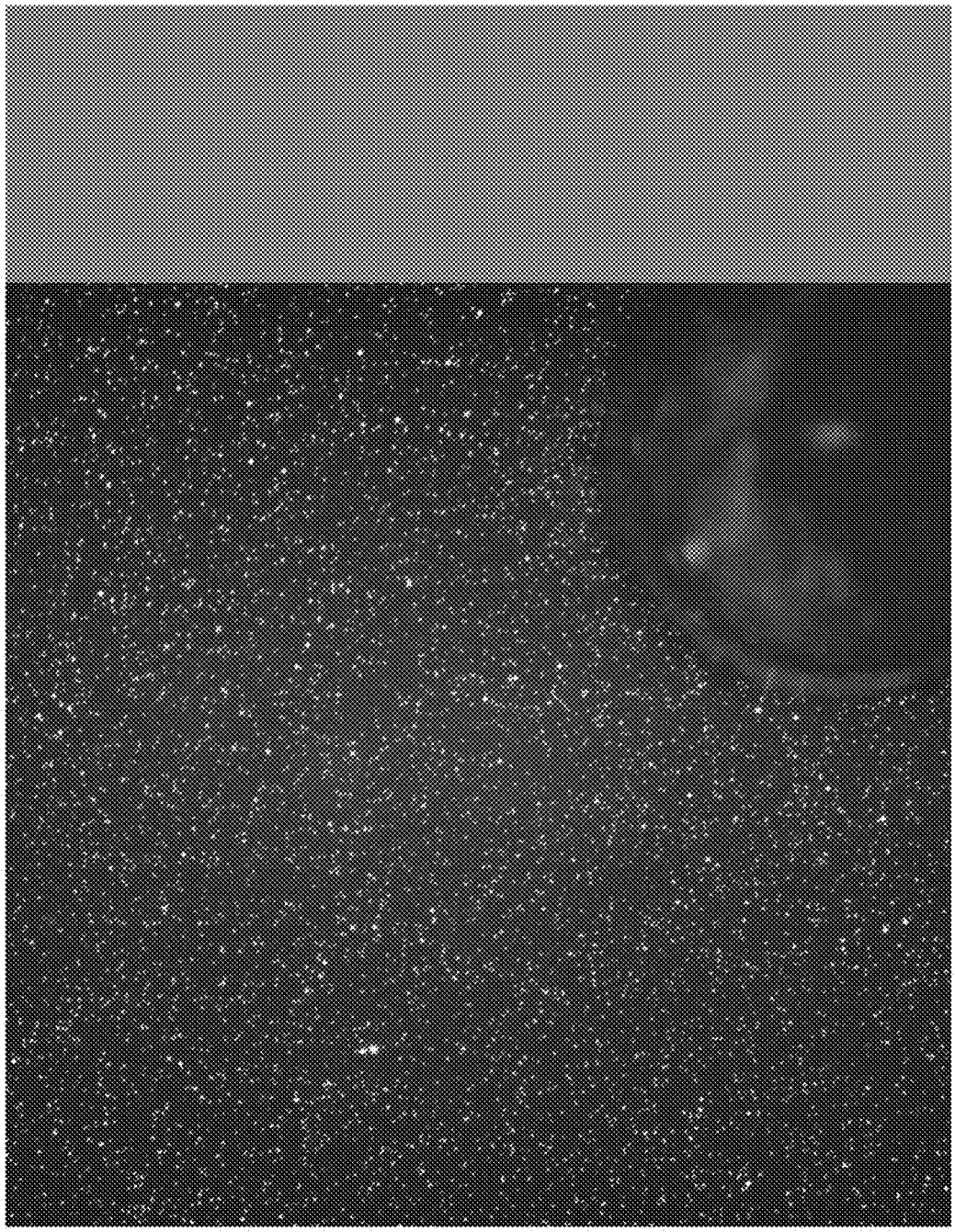
FIGS. 41A and 41B provide example images used to perform validation assays for a baseline, image-based cross-correlation registration algorithm and a GHT point-based image registration method in accordance with an embodiment of the present disclosure.
Figure 41B:
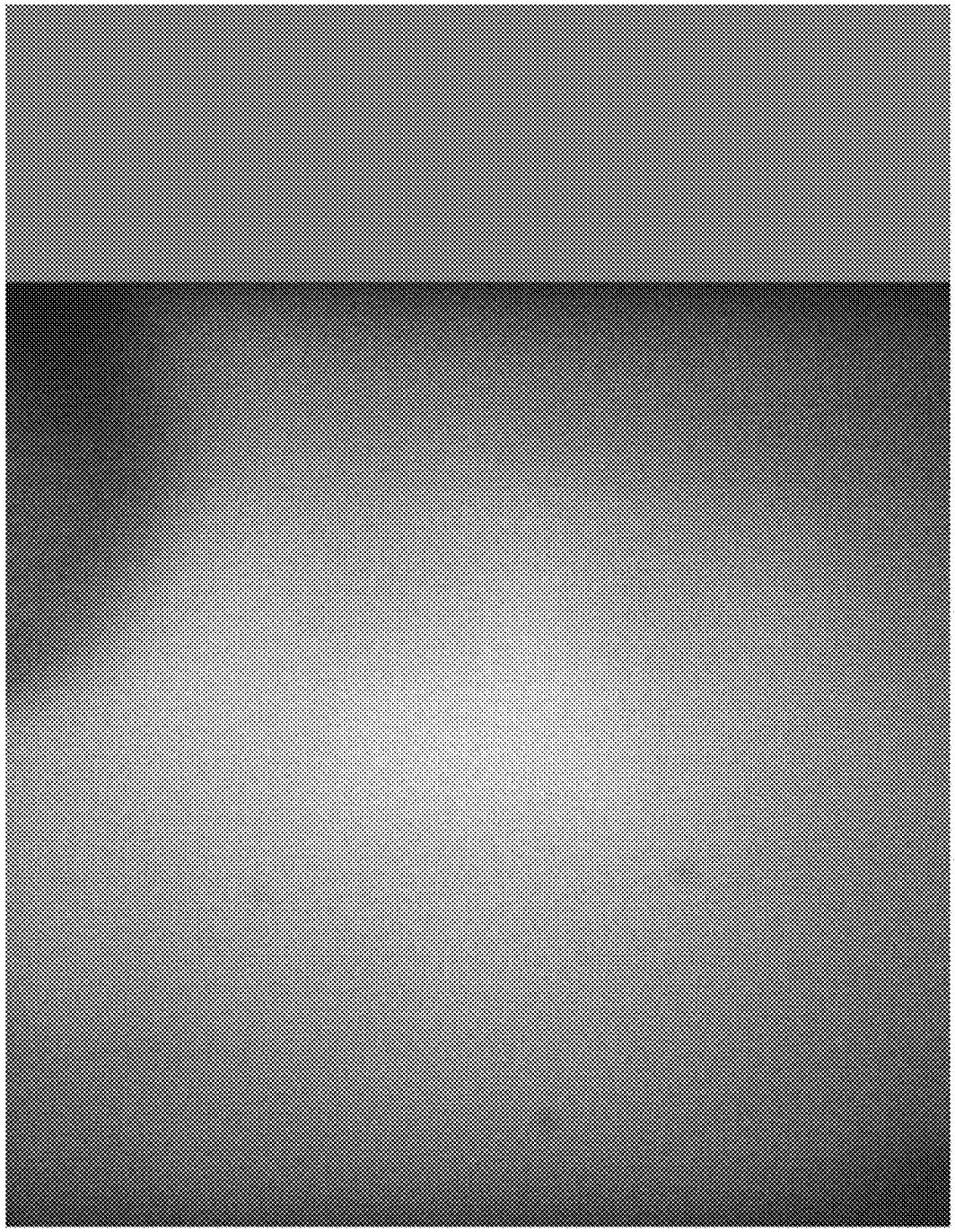

Registration succeeded in all cases in the first plot (FIG. 39C) and in many cases in the second plot (FIG. 39D). These results indicate dramatically improved image registration when using the GHT point-based image registration method compared to the baseline algorithm. Notably, failures in registration displayed in FIG. 39D indicate correct failures (e.g., true negatives), as described in further detail below with reference to FIGS. 41A-B.

Further investigation was performed to determine whether the increased success rate (e.g., successful identification of transforms for image registration) obtained from the GHT point-based image registration method was due in part to increased identification of false positives.

Accordingly, false positives were assessed by examining the consistency of transforms found for images within the same lane comparisons. Significant differences (e.g., poor consistency) were not expected because the imaging instrument was deemed to be relatively consistent, with stage motion varying by approximately a few pixels per step. Thus, any offsets found between the 30 pairs of images (e.g., for comparisons between two lobes along a given lane) were expected to be the same within that tolerance.

Figure 40A:
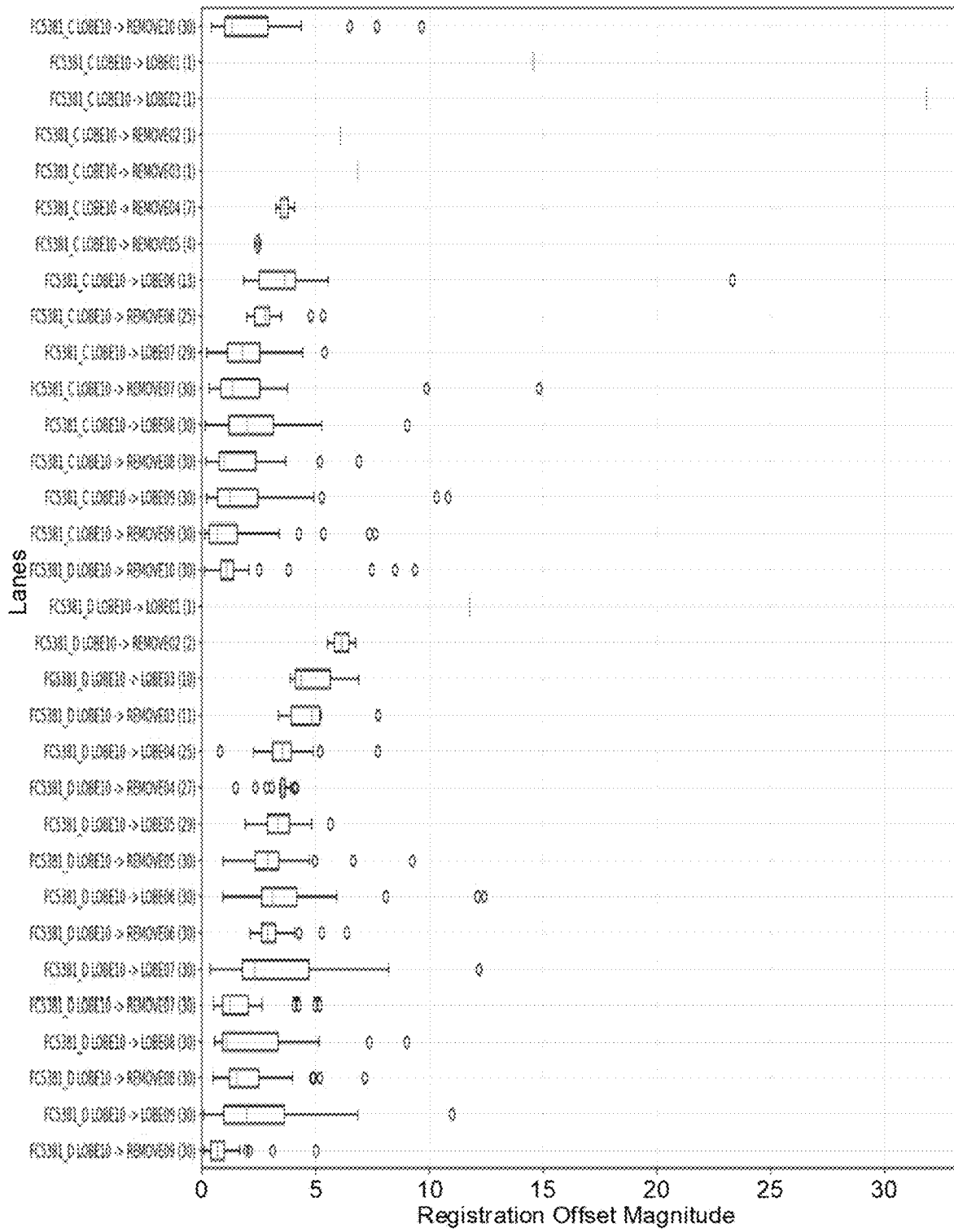
FIGS. 40A, 40B, 40C, and 40D illustrate registration offset plots and registration rotation plots indicating performance of a baseline, image-based cross-correlation registration algorithm and a GHT point-based image registration method in accordance with an embodiment of the present disclosure.
Figure 40B:
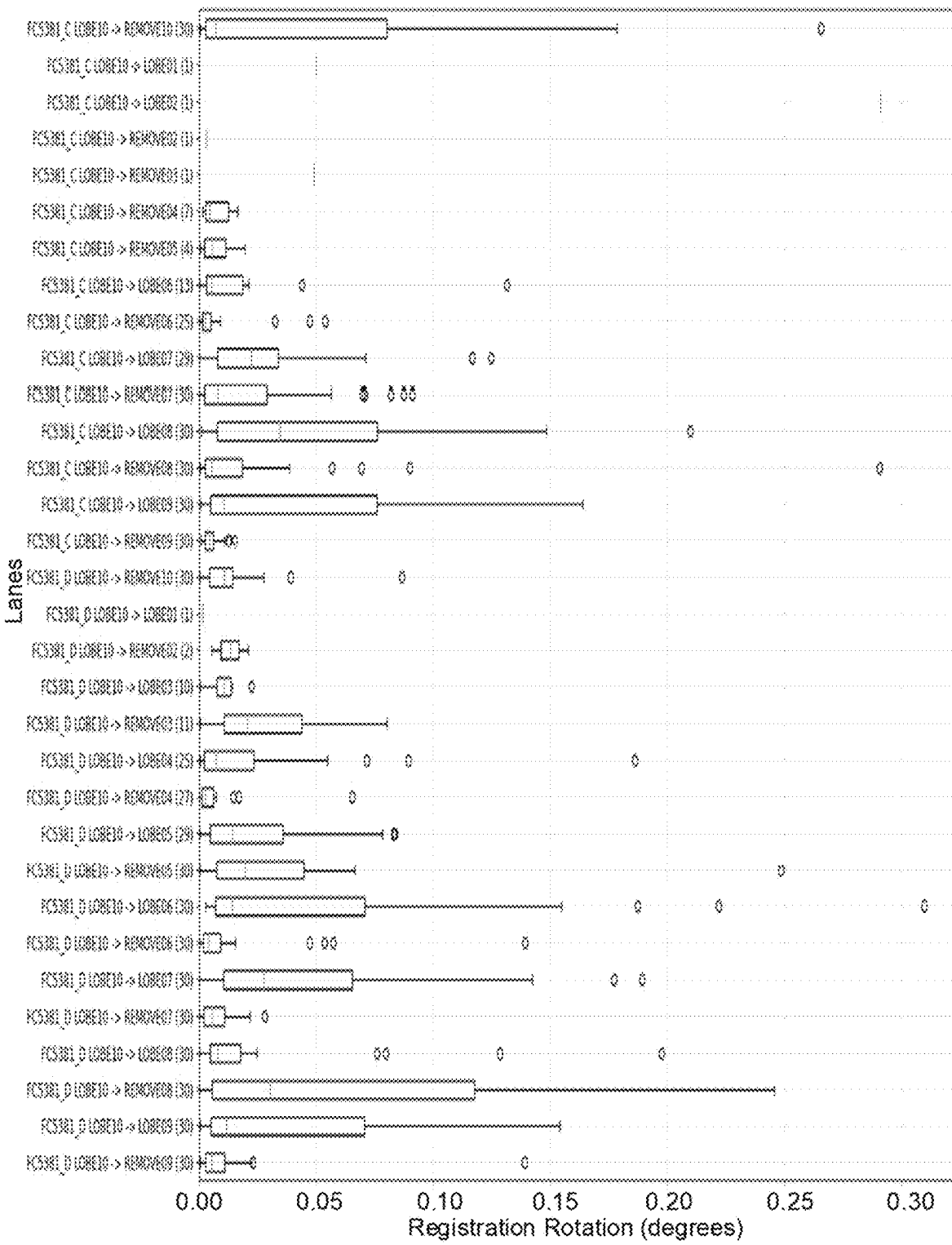
Figure 40C:
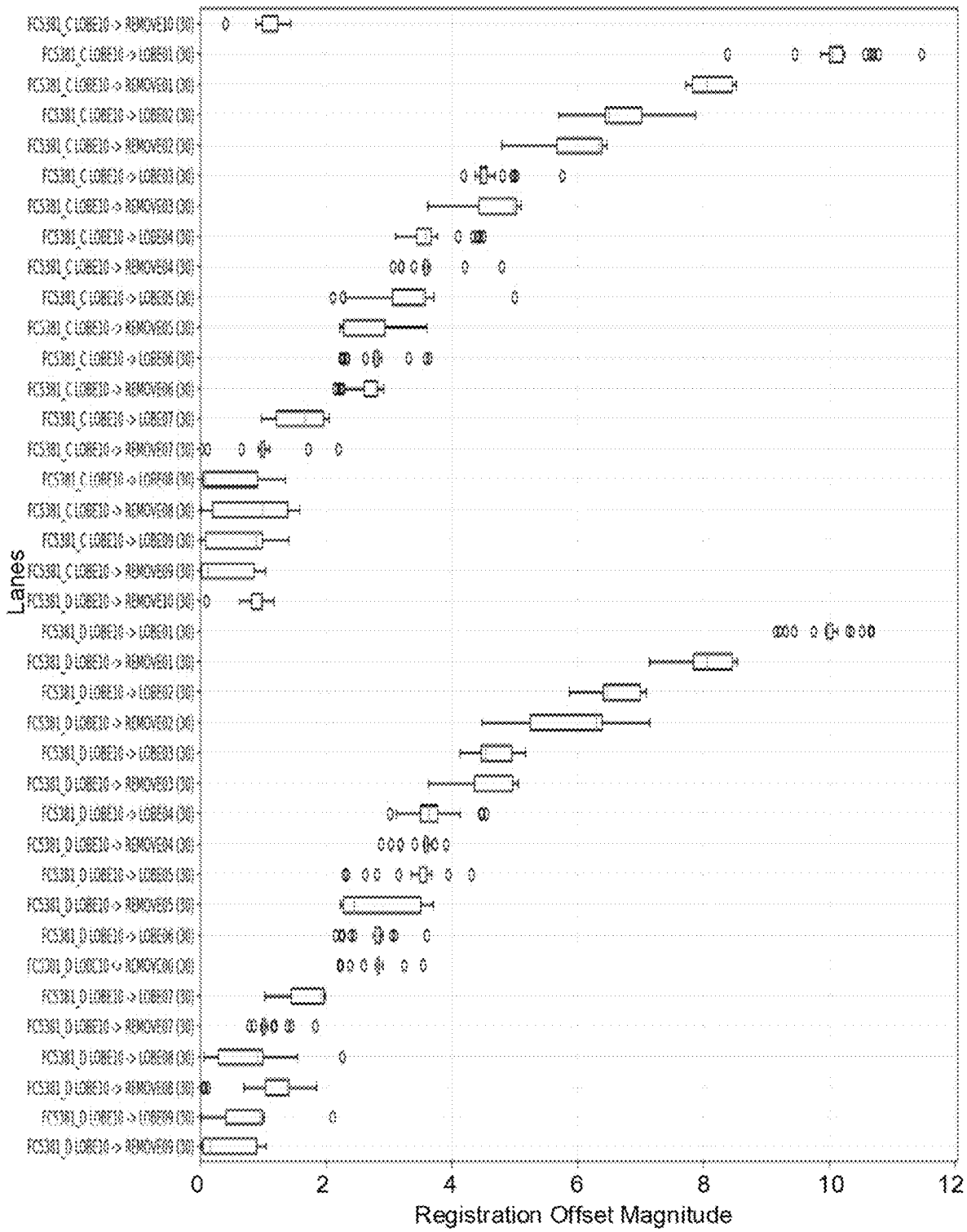
Figure 40D:
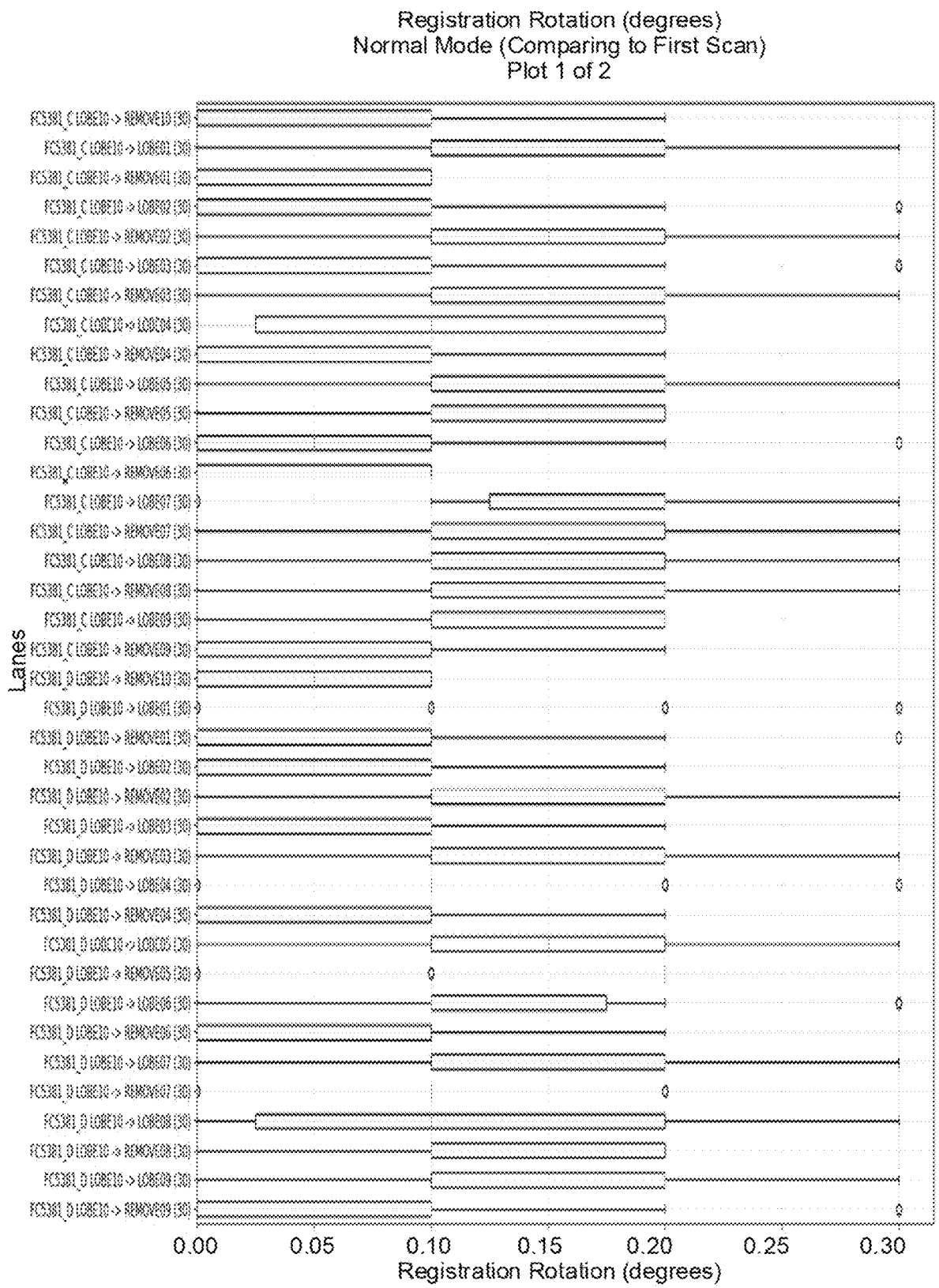

Plots of offset and rotations found for the image-based cross-correlation registration algorithm are shown in FIGS. 40A-B, and plots of offset and rotations found for the GHT point-based image registration method are shown in FIGS. 40C-D. Unlike the baseline offset and rotation plots illustrated in FIGS. 40A-B, which show a number of widely spaced outliers, the point-based registration plots illustrated in FIGS. 40C-D show good consistency and no significant outliers. Notably, the point-based rotation plots show consistent variation under 0.03° (e.g., less than 1 pixel of travel from center-to-corner), compared to baseline rotation plots showing variation exceeding 0.1°.

An example assessment to determine whether false positives were generated by the GHT point-based image registration method was performed using a selected lane having a mixed set (e.g., where some "steps" indicated failures and some "steps" indicated successes). The selected comparison is indicated in FIG. 40D as Lane F, LOBE05 vs. LOBE10 (502). Image registration using the point-based registration method was repeated for the subset of images corresponding to the Lane F, LOBE05 vs. LOBE10 comparison, and the images were visually inspected. As expected, images corresponding to successful registration (e.g., steps 0 to 12; "pass") contained an appropriate plurality of points, while the remaining images corresponding to failed registration (e.g., steps 13 to 29; "fail") were blank in and contained no detectable points for at least one of the lobes in the pair of lobes. For instance, for LOBE05, all images corresponding to steps 0 to 12 were acceptable (e.g., illustrated by exemplary step 12 in FIG. 41A), while all images corresponding to steps 13 to 29 were blank (e.g., illustrated by exemplary step 13 in FIG. 41B).

These results indicate that the image registration method was able to satisfactorily pass the manual validation, based on a comparison with results obtained from a conventional, image-based cross-correlation registration method.

Example 8: Fiducial Bead-Only Scan

An assay was performed to assess the performance of a GHT point-based image registration method, using a first image comprising a first plurality of points and a second image comprising a second plurality of points, in accordance with an embodiment of the present disclosure.

A first image A was obtained, including 100 randomly generated points, and a second image B was obtained for alignment to image A. The assay was performed by simulation, varying two parameters: lobe occupancy in image A (e.g., "Occupancy A %") and bead occupancy in image A (e.g., Bead A %). A one-time bead loss rate of 10% was applied in order to obviate the need to factor in a loss per cycle rate that is dependent on the cycle number used in the simulation. For image B, the lobe occupancy was fixed at 15%, and NSB for both images A and B was 1%. A comparison tolerance of 0.75 pixels was defined, such that a registration was successful if it returned an offset closer than that to the true offset. For identification of point pairs between image A and image B, a small search radius of 5 pixels was used, as it was deemed appropriate to MVP with landmarking.

Table 2

Successful Alignment of Image A Points in Image B using GHT Point-Based Image Registration

| Occupancy A % | Bead A % 0.2 | 0.4 | 0.6 | 0.8 | 1 | 1.2 | 1.4 | 1.6 | 1.8 | 2 |
| --- | --- | --- | --- | --- | --- | --- | --- | --- | --- | --- |
| 5 | 100 | 100 | 100 | 100 | 100 | 100 | 100 | 100 | 100 | 100 |
| 10 | 50 | 100 | 100 | 100 | 100 | 100 | 100 | 100 | 100 | 100 |
| 15 | 10 | 100 | 100 | 100 | 100 | 100 | 100 | 100 | 100 | 100 |
| 20 | 0 | 100 | 100 | 100 | 100 | 100 | 100 | 100 | 100 | 100 |
| 25 | 30 | 60 | 90 | 100 | 100 | 100 | 100 | 100 | 100 | 100 |
| 30 | 10 | 50 | 100 | 100 | 100 | 100 | 100 | 100 | 100 | 100 |
| 35 | 10 | 30 | 30 | 100 | 100 | 100 | 100 | 100 | 100 | 100 |
| 40 | 10 | 20 | 50 | 90 | 100 | 100 | 100 | 100 | 100 | 100 |
| 45 | 10 | 10 | 20 | 30 | 100 | 100 | 100 | 100 | 100 | 100 |
| 50 | 10 | 0 | 20 | 40 | 90 | 100 | 100 | 100 | 100 | 100 |

Table 2 illustrates the results from the simulation for varying parameter combinations. Accurate detection and alignment of matching points in image B were obtained for all 100 randomly generated points in image A when bead occupancy in image A was 1.2% or higher, lobe occupancy in image A was 50% or lower, cumulative bead loss was 10% or lower, and average lobe occupancy in image B was 15%, optionally with a maximum lobe occupancy of 50%.

A second assay was performed to assess the performance of a pixel-accumulation algorithm for implementing an image registration method without rotation, in accordance with an embodiment of the present disclosure. As described above, a first image A was obtained, including 100 randomly generated points, and a second image B was obtained for alignment to image A. The assay was performed by simulation, varying two parameters: lobe occupancy in image A (e.g., "Occupancy A %") and bead occupancy in image A (e.g., Bead A %).

The pixel-accumulation method includes, for each point in image A, selecting a neighborhood region of interest (ROI) around the respective point as overlaid on image B, where ROI size determines the search radius. The method further includes determining a sum of pixels values in image B over all of the ROIs corresponding to each point in image A. In other words, the pixel values in image B encompassed by each respective ROI are used to vote for each respective pixel location that is positioned relative to a frame of reference determined by the ROI size. Tallying pixel values from image B encompassed by each ROI can also be envisioned as "stacking" the ROIs and any corresponding pixel values obtained from image B. The method further includes determining the highest pixel value from the sums of pixel values (e.g., the brightest pixel).

The results of the second assay are provided in Table 3. Notably, the pixel-accumulation method was substantially more sensitive, with 100% of points accurately aligned when bead occupancy in image A was 0.6% or higher and lobe occupancy in image A was 50% or lower. Although this method does not account for rotation between a first image and a second image, it may be useful in a wide variety of applications where rotation is not expected to occur and/or where stage rotation error is low.

TABLE 3

Successful Alignment of Image A Points in Image B using Pixel Accumulation

| Occupancy A % | Bead A % 0.2 | 0.4 | 0.6 | 0.8 | 1 | 1.2 | 1.4 | 1.6 | 1.8 | 2 |
|---|---|---|---|---|---|---|---|---|---|---|
| 5 | 100 | 100 | 100 | 100 | 100 | 100 | 100 | 100 | 100 | 100 |
| 10 | 100 | 100 | 100 | 100 | 100 | 100 | 100 | 100 | 100 | 100 |
| 15 | 100 | 100 | 100 | 100 | 100 | 100 | 100 | 100 | 100 | 100 |
| 20 | 100 | 100 | 100 | 100 | 100 | 100 | 100 | 100 | 100 | 100 |
| 25 | 100 | 100 | 100 | 100 | 100 | 100 | 100 | 100 | 100 | 100 |
| 30 | 100 | 100 | 100 | 100 | 100 | 100 | 100 | 100 | 100 | 100 |
| 35 | 60 | 100 | 100 | 100 | 100 | 100 | 100 | 100 | 100 | 100 |
| 40 | 20 | 100 | 100 | 100 | 100 | 100 | 100 | 100 | 100 | 100 |
| 45 | 0 | 100 | 100 | 100 | 100 | 100 | 100 | 100 | 100 | 100 |
| 50 | 0 | 80 | 100 | 100 | 100 | 100 | 100 | 100 | 100 | 100 |

The foregoing assays illustrates a high rate of accuracy in point registration, particularly under at least threshold parameters for bead occupancy in the first image, lobe occupancy in the first and second image, and cumulative bead loss. These results suggest that image registration can be performed without the need for an initial scan to obtain an initial reference image that includes only fiducials (e.g., beads without the presence of labeled probes), for instance, in some implementations, when these parameters are met.

In some alternative implementations, however, an initial reference image that includes only fiducials provides a baseline for registration of subsequent images, including images that include labeled probes (e.g., lobes). This is due to the fact that it can be difficult to distinguish between points originating from fiducials and points originating from lobes in an image that comprises both fiducials and lobes, resulting in increased computational burden, an increased need for energy and processing power, and increased pressure on the registration method. Thus, in some embodiments, a fiducial-only reference image can advantageously be used to improve registration as well as improve performance of a computing system, e.g., by lowering the number of CPU cycles.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Notwithstanding the appended claims, the disclosure set forth herein is also defined by the following clauses:

1) A single-analyte array, comprising:
   a) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and
   b) a plurality of fiducial elements, wherein each fiducial element is located at a site of the plurality of sites, and wherein the plurality of fiducial elements is distributed on the solid support at random sites.

2. The single-analyte array of clause 1, wherein a first site of the plurality of sites is resolvable at single-analyte resolution.

3. The single-analyte array of clause 2, wherein a first signal originating from the first site is spatially distinguishable from a second signal originating from a second site of the plurality of sites, the first site being adjacent to the second site on the solid support.

4. The single-analyte array of clause 3, wherein the first signal and the second signal are spatially distinguishable from a third signal originating from an interstitial region that separates the first site from the second site.

5. The single-analyte array of clause 3 or 4, wherein the first site and the second site are separated by a distance of at least 100 nanometers (nm).

6. The single-analyte array of clause 5, wherein the first site and the second site are separated by a distance of at least 500 nm.

7. The single-analyte array of clause 6, wherein the first site and the second site are separated by a distance of at least 1000 nm.

8. The single-analyte array of any one of clauses 5-7, wherein the first site and the second site are separated by a distance of no more than 5000 nm.

9. The single-analyte array of any one of clauses 2-8, wherein each site of the plurality of sites is resolvable from any other site of the plurality of sites at single-analyte resolution.

10. The single-analyte array of any one of clauses 1-9, wherein a first site of the plurality of sites comprises a coupling moiety that is configured to couple a single analyte.

11. The single-analyte array of clause 10, wherein the coupling moiety is covalently coupled to the solid support.

12. The single-analyte array of clause 10, wherein the coupling moiety is non-covalently coupled to the solid support.

13. The single-analyte array of any one of clauses 10-12, wherein the coupling moiety is configured to covalently couple an analyte to the site.

14. The single-analyte array of any one of clauses 10-12, wherein the coupling moiety is configured to non-covalently couple an analyte to the site.

15. The single-analyte array of any one of clauses 10-14, wherein the site comprises a plurality of coupling moieties.

16. The single-analyte array of any one of clauses 10-15, wherein each site of a subset of the plurality of sites comprises a coupling moiety that is configured to couple a single analyte.

17. The single-analyte array of clause 16, wherein the subset of the plurality of sites comprises at least about 10% of the plurality of sites.

18. The single-analyte array of clause 17, wherein the subset of the plurality of sites comprises at least about 50% of the plurality of sites.

19. The single-analyte array of any one of clauses 10-18, wherein the first site comprises a first coupling moiety and a second site comprises a second coupling moiety, wherein reactivity of the first coupling moiety differs from reactivity of the second coupling moiety.

20. The single-analyte array of any one of clauses 1-19, wherein an interstitial region of the one or more interstitial regions comprises a passivating moiety that is configured to inhibit binding of an unbound moiety.

21. The single-analyte array of clause 20, wherein the passivating moiety comprises a hydrophilic moiety.

22. The single-analyte array of clause 20, wherein the passivating moiety comprises a hydrophobic moiety.

23. The single-analyte array of clause 20, wherein the passivating moiety comprises a moiety that sterically hinders or electrostatically hinders the binding of the uncoupled molecule.

24. The single-analyte array of any one of clauses 20-23, wherein the passivating moiety comprises a linear polyethylene glycol (PEG), a branched PEG, a linear alkyl moiety, a branched alkyl moiety, a fluorinated hydrocarbon, a linear polysaccharide, a branched polysaccharide, a dendrimer, or a combination thereof.

25. The single-analyte array of any one of clauses 20-24, wherein the interstitial region of the one or more interstitial regions comprises a first passivating moiety and a second passivating moiety, wherein the first passivating moiety differs from the second passivating moiety.

26. The single-analyte array of clause 25, wherein a chemical structure of the first passivating moiety differs from a chemical structure of the second passivating moiety.

27. The single-analyte array of clause 25, wherein a degree of branching of the first passivating moiety differs from a degree of branching of the second passivating moiety.

28. The single-analyte array of any one of clauses 1-27, wherein the one or more interstitial regions comprise a single continuous interstitial region.

29. The single-analyte array of any one of clauses 1-27, wherein the one or more interstitial regions comprise two or more non-continuous interstitial regions.

30. The single-analyte array of any one of clauses 1-29, wherein the unbound moiety is selected from the group consisting of a cell, a macromolecule, a nanoparticle, a small molecule, and a process substrate.

31. The single-analyte array of clause 30, wherein the macromolecule comprises a nucleic acid, a polypeptide, a polysaccharide, or a combination thereof.

32. The single-analyte array of clause 30, wherein the small molecule comprises a metabolite, a candidate therapeutic agent, a pharmaceutical compound, a binding ligand, an ionic species, or a combination thereof.

33. The single-analyte array of clause 30, wherein the process substrate comprises a moiety provided during a step of an analytical method.

34. The single-analyte array of clause 33, wherein the process substrate comprises an analyte, an affinity agent, a modifying agent, a stabilizing agent, a detection agent, or a combination thereof.

35. The single-analyte array of any one of clauses 1-34, wherein the plurality of sites comprises a patterned array of sites.

36. The single-analyte array of clause 35, wherein the patterned array of sites is formed on the solid support by a method selected from the group consisting of: photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, local oxidation nanolithography, deep-ultraviolet lithography, molecular self-assembly, stencil lithography, and electron-beam lithography.

37. The single-analyte array of clause 35 or 36, wherein the patterned array has a repeating pattern of sites.

38. The single-analyte array of clause 37, wherein the repeating pattern comprises a rectangular grid, a hexagonal grid, a polygonal grid, or a circular grid.

39. The single-analyte array of any one of clauses 35-38, wherein the plurality of sites of the patterned array comprise an axis of symmetry.

40. The single-analyte array of any one of clauses 35-38, wherein the plurality of sites of the patterned array comprise an asymmetric configuration.

41. The single-analyte array of any one of clauses 1-34, wherein the array comprises a non-repeating pattern of sites.

42. The single-analyte array of any one of clauses 1-41, wherein a fiducial element of the plurality of fiducial elements comprises an optically active moiety.

43. The single-analyte array of clause 42, wherein the optically active moiety comprises a light-emitting moiety, a light-absorbing moiety, or a photon transfer pair.

44. The single-analyte array of clause 43, wherein the light-emitting moiety comprises a fluorophore or a luminophore.

45. The single-analyte array of clause 44, wherein the fiducial element comprises a moiety selected from the group consisting of an organic nanoparticle, an inorganic nanoparticle, a nucleic acid, a polypeptide, and a combination thereof.

46. The single-analyte array of clause 44 or 45, wherein the light-emitting moiety is configured to emit light with a wavelength of less than 400 nanometers (nm).

47. The single-analyte array of clause 44 or 45, wherein the light-emitting moiety is configured to emit light with a wavelength in a range from 400 nm to 700 nm.

48. The single-analyte array of clause 44 or 45, wherein the light-emitting moiety is configured to emit light with a wavelength of greater than 700 nm.

49. The single-analyte array of clause 43, wherein the photon transfer pair comprises a Fluorescence Resonance Energy Transfer (FRET) pair.

50. The single-analyte array of any one of clauses 42-49, wherein the largest dimension of the optically active moiety is smaller than the largest dimension of the site to which the optically active moiety is coupled.

51. The single-analyte array of any one of clauses 42-49, wherein the largest dimension of the optically active moiety is greater than or equal to the largest dimension of the site to which the optically active moiety is coupled.

52. The single-analyte array of any one of clauses 42-51, wherein the optically active moiety is coupled to the site by an anchoring moiety.

53. The single-analyte array of clause 52, wherein the anchoring moiety is configured to inhibit contact of the optically active moiety with the site or an interstitial region of the one or more interstitial regions.

54. The single-analyte array of clause 52 or 53, wherein the anchoring moiety comprises a nucleic acid or a nanoparticle.

55. The single-analyte array of clause 54, wherein the nucleic acid comprises a single-stranded nucleic acid.

56. The single-analyte array of clause 54 or 55, wherein the nucleic acid comprises a structured nucleic acid particle.

57. The single-analyte array of clause 56, wherein the structured nucleic acid particle comprises a nucleic acid nanoball or a nucleic acid origami.

58. The single-analyte array of any one of clauses 52-57, wherein the anchoring moiety is coupled to the site by a covalent interaction.

59. The single-analyte array of any one of clauses 52-57, wherein the anchoring moiety is coupled to the site by a non-covalent interaction.

60. The single-analyte array of any one of clauses 52-59, wherein the anchoring moiety is coupled to the optically active moiety by a covalent interaction.

61. The single-analyte array of any one of clauses 52-59, wherein the anchoring moiety is coupled to the optically active moiety by a non-covalent interaction.

62. The single-analyte array of any one of clauses 42-52, wherein the optically active moiety is directly coupled to the site.

63. The single-analyte array of any one of clauses 42-51, wherein the optically active moiety is coupled to the site by a covalent interaction.

64. The single-analyte array of any one of clauses 52-57, wherein the optically active moiety is coupled to the site by a non-covalent interaction.

65. The single-analyte array of any one of clauses 1-41, wherein a fiducial element of the plurality of fiducial elements comprises an optically passive material.

66. The single-analyte array of clause 65, wherein the optically passive material is configured to reflect a photon of light, refract a photon of light, or scatter a photon of light.

67. The single-analyte array of clause 66, wherein the photon of light has a wavelength of less than 400 nanometers (nm).

68. The single-analyte array of clause 67, wherein the photon of light has a wavelength in a range from 400 nm to 700 nm.

69. The single-analyte array of clause 67, wherein the photon of light has a wavelength of greater than 700 nm.

70. The single-analyte array of any one of clauses 65-69, wherein the fiducial element comprises a metal, a metal oxide, a semiconductor, or a dielectric material.

71. The single-analyte array of any one of clauses 65-70, wherein the fiducial element comprises a topographical feature of the solid support.

72. The single-analyte array of clause 71, wherein the topographical feature comprises a raised feature.

73. The single-analyte array of clause 71, wherein the topographical feature comprises an indented feature.

74. The single-analyte array of any one of clauses 71-73, wherein the topographical feature comprises a contrast-enhancing feature.

75. The single-analyte array of clause 71, wherein the contrast enhancing feature comprises a non-diffuse edge between the fiducial element and the solid support.

76. The single-analyte array of any one of clauses 65-75, wherein a fiducial element of the plurality of fiducial elements comprises a material deposited on the solid support.

77. The single-analyte array of clause 76, wherein the material deposited on the solid support is further formed by a lithographic process.

78. The single-analyte array of any one of clauses 65-75, wherein a fiducial element of the plurality of fiducial elements comprises a feature formed from the solid support.

79. The single-analyte array of clause 78, wherein the feature formed from the solid support is formed by a lithographic process.

80. The single-analyte array of any one of clauses 1-79, wherein the largest dimension of a fiducial element of the plurality of fiducial elements is smaller than the largest dimension of the site at which the fiducial element is coupled.

81. The single-analyte array of clause 80, wherein the largest dimension comprises a length, a width, or a diameter.

82. The single-analyte array of clause 80 or 81, wherein the largest dimension has a value of no more than 500 nanometers (nm).

83. The single-analyte array of clause 82, wherein the largest dimension has a value of no more than 100 nm.

84. The single-analyte array of any one of clauses 1-79, wherein the largest dimension of a fiducial element of the plurality of fiducial elements is larger than the largest dimension of the site at which the fiducial element is coupled.

85. The single-analyte array of clause 84, wherein the largest dimension has a value of at least 100 nanometers (nm).

86. The single-analyte array of clause 85, wherein the largest dimension has a value of at least 500 nm.

87. The single-analyte array of any one of clauses 84-86, wherein the fiducial element is coupled to two or more sites.

88. The single-analyte array of any one of clauses 84-87, wherein the fiducial element is coupled to no more than one site.

89. The single-analyte array of any one of clauses 80-88, wherein the fiducial element is configured to produce a detectable signal, wherein the detectable signal is spatially resolvable to an area that is less than or equal to the area of the site.

90. The single-analyte array of any one of clauses 80-88, wherein the fiducial element is configured to produce a detectable signal, wherein the detectable signal is spatially resolvable to an area that is greater than the area of the site.

91. The single-analyte array of any one of clause 1-90, wherein a site of the plurality of sites comprises a mapping moiety.

92. The single-analyte array of clause 91, wherein the mapping moiety comprises a light-emitting moiety, a light-absorbing moiety, or a Forster resonance energy transfer pair.

93. The single-analyte array of clause 90 or 91, wherein the mapping moiety is covalently coupled to the site.

94. The single-analyte array of clause 90 or 91, wherein the mapping moiety is non-covalently coupled to the site.

95. The single-analyte array of any one of clauses 91-94, wherein the mapping moiety is removable from the analytical binding site.

96. The single-analyte array of any one of clauses 91-95, wherein each site of the plurality of sites comprises a mapping moiety.

97. The single-analyte array of clause 96, wherein the one or more interstitial regions do not comprise a mapping moiety.

98. The single-analyte array of any one of clauses 1-97, wherein the plurality of fiducial elements is distributed on the solid support in a random order as defined by a measure of randomness.

99. The single-analyte array of clause 98, wherein the measure of randomness comprises a measurement of an average distance between a first fiducial element and a second fiducial element, wherein the second fiducial element comprises the nearest fiducial element to the first fiducial element.

100. The single-analyte array of clause 98 wherein the measure of randomness comprises a likelihood of a first fiducial element and a second fiducial element being separated by a separation distance, wherein the second fiducial element comprises the nearest fiducial element to the first fiducial element.

101. The single-analyte array of clause 98, wherein the measure of randomness comprises a measurement of a quantity of fiducial elements N within a subset of the plurality of sites containing a first fiducial element, wherein the subset of the plurality of sites comprises M sites.

102. The single-analyte array of clause 98, wherein the measure of randomness comprises a likelihood of detecting N fiducial elements within a subset of the plurality of sites containing a first fiducial element, wherein the subset of the plurality of sites comprises M sites.

103. The single-analyte array of clause 101 or 102, wherein the subset of M sites is contiguous.

104. The single-analyte array of clause 101 or 102, wherein the subset of M sites is non-contiguous.

105. The single-analyte array of any one of clauses 98-102, wherein the measure of randomness is described by a probability distribution or a probability density function.

106. The single-analyte array of clause 98, wherein the measure of randomness comprises absence of a repeating pattern of spatial addresses for sites in the array.

107. The single-analyte array of any one of clauses 1-106, further comprising a landmarking region.

108. The single-analyte array of clause 107, wherein the landmarking region is configured to provide a measure of absolute position on the single-analyte array.

109. The single-analyte array of clause 107 or 108, wherein the landmarking region is configured to provide a measure of position for the beginning or end of an analytical method for the single-analyte array.

110. The single-analyte array of any one of clauses 107-109, wherein the landmarking region comprises a corner of the single-analyte array.

111. The single-analyte array of any one of clauses 107-110, wherein the landmarking region comprises an edge of the single-analyte array.

112. The single-analyte array of any one of clauses 107-111, wherein the landmarking region comprises a fiducial element.

113. The single-analyte array of clause 112, wherein the fiducial element comprises an optically active moiety, a metal fiducial material, a metal oxide fiducial material, or a combination thereof.

114. The single-analyte array of any one of clauses 1-113, wherein the plurality of sites comprises at least M sites, wherein M is at least 1000 sites.

115. The single-analyte array of clause 114, wherein the plurality of sites comprises at least M sites, wherein M is at least 10000000 sites.

116. The single-analyte array of clause 114, wherein the plurality of sites comprises at least M sites, wherein M is at least 1000000000 sites.

117. The single-analyte array of any one of clauses 114-116, wherein the plurality of fiducial elements is coupled to N sites, wherein N is no more than 10% of M.

118. The single-analyte array of clause 117, wherein the plurality of fiducial elements is coupled to N sites, wherein N is no more than 1% of M.

119. The single-analyte array of clause 118, wherein the plurality of fiducial elements is coupled to N sites, wherein N is no more than 0.1% of M.

120. The single-analyte array of any one of clauses 1-119, wherein the plurality of fiducial elements comprises a first fiducial element and a second fiducial element, wherein the first fiducial element comprises an optically active moiety and the second fiducial element comprises an optically passive moiety.

121. The single-analyte array of clause 120, wherein the plurality of fiducial elements comprises a first subset and a second subset, wherein the first subset comprises a plurality of optically active moieties and the second subset comprises a plurality of optically passive moieties.

122. The single-analyte array of clause 121, wherein the first subset is distributed to a non-repeating pattern of sites on the solid support.

123. The single-analyte array of clause 122, wherein the second subset is distributed to a repeating pattern of sites on the solid support.

124. The single-analyte array of clause 122, wherein the second subset is distributed to a non-repeating pattern of sites on the solid support.

125. The single-analyte array of any one of clauses 120-124, wherein a ratio of the number of fiducial elements in the first subset to the number of fiducial elements in the second subset is at least 5.

126. The single-analyte array of clause 125, wherein the ratio of the number of fiducial elements in the first subset to the number of fiducial elements in the second subset is at least 10.

127. The single-analyte array of clause 126, wherein the ratio of a number of fiducial elements in the first subset to the number of fiducial elements in the second subset is at least 100.

128. The single-analyte array of any one of clauses 120-127, wherein the ratio of the number of fiducial elements in the first subset to the number of fiducial elements in the second subset is no more than 1000000.

129. The single-analyte array of any one of clauses 120-128, wherein the solid support comprises a landmarking region, wherein the second fiducial element is located at the landmarking region, and wherein the first fiducial element is located at a region of the solid support other than the landmarking region.

130. The single-analyte array of any one of clauses 1-129, further comprising an identification tag.

131. The single-analyte array of clause 130, wherein the identification tag comprises an on-chip label.

132. The single-analyte array of clause 131, wherein the on-chip label comprises letters, numbers, symbols, shapes, colors, a serial number, a lot number, a radio frequency identification (RFID) tag, a printed barcode, a QR code, or a combination thereof.

133. The single-analyte array of clause 130, wherein the identification tag comprises a sample identification molecule.

134. The single-analyte array of clause 133, wherein the sample identification molecule comprises a nucleic acid, a polypeptide, or a combination thereof.

135. The single-analyte array of clause 134, wherein the nucleic acid or polypeptide is a synthetic biomolecule.

136. The single-analyte array of clause 134, wherein the nucleic acid or polypeptide is derived from a natural source.

137. The single-analyte array of any one of clauses 130-136, wherein the sample identification molecule is coupled to a sample identification region of the single-analyte array.

138. The single-analyte array of any one of clauses 1-137, wherein a site of the plurality of sites comprises two or more fiducial elements of the plurality of fiducial elements.

139. The single-analyte array of clause 138, wherein a subset of the plurality of sites comprises two or more fiducial elements of the plurality of fiducial elements.

140. The single-analyte array of clause 138, wherein the subset of the plurality of sites is distributed on the solid support in a random order as defined by a measure of randomness.

141. The single-analyte array of clause 139, wherein the measure of randomness comprises a measurement of an average distance between a first site of the subset of the plurality of sites and a second site of the subset of the plurality of sites, wherein the first fiducial element comprises only one fiducial element, wherein the second site comprises two or more fiducial elements, and wherein the second site is a nearest site comprising two or more fiducial elements to the first site.

142. The single-analyte array of clause 139, wherein the measure of randomness comprises a measurement of an average distance between a first site of the subset of the plurality of sites and a second site of the subset of the plurality of sites, wherein the first fiducial element comprises two or more fiducial elements, wherein the second site comprises two or more fiducial elements, and wherein the second site is a nearest site comprising two or more fiducial elements to the first site.

143. The single-analyte array of clause 139, wherein the measure of randomness comprises a likelihood that a sampling of M sites of the plurality of sites comprises N sites comprising two or more fiducial elements.

144. The single-analyte array of any one of clauses 1-143, further comprising a fluidic cartridge.

145. The single-analyte array of clause 144, wherein the single-analyte array is disposed within an internal volume of the fluidic cartridge.

146. The single-analyte array of clause 144 or 145, wherein the fluidic cartridge is configured to contact a fluid with the single-analyte array.

147. The single-analyte array of any one of clauses 144-146, wherein the fluidic cartridge further comprises one or more fluidic channels.

148. The single-analyte array of clause 147, wherein the one or more fluidic channels are configured to charge or discharge a fluid from an internal volume of the fluidic cartridge.

149. The single-analyte array of any one of clauses 1-148, wherein a fiducial element of the plurality of fiducial elements is co-located at a site with an analyte.

150. The single-analyte array of clause 149, wherein the analyte is not coupled to the fiducial element.

151. The single-analyte array of clause 149, wherein the analyte is coupled to the fiducial element.

152. The single-analyte array of clause 151, wherein the analyte is covalently coupled to the fiducial element.

153. The single-analyte array of clause 151, wherein the analyte is non-covalently coupled to the fiducial element.

154. A single-analyte array composition, comprising:
 a. a solid support, wherein the solid support comprises a plurality of addresses and one or more interstitial regions, wherein a subset of the addresses are sites that are configured to couple analytes of interest, wherein each interstitial region is configured to inhibit binding of the analytes of interest, and wherein each of the sites is separated from each other of the sites by an interstitial region of the one or more interstitial regions;
 b. a plurality of fiducial elements, wherein a second subset of addresses of the plurality of addresses comprises a coupled fiducial element of the plurality of fiducial elements, and wherein a spatial distribution of the second subset of addresses is random; and
 c. a plurality of the analytes of interest in contact with the solid support.

155. The single-analyte array composition of clause 154, wherein the plurality of analytes comprises a cell, a polypeptide, a nucleic acid, or a combination thereof.

156. The single-analyte array composition of clause 155, wherein the plurality of analytes comprises a plurality of cells, a plurality of polypeptides, a plurality of nucleic acids, or a combination thereof.

157. The single-analyte array composition of any one of clauses 154-156, wherein analytes of interest of the plurality of analytes of interest are each coupled to an anchoring moiety.

158. The single-analyte array composition of clause 157, wherein the anchoring moiety is configured to couple the analyte of interest to an address of the array.

159. The single-analyte array composition of clause 158, wherein the anchoring moiety is further configured to inhibit contact of the analyte with the address or an interstitial region of the one or more interstitial regions.

160. The single-analyte array composition of any one of clauses 157-159, wherein the anchoring moiety is configured to form a covalent interaction with the address.

161. The single-analyte array composition of any one of clauses 157-159, wherein the anchoring moiety is configured to form a non-covalent interaction with the site.

162. The single-analyte array composition of any one of clauses 157-161, wherein the anchoring moiety comprises a nucleic acid or a nanoparticle.

163. The single-analyte array composition of clause 162, wherein the nucleic acid comprises a structured nucleic acid particle.

164. The single-analyte array composition of clause 163, wherein the structured nucleic acid particle comprises a nucleic acid nanoball or a nucleic acid origami.

165. The single-analyte array composition of any one of clauses 157-164, wherein fiducial elements of the plurality of fiducial elements are each coupled to an anchoring moiety.

166. The single-analyte array composition of clause 165, wherein the anchoring moiety is configured to couple the fiducial to an address of the array.

167. The single-analyte array composition of any one of clauses 157-166, wherein the fiducial elements and the analytes of interest are coupled to the addresses via anchoring moieties that comprise structured nucleic acid particles.

168. The single-analyte array composition of any one of clauses 157-166, wherein the fiducial elements and the analytes of interest are coupled to the addresses via anchoring moieties that comprise non-nucleic acid particles.

169. The single-analyte array composition of any one of clauses 157-166, wherein the fiducial elements are coupled to the addresses via anchoring moieties that comprise non-nucleic acid particles and wherein the analytes of interest are coupled to the addresses via anchoring moieties that comprise structured nucleic acid particles.

170. The single-analyte array composition of any one of clauses 157-166, wherein the fiducial elements are coupled to the addresses via anchoring moieties that comprise structured nucleic acid particles and wherein the analytes of interest are coupled to the addresses via anchoring moieties that comprise non-nucleic acid particles.

171. The single-analyte array composition of any one of clauses 154-170, wherein the plurality of analytes is in fluidic communication with the solid support.

172. The single-analyte array composition of clause 171, further comprising a fluidic medium comprising the plurality of single analytes.

173. The single-analyte array composition of clause 172, wherein the fluidic medium is configured to facilitate coupling of an analyte of the plurality of analytes to a site of the plurality of sites.

174. The single-analyte array composition of any one of clauses 154-173, wherein an analyte of the plurality of analytes is coupled to a site of the plurality of sites.

175. The single-analyte array composition of clause 174, wherein the site does not comprise a fiducial element.

176. The single-analyte array composition of clause 174, wherein the site further comprises a fiducial element.

177. The single-analyte array composition of clause 174, wherein each analyte of the plurality of analytes is coupled to a site of a second subset of the plurality of sites, wherein the second subset comprises the plurality of sites excluding the first subset of sites.

178. The single-analyte array composition of clause 177, wherein a site of the second subset of sites comprises only one analyte.

179. The single-analyte array composition of clause 178, wherein each site of the second subset of sites comprises only one analyte.

180. The single-analyte array composition of clause 178, wherein a site of the second subset of sites comprises more than one analyte.

181. The single-analyte array composition of any one of clauses 177-180, further comprising a plurality of analytical reagents.

182. The single-analyte array composition of clause 181, wherein an analytical reagent of the plurality of analytical reagents is configured to form an interaction with an analyte of the plurality of analytes.

183. The single-analyte array composition of clause 182, wherein the interaction comprises a binding interaction, a chemical modification reaction, a structural modification reaction, or a combination thereof.

184. The single-analyte array composition of any one of clauses 181-183, wherein an analytical reagent of the plurality of analytical reagents comprises an affinity agent that recognizes an analyte of interest of the plurality of analytes of interest.

185. The single-analyte array composition of clause 184, wherein the plurality of analytical reagents comprises a plurality of affinity agents that recognize analytes of interest of the plurality of analytes of interest.

186. The single-analyte array composition of clause 185, wherein each affinity agent of the plurality of affinity agents is bound to an analyte of interest of the plurality of analytes of interest.

187. The single-analyte array composition of clause 186, wherein a subset of sites comprising M contiguous sites comprises at least one site comprising a fiducial element and no more than about 50% of sites of the subset of sites comprising an analyte coupled to an affinity agent.

188. The single-analyte array composition of clause 187, wherein a subset of sites comprising M contiguous sites comprises at least one site comprising a fiducial element and no more than about 10% of sites of the subset of sites comprising an analyte coupled to an affinity agent.

189. The single-analyte array composition of clause 188, wherein a subset of sites comprising M contiguous sites comprises at least one site comprising a fiducial element and no more than about 1% of sites of the subset of sites comprising an analyte coupled to an affinity agent.

190. A non-transitory computer-readable medium, comprising:
  a. an identification value corresponding to an identification tag of an array; and
  b. an array map, wherein the array map comprises a plurality of data units, in which each data unit comprises:
    i) a location tag, wherein the location tag comprises a datum corresponding to a site on the array; and
    ii) a signal datum for the site on the array, wherein the signal datum comprises information pertaining to presence or absence of a fiducial element at the site on the array.

191. A composition, comprising:
  a. a solid support comprising an address with a known spatial address;
  b. a fiducial element coupled to the address; and
  c. an analyte coupled to the address;
  wherein the fiducial element and the analyte are spatially non-resolvable at the address at single-analyte resolution, and wherein the fiducial element and the analyte are resolvable at the address via distinguishable optical characteristics.

192. The composition of clause 191, further comprising an affinity agent, wherein the affinity agent is coupled to the analyte.

193. The composition of clause 192, wherein the affinity agent comprises an optically-detectable label, wherein the optically-detectable label is configured to provide a detectable signal.

194. The composition of clause 193, wherein the optically detectable label is configured to provide a detectable signal that is distinguishable from a detectable signal provided by the fiducial element.

195. A single-analyte system, comprising:
  a. a single-analyte array of any one of clauses 1-153;
  b. a sensing device; and
  c. a retaining device, wherein the retaining device is configured to position a landmarking region of the single-analyte array relative to the sensing device.

196. The single-analyte system of clause 195, further comprising a translation device.

197. The single-analyte system of clause 196, wherein the translation device is configured to alter a position between the single-analyte array relative and the sensing device.

198. The single-analyte system of clause 196 or 197, wherein the single-analyte system comprises a first landmarking position corresponding to a first position between the single-analyte array and the sensing device and a second landmarking position corresponding to a second position between the single-analyte array and the sensing device.

199. The single-analyte array of clause 198, wherein the first landmarking position comprises an initial position between the single-analyte array and the sensing device.

200. The single-analyte array of clause 198 or 199, wherein the second landmarking position comprises a final position between the single-analyte array and the sensing device.

201. A non-transitory, computer-readable medium, comprising:
 a. a first subarray map comprising a first plurality of data units, wherein each data unit of the first plurality of data units comprises a signal datum for the site on the array, wherein the signal datum comprises information pertaining to presence or absence of a fiducial element at the site on the first subregion of the array;
 b. a second subarray map comprising a second plurality of data units, wherein each data unit of the second plurality of data units comprises a signal datum for the site on the array, wherein the signal datum comprises information pertaining to presence or absence of a fiducial element at the site on the second subregion of the array;
 wherein a first subset of signal data of the first plurality of data units corresponds to a first random spatial order of fiducial elements at sites of the array, wherein a second subset of signal data of the second plurality of data units corresponds to a second random spatial order of fiducial elements at sites of the array, and wherein the first random spatial order and the second random spatial order are the same.

202. A method of registering overlapping data sets, comprising:
 a. obtaining a first data set of an array of any one of clauses 1-153, wherein the first data set comprises a spatial distribution of detected signals in a first field-of-view of a sensing device, wherein the first field-of-view encompasses a first plurality of sites, wherein the first plurality of sites comprises a first pattern of detected signals from a plurality of fiducial elements, and wherein a first site of the first plurality of sites is optically non-resolvable;
 b. obtaining a second data set of the array, wherein the second data set comprises a spatial distribution of detected signals in a second field-of-view of the sensing device, wherein the second field-of-view encompasses a second plurality of sites, wherein the second plurality of sites, wherein the second plurality of sites comprises a second pattern of detected signals from the plurality of fiducial elements, and wherein a second site of the second plurality of sites is optically non-resolvable;
 c. aligning the first pattern of detected signals with the second pattern of detected signals; and
 d. after aligning the first pattern of detected signals with the second pattern of detected signals, identifying a first address of the first site, and identifying a second address of the second site.

203. The method of clause 202, wherein the address of the first site of the first plurality of sites or the address of the second site of the second plurality of sites is optically non-resolvable based upon a ratio of a magnitude of a detected signal from the first site or the second site to a magnitude of a detected background signal.

204. The method of clause 203, wherein the ratio of the magnitude of the signal from first site or the second site to the magnitude of the detected background signal is less than 2.

205. The method of clause 204, wherein the ratio of the magnitude of the signal from first site or the second site to the magnitude of the detected background signal is less than 1.5.

206. The method of clause 205, wherein the ratio of the magnitude of the signal from first site or the second site to the magnitude of the detected background signal is less than 1.1.

207. The method of any one of clauses 202-206, further comprising:
 a. collecting the first data set of an array on an array-based system comprising a sensing device; and
 b. collecting the second data set of the array on the array-based system comprising a sensing device.

208. The method of clause 207, wherein the sensing device comprises a sensor, wherein the sensor comprises a pixel array containing a plurality of pixels.

209. The method of clause 208, wherein collecting the first data set or collecting the second data set comprises distinguishing signal intensities at each pixel of the plurality of pixels of the pixel array.

210. The method of clause 209, wherein the signal intensities comprise signal magnitudes of signals derived from signal sources.

211. The method of clause 210, wherein the signal sources comprise analytes or affinity agents bound to the analytes.

212. The method of clause 210, wherein the signal sources comprise a fiducial element.

213. The method of any one of clauses 202-212, wherein the first plurality of sites or the second plurality of sites comprises at least 1000 sites.

214. The method of clause 213, wherein the first plurality of sites or the second plurality of sites comprises at least 10000 sites.

215. The method of any one of clauses 214, wherein the first plurality of sites or the second plurality of sites comprises at least 100000 sites.

216. The method of any one of clauses 213-215, wherein addresses of at least 75% of sites of the first plurality of sites are optically non-resolvable in the first data set.

217. The method of clause 216, wherein addresses of at least 90% of sites of the first plurality of sites are optically non-resolvable in the first data set.

218. The method of clause 217, wherein addresses of at least 99% of sites of the first plurality of sites are optically non-resolvable in the first data set.

219. The method of any one of clauses 216-218, wherein addresses of at least 75% of sites of the second plurality of sites are optically non-resolvable in the second data set.

220. The method of clause 219, wherein addresses of at least 90% of sites of the second plurality of sites are optically non-resolvable in the second data set.

221. The method of clause 220, wherein addresses of at least 99% of sites of the second plurality of sites are optically non-resolvable in the second data set.

222. The method of any one of clauses 202-221, wherein the first field-of-view has the same aspect ratio as the second field-of-view.

223. The method of clause 222, wherein the first field-of-view has the same length as the second field-of-view.

224. The method of clause 222, wherein the first field-of-view has a different length from the second field-of-view.

225. The method of clause 224, further comprising rescaling the first image or the second image to align with each other.

226. The method of any one of clauses 222-225, wherein the first field-of-view is rotated relative to the second field-of-view.

227. The method of clause 226, further comprising rotating the first image or the second image to align with each other.

228. The method of any one of clauses 222-227, wherein the first field-of-view is tilted relative to the second field-of-view.

229. The method of clause 228, further comprising re-tilting the first image or the second image to align with each other.

230. The method of any one of clauses 202-229, wherein aligning the first pattern of fiducial elements with the second pattern of fiducial elements further comprises:
　a. altering the second data set to form an altered second pattern of fiducial elements; and
　b. aligning the first pattern of fiducial elements with the altered second pattern of fiducial elements.

231. The method of clause 230, wherein altering the second data set comprises altering spatial information of the second data set.

232. The method of clause 231, wherein the altering spatial information of the second data set comprises a rotational transformation of spatial data within a focal plane, a rotational transformation of spatial data into or out of a focal plane, re-scaling the spatial data of the second data set, or a combination thereof.

233. The method of clause 230, wherein altering the second data set comprises altering signal information of the second data set.

234. The method of clause 233, wherein signal information of the second data set comprises filtering signal information, reducing noise of signal information, subtracting background from signal information, altering contrast of signal information, or a combination thereof.

235. The method of any one of clauses 202-234, further comprising identifying presence or absence of a detected signal at each site of the first plurality of sites and the second plurality of sites.

236. The method of any one of clauses 202-235, wherein the first data set or the second data set is derived from image data.

237. The method of clause 236, wherein the image data comprises unaltered image data.

238. The method of clause 236, wherein the image data comprises altered image data.

239. The method of clause 236, wherein the image data comprises a data structure derived from an image, in which the data structure comprises a plurality of data units, in which each data unit comprises: i) an address of a plurality of addresses, and ii) a detected signal at the address of the plurality of addresses.

240. The method of clause 239, wherein the address of the plurality of addresses corresponds to a pixel of a pixel array of a sensing device.

241. The method of any one of clauses 202-240, further comprising performing steps a)—d) with a third data set, wherein the third data set comprises a spatial distribution of detected signals in a third field-of-view of a sensing device, wherein the third field-of-view encompasses a third plurality of sites, wherein the third plurality of sites comprises a third pattern of detected signals from a plurality of fiducial elements, and wherein a third site of the third plurality of sites is optically non-resolvable.

242. The method of clause 241, further comprising, after registering the overlapping data sets, determining an array map based upon the overlapping data sets.

243. The method of clause 242, wherein the array map comprises a first plurality of addresses, wherein each address of the first plurality of addresses comprises a fiducial element.

244. The method of clause 242 or 243, wherein the array map comprises a second plurality of addresses, wherein each address of the second plurality of addresses comprises a signal from an analyte signal source.

245. The method of clause 244, wherein the analyte signal source comprises an analyte.

246. The method of clause 244, wherein the analyte signal source comprises an affinity agent bound to an analyte.

247. The method of any one of clauses 202-246, wherein the first pattern of the plurality of fiducial elements and the second pattern of fiducial elements are the same pattern based upon a measure of randomness.

248. The method of clause 247, wherein the measure of randomness is a local measure of randomness.

249. The method of clause 247, wherein the measure of randomness is a global measure of randomness.

250. A method of mapping an address of a site, comprising:
　a. providing a single-analyte array comprising a solid support, wherein the single-analyte array comprises a first site, a second site, and a third site, wherein the first site comprises a first address on the solid support, wherein the second site comprises a second address on the solid support, wherein the third site comprises a third address on the solid support, and wherein the first address, the second address, and the third address are resolvable at single-analyte resolution;
　b. coupling a first fiducial element to the third site;
　c. coupling a first locating moiety to the first site and a second locating moiety to the second site, wherein the locating moiety comprises a detectable label or a second fiducial element;
　d. detecting the first locating moiety, the second locating moiety, and the first fiducial element; and
　e. identifying the first address and the second address relative to the third address.

251. The method of clause 250, wherein the detectable label comprises a fluorophore or a luminophore.

252. The method of clause 251, wherein the detectable label further comprises a nucleic acid.

253. The method of clause 252, wherein the nucleic acid comprises a single-stranded nucleic acid, a double-stranded nucleic acid, or a combination thereof.

254. The method of clause 252 or 253, wherein the nucleic acid comprises a structured nucleic acid particle.

255. The method of any one of clauses 250-254, wherein coupling the first fiducial element to the third site further comprises simultaneously contacting the array with a pool of fiducial elements, wherein the pool of fiducial elements comprises the first fiducial element.

256. The method of clause 255, wherein coupling the first locating moiety to the first site and a second locating moiety to the second site further comprises contacting the array with a plurality of locating moieties, wherein the plurality of locating moieties comprises the first locating moiety and the second locating moiety.

257. The method of clause 256, wherein contacting the solid support with the plurality of locating moieties occurs before contacting the solid support with the pool of fiducial elements.

258. The method of clause 256, wherein contacting the solid support with the plurality of locating moieties occurs after contacting the solid support with the pool of fiducial elements.

259. The method of any one of clauses 250-258, wherein detecting the first locating moiety, the second locating moiety, and the first fiducial element comprises:
   i) sensing a first detectable signal emitted from the first locating moiety, sensing a second detectable signal emitted from the second locating moiety, and sensing a third detectable signal emitted from the first fiducial element.

260. A method of qualifying a single-analyte array, comprising:
   a. providing a single-analyte array, wherein the single-analyte array comprises:
      i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions;
      ii) a plurality of fiducial elements, wherein each fiducial element is located at a site of the plurality of sites, and wherein the plurality of fiducial elements is distributed on the solid support at spatially random addresses;
   b. determining a measure of spatial randomness for the plurality of fiducial elements; and
   c. selecting the single-analyte array if the measure of spatial randomness meets a selection criterion for the measure of spatial randomness.

261. A method of preparing a solid support, comprising:
   a. providing the solid support, wherein the solid support comprises a plurality of sites, wherein each site of the plurality of sites has a unique spatial address on a surface of the solid support, and wherein each site of the plurality of sites is configured to couple a moiety to the surface of the solid support;
   b. depositing a plurality of fiducial elements on the solid support, wherein each fiducial element of the plurality of fiducial elements is deposited at a random site of the plurality of sites; and
   c. identifying a spatial distribution of the plurality of fiducial elements on the solid support, wherein the spatial distribution comprises presence or absence of a fiducial element of the plurality of fiducial elements at each address of the plurality of addresses.

262. A method of forming a single-analyte array, comprising:
   a. providing a single-analyte array, wherein the single-analyte array comprises:
      i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions;
      ii) a plurality of fiducial elements, wherein each fiducial element is located at a site of the plurality of sites, and wherein the plurality of fiducial elements is distributed on the solid support at spatially random addresses; and
   b. depositing a plurality of single analytes on the solid support, wherein each single analyte of the plurality of single analytes is deposited at a site that does not comprise a fiducial element.

263. A method of aligning a single-analyte array, comprising:
   a. providing a single-analyte array, wherein the single-analyte array comprises:
      i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions;
      ii) a plurality of fiducial elements, wherein each fiducial element is located at a site of the plurality of sites, and wherein the plurality of fiducial elements is distributed on the solid support at spatially random addresses; and
      iii) a landmarking fiducial element;
   b. setting an initial position for the single-analyte array based upon a first identification of the landmarking fiducial element relative to the detection device;
   c. scanning the plurality of sites of the single-analyte array with the detection device, wherein scanning the plurality of sites comprises altering a position of the detection device relative to the single-analyte array; and
   d. returning the single-analyte array to the initial position relative to the detection device based upon a second identification of the landmarking fiducial element relative to the detection device.

264. A method of aligning multiple sensors, comprising:
   a. providing a single-analyte array, wherein the single-analyte array comprises:
      i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and
      ii) a plurality of fiducial elements, wherein each fiducial element is located at a site of the plurality of sites, and wherein the plurality of fiducial elements is distributed on the solid support at spatially random addresses;
   b. identifying in a first field-of-view on a first sensor a first plurality of signals from a subset of fiducial elements of the plurality of fiducial elements, in which the first plurality of signals comprises a unique spatial pattern;
   c. identifying in a second field-of-view on a second sensor a second plurality of signals from the subset of fiducial elements of the plurality of fiducial elements, in which the second plurality of signals comprises the unique spatial pattern; and
   d. determining a spatial offset between the first field-of-view and the second field-of-view.

265. A method of altering an optical detection device comprising:
   a. providing a single-analyte array, wherein the single-analyte array comprises:
      i) a solid support, wherein the solid support comprises a plurality of sites and one or more interstitial regions, wherein each site of the plurality of sites is configured to couple an analyte, wherein each interstitial region is configured to inhibit binding of an unbound moiety, and wherein each site is separated from each other site by an interstitial region of the one or more interstitial regions; and
ii) a plurality of fiducial elements, wherein each fiducial element is located at a site of the plurality of sites, and wherein the plurality of fiducial elements is distributed on the solid support at spatially random addresses;
b. obtaining a plurality of signals from the single-analyte array using a optical detection device, in which the plurality of signals comprise a spatial pattern of a subset of the plurality of fiducial elements;
c. determining an optical calibration parameter based upon the plurality of signals; and
d. based upon the optical calibration parameter, altering an optical setting of the optical detection device relative to the single-analyte array.

266. A method for registering a plurality of images of a substrate, the method comprising:
obtaining a first plurality of points within a first image in the plurality of images, the first image defining a first angular reference frame, wherein the first plurality of points comprises about 100 or more points and each respective point in the first plurality of points has respective two-dimensional coordinates defining a location of the respective point in the first image;
obtaining a second plurality of points within a second image in the plurality of images, the second image defining a second angular reference frame, wherein the second plurality of points comprises about 100 or more points, wherein each respective point in the second plurality of points has respective two-dimensional coordinates defining a location of the respective point in the second image, and wherein the first plurality of points and the second plurality of points are coplanar, and wherein
at least a first subset of the first plurality of points is not represented by the second plurality of points,
at least a second subset of the second plurality of points is not represented by the first plurality of points, and
at least a third subset of points in the first plurality of points is represented in the second plurality of points;
forming a transformation data structure that includes a respective counter for each transform candidate in a plurality of transform candidates, wherein
each transform candidate in the plurality of transform candidates includes a two-dimensional translation component and a planar rotational component,
the plurality of transform candidates collectively samples between a first angle and a second angle about an axis orthogonal to the first and second plurality of points, and
the plurality of transform candidates comprises about 5,000 or more different transform candidates;
for each respective point in one of the first and second plurality of points:
(i) pairing the respective point with a corresponding point in the other of the first and second plurality of points whose corresponding two-dimensional coordinates are within a query radius centered on the respective two-dimensional coordinates of the respective point, thereby identifying a respective point pair,
(ii) adding, for the respective point pair, a respective vote for each respective transform candidate in the plurality of transform candidates, having a respective angle represented by the transformation data structure, that maps the respective point onto the corresponding point, to the respective counter for the respective transform candidate in the transformation data structure, and
(iii) repeating the adding (ii) for the respective point pair for each respective angle represented by the transformation data structure thereby adding additional votes for respective transform candidates identified by the adding (ii), and
(iv) repeating the pairing (i), adding (ii), and repeating (iii) for the respective point with each other corresponding point in the second plurality of points that is within the query radius; and
registering the first and second images to each other using a respective transform candidate selected from the plurality of transform candidates in the transformation data structure based at least in part on a value of the respective counter associated with the respective transform candidate in the transformation data structure.

267. The method of clause 266, wherein the adding (ii) rotates a point in the respective point pair by the respective angle about the axis prior to determining each respective transform candidate in the plurality of transform candidates having the respective angle, represented by the transformation data structure, that maps the respective point onto the corresponding point.

268. The method of clause 266 or 267, wherein the query radius is at least 10 pixels, at least 20 pixels, or at least 50 pixels.

269. A method for registering a plurality of images of a substrate, the method comprising:
obtaining a first plurality of points within a first image in the plurality of images, the first image defining a first angular reference frame, wherein the first plurality of points comprises about 100 or more points;
obtaining a second plurality of points within a second image in the plurality of images, the second image defining a second angular reference frame, wherein the second plurality of points comprises about 100 or more points, and wherein the first plurality of points and the second plurality of points are coplanar, and wherein
at least a first subset of the first plurality of points is not represented by the second plurality of points,
at least a second subset of the second plurality of points is not represented by the first plurality of points, and
at least a third subset of points in the first plurality of points is represented in the second plurality of points;
forming a transformation data structure that includes a respective counter for each transform candidate in a plurality of transform candidates, wherein each transform candidate in the plurality of transform candidates includes a two-dimensional translation component and a planar rotational component, and wherein the plurality of transform candidates comprises about 5,000 or more different transform candidates;
for each respective transform candidate in the plurality of transform candidates, performing a procedure that comprises:
(i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition; and registering the first and second images to each other using a respective transform candidate selected from the plurality of transform candidates in the transformation data structure based at least in part on a value of the respective counter associated with the respective transform candidate in the transformation data structure.

270. The method of any one of clauses 266-269, wherein the substrate has a planar surface.

271. The method of any one of clauses 266-270, wherein each image in the plurality of images comprises more than 200,000 pixels.

272. The method of any one of clauses 266-271, where each image in the plurality of images comprises more than 500,000 pixels.

273. The method of any one of clauses 266-272, wherein
each image in the plurality of images comprises at least about 500 pixels in a first dimension,
each image in the plurality of images comprises at least about 500 pixels in a second dimension orthogonal to the first dimension, and
each transform candidate in the plurality of transform candidates transforms one of the first image or the second image between about 1 pixel and about 300 pixels.

274. The method of any one of clauses 266-273, wherein
each image in the plurality of images consists of 2048 pixels in a first dimension,
each image in the plurality of images consists of 2048 pixels in a second dimension orthogonal to the first dimension, and
each transform candidate in the plurality of transform candidates transforms one of the first image or the second image between about 1 pixel and about 256 pixels.

275. The method of any one of clauses 266-274, wherein each point in the first plurality of points represents optical activity localized to a corresponding position on the substrate.

276. The method of clause 275, wherein a first subplurality of the first plurality of points arises from respective optical measurements of a plurality of fiducials on the substrate, wherein points corresponding to the first subplurality of points is in the second plurality of points, and a second subplurality of the first plurality of points arises from respective optical measurements of a plurality of polypeptide molecules when bound to an affinity reagent, and each polypeptide molecule of said plurality of polypeptide molecules is coupled to a unique, spatially-separated location of a plurality of unique, spatially-separated locations on the substrate.

277. The method of clause 276, wherein the affinity reagent binds to more than one unique epitope present within one or more polypeptides in the plurality of polypeptide molecules.

278. The method of clause 276, wherein the affinity reagent comprises a known degree of binding nonspecificity.

279. The method of clause 276, wherein said plurality of polypeptide molecules comprises more than 500, more than 1000, more than 2000, more than 3000, more than 5000, more than 6000, or more than 7000 different polypeptide molecules.

280. The method of clause 276, wherein the first subplurality represents less than 10 percent, less than 5 percent, or less than 2 percent of the first plurality of points.

281. The method of any one of clauses 266-271, wherein each transform candidate in the plurality of transform candidates transforms one of the first image or the second image between about 1 pixel and about 500 pixels.

282. The method of any one of clauses 266-281, wherein the plurality of transform candidates comprises a sampling between a first limit angle and a second limit angle about the axis.

283. The method of clause 282, wherein the first limit angle is −0.5° and the second limit angle is +0.5°.

284. The method of clause 282, wherein the first limit angle is −5° and the second limit angle is +5°.

285. The method of clause 282, wherein the plurality of transform candidates samples between the first limit angle and the second limit angle with a constant step size, and where the constant step size is 0.01°.

286. The method of any one of clauses 266-285, wherein
the first plurality of points comprises about 200 or more, about 400 or more, about 600 or more, about 800 or more, or about 1000 or more points, and
the second plurality of points comprises about 200 or more, about 400 or more, about 600 or more, about 800 or more, or about 1000 or more points.

287. The method of any one of clauses 266-286, wherein at least about 5 percent, at least about 10 percent, at least about 15 percent, at least about 20 percent, at least about 25 percent, at least about 30 percent, at least about 35 percent, or at least about 40 percent of the first plurality of points is not represented by the second plurality of points.

288. The method of any one of clauses 266-287, wherein
each point in the first plurality of points occupies a corresponding single pixel in the first image; and
each point in the second plurality of points occupies a corresponding single pixel in the second image.

289. The method of any one of clauses 266-288, wherein selection of the respective transform candidate in the plurality of transform candidates in the transformation data structure based at least in part on a value of the respective counter associated with the respective transform candidate in the transformation data structure includes identifying an optimal planar rotational component by a procedure comprising:

for each different candidate planar rotational component represented in the plurality of transform candidates:
  (i) forming a corresponding Hough two-dimensional image, wherein each pixel in the corresponding Hough two-dimensional image is the corresponding count of points of a respective transform candidate in the plurality of transform candidates having the different candidate planar rotational component,
  (ii) applying a binomial distribution cumulative distribution function across the respective counts of each transform candidate in the respective image; and
  (iii) computing a respective z-score of the largest peak in the respective Hough two-dimensional image,
thereby forming a plurality of Hough two-dimensional images,
wherein the respective transform candidate is selected from among the plurality of transform candidates in the transformation data structure based on a respective z-score of each largest peak in each Hough two-dimensional image in the plurality of Hough two-dimensional images.

290. The method of clause 289, wherein the respective transform candidate is selected from among the plurality of transform candidates in the transformation data structure that is associated with a peak in the plurality of Hough two-dimensional images having the largest Z-score.

291. The method of clause 289 or 290, wherein the method further comprises applying a Gaussian filter to the respective Hough two-dimensional image prior to computing the respective z-score.

292. The method of any one of clauses 266-291, wherein at least about 5 percent, at least about 10 percent, at least about 15 percent, at least about 20 percent, at least about 25 percent, at least about 30 percent, at least about 35 percent, or at least about 40 percent of the first plurality of points is represented in the second plurality of points.

293. The method of any one of clauses 266-291, wherein between about 5 percent and about 10 percent, between about 15 percent and about 20 percent, between about 25 percent and about 30 percent, between about 35 percent and about 40 percent, between about 20 percent and about 90, or between about 5 percent and about 99 percent of the first plurality of points is represented in the second plurality of points.

294. The method of any one of clauses 266-293, wherein the registration is a rigid transformation.

295. The method of any one of clauses 266-294, wherein each point in the first plurality of points and in the second plurality of points represents an optical measurement of a corresponding position on the substrate.

296. The method of clause 295, wherein the optical measurement is of a fluorescence.

297. The method of clause 295, wherein the optical measurement is of a bioluminescence, a chemiluminescence, or a light scattering signal.

298. The method of any one of clauses 266-297, wherein
each image in the plurality of images comprises at least about 500 pixels in a first dimension, and
each image in the plurality of images comprises at least about 500 pixels in a second dimension orthogonal to the first dimension.

299. The method of any one of clauses 266-298, wherein
each image in the plurality of images consists of 2048 pixels in a first dimension, and
each image in the plurality of images consists of 2048 pixels in a second dimension orthogonal to the first dimension.

300. The method of clause 269, wherein
the plurality of transform candidates samples between about one and about 500 pixels in a first translational dimension with a constant first step size; and
the plurality of transform candidates samples between about one and about 500 pixels in a second translational dimension with a constant second step size.

301. The method of clause 300, wherein the constant first step size and the constant second step size is the same or different.

302. The method of clause 300, wherein the constant first step size and the constant second step size are each a single pixel.

303. The method of any one of clauses 300-302, wherein the plurality of transform candidates samples between a first angle and a second angle about the axis with a third constant step size.

304. The method of clause 303, wherein the first angle is −0.5° and the second angle is +0.5°.

305. The method of clause 303, wherein the first angle is −5° and the second angle is +5°.

306. A computer system comprising:
one or more processors;
memory; and
one or more programs, wherein the one or more programs are stored in the memory and are configured to be executed by the one or more processors, the one or more programs including instructions for registering a plurality of images of a substrate by a method comprising:
obtaining a first plurality of points within a first image in the plurality of images, the first image defining a first angular reference frame, wherein the first plurality of points comprises about 100 or more points and each respective point in the first plurality of points has respective two-dimensional coordinates defining a location of the respective point in the first image;
obtaining a second plurality of points within a second image in the plurality of images, the second image defining a second angular reference frame, wherein the second plurality of points comprises about 100 or more points, wherein each respective point in the second plurality of points has respective two-dimensional coordinates defining a location of the respective point in the second image, and wherein the first plurality of points and the second plurality of points are coplanar, and wherein
at least a first subset of the first plurality of points is not represented by the second plurality of points,
at least a second subset of the second plurality of points is not represented by the first plurality of points, and
at least a third subset of points in the first plurality of points is represented in the second plurality of points;
forming a transformation data structure that includes a respective counter for each transform candidate in a plurality of transform candidates, wherein each transform candidate in the plurality of transform candidates includes a two-dimensional translation component and a planar rotational component,
the plurality of transform candidates collectively samples between a first angle and a second angle about an axis orthogonal to the first and second plurality of points, and
the plurality of transform candidates comprises about 5,000 or more different transform candidates;
for each respective point in one of the first and second plurality of points:
(i) pairing the respective point with a corresponding point in the other of the first and second plurality of points whose corresponding two-dimensional coordinates are within a query radius centered on the respective two-dimensional coordinates of the respective point thereby identifying a respective point pair,
(ii) adding, for the respective point pair, a respective vote for each respective transform candidate in the plurality of transform candidates, having a respective angle represented by the transformation data structure, that maps the respective point onto the corresponding point, to the respective counter for the respective transform candidate in the transformation data structure, and
(iii) repeating the adding (ii) for the respective point pair for each respective angle represented by the transformation data structure thereby adding additional votes for respective transform candidates identified by the adding (ii), and (iv) repeating the pairing (i), adding (ii), and repeating (iii) for the respective point with each other corresponding point in the second plurality of points that is within the query radius; and registering the first and second images to each other using a respective transform candidate selected from the plurality of transform candidates in the transformation data structure based at least in part on a value of the respective counter associated with the respective transform candidate in the transformation data structure.

307. A computer readable storage medium storing one or more programs, the one or more programs comprising instructions that, when executed by an electronic device with one or more processors and a memory, cause the electronic device to perform a method for registering a plurality of images of a substrate, comprising:

obtaining a first plurality of points within a first image in the plurality of images, the first image defining a first angular reference frame, wherein the first plurality of points comprises about 100 or more points and each respective point in the first plurality of points has respective two-dimensional coordinates defining a location of the respective point in the first image;

obtaining a second plurality of points within a second image in the plurality of images, the second image defining a second angular reference frame, wherein the second plurality of points comprises about 100 or more points, wherein each respective point in the second plurality of points has respective two-dimensional coordinates defining a location of the respective point in the second image, and wherein the first plurality of points and the second plurality of points are coplanar, and wherein at least a first subset of the first plurality of points is not represented by the second plurality of points, at least a second subset of the second plurality of points is not represented by the first plurality of points, and at least a third subset of points in the first plurality of points is represented in the second plurality of points;

forming a transformation data structure that includes a respective counter for each transform candidate in a plurality of transform candidates, wherein each transform candidate in the plurality of transform candidates includes a two-dimensional translation component and a planar rotational component, the plurality of transform candidates collectively samples between a first angle and a second angle about an axis orthogonal to the first and second plurality of points, and the plurality of transform candidates comprises about 5,000 or more different transform candidates;

for each respective point in one of the first and second plurality of points:

(i) pairing the respective point with a corresponding point in the other of the first and second plurality of points whose corresponding two-dimensional coordinates are within a query radius centered on the respective two-dimensional coordinates of the respective point thereby identifying a respective point pair, (ii) adding, for the respective point pair, a respective vote for each respective transform candidate in the plurality of transform candidates, having a respective angle represented by the transformation data structure, that maps the respective point onto the corresponding point, to the respective counter for the respective transform candidate in the transformation data structure, and (iii) repeating the adding (ii) for the respective point pair for each respective angle represented by the transformation data structure thereby adding additional votes for respective transform candidates identified by the adding (ii), and (iv) repeating the pairing (i), adding (ii), and repeating (iii) for the respective point with each other corresponding point in the second plurality of points that is within the query radius; and registering the first and second images to each other using a respective transform candidate selected from the plurality of transform candidates in the transformation data structure based at least in part on a value of the respective counter associated with the respective transform candidate in the transformation data structure.

308. A computer system comprising:

one or more processors;

memory; and one or more programs, wherein the one or more programs are stored in the memory and are configured to be executed by the one or more processors, the one or more programs including instructions for registering a plurality of images of a substrate, by a method comprising:

obtaining a first plurality of points within a first image in the plurality of images, the first image defining a first angular reference frame, wherein the first plurality of points comprises about 100 or more points;

obtaining a second plurality of points within a second image in the plurality of images, the second image defining a second angular reference frame, wherein the second plurality of points comprises about 100 or more points, and wherein the first plurality of points and the second plurality of points are coplanar, and wherein at least a first subset of the first plurality of points is not represented by the second plurality of points, at least a second subset of the second plurality of points is not represented by the first plurality of points, and at least a third subset of points in the first plurality of points is represented in the second plurality of points;

forming a transformation data structure that includes a respective counter for each transform candidate in a plurality of transform candidates, wherein each transform candidate in the plurality of transform candidates includes a two-dimensional translation component and a planar rotational component, and wherein the plurality of transform candidates comprises about 5,000 or more different transform candidates;

for each respective transform candidate in the plurality of transform candidates, performing a procedure that comprises:

(i) superimposing the first and second plurality of points onto each other using the respective transform candidate to form a respective candidate superposition, and (ii) for each respective point, in the first plurality of points, adding to the respective counter for the transform candidate in the transformation data structure, a single vote when the respective point overlaps a corresponding point from the second plurality of points in the respective candidate superposition; and registering the first and second images to each other using a respective transform candidate selected from the plurality of transform candidates in the transformation data structure based at least in part on a value of the respective counter associated with the respective transform candidate in the transformation data structure.

309. A computer readable storage medium storing one or more programs, the one or more programs comprising instructions that, when executed by an electronic device with one or more processors and a memory, cause the electronic device to perform a method for registering a plurality of images of a substrate, comprising:
  obtaining a first plurality of points within a first image in the plurality of images, the first image defining a first angular reference frame, wherein the first plurality of points comprises about 100 or more points;
  obtaining a second plurality of points within a second image in the plurality of images, the second image defining a second angular reference frame, wherein the second plurality of points comprises about 100 or more points, and wherein the first plurality of points and the second plurality of points are coplanar, and wherein
    at least a first subset of the first plurality of points is not represented by the second plurality of points,
    at least a second subset of the second plurality of points is not represented by the first plurality of points, and
    at least a third subset of points in the first plurality of points is represented in the second plurality of points;
  forming a transformation data structure that includes a respective counter for each transform candidate in a plurality of transform candidates, wherein each transform candidate in the plurality of transform candidates includes a two-dimensional translation component and a planar rotational component, and wherein the plurality of transform candidates comprises about 5,000 or more different transform candidates;
  for each respective transform candidate in the plurality of transform candidates, performing a procedure that comprises:
    (i) superimposing the first and second plurality of points onto each other using the respective transform candidate to form a respective candidate superposition, and
    (ii) for each respective point, in the first plurality of points, adding to the respective counter for the transform candidate in the transformation data structure, a single vote when the respective point overlaps a corresponding point from the second plurality of points in the respective candidate superposition; and
  registering the first and second images to each other using a respective transform candidate selected from the plurality of transform candidates in the transformation data structure based at least in part on a value of the respective counter associated with the respective transform candidate in the transformation data structure.

What is claimed is:

1. A method of utilizing a single-analyte array, comprising:
  a) providing the single-analyte array, wherein the single-analyte array comprises first oligonucleotides at a plurality of sites, and wherein:
    each site of the plurality of sites is optically resolvable at single-analyte resolution,
    each site of the plurality of sites comprises a corresponding plurality of the first oligonucleotides, each of the first oligonucleotides comprising a first nucleotide sequence,
    each individual site of a first subset of the plurality of sites comprises a corresponding fiducial element of a plurality of fiducial elements, wherein the corresponding fiducial element is attached to a second oligonucleotide moiety, in a plurality of second oligonucleotide moieties, coupled to a first oligonucleotide of the corresponding plurality of first oligonucleotides for the individual site of the first subset of the plurality of sites by hybridization of the first nucleotide sequence of the first oligonucleotide with a second nucleotide sequence of the second oligonucleotide moiety, and wherein the first subset of the plurality of sites has a random spatial distribution,
    the single-analyte array further comprises a plurality of single analytes, wherein each individual single analyte in the plurality of single analytes is bound to an individual site in a second subset of the plurality of sites, wherein each single analyte of the plurality of single analytes is attached to a third oligonucleotide moiety, in a plurality of third oligonucleotide moieties, coupled to a first oligonucleotide of the corresponding plurality of first oligonucleotides for the individual site of the second subset of the plurality of sites by hybridization of the first nucleotide sequence of the first oligonucleotide with a second nucleotide sequence of the third oligonucleotide moiety, and wherein each site of the second subset of the plurality of sites comprises one and only one analyte of the plurality of single analytes, and
    the second nucleotide sequence of each respective second oligonucleotide moiety in the plurality of second oligonucleotide moieties and the second nucleotide sequence of each respective third oligonucleotide moiety in the plurality of third oligonucleotide moieties are the same;
  b) binding an analytical reagent to a single analyte of the plurality of single analytes;
  c) detecting optical signals from the first subset of the plurality of sites;
  d) detecting an optical signal from the analytical reagent bound to the single analyte; and
  e) based upon an address of the optical signal from the analytical reagent relative to the optical signals of the first subset of the plurality of sites, identifying a site of the second subset of the plurality of sites comprising the analytical reagent bound to the single analyte of the plurality of single analytes.

2. The method of claim 1, wherein providing the single-analyte array comprises: i) hybridizing the plurality of fiducial elements to the first subset of the plurality of sites; and ii) hybridizing the plurality of single-analytes to the second subset of the plurality of sites.

3. The method of claim 2, wherein the hybridizing i) occurs before the hybridizing ii).

4. The method of claim 2, wherein the hybridizing i) and the hybridizing ii) occur simultaneously.

5. The method of claim 1, wherein the first subset of the plurality of sites comprises no more than 1% of the plurality of sites.

6. The method of claim 5, wherein the first subset of the plurality of sites comprises no more than 0.1% of the plurality of sites.

7. The method of claim 1, wherein detecting the optical signals of the first subset of the plurality of sites comprises: iii) contacting the single-analyte array with electromagnetic radiation, wherein the electromagnetic radiation comprises light of a wavelength that produces optical signals from the plurality of fiducial elements; and iv) after contacting the single-analyte array with electromagnetic radiation, detecting the optical signals from fiducial elements of the plurality of fiducial elements at sites of the first subset of the plurality of sites.

8. The method of claim 1, wherein detecting the analytical reagent bound to the single analyte further comprises: v) contacting the single-analyte array with electromagnetic radiation, wherein the electromagnetic radiation comprises light of an excitation wavelength of a detectable label coupled to the analytical reagent.

9. The method of claim 8, wherein the excitation wavelength of the detectable label is the same wavelength as a wavelength that produces an optical signal from a fiducial element of the plurality of fiducial elements.

10. The method of claim 8, wherein detecting the analytical reagent bound to the single analyte further comprises: vi) detecting addresses of the optical signals from sites of the first subset of the plurality of sites.

11. The method of claim 10, wherein identifying the site of the second subset of the plurality of sites comprising the analytical reagent bound to the single analyte of the plurality of single analytes comprises: vii) providing the addresses of the optical signals from sites of the first subset of the plurality of sites to an image analysis algorithm; viii) matching a spatial distribution of the addresses of the optical signals from sites of the first subset of the plurality of sites to a subdistribution of the first subset of the plurality of sites using the image analysis algorithm; and ix) based upon the address of the optical signal from the analytical reagent relative to the subdistribution of the first subset of the plurality of sites, identifying the site of the second subset of the plurality of sites.

12. The method of claim 1, further comprising: f) for each site of the plurality of sites, identifying an address of the site on the single-analyte array.

13. The method of claim 12, wherein the identifying f) comprises: x) for each respective site in a third subset of the plurality of sites, coupling a mapping moiety to the respective site, and xi) detecting an address of a signal from the mapping moiety.

14. The method of claim 1, further comprising: g) identifying a site of the second subset of the plurality of sites comprising an absence of an analytical reagent bound to the single analyte of the plurality of single analytes.

15. The method of claim 1, wherein binding the analytical reagent to the single analyte of the plurality of single analytes comprises binding a first analytical reagent to a first single analyte, and binding a second analytical reagent to a second single analyte.

16. The method of claim 15, wherein the first analytical reagent comprises a first detectable label with a first excitation wavelength, wherein the second analytical reagent comprises a second detectable label with a second excitation wavelength, and wherein the first excitation wavelength differs from the second excitation wavelength.

17. The method of claim 16, wherein a fiducial element of the plurality of fiducial elements produces a first optical signal in the presence of light of the first excitation wavelength, and produces a second optical signal in the presence of light of the second excitation wavelength.

18. The method of claim 1, comprising, before binding the analytical reagent to the single analyte, identifying the random spatial distribution of the first subset of the plurality of sites.

19. The method of claim 1, wherein the single-analyte array further comprises an identification tag.

20. The method of claim 19, further comprising: xii) providing a datum from the identification tag to a database; xiii) after providing the datum to the database, obtaining an array map comprising the first subset of the plurality of sites.

21. The method of claim 20, further comprising matching the signals from the first subset of the plurality of sites to the array map of the first subset of the plurality of sites.

22. The method of claim 1, wherein a fiducial element of the plurality of fiducial elements comprises a fluorescent nanoparticle.

23. The method of claim 22, wherein the fluorescent nanoparticle comprises a fluorescent polymer nanoparticle or a quantum dot.

24. The method of claim 22 or 23, wherein the fluorescent nanoparticle comprises a multi-spectral nanoparticle.

25. The method of claim 24, wherein the binding b) comprises binding a first analytical reagent to a first single analyte of the plurality of single analytes, and binding a second analytical reagent to a second single analyte of the plurality of single analytes, wherein the first analytical reagent produces an optical signal at a first excitation wavelength, wherein the second analytical reagent produces an optical signal at a second excitation wavelength, and wherein the first excitation wavelength differs from the second excitation wavelength.

26. The method of claim 25, wherein the multi-spectral nanoparticle produces a first optical signal at the first excitation wavelength and a second optical signal at the second excitation wavelength.

27. The method of claim 1, further comprising repeating the binding b), detecting c), detecting d), and identifying e).

28. The method of claim 27, further comprising repeating the binding b), detecting c), detecting d), and identifying e) at least 50 times.

29. The method of claim 1, wherein, for an individual site of the first subset of the plurality of sites, the corresponding fiducial element of the plurality of fiducial elements is attached to two or more second oligonucleotide moieties in the plurality of second oligonucleotide moieties coupled to two or more first oligonucleotides of the corresponding plurality of first oligonucleotides for the individual site.

30. The method of claim 1, wherein a single analyte of the plurality of single analytes bound to an individual site in the second subset of the plurality of sites is attached to two or more third oligonucleotide moieties in the plurality of third oligonucleotide moieties coupled to two or more first oligonucleotides of the corresponding plurality of first oligonucleotides for the individual site.

* * * * *